United States Patent
Kaplan et al.

(10) Patent No.: US 11,306,144 B2
(45) Date of Patent: *Apr. 19, 2022

(54) B7-H4 ANTIBODIES AND METHODS OF USE THEREOF

(71) Applicant: Five Prime Therapeutics, Inc., South San Francisco, CA (US)

(72) Inventors: Charles Kaplan, San Francisco, CA (US); Derrick Houser, San Francisco, CA (US); Luis Borges, San Mateo, CA (US); Gloria Brattich, San Francisco, CA (US); David Bellovin, San Jose, CA (US); Felicia Kemp, San Jose, CA (US); Majid Ghoddusi, Walnut Creek, CA (US); Nels P. Nielson, Lebanon, NH (US); Kathy Miller, San Francisco, CA (US); Maike Schmidt, San Francisco, CA (US)

(73) Assignee: FIVE PRIME THERAPEUTICS, INC., South San Francisco, CA (US)

( * ) Notice: Subject to any disclaimer, the term of this patent is extended or adjusted under 35 U.S.C. 154(b) by 343 days.

This patent is subject to a terminal disclaimer.

(21) Appl. No.: 16/111,064

(22) Filed: Aug. 23, 2018

(65) Prior Publication Data

US 2019/0085080 A1    Mar. 21, 2019

Related U.S. Application Data

(60) Provisional application No. 62/656,789, filed on Apr. 12, 2018, provisional application No. 62/607,810, filed on Dec. 19, 2017, provisional application No. 62/579,774, filed on Oct. 31, 2017, provisional application No. 62/550,173, filed on Aug. 25, 2017.

(51) Int. Cl.

| C07K 16/28 | (2006.01) |
|---|---|
| A61K 39/395 | (2006.01) |
| A61P 35/00 | (2006.01) |
| G01N 33/574 | (2006.01) |
| A61K 39/00 | (2006.01) |

(52) U.S. Cl.
CPC .......... *C07K 16/2827* (2013.01); *A61P 35/00* (2018.01); *C07K 16/2818* (2013.01); *G01N 33/57492* (2013.01); *A61K 2039/505* (2013.01); *A61K 2039/507* (2013.01); *C07K 2317/21* (2013.01); *C07K 2317/24* (2013.01); *C07K 2317/40* (2013.01); *C07K 2317/41* (2013.01); *C07K 2317/52* (2013.01); *C07K 2317/56* (2013.01); *C07K 2317/565* (2013.01); *C07K 2317/73* (2013.01); *C07K 2317/732* (2013.01); *C07K 2317/74* (2013.01); *C07K 2317/75* (2013.01); *C07K 2317/76* (2013.01); *C07K 2317/92* (2013.01)

(58) Field of Classification Search
None
See application file for complete search history.

(56) References Cited

U.S. PATENT DOCUMENTS

| 3,817,837 | A | 6/1974 | Rubenstein |
|---|---|---|---|
| 3,850,752 | A | 11/1974 | Schuurs |
| 3,939,350 | A | 2/1976 | Kronick |
| 3,996,345 | A | 12/1976 | Ullman |
| 4,275,149 | A | 6/1981 | Litman |
| 4,277,437 | A | 7/1981 | Maggio |
| 4,366,241 | A | 12/1982 | Tom |
| 4,472,509 | A | 9/1984 | Gansow |
| 4,938,948 | A | 7/1990 | Ring |
| 5,122,464 | A | 6/1992 | Wilson |
| 5,196,066 | A | 3/1993 | Kusuda |
| 5,223,409 | A | 6/1993 | Ladner et al. |
| 5,225,539 | A | 7/1993 | Winter |
| 5,403,484 | A | 4/1995 | Ladner |
| 5,427,908 | A | 6/1995 | Dower |
| 5,516,637 | A | 5/1996 | Huang |
| 5,571,698 | A | 11/1996 | Ladner et al. |
| 5,580,717 | A | 12/1996 | Dower |
| 5,585,097 | A | 12/1996 | Bolt |

(Continued)

FOREIGN PATENT DOCUMENTS

| EP | 1331266 A1 | 7/2003 |
|---|---|---|
| WO | WO198605807 A1 | 10/1986 |

(Continued)

OTHER PUBLICATIONS

Podojil et al. (2017) Potential targeting of B7-H4 for the treatment of cancer. Immunol Rev. 276(1): 40-51.*
Wang et al. (2016) Could B7-H4 serve as a target to activate anti-cancer immunity? International Immunopharmacology 38: 97-103.*
MacGregor et al. (2017) Molecular Pathways: Evaluating the Potential for B7-H4 as an Immunoregulatory Target. Clin Cancer Res; 23(12): 2934-2941.*
Damschroder et al. Molecular Immunology (2004) 41: 985-1000.*
Khan et al. Sci. Rep. (2017) 7, 45163; doi: 10.1038/srep45163 (12 pages).*

(Continued)

*Primary Examiner* — Ilia I Ouspenski
(74) *Attorney, Agent, or Firm* — Marshall, Gerstein & Borun LLP

(57) ABSTRACT

The present disclosure provides antibodies and antigen-binding fragments thereof that specifically bind to human B7-H4 (and optionally cynomolgus monkey, mouse, and/or rat B7-H4) and compositions comprising such antibodies or antigen-binding fragments thereof. In a specific aspect, the antibodies or antigen-binding fragments thereof that specifically bind to human B7-H4 increase T cell proliferation, increase interferon-gamma production, and/or deplete B7-H4 expressing cells via ADCC activity. The present disclosure also provides methods for treating disorders, such as cancer, by administering an antibody or antigen-binding fragment thereof that specifically binds to human B7-H4.

45 Claims, 22 Drawing Sheets

Specification includes a Sequence Listing.

(56) References Cited

U.S. PATENT DOCUMENTS

| | | | |
|---|---|---|---|
| 5,624,821 A | 4/1997 | Winter | |
| 5,648,260 A | 7/1997 | Winter | |
| 5,658,727 A | 8/1997 | Barbas | |
| 5,677,425 A | 10/1997 | Bodmer | |
| 5,693,780 A | 12/1997 | Newman | |
| 5,698,426 A | 12/1997 | Huse | |
| 5,733,743 A | 3/1998 | Johnson et al. | |
| 5,750,753 A | 5/1998 | Kimae et al. | |
| 5,780,225 A | 7/1998 | Wigler | |
| 5,807,715 A | 9/1998 | Morrison | |
| 5,821,047 A | 10/1998 | Garrard et al. | |
| 5,869,046 A | 2/1999 | Presta | |
| 5,965,726 A | 10/1999 | Pavlakis | |
| 5,969,108 A | 10/1999 | Mccafferty | |
| 6,121,022 A | 9/2000 | Presta | |
| 6,165,745 A | 12/2000 | Ward | |
| 6,174,666 B1 | 1/2001 | Pavlakis | |
| 6,194,551 B1 | 2/2001 | Idusogie | |
| 6,277,022 B1 | 8/2001 | Melin | |
| 6,291,664 B1 | 9/2001 | Pavlakis | |
| 6,414,132 B1 | 7/2002 | Pavlakis | |
| 6,602,684 B1 | 8/2003 | Umana | |
| 6,737,056 B1 | 5/2004 | Presta | |
| 6,794,498 B2 | 9/2004 | Pavlakis | |
| 6,891,030 B2 | 5/2005 | Chen | |
| 6,946,292 B2 | 9/2005 | Kanda | |
| 7,214,775 B2 | 5/2007 | Hanai | |
| 7,304,149 B2 | 12/2007 | Murphy et al. | |
| 7,504,256 B1 | 3/2009 | Ogawa | |
| 7,619,068 B2 | 11/2009 | Pilkington et al. | |
| 7,622,565 B2 | 11/2009 | Chen | |
| 7,658,921 B2 | 2/2010 | Dall | |
| 7,687,061 B2 | 3/2010 | Hanai | |
| 7,709,226 B2 | 5/2010 | Foote | |
| 7,875,702 B2 | 1/2011 | Chen | |
| 7,888,477 B2 | 2/2011 | Bangur et al. | |
| 7,931,896 B2 | 4/2011 | Chen | |
| 7,964,195 B2 | 6/2011 | Papkoff et al. | |
| 8,129,347 B2 | 3/2012 | Chen | |
| 8,182,813 B2 | 5/2012 | Brasel | |
| 8,206,715 B2 | 6/2012 | Wong | |
| 8,236,767 B2 | 8/2012 | Chen | |
| 8,263,079 B2 | 9/2012 | Doody | |
| 8,323,645 B2 | 12/2012 | Veiby et al. | |
| 8,444,971 B2 | 5/2013 | Papkoff et al. | |
| 8,513,199 B2 | 8/2013 | Brasel | |
| 8,591,886 B2 | 11/2013 | Ponath | |
| 8,609,816 B2 | 12/2013 | Korman et al. | |
| 8,652,465 B2 | 2/2014 | Freeman et al. | |
| 8,703,916 B2 | 4/2014 | Chen | |
| 8,759,490 B2 | 6/2014 | Veiby et al. | |
| 8,906,369 B2 * | 12/2014 | Papkoff | A61K 51/1027 424/130.1 |
| 9,005,616 B2 | 4/2015 | Langermann et al. | |
| 9,011,853 B2 | 4/2015 | Langermann et al. | |
| 9,121,853 B2 | 9/2015 | Kwon et al. | |
| 9,221,910 B2 | 12/2015 | Fertig | |
| 9,279,008 B2 | 3/2016 | Scholler et al. | |
| 9,296,822 B2 * | 3/2016 | Korman | A61P 37/06 |
| 9,421,277 B2 | 8/2016 | Veiby et al. | |
| 9,422,351 B2 | 8/2016 | Scholler et al. | |
| 9,447,186 B2 | 9/2016 | Zang et al. | |
| 9,555,124 B2 | 1/2017 | Chen | |
| 9,562,099 B2 | 2/2017 | Leong et al. | |
| 9,574,000 B2 | 2/2017 | Langermann et al. | |
| 9,676,854 B2 * | 6/2017 | Liu | A61P 37/06 |
| 9,926,378 B2 | 3/2018 | Veiby et al. | |
| 9,957,312 B2 | 5/2018 | Langermann et al. | |
| 10,059,768 B2 | 8/2018 | Leong et al. | |
| 2003/0055224 A1 | 3/2003 | Gao | |
| 2003/0060612 A1 | 3/2003 | Goddard | |
| 2003/0165504 A1 | 9/2003 | Retter et al. | |
| 2003/0181692 A1 | 9/2003 | Ni | |
| 2003/0208058 A1 | 11/2003 | Fiscella | |
| 2004/0014194 A1 | 1/2004 | Beyer | |
| 2004/0126807 A1 | 7/2004 | Goddard | |
| 2005/0163772 A1 | 7/2005 | Dong et al. | |
| 2006/0088523 A1 | 4/2006 | Andya | |
| 2006/0223077 A1 | 10/2006 | Ni | |
| 2006/0253928 A1 | 11/2006 | Bakker | |
| 2007/0036783 A1 | 2/2007 | Humeau et al. | |
| 2007/0178551 A1 | 8/2007 | Gerngross | |
| 2007/0218032 A1 | 9/2007 | Kwon | |
| 2007/0248600 A1 | 10/2007 | Hansen | |
| 2008/0050370 A1 | 2/2008 | Glaser et al. | |
| 2008/0060092 A1 | 3/2008 | Dickey | |
| 2008/0206235 A1 | 8/2008 | Chen | |
| 2009/0005301 A1 | 1/2009 | Ni | |
| 2009/0118175 A1 | 5/2009 | Macina | |
| 2009/0176317 A1 | 7/2009 | Kwon et al. | |
| 2011/0020325 A1 | 1/2011 | Kwon et al. | |
| 2011/0085970 A1 | 4/2011 | Terrett et al. | |
| 2012/0014947 A1 | 1/2012 | Fu | |
| 2013/0078234 A1 | 3/2013 | Takahashi et al. | |
| 2014/0037551 A1 | 2/2014 | Zang et al. | |
| 2014/0294861 A1 | 10/2014 | Scholler et al. | |
| 2014/0322129 A1 | 10/2014 | Leong | |
| 2014/0335541 A1 | 11/2014 | Kwon et al. | |
| 2014/0356364 A1 | 12/2014 | Liu et al. | |
| 2014/0364585 A1 | 12/2014 | Zhang et al. | |
| 2015/0315275 A1 | 11/2015 | Liu et al. | |
| 2016/0017040 A1 | 1/2016 | Leong et al. | |
| 2016/0146806 A1 | 5/2016 | Langermann et al. | |
| 2016/0159910 A1 | 6/2016 | Leong et al. | |
| 2016/0185870 A1 | 6/2016 | Van et al. | |
| 2016/0304581 A1 | 10/2016 | Zang et al. | |
| 2016/0304607 A1 | 10/2016 | Sadineni et al. | |
| 2017/0015758 A1 | 1/2017 | Hammond et al. | |
| 2017/0029525 A1 | 2/2017 | Zang et al. | |
| 2017/0044268 A1 | 2/2017 | Gurney et al. | |
| 2017/0143827 A1 | 5/2017 | Sadineni et al. | |
| 2017/0158771 A1 | 6/2017 | Glennie et al. | |
| 2017/0204185 A1 | 7/2017 | Chen | |
| 2017/0233808 A1 | 8/2017 | Haining et al. | |
| 2017/0334999 A1 | 11/2017 | Sathyanarayanan et al. | |
| 2018/0118831 A1 | 5/2018 | Epstein et al. | |
| 2018/0186878 A1 | 7/2018 | Rosenthal | |
| 2019/0085080 A1 | 3/2019 | Kaplan et al. | |
| 2020/0255528 A1 * | 8/2020 | Kaplan | C07K 16/2827 |
| 2021/0070861 A1 * | 3/2021 | Quan | C07K 16/2827 |
| 2021/0070862 A1 * | 3/2021 | Inamdar | C07K 16/2827 |
| 2021/0079096 A1 * | 3/2021 | Kaplan | G01N 33/57492 |
| 2021/0332137 A1 * | 10/2021 | Inamdar | C07K 16/2818 |

FOREIGN PATENT DOCUMENTS

| | | |
|---|---|---|
| WO | WO198901036 A1 | 2/1989 |
| WO | WO199002809 A1 | 3/1990 |
| WO | WO199110737 A1 | 7/1991 |
| WO | WO199201047 A1 | 1/1992 |
| WO | WO199218619 A1 | 10/1992 |
| WO | WO199311236 A1 | 6/1993 |
| WO | WO199429351 A2 | 12/1994 |
| WO | WO199429351 A3 | 12/1994 |
| WO | WO199515982 A2 | 6/1995 |
| WO | WO199520401 A1 | 8/1995 |
| WO | WO199515982 A3 | 12/1995 |
| WO | WO199713844 A1 | 4/1997 |
| WO | WO199734631 A1 | 9/1997 |
| WO | WO199823289 A1 | 6/1998 |
| WO | WO199954342 A1 | 10/1999 |
| WO | WO200036107 A2 | 6/2000 |
| WO | WO200042072 A2 | 7/2000 |
| WO | WO200061739 A1 | 10/2000 |
| WO | WG200042072 A3 | 11/2000 |
| WO | WO200036107 A3 | 2/2001 |
| WO | WO200129246 A1 | 4/2001 |
| WO | WO200140269 A2 | 6/2001 |
| WO | WO200162891 A2 | 8/2001 |
| WO | WO200140269 A3 | 12/2001 |
| WO | WO200202587 A1 | 1/2002 |
| WO | WO200206317 A2 | 1/2002 |
| WO | WO200210187 A1 | 2/2002 |
| WO | WO200216581 A2 | 2/2002 |

(56) References Cited

FOREIGN PATENT DOCUMENTS

| | | |
|---|---|---|
| WO | WO200230954 A1 | 4/2002 |
| WO | WO200231140 A1 | 4/2002 |
| WO | WO2002060919 A2 | 8/2002 |
| WO | WO2002060919 A3 | 8/2002 |
| WO | WO2002062203 A2 | 8/2002 |
| WO | WO2002071928 A2 | 9/2002 |
| WO | WO200216581 A3 | 1/2003 |
| WO | WO2003004989 A2 | 1/2003 |
| WO | WG2002062203 A3 | 2/2003 |
| WO | WO2003011878 A2 | 2/2003 |
| WO | WO2002071928 A3 | 3/2003 |
| WO | WO2003004989 A3 | 3/2003 |
| WO | WO200162891 A3 | 7/2003 |
| WO | WO200206317 A3 | 7/2003 |
| WO | WO2003076579 A2 | 9/2003 |
| WO | WO2003011878 A3 | 11/2003 |
| WO | WO2003097802 A2 | 11/2003 |
| WO | WO2003097803 A2 | 11/2003 |
| WO | WO2003101400 A2 | 12/2003 |
| WO | WO2003104399 A2 | 12/2003 |
| WO | WO2003104438 A2 | 12/2003 |
| WO | WO2004000221 A2 | 12/2003 |
| WO | WO2004000221 A3 | 7/2004 |
| WO | WO2004058167 A2 | 7/2004 |
| WO | WO2004065540 A2 | 8/2004 |
| WO | WO2003076579 A3 | 9/2004 |
| WO | WO2004101756 A2 | 11/2004 |
| WO | WO2003097802 A3 | 12/2004 |
| WO | WO2004113500 A2 | 12/2004 |
| WO | WO2004058167 A3 | 1/2005 |
| WO | WO2004065540 A3 | 3/2005 |
| WO | WO2005035724 A2 | 4/2005 |
| WO | WO2004101756 A3 | 6/2005 |
| WO | WO2005051990 A2 | 6/2005 |
| WO | WO2005052121 A2 | 6/2005 |
| WO | WO2003104438 A3 | 7/2005 |
| WO | WO2005062788 A2 | 7/2005 |
| WO | WO2004113500 A3 | 8/2005 |
| WO | WO2005051990 A3 | 8/2005 |
| WO | WO2003101400 A3 | 9/2005 |
| WO | WO2003104399 A3 | 9/2005 |
| WO | WO2003097803 A3 | 5/2006 |
| WO | WO2006053110 A2 | 5/2006 |
| WO | WO2005035724 A3 | 6/2006 |
| WO | WO2005052121 A3 | 6/2006 |
| WO | WO2006074418 A2 | 7/2006 |
| WO | WO2006098887 A2 | 9/2006 |
| WO | WO2005062788 A3 | 10/2006 |
| WO | WO2006104677 A2 | 10/2006 |
| WO | WO2006105021 A2 | 10/2006 |
| WO | WO2006104677 A3 | 11/2006 |
| WO | WO2006121991 A2 | 11/2006 |
| WO | WO2006133396 A2 | 12/2006 |
| WO | WO2007001459 A2 | 1/2007 |
| WO | WO2007005874 A2 | 1/2007 |
| WO | WO2006053110 A3 | 3/2007 |
| WO | WO2006105021 A3 | 3/2007 |
| WO | WO2006074418 A3 | 4/2007 |
| WO | WO2006121991 A3 | 4/2007 |
| WO | WO2007039818 A2 | 4/2007 |
| WO | WO2007067991 A2 | 6/2007 |
| WO | WO2007005874 A3 | 7/2007 |
| WO | WO2007082154 A2 | 7/2007 |
| WO | WO2006098887 A3 | 8/2007 |
| WO | WO2006133396 A3 | 8/2007 |
| WO | WO2007039818 A3 | 8/2007 |
| WO | WO2007067991 A3 | 9/2007 |
| WO | WO2007001459 A3 | 10/2007 |
| WO | WO2008067283 A2 | 6/2008 |
| WO | WO-2008071447 A2 | 6/2008 |
| WO | WO2008083228 A2 | 7/2008 |
| WO | WO2008083239 A2 | 7/2008 |
| WO | WO2008083239 A3 | 8/2008 |
| WO | WO2008067283 A3 | 10/2008 |
| WO | WO2007082154 A3 | 11/2008 |
| WO | WO2008083228 A3 | 11/2008 |
| WO | WO2008154333 A2 | 12/2008 |
| WO | WO2007001459 A8 | 1/2009 |
| WO | WO2009009116 A2 | 1/2009 |
| WO | WO2009009116 A3 | 3/2009 |
| WO | WO-2009036379 A2 | 3/2009 |
| WO | WO2009073533 A2 | 6/2009 |
| WO | WO2008154333 A3 | 11/2009 |
| WO | WO2009073533 A3 | 11/2009 |
| WO | WO-2010105256 A1 | 9/2010 |
| WO | WO2011020024 A2 | 2/2011 |
| WO | WO2011028683 A1 | 3/2011 |
| WO | WO2011020024 A3 | 6/2011 |
| WO | WO-2012009568 A2 | 1/2012 |
| WO | WO2012130831 A1 | 10/2012 |
| WO | WO2012145493 A1 | 10/2012 |
| WO | WO2013025779 A1 | 2/2013 |
| WO | WO2013067492 A1 | 5/2013 |
| WO | WO2013079174 A1 | 6/2013 |
| WO | WO-2014100439 A2 | 6/2014 |
| WO | WO-2014100483 A2 | 6/2014 |
| WO | WO-2014100823 A1 | 6/2014 |
| WO | WO-2014159835 A1 | 10/2014 |
| WO | WO2015017600 A1 | 2/2015 |
| WO | WO2015031667 A2 | 3/2015 |
| WO | WO-2015069770 A1 | 5/2015 |
| WO | WO2015031667 A3 | 11/2015 |
| WO | WO2016040724 A1 | 3/2016 |
| WO | 2016/070001 A1 | 5/2016 |
| WO | WO-2016168771 A2 | 10/2016 |
| WO | WO-2016197204 A1 | 12/2016 |
| WO | WO2017015623 A2 | 1/2017 |
| WO | WO-2017019846 A1 | 2/2017 |
| WO | WO2017015623 A3 | 3/2017 |
| WO | WO-2017048878 A1 | 3/2017 |
| WO | WO-2017058754 A1 | 4/2017 |
| WO | WO2017079117 A1 | 5/2017 |
| WO | 2017106656 A1 | 6/2017 |
| WO | WO-2017129790 A1 | 8/2017 |
| WO | WO-2017147368 A1 | 8/2017 |
| WO | WO-2017149150 A1 | 9/2017 |
| WO | WO-2017201502 A1 | 11/2017 |
| WO | WO-2018049474 A1 | 3/2018 |
| WO | WO-2018075978 A1 | 4/2018 |
| WO | WO-2018078145 A1 | 5/2018 |
| WO | WO2018098363 A2 | 5/2018 |
| WO | 2018106862 A1 | 6/2018 |
| WO | 2018106864 A1 | 6/2018 |
| WO | WO2018098363 A3 | 9/2018 |
| WO | WO-2019040780 A1 | 2/2019 |
| WO | WO2019165075 A1 | 8/2019 |
| WO | WO2019165077 A1 | 8/2019 |
| WO | WO2019169212 A1 | 9/2019 |
| WO | 2020081497 A1 | 4/2020 |

OTHER PUBLICATIONS

Zhu et al. Cell (2015) 161: 1280-1292.*
Lee et al. Nature Medicine (2016) 22: 1456-1464.*
Abdiche et al. mAbs (2016) 8: 264-277.*
Konitzer et al. mAbs (2017) 9: 536-549.*
Ferrara et al. mAbs (2015) 7: 32-41.*
Parola et al. Immunology (2018) 153:31-41.*
Boyd et al. Current Opinion in Immunology 2016, 40: 103-109.*
Van Regenmortel MHV. Front. Immunol. (2018) vol. 8, Article 2009 (11 pages).*
Conroy et al. Methods (2017) 116: 12-22.*
Sheehan et al. Microbiol. Spectr. (2015) 3(1): AID-0028-2014; 17 pages.*
Kaplan et al. FPA150, a Novel B7-H4 Therapeutic Antibody With Checkpoint Blockade and ADCC Activities. Annals of Oncology (Sep. 2017) 28 (suppl_5): v2, Abstract 1548 (1 page).*
Kaplan et al. FPA150, a Novel B7-H4 Therapeutic Antibody With Checkpoint Blockade and ADCC Activities. ESMO 2017 Congress, Sep. 8-12, 2017, Madrid, Spain; Poster (1 page).*
Abadi, Y., et al., "Host B7x Promotes Pulmonary Metastasis of Breast Cancer," Journal of Immunology, 190(7):3806-3814, American Association of Immunologists, United States (Mar. 2013).

(56) References Cited

OTHER PUBLICATIONS

Anderson, G.L., et al., "Assessing Lead Time of Selected Ovarian Cancer Biomarkers: a Nested Case-control Study," Journal of the National Cancer Institute, 102(1):26-38, Oxford University Press, United States (Jan. 2010).

Arnold, J.N., et al., "The Impact of Glycosylation on the Biological Function and Structure of Human Immunoglobulins," Annual Review of Immunology, 25: 21-50, Annual Reviews Inc., United States (2007).

Awadallah, N., et al., "Detection of B7-H4 and P53 in Pancreatic Cancer: Potential Role as a Cytological Diagnostic Adjunct," Pancreas, 36(2):200-206, Lippincott Williams & Wilkins, United States (Mar. 2008).

Azuma, T., et al., "Potential Role of Decoy B7-H4 in the Pathogenesis of Rheumatoid Arthritis: a Mouse Model Informed by Clinical Data," PLOS Medicine, 6(10):e1000166, pp. 1-15, Public Library of Science, United States (Oct. 2009).

Bregar, A., et al., "Characterization of Immune Regulatory Molecules B7-H4 and PD-L1 in Low and High Grade Endometrial Tumors," Gynecologic Oncology, 145(3):446-452, Academic Press, United States (Mar. 2017).

Carreno, B., et al., "Therapeutic Opportunities in the B7/CD28 Family of Ligands and Receptors," Current Opinion in Pharmacology, 5(4):424-430, Elsevier Science, England (Jun. 2005).

Chen, C., et al., "Analysis of B7-H4 Expression in Metastatic Pleural Adenocarcinoma and Therapeutic Potential of Its Antagonists," BMC Cancer, 17(1):652 (6 pages), BioMed Central, England (Sep. 2017).

Chen, C., et al., "Increase of Circulating B7-H4-expressing CD68+ Macrophage Correlated With Clinical Stage of Lung Carcinomas," Journal of Immunotherapy, 35(4):354-358 (May 2012).

Chen, C., et al., "Induced Expression of B7-H4 on the Surface of Lung Cancer Cell by the Tumor-associated Macrophages: a Potential Mechanism of Immune Escape," Cancer Letters, 317(1):99-105, Elsevier Science Ireland, Ireland (2012).

Chen, C., et al., "Nuclear Localization of B7-H4 in Pulmonary Adenocarcinomas Presenting as a Solitary Pulmonary Nodule," Oncotarget, 7(36):58563-58568, Impact Journals, United States (Jul. 2016).

Chen, C., et al., "Overexpression of B7-H4 in Tumor Infiltrated Dendritic Cells," Journal of Immunoassay and Immunochemistry, 32(4):353-364, Taylor & Francis, England (2011).

Chen, L.J., et al., "B7-H4 Expression Associates With Cancer Progression and Predicts Patient's Survival in Human Esophageal Squamous Cell Carcinoma," Cancer Immunology Immunotherapy, 60(7):1047-1055, Springer Verlag, Germany (Apr. 2011).

Chen, X., et al., "Increased B7-H4 Expression During Esophageal Squamous Cell Carcinogenesis is Associated with IL-6/STAT3 Signaling Pathway Activation in Mice," Oncology Letters, 13(4):2207-2215, Spandidos Publications, Greece (Feb. 2017).

Chen, Y., et al., "The Coexpression and Clinical Significance of Costimulatory Molecules B7-H1, B7-H3, and B7-H4 in Human Pancreatic Cancer," OncoTargets and Therapy, 7:1465-1472, Dove Medical Press, c2008, New Zealand (2014).

Chinnadurai, R and Grakoui, A, "B7-H4 Mediates Inhibition of T Cell Responses by Activated Murine Hepatic Stellate Cells," Hepatology, 52(6):2177-2185, Williams and Wilkins, United States (Dec. 2010).

Choi, I.H., et al., "Genomic Organization and Expression Analysis of B7-H4, an Immune Inhibitory Molecule of the B7 Family," Journal of Immunology, 171(9):4650-4654, American Association of Immunologists, United States (2003).

Cui, Y and Li, Z.,, "B7-H4 is Predictive of Poor Prognosis in Patients With Gastric Cancer," Medical Science Monitor, 22:4233-4237, International Scientific Information, United States (2016).

Dangaj, D., et al., "Novel Recombinant Human B7-H4 Antibodies Overcome Tumoral Immune Escape to Potentiate T-cell Antitumor Responses," Cancer Research, 73(15):4820-4829, American Association for Cancer Research, United States (May 2013).

Epstein, A.L., "B7-H4 as a Target for Breast Cancer Immunotherapy," Research Grant W81XWH-11-1-0466, 2012, 18 pages.

Fan, M., et al., "B7-H4 Expression Is Correlated With Tumor Progression and Clinical Outcome in Urothelial Cell Carcinoma," International Journal of Clinical and Experimental Pathology, 7(10):6768-6775, E-century Publishing Corporation, United States (2014).

Fukuda, T., et al., "Higher Preoperative Serum Levels of PD-L1 and B7-H4 are Associated with Invasive and Metastatic Potential and Predictable for Poor Response to VEGF-targeted Therapy and Unfavorable Prognosis of Renal Cell Carcinoma," Cancer Medicine, 5(8):1810-1820, John Wiley & Sons Limited, United States (2016).

Gao, A., et al., "Effect of VTCN1 on Progression and Metastasis of Ovarian Carcinoma in Vitro and Vivo," Biomedicine & Pharmacotherapy, 73:129-134, Editions Scientifiques Elsevier, France (2015).

Geng, Y., et al., "Expression of Costimulatory Molecules B7-H1, B7-H4 and Foxp3+ Tregs in Gastric Cancer and Its Clinical Significance," International Journal of Clinical Oncology, 20(2):273-281, Springer-Verlag Tokyo, Japan (2015).

Han, S., et al., "Negative Roles of B7-H3 and B7-H4 in the Microenvironment of Cervical Cancer," Experimental Cell Research, Author's Accepted Manuscript, Academic Press, United States (Aug. 2018).

Han, S., et al., "Roles of Immune Inhibitory Molecule B7-H4 in Cervical Cancer," Oncology Reports, 37(4):2308-2316, D.A. Spandidos, Greece (Apr. 2017).

Hansen, J.D., et al., "The B7 Family of Immunoregulatory Receptors: A Comparative and Evolutionary Perspective," Molecular Immunology, 46(3):457-472, Pergamon Press, England (2009).

He, C., et al., "The Inhibitory Role of B7-H4 in Antitumor Immunity: Association With Cancer Progression and Survival," Clinical & Developmental Immunology, 2011:695834 (8 pages), Hindawi Publishing Corporation, Egypt (2011).

Horsten, H., et al., "Production of Non-Fucosylated Antibodies by Co-expression of Heterologous GDP-6-Deoxy-D-Lyxo-4-Hexulose Reductase," Glycobiology, 20(12):1607-1618, IRL Press at Oxford University Press, England (2010).

Huang, C., et al., "B7-H3, B7-H4, Foxp3 and IL-2 Expression in Cervical Cancer: Associations With Patient Outcome and Clinical Significance," Oncology reports, 35(4):2183-2190, D.A. Spandidos, Greece (Apr. 2016).

Huang, H., et al., "Clinical Significance of the B7-H4 as a Novel Prognostic Marker in Breast Cancer," Gene, Author's Manuscript, Elsevier, Netherlands (Apr. 2017).

Iida, S., et al., "Two Mechanisms of the Enhanced Antibody-dependent Cellular Cytotoxicity (ADCC) Efficacy of Non-fucosylated Therapeutic Antibodies in Human Blood," BMC Cancer, 9:58 (12 pages), BioMed Central, England (Feb. 2009).

Iizuka, A., et al., "Unstable B7-H4 Cell Surface Expression and T-cell Redirection as a Means of Cancer Therapy," Oncology Reports, 36(5):2625-2632, D.A. Spandidos, Greece (Nov. 2016).

Janakiram, M., et al., "The Third Group of the B7-CD28 Immune Checkpoint Family: HHLA2, TMIGD2, B7x, and B7-H3," Immunological Reviews, 276(1):26-39, Blackwell, England (Mar. 2017).

Jennewein, M and Alter G., et al., "The Immunoregulatory Roles of Antibody Glycosylation," Trends in Immunology, 38(5):358-372, Elsevier Science, England (May 2017).

Jeon, H., et al., "Structure and Cancer Immunotherapy of the B7 Family Member B7x," Cell Reports, 9(3):1089-1098, Cell Press, United States (Nov. 2014).

Jiang, J., et al., "Tumor Expression of B7-H4 Predicts Poor Survival of Patients Suffering From Gastric Cancer," Cancer Immunology, 59(11):1707-1714, Springer Verlag, Germany (2010).

Jiang, J.T., et al.,, "B7-H4 Expression and Increased Death Risk of Cancer Patients: A Meta-Analysis," Journal of Cancer Research and Clinical Oncology, 8:229-234 (2011).

Kamimura, Y., et al., "Possible Involvement of Soluble B7-H4 in T Cell-mediated Inflammatory Immune Responses," Biochemical and Biophysical Research Communications, 389(2):349-353, Elsevier, United States (Aug. 2009).

(56) References Cited

OTHER PUBLICATIONS

Kim, J.Y., et al., "Immune Signature of Metastatic Breast Cancer: Identifying Predictive Markers of Immunotherapy Response," Oncotarget, Advance Publications:1-12, Impact Journals, United States (May 2017).

Krambeck, A.E., et al., "B7-H4 Expression in Renal Cell Carcinoma and Tumor Vasculature: Associations With Cancer Progression and Survival," Proceedings of the National Academy of Sciences of the United States of America, 103(27):10391-10396, National Academy of Sciences, United States (Jul. 2006).

Kryczek, I., et al., "B7-H4 Expression Identifies a Novel Suppressive Macrophage Population in Human Ovarian Carcinoma," The Journal of Experimental Medicine, 203(4):871-881, Rockefeller University Press, United States (Apr. 2006).

Kryczek, I., et al., "Relationship Between B7-H4, Regulatory T Cells, and Patient Outcome in Human Ovarian Carcinoma," Cancer Research, 67(18):8900-8905, American Association for Cancer Research, United States (Sep. 2007).

Leong, S., et al., "An Anti-B7-H4 Antibody-drug Conjugate for the Treatment of Breast Cancer," Molecular Pharmaceutics, 12(6):1717-1729, American Chemical Society, United States (Apr. 2015).

Leung, J., et al., "Host B7-H4 Regulates Antitumor T Cell Responses Through Inhibition of Myeloid-derived Suppressor Cells in a 4T1 Tumor Transplantation Model," Journal of Immunology, 190(12):6651-6661, American Association of Immunologists, United States (Jun. 2013), and supplemental information.

Leung, J., et al., "Synergistic Effects of Host B7-H4 Deficiency and Gemcitabine Treatment on Tumor Regression and Anti-tumor T Cell Immunity in a Mouse Model," Cancer Immunology, 66(4):491-502, Springer Verlag, Germany (Jan. 2017).

Li, J., et al., "Co-inhibitory Molecule B7 Superfamily Member 1 Expressed by Tumor-infiltrating Myeloid Cells Induces Dysfunction of Anti-tumor CD8+ T Cells," Immunity Cell Press, 48:1-14, Elsevier, Netherlands (Apr. 2018).

Liu, J., et al., "Expression of Immune Checkpoint Molecules in Endometrial Carcinoma," Experimental and Therapeutic Medicine, 10(5):1947-1952, Spandidos Publications, Greece (2015).

Liu, L., et al., "B7-H4 Expression in Human Infiltrating Ductal Carcinoma-associated Macrophages," Molecular Medicine Report, 14(3):2135-2142, Spandidos Publications, Greece (2016).

Liu, W-H., et al., "B7-H4 Expression in Bladder Urothelial Carcinoma and Immune Escape Mechanisms," Oncology Letters, 8(6):2527-2534, Spandidos Publications, Greece (2014).

MacGregor, H-L and Ohashi, P-S., "Molecular Pathways: Evaluating the Potential for B7-H4 as an Immunoregulatory Target," Clinical Cancer Research, 23(12):2934-2941, Denville, United States (Jun. 2017).

Mao, Y., et al., "Recombinant Human B7-H4 Expressed in *Escherichia coli* Inhibits T Lymphocyte Proliferation and IL-2 Secretion in Vitro," Acta Pharmacologica Sinica, 27(6):741-746, Blackwell Publishing Group, United States (Jun. 2006).

Matsunaga, T., et al., "Increased B7-H1 and B7-H4 Expressions on Circulating Monocytes and Tumor-associated Macrophages Are Involved in Immune Evasion in Patients With Gastric Cancer," Yonago Acta Medica, 54(1):1-10, Tottori University Medical Press, Japan (2011).

Meng, Z., et al., "B7-H4 as an Independent Prognostic Indicator of Cancer Patients: a Meta-analysis," Oncotarget, 8(40):68825-68836, Impact Journals, United States (Jun. 2017).

Miyatake, T., et al., "B7-H4 (DD-O110) Is Overexpressed in High Risk Uterine Endometrioid Adenocarcinomas and Inversely Correlated With Tumor T-cell Infiltration," Gynecologic Oncology, 106(1):119-127, Academic Press, United States (2007).

Mugler, K., et al., "B7-H4 Expression in a Range of Breast Pathology: Correlation With Tumor T-cell Infiltration," Applied Immunohistochemistry and Molecular Morphology, 15(4):363-370, Lippincott Williams & Wilkins, United States (Dec. 2007).

Niwa R., et al., "Enhanced Natural Killer Cell Binding and Activation by Low-fucose IgG1 Antibody Results in Potent Antibody-dependent Cellular Cytotoxicity Induction at Lower Antigen Density," Clinical Cancer Research, 11(6):2327-2336, Denville, United States (Mar. 2005).

Ohaegbulam, K., et al., "Tumor-expressed Immune Checkpoint B7X Promotes Cancer Progression and Antigen-specific CD8 T Cell Exhaustion and Suppressive Innate Immune Cells," Oncotarget, 8(47):82740-82753, Impact Journals, United States (Sep. 2017).

Kaplan, C., et al., "FPA 150, a Novel B7-H4 Therapeutic Antibody with Checkpoint Blockade and ADCC Activities," Five Prime Therapeutics, ADIMAB, 2017, 1 page.

MacGregor, H.L., et al., "Molecular Pathways: Evaluating the Potential for B7-H4 as an Immunoregulatory Target," Clinical Cancer Research: 23 pages, American Association of Cancer Research, United States (Mar. 2017).

Podojil, J and Miller, S., et al., "Potential Targeting of B7-H4 for the Treatment of Cancer," Immunological Reviews, 276(1):40-51, Blackwell, England (Mar. 2017).

Prasad, D., et al., "B7S1, a Novel B7 Family Member That Negatively Regulates T Cell Activation.," Immunity, 18(6):863-873, Cell Press, United States (Jun. 2003).

Tringler, B., et al., "B7-H4 is Highly Expressed in Ductal and Lobular Breast Cancer," Clinical Cancer Research, 11(5):1842-1848, The Association, 1995, United States (Mar. 2005).

Qian, Y., et al., "B7-H4 Expression in Various Tumors Determined Using a Novel Developed Monoclonal Antibody," Clinical and Experimental Medicine, 11(3):163-170, Milano, Italy (2011).

Qian, Y., et al., "Development of a Novel Monoclonal Antibody to B7-H4: Characterization and Biological Activity," European Journal of Medical Research, 16(7):295-302, BioMed Central, England (Jul. 2011).

Rahbar, R., et al., "B7-H4 Expression by Nonhematopoietic Cells in the Tumor Microenvironment Promotes Antitumor Immunity," Cancer Immunology Research, 3(2):184-195, American Association for Cancer Research, United States (Feb. 2015).

Rahbar, R., et al., "B7-H4 Is a Positive Regulator of Antitumor Immunity," Oncoimmunology, 5(1):e1050575 (2 pages), Taylor & Francis, United States (Jan. 2016).

Salceda, S., et al., "The Immunomodulatory Protein B7-H4 Is Overexpressed in Breast and Ovarian Cancers and Promotes Epithelial Cell Transformation," Experimental Cell Research, 306(1):128-141, Academic Press, United States (May 2005).

Sankin, A., et al., "The Expanding Repertoire of Targets for Immune Checkpoint Inhibition in Bladder Cancer: What Lies Beneath the Tip of the Iceberg, PD-L1," Urologic Oncology, 36(10):459-468, Elsevier Science, United States (Oct. 2018).

Schalper, K., et al., "Differential Expression and Significance of PD-L1, IDO-1, and B7-H4 in Human Lung Cancer," Clinical Cancer Research, 23(2):370-378, Denville, United States (Jan. 2017).

Shaffer, D., et al., "Dissecting the Tumor Micro-environment in Triple Negative Breast Cancer Identifies a Mutually Exclusive Expression Pattern of the Immune Co-inhibitory Molecules B7-H 4 and PD-L1," Journal for Immunotherapy of Cancer, 3(2):O17 (1 page), BioMed Central, England (2015).

Shen, L., et al., "B7-H4 Is a Prognostic Biomarker for Poor Survival in Patients With Pancreatic Cancer," Human Pathology, 66:79-85, W B Saunders, United States (Aug. 2017).

Shi, H., et al., "Serum B7-H4 Expression Is a Significant Prognostic Indicator for Patients With Gastric Cancer," World Journal of Surgical Oncology, 12:188 (5 pages) BioMed Central, England (2014).

Shrestha, R., et al., "Monitoring Immune Checkpoint Regulators as Predictive Biomarkers in Hepatocellular Carcinoma," Frontiers in Oncology, 8:269 (17 pages), Frontiers Research Foundation, Switzerland (Jul. 2018).

Sica, G., et al., "B7-H4, a Molecule of the B7 Family, Negatively Regulates T Cell Immunity," Immunity, 18(6):849-861, Cell Press, United States (Jun. 2003).

Simon, I., et al., "B7-H4 Is a Novel Membrane-bound Protein and a Candidate Serum and Tissue Biomarker for Ovarian Cancer," Cancer Research, 66(3):1570-1575, American Association for Cancer Research, United States (Feb. 2006).

(56) References Cited

OTHER PUBLICATIONS

Simon, I., et al., "B7-H4 Is Over-expressed in Early-stage Ovarian Cancer and is Independent of CA125 Expression," Gynecologic Oncology, 106(2):334-341, Academic Press, United States (Aug. 2007).
Smith, J., et al., "B7-H4 as a Potential Target for Immunotherapy for Gynecologic Cancers: a Closer Look," Gynecologic Oncology, 134(1):181-189, Academic Press, United States (Jul. 2014).
Smith, J., et al., "Tumor Regression and Delayed Onset Toxicity Following B7-H4 Car T Cell Therapy," Molecular Therapy, 24(11):1987-1999, Cell Press, United States (Nov. 2016).
Song, X., et al., "Prognostic Role of High B7-H4 Expression in Patients With Solid Tumors: a Meta-analysis," Oncotarget, Advance Publications:1-11, Impact Journals, United States (Apr. 5, 2016).
Kaplan, C.D., et al., FPA150, a Novel B7-H4 Therapeutic Antibody with Checkpoint Blockade and ADCC Activities, Aug. 31, 2017, 2 pages, European Society for Medical Oncology (Abstract). FM2.
Sun, Y., et al., "B7-H3 and B7-H4 Expression in Non-small-cell Lung Cancer," Lung Cancer, 53(2):143-151, Elsevier Scientific Publishers, Ireland (Aug. 2006).
Tan, Z and Shen, Weixi, "Prognostic Role of B7-H4 in Patients With Non-small Cell Lung Cancer: a Meta-analysis," Oncotarget, 8(16):27137-27144, Impact Journals, United States (Apr. 2017).
Thompson, R., et al., "Serum-Soluble B7x Is Elevated in Renal Cell Carcinoma Patients and Is Associated With Advanced Stage," Cancer Research, 68(15):6054-6058, American Association for Cancer Research, United States (Aug. 2008).
Tringler, B., et al., "B7-H4 Overexpression in Ovarian Tumors," Gynecologic Oncology, 100(1):44-52, Academic Press, United States (Jan. 2006).
Wang, L., et al., "B7-H4 Overexpression Contributes to Poor Prognosis and Drug-resistance in Triple-negative Breast Cancer," Cancer Cell International, 18:100 (12 pages), BioMed Central, England (Jul. 2018).
Wang, L., et al., "Roles of Coinhibitory Molecules B7-H3 and B7-H4 in Esophageal Squamous Cell Carcinoma," Tumour Biology, Online Publication, pp. 1-11, Springer Publishing, United States (Sep. 2015).
Xu, H., et al., "B7-H3 and B7-H4 Are Independent Predictors of a Poor Prognosis in Patients With Pancreatic Cancer," Oncology Letters, 11(3):1841-1846, Spandidos Publications, Greece (Mar. 2016).
Yamane-Ohnuki, N., et al., "Establishment of FUT8 Knockout Chinese Hamster Ovary Cells: an Ideal Host Cell Line for Producing Completely Defucosylated Antibodies With Enhanced Antibody-dependent Cellular Cytotoxicity," Wiley Interscience, Advance Publication Online, pp. 1-9, Wiley, United States (Aug. 6, 2004).
Ye, Y., et al., "Does B7-H4 Expression Correlate With Clinicopathologic Characteristics and Survival in Ovarian Cancer?: a Systematic Review and Prisma-compliant Meta-analysis," Medicine, 97(32):e11821 (8 pages), Lippincott Williams & Wilkins, United States (Aug. 2018).
Zang, X., et al., "B7-H3 and B7x Are Highly Expressed in Human Prostate Cancer and Associated With Disease Spread and Poor Outcome," Proceedings of the National Academy of Sciences of the United States of America, 104(49):19458-19463, National Academy of Sciences, United States (Dec. 2007).
Zang, X., et al., "B7x: a Widely Expressed B7 Family Member That Inhibits T Cell Activation," Proceedings of the National Academy of Sciences of the United States of America, 100(18):10388-10392, National Academy of Sciences, United States (Sep. 2003).
Zhang, L., et al., "The Costimulatory Molecule B7-H4 Promote Tumor Progression and Cell Proliferation Through Translocating Into Nucleus," Oncogene, 32(46): 5347-5358, Nature Publishing Group, England (Nov. 2013).
Zhang, N., et al., "Preparation and Characterization of Monoclonal Antibody Against Human B7-H4 Molecule," Monoclonal Antibodies in Immunodiagnosis and Immunotherapy, 33(4):270-274, Mary Ann Liebert, United States (Aug. 2014).
Zhang, S., et al., "Circulating B7-H4 in Serum Predicts Prognosis in Patients With Hepatocellular Carcinoma," Genetics and Molecular Research, 14(4):13041-13048, FUNPEC, Brazil (Oct. 2015).
Zhang, X., et al., "B7-H4 Promotes Tumor Growth and Metastatic Progression in Lung Cancer by Impacting Cell Proliferation and Survival," Oncotarget, Advance Publication:1-11, Impact Journals, United States (Mar. 2017).
Zhou, D., et al., "Silencing of B7-H4 Suppresses the Tumorigenicity of the Mgc-803 Human Gastric Cancer Cell Line and Promotes Cell Apoptosis via the Mitochondrial Signaling Pathway," International Journal of Oncology, 52(4):1267-1276, Spandidos Publishing, Greece (Apr. 2018).
Zhu, J., et al., "B7-H4 Expression Is Associated With Cancer Progression and Predicts Patient Survival in Human Thyroid Cancer," Asian Pacific Journal of Cancer Prevention, 14(5):3011-3015, Asian Pacific Organization for Cancer Prevention, Thailand (May 2013).
B7-H4 mouse monoclonal antibody A57.1 (ATCC Catalog No. PTA-5180), accessed at https://www.atcc.org/products/all/PTA-5180. aspx, accessed on May 14, 2019, date of deposit May 8, 2003.
Nida, S. et al., "Detection of B7-H4 and p53 in Pancreatic Cancer", Pancreas 36(2):200-206, Lippincott Williams & Wilkins, United States (Mar. 2008).
Estep, P., et al., "High throughput solution-based measurement of antibody—antigen affinity and epitope binning," MAbs 5(2):270-278, Landes Biosciences, United States (2013).
Liu, Y., et al., "High-throughput screening for developability during early-stage antibody discovery using self-interaction nanoparticle spectroscopy," MAbs 6(2):483-492, Landes Bioscience, United States (2014).
Siegel, R.W., et al., "High efficiency recovery and epitope-specific sorting of an scFv yeast display library," J Immunol Methods 286(1-2):141-153, Elsevier, Netherlands (2004).
Xu, Y., et al., "Addressing polyspecificity of antibodies selected from an in vitro yeast presentation system: a FACS-based, high-throughput selection and analytical tool," PEDS (26)10: 663-70, Oxford Academic, United Kingdom (2013).
Dangaj, D., et al., "Blocking the B7-H4 pathway with novel recombinant antibodies enhances T cell-mediated antitumor responses," OncoImmunology 2:8 e25913, 3 pages, Landes Bioscience, United States (Aug. 2013).
International Search Report and Written Opinion for International Application No. PCT/US2018/047805, International Search Authority, United States, dated Dec. 12, 2018, 25 pages.
Abdiche, Y.N. et al. (Mar. 15, 2009, e-pub. Dec. 7, 2008). "Exploring Blocking Assays Using Octet, ProteOn, and Biacore Biosensors," Analytical Biochem 386(2):172-180.
Al-Lazikani, B. et al. (1997). "Standard Conformations for the Canonical Structures of Immunoglobulins," J. Mol. Biol. 273:927-948.
Ames, R.S. et al. (Aug. 18, 1995). "Conversion of Murine Fabs Isolated From a Combinatorial Phage Display Library to Full Length Immunoglobulins," J. Immunol. Methods 184(2):177-186.
Arigami, T. et al. (2010). "Expression of B7-H4 in Blood of Patients With Gastric Cancer Predicts Tumor Progression and Prognosis," J. Surgical Oncology 102:748-752.
Ausubel, F. et al., (1987). Current Protocols in Molecular Biology, Greene Publishing and Wiley Interscience, New York, TOC, 7 pages.
Balwit, J.M. et al. (2011). "The iSBTc/SITC Primer on Tumor Immunology and Biological Therapy of Cancer: A Summary of the 2010 Program," J. Translational Medicine 9:18, 15 pages.
Barach, Y.S. et al. (Jan. 2011). "T Cell Conihibition in Prostate Cancer: New Immune Evasion Pathways and Emerging Therapeutics," Trends Mo. Med. 17(1):47-55.
Bricogne, G. (1997). "Bayesian Statistical Viewpoint on Structure Determination: Basic Concepts and Examples," Meth Enzymol 276:361-423.
Bricogne, G. (Jan. 1, 1993), "Direct Phase Determination by Entropy Maximization and Likelihood Ranking: Status Report and Perspectives," Acta Crystallogr D Biol Ciystallogr D49(Pt 1):37-60.
Brinkman, U. et al. (May 11, 1995). Phage Display of Disulfide-Stabilized Fv Fragments, J Immunol Methods 182:41-50.

(56) References Cited

OTHER PUBLICATIONS

Burton, D.R. et al. (1994). "Human Antibodies From Combinatorial Libraries," Advances in Imniunology 57:191-280.
Champe, M. et al. (1995). "Monoclonal Antibodies That Block the Activity of Leukocyte Function-Associated Antigen 1 Recognize Three Discrete Epitopes in the Inserted Domain of CD11a," J Biol Chem 270:1388-1394.
Chayen, N.E. (Oct. 15, 1997). The Role of Oil in Macromolecular Crystallization, Structure 5(10):1269-1274.
Cheung, R.C. et al. (Jun. 1990). "Epitope-Specific Antibody Response to the Surface Antigen of Duck Hepatitis B Virus in Infected Ducks," Virology 176(2):546-552.
Chothia, C. et al. (Aug. 20, 1987). "Canonical Structures for the Hypervariable Regions of Immunoglobulins," J. Mol. Biol. 196(4):901-917.
Chothia, C. et al. (Oct. 5, 1992). "Structural Repertoire of the Human VH Segments," J Mol Biol 227(3):799-817.
Chumsae, C. et al. (Aug. 19, 2014). "Discovery of a Chemical Modification by Citric Acid in a Recombinant Monoclonal Antibody," Analytical Chemistry 86(18):8932-8936.
Clackson, T. et al. (Aug. 15, 1991). "Making Antibody Fragments Using Phage Display Libraries," Nature 352:624-628.
Coales, S.J. et al. (Mar. 2009). "Epitope Mapping by Amide Hydrogen/Deuterium Exchange Coupled With Immobilization of Antibody, On-Line Proteolysis, Liquid Chromatography and Mass Spectrometry," Rapid Commun. Mass Spectrom. 23(5):639-647.
Cockett, M.I. et al. (Jul. 1990). "High Level Expression of Tissue Inhibitor of Metalloproteinases in Chinese Hamster Ovary Cells Using Glutamine Synthetase Gene Amplification," Bio/Technology 8(7):662-667 (Jul. 1990).
Cunningham, B.C. et al. (Jun. 2, 1989). "High-Resolution Epitope Mapping of hGH-Receptor Interactions by Alanine-Scanning Mutagenesis," Science 244:1081-1085.
Dall'Acqua, W.F. et al. (Aug. 18, 2006). "Properties of Human IgG1s Engineered for Enhanced Binding to the Neonatal Fc Receptor (FcRn)," J Biol Chem 281(33):23514-23524.
Davies, J. et al. (Aug. 2001). "Expression of GnTIII in a Recombinant Anti-CD20 CHO Production Cell Line: Expression of Antibodies With Altered Glycoforms Leads to an Increase in ADCC Through Higher Affinity for FC gamma RIII," Biotechnol. Bioeng. 74(4):288-294.
Driessens, G. et al. (May 2009), "Costimulatory and Coinhibitory Receptors in Anti-Tumor Immunity," Immunol. Rev. 229(1):126-144, 28 pages.
D'Aria, M. et al. (May 2009). "Abstract# 1601: B7-H4 (DD-O110) is Overexpressed in Endocervical Adenorcarcinoma in situ and invasive Adenocarcinoma," Cancer Research, retrieved from https//cacerres.aacrjournals.org/content/59/9_Supplement/1601 , last visited Apr. 30, 2020, 4 pages.
Ferrara, C. et al. (2006, e-pub. Jan. 24, 2006). "Modulation of Therapeutic Antibody Effector Functions by Glycosylation Engineering: Influence of Golgi Enzyme Localization Domain and Co-Expression of Heterologous β1,4-N-Acetylglucosaminyltransferase III and Golgi α-Mannosidase," Biotechnology and Bioengineering 93(5):851-861.
Filies, D. B. et al. (2007). "The New B7s: Playing a Pivotal Role in Tumor Immunity," J. Immunother. 30:251-260.
Foecking, M.K. et al. (1986). "Powerful and Versatile Enhancer-Promoter Unit for Mammalian Expression Vectors," Gene 45(1):101-105.
GCC Office Action, dated Jan. 20, 2020, for GCC Patent Application No. GC2018-35987, 6 pages.
Giegé, R. et al. (Jul. 1, 1994). Crystallogenesis of Biological Macromolecules: Facts and Perspectives, Acta Crystallogr D Biol Crystallogr 50(Pt 4):339-350.
Goldberg, A. et al. (Dec. 2009). "Abstract C243: B7-H4 Protein Expression in Invasive Ductal Carcinoma and its Association With Tumor Progression," Molecular Cancer Therapeutics, retrieved from https://mct.aacrjournals.org/content/8/12_Supplement/C243, last visited Apr. 30, 2020, 4 pages.

Hammerling, G.J. et al. (1981). "Production of Antibody-Producing Hybridomas in the Rodent Systems," in Research Monographs in Immunology, Elsevier/North-Holland Biomedical Press 3:563-587.
Harlow, E. et al. (1988). Antibodies: A Laboratory Manual, Cold Spring Harbor Press, 89 pages.
Herber, D.L. et al. (Jun. 1, 2007). "Meeting Report: Mechanism and Therapeutic Reversal of Immune Suppression in Cancer," Cancer Res. 67(11):5067-5069.
Ichikawa, M. et al. (Sep. 1, 2005). "Role of B7-H1 and B7-H4 Molecules in Down-Regulating Effector Phase of T-Cell Immunity: Novel Cancer Escaping Mechanisms," Frontiers in Bioscience 10:2856-2860.
Imai-Nishinya, Harue et al. "Double Knockdown of a1 ,6-Fucosyltransferase (FUT8) and GDP-Mannose 4,6-Dehydratase (GMD) in Antibody-Producing Cells: A New Strategy for Generating Fully Non-Fucosylated Therapeutic Antibodies With Enhanced ADCC," BMC Biotechnology (Nov. 30, 2007); 7:84; 13 pages.
International Search Report and Written Opinion, dated Jun. 12, 2019, for PCT Application No. PCT/US2019/018965, filed Feb. 21, 2019, 11 pages.
International Search Report and Written Opinion, dated Jun. 14, 2019, for PCT Application No. PCT/US2019/018963, filed Feb. 21, 2019, 11 pages.
Jones, P.T. et al. (May 29, 1986). "Replacing the Complementarity-Determing Regions in a Human Antibody With Those From a Mouse," Nature 321:522-525.
Kabat, E.A. et al. (1971). "Attempts to Locate Complementarity-Determining Residues in the Variable Positions of Light and Heavy Chains," Ann NY Acad Sci 190:382-391.
Kabat, E.A. et al. (1991). Sequences of Proteins of Immunological Interest, 5th ed., Public Health Service, National Institutes of Health, Bethesda, MD. TOC, 21 pages.
Kanda, Y. et al. (Jan. 2007, e-pub. Sep. 29, 2006). "Comparison of Biological Activity Among Nonfucosylated Therapeutic Igg1 Antibodies With Three Different N-Linked Fc Oligosaccharides: The High-Mannose, Hybrid, and Complex Types," Glycobiology 17(1):104-118.
Kettleborough, C.A. et al. (Apr. 1994). "Isolation of Tumor Cell-Specific Single-Chain Fv From Immunized Mice Using Phage-Antibody Libraries and the Re-Construction of Whole Antibodies From These Antibody Fragments," Eur. J. Immunol. 24(4):952-958.
Kim, S.J. et al. (Dec. 2007). "Guided Selection of Human Antibody Light Chains Against TAG-72 Using a Phage Display Chain Shuffling Approach," J Microbiol 45:572-577.
Kirkland, T.N. et al. (Dec. 1, 1986). "Analysis of the Fine Specificity and Cross-Reactivity of Monoclonal Anti-Lipid A Antibodies," J Immunol 137(11):3614-3619.
Kitamura, H. et al. (Jan.-Mar. 2008). "Prognostic Biomarkers of Renal Cell Carcinoma: Recent Advances," Indian J. Urol. 24(1):10-15, retrieved from https://www.ncbi.nlm.gove/pmc/articles/PMC2684243/?report-printabie, last visited Apr. 30, 2020, 12 pages.
Klatte, T et al. (May 20-25, 2006). Best of the 2006 AUA Annual Meeting: Highlights from the 2006 Annual Meeting of the Am. Urological Assoc, 8(3):120-164.
Kuroki, M et al. (Aug. 1992). "Biochemical Characterization of 25 Distinct Carcinoembryonic Antigen (CEA) Epitopes Recognized by 57 Monoclonal Antibodies and Categorized Into Seven Groups in Terms of Domain Structure of the CEA Molecule," Hybridoma 11(4):391-407.
Kuroki, M et al. (Oct. 1992, e-pub. Jul. 7, 2009). "Determination of Epitope Specificities of a Large Number of Monoclonal Antibodies by Solid-Phase Mutual Inhibition Assays Using Biotinylated Antigen," Immunol Invest 21 (6):523-538.
Kuroki, M. et al. (Aug. 15, 1990). "Serological Mapping of the TAG-72 Tumor-associated Antigen Using 19 Distinct Monoclonal Antibodies," Cancer Res 50:4872-4879.
Köhler, G. et al. (Aug. 7, 1975). "Continuous Cultures of Fused Cells Secreting Antibody of Predefined Specificity," Nature 256:495-497.
Lefranc, M.-P. (1999), "The IMGT Unique Numbering for Immunoglobulins, T-Cell Receptors, and Ig-Like Domains," The Immunologist 7(4):132-136.

(56) References Cited

OTHER PUBLICATIONS

Lefranc, M.-P. et al. (1999). "IMGT, The International ImMunoGeneTics Databse," Nucleic Acids Res 27(1):209-212.

Li, Y. et al. (Jan. 28, 2009). "Summary of the Primer on Tumor Immunology and the Biological Therapy of Cancer," J. Translational Medicine 7:11, 5 pages.

Loke, P. et al. (Aug. 6, 2004). "Emerging Mechanisms of Immune Regulation: The Extended B7 Family and Regulatory T Ceils," Arthritis Research & Therapy 6(5):208-214.

Longmore, G.D. et al. (Mar. 1, 1982). "Product-Identification and Substrate-Specificity Studies of the GDP-L-fucose:2-acetamido-2-deoxy-beta-D-glucoside (FUC to Asn-Linked GlcNAc) 6-alpha-L-fucosyitransferase in a Golgi-Rich Fraction From Porcine Liver," Carbohydr Res 100:365-392.

MacCallum, R.M. et al. (1996). "Antibody-Antigen Interactions: Contact Analysis and Binding Site Topography," J. Mol. Biol. 262:732-745.

Martin, A.C.R. (2001). "Protein Sequence and Structure Analysis of Antibody Variable Domains," in Antibody Engineering, Kontermann and Dithel, eds., Chapter 31, pp. 422-439.

McPherson, A. (1990). "Current Approaches to Macromolecular Crystallization," Eur J Biochem 189:1-23.

McPherson, A. (Oct. 25, 1976). "Crystallization of Proteins from Polyethylene Glycol," J Biol Chem 251 (20):6300-6303.

Miyatake, T. et al. (Apr. 2006). "B7-H4 (DD-O110) Immunocytochemistry Improves the Sensitivity of Cancer Cell Detection in Pelvic Wash Specimens of Metastatic Ovarian Cancer," Cancer Research, Abstract 4502, retrieved from https://cancerres.aacrjounals.org/content/66/8_Supplement/1056.4, last visited Apr. 30, 2020, 4 pages.

Miyatake, T. et al. (May 2005). "B7-H4 (DD-0110) is Overexpressed in Uterine Endometrioid Carcinomas Independent of Tumor Grade, T Cell Infiltration, or Apoptotic Index," Cancer Research, Abstract 3604, retrieved from https://canceres.aacrjournals.org/content/65/9_Supplement/849.5, last visited May 1, 2020, 4 pages.

Moldenhauer, G. et al. (Aug. 1990). "Identity of HML-1 Antigen on Intestinal Intraepithelial T Cells and of B-ly7 Antigen on Hairy Cell Leukaemia," Scand J Immunol 32(2):77-82.

Morel, G.A. et al. (Jan. 1988). "Monoclonal Antibodies to Bovine Serum Albumin: Affinity and Specificity Determinations," Mol Immunol 25(1):7-15.

Murillo, O. et al. (Nov. 15, 2013). "Potentiation of Therapeutic Immune Responses Against Malignancies With Monoclonal Antibodies," Clinical Cancer Research 9:5454-5464.

Niwa, R. et al. (Sep. 15, 2004). "Enhlancement of the Antibody-Dependent Cellular Cytotoxicity of Low-Fucose IgG1 is independent of FcγRIIIa Functional Polymorphism," Clin Cancer Res 10:6248-6255.

Palena, C. et al. (2010), "Review Article: Vaccines Against Human Carcinomas: Strategies to Improve Antitumor Immune Responses," J. Biomedicine and Biotechnology 2010(380697):1-12.

Persic, L. et al. (Mar. 10, 1997). "An Integrated Vector System for the Eukaryotic Expression of Antibodies or Their Fragments After Selection From Phage Display Libraries," Gene 187(1):9-18. Abstract Only.

Presta, L.G. et al. (2002). "Engineering Therapeutic Antibodies for Improved Function," Biochemical Society Transactions 30(4):487-490.

Rabinovich, G.A. et al. (2007). "Immunosuppressive Strategies That Are Mediated by Tumor Cells," Annu. Rev. Immunol. 25:267-296, 34 pages.

Rader, C. et al. (Jul. 1998). ". A Phage Display Approach for Rapid Antibody Humanization: Designed Combinatorial V Gene Libraries," PNAS 95:8910-8915.

Raju, T.S. (Apr. 2003). "Glycosylation Variations with Expression Systems and Their Impact on Biological Activity of Therapeutic Immunoglobulins," BioProcess International 1(4): 44-53.

Riechmann, L. et al. (Mar. 24, 1988). "Reshaping Human Antibodies for Therapy," Nature 332:323-329.

Roguska, M.A. et al. (Feb. 1, 1994), "Humanization of Murine Monoclonal Antibodies Through Variable Domain Resurfacing," Proc. Natl. Acad. Sci. USA 91(3):969-973.

Roguska, M.A. et al. (Oct. 1996). "A Comparison of Two Murine Monoclonal Antibodies Humanized by CDR-Grafting and Variable Domain Resurfacing," Protein Eng. 9(10):895-904.

Routier, F.H. et al. (1997). "The Glycosylation Pattern of a Humanized IgGI Antibody (D1.3) Expressed in CHO Cells," Glycoconjugate Journal 14:201-207.

Roversi, P et al. (2000). "Modelling Prior Distributions of Atoms for Macro-Molecular Refinement and Completion," Acta Crystallogr D Biol Crystallogr 56(Pt 10):1316-1323.

Sadun, R.E. et al. (Jul. 1, 2007). "Immune Signatures of Murine and Human Cancers Reveal Unique Mechanisms of Tumor Escape and New Targets for Cancer Immunotherapy," Cancer Therapy: Preclinical 13(13):4016-4025.

Sambrook, J. et al. (2001). "Molecular Cloning: A Laboratory Manual," 3rd edition, J.F. Sambrook and D.W. Russell, ed., Cold Spring Harbor Laboratory Press: Cold Spring Harbor, NY, 2:107 pages.

Seliger, B. et al. (Dec. 2008). "The Complex Role of B7 Molecules in Tumor Immunology," Trends Mol. Med. 14(12):550-559, 19 pages.

Shields, R.L. et al. (Jul. 26, 2002, e-pub. May 1, 2002), "Lack of Fucose on Human IgG1 N-Linked Oligosaccharide Improves Binding to Human FcγRIII and Antibody-dependent Cellular Toxicity," J. Biol. Chem. 277:26733-26740.

Shields, R.L. et al. (Mar. 2, 2001), "High Resolution Mapping of the Binding Site on Human IgG1 for FcγRI, FcγII. FcγIII, and FcRn and Design of IgG1 Variants With Improved Binding to the FcγR," J. Biol.Chem. 276(9):6591-6604.

Shinkawa, T. et al. (Jan. 31, 2003). "The Absence of Fucose but Not the Presence of Galactose or Bisecting N-Acetylglucosamine of Human IgG1 Complex-Type Oligosaccharides Shows the Critical Role of Enhancing Antibody-Dependent Cellular Cytotoxicity," Journal of Biologicai Chemistry, 278(5):3466-3473.

Simon, I. et al. (May 2005). "Evaluation of B7-H4 (DD-O110) as a Prognostic Marker in Tissue and Serum of Ovarian Cancer Patients," Cancer Research, Abstract 4882, retrieved from https://cancerres.aacrjournals.org/content/65/9_Supplement/1153.2, last visited Apr. 30, 2020, 4 pages.

Smith, P. et al. (Apr. 17, 2012, e-pub. Apr. 2, 2012). "Mouse Model Recapitulating Human Fcγ Receptor Structural and Functional Diversity," PNAS 109(16):6181-6186, 6 pages.

Sood, A.K. (2010, e-pub. Sep. 10, 2009). "PDEF and PDEF-Induced Proteins as Candidate Tumor Antigens for T Cell and Antibody-Mediated Immunotherapy of Breast Cancer," Immunol. Res. 46:206-215.

Terrett, J. et al., (May 2008). "Preclinical Development of Anti B7-H4 Therapeutic Antibodies," Cancer Research, Abstract 4986, retrieved from https://canerres.accrjournals.org/content/68/9_Supplement/4986, last visited Apr. 30, 2020, 3 pages.

Thompson, R.H. et al. (2005). "B7-H1, Glycoprotein Blockade: A Novel Strategy to Enhance Immunotherapy in Patients With Renal Cell Carcinoma," Urology 66(Suppl. 5A):10-14.

Tramontano, A et al. (Sep. 1990). "Framework Residue 71 Is a Major Determinant of the Position and Conformation of the Second Hypervariable Region in the VH Domains of Immunoglobulins," J Mol Biol 215 (1):175-182.

Umaña, P. et al., (Feb. 1999). "Engineered Glycoforms of an Antineuro-Blastoma IgG 1 With Optimized Antibody-Dependent Cellular Cytotoxic Activity," Nat. Biotechnol. 17:176-180.

Verhoeyen, M. et al. (Mar. 25, 1988). "Reshaping Human Antibodies: Grafting an Antilysozyme Activity," Science 239(4857):1534-1536.

Wagener, C et al. (Mar. 30, 1984). "Use of Biotin-Labeled Monoclonal Antibodies and Avidin-Peroxidase Conjugates for the Determination of Epitope Specificities in a Solid-Phase Competitive Enzyme Immunoassay," J Immunol Methods 68(1-2):269-274.

Wagener, C. et al. (May 1983). "Monoclonal Antibodies for Carcinoembryonic Antigen and Related Antigens as a Model Sys-

(56) References Cited

OTHER PUBLICATIONS tem: A Systematic Approach for the Determination of Epitope Specificities of Monoclonal Antibodies," J Immunol 130(5):2308-2315.

Wilcox, R.A. et al. (2009). "CD14+ hla-DR-/Lo Myeloid-Derived Suppressor Cells Express Immunosuppressive B7-H Family Members and Are Depleted Following Taxane-Based Chemotherapy in Melanoma," Blood 114(22):464, Abstract 464, retrieved from https://ashpublication.org/blood/article/114/22/464/64311/CD14-hlaDRlo-MyeloidDerived-Suppressor-Cell, last, visited Apr. 30, 2020, 6 pages.

Wu, T.C. et al. (No Date). "Abstract 547: Development of Antigen-Targeted Vaccines and Immune Checkpoint Inhibitors for Cancer Therapy," Immune Response Modifiers: Cancer Vaccines, 1 page.

Zou, W. (Apr. 2005, e-pub. Mar. 18, 2015), "Immunosuppressive Networks in the Tumour Environment and Their Therapeutic Relevance," Nature Reviews 5:263-274.

Ferreira, M.M. et al. (Mar. 2016, e-pub. Jan. 28, 2016). "Circulating Tumor Cell Technologies," Molecular Oncology 10(3):374-394.

Goding, J.W. (1936). "Production of Monoclonal Antibodies," Chapter 3 in Monoclonal Antibodies: Principles and Practice, Academic Press, New York, pp. 59-103.

International Preliminary Report on Patentability, dated Aug. 27, 2020, for PCT Application No. PCT/US2019/018965, filed Feb. 21, 2019, 7 pages.

International Preliminary Report on Patentability, dated Aug. 27, 2020, for PCT Application No. PCT/US2019/018966, filed Feb. 21, 2019, 11 pages.

International Preliminary Report on Patentability, dated Sep. 8, 2020, for PCT Application No. PCT/US2019/020189, filed Mar. 1, 2019, 6 pages.

International Search Report and Written Opinion, dated Jan. 28, 2020, for PCT Application No. PCT/US2019/056210, filed Oct. 15, 2019, 14 pages.

International Search Report and Written Opinion, dated May 17, 2019, for PCT Application No. PCT/US2019/020189, filed Mar. 1, 2019, 9 pages.

Abdiche. et a "Exploring Blocking Assays Using Octet, ProteOn, and Biacore Biosensors," Analytical Biochem 386(2):172-180 (2009).

\* cited by examiner

FIG. 12A  4T1-moB7H4/H3 Tumor Growth

FIG. 12B  Day 33 Tumor volumes

B7-H4 ANTIBODIES AND METHODS OF USE THEREOF

CROSS REFERENCE TO RELATED APPLICATIONS

This application claims the benefit of U.S. Provisional Application No. 62/550,173, filed Aug. 25, 2017, U.S. Provisional Application No. 62/579,774, filed Oct. 31, 2017, U.S. Provisional Application No. 62/607,810, filed Dec. 19, 2017, and U.S. Provisional Application No. 62/656,789, filed Apr. 12, 2018, which are each hereby incorporated in its entirety by reference.

REFERENCE TO A SEQUENCE LISTING SUBMITTED ELECTRONICALLY VIA EFS-WEB

The content of the electronically submitted sequence listing (Name: 3986.0090004_SL_ST25.txt; Size: 331,354 bytes; Date of Creation: Aug. 3, 2018) is herein incorporated by reference in its entirety.

BACKGROUND OF THE INVENTION

Field

The present disclosure relates to antibodies that specifically bind to human B7-H4 compositions comprising such antibodies, and methods of producing and using antibodies that specifically bind to B7-H4.

Description of the Related Art

B7-H4 (also known as B7x, B7-S1, and VTCN1) is an immune regulatory molecule that shares homology with other B7 family members, include PD-L1. It is a type I transmembrane protein comprised of both IgV and IgC ectodomains. While B7-H4 expression in healthy tissues is relatively limited at the protein level, B7-H4 is expressed in several solid tumors such as gynecological carcinomas of the breast, ovary, and endometrium. Expression of B7-H4 in tumors tends to correlate with poor prognosis. The receptor for B7-H4 is unknown, but it is believed to be expressed on T cells. B7-H4 is believed to directly inhibit T cell activity. Given the expression and function of B7-H4, provided herein are antibodies that specifically bind to B7-H4 and the use of these antibodies to modulate B7-H4 activity, including, e.g., in the treatment of cancer.

SUMMARY

Provided herein is an isolated antibody or antigen-binding fragment thereof that specifically binds to human B7-H4, comprising heavy chain variable region (VH) complementarity determining region (CDR) 1, VH CDR2, VH CDR3 and light chain variable region (VL) CDR1, CDR2, and CDR3 sequences selected from the group consisting of: SEQ ID NOs:5-10, respectively; SEQ ID NOs:15-20, respectively; SEQ ID NOs:25-30, respectively; SEQ ID NOs:35-40, respectively; SEQ ID NOs:458-463, respectively; SEQ ID NOs:45-50, respectively; SEQ ID NOs:55-60, respectively; SEQ ID NOs:65-70, respectively; SEQ ID NOs:75-80, respectively; SEQ ID NOs:85-90, respectively; SEQ ID NOs:95-100, respectively; SEQ ID NOs:105-110, respectively; SEQ ID NOs:115-120, respectively; SEQ ID NOs:125-130, respectively; SEQ ID NOs:135-140, respectively; SEQ ID NOs:145-150, respectively; SEQ ID NOs:155-160, respectively; SEQ ID NOs:165-170, respectively; SEQ ID NOs:175-180, respectively; SEQ ID NOs:185-190, respectively; and SEQ ID NOs:195-200, respectively.

In one embodiment, the antibody or antigen-binding fragment thereof comprises a VH comprising the amino acid sequence of SEQ ID NO:11, 21, 31, 41, 464, 51, 61, 71, 81, 91, 101, 111, 121, 131, 141, 151, 161, 171, 181, 191, or 201.

In one embodiment, the antibody or antigen-binding fragment thereof comprises a VL comprising the amino acid sequence of SEQ ID NO:12, 22, 32, 42, 52, 62, 72, 82, 92, 102, 112, 122, 132, 142, 152, 162, 172, 182, 192, or 202.

In one embodiment, the antibody or antigen-binding fragment thereof comprises a heavy chain variable region and a light chain variable region, wherein the heavy chain variable region comprises the amino acid sequence of SEQ ID NO:11, 21, 31, 41, 464, 51, 61, 71, 81, 91, 101, 111, 121, 131, 141, 151, 161, 171, 181, 191, or 201.

Also provided herein is an isolated antibody or antigen-binding fragment thereof that specifically binds to human B7-H4, wherein the antibody comprises a heavy chain variable region and a light chain variable region, wherein the light chain variable region comprises the amino acid sequence of SEQ ID NO:12, 22, 32, 42, 52, 62, 72, 82, 92, 102, 112, 122, 132, 142, 152, 162, 172, 182, 192, or 202.

Also provided herein is an isolated antibody or antigen-binding fragment thereof that specifically binds to human B7-H4, comprising a heavy chain variable region and a light chain variable region comprising the amino acid sequences of: SEQ ID NOs:11 and 12, respectively; SEQ ID NOs:21 and 22, respectively; SEQ ID NOs:31 and 32, respectively; SEQ ID NOs:41 and 42, respectively; SEQ ID NOs:464 and 42, respectively, SEQ ID NOs:51 and 52, respectively; SEQ ID NOs:61 and 62, respectively; SEQ ID NOs:71 and 72, respectively; SEQ ID NOs:81 and 82, respectively; SEQ ID NOs:91 and 92, respectively; SEQ ID NOs:101 and 102, respectively; SEQ ID NOs:111 and 112, respectively; SEQ ID NOs:121 and 122, respectively; SEQ ID NOs:131 and 132, respectively; SEQ ID NOs:141 and 142, respectively; SEQ ID NOs:151 and 152, respectively; SEQ ID NOs:161 and 162, respectively; SEQ ID NOs:171 and 172, respectively; SEQ ID NOs:181 and 182, respectively; SEQ ID NOs:191 and 192, respectively; or SEQ ID NOs:201 and 202, respectively.

In one embodiment, the antibody or antigen-binding fragment thereof further comprises a heavy chain constant region. In one embodiment, the heavy chain constant region is selected from the group consisting of human immunoglobulins $IgG_1$, $IgG_2$, $IgG_3$, $IgG_4$, $IgA_1$, and $IgA_2$ heavy chain constant regions.

In one embodiment, the antibody or antigen-binding fragment further comprises a light chain constant region. In one embodiment, the light chain constant region is selected from the group consisting of human immunoglobulins IgGκ and IgGλ light chain constant regions.

In one embodiment, the antibody or antigen-binding fragment further comprises a heavy chain constant region and a light chain constant region, wherein the heavy chain constant region is a human $IgG_1$ heavy chain constant region, and wherein the light chain constant region is a human IgGκ light chain constant region.

In one embodiment, the antibody or antigen-binding fragment thereof comprises a heavy chain comprising the amino acid sequence of SEQ ID NO:13, 23, 33, 43, 469, 53, 63, 73, 83, 93, 103, 113, 123, 133, 143, 153, 163, 173, 183, 193, or 203.

In one embodiment, the antibody or antigen-binding fragment thereof comprises a light chain comprising the amino acid sequence of SEQ ID NO:14, 24, 34, 44, 54, 64, 74, 84, 94, 104, 114, 124, 134, 144, 154, 164, 174, 184, 194, or 204.

In one embodiment, the antibody or antigen-binding fragment thereof comprises a heavy chain and light chain comprising the amino acid sequences of: SEQ ID NOs:13 and 14, respectively; SEQ ID NOs:23 and 24, respectively; SEQ ID NOs:33 and 34, respectively; SEQ ID NOs:43 and 44, respectively; SEQ ID NOs:469 and 44, respectively; SEQ ID NOs:53 and 54, respectively; SEQ ID NOs:63 and 64, respectively; SEQ ID NOs:73 and 74, respectively; SEQ ID NOs:83 and 84, respectively; SEQ ID NOs:93 and 94, respectively; SEQ ID NOs:103 and 104, respectively; SEQ ID NOs:113 and 114, respectively; SEQ ID NOs:123 and 124, respectively; SEQ ID NOs:133 and 134, respectively; SEQ ID NOs:143 and 144, respectively; SEQ ID NOs:153 and 154, respectively; SEQ ID NOs:163 and 164, respectively; SEQ ID NOs:173 and 174, respectively; SEQ ID NOs:183 and 184, respectively; SEQ ID NOs:193 and 194, respectively; or SEQ ID NOs:203 and 204, respectively.

Also provided herein is an isolated antibody or antigen-binding fragment thereof that specifically binds to human B7-H4, wherein the antibody or antigen-binding fragment thereof comprises the VH CDR1, VH CDR2, VH CDR3, VL CDR1, VL CDR2, and VL CDR3 of an antibody selected from the group consisting of 15461, 20500, 20501, 20502, 20502.1, 22208, 15462, 22213, 15465, 20506, 15483, 20513, 22216, 15489, 20516, 15472, 15503, 15495, 15478, 15441, and 20496. In one embodiment, the CDRs are the Kabat-defined CDRs, the Chothia-defined CDRs, or the AbM-defined CDRs.

Also provided herein is an isolated antibody or antigen-binding fragment thereof that specifically binds to human B7-H4, comprising the heavy chain variable region (VH) complementarity determining region (CDR) 1, VH CDR2, VH CDR3 and light chain variable region (VL) CDR1, CDR2, and CDR3 sequences of SEQ ID NOs:458-463, respectively. In one embodiment, (i) the antibody or antigen-binding fragment thereof comprises a variable heavy chain region comprising the amino acid sequence of SEQ ID NO:464 and a variable light chain region comprising the amino acid sequence of SEQ ID NO:42 or (ii) the antibody comprises a heavy chain comprising the amino acid sequence of SEQ ID NO:469 and a light chain comprising the amino acid sequence of SEQ ID NO:44.

Also provided herein is an isolated antibody or antigen-binding fragment thereof that specifically binds to human B7-H4, comprising the heavy chain variable region (VH) complementarity determining region (CDR) 1, VH CDR2, VH CDR3 and light chain variable region (VL) CDR1, CDR2, and CDR3 sequences of SEQ ID NOs:35-40, respectively. In one embodiment, (i) the antibody or antigen-binding fragment thereof comprises a variable heavy chain region comprising the amino acid sequence of SEQ ID NO:41 and a variable light chain region comprising the amino acid sequence of SEQ ID NO:42 or (ii) the antibody comprises a heavy chain comprising the amino acid sequence of SEQ ID NO:43 and a light chain comprising the amino acid sequence of SEQ ID NO:44.

Also provided herein is an isolated antibody or antigen-binding fragment thereof that specifically binds to human B7-H4, comprising the heavy chain variable region (VH) complementarity determining region (CDR) 1, VH CDR2, VH CDR3 and light chain variable region (VL) CDR1, CDR2, and CDR3 sequences of SEQ ID NOs:65-70, respectively. In one embodiment, (i) the antibody or antigen-binding fragment thereof comprises a variable heavy chain region comprising the amino acid sequence of SEQ ID NO:71 and a variable light chain region comprising the amino acid sequence of SEQ ID NO:72 or (ii) wherein the antibody comprises a heavy chain comprising the amino acid sequence of SEQ ID NO:73 and a light chain comprising the amino acid sequence of SEQ ID NO:74.

Also provided herein is an isolated antibody or antigen-binding fragment thereof that binds to the same epitope of human B7-H4 as the antibody or antigen-binding fragment thereof of any one of claims 1-20. In one embodiment, the antibody or antigen-binding fragment thereof binds to the same epitope of human B7-H4 as determined by SPR.

In one embodiment, the antibody or antigen-binding fragment thereof is a human antibody or antigen-binding fragment thereof. In one embodiment, the antibody or antigen-binding fragment thereof is a murine, humanized, or chimeric antibody or antigen-binding fragment thereof.

In one embodiment, the antibody or antigen-binding fragment thereof induces T cell proliferation. In one embodiment, the antibody or antigen-binding fragment increases T-cell proliferation by at least 21% as compared to treatment with a control antibody. In one embodiment, the antibody or antigen-binding fragment increases T-cell proliferation by about 5% to about 35% as compared to treatment with a control antibody. In one embodiment, the antibody or antigen-binding fragment thereof induces CD4+ T cell proliferation. In one embodiment, the antibody or antigen-binding fragment thereof increases CD4+ T cell proliferation by at least 9% as compared to treatment with a control antibody. In one embodiment, the antibody or antigen-binding fragment thereof increases CD4+ T cell proliferation by about 5% to about 15% as compared to treatment with a control antibody. In one embodiment, the antibody or antigen-binding fragment thereof induces CD8+ T cell proliferation. In one embodiment, the antibody or antigen-binding fragment thereof increases CD8+ T cell proliferation by at least 11% as compared to treatment with a control antibody. In one embodiment, the antibody or antigen-binding fragment thereof increases CD8+ T cell proliferation by about 5% to about 15% as compared to treatment with a control antibody.

In one embodiment, the antibody or antigen-binding fragment thereof induces interferon-gamma (IFNγ) production. In one embodiment, the antibody or antigen-binding fragment thereof is capable of increasing production of IFNγ by at least 2 fold, at least 3 fold, at least 4 fold, and at least 5 fold, at least 6 fold, at least 7 fold, at least 8 fold, about 2 fold to about 10 fold, or about 3 fold to about 10 fold.

In one embodiment, the antibody or antigen-binding fragment thereof is capable of inducing antibody dependent cell mediated cytotoxicity (ADCC) in a B7-H4-expressing cell. In one embodiment, the antibody or antigen-binding fragment thereof induces specific lysis in at least 20%, at least 30%, at least 40%, about 20% to about 50%, or about 30% to about 50% of B7-H4 expressing cells.

In one embodiment, the antibody or antigen-binding fragment thereof inhibits tumor growth in a murine CT26 colorectal carcinoma model, a murine breast carcinoma 4T1 model, or a melanoma cell line B16-moB7-H4/H3 model. In one embodiment, the antibody or antigen-binding fragment thereof reduces tumor growth by at least 25%, at least 30%, at least 40%, at least 45%, or at least 50% as compared to treatment with a control antibody.

In one embodiment, the induction of T cell proliferation, the induction of CD4+ T cell proliferation, the induction of CD8+ T cell proliferation, the induction of IFNγ production, the ADCC activity, and/or in the inhibition of tumor growth is dose-dependent.

In one embodiment, the antibody or antigen-binding fragment thereof binds to cynomolgus monkey B7-H4. In one embodiment, the antibody or antigen-binding fragment thereof binds to rat B7-H4. In one embodiment, the antibody or antigen-binding fragment thereof binds to mouse B7-H4. In one embodiment, the antibody or antigen-binding fragment thereof binds to human B7-H4, cynomolgus monkey B7-H4, rat B7-H4 and mouse B7-H4.

In one embodiment, the antibody or antigen-binding fragment thereof binds to the IgV domain of human B7-H4.

In one embodiment, the antibody or antigen-binding fragment thereof is afucosylated.

In one embodiment, the antibody or antigen binding fragment thereof is a full length antibody. In one embodiment, the antibody or antigen binding fragment thereof is an antigen binding fragment. In one embodiment, the antigen binding fragment comprises a Fab, Fab', F(ab)$_2$, single chain Fv (scFv), disulfide linked Fv, V-NAR domain, IgNar, intrabody, IgGΔCH2, minibody, F(ab')$_3$, tetrabody, triabody, diabody, single-domain antibody, DVD-Ig, Fcab, mAb$^2$, (scFv)$_2$, or scFv-Fc.

In one embodiment, the antibody or antigen-binding fragment thereof further comprises a detectable label.

Also provided herein is an isolated polynucleotide comprising a nucleic acid molecule encoding the heavy chain variable region or heavy chain of an antibody or antigen-biding fragment thereof provided herein. In one embodiment, the nucleic acid molecule encodes the VH of SEQ ID NO:11, 21, 31, 41, 464, 51, 61, 71, 81, 91, 101, 111, 121, 131, 141, 151, 161, 171, 181, 191, or 201 or the heavy chain of SEQ ID NO:13, 23, 33, 43, 469, 53, 63, 73, 83, 93, 103, 113, 123, 133, 143, 153, 163, 173, 183, 193, or 203. In one embodiment, the nucleic acid molecule comprises the sequence of SEQ ID NO:213, 223, 233, 243, 470, 253, 263, 273, 283, 293, 303, 313, 323, 333, 343, 353, 363, 373, 383, 393, or 403. In one embodiment, the nucleic acid molecule comprises (i) the sequence of SEQ ID NO:213, 223, 233, 243, 470, 253, 263, 273, 283, 293, 303, 313, 323, 333, 343, 353, 363, 373, 383, 393, or 403 and (ii) the sequence of SEQ ID NO:408.

Also provided herein is an isolated polynucleotide comprising a nucleic acid molecule encoding the light chain variable region or light chain of an antibody or antigen-biding fragment thereof provided herein. In one embodiment, the nucleic acid molecule encodes the VL of SEQ ID NO:12, 22, 32, 42, 52, 62, 72, 82, 92, 102, 112, 122, 132, 142, 152, 162, 172, 182, 192, or 202 or the light chain of SEQ ID NO:14, 24, 34, 44, 54, 64, 74, 84, 94, 104, 114, 124, 134, 144, 154, 164, 174, 184, 194, or 204. In one embodiment, the nucleic acid molecule comprises the sequence of SEQ ID NO:214, 224, 234, 244, 254, 264, 274, 284, 294, 304, 314, 324, 334, 344, 354, 364, 374, 384, 394, or 404. In one embodiment, the nucleic acid molecule comprises (i) the sequence of SEQ ID NO:214, 224, 234, 244, 254, 264, 274, 284, 294, 304, 314, 324, 334, 344, 354, 364, 374, 384, 394, or 404 and (ii) the sequence of SEQ ID NO:406.

Also provided herein is an isolated polynucleotide comprising a nucleic acid molecule encoding the heavy chain variable region or heavy chain of an antibody or antigen-biding fragment provided herein and the light chain variable region or light chain of the antibody or antigen-biding fragment thereof.

Also provided herein is an isolated vector comprising a polynucleotide provided herein.

Also provided herein is a host cell comprising a polynucleotide provided herein, a vector provided herein, a first vector comprising one polynucleotide provided herein (e.g., a polynucleotide comprising a variable heavy chain or heavy chain encoding nucleic acid) and a second vector comprising another polynucleotide provided herein (e.g., a polynucleotide comprising variable light chain or light chain encoding nucleic acid). In one embodiment, the host cell is a cell selected from the group consisting of *E. coli, Pseudomonas, Bacillus, Streptomyces*, yeast, CHO, YB/20, NS0, PER-C6, HEK-293T, NIH-3T3, HeLa, BHK, Hep G2, SP2/0, R1.1, B-W, L-M, COS 1, COS 7, BSC1, BSC40, BMT10 cell, plant cell, insect cell, and human cell in tissue culture. In one embodiment, the host cell is a CHO cell. In one embodiment, the host cell (e.g., a mammalian host cell, such as a CHO cell) lacks a functional alpha-1,6-fucosyltransferase gene (FUT8) gene.

Also provided herein is a method (e.g., an in vitro method) of producing an antibody or antigen-binding fragment thereof that binds to human B7-H4 comprising culturing a host cell provided herein so that the nucleic acid molecule is expressed and the antibody or antigen-biding fragment thereof is produced.

Also provided herein is an isolated antibody or antigen-binding fragment thereof that specifically binds to human B7-H4 and is encoded by a polynucleotide provided herein.

Also provided herein is a pharmaceutical composition comprising an antibody or antigen-binding fragment thereof provided herein, a polynucleotide provided herein, a vector provided herein, or a host cell provided herein; and a pharmaceutically acceptable excipient.

Also provided herein is a pharmaceutical composition comprising (i) antibodies or antigen-binding fragments provided herein and (ii) a pharmaceutically acceptable excipient, wherein at least 80%, at least 85%, at least 90%, at least 95%, at least 96%, at least 97%, at least 98%, or at least 99% of the antibodies or antigen-binding fragments thereof in the composition are afucosylated.

Also provided herein is a pharmaceutical composition comprising (i) antibodies or antigen-binding fragments provided herein and (ii) a pharmaceutically acceptable excipient, wherein at least 95% of the antibodies or antigen-binding fragments thereof in the composition are afucosylated.

Also provided herein is a pharmaceutical composition comprising (i) antibodies or antigen-binding fragments thereof that specifically bind to human B7-H4 and comprise the heavy chain variable region (VH) complementarity determining region (CDR) 1, VH CDR2, VH CDR3 and light chain variable region (VL) CDR1, CDR2, and CDR3 sequences of SEQ ID NOs:458-463, respectively and (ii) a pharmaceutically acceptable excipient, wherein at least 80%, at least 85%, at least 90%, at least 95%, at least 96%, at least 97%, at least 98%, or at least 99% of the antibodies or antigen-binding fragments thereof in the composition are afucosylated. In one embodiment, (i) the antibody or antigen-binding fragment thereof comprises a variable heavy chain region comprising the amino acid sequence of SEQ ID NO:464 and a variable light chain region comprising the amino acid sequence of SEQ ID NO:42 or (ii) the antibody comprises a heavy chain comprising the amino acid sequence of SEQ ID NO:469 and a light chain comprising the amino acid sequence of SEQ ID NO:44.

Also provided herein is a pharmaceutical composition comprising (i) antibodies or antigen-binding fragments thereof that specifically bind to human B7-H4 and comprise the heavy chain variable region (VH) complementarity determining region (CDR) 1, VH CDR2, VH CDR3 and light chain variable region (VL) CDR1, CDR2, and CDR3 sequences of SEQ ID NOs: 458-463, respectively and (ii) a pharmaceutically acceptable excipient, wherein at least 95% of the antibodies or antigen-binding fragments thereof in the composition are afucosylated. In one embodiment, (i) the antibody or antigen-binding fragment thereof comprises a variable heavy chain region comprising the amino acid sequence of SEQ ID NO: 464 and a variable light chain region comprising the amino acid sequence of SEQ ID NO:42 or (ii) the antibody comprises a heavy chain comprising the amino acid sequence of SEQ ID NO: 469 and a light chain comprising the amino acid sequence of SEQ ID NO:44.

Also provided herein is a pharmaceutical composition comprising (i) antibodies or antigen-binding fragments thereof that specifically bind to human B7-H4 and comprise the heavy chain variable region (VH) complementarity determining region (CDR) 1, VH CDR2, VH CDR3 and light chain variable region (VL) CDR1, CDR2, and CDR3 sequences of SEQ ID NOs:35-40, respectively and (ii) a pharmaceutically acceptable excipient, wherein at least 80%, at least 85%, at least 90%, at least 95%, at least 96%, at least 97%, at least 98%, or at least 99% of the antibodies or antigen-binding fragments thereof in the composition are afucosylated. In one embodiment, (i) the antibody or antigen-binding fragment thereof comprises a variable heavy chain region comprising the amino acid sequence of SEQ ID NO:41 and a variable light chain region comprising the amino acid sequence of SEQ ID NO:42 or (ii) the antibody comprises a heavy chain comprising the amino acid sequence of SEQ ID NO:43 and a light chain comprising the amino acid sequence of SEQ ID NO:44.

Also provided herein is a pharmaceutical composition comprising (i) antibodies or antigen-binding fragments thereof that specifically bind to human B7-H4 and comprise the heavy chain variable region (VH) complementarity determining region (CDR) 1, VH CDR2, VH CDR3 and light chain variable region (VL) CDR1, CDR2, and CDR3 sequences of SEQ ID NOs:35-40, respectively and (ii) a pharmaceutically acceptable excipient, wherein at least 95% of the antibodies or antigen-binding fragments thereof in the composition are afucosylated. In one embodiment, (i) the antibody or antigen-binding fragment thereof comprises a variable heavy chain region comprising the amino acid sequence of SEQ ID NO:41 and a variable light chain region comprising the amino acid sequence of SEQ ID NO:42 or (ii) the antibody comprises a heavy chain comprising the amino acid sequence of SEQ ID NO:43 and a light chain comprising the amino acid sequence of SEQ ID NO:44.

Also provided herein is a pharmaceutical composition comprising (i) antibodies or antigen-binding fragments thereof that specifically bind to human B7-H4 and comprise the heavy chain variable region (VH) complementarity determining region (CDR) 1, VH CDR2, VH CDR3 and light chain variable region (VL) CDR1, CDR2, and CDR3 sequences of SEQ ID NOs:65-70, respectively and (ii) a pharmaceutically acceptable excipient, wherein at least 80%, at least 85%, at least 90%, at least 95%, at least 96%, at least 97%, at least 98%, or at least 99% of the antibodies or antigen-binding fragments thereof in the composition are afucosylated. In one embodiment, (i) the antibody or antigen-binding fragment thereof comprises a variable heavy chain region comprising the amino acid sequence of SEQ ID NO:71 and a variable light chain region comprising the amino acid sequence of SEQ ID NO:72 or (ii) wherein the antibody comprises a heavy chain comprising the amino acid sequence of SEQ ID NO:73 and a light chain comprising the amino acid sequence of SEQ ID NO:74.

Also provided herein is a pharmaceutical composition comprising (i) antibodies or antigen-binding fragments thereof that specifically bind to human B7-H4 and comprise the heavy chain variable region (VH) complementarity determining region (CDR) 1, VH CDR2, VH CDR3 and light chain variable region (VL) CDR1, CDR2, and CDR3 sequences of SEQ ID NOs:65-70, respectively and (ii) a pharmaceutically acceptable excipient, wherein at least 95% of the antibodies or antigen-binding fragments thereof in the composition are afucosylated. In one embodiment, (i) the antibody or antigen-binding fragment thereof comprises a variable heavy chain region comprising the amino acid sequence of SEQ ID NO:71 and a variable light chain region comprising the amino acid sequence of SEQ ID NO:72 or (ii) wherein the antibody comprises a heavy chain comprising the amino acid sequence of SEQ ID NO:73 and a light chain comprising the amino acid sequence of SEQ ID NO:74.

In one embodiment, fucosylation is undetectable in the composition.

Also provided herein is a method for inducing T cell proliferation comprising contacting a T cell with an antibody or antigen-binding fragment thereof provided herein, a polynucleotide provided herein, a vector provided herein, a host cell provided herein, or a pharmaceutical composition provided herein. In one embodiment, T cell proliferation is reduced by at least 30%, at least 40%, at least 50%, at least 60%, at least 70%, or at least 80% (e.g., as compared to treatment with a control antibody).

Also provided herein is a method for inducing CD4+ T cell proliferation comprising contacting a CD4+ T cell with an antibody or antigen-binding fragment thereof provided herein, a polynucleotide provided herein, a vector provided herein, a host cell provided herein, or a pharmaceutical composition provided herein. In one embodiment, CD4+ T cell proliferation is reduced by at least 30%, at least 40%, at least 50%, at least 60%, at least 70%, or at least 80% (e.g., as compared to treatment with a control antibody).

Also provided herein is a method for inducing CD8+ T cell proliferation comprising contacting a CD8+ T cell with an antibody or antigen-binding fragment thereof provided herein, a polynucleotide provided herein, a vector provided herein, a host cell provided herein, or a pharmaceutical composition provided herein. In one embodiment, CD8+ T cell proliferation is reduced by at least 30%, at least 40%, at least 50%, at least 60%, at least 70%, or at least 80% (e.g., as compared to treatment with a control antibody).

Also provided herein is a method for inducing interferon gamma production comprising contacting a T cell with an antibody or antigen-binding fragment thereof provided herein, a polynucleotide provided herein, a vector provided herein, a host cell provided herein, or a pharmaceutical composition provided herein. In one embodiment, interferon gamma production is increased by at least 30%, at least 40%, at least 50%, at least 60%, at least 70%, or at least 80% (e.g., as compared to treatment with a control antibody).

Also provided herein is a method for killing a cell expressing B7-H4 comprising contacting the cell with an antibody or antigen-binding fragment thereof provided herein, a polynucleotide provided herein, a vector provided herein, a host cell provided herein, or a pharmaceutical composition provided herein.

Also provided herein is a method for depleting B7-H4-expressing cells from a population of cells comprising contacting the population of cells with an antibody or antigen-binding fragment thereof provided herein, a polynucleotide provided herein, a vector provided herein, a host cell provided herein, or a pharmaceutical composition provided herein.

In one embodiment, the killing or depletion occurs via ADCC.

In one embodiment, the contacting is in vitro. In one embodiment, the contacting is in a subject.

Also provided herein is a method of treating cancer in a subject, the method comprising administering to the subject an effective amount of an antibody or antigen-binding fragment thereof provided herein, a polynucleotide provided herein, a vector provided herein, a host cell provided herein, or a pharmaceutical composition provided herein. In one embodiment, the cancer is selected from the group consisting of breast cancer, such as triple negative breast cancer or invasive ductal carcinoma, endometrial carcinoma, ovarian cancer, non-small cell lung cancer, pancreatic cancer, thyroid cancer, kidney cancer and bladder cancer. In one embodiment, the breast cancer is triple negative breast cancer or wherein the non-small cell lung cancer is squamous cell carcinoma. In one embodiment, the non-small cell lung cancer is an adenocarcinoma. In one embodiment, the cancer is selected from the group consisting of head and neck cancer, small cell lung cancer, gastric cancer, and melanoma. In one embodiment, the ovarian cancer is a serous adenocarcinoma. In one embodiment, the breast cancer is a ductal adenocarcinoma.

In one embodiment, the cancer is a PD-1 inhibitor inadequate responder and/or PD-L1 inhibitor inadequate responder. In one embodiment, the cancer expresses a low level of PD-L1.

In one embodiment, the subject is human.

Also provided herein is a method for detecting B7-H4 in a sample comprising contacting said sample with an antibody or antigen-binding fragment thereof provided herein. In one embodiment, the sample is obtained from a cancer in a human subject.

Also provided herein is a kit comprising an antibody or antigen-binding fragment thereof provided herein, a polynucleotide provided herein, a vector provided herein, a host cell provided herein, or a pharmaceutical composition provided herein and a) a detection reagent, b) a B7-H4 antigen, c) a notice that reflects approval for use or sale for human administration, or d) a combination thereof.

Also provided herein is an isolated antibody or antigen-binding fragment, wherein the antibody or antigen-binding fragment thereof inhibits T cell checkpoint blockade activity of B7-H4. In one embodiment, the T cell checkpoint blockade activity is measured by an increase in IL-2 production relative to control cells.

Also provided herein is a pharmaceutical composition comprising (i) antibodies or antigen-binding fragments and (ii) a pharmaceutically acceptable excipient, wherein the antibodies or antigen-binding fragments inhibit T cell checkpoint blockade activity of B7-H4. In an embodiment, the T cell checkpoint blockade activity is measured by an increase in IL-2 production relative to control cells.

BRIEF DESCRIPTION OF THE FIGURES

FIGS. 12A-12C show the in vivo anti-tumor efficacy of 20502-msIgG2a-F administered on the same day as an anti-PD-1 antibody. (See Example 15.) * indicates $p<0.05$; and **** indicates $p<0.0001$.

DETAILED DESCRIPTION

Figure 1A:
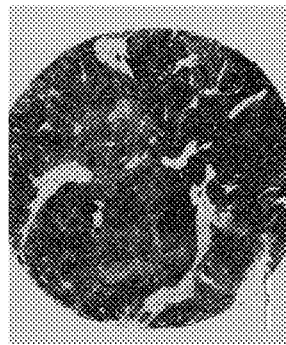
FIG. 1A shows B7-H4 expression in a variety of tumor tissues. (See Example 1.)
Figure 1A:
Figure 1A:
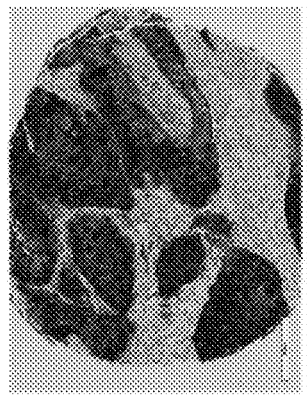
Figure 1A:
Figure 1A:
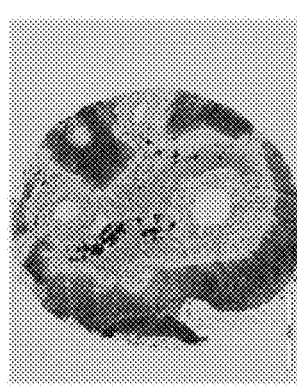

Provided herein are antibodies (e.g., monoclonal antibodies) and antigen-binding fragments thereof that specifically bind to B7-H4 (e.g., human B7-H4). The anti-B7-H4 antibodies and antigen-binding fragments thereof can, for example, result in T cell checkpoint blockade activity (e.g., as measured by an increase in interferon-gamma (IFNγ), CD4 T-cell proliferation, CD8 T-cell proliferation, and/or total T-cell proliferation) and/or have antibody-dependent cellular cytotoxicity (ADCC activity).

Also provided are isolated nucleic acids (polynucleotides), such as complementary DNA (cDNA), encoding such antibodies and antigen-binding fragments thereof. Further provided are vectors (e.g., expression vectors) and cells (e.g., host cells) comprising nucleic acids (polynucleotides) encoding such antibodies and antigen-binding fragments thereof. Also provided are methods of making such antibodies and antigen-binding fragments thereof. In other aspects, provided herein are methods for treating certain conditions, such as cancer. Related compositions (e.g., pharmaceutical compositions), kits, and detection methods are also provided.

1.1 Terminology

As used herein, the term "B7-H4" refers to mammalian B7-H4 polypeptides including, but not limited to, native B7-H4 polypeptides and isoforms of B7-H4 polypeptides. "B7-H4" encompasses full-length, unprocessed B7-H4 polypeptides as well as forms of B7-H4 polypeptides that result from processing within the cell. As used herein, the term "human B7-H4" refers to a polypeptide comprising the amino acid sequence of SEQ ID NO:1. A "B7-H4 polynucleotide," "B7-H4 nucleotide," or "B7-H4 nucleic acid" refer to a polynucleotide encoding B7-H4.

The term "PD-1" as used herein, refers to mammalian PD-1 polypeptides, including, but not limited to, native PD-1 polypeptides and isoforms of PD-1 polypeptides. PD-1 is also referred to as Programmed death protein 1 or Programmed cell death protein 1. "PD-1" encompasses full-length, unprocessed PD-1 polypeptides as well as forms of PD-1 polypeptides that result from processing in the cell. As used herein, the term "human PD-1" refers to a polypeptide comprising the amino acid sequence of SEQ ID NO:439: PGWFLDSPDR PWNPPTFSPA LLVVTEGDNA TFTCSFSNTS ESFVLNWYRM SPSNQTDKLA AFPEDRSQPG QDCRFRVTQL PNGRDFHMSV VRARRNDSGT YLCGAISLAP KAQIKESLRA ELRVTERRAE VPTAHPSPSP RPAGQFQTLV VGVVGGLLGS LVLLVWVLAV ICSRAARGTI GARRTGQPLK EDPSAVPVFS VDYGELDFQW REKTPEPPVP CVPEQTEYAT IVFPSGMGTS SPARRGSADG PRSAQPLRPE DGHCSWPL (SEQ ID NO:439) (mature human PD-1 without a signal sequence). A "PD-1 polynucleotide," "PD-1 nucleotide" or "PD-1 nucleic acid" refers to a polynucleotide encoding PD-1.

The term "antibody" means an immunoglobulin molecule that recognizes and specifically binds to a target, such as a protein, polypeptide, peptide, carbohydrate, polynucleotide, lipid, or combinations of the foregoing through at least one antigen recognition site within the variable region of the immunoglobulin molecule. As used herein, the term "antibody" encompasses intact polyclonal antibodies, intact monoclonal antibodies, chimeric antibodies, humanized antibodies, human antibodies, fusion proteins comprising an antibody, and any other modified immunoglobulin molecule so long as the antibodies exhibit the desired biological activity. An antibody can be of any the five major classes of immunoglobulins: IgA, IgD, IgE, IgG, and IgM, or subclasses (isotypes) thereof (e.g. IgG1, IgG2, IgG3, IgG4, IgA1 and IgA2), based on the identity of their heavy-chain constant domains referred to as alpha, delta, epsilon, gamma, and mu, respectively. The different classes of immunoglobulins have different and well known subunit structures and three-dimensional configurations. Antibodies can be naked or conjugated to other molecules such as toxins, radioisotopes, etc.

The term "antibody fragment" refers to a portion of an intact antibody. An "antigen-binding fragment," "antigen-binding domain," or "antigen-binding region," refers to a portion of an intact antibody that binds to an antigen. An antigen-binding fragment can contain the antigenic determining regions of an intact antibody (e.g., the complementarity determining regions (CDR)). Examples of antigen-binding fragments of antibodies include, but are not limited to Fab, Fab', F(ab')2, and Fv fragments, linear antibodies, and single chain antibodies. An antigen-binding fragment of an antibody can be derived from any animal species, such as rodents (e.g., mouse, rat, or hamster) and humans or can be artificially produced.

The terms "anti-B7-H4 antibody," "B7-H4 antibody" and "antibody that binds to B7-H4" refer to an antibody that is capable of binding B7-H4 with sufficient affinity such that the antibody is useful as a diagnostic and/or therapeutic agent in targeting B7-H4. The extent of binding of an anti-B7-H4 antibody to an unrelated, non-B7-H4 protein can be less than about 10% of the binding of the antibody to B7-H4 as measured, e.g., by a radioimmunoassay (RIA).

The terms "anti-PD-1 antibody," "PD-1 antibody" and "antibody that binds to PD-1" refer to an antibody that is capable of binding PD-1 with sufficient affinity such that the antibody is useful as a diagnostic and/or therapeutic agent in targeting PD-1. The extent of binding of an anti-PD-1 antibody to an unrelated, non-PD-1 protein can be less than about 10% of the binding of the antibody to PD-1 as measured, e.g., by a radioimmunoassay (RIA).

A "monoclonal" antibody or antigen-binding fragment thereof refers to a homogeneous antibody or antigen-binding fragment population involved in the highly specific recognition and binding of a single antigenic determinant, or epitope. This is in contrast to polyclonal antibodies that typically include different antibodies directed against different antigenic determinants. The term "monoclonal" antibody or antigen-binding fragment thereof encompasses both intact and full-length monoclonal antibodies as well as antibody fragments (such as Fab, Fab', F(ab')2, Fv), single chain (scFv) mutants, fusion proteins comprising an antibody portion, and any other modified immunoglobulin molecule comprising an antigen recognition site. Furthermore, "monoclonal" antibody or antigen-binding fragment thereof refers to such antibodies and antigen-binding fragments thereof made in any number of manners including but not limited to by hybridoma, phage selection, recombinant expression, and transgenic animals.

As used herein, the terms "variable region" or "variable domain" are used interchangeably and are common in the art. The variable region typically refers to a portion of an antibody, generally, a portion of a light or heavy chain, typically about the amino-terminal 110 to 120 amino acids or 110 to 125 amino acids in the mature heavy chain and about 90 to 115 amino acids in the mature light chain, which differ extensively in sequence among antibodies and are used in the binding and specificity of a particular antibody for its particular antigen. The variability in sequence is concentrated in those regions called complementarity determining regions (CDRs) while the more highly conserved regions in the variable domain are called framework regions (FR). Without wishing to be bound by any particular mechanism or theory, it is believed that the CDRs of the light and heavy chains are primarily responsible for the interaction and specificity of the antibody with antigen. In certain embodiments, the variable region is a human variable region. In certain embodiments, the variable region comprises rodent or murine CDRs and human framework regions (FRs). In particular embodiments, the variable region is a primate (e.g., non-human primate) variable region. In certain embodiments, the variable region comprises rodent or murine CDRs and primate (e.g., non-human primate) framework regions (FRs).

The terms "VL" and "VL domain" are used interchangeably to refer to the light chain variable region of an antibody.

The terms "VH" and "VH domain" are used interchangeably to refer to the heavy chain variable region of an antibody.

The term "Kabat numbering" and like terms are recognized in the art and refer to a system of numbering amino acid residues in the heavy and light chain variable regions of an antibody or an antigen-binding fragment thereof. In certain aspects, CDRs can be determined according to the Kabat numbering system (see, e.g., Kabat E A & Wu T T (1971) Ann NY Acad Sci 190: 382-391 and Kabat E A et al., (1991) Sequences of Proteins of Immunological Interest, Fifth Edition, U.S. Department of Health and Human Services, NIH Publication No. 91-3242). Using the Kabat numbering system, CDRs within an antibody heavy chain molecule are typically present at amino acid positions 31 to 35, which optionally can include one or two additional amino acids, following 35 (referred to in the Kabat numbering scheme as 35A and 35B) (CDR1), amino acid positions 50 to 65 (CDR2), and amino acid positions 95 to 102 (CDR3). Using the Kabat numbering system, CDRs within an antibody light chain molecule are typically present at amino acid positions 24 to 34 (CDR1), amino acid positions 50 to 56 (CDR2), and amino acid positions 89 to 97 (CDR3). In a specific embodiment, the CDRs of the antibodies described herein have been determined according to the Kabat numbering scheme.

Chothia refers instead to the location of the structural loops (Chothia and Lesk, J. Mol. Biol. 196:901-917 (1987)). The end of the Chothia CDR-H1 loop when numbered using the Kabat numbering convention varies between H32 and H34 depending on the length of the loop (this is because the Kabat numbering scheme places the insertions at H35A and H35B; if neither 35A nor 35B is present, the loop ends at 32; if only 35A is present, the loop ends at 33; if both 35A and 35B are present, the loop ends at 34). The AbM hypervariable regions represent a compromise between the Kabat CDRs and Chothia structural loops, and are used by Oxford Molecular's AbM antibody modeling software.

| Loop | Kabat | AbM | Chothia |
|------|-------|-----|---------|
| L1 | L24-L34 | L24-L34 | L24-L34 |
| L2 | L50-L56 | L50-L56 | L50-L56 |
| L3 | L89-L97 | L89-L97 | L89-L97 |
| H1 | H31-H35B | H26-H35B | H26-H32..34 |
| | | | (Kabat Numbering) |
| H1 | H31-H35 | H26-H35 | H26-H32 |
| | | | (Chothia Numbering) |
| H2 | H50-H65 | H50-H58 | H52-H56 |
| H3 | H95-H102 | H95-H102 | H95-H102 |

As used herein, the term "constant region" or "constant domain" are interchangeable and have its meaning common in the art. The constant region is an antibody portion, e.g., a carboxyl terminal portion of a light and/or heavy chain which is not directly involved in binding of an antibody to antigen but which can exhibit various effector functions, such as interaction with the Fc receptor. The constant region of an immunoglobulin molecule generally has a more conserved amino acid sequence relative to an immunoglobulin variable domain. In certain aspects, an antibody or antigen-binding fragment comprises a constant region or portion thereof that is sufficient for antibody-dependent cell-mediated cytotoxicity (ADCC).

As used herein, the term "heavy chain" when used in reference to an antibody can refer to any distinct type, e.g., alpha (α), delta (δ), epsilon (ε), gamma (γ), and mu (μ), based on the amino acid sequence of the constant domain, which give rise to IgA, IgD, IgE, IgG, and IgM classes of antibodies, respectively, including subclasses of IgG, e.g., $IgG_1$, $IgG_2$, $IgG_3$, and $IgG_4$. Heavy chain amino acid sequences are well known in the art. In specific embodiments, the heavy chain is a human heavy chain.

As used herein, the term "light chain" when used in reference to an antibody can refer to any distinct type, e.g., kappa (κ) or lambda (λ) based on the amino acid sequence of the constant domains. Light chain amino acid sequences are well known in the art. In specific embodiments, the light chain is a human light chain.

The term "chimeric" antibodies or antigen-binding fragments thereof refers to antibodies or antigen-binding fragments thereof wherein the amino acid sequence is derived from two or more species. Typically, the variable region of both light and heavy chains corresponds to the variable region of antibodies or antigen-binding fragments thereof derived from one species of mammals (e.g. mouse, rat, rabbit, etc.) with the desired specificity, affinity, and capability while the constant regions are homologous to the sequences in antibodies or antigen-binding fragments thereof derived from another (usually human) to avoid eliciting an immune response in that species.

The term "humanized" antibody or antigen-binding fragment thereof refers to forms of non-human (e.g. murine) antibodies or antigen-binding fragments that are specific immunoglobulin chains, chimeric immunoglobulins, or fragments thereof that contain minimal non-human (e.g., murine) sequences. Typically, humanized antibodies or antigen-binding fragments thereof are human immunoglobulins in which residues from the complementary determining region (CDR) are replaced by residues from the CDR of a non-human species (e.g. mouse, rat, rabbit, hamster) that have the desired specificity, affinity, and capability ("CDR grafted") (Jones et al., Nature 321:522-525 (1986); Riechmann et al., Nature 332:323-327 (1988); Verhoeyen et al., Science 239:1534-1536 (1988)). In some instances, the Fv framework region (FR) residues of a human immunoglobulin are replaced with the corresponding residues in an antibody or fragment from a non-human species that has the desired specificity, affinity, and capability. The humanized antibody or antigen-binding fragment thereof can be further modified by the substitution of additional residues either in the Fv framework region and/or within the replaced non-human residues to refine and optimize antibody or antigen-binding fragment thereof specificity, affinity, and/or capability. In general, the humanized antibody or antigen-binding fragment thereof will comprise substantially all of at least one, and typically two or three, variable domains containing all or substantially all of the CDR regions that correspond to the non-human immunoglobulin whereas all or substantially all of the FR regions are those of a human immunoglobulin consensus sequence. The humanized antibody or antigen-binding fragment thereof can also comprise at least a portion of an immunoglobulin constant region or domain (Fc), typically that of a human immunoglobulin. Examples of methods used to generate humanized antibodies are described in U.S. Pat. No. 5,225,539; Roguska et al., Proc. Natl. Acad. Sci., USA, 91(3):969-973 (1994), and Roguska et al., Protein Eng. 9(10):895-904 (1996). In some embodiments, a "humanized antibody" is a resurfaced antibody.

The term "human" antibody or antigen-binding fragment thereof means an antibody or antigen-binding fragment thereof having an amino acid sequence derived from a human immunoglobulin gene locus, where such antibody or antigen-binding fragment is made using any technique known in the art. This definition of a human antibody or antigen-binding fragment thereof includes intact or full-length antibodies and fragments thereof.

An "afucosylated" antibody or antigen-binding fragment thereof or an antibody or antigen-binding fragment thereof "lacking fucose" refers to an IgG1 or IgG3 isotype antibody or antigen-binding fragment thereof that lacks fucose in its constant region glycosylation. Glycosylation of human IgG1 or IgG3 occurs at Asn297 as core fucosylated biantennary complex oligosaccharide glycosylation terminated with up to 2 Gal residues. In some embodiments, an afucosylated antibody lacks fucose at Asn297. These structures are designated as G0, G1 (a 1,6 or a 1,3), or G2 glycan residues, depending on the amount of terminal Gal residues. See, e.g., Raju, T. S., BioProcess Int. 1: 44-53 (2003). CHO type glycosylation of antibody Fc is described, e.g., in Routier, F. FL, Glycoconjugate J. 14: 201-207 (1997).

Methods of measuring fucose include any methods known in the art. For purposes herein, fucose is detected by the method described in Example 1 of WO2015/017600, which is herein incorporated by reference in its entirety. Briefly, glycan analysis is performed by releasing glycans from the antibody (e.g., by enzymatic release), labeling the glycans with anthranilic acid (2-AA), and then purifying the labeled glycans. Normal phase HPLC with fluorescent detection is used to separate the glycans and measure the relative amount of each glycan in the antibody. The glycans may be positively identified as lacking or including fucose by mass spectrometry. In some embodiments, fucose is undetectable in a composition comprising a plurality of afucosylated antibodies or antigen-binding fragments thereof. In some embodiments, an afucosylated antibody or antigen-binding fragment thereof has enhanced ADCC activity, which may be measured by the assay provided in Example 12 herein. In some embodiments, an afucosylated antibody or antigen-binding fragment thereof has enhanced affinity for Fc gamma RIIIA. In some embodiments, an afucosylated antibody or antigen-binding fragment thereof has enhanced affinity for Fc gamma RIIIA(V158). In some embodiments, an afucosylated antibody or antigen-binding fragment thereof has enhanced affinity for Fc gamma RIIIA(F158). Affinity for Fc gamma RIIIA or its alleles may be measure by the assay provided in Example 10 herein.

"Binding affinity" generally refers to the strength of the sum total of non-covalent interactions between a single binding site of a molecule (e.g., an antibody or antigen-binding fragment thereof) and its binding partner (e.g., an antigen). Unless indicated otherwise, as used herein, "binding affinity" refers to intrinsic binding affinity which reflects a 1:1 interaction between members of a binding pair (e.g., antibody or antigen-binding fragment thereof and antigen). The affinity of a molecule X for its partner Y can generally be represented by the dissociation constant ($K_D$). Affinity can be measured and/or expressed in a number of ways known in the art, including, but not limited to, equilibrium dissociation constant ($K_D$), and equilibrium association constant ($K_A$). The $K_D$ is calculated from the quotient of $k_{off}/k_{on}$, whereas $K_A$ is calculated from the quotient of $k_{on}/k_{off}$. $k_{on}$ refers to the association rate constant of, e.g., an antibody or antigen-binding fragment thereof to an antigen, and $k_{off}$ refers to the dissociation of, e.g., an antibody or antigen-binding fragment thereof from an antigen. The $k_{on}$ and $k_{off}$ can be determined by techniques known to one of ordinary skill in the art, such as BIAcore® or KinExA.

As used herein, an "epitope" is a term in the art and refers to a localized region of an antigen to which an antibody or antigen-binding fragment thereof can specifically bind. An epitope can be, for example, contiguous amino acids of a polypeptide (linear or contiguous epitope) or an epitope can, for example, come together from two or more non-contiguous regions of a polypeptide or polypeptides (conformational, non-linear, discontinuous, or non-contiguous epitope). In certain embodiments, the epitope to which an antibody or antigen-binding fragment thereof binds can be determined by, e.g., NMR spectroscopy, X-ray diffraction crystallography studies, ELISA assays, hydrogen/deuterium exchange coupled with mass spectrometry (e.g., liquid chromatography electrospray mass spectrometry), array-based oligo-peptide scanning assays, and/or mutagenesis mapping (e.g., site-directed mutagenesis mapping). For X-ray crystallography, crystallization may be accomplished using any of the known methods in the art (e.g., Giegé R et al., (1994) Acta Crystallogr D Biol Crystallogr 50(Pt 4): 339-350; McPherson A (1990) Eur J Biochem 189: 1-23; Chayen N E (1997) Structure 5: 1269-1274; McPherson A (1976) J Biol Chem 251: 6300-6303). Antibody/antigen-binding fragment thereof: antigen crystals can be studied using well known X-ray diffraction techniques and can be refined using computer software such as X-PLOR (Yale University, 1992, distributed by Molecular Simulations, Inc.; see, e.g., Meth Enzymol (1985) volumes 114 & 115, eds Wyckoff H W et al.; U.S. 2004/0014194), and BUSTER (Bricogne G (1993) Acta Crystallogr D Biol Crystallogr 49(Pt 1): 37-60; Bricogne G (1997) Meth Enzymol 276A: 361-423, ed Carter C W; Roversi P et al., (2000) Acta Crystallogr D Biol Crystallogr 56(Pt 10): 1316-1323). Mutagenesis mapping studies can be accomplished using any method known to one of skill in the art. See, e.g., Champe M et al., (1995) J Biol Chem 270: 1388-1394 and Cunningham B C & Wells J A (1989) Science 244: 1081-1085 for a description of mutagenesis techniques, including alanine scanning mutagenesis techniques.

A B7-H4 antibody that "binds to the same epitope" as a reference B7-H4 antibody refers to an antibody that binds to the same B7-H4 amino acid residues as the reference B7-H4 antibody. The ability of a B7-H4 antibody to bind to the same epitope as a reference B7-4 antibody is determined by a hydrogen/deuterium exchange assay (see Coales et al. Rapid Commun. Mass Spectrom. 2009; 23: 639-647).

As used herein, the terms "immunospecifically binds," "immunospecifically recognizes," "specifically binds," and "specifically recognizes" are analogous terms in the context of antibodies or antigen-binding fragments thereof. These terms indicate that the antibody or antigen-binding fragment thereof binds to an epitope via its antigen-binding domain and that the binding entails some complementarity between the antigen binding domain and the epitope. Accordingly, an antibody that "specifically binds" to human B7-H4 (SEQ ID NO:1) may also bind to B7-H4 from other species (e.g., cynomolgous monkey, mouse, and/or rat B7-H4) and/or B7-H4 proteins produced from other human alleles, but the extent of binding to an un-related, non-B7-H4 protein (e.g., other B7 protein family members such as PD-L1) is less than about 10% of the binding of the antibody to B7-H4 as measured, e.g., by a radioimmunoassay (RIA).

In a specific embodiment, provided herein is an antibody or antigen-binding fragment thereof that binds to human, cynomolgus monkey, mouse, and rat B7-H4.

An antibody is said to "competitively inhibit" binding of a reference antibody to a given epitope if it preferentially binds to that epitope or an overlapping epitope to the extent that it blocks, to some degree, binding of the reference antibody to the epitope. Competitive inhibition may be determined by any method known in the art, for example, competition ELISA assays. An antibody may be said to competitively inhibit binding of the reference antibody to a given epitope by at least 90%, at least 80%, at least 70%, at least 60%, or at least 50%.

A polypeptide, antibody, polynucleotide, vector, cell, or composition which is "isolated" is a polypeptide, antibody, polynucleotide, vector, cell, or composition which is in a form not found in nature. Isolated polypeptides, antibodies, polynucleotides, vectors, cell or compositions include those which have been purified to a degree that they are no longer in a form in which they are found in nature. In some embodiments, an antibody, polynucleotide, vector, cell, or composition which is isolated is substantially pure. As used herein, "substantially pure" refers to material which is at least 50% pure (i.e., free from contaminants), at least 90% pure, at least 95% pure, at least 98% pure, or at least 99% pure.

The terms "polypeptide," "peptide," and "protein" are used interchangeably herein to refer to polymers of amino acids of any length. The polymer can be linear or branched, it can comprise modified amino acids, and it can be interrupted by non-amino acids. The terms also encompass an amino acid polymer that has been modified naturally or by intervention; for example, disulfide bond formation, glycosylation, lipidation, acetylation, phosphorylation, or any other manipulation or modification, such as conjugation with a labeling component. Also included within the definition are, for example, polypeptides containing one or more analogs of an amino acid (including, for example, unnatural amino acids, etc.), as well as other modifications known in the art. It is understood that, because the polypeptides of this invention are based upon antibodies, in certain embodiments, the polypeptides can occur as single chains or associated chains.

"Percent identity" refers to the extent of identity between two sequences (e.g., amino acid sequences or nucleic acid sequences). Percent identity can be determined by aligning two sequences, introducing gaps to maximize identity between the sequences. Alignments can be generated using programs known in the art. For purposes herein, alignment of nucleotide sequences can be performed with the blastn program set at default parameters, and alignment of amino acid sequences can be performed with the blastp program set at default parameters (see National Center for Biotechnology Information (NCBI) on the worldwide web, ncbi.nlm.nih.gov).

As used herein, the term "host cell" can be any type of cell, e.g., a primary cell, a cell in culture, or a cell from a cell line. In specific embodiments, the term "host cell" refers to a cell transfected with a nucleic acid molecule and the progeny or potential progeny of such a cell. Progeny of such a cell may not be identical to the parent cell transfected with the nucleic acid molecule, e.g., due to mutations or environmental influences that may occur in succeeding generations or integration of the nucleic acid molecule into the host cell genome.

The term "pharmaceutical formulation" refers to a preparation which is in such form as to permit the biological activity of the active ingredient to be effective, and which contains no additional components which are unacceptably toxic to a subject to which the formulation would be administered. The formulation can be sterile.

The terms "administer", "administering", "administration", and the like, as used herein, refer to methods that may be used to enable delivery of a drug, e.g., an anti-B7-H4 antibody or antigen-binding fragment thereof to the desired site of biological action (e.g., intravenous administration). Administration techniques that can be employed with the agents and methods described herein are found in e.g., Goodman and Gilman, The Pharmacological Basis of Therapeutics, current edition, Pergamon; and Remington's, Pharmaceutical Sciences, current edition, Mack Publishing Co., Easton, Pa.

Administration "in combination with" one or more further therapeutic agents includes simultaneous (concurrent) or consecutive administration in any order.

The combination therapy can provide "synergy," i.e., the effect achieved when the active agents used together is greater than the sum of the effects that result from using the active agents separately. A synergistic effect can be attained when the active agents are: (1) co-formulated and administered or delivered simultaneously in a combined, unit dosage formulation; (2) delivered serially, by alternation, or in parallel as separate formulations; or (3) by some other regimen. When delivered in alternation therapy, a synergistic effect can be attained when the active agents are administered or delivered sequentially, e.g., by different injections in separate syringes. A "synergistic combination" produces an effect that is greater than the sum of the effects of the individual active agents of the combination.

The combination therapy can provide an "additive" effect, i.e., the effect achieved when the active agents used together is equal to the sum of the effects the result from using the active agents separately.

As used herein, the terms "subject" and "patient" are used interchangeably. The subject can be an animal. In some embodiments, the subject is a mammal such as a non-human animal (e.g., cow, pig, horse, cat, dog, rat, mouse, monkey or other primate, etc.). In some embodiments, the subject is a cynomolgus monkey. In some embodiments, the subject is a human.

The term "therapeutically effective amount" refers to an amount of a drug, e.g., an anti-B7-H4 antibody or antigen-binding fragment thereof effective to treat a disease or disorder in a subject. In the case of cancer, the therapeutically effective amount of the drug can reduce the number of cancer cells; reduce the tumor size or burden; inhibit (i.e., slow to some extent and in a certain embodiment, stop) cancer cell infiltration into peripheral organs; inhibit (i.e., slow to some extent and in a certain embodiment, stop) tumor metastasis; inhibit, to some extent, tumor growth; relieve to some extent one or more of the symptoms associated with the cancer; and/or result in a favorable response such as increased progression-free survival (PFS), disease-free survival (DFS), or overall survival (OS), complete response (CR), partial response (PR), or, in some cases, stable disease (SD), a decrease in progressive disease (PD), a reduced time to progression (TTP), or any combination thereof. To the extent the drug can prevent growth and/or kill existing cancer cells, it can be cytostatic and/or cytotoxic.

Terms such as "treating" or "treatment" or "to treat" or "alleviating" or "to alleviate" refer to therapeutic measures that cure, slow down, lessen symptoms of, and/or halt progression of a diagnosed pathologic condition or disorder. Thus, those in need of treatment include those already diagnosed with or suspected of having the disorder. In certain embodiments, a subject is successfully "treated" for cancer according to the methods of the present invention if the patient shows one or more of the following: a reduction in the number of or complete absence of cancer cells; a reduction in the tumor size; inhibition of or an absence of cancer cell infiltration into peripheral organs including, for example, the spread of cancer into soft tissue and bone; inhibition of or an absence of tumor metastasis; inhibition or an absence of tumor growth; relief of one or more symptoms associated with the specific cancer; reduced morbidity and mortality; improvement in quality of life; reduction in tumorigenicity, tumorigenic frequency, or tumorigenic capacity, of a tumor; reduction in the number or frequency of cancer stem cells in a tumor; differentiation of tumorigenic cells to a non-tumorigenic state; increased progression-free survival (PFS), disease-free survival (DFS), or overall survival (OS), complete response (CR), partial response (PR), stable disease (SD), a decrease in progressive disease (PD), a reduced time to progression (TTP), or any combination thereof.

The terms "cancer" and "cancerous" refer to or describe the physiological condition in mammals in which a population of cells are characterized by unregulated cell growth. Examples of cancer include, but are not limited to, gynecological cancers (e.g., breast cancer (including triple negative breast cancer, ductal carcinoma), ovarian cancer, and endometrial cancer), non-small cell lung cancer, pancreatic cancer, thyroid cancer, kidney cancer (e.g., renal cell carcinoma), and bladder cancer (e.g., urothelial cell carcinoma). A non-small cell lung cancer can be e.g., an adenocarcinoma. Additional examples of cancer include, e.g., head and neck cancer, small cell lung cancer, gastric cancer, melanoma, cholangiocarcinoma, glioblastoma or glioblastoma multiforme (GBM), and merkel cell carcinoma. In one embodiment, the ovarian cancer is a serous adenocarcinoma. In one embodiment, the breast cancer is a ductal adenocarcinoma. The cancer can be a "cancer that expresses B7-H4" or a "B7-H4 expressing cancer." Such terms refer to a cancer comprising cells that express B7-H4. The cancer may be a primary tumor or may be advanced or metastatic cancer.

A "refractory" cancer is one that progresses even though an anti-tumor treatment, such as a chemotherapy, is administered to the cancer patient.

A "recurrent" cancer is one that has regrown, either at the initial site or at a distant site, after a response to initial therapy.

A "relapsed" patient is one who has signs or symptoms of cancer after remission. Optionally, the patient has relapsed after adjuvant or neoadjuvant therapy.

"T cell checkpoint blockade activity" refers to blocking or inhibition of a T cell checkpoint activity or response. T cell checkpoint blockade activity can be measured in an artificial antigen presenting cells (aAPC) assay based on changes in IFNγ production. Primary human T cells can be enriched from PBMCs using a T cell enrichment kit (such as an EasySep™ Human T Cell Enrichment Kit or similar kit). Enriched T cells are incubated with beads (e.g., anti-CD3/anti-CD28 beads). After a period of time, the beads are magnetically removed, and T cells are washed and incubated. Next, T cells are washed and incubated along with artificial antigen presenting cells (aAPCs) in the presence of B7-H4 antibody dose titration. aAPCs can be treated with Mitomycin C and then thoroughly washed prior to adding to the T cell co-culture. After co-culture of T cells, aAPCs, and B7-H4 antibodies, plates can be centrifuged, and supernatants can be harvested and assessed for IFNγ production by ELISA. IFNγ production can be plotted vs. antibody concentration, and the EC50 potency can be calculated using nonlinear regression curve fit. Results can be measured as EC50+/− STD in nM. T cell checkpoint blockade activity by B7-H4 antibodies can be demonstrated by an increase in IFNγ production. "T cell checkpoint blockade activity" can also be measured in an assay using cells that endogenously express B7-H4. Primary human T cells can be enriched from HLA-A2+ donor PBMCs using a T cell isolation kit (e.g., Human Pan T Cell Isolation Kit). MART-I TCR expressing T cells can be generated by first activating enriched Pan T cells with beads (e.g., anti-CD3/anti-CD28 Dynabeads), IL-2 and IL-7 for 48 hours. Activated T cells can then be transduced with MART-I TCR lentiviral particles in the presence of IL-2, IL-7 and polybrene. After transduction, MART-I TCR+ Pan T cells can be expanded over a period of time in the presence of IL-2 and IL-7. To generate HLA-A2 expressing target cell lines, the endogenous B7-H4 expressing cancer cell lines can be transduced with HLA-A2 lentiviral particles for a period of time (e.g., 48 hours). Furthermore, B7-H4 can be knocked-out of the HLA-A2+ cell line. Then, MART-I TCR+ Pan T cells can be co-cultured in the presence of the various target cell lines at a 1:1 E:T ratio, MART-I peptide and a B7-H4 antibody or a human isotype control. After co-incubation, plates can be centrifuged, and supernatants can be harvested and assessed for IL-2 production. IL-2 production can be measured by a standard immunoassay kit (such as an AlphaLISA assay or similar assay).

As used in the present disclosure and claims, the singular forms "a," "an," and "the" include plural forms unless the context clearly dictates otherwise.

It is understood that wherever embodiments are described herein with the language "comprising," otherwise analogous embodiments described in terms of "consisting of" and/or "consisting essentially of" are also provided. In this disclosure, "comprises," "comprising," "containing" and "having" and the like can have the meaning ascribed to them in U.S. Patent law and can mean "includes," "including," and the like; "consisting essentially of" or "consists essentially" likewise has the meaning ascribed in U.S. Patent law and the term is open-ended, allowing for the presence of more than that which is recited so long as basic or novel characteristics of that which is recited is not changed by the presence of more than that which is recited, but excludes prior art embodiments Unless specifically stated or obvious from context, as used herein, the term "or" is understood to be inclusive. The term "and/or" as used in a phrase such as "A and/or B" herein is intended to include both "A and B," "A or B," "A," and "B." Likewise, the term "and/or" as used in a phrase such as "A, B, and/or C" is intended to encompass each of the following embodiments: A, B, and C; A, B, or C; A or C; A or B; B or C; A and C; A and B; B and C; A (alone); B (alone); and C (alone).

As used herein, the terms "about" and "approximately," when used to modify a numeric value or numeric range, indicate that deviations of 5% to 10% above and 5% to 10% below the value or range remain within the intended meaning of the recited value or range.

Any compositions or methods provided herein can be combined with one or more of any of the other compositions and methods provided herein.

1.2 Antibodies

In a specific aspect, provided herein are antibodies (e.g., monoclonal antibodies, such as chimeric, humanized, or human antibodies) and antigen-binding fragments thereof which specifically bind to B7-H4 (e.g., human B7-H4). The amino acid sequences for human, cynomolgus monkey, murine, and rat B7-H4 are known in the art and also provided herein as represented by SEQ ID NOs:1-4, respectively.

```
Human B7-H4:
                                           (SEQ ID NO: 1)
MASLGQILFWSIISIIIILAGAIALIIGFGISGRHSITVTTVASAGNIGE

DGILSCTFEPDIKLSDIVIQWLKEGVLGLVHEFKEGKDELSEQDEMERGR

TAVFADQVIVGNASLRLKNVQLTDAGTYKCYIITSKGKGNANLEYKTGAF

SMPEVNVDYNASSETLRCEAPRWFPQPTVVWASQVDQGANFSEVSNTSFE

LNSENVTMKVVSVLYNVTINNTYSCMIENDIAKATGDIKVTESEIKRRSH

LQLLNSKASLCVSSFFAISWALLPLSPYLMLK

Cynomolgus monkey B7-H4:
                                           (SEQ ID NO: 2)
MASLGQILFWSIISIIFILAGAIALIIGFGISGRHSITVTTVASAGNIGE

DGILSCTFEPDIKLSDIVIQWLKEGVIGLVHEFKEGKDELSEQDEMFRGR

TAVFADQVIVGNASLRLKNVQLTDAGTYKCYIITSKGKGNANLEYKTGAF

SMPEVNVDYNASSETLRCEAPRWFPQPTVVWASQVDQGANFSEVSNTSFE

LNSENVTMKVVSVLYNVTINNTYSCMIENDIAKATGDIKVTESEIKRRSH

LQLLNSKASLCVSSFLAISWALLPLAPYLMLK

Murine B7-H4
                                           (SEQ ID NO: 3)
MASLGQIIFWSIINIIIILAGAIALIIGFGISGKHFITVTTFTSAGNIGE

DGTLSCTFEPDIKLNGIVIQWLKEGIKGLVHEFKEGKDDLSQQHEMFRGR

TAVFADQVVVGNASLRLKNVQLTDAGTYTCYIRTSKGKGNANLEYKTGAF

SMPEINVDYNASSESLRCEAPRWFPQPTVAWASQVDQGANFSEVSNTSFE

LNSENVTMKVVSVLYNVTINNTYSCMIENDIAKATGDIKVTDSEVKRRSQ

LQLLNSGPSPCVFSSAFVAGWALLSLSCCLMLR

Rat B7-H4
                                           (SEQ ID NO: 4)
MASLGQIIFWSIINVIIILAGAIVLIIGFGISGKHFITVTTFTSAGNIGE

DGTLSCTFEPDIKLNGIVIQWLKEGIKGLVHEFKEGKDDLSQQHEMFRGR

TAVFADQVVVGNASLRLKNVQLTDAGTYTCYIHTSKGKGNANLEYKTGAF

SMPEINVDYNASSESLRCEAPRWFPQPTVAWASQVDQGANFSEVSNTSFE

LNSENVTMKVVSVLYNVTINNTYSCMIENDIAKATGDIKVTDSEVKRRSQ

LELLNSGPSPCVSSVSAAGWALLSLSCCLMLR
```

In certain embodiments, an antibody or antigen-binding fragment thereof described herein binds to human B7-H4. In certain embodiments, an antibody or antigen-binding fragment thereof binds to human and cynomolgus monkey B7-H4. In certain embodiments, an antibody or antigen-binding fragment thereof binds to human, murine, and rat B7-H4. In certain embodiments, an antibody or antigen-binding fragment thereof binds to human, cynomolgus monkey, murine, and rat B7-H4.

B7-H4 contains an IgC ectodomain (amino acids 153-241 of SEQ ID NO:1) and an IgV domain (amino acids 35-146 of SEQ ID NO:1).

In certain embodiments, an antibody or antigen-binding fragment thereof described herein binds to the IgV domain of human B7-H4. Accordingly, provided herein are antibodies and antigen-binding fragments thereof that bind to a polypeptide consisting of amino acids 35-146 of SEQ ID NO:1.

In certain embodiments, an antibody or antigen-binding fragment thereof described herein binds to human B7-H4 and comprises the six CDRs of an antibody listed in Tables 1 and 2 (i.e., the three VH CDRs of the antibody listed in Table 1 and the three VL CDRs of the same antibody listed in Table 2).

TABLE 1

VH CDR Amino Acid Sequences[1]

| Antibody | VH CDR1 (SEQ ID NO:) | VH CDR2 (SEQ ID NO:) | VH CDR3 (SEQ ID NO:) |
|---|---|---|---|
| 15461 | GSISSSSYYWG (SEQ ID NO: 5) | NIYYSGSTYYNPSLKS (SEQ ID NO: 6) | AREGSYPNWFDP (SEQ ID NO: 7) |
| 20500 | GSIKSGSHYWG (SEQ ID NO: 15) | NIYYSGSTYYNPSLRS (SEQ ID NO: 16) | AREGSYPNWFDP (SEQ ID NO: 17) |
| 20501 | GSIKSGSHYWG (SEQ ID NO: 25) | NIYYSGSTYYNPSLKS (SEQ ID NO: 26) | AREGSYPNWLDP (SEQ ID NO: 27) |
| 20502 | GSIKSGSYYWG (SEQ ID NO: 458) | NIYYSGSTYYNPSLRS (SEQ ID NO: 459) | AREGSYPNQFDP (SEQ ID NO: 460) |

TABLE 1-continued

VH CDR Amino Acid Sequences[1]

| Antibody | VH CDR1 (SEQ ID NO:) | VH CDR2 (SEQ ID NO:) | VH CDR3 (SEQ ID NO:) |
|---|---|---|---|
| 20502.1 | GSIKSGSYYWG (SEQ ID NO: 35) | NIYYSGSTYYNPSLKS (SEQ ID NO: 36) | AREGSYPNQFDP (SEQ ID NO: 37) |
| 22208 | GSIKSGSHYWG (SEQ ID NO: 45) | NIYYSGSTYYNPSLKS (SEQ ID NO: 46) | AREGSYPNWFDP (SEQ ID NO: 47) |
| 15462 | GSISSSSYYWG (SEQ ID NO: 55) | NIYYSGSTYYNPSLKS (SEQ ID NO: 56) | AREGSYTTVLNV (SEQ ID NO: 57) |
| 22213 | GSIGRGSYYWG (SEQ ID NO: 65) | NIYYSGSTYYNPSLKS (SEQ ID NO: 66) | AREGSYTTVLNV (SEQ ID NO: 67) |
| 15465 | GSISSGGYYWS (SEQ ID NO: 75) | NIYYSGSTYYNPSLKS (SEQ ID NO: 76) | ARESSTISADFDL (SEQ ID NO: 77) |
| 20506 | GSISHGGYYWS (SEQ ID NO: 85) | NIYYSGSTYYNPSLKS (SEQ ID NO: 86) | ARESSTISADFDL (SEQ ID NO: 87) |
| 15483 | GSISSGGYYWS (SEQ ID NO: 95) | NIYYSGSTYYNPSLKS (SEQ ID NO: 96) | ARGLSTIDEAFDP (SEQ ID NO: 97) |
| 20513 | GSISDGSYYWS (SEQ ID NO: 105) | NIYYSGSTYYNPSLRS (SEQ ID NO: 106) | ARGLSTIDEAFDP (SEQ ID NO: 107) |
| 22216 | GSISDGSYYWS (SEQ ID NO: 115) | NIYYSGSTYYNPSLRS (SEQ ID NO: 116) | ARGLSTIDEAFDP (SEQ ID NO: 117) |
| 15489 | GSISSYYWS (SEQ ID NO: 125) | YIYSSGSTNYNPSLKS (SEQ ID NO: 126) | ARGSGQYAAPDYGMDV (SEQ ID NO: 127) |
| 20516 | GSIISYYWG (SEQ ID NO: 135) | YIYSSGSTSYNPSLKS (SEQ ID NO: 136) | ARGSGLYAAPDYGLDV (SEQ ID NO: 137) |
| 15472 | FTFSSYAMS (SEQ ID NO: 145) | TISGSGGSTYYADSVKG (SEQ ID NO: 146) | ARGAGHYDLVGRY (SEQ ID NO: 147) |
| 15503 | FTFSSYAMS (SEQ ID NO: 155) | AISGSGGSTYYADSVKG (SEQ ID NO: 156) | ARVGFRALNY (SEQ ID NO: 157) |
| 15495 | GTFSSYAIS (SEQ ID NO: 165) | GIIPIFGTASYAQKFQG (SEQ ID NO: 166) | ARQQYDGRRYFGL (SEQ ID NO: 167) |
| 15478 | GTFSSYAIS (SEQ ID NO: 175) | GIIPIFGTANYAQKFQG (SEQ ID NO: 176) | ARGGPWFDP (SEQ ID NO: 177) |
| 15441 | FTFSSYAMS (SEQ ID NO: 185) | AISGSGGSTSYADSVKG (SEQ ID NO: 186) | AKPSLATMLAFDI (SEQ ID NO: 187) |
| 20496 | GSISSSVYYWS (SEQ ID NO: 195) | SILVSGSTYYNPSLKS (SEQ ID NO: 196) | ARAVSFLDV (SEQ ID NO: 197) |

[1]The VH CDRs in Table 1 are determined according to Kabat.

TABLE 2

VL CDR Amino Acid Sequences[2]

| Antibody | VL CDR1 (SEQ ID NO:) | VL CDR2 (SEQ ID NO:) | VL CDR3 (SEQ ID NO:) |
|---|---|---|---|
| 15461 | RASQSVSSNLA (SEQ ID NO: 8) | GASTRAT (SEQ ID NO: 9) | QQYHSFPFT (SEQ ID NO: 10) |
| 20500 | RASQSVSSNLA (SEQ ID NO: 18) | GASTRAT (SEQ ID NO: 19) | QQYHSFPFT (SEQ ID NO: 20) |
| 20501 | RASQSVSSNLA (SEQ ID NO: 28) | GASTRAT (SEQ ID NO: 29) | QQYHSFPFT (SEQ ID NO: 30) |
| 20502 | RASQSVSSNLA (SEQ ID NO: 461) | GASTRAT (SEQ ID NO: 462) | QQYHSFPFT (SEQ ID NO: 463) |

TABLE 2-continued

VL CDR Amino Acid Sequences[2]

| Antibody | VL CDR1 (SEQ ID NO:) | VL CDR2 (SEQ ID NO:) | VL CDR3 (SEQ ID NO:) |
|---|---|---|---|
| 20502.1 | RASQSVSSNLA (SEQ ID NO: 38) | GASTRAT (SEQ ID NO: 39) | QQYHSFPFT (SEQ ID NO: 40) |
| 22208 | RASQSVSTNLA (SEQ ID NO: 48) | DASARVT (SEQ ID NO: 49) | QQYHSFPFT (SEQ ID NO: 50) |
| 15462 | RASQSVSSSYLA (SEQ ID NO: 58) | GASSRAT (SEQ ID NO: 59) | QQAASYPLT (SEQ ID NO: 60) |
| 22213 | RASQSVASSHLA (SEQ ID NO: 68) | DAVSRAT (SEQ ID NO: 69) | QQAASYPLT (SEQ ID NO: 70) |
| 15465 | RASQGISRWLA (SEQ ID NO: 78) | AASSLQS (SEQ ID NO: 79) | QQAHTFPYT (SEQ ID NO: 80) |
| 20506 | RASQGISRWLA (SEQ ID NO: 88) | AASSLQS (SEQ ID NO: 89) | QQAHTFPYT (SEQ ID NO: 90) |
| 15483 | RASQSISSWLA (SEQ ID NO: 98) | KASSLES (SEQ ID NO: 99) | QQDNSYPYT (SEQ ID NO: 100) |
| 20513 | RASQSISSWLA (SEQ ID NO: 108) | KASSLES (SEQ ID NO: 109) | QQDNSYPYT (SEQ ID NO: 110) |
| 22216 | RASKSISSWLA (SEQ ID NO: 118) | EASSLHS (SEQ ID NO: 119) | QQDNSYPYT (SEQ ID NO: 120) |
| 15489 | RASQSISSWLA (SEQ ID NO: 128) | KASSLES (SEQ ID NO: 129) | QQDNSFPFT (SEQ ID NO: 130) |
| 20516 | RASQSISSWLA (SEQ ID NO: 138) | KASSLES (SEQ ID NO: 139) | QQDNSFPFT (SEQ ID NO: 140) |
| 15472 | RASQSISSYLN (SEQ ID NO: 148) | AASSLQS (SEQ ID NO: 149) | QQLYSLPPT (SEQ ID NO: 150) |
| 15503 | RASQDISSWLA (SEQ ID NO: 158) | AASSLQS (SEQ ID NO: 159) | QQATSYPPWT (SEQ ID NO: 160) |
| 15495 | RASQSVSSNLA (SEQ ID NO: 168) | SASTRAT (SEQ ID NO: 169) | QQVNVWPPT (SEQ ID NO: 170) |
| 15478 | RASQSISSWLA (SEQ ID NO: 178) | KASSLES (SEQ ID NO: 179) | QQYNSYPPFT (SEQ ID NO: 180) |
| 15441 | RASQSISSWLA (SEQ ID NO: 188) | DASSLES (SEQ ID NO: 189) | QQSKSYPRT (SEQ ID NO: 190) |
| 20496 | RASQSISSYLN (SEQ ID NO: 198) | GASSLQS (SEQ ID NO: 199) | QQSYDPPWT (SEQ ID NO: 200) |

[2]The VL CDRs in Table 2 are determined according to Kabat.

In certain embodiments, an antibody or antigen-binding fragment thereof described herein binds to human B7-H4 and comprises the VH of an antibody listed in Table 3.

TABLE 3

Variable Heavy Chain (VH) Amino Acid Sequences

| Antibody | VH Amino Acid Sequence (SEQ ID NO) |
|---|---|
| 15461 | QLQLQESGPGLVKPSETLSLTCTVSGGSISSSSYYWGWIRQPPGKGLE WIGNIYYSGSTYYNPSLKSRVTISVDTSKNQFSLKLSSVTAADTAVYY CAREGSYPNWFDPWGQGTLVTVSS (SEQ ID NO: 11) |
| 20500 | QLQLQESGPGLVKPSETLSLTCTVSGGSIKSGSHYWGWIRQPPGKGLE WIGNIYYSGSTYYNPSLRSRVTISVDTSKNQFSLKLSSVTAADTAVYY CAREGSYPNWFDPWGQGTLVTVSS (SEQ ID NO: 21) |

TABLE 3-continued

Variable Heavy Chain (VH) Amino Acid Sequences

| Antibody | VH Amino Acid Sequence (SEQ ID NO) |
|---|---|
| 20501 | QLQLQESGPGLVKPSETLSLTCTVSGGSIKSGSHYWGWIRQPPGKGLE WIGNIYYSGSTYYNPSLKSRVTISVDTSKNQFSLKLSSVTAADTAVYY CAREGSYPNWLDPWGQGTLVTVSS (SEQ ID NO: 31) |
| 20502 | QLQLQESGPGLVKPSETLSLTCTVSGGSIKSGSYYWGWIRQPPGKGLE WIGNIYYSGSTYYNPSLRSRVTISVDTSKNQFSLKLSSVTAADTAVYY CAREGSYPNQFDPWGQGTLVTVSS (SEQ ID NO: 464) |
| 20502.1 | QLQLQESGPGLVKPSETLSLTCTVSGGSIKSGSYYWGWIRQPPGKGLE WIGNIYYSGSTYYNPSLKSRVTISVDTSKNQFSLKLSSVTAADTAVYY CAREGSYPNQFDPWGQGILVTVSS (SEQ ID NO: 41) |
| 22208 | QLQLQESGPGLVKPSETLSLTCTVSGGSIKSGSHYWGWIRQPPGKGLE WIGNIYYSGSTYYNPSLKSRVTMSVDTSKNQFSLKLSSVTAADTAVY YCAREGSYPNWFDPWGQGTLVTVSS (SEQ ID NO: 51) |
| 15462 | QLQLQESGPGLVKPSETLSLTCTVSGGSISSSSYYWGWIRQPPGKGLE WIGNIYYSGSTYYNPSLKSRVTISVDTSKNQFSLKLSSVTAADTAVYY CAREGSYTTVLNVWGQGTMVTVSS (SEQ ID NO: 61) |
| 22213 | QLQLQESGPGLVKPSETLSLTCTVSGGSIGRGSYYWGWIRQPPGKGLE WIGNIYYSGSTYYNPSLKSRVTISVDTSKNQFSLKLSSVTAADTAVYY CAREGSYTTVLNVWGQGTMVTVSS (SEQ ID NO: 71) |
| 15465 | QVQLQESGPGLVKPSQTLSLTCTVSGGSISSGGYYWSWIRQHPGKGL EWIGNIYYSGSTYYNPSLKSRVTISVDTSKNQFSLKLSSVTAADTAVY YCARESSTISADFDLWGRGTLVTVSS (SEQ ID NO: 81) |
| 20506 | QLQLQESGPGLVKPSETLSLTCTASGGSISHGGYYWSWIRQHPGKGL EWIGNIYYSGSTYYNPSLKSRVTMSVDTSKNQFSLKLSSVTAADTAV YYCARESSTISADFDLWGRGTLVTVSS (SEQ ID NO: 91) |
| 15483 | QVQLQESGPGLVKPSQTLSLTCTVSGGSISSGGYYWSWIRQHPGKGL EWIGNIYYSGSTYYNPSLKSRVTISVDTSKNQFSLKLSSVTAADTAVY YCARGLSTIDEAFDPWGQGTLVTVSS (SEQ ID NO: 101) |
| 20513 | QLQLQESGPGLVKPSETLSLTCTVSGGSISDGSYYWSWIRQHPGKGLE WIGNIYYSGSTYYNPSLRSRVTMSVDTSKNQFSLKLSSVTAADTAVY YCARGLSTIDEAFDPWGQGTLVTVSS (SEQ ID NO: 111) |
| 22216 | QVQLQESGPGLVKPSQTLSLTCTVSGGSISDGSYYWSWIRQHPGKGL EWIGNIYYSGSTYYNPSLRSRVTMSVDTSKNQFSLKLSSVTAADTAV YYCARGLSTIDEAFDPWGQGTLVTVSS (SEQ ID NO: 121) |
| 15489 | QVQLQESGPGLVKPSETLSLTCTVSGGSISSYYWSWIRQPPGKGLEWI GYIYSSGSTNYNPSLKSRVTISVDTSKNQFSLKLSSVTAADTAVYYCA RGSGQYAAPDYGMDVWGQGTTVTVSS (SEQ ID NO: 131) |
| 20516 | QVQLQESGPGLVKPSETLSLTCTVSGGSIISYYWGWIRQPPGKGLEWI GYIYSSGSTSYNPSLKSRVTISVDTSKNQFSLKLSSVTAADTAVYYCA RGSGLYAAPDYGLDVWGQGTTVTVSS (SEQ ID NO: 141) |
| 15472 | EVQLLESGGGLVQPGGSLRLSCAASGFTFSSYAMSWVRQAPGKGLE WVSTISGSGGSTYYADSVKGRFTISRDNSKNTLYLQMNSLRAEDTAV YYCARGAGHYDLVGRYWGQGTLVTVSS (SEQ ID NO: 151) |
| 15503 | EVQLLESGGGLVQPGGSLRLSCAASGFTFSSYAMSWVRQAPGKGLE WVSAISGSGGSTYYADSVKGRFTISRDNSKNTLYLQMNSLRAEDTAV YYCARVGFRALNYWGQGTTVTVSS (SEQ ID NO: 161) |
| 15495 | QVQLVQSGAEVKKPGSSVKVSCKASGGTFSSYAISWVRQAPGQGLE WMGGIIPIFGTASYAQKFQGRVTITADESTSTAYMELSSLRSEDTAVY YCARQQYDGRRYFGLWGRGTLVTVSS (SEQ ID NO: 171) |
| 15478 | QVQLVQSGAEVKKPGSSVKVSCKASGGTFSSYAISWVRQAPGQGLE WMGGIIPIFGTANYAQKFQGRVTITADESTSTAYMELSSLRSEDTAVY YCARGGPWFDPWGQGTLVTVSS (SEQ ID NO: 181) |
| 15441 | EVQLLESGGGLVQPGGSLRLSCAASGFTFSSYAMSWVRQAPGKGLE WVSAISGSGGSTSYADSVKGRFTISRDNSKNTLYLQMNSLRAEDTAV YYCAKPSLATMLAFDIWGQGTMVTVSS (SEQ ID NO: 191) |
| 20496 | QLQLQESGPGLVKPSETLSLTCTVSGGSISSSVYYWSWIRQPPGKGLE WIGSILVSGSTYYNPSLKSRVTISVDTSKNQFSLKLSSVTAADTAVYY CARAVSFLDVWGQGTMVIVSS (SEQ ID NO: 201) |

In certain embodiments, an antibody or antigen-binding fragment thereof described herein binds to human B7-H4 and comprises the VL of an antibody listed in Table 4.

TABLE 4

Variable Light Chain (VL) Amino Acid Sequences

| Antibody | VL Amino Acid Sequence (SEQ ID NO) |
|---|---|
| 15461 | EIVMTQSPATLSVSPGERATLSCRASQSVSSNLAWYQQKPGQAPRLLI YGASTRATGIPARFSGSGSGTEFTLTISSLQSEDFAVYYCQQYHSFPFT FGGGTKVEIK (SEQ ID NO: 12) |
| 20500 | EIVMTQSPATLSVSPGERATLSCRASQSVSSNLAWYQQKPGQAPRLLI YGASTRATGIPARFSGSGSGTEFTLTISSLQSEDFAVYYCQQYHSFPFT FGGGTKVEIK (SEQ ID NO: 22) |
| 20501 | EIVMTQSPATLSVSPGERATLSCRASQSVSSNLAWYQQKPGQAPRLLI YGASTRATGIPARFSGSGSGTEFTLTISSLQSEDFAVYYCQQYHSFPFT FGGGTKVEIK (SEQ ID NO: 32) |
| 20502 and 20502.1 | EIVMTQSPATLSVSPGERATLSCRASQSVSSNLAWYQQKPGQAPRLLI YGASTRATGIPARFSGSGSGTEFTLTISSLQSEDFAVYYCQQYHSFPFT FGGGTKVEIK (SEQ ID NO: 42) |
| 22208 | EIVMTQSPATLSVSPGERATLSCRASQSVSTNLAWYQQKPGQAPRLLI YDASARVTGIPARFSGSGSGTEFTLTISSLQSEDFAVYYCQQYHSFPFT FGGGTKVEIK (SEQ ID NO: 52) |
| 15462 | EIVLTQSPGTLSLSPGERATLSCRASQSVSSSYLAWYQQKPGQAPRLLI YGASSRATGIPDRFSGSGSGTDFTLTISRLEPEDFAVYYCQQAASYPLT FGGGTKVEIK (SEQ ID NO: 62) |
| 22213 | EIVLTQSPGTLSLSPGERATLSCRASQSVASSHLAWYQQKPGQAPRLL IYDAVSRATGIPDRFSGSGSGTDFTLTISRLEPEDFAVYYCQQAASYPL TFGGGTKVEIK (SEQ ID NO: 72) |
| 15465 | DIQMTQSPSSVSASVGDRVTITCRASQGISRWLAWYQQKPGKAPKLLI YAASSLQSGVPSRFSGSGSGTDFTLTISSLQPEDFATYYCQQAHTFPYT FGGGTKVEIK (SEQ ID NO: 82) |
| 20506 | DIQMTQSPSSVSASVGDRVTITCRASQGISRWLAWYQQKPGKAPKLLI YAASSLQSGVPSRFSGSGSGTDFTLTISSLQPEDFATYYCQQAHTFPYT FGGGTKVEIK (SEQ ID NO: 92) |
| 15483 | DIQMTQSPSTLSASVGDRVTITCRASQSISSWLAWYQQKPGKAPKLLI YKASSLESGVPSRFSGSGSGTEFTLTISSLQPDDFATYYCQQDNSYPYT FGGGTKVEIK (SEQ ID NO: 102) |
| 20513 | DIQMTQSPSTLSASVGDRVTITCRASQSISSWLAWYQQKPGKAPKLLI YKASSLESGVPSRFSGSGSGTEFTLTISSLQPDDFATYYCQQDNSYPYT FGGGTKVEIK (SEQ ID NO: 112) |
| 22216 | DIQMTQSPSTLSASVGDRVTITCRASKSISSWLAWYQQKPGKAPKLLI YEASSLHSGVPSRFSGSGSGTEFTLTISSLQPDDFATYYCQQDNSYPYT FGGGTKVEIK (SEQ ID NO: 122) |
| 15489 | DIQMTQSPSTLSASVGDRVTITCRASQSISSWLAWYQQKPGKAPKLLI YKASSLESGVPSRFSGSGSGTEFTLTISSLQPDDFATYYCQQDNSFPFT FGGGTKVEIK (SEQ ID NO: 132) |
| 20516 | DIQMTQSPSTLSASVGDRVTITCRASQSISSWLAWYQQKPGKAPKLLI YKASSLESGVPSRFSGSGSGTEFTLTISSLQPDDFATYYCQQDNSFPFT FGGGTKVEIK (SEQ ID NO: 142) |
| 15472 | DIQMTQSPSSLSASVGDRVTITCRASQSISSYLNWYQQKPGKAPKLLI YAASSLQSGVPSRFSGSGSGTDFTLTISSLQPEDFATYYCQQLYSLPPT FGGGTKVEIK (SEQ ID NO: 152) |
| 15503 | DIQLTQSPSSVSASVGDRVTITCRASQDISSWLAWYQQKPGKAPKLLI YAASSLQSGVPSRFSGSGSGTDFTLTISSLQPEDFATYYCQQATSYPP WTFGGGTKVEIK (SEQ ID NO: 162) |
| 15495 | EIVMTQSPATLSVSPGERATLSCRASQSVSSNLAWYQQKPGQAPRLLI YSASTRATGIPARFSGSGSGTEFTLTISSLQSEDFAVYYCQQVNVWPP TFGGGTKVEIK (SEQ ID NO: 172) |
| 15478 | DIQMTQSPSTLSASVGDRVTITCRASQSISSWLAWYQQKPGKAPKLLI YKASSLESGVPSRFSGSGSGTEFTLTISSLQPDDFATYYCQQYNSYPPF TFGGGTKVEIK (SEQ ID NO: 182) |

TABLE 4-continued

Variable Light Chain (VL) Amino Acid Sequences

| Antibody | VL Amino Acid Sequence (SEQ ID NO) |
|---|---|
| 15441 | DIQMTQSPSTLSASVGDRVTITCRASQSISSWLAWYQQKPGKAPKLLI YDASSLESGVPSRFSGSGSGTEFTLTISSLQPDDFATYYCQQSKSYPRT FGGGTKVEIK (SEQ ID NO: 192) |
| 20496 | DIQMTQSPSSLSASVGDRVTITCRASQSISSYLNWYQQKPGKAPKLLI YGASSLQSGVPSRFSGSGSGTDFTLTISSLQPEDFATYYCQQSYDPPW TFGGGTKVEIK (SEQ ID NO: 202) |

In certain embodiments, an antibody or antigen-binding fragment thereof described herein binds to human B7-H4 and comprises the VH and the VL of an antibody listed in Tables 3 and 4 (i.e., the VH of the antibody listed in Table 3 and the VL of the same antibody listed in Table 4).

In certain embodiments, an antibody or antigen-binding fragment thereof described herein binds to human B7-H4 and comprises the VH framework regions of an antibody listed in Table 5.

TABLE 5

VH FR Amino Acid Sequences[4]

| Antibody | VH FR1 (SEQ ID NO:) | VH FR2 (SEQ ID NO:) | VH FR3 (SEQ ID NO:) | VH FR4 (SEQ ID NO:) |
|---|---|---|---|---|
| 15461 | QLQLQESGPGLVK PSETLSLTCTVSG (SEQ ID NO: 205) | WIRQPPGKGLE WIG (SEQ ID NO: 206) | RVTISVDTSKNQFSL KLSSVTAADTAVYY C (SEQ ID NO: 207) | WGQGTLVT VSS (SEQ ID NO: 208) |
| 20500 | QLQLQESGPGLVK PSETLSLTCTVSG (SEQ ID NO: 215) | WIRQPPGKGLE WIG (SEQ ID NO: 216) | RVTISVDTSKNQFSL KLSSVTAADTAVYY C (SEQ ID NO: 217) | WGQGTLVT VSS (SEQ ID NO: 218) |
| 20501 | QLQLQESGPGLVK PSETLSLTCTVSG (SEQ ID NO: 225) | WIRQPPGKGLE WIG (SEQ ID NO: 226) | RVTISVDTSKNQFSL KLSSVTAADTAVYY C (SEQ ID NO: 227) | WGQGTLVT VSS (SEQ ID NO: 228) |
| 20502 | QLQLQESGPGLVK PSETLSLTCTVSG (SEQ ID NO: 465) | WIRQPPGKGLE WIG (SEQ ID NO: 466) | RVTISVDTSKNQFSL KLSSVTAADTAVYY C (SEQ ID NO: 467) | WGQGTLVT VSS (SEQ ID NO: 468) |
| 20502.1 | QLQLQESGPGLVK PSETLSLTCTVSG (SEQ ID NO: 235) | WIRQPPGKGLE WIG (SEQ ID NO: 236) | RVTISVDTSKNQFSL KLSSVTAADTAVYY C (SEQ ID NO: 237) | WGQGILVTV SS (SEQ ID NO: 238) |
| 22208 | QLQLQESGPGLVK PSETLSLTCTVSG (SEQ ID NO: 245) | WIRQPPGKGLE WIG (SEQ ID NO: 246) | RVTMSVDTSKNQFS LKLSSVTAADTAVY YC (SEQ ID NO: 247) | WGQGTLVT VSS (SEQ ID NO: 248) |
| 15462 | QLQLQESGPGLVK PSETLSLTCTVSG (SEQ ID NO: 255) | WIRQPPGKGLE WIG (SEQ ID NO: 256) | RVTISVDTSKNQFSL KLSSVTAADTAVYY C (SEQ ID NO: 257) | WGQGTMVT VSS (SEQ ID NO: 258) |
| 22213 | QLQLQESGPGLVK PSETLSLTCTVSG (SEQ ID NO: 265) | WIRQPPGKGLE WIG (SEQ ID NO: 266) | RVTISVDTSKNQFSL KLSSVTAADTAVYY C (SEQ ID NO: 267) | WGQGTMVT VSS (SEQ ID NO: 268) |
| 15465 | QVQLQESGPGLVK PSQTLSLTCTVSG (SEQ ID NO: 275) | WIRQHPGKGLE WIG (SEQ ID NO: 276) | RVTISVDTSKNQFSL KLSSVTAADTAVYY C (SEQ ID NO: 277) | WGRGTLVT VSS (SEQ ID NO: 278) |
| 20506 | QLQLQESGPGLVK PSETLSLTCTASG (SEQ ID NO: 285) | WIRQHPGKGLE WIG (SEQ ID NO: 286) | RVTMSVDTSKNQFS LKLSSVTAADTAVY YC (SEQ ID NO: 287) | WGRGTLVT VSS (SEQ ID NO: 288) |
| 15483 | QVQLQESGPGLVK PSQTLSLTCTVSG (SEQ ID NO: 295) | WIRQHPGKGLE WIG (SEQ ID NO: 296) | RVTISVDTSKNQFSL KLSSVTAADTAVYY C (SEQ ID NO: 297) | WGQGTLVT VSS (SEQ ID NO: 298) |
| 20513 | QLQLQESGPGLVK PSETLSLTCTVSG (SEQ ID NO: 305) | WIRQHPGKGLE WIG (SEQ ID NO: 306) | RVTMSVDTSKNQFS LKLSSVTAADTAVY YC (SEQ ID NO: 307) | WGQGTLVT VSS (SEQ ID NO: 308) |
| 22216 | QVQLQESGPGLVK PSQTLSLTCTVSG (SEQ ID NO: 315) | WIRQHPGKGLE WIG (SEQ ID NO: 316) | RVTMSVDTSKNQFS LKLSSVTAADTAVY YC (SEQ ID NO: 317) | WGQGTLVT VSS (SEQ ID NO: 318) |

TABLE 5-continued

VH FR Amino Acid Sequences[4]

| Antibody | VH FR1 (SEQ ID NO:) | VH FR2 (SEQ ID NO:) | VH FR3 (SEQ ID NO:) | VH FR4 (SEQ ID NO:) |
|---|---|---|---|---|
| 15489 | QVQLQESGPGLVKPSETLSLTCTVSG (SEQ ID NO: 325) | WIRQPPGKGLEWIG (SEQ ID NO: 326) | RVTISVDTSKNQFSLKLSSVTAADTAVYYC (SEQ ID NO: 327) | WGQGTTVTVSS (SEQ ID NO: 328) |
| 20516 | QVQLQESGPGLVKPSETLSLTCTVSG (SEQ ID NO: 335) | WIRQPPGKGLEWIG (SEQ ID NO: 336) | RVTISVDTSKNQFSLKLSSVTAADTAVYYC (SEQ ID NO: 337) | WGQGTTVTVSS (SEQ ID NO: 338) |
| 15472 | EVQLLESGGGLVQPGGSLRLSCAASG (SEQ ID NO: 345) | WVRQAPGKGLEWVS (SEQ ID NO: 346) | RFTISRDNSKNTLYLQMNSLRAEDTAVYYC (SEQ ID NO: 347) | WGQGTLVTVSS (SEQ ID NO: 348) |
| 15503 | EVQLLESGGGLVQPGGSLRLSCAASG (SEQ ID NO: 355) | WVRQAPGKGLEWVS (SEQ ID NO: 356) | RFTISRDNSKNTLYLQMNSLRAEDTAVYYC (SEQ ID NO: 357) | WGQGTTVTVSS (SEQ ID NO: 358) |
| 15495 | QVQLVQSGAEVKKPGSSVKVSCKASG (SEQ ID NO: 365) | WVRQAPGQGLEWMG (SEQ ID NO: 366) | RVTITADESTSTAYMELSSLRSEDTAVYYC (SEQ ID NO: 367) | WGRGTLVTVSS (SEQ ID NO: 368) |
| 15478 | QVQLVQSGAEVKKPGSSVKVSCKASG (SEQ ID NO: 375) | WVRQAPGQGLEWMG (SEQ ID NO: 376) | RVTITADESTSTAYMELSSLRSEDTAVYYC (SEQ ID NO: 377) | WGQGTLVTVSS (SEQ ID NO: 378) |
| 15441 | EVQLLESGGGLVQPGGSLRLSCAASG (SEQ ID NO: 385) | WVRQAPGKGLEWVS (SEQ ID NO: 386) | RFTISRDNSKNTLYLQMNSLRAEDTAVYYC (SEQ ID NO: 387) | WGQGTMVTVSS (SEQ ID NO: 388) |
| 20496 | QLQLQESGPGLVKPSETLSLTCTVSG (SEQ ID NO: 395) | WIRQPPGKGLEWIG (SEQ ID NO: 396) | RVTISVDTSKNQFSLKLSSVTAADTAVYYC (SEQ ID NO: 397) | WGQGTMVIVSS (SEQ ID NO: 398) |

[4]The VH framework regions described in Table 5 are determined based upon the boundaries of the Kabat numbering system for CDRs. In other words, the VH CDRs are determined by Kabat and the framework regions are the amino acid residues surrounding the CDRs in the variable region in the format FR1, CDR1, FR2, CDR2, FR3, CDR3, and FR4.

In certain embodiments, an antibody or antigen-binding fragment thereof described herein binds to human B7-H4 and comprises the VL framework regions of an antibody listed in Table 6.

TABLE 6

VL FR Amino Acid Sequences[3]

| Antibody | VL FR1 (SEQ ID NO:) | VL FR2 (SEQ ID NO:) | VL FR3 (SEQ ID NO:) | VL FR4 (SEQ ID NO:) |
|---|---|---|---|---|
| 15461 | EIVMTQSPATLSVSPGERATLSC (SEQ ID NO: 209) | WYQQKPGQAPRLLIY (SEQ ID NO: 210) | GIPARFSGSGSGTEFTLTISSLQSEDFAVYYC (SEQ ID NO: 211) | FGGGTKVEIK (SEQ ID NO: 212) |
| 20500 | EIVMTQSPATLSVSPGERATLSC (SEQ ID NO: 219) | WYQQKPGQAPRLLIY (SEQ ID NO: 220) | GIPARFSGSGSGTEFTLTISSLQSEDFAVYYC (SEQ ID NO: 221) | FGGGTKVEIK (SEQ ID NO: 222) |
| 20501 | EIVMTQSPATLSVSPGERATLSC (SEQ ID NO: 229) | WYQQKPGQAPRLLIY (SEQ ID NO: 230) | GIPARFSGSGSGTEFTLTISSLQSEDFAVYYC (SEQ ID NO: 231) | FGGGTKVEIK (SEQ ID NO: 232) |
| 20502 and 20502.1 | EIVMTQSPATLSVSPGERATLSC (SEQ ID NO: 239) | WYQQKPGQAPRLLIY (SEQ ID NO: 240) | GIPARFSGSGSGTEFTLTISSLQSEDFAVYYC (SEQ ID NO: 241) | FGGGTKVEIK (SEQ ID NO: 242) |
| 22208 | EIVMTQSPATLSVSPGERATLSC (SEQ ID NO: 249) | WYQQKPGQAPRLLIY (SEQ ID NO: 250) | GIPARFSGSGSGTEFTLTISSLQSEDFAVYYC (SEQ ID NO: 251) | FGGGTKVEIK (SEQ ID NO: 252) |

TABLE 6-continued

VL FR Amino Acid Sequences[3]

| Anti-body | VL FR1 (SEQ ID NO:) | VL FR2 (SEQ ID NO:) | VL FR3 (SEQ ID NO:) | VL FR4 (SEQ ID NO:) |
|---|---|---|---|---|
| 15462 | EIVLTQSPGTLSLSPGERATLSC (SEQ ID NO: 259) | WYQQKPGQAPRLLIY (SEQ ID NO: 260) | GIPDRFSGSGSGTDFTLTISRLEPEDFAVYYC (SEQ ID NO: 261) | FGGGTKVEIK (SEQ ID NO: 262) |
| 22213 | EIVLTQSPGTLSLSPGERATLSC (SEQ ID NO: 269) | WYQQKPGQAPRLLIY (SEQ ID NO: 270) | GIPDRFSGSGSGTDFTLTISRLEPEDFAVYYC (SEQ ID NO: 271) | FGGGTKVEIK (SEQ ID NO: 272) |
| 15465 | DIQMTQSPSSVSASVGDRVTITC (SEQ ID NO: 279) | WYQQKPGKAPKLLIY (SEQ ID NO: 280) | GVPSRFSGSGSGTDFTLTISSLQPEDFATYYC (SEQ ID NO: 281) | FGGGTKVEIK (SEQ ID NO: 282) |
| 20506 | DIQMTQSPSSVSASVGDRVTITC (SEQ ID NO: 289) | WYQQKPGKAPKLLIY (SEQ ID NO: 290) | GVPSRFSGSGSGTDFTLTISSLQPEDFATYYC (SEQ ID NO: 291) | FGGGTKVEIK (SEQ ID NO: 292) |
| 15483 | DIQMTQSPSTLSASVGDRVTITC (SEQ ID NO: 299) | WYQQKPGKAPKLLIY (SEQ ID NO: 300) | GVPSRFSGSGSGTEFTLTISSLQPDDFATYYC (SEQ ID NO: 301) | FGGGTKVEIK (SEQ ID NO: 302) |
| 20513 | DIQMTQSPSTLSASVGDRVTITC (SEQ ID NO: 309) | WYQQKPGKAPKLLIY (SEQ ID NO: 310) | GVPSRFSGSGSGTEFTLTISSLQPDDFATYYC (SEQ ID NO: 311) | FGGGTKVEIK (SEQ ID NO: 312) |
| 22216 | DIQMTQSPSTLSASVGDRVTITC (SEQ ID NO: 319) | WYQQKPGKAPKLLIY (SEQ ID NO: 320) | GVPSRFSGSGSGTEFTLTISSLQPDDFATYYC (SEQ ID NO: 321) | FGGGTKVEIK (SEQ ID NO: 322) |
| 15489 | DIQMTQSPSTLSASVGDRVTITC (SEQ ID NO: 329) | WYQQKPGKAPKLLIY (SEQ ID NO: 330) | GVPSRFSGSGSGTEFTLTISSLQPDDFATYYC (SEQ ID NO: 331) | FGGGTKVEIK (SEQ ID NO: 332) |
| 20516 | DIQMTQSPSTLSASVGDRVTITC (SEQ ID NO: 339) | WYQQKPGKAPKLLIY (SEQ ID NO: 340) | GVPSRFSGSGSGTEFTLTISSLQPDDFATYYC (SEQ ID NO: 341) | FGGGTKVEIK (SEQ ID NO: 342) |
| 15472 | DIQMTQSPSSLSASVGDRVTITC (SEQ ID NO: 349) | WYQQKPGKAPKLLIY (SEQ ID NO: 350) | GVPSRFSGSGSGTDFTLTISSLQPEDFATYYC (SEQ ID NO: 351) | FGGGTKVEIK (SEQ ID NO: 352) |
| 15503 | DIQLTQSPSSVSASVGDRVTITC (SEQ ID NO: 359) | WYQQKPGKAPKLLIY (SEQ ID NO: 360) | GVPSRFSGSGSGTDFTLTISSLQPEDFATYYC (SEQ ID NO: 361) | FGGGTKVEIK (SEQ ID NO: 362) |
| 15495 | EIVMTQSPATLSVSPGERATLSC (SEQ ID NO: 369) | WYQQKPGQAPRLLIY (SEQ ID NO: 370) | GIPARFSGSGSGTEFTLTISSLQSEDFAVYYC (SEQ ID NO: 371) | FGGGTKVEIK (SEQ ID NO: 372) |
| 15478 | DIQMTQSPSTLSASVGDRVTITC (SEQ ID NO: 379) | WYQQKPGKAPKLLIY (SEQ ID NO: 380) | GVPSRFSGSGSGTEFTLTISSLQPDDFATYYC (SEQ ID NO: 381) | FGGGTKVEIK (SEQ ID NO: 382) |
| 15441 | DIQMTQSPSTLSASVGDRVTITC (SEQ ID NO: 389) | WYQQKPGKAPKLLIY (SEQ ID NO: 390) | GVPSRFSGSGSGTEFTLTISSLQPDDFATYYC (SEQ ID NO: 391) | FGGGTKVEIK (SEQ ID NO: 392) |

TABLE 6-continued

VL FR Amino Acid Sequences[3]

| Anti-body | VL FR1 (SEQ ID NO:) | VL FR2 (SEQ ID NO:) | VL FR3 (SEQ ID NO:) | VL FR4 (SEQ ID NO:) |
| --- | --- | --- | --- | --- |
| 20496 | DIQMTQSPSSLSAS VGDRVTITC (SEQ ID NO: 399) | WYQQKPGKAP KLLIY (SEQ ID NO: 400) | GVPSRFSGSGSGT DFTLTISSLQPEDF ATYYC (SEQ ID NO: 401) | FGGGTKVEI K (SEQ ID NO: 402) |

[3] The VL framework regions described in Table 6 are determined based upon the boundaries of the Kabat numbering system for CDRs. In other words, the VL CDRs are determined by Kabat and the framework regions are the amino acid residues surrounding the CDRs in the variable region in the format FR1, CDR1, FR2, CDR2, FR3, CDR3, and FR4.

In certain embodiments, an antibody or antigen-binding fragment thereof described herein binds to human B7-H4 and comprises the four VH framework regions and the four VL framework regions of an antibody listed in Tables 5 and 6 (i.e., the four VH framework regions of the antibody listed in Table 5 and the four VL framework regions of the same antibody listed in Table 6.)

In certain embodiments, an antibody or antigen-binding fragment thereof described herein binds to human B7-H4 and comprises the heavy chain sequence of an antibody listed in Table 7.

TABLE 7

Full-length heavy chain amino acid sequences

| Antibody | Full-Length Heavy Chain Amino Acid Sequence (SEQ ID NO) |
| --- | --- |
| 15461 | QLQLQESGPGLVKPSETLSLTCTVSGGSISSSSYYWGWIRQPPGKGLE WIGNIYYSGSTYYNPSLKSRVTISVDTSKNQFSLKLSSVTAADTAVY YCAREGSYPNWFDPWGQGTLVTVSSASTKGPSVFPLAPSSKSTSGGT AALGCLVKDYFPEPVTVSWNSGALTSGVHTFPAVLQSSGLYSLSSV VTVPSSSLGTQTYICNVNHKPSNTKVDKKVEPKSCDKTHTCPPCPAP ELLGGPSVFLFPPKPKDTLMISRTPEVTCVVVDVSHEDPEVKFNWYV DGVEVHNAKTKPREEQYNSTYRVVSVLTVLHQDWLNGKEYKCKVS NKALPAPIEKTISKAKGQPREPQVYTLPPSRDELTKNQVSLTCLVKGF YPSDIAVEWESNGQPENNYKTTPPVLDSGSFFLYSKLTVDKSRWQ QGNVFSCSVMHEALHNHYTQKSLSLSPGK (SEQ ID NO: 13) |
| 20500 | QLQLQESGPGLVKPSETLSLTCTVSGGSIKSGSHYWGWIRQPPGKGL EWIGNIYYSGSTYYNPSLRSRVTISVDTSKNQFSLKLSSVTAADTAVY YCAREGSYPNWFDPWGQGTLVTVSSASTKGPSVFPLAPSSKSTSGGT AALGCLVKDYFPEPVTVSWNSGALTSGVHTFPAVLQSSGLYSLSSV VTVPSSSLGTQTYICNVNHKPSNTKVDKKVEPKSCDKTHTCPPCPAP ELLGGPSVFLFPPKPKDTLMISRTPEVTCVVVDVSHEDPEVKFNWYV DGVEVHNAKTKPREEQYNSTYRVVSVLTVLHQDWLNGKEYKCKVS NKALPAPIEKTISKAKGQPREPQVYTLPPSRDELTKNQVSLTCLVKGF YPSDIAVEWESNGQPENNYKTTPPVLDSDGSFFLYSKLTVDKSRWQ QGNVFSCSVMHEALHNHYTQKSLSLSPGK (SEQ ID NO: 23) |
| 20501 | QLQLQESGPGLVKPSETLSLTCTVSGGSIKSGSHYWGWIRQPPGKGL EWIGNIYYSGSTYYNPSLKSRVTISVDTSKNQFSLKLSSVTAADTAV YYCAREGSYPNWLDPWGQGTLVTVSSASTKGPSVFPLAPSSKSTSG GTAALGCLVKDYFPEPVTVSWNSGALTSGVHTFPAVLQSSGLYSLSS VVTVPSSSLGTQTYICNVNHKPSNTKVDKKVEPKSCDKTHTCPPCPA PELLGGPSVFLFPPKPKDTLMISRTPEVTCVVVDVSHEDPEVKFNWY VDGVEVHNAKTKPREEQYNSTYRVVSVLTVLHQDWLNGKEYKCK VSNKALPAPIEKTISKAKGQPREPQVYTLPPSRDELTKNQVSLTCLVK GFYPSDIAVEWESNGQPENNYKTTPPVLDSDGSFFLYSKLTVDKSRW QQGNVFSCSVMHEALHNHYTQKSLSLSPGK (SEQ ID NO: 33) |
| 20502 | QLQLQESGPGLVKPSETLSLTCTVSGGSIKSGSYYWGWIRQPPGKGL EWIGNIYYSGSTYYNPSLRSRVTISVDTSKNQFSLKLSSVTAADTAVY YCAREGSYPNQFDPWGQGTLVTVSSASTKGPSVFPLAPSSKSTSGGT AALGCLVKDYFPEPVTVSWNSGALTSGVHTFPAVLQSSGLYSLSSV VTVPSSSLGTQTYICNVNHKPSNTKVDKKVEPKSCDKTHTCPPCPAP ELLGGPSVFLFPPKPKDTLMISRTPEVTCVVVDVSHEDPEVKFNWYV DGVEVHNAKTKPREEQYNSTYRVVSVLTVLHQDWLNGKEYKCKVS NKALPAPIEKTISKAKGQPREPQVYTLPPSRDELTKNQVSLTCLVKGF YPSDIAVEWESNGQPENNYKTTPPVLDSDGSFFLYSKLTVDKSRWQ QGNVFSCSVMHEALHNHYTQKSLSLSPGK (SEQ ID NO: 469) |
| 20502.1 | QLQLQESGPGLVKPSETLSLTCTVSGGSIKSGSYYWGWIRQPPGKGL EWIGNIYYSGSTYYNPSLKSRVTISVDTSKNQFSLKLSSVTAADTAV YYCAREGSYPNQFDPWGQGILVTVSSASTKGPSVFPLAPSSKSTSGG TAALGCLVKDYFPEPVTVSWNSGALTSGVHTFPAVLQSSGLYSLSSV |

TABLE 7-continued

Full-length heavy chain amino acid sequences

Antibody | Full-Length Heavy Chain Amino Acid Sequence (SEQ ID NO)
---|---
 | VTVPSSSLGTQTYICNVNHKPSNTKVDKKVEPKSCDKTHTCPPCPAP
ELLGGPSVFLFPPKPKDTLMISRTPEVTCVVVDVSHEDPEVKFNWYV
DGVEVHNAKTKPREEQYNSTYRVVSVLTVLHQDWLNGKEYKCKVS
NKALPAPIEKTISKAKGQPREPQVYTLPPSRDELTKNQVSLTCLVKGF
YPSDIAVEWESNGQPENNYKTTPPVLDSDGSFFLYSKLTVDKSRWQ
QGNVFSCSVMHEALHNHYTQKSLSLSPGK (SEQ ID NO: 43)
22208 | QLQLQESGPGLVKPSETLSLTCTVSGGSIKSGSHYWGWIRQPPGKGL
EWIGNIYYSGSTYYNPSLKSRVTMSVDTSKNQFSLKLSSVTAADTAV
YYCAREGSYPNWFDPWGQGTLVTVSSASTKGPSVFPLAPSSKSTSG
GTAALGCLVKDYFPEPVTVSWNSGALTSGVHTFPAVLQSSGLYSLSS
VVTVPSSSLGTQTYICNVNHKPSNTKVDKKVEPKSCDKTHTCPPCPA
PELLGGPSVFLFPPKPKDTLMISRTPEVTCVVVDVSHEDPEVKFNWY
VDGVEVHNAKTKPREEQYNSTYRVVSVLTVLHQDWLNGKEYKCK
VSNKALPAPIEKTISKAKGQPREPQVYTLPPSRDELTKNQVSLTCLVK
GFYPSDIAVEWESNGQPENNYKTTPPVLDSDGSFFLYSKLTVDKSRW
QQGNVFSCSVMHEALHNHYTQKSLSLSPGK (SEQ ID NO: 53)
15462 | QLQLQESGPGLVKPSETLSLTCTVSGGSISSSSYYWGWIRQPPGKGLE
WIGNIYYSGSTYYNPSLKSRVTISVDTSKNQFSLKLSSVTAADTAVY
YCAREGSYTTVLNVWGQGTMVTVSSASTKGPSVFPLAPSSKSTSGG
TAALGCLVKDYFPEPVTVSWNSGALTSGVHTFPAVLQSSGLYSLSSV
VTVPSSSLGTQTYICNVNHKPSNTKVDKKVEPKSCDKTHTCPPCPAP
ELLGGPSVFLFPPKPKDTLMISRTPEVTCVVVDVSHEDPEVKFNWYV
DGVEVHNAKTKPREEQYNSTYRVVSVLTVLHQDWLNGKEYKCKVS
NKALPAPIEKTISKAKGQPREPQVYTLPPSRDELTKNQVSLTCLVKGF
YPSDIAVEWESNGQPENNYKTTPPVLDSDGSFFLYSKLTVDKSRWQ
QGNVFSCSVMHEALHNHYTQKSLSLSPGK (SEQ ID NO: 63)
22213 | QLQLQESGPGLVKPSETLSLTCTVSGGSIGRGSYYWGWIRQPPGKGL
EWIGNIYYSGSTYYNPSLKSRVTISVDTSKNQFSLKLSSVTAADTAV
YYCAREGSYTTVLNVWGQGTMVTVSSASTKGPSVFPLAPSSKSTSG
GTAALGCLVKDYFPEPVTVSWNSGALTSGVHTFPAVLQSSGLYSLSS
VVTVPSSSLGTQTYICNVNHKPSNTKVDKKVEPKSCDKTHTCPPCPA
PELLGGPSVFLFPPKPKDTLMISRTPEVTCVVVDVSHEDPEVKFNWY
VDGVEVHNAKTKPREEQYNSTYRVVSVLTVLHQDWLNGKEYKCK
VSNKALPAPIEKTISKAKGQPREPQVYTLPPSRDELTKNQVSLTCLVK
GFYPSDIAVEWESNGQPENNYKTTPPVLDSDGSFFLYSKLTVDKSRW
QQGNVFSCSVMHEALHNHYTQKSLSLSPGK (SEQ ID NO: 73)
15465 | QVQLQESGPGLVKPSQTLSLTCTVSGGSISSGGYYWSWIRQHPGKGL
EWIGNIYYSGSTYYNPSLKSRVTISVDTSKNQFSLKLSSVTAADTAV
YYCARESSTISADFDLWGRGTLVTVSSASTKGPSVFPLAPSSKSTSGG
TAALGCLVKDYFPEPVTVSWNSGALTSGVHTFPAVLQSSGLYSLSSV
VTVPSSSLGTQTYICNVNHKPSNTKVDKKVEPKSCDKTHTCPPCPAP
ELLGGPSVFLFPPKPKDTLMISRTPEVTCVVVDVSHEDPEVKFNWYV
DGVEVHNAKTKPREEQYNSTYRVVSVLTVLHQDWLNGKEYKCKVS
NKALPAPIEKTISKAKGQPREPQVYTLPPSRDELTKNQVSLTCLVKGF
YPSDIAVEWESNGQPENNYKTTPPVLDSDGSFFLYSKLTVDKSRWQ
QGNVFSCSVMHEALHNHYTQKSLSLSPGK (SEQ ID NO: 83)
20506 | QLQLQESGPGLVKPSETLSLTCTASGGSISHGGYYWSWIRQHPGKGL
EWIGNIYYSGSTYYNPSLKSRVTMSVDTSKNQFSLKLSSVTAADTAV
YYCARESSTISADFDLWGRGTLVTVSSASTKGPSVFPLAPSSKSTSGG
TAALGCLVKDYFPEPVTVSWNSGALTSGVHTFPAVLQSSGLYSLSSV
VTVPSSSLGTQTYICNVNHKPSNTKVDKKVEPKSCDKTHTCPPCPAP
ELLGGPSVFLFPPKPKDTLMISRTPEVTCVVVDVSHEDPEVKFNWYV
DGVEVHNAKTKPREEQYNSTYRVVSVLTVLHQDWLNGKEYKCKVS
NKALPAPIEKTISKAKGQPREPQVYTLPPSRDELTKNQVSLTCLVKGF
YPSDIAVEWESNGQPENNYKTTPPVLDSDGSFFLYSKLTVDKSRWQ
QGNVFSCSVMHEALHNHYTQKSLSLSPGK (SEQ ID NO: 93)
15483 | QVQLQESGPGLVKPSQTLSLTCTVSGGSISSGGYYWSWIRQHPGKGL
EWIGNIYYSGSTYYNPSLKSRVTISVDTSKNQFSLKLSSVTAADTAV
YYCARGLSTIDEAFDPWGQGTLVTVSSASTKGPSVFPLAPSSKSTSG
GTAALGCLVKDYFPEPVTVSWNSGALTSGVHTFPAVLQSSGLYSLSS
VVTVPSSSLGTQTYICNVNHKPSNTKVDKKVEPKSCDKTHTCPPCPA
PELLGGPSVFLFPPKPKDTLMISRTPEVTCVVVDVSHEDPEVKFNWY
VDGVEVHNAKTKPREEQYNSTYRVVSVLTVLHQDWLNGKEYKCK
VSNKALPAPIEKTISKAKGQPREPQVYTLPPSRDELTKNQVSLTCLVK
GFYPSDIAVEWESNGQPENNYKTTPPVLDSDGSFFLYSKLTVDKSRW
QQGNVFSCSVMHEALHNHYTQKSLSLSPGK (SEQ ID NO: 103)
20513 | QLQLQESGPGLVKPSETLSLTCTVSGGSISDGSYYWSWIRQHPGKGL
EWIGNIYYSGSTYYNPSLRSRVTMSVDTSKNQFSLKLSSVTAADTAV
YYCARGLSTIDEAFDPWGQGTLVTVSSASTKGPSVFPLAPSSKSTSG TABLE 7-continued Full-length heavy chain amino acid sequences

| Antibody | Full-Length Heavy Chain Amino Acid Sequence (SEQ ID NO) |
|---|---|
| | GTAALGCLVKDYFPEPVTVSWNSGALTSGVHTFPAVLQSSGLYSLSS<br>VVTVPSSSLGTQTYICNVNHKPSNTKVDKKVEPKSCDKTHTCPPCPA<br>PELLGGPSVFLFPPKPKDTLMISRTPEVTCVVVDVSHEDPEVKFNWY<br>VDGVEVHNAKTKPREEQYNSTYRVVSVLTVLHQDWLNGKEYKCK<br>VSNKALPAPIEKTISKAKGQPREPQVYTLPPSRDELTKNQVSLTCLVK<br>GFYPSDIAVEWESNGQPENNYKTTPPVLDSDGSFFLYSKLTVDKSRW<br>QQGNVFSCSVMHEALHNHYTQKSLSLSPGK (SEQ ID NO: 113) |
| 22216 | QVQLQESGPGLVKPSQTLSLTCTVSGGSISDGSYYWSWIRQHPGKGL<br>EWIGNIYYSGSTYYNPSLRSRVTMSVDTSKNQFSLKLSSVTAADTAV<br>YYCARGLSTIDEAFDPWGQGTLVTVSSASTKGPSVFPLAPSSKSTSG<br>GTAALGCLVKDYFPEPVTVSWNSGALTSGVHTFPAVLQSSGLYSLSS<br>VVTVPSSSLGTQTYICNVNHKPSNTKVDKKVEPKSCDKTHTCPPCPA<br>PELLGGPSVFLFPPKPKDTLMISRTPEVTCVVVDVSHEDPEVKFNWY<br>VDGVEVHNAKTKPREEQYNSTYRVVSVLTVLHQDWLNGKEYKCK<br>VSNKALPAPIEKTISKAKGQPREPQVYTLPPSRDELTKNQVSLTCLVK<br>GFYPSDIAVEWESNGQPENNYKTTPPVLDSDGSFFLYSKLTVDKSRW<br>QQGNVFSCSVMHEALHNHYTQKSLSLSPGK (SEQ ID NO: 123) |
| 15489 | QVQLQESGPGLVKPSETLSLTCTVSGGSISSYYWSWIRQPPGKGLEW<br>IGYIYSSGSTNYNPSLKSRVTISVDTSKNQFSLKLSSVTAADTAVYYC<br>ARGSGQYAAPDYGMDVWGQGTTVTVSSASTKGPSVFPLAPSSKSTS<br>GGTAALGCLVKDYFPEPVTVSWNSGALTSGVHTFPAVLQSSGLYSL<br>SSVVTVPSSSLGTQTYICNVNHKPSNTKVDKKVEPKSCDKTHTCPPC<br>PAPELLGGPSVFLFPPKPKDTLMISRTPEVTCVVVDVSHEDPEVKFN<br>WYVDGVEVHNAKTKPREEQYNSTYRVVSVLTVLHQDWLNGKEYK<br>CKVSNKALPAPIEKTISKAKGQPREPQVYTLPPSRDELTKNQVSLTCL<br>VKGFYPSDIAVEWESNGQPENNYKTTPPVLDSDGSFFLYSKLTVDKS<br>RWQQGNVFSCSVMHEALHNHYTQKSLSLSPGK (SEQ ID NO: 133) |
| 20516 | QVQLQESGPGLVKPSETLSLTCTVSGGSIISYYWGWIRQPPGKGLEWI<br>GYIYSSGSTSYNPSLKSRVTISVDTSKNQFSLKLSSVTAADTAVYYCA<br>RGSGLYAAPDYGLDVWGQGTTVTVSSASTKGPSVFPLAPSSKSTSG<br>GTAALGCLVKDYFPEPVTVSWNSGALTSGVHTFPAVLQSSGLYSLSS<br>VVTVPSSSLGTQTYICNVNHKPSNTKVDKKVEPKSCDKTHTCPPCPA<br>PELLGGPSVFLFPPKPKDTLMISRTPEVTCVVVDVSHEDPEVKFNWY<br>VDGVEVHNAKTKPREEQYNSTYRVVSVLTVLHQDWLNGKEYKCK<br>VSNKALPAPIEKTISKAKGQPREPQVYTLPPSRDELTKNQVSLTCLVK<br>GFYPSDIAVEWESNGQPENNYKTTPPVLDSDGSFFLYSKLTVDKSRW<br>QQGNVFSCSVMHEALHNHYTQKSLSLSPGK (SEQ ID NO: 143) |
| 15472 | EVQLLESGGGLVQPGGSLRLSCAASGFTFSSYAMSWVRQAPGKGLE<br>WVSTISGSGGSTYYADSVKGRFTISRDNSKNTLYLQMNSLRAEDTA<br>VYYCARGAGHYDLVGRYWGQGTLVTVSSASTKGPSVFPLAPSSKST<br>SGGTAALGCLVKDYFPEPVTVSWNSGALTSGVHTFPAVLQSSGLYS<br>LSSVVTVPSSSLGTQTYICNVNHKPSNTKVDKKVEPKSCDKTHTCPP<br>CPAPELLGGPSVFLFPPKPKDTLMISRTPEVTCVVVDVSHEDPEVKFN<br>WYVDGVEVHNAKTKPREEQYNSTYRVVSVLTVLHQDWLNGKEYK<br>CKVSNKALPAPIEKTISKAKGQPREPQVYTLPPSRDELTKNQVSLTCL<br>VKGFYPSDIAVEWESNGQPENNYKTTPPVLDSDGSFFLYSKLTVDKS<br>RWQQGNVFSCSVMHEALHNHYTQKSLSLSPGK (SEQ ID NO: 153) |
| 15503 | EVQLLESGGGLVQPGGSLRLSCAASGFTFSSYAMSWVRQAPGKGLE<br>WVSAISGSGGSTYYADSVKGRFTISRDNSKNTLYLQMNSLRAEDTA<br>VYYCARVGFRALNYWGQGTTVTVSSASTKGPSVFPLAPSSKSTSGG<br>TAALGCLVKDYFPEPVTVSWNSGALTSGVHTFPAVLQSSGLYSLSSV<br>VTVPSSSLGTQTYICNVNHKPSNTKVDKKVEPKSCDKTHTCPPCPAP<br>ELLGGPSVFLFPPKPKDTLMISRTPEVTCVVVDVSHEDPEVKFNWYV<br>DGVEVHNAKTKPREEQYNSTYRVVSVLTVLHQDWLNGKEYKCKVS<br>NKALPAPIEKTISKAKGQPREPQVYTLPPSRDELTKNQVSLTCLVKGF<br>YPSDIAVEWESNGQPENNYKTTPPVLDSDGSFFLYSKLTVDKSRWQ<br>QGNVFSCSVMHEALHNHYTQKSLSLSPGK (SEQ ID NO: 163) |
| 15495 | QVQLVQSGAEVKKPGSSVKVSCKASGGTFSSYAISWVRQAPGQGLE<br>WMGGIIPIFGTASYAQKFQGRVTITADESTSTAYMELSSLRSEDTAV<br>YYCARQQYDGRRYFGLWGRGTLVTVSSASTKGPSVFPLAPSSKSTS<br>GGTAALGCLVKDYFPEPVTVSWNSGALTSGVHTFPAVLQSSGLYSL<br>SSVVTVPSSSLGTQTYICNVNHKPSNTKVDKKVEPKSCDKTHTCPPC<br>PAPELLGGPSVFLFPPKPKDTLMISRTPEVTCVVVDVSHEDPEVKFN<br>WYVDGVEVHNAKTKPREEQYNSTYRVVSVLTVLHQDWLNGKEYK<br>CKVSNKALPAPIEKTISKAKGQPREPQVYTLPPSRDELTKNQVSLTCL<br>VKGFYPSDIAVEWESNGQPENNYKTTPPVLDSDGSFFLYSKLTVDKS<br>RWQQGNVFSCSVMHEALHNHYTQKSLSLSPGK (SEQ ID NO: 173) |
| 15478 | QVQLVQSGAEVKKPGSSVKVSCKASGGTFSSYAISWVRQAPGQGLE<br>WMGGIIPIFGTANYAQKFQGRVTITADESTSTAYMELSSLRSEDTAV |

TABLE 7-continued

Full-length heavy chain amino acid sequences

| Antibody | Full-Length Heavy Chain Amino Acid Sequence (SEQ ID NO) |
|---|---|
| | YYCARGGPWFDPWGQGTLVTVSSASTKGPSVFPLAPSSKSTSGGTA<br>ALGCLVKDYFPEPVTVSWNSGALTSGVHTFPAVLQSSGLYSLSSVVT<br>VPSSSLGTQTYICNVNHKPSNTKVDKKVEPKSCDKTHTCPPCPAPEL<br>LGGPSVFLFPPKPKDTLMISRTPEVTCVVVDVSHEDPEVKFNWYVD<br>GVEVHNAKTKPREEQYNSTYRVVSVLTVLHQDWLNGKEYKCKVSN<br>KALPAPIEKTISKAKGQPREPQVYTLPPSRDELTKNQVSLTCLVKGFY<br>PSDIAVEWESNGQPENNYKTTPPVLDSDGSFFLYSKLTVDKSRWQQ<br>GNVFSCSVMHEALHNHYTQKSLSLSPGK (SEQ ID NO: 183) |
| 15441 | EVQLLESGGGLVQPGGSLRLSCAASGFTFSSYAMSWVRQAPGKGLE<br>WVSAISGSGGSTSYADSVKGRFTISRDNSKNTLYLQMNSLRAEDTA<br>VYYCAKPSLATMLAFDIWGQGTMVTVSSASTKGPSVFPLAPSSKSTS<br>GGTAALGCLVKDYFPEPVTVSWNSGALTSGVHTFPAVLQSSGLYSL<br>SSVVTVPSSSLGTQTYICNVNHKPSNTKVDKKVEPKSCDKTHTCPPC<br>PAPELLGGPSVFLFPPKPKDTLMISRTPEVTCVVVDVSHEDPEVKFN<br>WYVDGVEVHNAKTKPREEQYNSTYRVVSVLTVLHQDWLNGKEYK<br>CKVSNKALPAPIEKTISKAKGQPREPQVYTLPPSRDELTKNQVSLTCL<br>VKGFYPSDIAVEWESNGQPENNYKTTPPVLDSDGSFFLYSKLTVDKS<br>RWQQGNVFSCSVMHEALHNHYTQKSLSLSPGK (SEQ ID NO: 193) |
| 20496 | QLQLQESGPGLVKPSETLSLTCTVSGGSISSSVYYWSWIRQPPGKGLE<br>WIGSILVSGSTYYNPSLKSRVTISVDTSKNQFSLKLSSVTAADTAVYY<br>CARAVSFLDVWGQGTMVIVSSASTKGPSVFPLAPSSKSTSGGTAALG<br>CLVKDYFPEPVTVSWNSGALTSGVHTFPAVLQSSGLYSLSSVVTVPS<br>SSLGTQTYICNVNHKPSNTKVDKKVEPKSCDKTHTCPPCPAPELLGG<br>PSVFLFPPKPKDTLMISRTPEVTCVVVDVSHEDPEVKFNWYVDGVE<br>VHNAKTKPREEQYNSTYRVVSVLTVLHQDWLNGKEYKCKVSNKAL<br>PAPIEKTISKAKGQPREPQVYTLPPSRDELTKNQVSLTCLVKGFYPSD<br>IAVEWESNGQPENNYKTTPPVLDSDGSFFLYSKLTVDKSRWQQGNV<br>FSCSVMHEALHNHYTQKSLSLSPGK (SEQ ID NO: 203) |

In certain embodiments, an antibody or antigen-binding fragment thereof described herein binds to human B7-H4 and comprises the light chain sequence of an antibody listed in Table 8.

TABLE 8

Full-length light chain amino acid sequences

| Antibody | Full-Length Light Chain Amino Acid Sequence (SEQ ID NO) |
|---|---|
| 15461 | EIVMTQSPATLSVSPGERATLSCRASQSVSSNLAWYQQKPGQAPRLL<br>IYGASTRATGIPARFSGSGSGTEFTLTISSLQSEDFAVYYCQQYHSFPF<br>TFGGGTKVEIKRTVAAPSVFIFPPSDEQLKSGTASVVCLLNNFYPREA<br>KVQWKVDNALQSGNSQESVTEQDSKDSTYSLSSTLTLSKADYEKHK<br>VYACEVTHQGLSSPVTKSFNRGEC (SEQ ID NO: 14) |
| 20500 | EIVMTQSPATLSVSPGERATLSCRASQSVSSNLAWYQQKPGQAPRLL<br>IYGASTRATGIPARFSGSGSGTEFTLTISSLQSEDFAVYYCQQYHSFPF<br>TFGGGTKVEIKRTVAAPSVFIFPPSDEQLKSGTASVVCLLNNFYPREA<br>KVQWKVDNALQSGNSQESVTEQDSKDSTYSLSSTLTLSKADYEKHK<br>VYACEVTHQGLSSPVTKSFNRGEC (SEQ ID NO: 24) |
| 20501 | EIVMTQSPATLSVSPGERATLSCRASQSVSSNLAWYQQKPGQAPRLL<br>IYGASTRATGIPARFSGSGSGTEFTLTISSLQSEDFAVYYCQQYHSFPF<br>TFGGGTKVEIKRTVAAPSVFIFPPSDEQLKSGTASVVCLLNNFYPREA<br>KVQWKVDNALQSGNSQESVTEQDSKDSTYSLSSTLTLSKADYEKHK<br>VYACEVTHQGLSSPVTKSFNRGEC (SEQ ID NO: 34) |
| 20502 and 20502.1 | EIVMTQSPATLSVSPGERATLSCRASQSVSSNLAWYQQKPGQAPRLL<br>IYGASTRATGIPARFSGSGSGTEFTLTISSLQSEDFAVYYCQQYHSFPF<br>TFGGGTKVEIKRTVAAPSVFIFPPSDEQLKSGTASVVCLLNNFYPREA<br>KVQWKVDNALQSGNSQESVTEQDSKDSTYSLSSTLTLSKADYEKHK<br>VYACEVTHQGLSSPVTKSFNRGEC (SEQ ID NO: 44) |
| 22208 | EIVMTQSPATLSVSPGERATLSCRASQSVSTNLAWYQQKPGQAPRLL<br>IYDASARVTGIPARFSGSGSGTEFTLTISSLQSEDFAVYYCQQYHSFPF<br>TFGGGTKVEIKRTVAAPSVFIFPPSDEQLKSGTASVVCLLNNFYPREA<br>KVQWKVDNALQSGNSQESVTEQDSKDSTYSLSSTLTLSKADYEKHK<br>VYACEVTHQGLSSPVTKSFNRGEC (SEQ ID NO: 54) |

TABLE 8-continued

Full-length light chain amino acid sequences

| Antibody | Full-Length Light Chain Amino Acid Sequence (SEQ ID NO) |
|---|---|
| 15462 | EIVLTQSPGTLSLSPGERATLSCRASQSVSSSYLAWYQQKPGQAPRLL<br>IYGASSRATGIPDRFSGSGSGTDFTLTISRLEPEDFAVYYCQQAASYP<br>LTFGGGTKVEIKRTVAAPSVFIFPPSDEQLKSGTASVVCLLNNFYPRE<br>AKVQWKVDNALQSGNSQESVTEQDSKDSTYSLSSTLTLSKADYEKH<br>KVYACEVTHQGLSSPVTKSFNRGEC (SEQ ID NO: 64) |
| 22213 | EIVLTQSPGTLSLSPGERATLSCRASQSVASSHLAWYQQKPGQAPRL<br>LIYDAVSRATGIPDRFSGSGSGTDFTLTISRLEPEDFAVYYCQQAASY<br>PLTFGGGTKVEIKRTVAAPSVFIFPPSDEQLKSGTASVVCLLNNFYPR<br>EAKVQWKVDNALQSGNSQESVTEQDSKDSTYSLSSTLTLSKADYEK<br>HKVYACEVTHQGLSSPVTKSFNRGEC (SEQ ID NO: 74) |
| 15465 | DIQMTQSPSSVSASVGDRVTITCRASQGISRWLAWYQQKPGKAPKL<br>LIYAASSLQSGVPSRFSGSGSGTDFTLTISSLQPEDFATYYCQQAHTFP<br>YTFGGGTKVEIKRTVAAPSVFIFPPSDEQLKSGTASVVCLLNNFYPRE<br>AKVQWKVDNALQSGNSQESVTEQDSKDSTYSLSSTLTLSKADYEKH<br>KVYACEVTHQGLSSPVTKSFNRGEC (SEQ ID NO: 84) |
| 20506 | DIQMTQSPSSVSASVGDRVTITCRASQGISRWLAWYQQKPGKAPKL<br>LIYAASSLQSGVPSRFSGSGSGTDFTLTISSLQPEDFATYYCQQAHTFP<br>YTFGGGTKVEIKRTVAAPSVFIFPPSDEQLKSGTASVVCLLNNFYPRE<br>AKVQWKVDNALQSGNSQESVTEQDSKDSTYSLSSTLTLSKADYEKH<br>KVYACEVTHQGLSSPVTKSFNRGEC (SEQ ID NO: 94) |
| 15483 | DIQMTQSPSTLSASVGDRVTITCRASQSISSWLAWYQQKPGKAPKLL<br>IYKASSLESGVPSRFSGSGSGTEFTLTISSLQPDDFATYYCQQDNSYP<br>YTFGGGTKVEIKRTVAAPSVFIFPPSDEQLKSGTASVVCLLNNFYPRE<br>AKVQWKVDNALQSGNSQESVTEQDSKDSTYSLSSTLTLSKADYEKH<br>KVYACEVTHQGLSSPVTKSFNRGEC (SEQ ID NO: 104) |
| 20513 | DIQMTQSPSTLSASVGDRVTITCRASQSISSWLAWYQQKPGKAPKLL<br>IYKASSLESGVPSRFSGSGSGTEFTLTISSLQPDDFATYYCQQDNSYP<br>YTFGGGTKVEIKRTVAAPSVFIFPPSDEQLKSGTASVVCLLNNFYPRE<br>AKVQWKVDNALQSGNSQESVTEQDSKDSTYSLSSTLTLSKADYEKH<br>KVYACEVTHQGLSSPVTKSFNRGEC (SEQ ID NO: 114) |
| 22216 | DIQMTQSPSTLSASVGDRVTITCRASKSISSWLAWYQQKPGKAPKLL<br>IYEASSLHSGVPSRFSGSGSGTEFTLTISSLQPDDFATYYCQQDNSYP<br>YTFGGGTKVEIKRTVAAPSVFIFPPSDEQLKSGTASVVCLLNNFYPRE<br>AKVQWKVDNALQSGNSQESVTEQDSKDSTYSLSSTLTLSKADYEKH<br>KVYACEVTHQGLSSPVTKSFNRGEC (SEQ ID NO: 124) |
| 15489 | DIQMTQSPSTLSASVGDRVTITCRASQSISSWLAWYQQKPGKAPKLL<br>IYKASSLESGVPSRFSGSGSGTEFTLTISSLQPDDFATYYCQQDNSFPF<br>TFGGGTKVEIKRTVAAPSVFIFPPSDEQLKSGTASVVCLLNNFYPREA<br>KVQWKVDNALQSGNSQESVTEQDSKDSTYSLSSTLTLSKADYEKHK<br>VYACEVTHQGLSSPVTKSFNRGEC (SEQ ID NO: 134) |
| 20516 | DIQMTQSPSTLSASVGDRVTITCRASQSISSWLAWYQQKPGKAPKLL<br>IYKASSLESGVPSRFSGSGSGTEFTLTISSLQPDDFATYYCQQDNSFPF<br>TFGGGTKVEIKRTVAAPSVFIFPPSDEQLKSGTASVVCLLNNFYPREA<br>KVQWKVDNALQSGNSQESVTEQDSKDSTYSLSSTLTLSKADYEKHK<br>VYACEVTHQGLSSPVTKSFNRGEC (SEQ ID NO: 144) |
| 15472 | DIQMTQSPSSLSASVGDRVTITCRASQSISSYLNWYQQKPGKAPKLLI<br>YAASSLQSGVPSRFSGSGSGTDFTLTISSLQPEDFATYYCQQLYSLPP<br>TFGGGTKVEIKRTVAAPSVFIFPPSDEQLKSGTASVVCLLNNFYPREA<br>KVQWKVDNALQSGNSQESVTEQDSKDSTYSLSSTLTLSKADYEKHK<br>VYACEVTHQGLSSPVTKSFNRGEC (SEQ ID NO: 154) |
| 15503 | DIQLTQSPSSVSASVGDRVTITCRASQDISSWLAWYQQKPGKAPKLLI<br>YAASSLQSGVPSRFSGSGSGTDFTLTISSLQPEDFATYYCQQATSYPP<br>WTFGGGTKVEIKRTVAAPSVFIFPPSDEQLKSGTASVVCLLNNFYPR<br>EAKVQWKVDNALQSGNSQESVTEQDSKDSTYSLSSTLTLSKADYEK<br>HKVYACEVTHQGLSSPVTKSFNRGEC (SEQ ID NO: 164) |
| 15495 | EIVMTQSPATLSVSPGERATLSCRASQSVSSNLAWYQQKPGQAPRLL<br>IYSASTRATGIPARFSGSGSGTEFTLTISSLQSEDFAVYYCQQVNVWP<br>PTFGGGTKVEIKRTVAAPSVFIFPPSDEQLKSGTASVVCLLNNFYPRE<br>AKVQWKVDNALQSGNSQESVTEQDSKDSTYSLSSTLTLSKADYEKH<br>KVYACEVTHQGLSSPVTKSFNRGEC (SEQ ID NO: 174) |

TABLE 8-continued

Full-length light chain amino acid sequences

| Antibody | Full-Length Light Chain Amino Acid Sequence (SEQ ID NO) |
|---|---|
| 15478 | DIQMTQSPSTLSASVGDRVTITCRASQSISSWLAWYQQKPGKAPKLL<br>IYKASSLESGVPSRFSGSGSGTEFTLTISSLQPDDFATYYCQQYNSYPP<br>FTFGGGTKVEIKRTVAAPSVFIFPPSDEQLKSGTASVVCLLNNFYPRE<br>AKVQWKVDNALQSGNSQESVTEQDSKDSTYSLSSTLTLSKADYEKH<br>KVYACEVTHQGLSSPVTKSFNRGEC (SEQ ID NO: 184) |
| 15441 | DIQMTQSPSTLSASVGDRVTITCRASQSISSWLAWYQQKPGKAPKLL<br>IYDASSLESGVPSRFSGSGSGTEFTLTISSLQPDDFATYYCQQSKSYPR<br>TFGGGTKVEIKRTVAAPSVFIFPPSDEQLKSGTASVVCLLNNFYPREA<br>KVQWKVDNALQSGNSQESVTEQDSKDSTYSLSSTLTLSKADYEKHK<br>VYACEVTHQGLSSPVTKSFNRGEC (SEQ ID NO: 194) |
| 20496 | DIQMTQSPSSLSASVGDRVTITCRASQSISSYLNWYQQKPGKAPKLLI<br>YGASSLQSGVPSRFSGSGSGTDFTLTISSLQPEDFATYYCQQSYDPPW<br>TFGGGTKVEIKRTVAAPSVFIFPPSDEQLKSGTASVVCLLNNFYPREA<br>KVQWKVDNALQSGNSQESVTEQDSKDSTYSLSSTLTLSKADYEKHK<br>VYACEVTHQGLSSPVTKSFNRGEC (SEQ ID NO: 204) |

In certain embodiments, an antibody or antigen-binding fragment thereof described herein binds to human B7-H4 and comprises the heavy chain sequence and the light chain sequence of an antibody listed in Tables 7 and 8 (i.e., the heavy chain sequence of the antibody listed in Table 7 and the light chain sequence of the same antibody listed in Table 8).

In certain embodiments, an antibody or antigen-binding fragment thereof described herein binds to human B7-H4, comprises the six CDRs of an antibody listed in Tables 1 and 2 (i.e., the three VH CDRs of the antibody listed in Table 1 and the three VL CDRs of the same antibody listed in Table 2), and comprises a VH comprising a sequence at least 80% identical to the VH sequence of the same antibody in Table 3 and a VL comprising a sequence at least 80% identical to the VL sequence of the same antibody in Table 4. In certain embodiments, an antibody or antigen-binding fragment thereof described herein binds to human B7-H4, comprises the six CDRs of an antibody listed in Tables 1 and 2 (i.e., the three VH CDRs of the antibody listed in Table 1 and the three VL CDRs of the same antibody listed in Table 2), and comprises a VH comprising a sequence at least 85% identical to the VH sequence of the same antibody in Table 3 and a VL comprising a sequence at least 85% identical to the VL sequence of the same antibody in Table 4.

In certain embodiments, an antibody or antigen-binding fragment thereof described herein binds to human B7-H4, comprises the six CDRs of an antibody listed in Tables 1 and 2 (i.e., the three VH CDRs of the antibody listed in Table 1 and the three VL CDRs of the same antibody listed in Table 2), and comprises a VH comprising a sequence at least 90% identical to the VH sequence of the same antibody in Table 3 and a VL comprising a sequence at least 90% identical to the VL sequence of the same antibody in Table 4. In certain embodiments, an antibody or antigen-binding fragment thereof described herein binds to human B7-H4, comprises the six CDRs of an antibody listed in Tables 1 and 2 (i.e., the three VH CDRs of the antibody listed in Table 1 and the three VL CDRs of the same antibody listed in Table 2), and comprises a VH comprising a sequence at least 95% identical to the VH sequence of the same antibody in Table 3 and a VL comprising a sequence at least 95% identical to the VL sequence of the same antibody in Table 4.

In certain embodiments, an antibody or antigen-binding fragment thereof described herein binds to human B7-H4, comprises the six CDRs of an antibody listed in Tables 1 and 2 (i.e., the three VH CDRs of the antibody listed in Table 1 and the three VL CDRs of the same antibody listed in Table 2), and comprises a VH comprising a sequence at least 96% identical to the VH sequence of the same antibody in Table 3 and a VL comprising a sequence at least 96% identical to the VL sequence of the same antibody in Table 4. In certain embodiments, an antibody or antigen-binding fragment thereof described herein binds to human B7-H4, comprises the six CDRs of an antibody listed in Tables 1 and 2 (i.e., the three VH CDRs of the antibody listed in Table 1 and the three VL CDRs of the same antibody listed in Table 2), and comprises a VH comprising a sequence at least 97% identical to the VH sequence of the same antibody in Table 3 and a VL comprising a sequence at least 97% identical to the VL sequence of the same antibody in Table 4. In certain embodiments, an antibody or antigen-binding fragment thereof described herein binds to human B7-H4, comprises the six CDRs of an antibody listed in Tables 1 and 2 (i.e., the three VH CDRs of the antibody listed in Table 1 and the three VL CDRs of the same antibody listed in Table 2), and comprises a VH comprising a sequence at least 98% identical to the VH sequence of the same antibody in Table 3 and a VL comprising a sequence at least 98% identical to the VL sequence of the same antibody in Table 4. In certain embodiments, an antibody or antigen-binding fragment thereof described herein binds to human B7-H4, comprises the six CDRs of an antibody listed in Tables 1 and 2 (i.e., the three VH CDRs of the antibody listed in Table 1 and the three VL CDRs of the same antibody listed in Table 2), and comprises a VH comprising a sequence at least 99% identical to the VH sequence of the same antibody in Table 3 and a VL comprising a sequence at least 99% identical to the VL sequence of the same antibody in Table 4.

In certain embodiments, an antibody or antigen-binding fragment thereof described herein binds to human B7-H4, comprises the six CDRs of an antibody listed in Tables 1 and 2 (i.e., the three VH CDRs of the antibody listed in Table 1 and the three VL CDRs of the same antibody listed in Table 2), comprises a VH comprising a sequence at least 80% identical to the VH sequence of the same antibody in Table 3 and a VL comprising a sequence at least 80% identical to the VL sequence of the same antibody in Table 4, and binds to human, cynomolgus monkey, rat, and/or mouse B7-H4. In certain embodiments, an antibody or antigen-binding fragment thereof described herein binds to human B7-H4, comprises the six CDRs of an antibody listed in Tables 1 and 2

(i.e., the three VH CDRs of the antibody listed in Table 1 and the three VL CDRs of the same antibody listed in Table 2), comprises a VH comprising a sequence at least 85% identical to the VH sequence of the same antibody in Table 3 and a VL comprising a sequence at least 85% identical to the VL sequence of the same antibody in Table 4, and binds to human, cynomolgus monkey, rat, and/or mouse B7-H4.

In certain embodiments, an antibody or antigen-binding fragment thereof described herein binds to human B7-H4, comprises the six CDRs of an antibody listed in Tables 1 and 2 (i.e., the three VH CDRs of the antibody listed in Table 1 and the three VL CDRs of the same antibody listed in Table 2), comprises a VH comprising a sequence at least 90% identical to the VH sequence of the same antibody in Table 3 and a VL comprising a sequence at least 90% identical to the VL sequence of the same antibody in Table 4, and binds to human, cynomolgus monkey, rat, and/or mouse B7-H4. In certain embodiments, an antibody or antigen-binding fragment thereof described herein binds to human B7-H4, comprises the six CDRs of an antibody listed in Tables 1 and 2 (i.e., the three VH CDRs of the antibody listed in Table 1 and the three VL CDRs of the same antibody listed in Table 2), comprises a VH comprising a sequence at least 95% identical to the VH sequence of the same antibody in Table 3 and a VL comprising a sequence at least 95% identical to the VL sequence of the same antibody in Table 4, and binds to human, cynomolgus monkey, rat, and/or mouse B7-H4.

In certain embodiments, an antibody or antigen-binding fragment thereof described herein binds to human B7-H4, comprises the six CDRs of an antibody listed in Tables 1 and 2 (i.e., the three VH CDRs of the antibody listed in Table 1 and the three VL CDRs of the same antibody listed in Table 2), comprises a VH comprising a sequence at least 96% identical to the VH sequence of the same antibody in Table 3 and a VL comprising a sequence at least 96% identical to the VL sequence of the same antibody in Table 4, and binds to human, cynomolgus monkey, rat, and/or mouse B7-H4. In certain embodiments, an antibody or antigen-binding fragment thereof described herein binds to human B7-H4, comprises the six CDRs of an antibody listed in Tables 1 and 2 (i.e., the three VH CDRs of the antibody listed in Table 1 and the three VL CDRs of the same antibody listed in Table 2), comprises a VH comprising a sequence at least 97% identical to the VH sequence of the same antibody in Table 3 and a VL comprising a sequence at least 97% identical to the VL sequence of the same antibody in Table 4, and binds to human, cynomolgus monkey, rat, and/or mouse B7-H4. In certain embodiments, an antibody or antigen-binding fragment thereof described herein binds to human B7-H4, comprises the six CDRs of an antibody listed in Tables 1 and 2 (i.e., the three VH CDRs of the antibody listed in Table 1 and the three VL CDRs of the same antibody listed in Table 2), comprises a VH comprising a sequence at least 98% identical to the VH sequence of the same antibody in Table 3 and a VL comprising a sequence at least 98% identical to the VL sequence of the same antibody in Table 4, and binds to human, cynomolgus monkey, rat, and/or mouse B7-H4. In certain embodiments, an antibody or antigen-binding fragment thereof described herein binds to human B7-H4, comprises the six CDRs of an antibody listed in Tables 1 and 2 (i.e., the three VH CDRs of the antibody listed in Table 1 and the three VL CDRs of the same antibody listed in Table 2), comprises a VH comprising a sequence at least 99% identical to the VH sequence of the same antibody in Table 3 and a VL comprising a sequence at least 99% identical to the VL sequence of the same antibody in Table 4, and binds to human, cynomolgus monkey, rat, and/or mouse B7-H4.

In certain embodiments, an antibody or antigen-binding fragment thereof described herein binds to human B7-H4, comprises the six CDRs of an antibody listed in Tables 1 and 2 (i.e., the three VH CDRs of the antibody listed in Table 1 and the three VL CDRs of the same antibody listed in Table 2), comprises a VH comprising a sequence at least 80% identical to the VH sequence of the same antibody in Table 3 and a VL comprising a sequence at least 80% identical to the VL sequence of the same antibody in Table 4, increases T cell proliferation, increases IFNγ production, and mediates ADCC activity against B7-H4-expressing cells. In certain embodiments, an antibody or antigen-binding fragment thereof described herein binds to human B7-H4, comprises the six CDRs of an antibody listed in Tables 1 and 2 (i.e., the three VH CDRs of the antibody listed in Table 1 and the three VL CDRs of the same antibody listed in Table 2), comprises a VH comprising a sequence at least 85% identical to the VH sequence of the same antibody in Table 3 and a VL comprising a sequence at least 85% identical to the VL sequence of the same antibody in Table 4, increases T cell proliferation, increases IFNγ production, and mediates ADCC activity against B7-H4-expressing cells.

In certain embodiments, an antibody or antigen-binding fragment thereof described herein binds to human B7-H4, comprises the six CDRs of an antibody listed in Tables 1 and 2 (i.e., the three VH CDRs of the antibody listed in Table 1 and the three VL CDRs of the same antibody listed in Table 2), comprises a VH comprising a sequence at least 90% identical to the VH sequence of the same antibody in Table 3 and a VL comprising a sequence at least 90% identical to the VL sequence of the same antibody in Table 4, increases T cell proliferation, increases IFNγ production, and/or mediates ADCC activity against B7-H4-expressing cells. In certain embodiments, an antibody or antigen-binding fragment thereof described herein binds to human B7-H4, comprises the six CDRs of an antibody listed in Tables 1 and 2 (i.e., the three VH CDRs of the antibody listed in Table 1 and the three VL CDRs of the same antibody listed in Table 2), comprises a VH comprising a sequence at least 95% identical to the VH sequence of the same antibody in Table 3 and a VL comprising a sequence at least 95% identical to the VL sequence of the same antibody in Table 4, increases T cell proliferation, increases IFNγ production, and mediates ADCC activity against B7-H4-expressing cells.

In certain embodiments, an antibody or antigen-binding fragment thereof described herein binds to human B7-H4, comprises the six CDRs of an antibody listed in Tables 1 and 2 (i.e., the three VH CDRs of the antibody listed in Table 1 and the three VL CDRs of the same antibody listed in Table 2), comprises a VH comprising a sequence at least 96% identical to the VH sequence of the same antibody in Table 3 and a VL comprising a sequence at least 96% identical to the VL sequence of the same antibody in Table 4, increases T cell proliferation, increases IFNγ production, and mediates ADCC activity against B7-H4-expressing cells. In certain embodiments, an antibody or antigen-binding fragment thereof described herein binds to human B7-H4, comprises the six CDRs of an antibody listed in Tables 1 and 2 (i.e., the three VH CDRs of the antibody listed in Table 1 and the three VL CDRs of the same antibody listed in Table 2), comprises a VH comprising a sequence at least 97% identical to the VH sequence of the same antibody in Table 3 and a VL comprising a sequence at least 97% identical to the VL sequence of the same antibody in Table 4, increases T cell proliferation, increases IFNγ production, and mediates ADCC activity against B7-H4-expressing cells. In certain embodiments, an antibody or antigen-binding fragment thereof described herein binds to human B7-H4, comprises the six CDRs of an antibody listed in Tables 1 and 2 (i.e., the three VH CDRs of the antibody listed in Table 1 and the three VL CDRs of the same antibody listed in Table 2), comprises a VH comprising a sequence at least 98% identical to the VH sequence of the same antibody in Table 3 and a VL comprising a sequence at least 98% identical to the VL sequence of the same antibody in Table 4, increases T cell proliferation, increases IFNγ production, and mediates ADCC activity against B7-H4-expressing cells. In certain embodiments, an antibody or antigen-binding fragment thereof described herein binds to human B7-H4, comprises the six CDRs of an antibody listed in Tables 1 and 2 (i.e., the three VH CDRs of the antibody listed in Table 1 and the three VL CDRs of the same antibody listed in Table 2), comprises a VH comprising a sequence at least 99% identical to the VH sequence of the same antibody in Table 3 and a VL comprising a sequence at least 99% identical to the VL sequence of the same antibody in Table 4, increases T cell proliferation, increases IFNγ production, and mediates ADCC activity against B7-H4-expressing cells.

In certain aspects, an antibody or antigen-binding fragment thereof described herein may be described by its VL domain alone, or its VH domain alone, or by its 3 VL CDRs alone, or its 3 VH CDRs alone. See, for example, Rader C et al., (1998) PNAS 95: 8910-8915, which is incorporated herein by reference in its entirety, describing the humanization of the mouse anti-αvβ3 antibody by identifying a complementing light chain or heavy chain, respectively, from a human light chain or heavy chain library, resulting in humanized antibody variants having affinities as high or higher than the affinity of the original antibody. See also Clackson T et al., (1991) Nature 352: 624-628, which is incorporated herein by reference in its entirety, describing methods of producing antibodies that bind a specific antigen by using a specific VL domain (or VH domain) and screening a library for the complementary variable domains. The screen produced 14 new partners for a specific VH domain and 13 new partners for a specific VL domain, which were strong binders, as determined by ELISA. See also Kim S J & Hong H J, (2007) J Microbiol 45: 572-577, which is incorporated herein by reference in its entirety, describing methods of producing antibodies that bind a specific antigen by using a specific VH domain and screening a library (e.g., human VL library) for complementary VL domains; the selected VL domains in turn could be used to guide selection of additional complementary (e.g., human) VH domains.

In certain aspects, the CDRs of an antibody or antigen-binding fragment thereof can be determined according to the Chothia numbering scheme, which refers to the location of immunoglobulin structural loops (see, e.g., Chothia C & Lesk A M, (1987), J Mol Biol 196: 901-917; Al-Lazikani B et al., (1997) J Mol Biol 273: 927-948; Chothia C et al., (1992) J Mol Biol 227: 799-817; Tramontano A et al., (1990) J Mol Biol 215(1): 175-82; and U.S. Pat. No. 7,709,226). Typically, when using the Kabat numbering convention, the Chothia CDR-H1 loop is present at heavy chain amino acids 26 to 32, 33, or 34, the Chothia CDR-H2 loop is present at heavy chain amino acids 52 to 56, and the Chothia CDR-H3 loop is present at heavy chain amino acids 95 to 102, while the Chothia CDR-L1 loop is present at light chain amino acids 24 to 34, the Chothia CDR-L2 loop is present at light chain amino acids 50 to 56, and the Chothia CDR-L3 loop is present at light chain amino acids 89 to 97. The end of the Chothia CDR-H1 loop when numbered using the Kabat numbering convention varies between H32 and H34 depending on the length of the loop (this is because the Kabat numbering scheme places the insertions at H35A and H35B; if neither 35A nor 35B is present, the loop ends at 32; if only 35A is present, the loop ends at 33; if both 35A and 35B are present, the loop ends at 34).

In certain aspects, provided herein are antibodies and antigen-binding fragments thereof that specifically bind to B7-H4 (e.g., human B7-H4) and comprise the Chothia VH and VL CDRs of an antibody listed in Tables 3 and 4. In certain embodiments, antibodies or antigen-binding fragments thereof that specifically bind to B7-H4 (e.g., human B7-H4) comprise one or more CDRs, in which the Chothia and Kabat CDRs have the same amino acid sequence. In certain embodiments, provided herein are antibodies and antigen-binding fragments thereof that specifically bind to B7-H4 (e.g., human B7-H4) and comprise combinations of Kabat CDRs and Chothia CDRs.

In certain aspects, the CDRs of an antibody or antigen-binding fragment thereof can be determined according to the IMGT numbering system as described in Lefranc M-P, (1999) The Immunologist 7: 132-136 and Lefranc M-P et al., (1999) Nucleic Acids Res 27: 209-212. According to the IMGT numbering scheme, VH-CDR1 is at positions 26 to 35, VH-CDR2 is at positions 51 to 57, VH-CDR3 is at positions 93 to 102, VL-CDR1 is at positions 27 to 32, VL-CDR2 is at positions 50 to 52, and VL-CDR3 is at positions 89 to 97. In a particular embodiment, provided herein are antibodies and antigen-binding fragments thereof that specifically bind to B7-H4 (e.g., human B7-H4) and comprise the IMGT VH and VL CDRs of an antibody listed in Tables 3 and 4, for example, as described in Lefranc M-P (1999) supra and Lefranc M-P et al., (1999) supra).

In certain aspects, the CDRs of an antibody or antigen-binding fragment thereof can be determined according to MacCallum R M et al., (1996) J Mol Biol 262: 732-745. See also, e.g., Martin A. "Protein Sequence and Structure Analysis of Antibody Variable Domains," in Antibody Engineering, Kontermann and Dübel, eds., Chapter 31, pp. 422-439, Springer-Verlag, Berlin (2001). In a particular embodiment, provided herein are antibodies or antigen-binding fragments thereof that specifically bind to B7-H4 (e.g., human B7-H4) and comprise VH and VL CDRs of an antibody listed in Tables 3 and 4 as determined by the method in MacCallum R M et al.

In certain aspects, the CDRs of an antibody or antigen-binding fragment thereof can be determined according to the AbM numbering scheme, which refers AbM hypervariable regions which represent a compromise between the Kabat CDRs and Chothia structural loops, and are used by Oxford Molecular's AbM antibody modeling software (Oxford Molecular Group, Inc.). In a particular embodiment, provided herein are antibodies or antigen-binding fragments thereof that specifically bind to B7-H4 (e.g., human B7-H4) and comprise VH and VL CDRs of an antibody listed in Tables 3 and 4 as determined by the AbM numbering scheme.

In specific aspects, provided herein are antibodies that comprise a heavy chain and a light chain. With respect to the heavy chain, in a specific embodiment, the heavy chain of an antibody described herein can be an alpha (α), delta (δ), epsilon (ε), gamma (γ) or mu (μ) heavy chain. In another specific embodiment, the heavy chain of an antibody described can comprise a human alpha (α), delta (δ), epsilon (ε), gamma (γ) or mu (μ) heavy chain. In a particular embodiment, an antibody described herein, which immuno-specifically binds to B7-H4 (e.g., human B7-H4), comprises a heavy chain wherein the amino acid sequence of the VH domain comprises an amino acid sequence set forth in Table 3 and wherein the constant region of the heavy chain comprises the amino acid sequence of a human gamma (γ) heavy chain constant region. In a specific embodiment, an antibody described herein, which specifically binds to B7-H4 (e.g., human B7-H4), comprises a heavy chain wherein the amino acid sequence of the VH domain comprises a sequence set forth in Table 3, and wherein the constant region of the heavy chain comprises the amino acid of a human heavy chain described herein or known in the art. Non-limiting examples of human constant region sequences have been described in the art, e.g., see U.S. Pat. No. 5,693,780 and Kabat E A et al., (1991) supra.

With respect to the light chain, in a specific embodiment, the light chain of an antibody described herein is a kappa light chain. The constant region of a human kappa light chain can comprise the following amino acid sequence:

(SEQ ID NO: 405)
RTVAAPSVFIFPPSDEQLKSGTASVVCLLNNFYPREAKVQWKVDNALQSG

NSQESVTEQDSKDSTYSLSSTLTLSKADYEKHKVYACEVTHQGLSSPVTK

SFNRGEC.

The constant region of a human kappa light chain can be encoded by the following nucleotide sequence:

(SEQ ID NO: 406)
CGGACCGTGGCTGCACCATCTGTCTTCATCTTCCCGCCATCTGATGAGCA

GTTGAAATCTGGAACTGCCTCTGTTGTGTGCCTGCTGAATAACTTCTATC

CCAGAGAGGCCAAAGTACAGTGGAAGGTGGATAACGCCCTCCAATCGGGT

AACTCCCAGGAGAGTGTCACAGAGCAGGACAGCAAGGACAGCACCTACAG

CCTCAGCAGCACCCTGACGCTGAGCAAAGCAGACTACGAGAAACACAAAG

TCTACGCCTGCGAAGTCACCCATCAGGGCCTGAGCTCGCCCGTCACAAAG

AGCTTCAACAGGGGAGAGTGT.

In another specific embodiment, the light chain of an antibody described herein is a lambda light chain. In yet another specific embodiment, the light chain of an antibody described herein is a human kappa light chain or a human lambda light chain. In a particular embodiment, an antibody described herein, which immunospecifically binds to a B7-H4 polypeptide (e.g., human B7-H4) comprises a light chain wherein the amino acid sequence of the VL domain comprises a sequence set forth in Table 4, and wherein the constant region of the light chain comprises the amino acid sequence of a human kappa light chain constant region. In another particular embodiment, an antibody described herein, which immunospecifically binds to B7-H4 (e.g., human B7-H4) comprises a light chain wherein the amino acid sequence of the VL domain comprises a sequence set forth in Table 4 and wherein the constant region of the light chain comprises the amino acid sequence of a human lambda light chain constant region. In a specific embodiment, an antibody described herein, which immunospecifically binds to B7-H4 (e.g., human B7-H4) comprises a light chain wherein the amino acid sequence of the VL domain comprises a sequence set forth in Table 4 and wherein the constant region of the light chain comprises the amino acid sequence of a human kappa or lambda light chain constant region. Non-limiting examples of human constant region sequences have been described in the art, e.g., see U.S. Pat. No. 5,693,780 and Kabat E A et al., (1991) supra.

In a specific embodiment, an antibody described herein, which immunospecifically binds to B7-H4 (e.g., human B7-H4) comprises a VH domain and a VL domain comprising any amino acid sequence described herein, and wherein the constant regions comprise the amino acid sequences of the constant regions of an IgG, IgE, IgM, IgD, IgA, or IgY immunoglobulin molecule, or a human IgG, IgE, IgM, IgD, IgA, or IgY immunoglobulin molecule. In another specific embodiment, an antibody described herein, which immunospecifically binds to B7-H4 (e.g., human B7-H4) comprises a VH domain and a VL domain comprising any amino acid sequence described herein, and wherein the constant regions comprise the amino acid sequences of the constant regions of an IgG, IgE, IgM, IgD, IgA, or IgY immunoglobulin molecule, any class (e.g., IgG1, IgG2, IgG3, IgG4, IgA1, and IgA2), or any subclass (e.g., IgG2a and IgG2b) of immunoglobulin molecule. In a particular embodiment, the constant regions comprise the amino acid sequences of the constant regions of a human IgG, IgE, IgM, IgD, IgA, or IgY immunoglobulin molecule, any class (e.g., IgG1, IgG2, IgG3, IgG4, IgA1, and IgA2), or any subclass (e.g., IgG2a and IgG2b) of immunoglobulin molecule.

The constant region of a human IgG1 heavy chain can comprise the following amino acid sequence:

(SEQ ID NO: 407)
ASTKGPSVFPLAPSSKSTSGGTAALGCLVKDYFPEPVTVSWNSGALTSGV

HTFPAVLQSSGLYSLSSVVTVPSSSLGTQTYICNVNHKPSNTKVDKKVEP

KSCDKTHTCPPCPAPELLGGPSVFLFPPKPKDTLMISRTPEVTCVVVDVS

HEDPEVKFNWYVDGVEVHNAKTKPREEQYNSTYRVVSVLTVLHQDWLNGK

EYKCKVSNKALPAPIEKTISKAKGQPREPQVYTLPPSRDELTKNQVSLTC

LVKGFYPSDIAVEWESNGQPENNYKTTPPVLDSDGSFFLYSKLTVDKSRW

QQGNVFSCSVMHEALHNHYTQKSLSLSPGK.

The constant region of a human IgG$_1$ heavy chain can be encoded by the following nucleotide sequence:

(SEQ ID NO: 408)
GCCTCCACCAAGGGCCCATCGGTCTTCCCCCTGGCACCCTCCTCCAAGAG

CACCTCTGGGGGCACAGCGGCCCTGGGCTGCCTGGTCAAGGACTACTTCC

CCGAACCGGTGACGGTGTCGTGGAACTCAGGCGCCCTGACCAGCGGCGTG

CACACCTTCCCGGCTGTCCTACAGTCCTCAGGACTCTACTCCCTCAGCAG

CGTGGTGACCGTGCCCTCCAGCAGCTTGGGCACCCAGACCTACATCTGCA

ACGTGAATCACAAGCCCAGCAACACCAAGGTGGACAAGAAAGTTGAGCCC

AAATCTTGTGACAAAACTCACACATGCCCACCGTGCCCAGCACCTGAACT

CCTGGGGGGACCGTCAGTCTTCCTCTTCCCCCCAAAACCCAAGGACACCC

TCATGATCTCCCGGACCCCTGAGGTCACATGCGTGGTGGTGGACGTGAGC

CACGAAGACCCTGAGGTCAAGTTCAACTGGTACGTGGACGGCGTGGAGGT

GCATAATGCCAAGACAAAGCCGCGGGAGGAGCAGTACAACAGCACGTACC

GGGTGGTCAGCGTCCTCACCGTCCTGCACCAGGACTGGCTGAATGGCAAG

GAGTACAAGTGCAAGGTCTCCAACAAAGCCCTCCCAGCCCCCATCGAGAA

AACCATCTCCAAAGCCAAAGGGCAGCCCCGAGAACCACAGGTGTACACCC

TGCCCCCATCCCGGGATGAGCTGACCAAGAACCAGGTCAGCCTGACCTGC

-continued

```
CTGGTCAAAGGCTTCTATCCCAGCGACATCGCCGTGGAGTGGGAGAGCAA

TGGGCAGCCGGAGAACAACTACAAGACCACGCCTCCCGTGCTGGACTCCG

ACGGCTCCTTCTTCCTCTACAGCAAGCTCACCGTGGACAAGAGCAGGTGG

CAGCAGGGGAACGTCTTCTCATGCTCCGTGATGCATGAGGCTCTGCACAA

CCACTACACGCAGAAGAGCCTCTCCCTGTCTCCGGGTAAA.
```

Non-limiting examples of human constant regions are described in the art, e.g., see Kabat E A et al., (1991) supra.

In certain embodiments, one, two, or more mutations (e.g., amino acid substitutions) are introduced into the Fc region of an antibody or antigen-binding fragment thereof described herein (e.g., CH2 domain (residues 231-340 of human $IgG_1$) and/or CH3 domain (residues 341-447 of human $IgG_1$) and/or the hinge region, with numbering according to the Kabat numbering system (e.g., the EU index in Kabat)) to alter one or more functional properties of the antibody or antigen-binding fragment thereof, such as serum half-life, complement fixation, Fc receptor binding, and/or antigen-dependent cellular cytotoxicity.

In certain embodiments, one, two, or more mutations (e.g., amino acid substitutions) are introduced into the hinge region of the Fc region (CH1 domain) such that the number of cysteine residues in the hinge region are altered (e.g., increased or decreased) as described in, e.g., U.S. Pat. No. 5,677,425. The number of cysteine residues in the hinge region of the CH1 domain may be altered to, e.g., facilitate assembly of the light and heavy chains, or to alter (e.g., increase or decrease) the stability of the antibody or antigen-binding fragment thereof.

In some embodiments, one, two, or more mutations (e.g., amino acid substitutions) are introduced into the Fc region of an antibody or antigen-binding fragment thereof described herein (e.g., CH2 domain (residues 231-340 of human IgG1) and/or CH3 domain (residues 341-447 of human IgG1) and/or the hinge region, with numbering according to the Kabat numbering system (e.g., the EU index in Kabat)) to increase or decrease the affinity of the antibody or antigen-binding fragment thereof for an Fc receptor (e.g., an activated Fc receptor) on the surface of an effector cell. Mutations in the Fc region that decrease or increase affinity for an Fc receptor and techniques for introducing such mutations into the Fc receptor or fragment thereof are known to one of skill in the art. Examples of mutations in the Fc receptor that can be made to alter the affinity of the antibody or antigen-binding fragment thereof for an Fc receptor are described in, e.g., Smith P et al., (2012) PNAS 109: 6181-6186, U.S. Pat. No. 6,737,056, and International Publication Nos. WO 02/060919; WO 98/23289; and WO 97/34631, which are incorporated herein by reference.

In a specific embodiment, one, two, or more amino acid mutations (i.e., substitutions, insertions or deletions) are introduced into an IgG constant domain, or FcRn-binding fragment thereof (preferably an Fc or hinge-Fc domain fragment) to alter (e.g., decrease or increase) half-life of the antibody or antigen-binding fragment thereof in vivo. See, e.g., International Publication Nos. WO 02/060919; WO 98/23289; and WO 97/34631; and U.S. Pat. Nos. 5,869,046, 6,121,022, 6,277,375 and 6,165,745 for examples of mutations that will alter (e.g., decrease or increase) the half-life of an antibody or antigen-binding fragment thereof in vivo. In some embodiments, one, two or more amino acid mutations (i.e., substitutions, insertions, or deletions) are introduced into an IgG constant domain, or FcRn-binding fragment thereof (preferably an Fc or hinge-Fc domain fragment) to decrease the half-life of the antibody or antigen-binding fragment thereof in vivo. In other embodiments, one, two or more amino acid mutations (i.e., substitutions, insertions or deletions) are introduced into an IgG constant domain, or FcRn-binding fragment thereof (preferably an Fc or hinge-Fc domain fragment) to increase the half-life of the antibody or antigen-binding fragment thereof in vivo. In a specific embodiment, the antibodies or antigen-binding fragments thereof may have one or more amino acid mutations (e.g., substitutions) in the second constant (CH2) domain (residues 231-340 of human IgG1) and/or the third constant (CH3) domain (residues 341-447 of human IgG1), with numbering according to the EU index in Kabat (Kabat E A et al., (1991) supra). In a specific embodiment, the constant region of the IgG1 comprises a methionine (M) to tyrosine (Y) substitution in position 252, a serine (S) to threonine (T) substitution in position 254, and a threonine (T) to glutamic acid (E) substitution in position 256, numbered according to the EU index as in Kabat. See U.S. Pat. No. 7,658,921, which is incorporated herein by reference. This type of mutant IgG, referred to as "YTE mutant" has been shown to display fourfold increased half-life as compared to wild-type versions of the same antibody (see Dall'Acqua W F et al., (2006) J Biol Chem 281: 23514-24). In certain embodiments, an antibody or antigen-binding fragment thereof comprises an IgG constant domain comprising one, two, three or more amino acid substitutions of amino acid residues at positions 251-257, 285-290, 308-314, 385-389, and 428-436, numbered according to the EU index as in Kabat.

In a further embodiment, one, two, or more amino acid substitutions are introduced into an IgG constant domain Fc region to alter the effector function(s) of the antibody or antigen-binding fragment thereof. For example, one or more amino acids selected from amino acid residues 234, 235, 236, 237, 297, 318, 320 and 322, numbered according to the EU index as in Kabat, can be replaced with a different amino acid residue such that the antibody or antigen-binding fragment thereof has an altered affinity for an effector ligand but retains the antigen-binding ability of the parent antibody. The effector ligand to which affinity is altered can be, for example, an Fc receptor or the C1 component of complement. This approach is described in further detail in U.S. Pat. Nos. 5,624,821 and 5,648,260. In some embodiments, the deletion or inactivation (through point mutations or other means) of a constant region domain may reduce Fc receptor binding of the circulating antibody or antigen-binding fragment thereof thereby increasing tumor localization. See, e.g., U.S. Pat. Nos. 5,585,097 and 8,591,886 for a description of mutations that delete or inactivate the constant domain and thereby increase tumor localization. In certain embodiments, one or more amino acid substitutions can be introduced into the Fc region to remove potential glycosylation sites on Fc region, which may reduce Fc receptor binding (see, e.g., Shields R L et al., (2001) J Biol Chem 276: 6591-604).

In certain embodiments, one or more amino acids selected from amino acid residues 329, 331, and 322 in the constant region, numbered according to the EU index as in Kabat, can be replaced with a different amino acid residue such that the antibody or antigen-binding fragment thereof has altered C1q binding and/or reduced or abolished complement dependent cytotoxicity (CDC). This approach is described in further detail in U.S. Pat. No. 6,194,551 (Idusogie et al). In some embodiments, one or more amino acid residues within amino acid positions 231 to 238 in the N-terminal region of the CH2 domain are altered to thereby alter the ability of the antibody to fix complement. This approach is described further in International Publication No. WO 94/29351. In certain embodiments, the Fc region is modified to increase the ability of the antibody or antigen-binding fragment thereof to mediate antibody dependent cellular cytotoxicity (ADCC) and/or to increase the affinity of the antibody or antigen-binding fragment thereof for an Fcy receptor by mutating one or more amino acids (e.g., introducing amino acid substitutions) at the following positions: 238, 239, 248, 249, 252, 254, 255, 256, 258, 265, 267, 268, 269, 270, 272, 276, 278, 280, 283, 285, 286, 289, 290, 292, 293, 294, 295, 296, 298, 301, 303, 305, 307, 309, 312, 315, 320, 322, 324, 326, 327, 328, 329, 330, 331, 333, 334, 335, 337, 338, 340, 360, 373, 376, 378, 382, 388, 389, 398, 414, 416, 419, 430, 434, 435, 437, 438, or 439, numbered according to the EU index as in Kabat. This approach is described further in International Publication No. WO 00/42072.

In certain embodiments, an antibody or antigen-binding fragment thereof described herein comprises the constant domain of an IgG1 with a mutation (e.g., substitution) at position 267, 328, or a combination thereof, numbered according to the EU index as in Kabat. In certain embodiments, an antibody or antigen-binding fragment thereof described herein comprises the constant domain of an IgG1 with a mutation (e.g., substitution) selected from the group consisting of S267E, L328F, and a combination thereof. In certain embodiments, an antibody or antigen-binding fragment thereof described herein comprises the constant domain of an IgG1 with a S267E/L328F mutation (e.g., substitution). In certain embodiments, an antibody or antigen-binding fragment thereof described herein comprising the constant domain of an IgG1 with a S267E/L328F mutation (e.g., substitution) has an increased binding affinity for FcγRIIA, FcγRIIB, or FcγRIIA and FcγRIIB.

Antibodies with reduced fucose content have been reported to have an increased affinity for Fc receptors, such as, e.g., FcγRIIIA Accordingly, in certain embodiments, an antibody or antigen-binding fragment thereof described herein has reduced fucose content or lacks fucose (i.e., is "afucosylated"). Such antibodies or antigen-binding fragments thereof can be produced using techniques known to one skilled in the art. For example, they can be expressed in cells deficient or lacking the ability to fucosylate. In a specific example, cell lines with a knockout of both alleles of α1,6-fucosyltransferase can be used to produce antibodies or antigen-binding fragments thereof with reduced fucose content. The Potelligent® system (Lonza) is an example of such a system that can be used to produce antibodies and antigen-binding fragments thereof with reduced fucose content. Alternatively, antibodies or antigen-binding fragments thereof with reduced fucose content or no fucose content can be produced by, e.g.: (i) culturing cells under conditions which prevent or reduce fucosylation; (ii) posttranslational removal of fucose (e.g., with a fucosidase enzyme); (iii) post-translational addition of the desired carbohydrate, e.g., after recombinant expression of a non-glycosylated glycoprotein; or (iv) purification of the glycoprotein so as to select for antibodies or antigen-binding fragments thereof which are not fucsoylated. See, e.g., Longmore G D & Schachter H (1982) Carbohydr Res 100: 365-92 and Imai-Nishiya H et al., (2007) BMC Biotechnol. 7: 84 for methods for producing antibodies thereof with no fucose content or reduced fucose content. See also Example 8 herein describing the production of afucosylated B7-H4 antibodies.

In some embodiments, the B7-H4 antibody or antigen-binding fragment thereof has enhanced ADCC activity in vitro compared to fucosylated B7-H4 antibodies or antigen-binding fragments thereof having the same amino acid sequence. In some embodiments, the afucosylated B7-H4 antibodies or antigen-binding fragments thereof cause specific lysis that is at least 10, at least 15, at least 20, at least 25, at least 30, at least 35, at least 40, at least 45, at least 50, at least 60, at least 65, at least 70, or at least 75 percentage points greater than specific lysis with fucosylated B7-H4 antibodies.

In some embodiments, the B7-H4 antibody or antigen-binding fragment thereof has enhanced affinity for Fc gamma RIIIA compared to fucosylated B7-H4 antibodies or antigen-binding fragments thereof having the same amino acid sequence. In some embodiments, the afucosylated B7-H4 antibodies or antigen-binding fragments thereof bind to Fc gamma RIIIA with at least 2-fold, at least 3-fold, at least 4-fold, at least 5-fold, at least 7-fold, at least 10-fold, at least 12-fold, at least 15-fold, at least 17-fold, or at least 20-fold greater affinity than fucosylated B7-H4 antibodies or antigen-binding fragments thereof. In some embodiments, affinity for Fc gamma RIIIA is determined using surface plasmon resonance. In some embodiments, Fc gamma RIIIA is selected from Fc gamma RIIIA(V158) and Fc gamma RIIIA(F158). In some embodiments, Fc gamma RIIIA is Fc gamma RIIIA(V158).

In some embodiments, the presence of fucose can be determined by a method comprising high performance liquid chromatography (HPLC), capillary electrophoresis, or MALDI-TOF mass spectrometry.

In specific embodiments, an antibody or antigen-binding fragment thereof (i) comprises the CDR sequences of 20502 (e.g., the amino acid sequences of SEQ ID NOs:458-463), the VH and VL sequences of 20502 (the amino acid sequences of SEQ ID NOs:464 and 42, respectively), or the heavy and light chain sequences of 20502 (the amino acid sequences of SEQ ID NOs:469 and 44, respectively) and (ii) is afucosylated.

In specific embodiments, a composition comprises antibodies or antigen-binding fragments thereof that (i) comprises the CDR sequences of 20502 (e.g., the amino acid sequences of SEQ ID NOs:458-463), the VH and VL sequences of 20502 (the amino acid sequences of SEQ ID NOs:464 and 42, respectively), or the heavy and light chain sequences of 20502 (the amino acid sequences of SEQ ID NOs:469 and 44, respectively) and (ii) are afucosylated, e.g., wherein at least 95% of the antibodies in the composition are afucosylated or wherein fucosylation is undetectable in the composition.

In specific embodiments, an antibody or antigen-binding fragment thereof (i) comprises the CDR sequences of 20502.1 (e.g., the amino acid sequences of SEQ ID NOs: 35-40), the VH and VL sequences of 20502.1 (the amino acid sequences of SEQ ID NOs:41 and 42, respectively), or the heavy and light chain sequences of 20502.1 (the amino acid sequences of SEQ ID NOs:43 and 44, respectively) and (ii) is afucosylated.

In specific embodiments, a composition comprises antibodies or antigen-binding fragments thereof that (i) comprises the CDR sequences of 20502.1 (e.g., the amino acid sequences of SEQ ID NOs:35-40), the VH and VL sequences of 20502.1 (the amino acid sequences of SEQ ID NOs:41 and 42, respectively), or the heavy and light chain sequences of 20502.1 (the amino acid sequences of SEQ ID NOs:43 and 44, respectively) and (ii) are afucosylated, e.g., wherein at least 95% of the antibodies in the composition are afucosylated or wherein fucosylation is undetectable in the composition.

In specific embodiments, an antibody or antigen-binding fragment thereof (i) comprises the CDR sequences of 22213 (e.g., the amino acid sequences of SEQ ID NOs:65-70), the VH and VL sequences of 22213 (the amino acid sequences of SEQ ID NOs:71 and 72, respectively), or the heavy and light chain sequences of 22213 (the amino acid sequences of SEQ ID NOs:73 and 74, respectively) and (ii) is afucosylated.

In specific embodiments, a composition comprises antibodies or antigen-binding fragments thereof that (i) comprises the CDR sequences of 22213 (e.g., the amino acid sequences of SEQ ID NOs:65-70), the VH and VL sequences of 22213 (the amino acid sequences of SEQ ID NOs:71 and 72, respectively), or the heavy and light chain sequences of 22213 (the amino acid sequences of SEQ ID NOs:73 and 74, respectively) and (ii) are afucosylated, e.g., wherein at least 95% of the antibodies in the composition are afucosylated or wherein fucosylation is undetectable in the composition.

Engineered glycoforms may be useful for a variety of purposes, including but not limited to enhancing or reducing effector function. Methods for generating engineered glycoforms in an antibody or antigen-binding fragment thereof described herein include but are not limited to those disclosed, e.g., in Umalia P et al., (1999) Nat Biotechnol 17: 176-180; Davies J et al., (2001) Biotechnol Bioeng 74: 288-294; Shields R L et al., (2002) J Biol Chem 277: 26733-26740; Shinkawa T et al., (2003) J Biol Chem 278: 3466-3473; Niwa R et al., (2004) Clin Cancer Res 1: 6248-6255; Presta L G et al., (2002) Biochem Soc Trans 30: 487-490; Kanda Y et al., (2007) Glycobiology 17: 104-118; U.S. Pat. Nos. 6,602,684; 6,946,292; and 7,214,775; U.S. Patent Publication Nos. US 2007/0248600; 2007/0178551; 2008/0060092; and 2006/0253928; International Publication Nos. WO 00/61739; WO 01/292246; WO 02/311140; and WO 02/30954; Potillegent™ technology (Biowa, Inc. Princeton, N.J.); and GlycoMAb® glycosylation engineering technology (Glycart biotechnology AG, Zurich, Switzerland). See also, e.g., Ferrara C et al., (2006) Biotechnol Bioeng 93: 851-861; International Publication Nos. WO 07/039818; WO 12/130831; WO 99/054342; WO 03/011878; and WO 04/065540.

In certain embodiments, any of the constant region mutations or modifications described herein can be introduced into one or both heavy chain constant regions of an antibody or antigen-binding fragment thereof described herein having two heavy chain constant regions.

In another particular embodiment, an antibody or antigen-binding fragment thereof described herein, which immunospecifically binds to B7-H4 (e.g., human B7-H4), comprises a heavy chain and a light chain, wherein (i) the heavy chain comprises a VH domain comprising the VH CDR1, VL CDR2, and VL CDR3 amino acid sequences of an antibody listed in Table 1 (e.g., SEQ ID NOs:458-460, 35-37, or 65-67); (ii) the light chain comprises a VL domain comprising the VL CDR1, VH CDR2, and VH CDR3 amino acid sequences of the same antibody listed in Table 2 (e.g., SEQ ID NOs:461-463, 38-40, or 68-70); (iii); and the heavy chain further comprises a constant heavy chain domain comprising the amino acid sequence of the constant domain of a human IgG1 heavy chain (iv); the light chain further comprises a constant light chain domain comprising the amino acid sequence of the constant domain of a human kappa light chain.

In another particular embodiment, an antibody or antigen-binding fragment thereof described herein, which immunospecifically binds to B7-H4 (e.g., human B7-H4), comprises a heavy chain and a light chain, wherein (i) the heavy chain comprises a VH domain comprising the amino acid sequence of an antibody listed in Table 3 (e.g., SEQ ID NO:464, 41, or 71); (ii) the light chain comprises a VL domain comprising the amino acid sequence of the same antibody listed in Table 4 (e.g., SEQ ID NO:42 or 73); (iii); and the heavy chain further comprises a constant heavy chain domain comprising the amino acid sequence of the constant domain of a human IgG1 heavy chain (iv); the light chain further comprises a constant light chain domain comprising the amino acid sequence of the constant domain of a human kappa light chain.

In specific embodiments, an antibody or antigen-binding fragment thereof described herein, which immunospecifically binds to B7-H4 (e.g., human B7-H4) exhibits T cell checkpoint blockade activity. Exemplary methods of measuring T cell checkpoint blockade activity are provided herein in Examples 7 and 11. In specific embodiments, an antibody or antigen-binding fragment thereof described herein, which immunospecifically binds to B7-H4 (e.g., human B7-H4) increases interferon-gamma (IFNγ) production in T cells. Exemplary methods of measuring IFNγ production are provided herein in Examples 7 and 11. In specific embodiments, an antibody or antigen-binding fragment thereof described herein, which immunospecifically binds to B7-H4 (e.g., human B7-H4) increases T cell proliferation. Exemplary methods of measuring T-cell proliferation are provided herein in Example 7. In specific embodiments, an antibody or antigen-binding fragment thereof described herein, which immunospecifically binds to B7-H4 (e.g., human B7-H4) increases CD4+ T cell proliferation. Exemplary methods of measuring CD4+ T-cell proliferation are provided herein in Example 7. In specific embodiments, an antibody or antigen-binding fragment thereof described herein, which immunospecifically binds to B7-H4 (e.g., human B7-H4) increases CD8+ T cell proliferation. Exemplary methods of measuring CD8+ T-cell proliferation are provided herein in Example 7.

In specific embodiments, an antibody or antigen-binding fragment thereof described herein, which immunospecifically binds to B7-H4 (e.g., human B7-H4) exhibits antibody-dependent cellular cytotoxicity (ADCC) activity. In specific embodiments, an antibody or antigen-binding fragment thereof described herein, which immunospecifically binds to B7-H4 (e.g., human B7-H4) exhibits antibody-dependent cellular cytotoxicity (ADCC) activity on cell lines with at least 300,000 cell surface B7-H4 molecules (e.g., SK-BR-3 cells). In specific embodiments, an antibody or antigen-binding fragment thereof described herein, which immunospecifically binds to B7-H4 (e.g., human B7-H4) exhibits antibody-dependent cellular cytotoxicity (ADCC) activity on cell lines with at least 100,000 cell surface B7-H4 molecules (e.g., HCC 1569 cells). In specific embodiments, an antibody or antigen-binding fragment thereof described herein, which immunospecifically binds to B7-H4 (e.g., human B7-H4) exhibits antibody-dependent cellular cytotoxicity (ADCC) activity on cell lines with at least 50,000 cell surface B7-H4 molecules (e.g., ZR-75-1 cells). In specific embodiments, an antibody or antigen-binding fragment thereof described herein, which immunospecifically binds to B7-H4 (e.g., human B7-H4) exhibits antibody-dependent cellular cytotoxicity (ADCC) activity on cell lines with at least 30,000 cell surface B7-H4 molecules (e.g., MDA-MB-468 cells). In specific embodiments, an antibody or antigen-binding fragment thereof described herein, which immunospecifically binds to B7-H4 (e.g., human B7-H4) exhibits antibody-dependent cellular cytotoxicity (ADCC)

activity on cell lines with at least 15,000 cell surface B7-H4 molecules (e.g., HCC1964 cells). Exemplary methods of measuring ADCC activity are provided herein in Example 13.

In specific embodiments, an antibody or antigen-binding fragment thereof described herein, which immunospecifically binds to B7-H4 (e.g., human B7-H4), comprises framework regions (e.g., framework regions of the VH domain and/or VL domain) that are human framework regions or derived from human framework regions. Non-limiting examples of human framework regions are described in the art, e.g., see Kabat E A et al., (1991) supra). In certain embodiment, an antibody or antigen-binding fragment thereof described herein comprises framework regions (e.g., framework regions of the VH domain and/or VL domain) that are primate (e.g., non-human primate) framework regions or derived from primate (e.g., non-human primate) framework regions.

In certain embodiments, an antibody or antigen-binding fragment thereof described herein, which specifically binds to B7-H4 (e.g., human B7-H4), comprises one, two, or more VH framework regions (FRs) having the amino acid sequences described herein for an antibody set forth in Table 5, supra (e.g., SEQ ID NOs: 465, 466, 467, and/or 469; SEQ ID NOs:235, 236, 237 and/or 238; or SEQ ID NOs:265, 266, 267, and/or 268). In some embodiments, an antibody or antigen-binding fragment thereof described herein, which specifically binds to B7-H4 (e.g., human B7-H4), comprises one, two, or more VL framework regions (FRs) having the amino acid sequences described herein for an antibody set forth in Table 6, supra (e.g., SEQ ID NOs:239, 240, 241, and/or 242 or SEQ ID NOs:269, 270, 271, and/or 272). In specific embodiments, an antibody or antigen-binding fragment thereof described herein, which specifically binds to B7-H4 (e.g., human B7-H4), comprises one, two, or more VH framework regions having the amino acid sequences described herein for an antibody set forth in Table 5, supra, and one, two, or more VL framework regions having the amino acid sequences described herein for the same antibody set forth in Table 6, supra (e.g., (i) SEQ ID NOs: 465, 466, 467, and/or 469 and SEQ ID NOs:239, 240, 241, and/or 242; (ii) SEQ ID NOs:235, 236, 237 and/or 238 and SEQ ID NOs:239, 240, 241, and/or 242 or (iii) SEQ ID NOs:265, 266, 267, and/or 268 and SEQ ID NOs:269, 270, 271, and/or 272).

In certain embodiments, an antibody or antigen-binding fragment thereof described herein, which specifically binds to B7-H4 (e.g., human B7-H4), comprises VH framework regions (FRs) having at least 70%, at least 75%, at least 80%, at least 85%, at least 90%, at least 95%, or at least 98% sequence identity to the VH framework regions described herein in Table 5, supra. In certain embodiments, an antibody or antigen-binding fragment thereof described herein, which specifically binds to B7-H4 (e.g., human B7-H4), comprises VL framework regions (FRs) having at least 70%, at least 75%, at least 80%, at least 85%, at least 90%, at least 95%, or at least 98% sequence identity to the VL framework regions described herein Table 6, supra. In some embodiments, an antibody or antigen-binding fragment thereof described herein, which specifically binds to B7-H4 (e.g., human B7-H4), comprises VH framework regions (FRs) having at least 70%, at least 75%, at least 80%, at least 85%, at least 90%, at least 95%, or at least 98% sequence identity to the VH framework regions described herein Table 5, supra, and VL framework regions (FRs) having at least 70%, at least 75%, at least 80%, at least 85%, at least 90%, at least 95%, or at least 98% sequence identity to the VL framework regions described herein Table 6, supra.

In certain embodiments, an antibody or antigen-binding fragment thereof described herein, which immunospecifically binds to B7-H4 (e.g., human B7-H4), comprises a VH domain having at least 70%, at least 75%, at least 80%, at least 85%, at least 90%, at least 95%, or at least 98% sequence identity to the amino acid sequence of the VH domain of 20502 or 22213 (e.g., SEQ ID NO:464 or 71), wherein the antibody comprises VH CDRs that are identical to the VH CDRs of 20502 or 22213 (e.g., SEQ ID NOs: 458-460 or 65-67).

In certain embodiments, an antibody or antigen-binding fragment thereof described herein, which immunospecifically binds to B7-H4 (e.g., human B7-H4), comprises a VL domain having at least 70%, at least 75%, at least 80%, at least 85%, at least 90%, at least 95%, or at least 98% sequence identity to the amino acid sequence of the VL domain of 20502 or 22213 (e.g., SEQ ID NO:42 or 72), wherein the antibody or antigen-binding fragment thereof comprises VL CDRs that are identical to the VL CDRs of 20502 or 22213 (e.g., SEQ ID NO:461-463 or 68-70).

In certain embodiments, an antibody or antigen-binding fragment thereof described herein, which immunospecifically binds to B7-H4 (e.g., human B7-H4), comprises: (i) a VH domain having at least 70%, at least 75%, at least 80%, at least 85%, at least 90%, at least 95%, or at least 98% sequence identity to the amino acid sequence of the VH domain of 20502 or 22213 (e.g., SEQ ID NO:464 or 71); and (ii) a VL domain having at least 70%, at least 75%, at least 80%, at least 85%, at least 90%, at least 95%, or at least 98% sequence identity to the amino acid sequence of the VL domain of 20502 or 22213 (e.g., SEQ ID NO:42 or 72), wherein the antibody comprises VH CDRs and VL CDRs that are identical to the VH CDRs and VL CDRs of 20502 or 22213 (e.g., SEQ ID NOs:458-463 or SEQ ID NOs:65-70).

In another aspect, provided herein are antibodies or antigen-binding fragments thereof that bind the same epitope of B7-H4 (e.g., an epitope of human B7-H4) as an antibody or antigen-binding fragment thereof described herein (e.g., 20502 or 22213).

In certain embodiments, an antibody or antigen-binding fragment thereof described herein, which immunospecifically binds to B7-H4 (e.g., human B7-H4), comprises a VH domain having at least 70%, at least 75%, at least 80%, at least 85%, at least 90%, at least 95%, or at least 98% sequence identity to the amino acid sequence of the VH domain of 20502.1 or 22213 (e.g., SEQ ID NO:41 or 71), wherein the antibody comprises VH CDRs that are identical to the VH CDRs of 20502.1 or 22213 (e.g., SEQ ID NOs: 35-37 or 65-67).

In certain embodiments, an antibody or antigen-binding fragment thereof described herein, which immunospecifically binds to B7-H4 (e.g., human B7-H4), comprises a VL domain having at least 70%, at least 75%, at least 80%, at least 85%, at least 90%, at least 95%, or at least 98% sequence identity to the amino acid sequence of the VL domain of 20502.1 or 22213 (e.g., SEQ ID NO:42 or 72), wherein the antibody or antigen-binding fragment thereof comprises VL CDRs that are identical to the VL CDRs of 20502.1 or 22213 (e.g., SEQ ID NO:38-40 or 68-70).

In certain embodiments, an antibody or antigen-binding fragment thereof described herein, which immunospecifically binds to B7-H4 (e.g., human B7-H4), comprises: (i) a VH domain having at least 70%, at least 75%, at least 80%, at least 85%, at least 90%, at least 95%, or at least 98% sequence identity to the amino acid sequence of the VH domain of 20502.1 or 22213 (e.g., SEQ ID NO:41 or 71); and (ii) a VL domain having at least 70%, at least 75%, at least 80%, at least 85%, at least 90%, at least 95%, or at least 98% sequence identity to the amino acid sequence of the VL domain of 20502.1 or 22213 (e.g., SEQ ID NO:42 or 72), wherein the antibody comprises VH CDRs and VL CDRs that are identical to the VH CDRs and VL CDRs of 20502.1 or 22213 (e.g., SEQ ID NOs:35-40 or SEQ ID NOs:65-70).

In another aspect, provided herein are antibodies or antigen-binding fragments thereof that bind the same epitope of B7-H4 (e.g., an epitope of human B7-H4) as an antibody or antigen-binding fragment thereof described herein (e.g., 20502.1 or 22213).

Competition binding assays can be used to determine whether two antibodies bind to overlapping epitopes. Competitive binding can be determined in an assay in which the immunoglobulin under test inhibits specific binding of a reference antibody to a common antigen, such as B7-H4. Numerous types of competitive binding assays are known, for example: solid phase direct or indirect radioimmunoassay (RIA), solid phase direct or indirect enzyme immunoassay (EIA), sandwich competition assay (see Stahli C et al., (1983) Methods Enzymol 9: 242-253); solid phase direct biotin-avidin EIA (see Kirkland T N et al., (1986) J Immunol 137: 3614-9); solid phase direct labeled assay, solid phase direct labeled sandwich assay (see Harlow E & Lane D, (1988) Antibodies: A Laboratory Manual, Cold Spring Harbor Press); solid phase direct label RIA using I-125 label (see Morel G A et al., (1988) Mol Immunol 25(1): 7-15); solid phase direct biotin-avidin EIA (Cheung R C et al., (1990) Virology 176: 546-52); and direct labeled RIA. (Moldenhauer G et al., (1990) Scand J Immunol 32: 77-82). Typically, such an assay involves the use of purified antigen (e.g., B7-H4 such as human B7-H4) bound to a solid surface or cells bearing either of these, an unlabeled test immunoglobulin and a labeled reference immunoglobulin. Competitive inhibition can be measured by determining the amount of label bound to the solid surface or cells in the presence of the test immunoglobulin. Usually the test immunoglobulin is present in excess. Usually, when a competing antibody is present in excess, it will inhibit specific binding of a reference antibody to a common antigen by at least 50-55%, 55-60%, 60-65%, 65-70%, 70-75% or more. A competition binding assay can be configured in a large number of different formats using either labeled antigen or labeled antibody. In a common version of this assay, the antigen is immobilized on a 96-well plate. The ability of unlabeled antibodies to block the binding of labeled antibodies to the antigen is then measured using radioactive or enzyme labels. For further details see, for example, Wagener C et al., (1983) J Immunol 130: 2308-2315; Wagener C et al., (1984) J Immunol Methods 68: 269-274; Kuroki M et al., (1990) Cancer Res 50: 4872-4879; Kuroki M et al., (1992) Immunol Invest 21: 523-538; Kuroki M et al., (1992) Hybridoma 11: 391-407 and Antibodies: A Laboratory Manual, Ed Harlow E & Lane D editors supra, pp. 386-389.

In one embodiment, a competition assay is performed using surface plasmon resonance (BIAcore®), e.g., by an 'in tandem approach' such as that described by Abdiche Y N et al., (2009) Analytical Biochem 386: 172-180, whereby B7-H4 antigen is immobilized on the chip surface, for example, a CM5 sensor chip and the anti-B7-H4 antibodies are then run over the chip. To determine if an antibody or antigen-binding fragment thereof competes with an anti-B7-H4 antibody described herein, the anti-B7-H4 antibody is first run over the chip surface to achieve saturation and then the potential, competing antibody is added. Binding of the competing antibody or antigen-binding fragment thereof can then be determined and quantified relative to a non-competing control.

In one embodiment, Fortebio Octet competition binding (e.g., as described in Example 2 below) is used to determine that a B7-H4 antibody or antigen-binding fragment thereof competitively inhibits the binding of another B7-H4 antibody or antigen-binding fragment thereof to B7-H4.

In another aspect, provided herein are antibodies that competitively inhibit (e.g., in a dose dependent manner) an antibody or antigen-binding fragment thereof described herein (e.g., 20502, 20502.1 or 22213) from binding to B7-H4 (e.g., human B7-H4), as determined using assays known to one of skill in the art or described herein (e.g., ELISA competitive assays, or suspension array or surface plasmon resonance assay).

In specific aspects, provided herein is an antibody or antigen-binding fragment which competitively inhibits (e.g., in a dose dependent manner) binding to B7-H4 (e.g., human B7-H4), of an antibody comprising a VH domain having the amino acid sequence set forth in SEQ ID NO:464, and a VL domain having the amino acid sequence set for the in SEQ ID NO:42.

In specific aspects, provided herein is an antibody or antigen-binding fragment which competitively inhibits (e.g., in a dose dependent manner) binding to B7-H4 (e.g., human B7-H4), of an antibody comprising a VH domain having the amino acid sequence set forth in SEQ ID NO:41, and a VL domain having the amino acid sequence set for the in SEQ ID NO:42.

In specific aspects, provided herein is an antibody or antigen-binding fragment which competitively inhibits (e.g., in a dose dependent manner) binding to B7-H4 (e.g., human B7-H4), of an antibody comprising a VH domain having the amino acid sequence set forth in SEQ ID NO:71, and a VL domain having the amino acid sequence set for the in SEQ ID NO:72.

In specific aspects, provided herein is an antibody or antigen-binding fragment thereof which competitively inhibits (e.g., in a dose dependent manner) binding to B7-H4 (e.g., human B7-H4), with an antibody comprising (i) a VH domain comprising a VH CDR1, VH CDR2, and VH CDR3 having the amino acid sequences of the VH CDRs listed in Table 1; and (ii) a VL domain comprising a VL CDR1, VL CDR2, and VL CDR3 having the amino acid sequences of the CDRs listed in Table 2.

In specific aspects, provided herein is an antibody or antigen-binding fragment thereof, which immunospecifically binds to the same B7-H4 (e.g., human B7-H4) epitope as that of 20502, 20502.1, or 22213.

In another specific embodiment, an antibody or antigen-binding fragment thereof described herein, immunospecifically binds to the same B7-H4 (e.g., human B7-H4) epitope as that of an antibody comprising (i) a VH domain comprising a VH CDR1, VH CDR2, and VH CDR3 having the amino acid sequences of the CDRs listed in Table 1 and (ii) a VL domain comprising a VL CDR1, VL CDR2, and VL CDR3 having the amino acid sequences of the CDRs listed in Table 2.

In a specific aspect, an antigen-binding fragment as described herein, which immunospecifically binds to B7-H4 (e.g., human B7-H4), is selected from the group consisting of a Fab, Fab', F(ab')2, and scFv, wherein the Fab, Fab', F(ab')2, or scFv comprises a heavy chain variable region sequence and a light chain variable region sequence of an anti-B7-H4 antibody or antigen-binding fragment thereof as described herein. A Fab, Fab', F(ab')2, or scFv can be produced by any technique known to those of skill in the art, including, but not limited to, those discussed in Section 5.3, infra. In certain embodiments, the Fab, Fab', F(ab')2, or scFv further comprises a moiety that extends the half-life of the antibody in vivo. The moiety is also termed a "half-life extending moiety." Any moiety known to those of skill in the art for extending the half-life of a Fab, Fab', F(ab')2, or scFv in vivo can be used. For example, the half-life extending moiety can include a Fc region, a polymer, an albumin, or an albumin binding protein or compound. The polymer can include a natural or synthetic, optionally substituted straight or branched chain polyalkylene, polyalkenylene, polyoxylalkylene, polysaccharide, polyethylene glycol, polypropylene glycol, polyvinyl alcohol, methoxypolyethylene glycol, lactose, amylose, dextran, glycogen, or derivative thereof. Substituents can include one or more hydroxy, methyl, or methoxy groups. In certain embodiments, the Fab, Fab', F(ab')2, or scFv can be modified by the addition of one or more C-terminal amino acids for attachment of the half-life extending moiety. In certain embodiments the half-life extending moiety is polyethylene glycol or human serum albumin. In certain embodiments, the Fab, Fab', F(ab')2, or scFv is fused to a Fc region.

An anti-B7-H4 antibody or antigen-binding fragment thereof can be fused or conjugated (e.g., covalently or noncovalently linked) to a detectable label or substance. Examples of detectable labels or substances include enzyme labels, such as, glucose oxidase; radioisotopes, such as iodine ($125I$, $121I$), carbon ($14C$), sulfur ($35S$), tritium ($3H$), indium ($121In$), and technetium ($99Tc$); luminescent labels, such as luminol; and fluorescent labels, such as fluorescein and rhodamine, and biotin. Such labeled antibodies or antigen-binding fragments thereof can be used to detect B7-H4 (e.g., human B7-H4) protein. See, e.g., Section 5.5.2, infra.

Antibody Production

Antibodies and antigen-binding fragments thereof that immunospecifically bind to B7-H4 (e.g., human B7-H4) can be produced by any method known in the art for the synthesis of antibodies and antigen-binding fragments thereof, for example, by chemical synthesis or by recombinant expression techniques. The methods described herein employ, unless otherwise indicated, conventional techniques in molecular biology, microbiology, genetic analysis, recombinant DNA, organic chemistry, biochemistry, PCR, oligonucleotide synthesis and modification, nucleic acid hybridization, and related fields within the skill of the art. These techniques are described, for example, in the references cited herein and are fully explained in the literature. See, e.g., Sambrook J et al., (2001) Molecular Cloning: A Laboratory Manual, Cold Spring Harbor Laboratory Press, Cold Spring Harbor, N.Y.; Ausubel F M et al., Current Protocols in Molecular Biology, John Wiley & Sons (1987 and annual updates); Current Protocols in Immunology, John Wiley & Sons (1987 and annual updates) Gait (ed.) (1984) Oligonucleotide Synthesis: A Practical Approach, IRL Press; Eckstein (ed.) (1991) Oligonucleotides and Analogues: A Practical Approach, IRL Press; Birren B et al., (eds.) (1999) Genome Analysis: A Laboratory Manual, Cold Spring Harbor Laboratory Press.

In a certain aspect, provided herein is a method of making an antibody or antigen-binding fragment which immunospecifically binds to B7-H4 (e.g., human B7-H4) comprising culturing a cell or host cell described herein. In a certain aspect, provided herein is a method of making an antibody or antigen-binding fragment thereof which immunospecifically binds to B7-H4 (e.g., human B7-H4) comprising expressing (e.g., recombinantly expressing) the antibody or antigen-binding fragment thereof using a cell or host cell described herein (e.g., a cell or a host cell comprising polynucleotides encoding an antibody or antigen-binding fragment thereof described herein). In a particular embodiment, the cell is an isolated cell. In a particular embodiment, the exogenous polynucleotides have been introduced into the cell. In a particular embodiment, the method further comprises the step of purifying the antibody or antigen-binding fragment obtained from the cell or host cell.

Methods for producing polyclonal antibodies are known in the art (see, for example, Chapter 11 in: Short Protocols in Molecular Biology, (2002) 5th Ed., Ausubel F M et al., eds., John Wiley and Sons, New York).

Monoclonal antibodies or antigen-binding fragments thereof can be prepared using a wide variety of techniques known in the art including the use of hybridoma, recombinant, and phage display technologies, yeast-based presentation technologies, or a combination thereof. For example, monoclonal antibodies or antigen-binding fragments thereof can be produced using hybridoma techniques including those known in the art and taught, for example, in Harlow E & Lane D, Antibodies: A Laboratory Manual, (Cold Spring Harbor Laboratory Press, 2nd ed. 1988); Hammerling G J et al., in: Monoclonal Antibodies and T-Cell Hybridomas 563 681 (Elsevier, N.Y., 1981), or as described in Kohler G & Milstein C (1975) Nature 256: 495. Examples of yeast-based presentation methods that can be employed to select and generate the antibodies described herein include those disclosed in, for example, WO2009/036379A2; WO2010/105256; and WO2012/009568, each of which is herein incorporated by reference in its entirety.

In specific embodiments, a monoclonal antibody or antigen-binding fragment is an antibody or antigen-binding fragment produced by a clonal cell (e.g., hybridoma or host cell producing a recombinant antibody or antigen-binding fragment), wherein the antibody or antigen-binding fragment immunospecifically binds to B7-H4 (e.g., human B7-H4) as determined, e.g., by ELISA or other antigen-binding assays known in the art or in the Examples provided herein. In particular embodiments, a monoclonal antibody or antigen-binding fragment thereof can be a chimeric or a humanized antibody or antigen-binding fragment thereof. In certain embodiments, a monoclonal antibody or antigen-binding fragment thereof can be a Fab fragment or a F(ab')2 fragment. Monoclonal antibodies or antigen-binding fragments thereof described herein can, for example, be made by the hybridoma method as described in Kohler G & Milstein C (1975) Nature 256: 495 or can, e.g., be isolated from phage libraries using the techniques as described herein, for example. Other methods for the preparation of clonal cell lines and of monoclonal antibodies and antigen-binding fragments thereof expressed thereby are well known in the art (see, for example, Chapter 11 in: Short Protocols in Molecular Biology, (2002) 5th Ed., Ausubel F M et al., supra).

Antigen-binding fragments of antibodies described herein can be generated by any technique known to those of skill in the art. For example, Fab and F(ab')2 fragments described herein can be produced by proteolytic cleavage of immunoglobulin molecules, using enzymes such as papain (to produce Fab fragments) or pepsin (to produce F(ab')2 fragments). A Fab fragment corresponds to one of the two identical arms of a tetrameric antibody molecule and contains the complete light chain paired with the VH and CH1 domains of the heavy chain. A F(ab')2 fragment contains the two antigen-binding arms of a tetrameric antibody molecule linked by disulfide bonds in the hinge region.

Further, the antibodies or antigen-binding fragments thereof described herein can also be generated using various phage display and/or yeast-based presentation methods known in the art. In phage display methods, proteins are displayed on the surface of phage particles which carry the polynucleotide sequences encoding them. In particular, DNA sequences encoding VH and VL domains are amplified from animal cDNA libraries (e.g., human or murine cDNA libraries of affected tissues). The DNA encoding the VH and VL domains are recombined together with a scFv linker by PCR and cloned into a phagemid vector. The vector is electroporated in *E. coli* and the *E. coli* is infected with helper phage. Phage used in these methods are typically filamentous phage including fd and M13, and the VH and VL domains are usually recombinantly fused to either the phage gene III or gene VIII. Phage expressing an antibody or antigen-binding fragment thereof that binds to a particular antigen can be selected or identified with antigen, e.g., using labeled antigen or antigen bound or captured to a solid surface or bead. Examples of phage display methods that can be used to make the antibodies or fragments described herein include those disclosed in Brinkman U et al., (1995) J Immunol Methods 182: 41-50; Ames R S et al., (1995) J Immunol Methods 184: 177-186; Kettleborough C A et al., (1994) Eur J Immunol 24: 952-958; Persic L et al., (1997) Gene 187: 9-18; Burton D R & Barbas C F (1994) Advan Immunol 57: 191-280; PCT Application No. PCT/GB91/001134; International Publication Nos. WO 90/02809, WO 91/10737, WO 92/01047, WO 92/18619, WO 93/1 1236, WO 95/15982, WO 95/20401, and WO 97/13844; and U.S. Pat. Nos. 5,698,426, 5,223,409, 5,403,484, 5,580,717, 5,427,908, 5,750,753, 5,821,047, 5,571,698, 5,427,908, 5,516,637, 5,780,225, 5,658,727, 5,733,743, and 5,969,108.

A humanized antibody or antigen-binding fragment thereof can be selected from any class of immunoglobulins, including IgM, IgG, IgD, IgA and IgE, and any isotype, including IgG1, IgG2, IgG3 and IgG4.

1.2.1 Polynucleotides

In certain aspects, provided herein are polynucleotides comprising a nucleotide sequence encoding an antibody or antigen-binding fragment thereof described herein or a domain thereof (e.g., a variable light chain region and/or variable heavy chain region) that immunospecifically binds to a B7-H4 (e.g., human B7-H4) antigen, and vectors, e.g., vectors comprising such polynucleotides for recombinant expression in host cells (e.g., *E. coli* and mammalian cells).

In particular aspects, provided herein are polynucleotides comprising nucleotide sequences encoding antibodies or antigen-binding fragments thereof, which immunospecifically bind to a B7-H4 polypeptide (e.g., human B7-H4) and comprise an amino acid sequence as described herein, as well as antibodies or antigen-binding fragments that compete with such antibodies or antigen-binding fragments for binding to a B7-H4 polypeptide (e.g., in a dose-dependent manner), or which bind to the same epitope as that of such antibodies or antigen-binding fragments.

Also provided herein is a polynucleotide comprising a nucleotide sequence encoding a polypeptide comprising a sequence selected from the group consisting of SEQ ID NOs:11, 12, 21, 22, 31, 32, 41, 464, 42, 51, 52, 61, 62, 71, 72, 81, 82, 91, 92, 101, 102, 111, 112, 121, 122, 131, 132, 141, 142, 151, 152, 161, 162, 171, 172, 181, 182, 191, 192, 201, and 202. In some embodiments, an antibody or antigen-binding fragment thereof comprising the polypeptide immunospecifically binds to B7-H4.

Also provided herein is a polynucleotide comprising a nucleotide sequence encoding a polypeptide comprising a sequence selected from the group consisting of SEQ ID NOs:13, 14, 23, 24, 33, 34, 43, 469, 44, 53, 54, 63, 64, 73, 74, 83, 84, 93, 94, 103, 104, 113, 114, 123, 124, 133, 134, 143, 144, 153, 154, 163, 164, 173, 174, 183, 184, 193, 194, 203, and 204. In some embodiments, an antibody or antigen-binding fragment thereof comprising the polypeptide immunospecifically binds to B7-H4.

Also provided herein are polynucleotides comprising a variable heavy chain-encoding nucleotide sequence shown in Table 9, e.g., wherein an antibody or antigen-binding fragment thereof comprising the encoded variable heavy chain binds to B7-H4.

TABLE 9

Variable heavy chain-encoding polynucleotide sequences

| Antibody | Variable Heavy Chain-Encoding Polynucleotide Sequence (SEQ ID NO) |
|---|---|
| 15461 | CAGCTGCAGCTGCAGGAGTCGGGCCCAGGACTGGTGAAGCCTTCGGAG<br>ACCCTGTCCCTCACCTGCACTGTCTCTGGTGGCTCCATCAGCAGTAGTA<br>GTTACTACTGGGGCTGGATCCGCCAGCCCCCAGGGAAGGGGCTGGAGT<br>GGATTGGGAACATCTATTATAGTGGGAGCACCTACTACAACCCGTCCCT<br>CAAGAGTCGAGTCACCATATCCGTAGACACGTCCAAGAACCAGTTCTC<br>CCTGAAGCTGAGTTCTGTGACCGCCGCAGACACGGCGGTGTACTACTG<br>CGCCAGAGAAGGATCTTACCCCAATTGGTTTGATCCATGGGGACAGGG<br>TACATTGGTCACCGTCTCCTCA (SEQ ID NO: 213) |
| 20500 | CAGCTGCAGCTGCAGGAGTCGGGCCCAGGACTGGTGAAGCCTTCGGAG<br>ACCCTGTCCCTCACCTGCACTGTCTCTGGTGGCTCCATCAAGAGTGGTA<br>GTCACTACTGGGGCTGGATCCGCCAGCCCCCAGGGAAGGGGCTGGAGT<br>GGATTGGGAACATCTATTATAGTGGGAGCACCTACTACAACCCGTCCCT<br>CAGGAGTCGAGTCACCATATCCGTAGACACGTCCAAGAACCAGTTCTC<br>CCTGAAGCTGAGTTCTGTGACCGCCGCAGACACGGCGGTGTACTACTG<br>CGCCAGGGAAGGATCTTACCCCAATTGGTTTGATCCATGGGGACAGGG<br>TACATTGGTCACCGTCTCCTCA (SEQ ID NO: 223) |
| 20501 | CAGCTGCAGCTGCAGGAGTCGGGCCCAGGACTGGTGAAGCCTTCGGAG<br>ACCCTGTCCCTCACCTGCACTGTCTCTGGTGGCTCCATCAAGAGTGGTA<br>GTCACTACTGGGGCTGGATCCGCCAGCCCCCAGGGAAGGGGCTGGAGT<br>GGATTGGGAACATCTATTATAGTGGGAGCACCTACTACAACCCGTCCCT<br>CAAGAGTCGAGTCACCATATCCGTAGACACGTCCAAGAACCAGTTCTC |

TABLE 9-continued

Variable heavy chain-encoding polynucleotide sequences

| Antibody | Variable Heavy Chain-Encoding Polynucleotide Sequence (SEQ ID NO) |
|---|---|
| | CCTGAAGCTGAGTTCTGTGACCGCCGCAGACACGGCGGTGTACTACTG<br>CGCCAGAGAAGGATCTTACCCCAATTGGTTGGATCCATGGGGACAGGG<br>TACATTGGTCACCGTCTCCTCA (SEQ ID NO: 233) |
| 20502 | CAGCTGCAGCTGCAGGAGTCGGGCCCAGGACTGGTGAAGCCTTCGGAG<br>ACCCTGTCCCTCACCTGCACTGTCTCTGGTGGCTCCATCAAAAGTGGTA<br>GTTACTACTGGGGCTGGATCCGCCAGCCCCAGGGAAGGGGCTGGAGT<br>GGATTGGGAACATCTATTATAGTGGGAGCACCTACTACAACCCGTCCCT<br>CAGAAGTCGAGTCACCATATCCGTAGACACGTCCAAGAACCAGTTCTC<br>CCTGAAGCTGAGTTCTGTGACCGCCGCAGACACGGCGGTGTACTACTG<br>CGCCAGAGAAGGATCTTACCCCAATCAGTTTGATCCATGGGGACAGGG<br>TACATTGGTCACCGTCTCCTCA (SEQ ID NO: 470) |
| 20502.1 | CAGCTGCAGCTGCAGGAGTCGGGCCCAGGACTGGTGAAGCCTTCGGAG<br>ACCCTGTCCCTCACCTGCACTGTCTCTGGTGGCTCCATCAAGAGTGGTA<br>GTTACTACTGGGGCTGGATCCGCCAGCCCCAGGGAAGGGGCTGGAGT<br>GGATTGGGAACATCTATTATAGTGGGAGCACCTACTACAACCCGTCCCT<br>CAAGAGTCGAGTCACCATATCCGTAGACACGTCCAAGAACCAGTTCTC<br>CCTGAAGCTGAGTTCTGTGACCGCCGCAGACACGGCGGTGTACTACTG<br>CGCCAGAGAAGGATCTTACCCCAATCAGTTTGATCCATGGGGACAGGG<br>TATATTGGTCACCGTCTCCTCA (SEQ ID NO: 243) |
| 22208 | CAGCTGCAGCTGCAGGAGTCGGGCCCAGGACTGGTGAAGCCTTCGGAG<br>ACCCTGTCCCTCACCTGCACTGTCTCTGGTGGCTCCATCAAGAGTGGTA<br>GTCACTACTGGGGCTGGATCCGCCAGCCCCAGGGAAGGGGCTGGAGT<br>GGATTGGGAACATCTATTATAGTGGGAGCACCTACTACAACCCGTCCCT<br>CAAGAGTCGAGTCACCATGTCCGTAGACACGTCCAAGAACCAGTTCTC<br>CCTGAAGCTGAGTTCTGTGACCGCCGCAGACACGGCGGTGTACTACTG<br>CGCCAGAGAAGGATCTTACCCCAATTGGTTTGATCCATGGGGACAGGG<br>TACATTGGTCACCGTCTCCTCA (SEQ ID NO: 253) |
| 15462 | CAGCTGCAGCTGCAGGAGTCGGGCCCAGGACTGGTGAAGCCTTCGGAG<br>ACCCTGTCCCTCACCTGCACTGTCTCTGGTGGCTCCATCAGCAGTAGTA<br>GTTACTACTGGGGCTGGATCCGCCAGCCCCAGGGAAGGGGCTGGAGT<br>GGATTGGGAACATCTATTATAGTGGGAGCACCTACTACAACCCGTCCCT<br>CAAGAGTCGAGTCACCATATCCGTAGACACGTCCAAGAACCAGTTCTC<br>CCTGAAGCTGAGTTCTGTGACCGCCGCAGACACGGCGGTGTACTACTG<br>CGCCAGAGAAGGATCTTACACAACCGTGTTAAACGTATGGGGTCAGGG<br>TACAATGGTCACCGTCTCCTCA (SEQ ID NO: 263) |
| 22213 | CAGCTGCAGCTGCAGGAGTCGGGCCCAGGACTGGTGAAGCCTTCGGAG<br>ACCCTGTCCCTCACCTGCACTGTCTCTGGTGGCTCCATCGGGAGGGGA<br>GTTACTACTGGGGCTGGATCCGCCAGCCCCAGGGAAGGGGCTGGAGT<br>GGATTGGGAACATCTATTATAGTGGGAGCACCTACTACAACCCGTCCCT<br>CAAGAGTCGAGTCACCATATCCGTAGACACGTCCAAGAACCAGTTCTC<br>CCTGAAGCTGAGTTCTGTGACCGCCGCAGACACGGCGGTGTACTACTG<br>CGCCAGAGAAGGATCTTACACAACCGTGTTAAACGTATGGGGTCAGGG<br>TACAATGGTCACCGTCTCCTCA (SEQ ID NO: 273) |
| 15465 | CAGGTGCAGCTGCAGGAGTCGGGCCCAGGACTGGTGAAGCCTTCACAG<br>ACCCTGTCCCTCACCTGTACTGTCTCTGGTGGCTCCATCAGCAGTGGTG<br>GTTACTACTGGAGCTGGATCCGCCAGCACCCAGGGAAGGGCCTGGAGT<br>GGATTGGGAACATCTATTACAGTGGGAGCACCTACTACAACCCGTCCT<br>CAAGAGTCGAGTTACCATATCAGTAGACACGTCTAAGAACCAGTTCTC<br>CCTGAAGCTGAGTTCTGTGACCGCCGCAGACACGGCGGTGTACTACTG<br>CGCCAGAGAATCTAGCACCATATCTGCCGACTTCGACCTATGGGGAG<br>AGGTACCTTGGTCACCGTCTCCTCA (SEQ ID NO: 283) |
| 20506 | CAGCTGCAGCTGCAGGAGTCGGGCCCAGGACTGGTGAAGCCTTCGGAG<br>ACCCTGTCCCTCACCTGTACTGCCTCTGGTGGCTCCATCAGCCATGGTG<br>GTACTACTGGAGCTGGATCCGCCAGCACCCAGGGAAGGGCCTGGAGT<br>GGATTGGGAACATCTATTACAGTGGGAGCACCTACTACAATCCGTCCT<br>CAAGAGTCGAGTTACCATGTCAGTAGACACGTCTAAGAACCAGTTCTC<br>CCTGAAGCTGAGTTCTGTGACCGCCGCAGACACGGCGGTGTACTACTG<br>CGCCAGAGAATCTAGCACCATATCTGCCGACTTCGACCTATGGGGAG<br>AGGTACCTTGGTCACCGTCTCCTCA (SEQ ID NO: 293) |
| 15483 | CAGGTGCAGCTGCAGGAGTCGGGCCCAGGACTGGTGAAGCCTTCACAG<br>ACCCTGTCCCTCACCTGTACTGTCTCTGGTGGCTCCATCAGCAGTGGTG<br>GTTACTACTGGAGCTGGATCCGCCAGCACCCAGGGAAGGGCCTGGAGT<br>GGATTGGGAACATCTATTACAGTGGGAGCACCTACTACAACCCGTCCT<br>CAAGAGTCGAGTTACCATATCAGTAGACACGTCTAAGAACCAGTTCTC<br>CCTGAAGCTGAGTTCTGTGACCGCCGCAGACACGGCGGTGTACTACTG<br>CGCCAGAGGGTTGAGCACCATAGACGAGGCATTCGACCCATGGGGACA<br>GGGTACATTGGTCACCGTCTCCTCA (SEQ ID NO: 303) |

TABLE 9-continued

Variable heavy chain-encoding polynucleotide sequences

| Antibody | Variable Heavy Chain-Encoding Polynucleotide Sequence (SEQ ID NO) |
|---|---|
| 20513 | CAGCTGCAGCTGCAGGAGTCGGGCCCAGGACTGGTGAAGCCTTCGGAG<br>ACCCTGTCCCTCACCTGCACTGTCTCTGGTGGCTCCATCAGCGATGGTA<br>GTTACTACTGGAGCTGGATCCGCCAGCACCCAGGGAAGGGCCTGGAGT<br>GGATTGGGAACATCTATTACAGTGGGAGCACCTACTACAACCCGTCCCT<br>CAGGAGTCGAGTTACCATGTCAGTAGACACGTCTAAGAACCAGTTCTC<br>CCTGAAGCTGAGTTCTGTGACCGCCGCAGACACGGCGGTGTACTACTG<br>CGCCAGAGGGTTGAGCACCATAGACGAGGCATTCGACCCATGGGGACA<br>GGGTACATTGGTCACCGTCTCCTCA (SEQ ID NO: 313) |
| 22216 | CAGGTGCAGCTGCAGGAGTCGGGCCCAGGACTGGTGAAGCCTTCACAG<br>ACCCTGTCCCTCACCTGTACTGTCTCTGGTGGCTCCATCAGCGATGGTA<br>GTTACTACTGGAGCTGGATCCGCCAGCACCCAGGGAAGGGCCTGGAGT<br>GGATTGGGAACATCTATTACAGTGGGAGCACCTACTACAACCCGTCCCT<br>CAGGAGTCGAGTTACCATGTCAGTAGACACGTCTAAGAACCAGTTCTC<br>CCTGAAGCTGAGTTCTGTGACCGCCGCAGACACGGCGGTGTACTACTG<br>CGCCAGAGGGTTGAGCACCATAGACGAGGCATTCGACCCATGGGGACA<br>GGGTACATTGGTCACCGTCTCCTCA (SEQ ID NO: 323) |
| 15489 | CAGGTGCAGCTGCAGGAGTCGGGCCCAGGACTGGTGAAGCCTTCGGAG<br>ACCCTGTCCCTCACCTGCACTGTCTCTGGTGGCTCCATCAGTAGTTACT<br>ACTGGAGCTGGATCCGGCAGCCCCAGGGAAGGGACTGGAGTGGATTG<br>GGTATATCTATAGTAGTGGGAGCACCAACTACAACCCCTCCCTCAAGA<br>GTCGAGTCACCATATCAGTAGACACGTCCAAGAACCAGTTCTCCCTGA<br>AGCTGAGTTCTGTGACCGCCGCAGACACGGCGGTGTACTACTGCGCCA<br>GAGGCTCTGGACAGTATGCAGCTCCTGATTATGGAATGGACGTATGGG<br>GCCAGGGAACAACTGTCACCGTCTCCTCA (SEQ ID NO: 333) |
| 20516 | CAGGTGCAGCTGCAGGAGTCGGGCCCAGGACTGGTGAAGCCTTCGGAG<br>ACCCTGTCCCTCACCTGCACTGTCTCTGGTGGCTCCATCATTAGTTACTA<br>CTGGGGGTGGATCCGGCAGCCCCAGGGAAGGGACTGGAGTGGATTGG<br>GTATATCTATTCTAGTGGGAGCACCTCGTACAACCCCTCCCTCAAGAGT<br>CGAGTCACCATATCAGTAGACACGTCCAAGAACCAGTTCTCCCTGAAG<br>CTGAGTTCTGTGACCGCCGCAGACACGGCGGTGTACTACTGCGCCAGA<br>GGCTCTGGACTGTATGCAGCTCCTGATTATGGACTTGACGTATGGGGTC<br>AGGGAACAACTGTCACCGTCTCCTCA (SEQ ID NO: 343) |
| 15472 | GAGGTGCAGCTGTTGGAGTCTGGGGGAGGCTTGGTACAGCCTGGGGGG<br>TCCCTGAGACTCTCCTGTGCAGCCTCTGGATTCACCTTTAGCAGCTATG<br>CCATGAGCTGGGTCCGCCAGGCTCCAGGGAAGGGGCTGGAGTGGGTCT<br>CAACCATTAGTGGTAGTGGTGGTAGCACATACTACGCAGACTCCGTGA<br>AGGGCCGGTTCACCATCTCCAGAGACAATTCCAAGAACACGCTGTATC<br>TGCAAATGAACAGCCTGAGAGCCGAGGACACGGCGGTGTACTACTGCG<br>CCAGAGGTGCCGGACACTACGACCTCGTCGGACGATACTGGGGACAGG<br>GTACATTGGTCACCGTCTCCTCA (SEQ ID NO: 353) |
| 15503 | GAGGTGCAGCTGTTGGAGTCTGGGGGAGGCTTGGTACAGCCTGGGGGG<br>TCCCTGAGACTCTCCTGTGCAGCCTCTGGATTCACCTTTAGCAGCTATG<br>CCATGAGCTGGGTCCGCCAGGCTCCAGGGAAGGGGCTGGAGTGGGTCT<br>CAGCTATTAGTGGTAGTGGTGGTAGCACATACTACGCAGACTCCGTGA<br>AGGGCCGGTTCACCATCTCCAGAGACAATTCCAAGAACACGCTGTATC<br>TGCAAATGAACAGCCTGAGAGCCGAGGACACGGCGGTGTACTACTGCG<br>CCAGAGTGGGATTCAGAGCATTAAACTACTGGGGACAGGGTACAACTG<br>TCACCGTCTCCTCA (SEQ ID NO: 363) |
| 15495 | CAGGTGCAGCTGGTGCAGTCTGGGGCTGAGGTGAAGAAGCCTGGGTCC<br>TCGGTGAAGGTCTCCTGCAAGGCTTCTGGAGGCACCTTCAGCAGCTATG<br>CTATCAGCTGGGTGCGACAGGCCCCTGGACAAGGGCTTGAGTGGATGG<br>GAGGGATCATCCCTATCTTTGGTACAGCAAGCTACGCACAGAAGTTCC<br>AGGGCAGAGTCACGATTACCGCGGACGAATCCACGAGCACAGCCTACA<br>TGGAGCTGAGCAGCCTGAGATCTGAGGACACGGCGGTGTACTACTGCG<br>CAAGACAGCAATACGACGGTAGACGATACTTCGGCCTATGGGGGAGAG<br>GTACCTTGGTCACCGTCTCCTCA (SEQ ID NO: 373) |
| 15478 | CAGGTGCAGCTGGTGCAGTCTGGGGCTGAGGTGAAGAAGCCTGGGTCC<br>TCGGTGAAGGTCTCCTGCAAGGCTTCTGGAGGCACCTTCAGCAGCTATG<br>CTATCAGCTGGGTGCGACAGGCCCCTGGACAAGGGCTTGAGTGGATGG<br>GAGGGATCATCCCTATCTTTGGTACAGCAAACTACGCACAGAAGTTCC<br>AGGGCAGAGTCACGATTACCGCGGACGAATCCACGAGCACAGCCTACA<br>TGGAGCTGAGCAGCCTGAGATCTGAGGACACGGCGGTGTACTACTGCG<br>CCAGAGGTGGGCCTTGGTTTGATCCATGGGGACAGGGTACATTGGTCA<br>CCGTCTCCTCA (SEQ ID NO: 383) |
| 15441 | GAGGTGCAGCTGTTGGAGTCTGGGGGAGGCTTGGTACAGCCTGGGGGG<br>TCCCTGAGACTCTCCTGTGCAGCCTCTGGATTCACCTTTAGCAGCTATG |

TABLE 9-continued

Variable heavy chain-encoding polynucleotide sequences

| Antibody | Variable Heavy Chain-Encoding Polynucleotide Sequence (SEQ ID NO) |
|---|---|
|  | CCATGAGCTGGGTCCGCCAGGCTCCAGGGAAGGGGCTGGAGTGGGTCT<br>CAGCTATTAGTGGTAGTGGTGGTAGCACATCCTACGCAGACTCCGTGA<br>AGGGCCGGTTCACCATCTCCAGAGACAATTCCAAGAACACGCTGTATC<br>TGCAAATGAACAGCCTGAGAGCCGAGGACACGGCGGTGTACTACTGCG<br>CCAAGCCTTCTTTGGCAACAATGTTAGCCTTCGATATCTGGGGTCAGGG<br>TACAATGGTCACCGTCTCCTCA (SEQ ID NO: 393) |
| 20496 | CAGCTGCAGCTGCAGGAGTCGGGCCCAGGACTGGTGAAGCCTTCGGAG<br>ACCCTGTCCCTCACCTGCACTGTCTCTGGTGGCTCCATCAGCAGTAGTG<br>TTTACTACTGGAGTTGGATCCGCCAGCCCCCAGGGAAGGGGTTGGAGT<br>GGATTGGGAGTATCCTGGTGAGTGGGAGCACCTACTACAACCCGTCCC<br>TCAAGAGTCGAGTCACCATATCCGTAGACACGTCCAAGAACCAGTTCT<br>CCCTGAAGCTGAGTTCTGTGACCGCCGCAGACACGGCGGTGTACTACT<br>GCGCCAGAGCTGTATCCTTCTTAGACGTATGGGGTCAGGGTACAATGGT<br>CATCGTCTCCTCA (SEQ ID NO: 403) |

Also provided herein are polynucleotides comprising a variable light chain-encoding nucleotide sequence shown in Table 10, e.g., wherein an antibody or antigen-binding fragment thereof comprising the encoded variable light chain binds to B7-H4.

TABLE 10

Variable light chain-encoding polynucleotide sequences

| Antibody | Variable Light Chain-Encoding Polynucleotide Sequence (SEQ ID NO) |
|---|---|
| 15461 | GAAATAGTGATGACGCAGTCTCCAGCCACCCTGTCTGTGTCTCCAGGG<br>GAAAGAGCCACCCTCTCCTGCAGGGCCAGTCAGAGTGTTAGCAGCAA<br>CTTAGCCTGGTACCAGCAGAAACCTGGCCAGGCTCCCAGGCTCCTCAT<br>CTATGGTGCATCCACCAGGGCCACTGGTATCCCAGCCAGGTTCAGTGG<br>CAGTGGGTCTGGGACAGAGTTCACTCTCACCATCAGCAGCCTGCAGTC<br>TGAAGATTTTGCAGTTTATTACTGTCAGCAGTACCACTCCTTCCCTTTC<br>ACTTTTGGCGGAGGGACCAAGGTTGAGATCAAA (SEQ ID NO: 214) |
| 20500 | GAAATAGTGATGACGCAGTCTCCAGCCACCCTGTCTGTGTCTCCAGGG<br>GAAAGAGCCACCCTCTCCTGCAGGGCCAGTCAGAGTGTTAGCAGCAA<br>CTTAGCCTGGTACCAGCAGAAACCTGGCCAGGCTCCCAGGCTCCTCAT<br>CTATGGTGCATCCACCAGGGCCACTGGTATCCCAGCCAGGTTCAGTGG<br>CAGTGGGTCTGGGACAGAGTTCACTCTCACCATCAGCAGCCTGCAGTC<br>TGAAGATTTTGCAGTTTATTACTGTCAGCAGTACCACTCCTTCCCTTTC<br>ACTTTTGGCGGAGGGACCAAGGTTGAGATCAAA (SEQ ID NO: 224) |
| 20501 | GAAATAGTGATGACGCAGTCTCCAGCCACCCTGTCTGTGTCTCCAGGG<br>GAAAGAGCCACCCTCTCCTGCAGGGCCAGTCAGAGTGTTAGCAGCAA<br>CTTAGCCTGGTACCAGCAGAAACCTGGCCAGGCTCCCAGGCTCCTCAT<br>CTATGGTGCATCCACCAGGGCCACTGGTATCCCAGCCAGGTTCAGTGG<br>CAGTGGGTCTGGGACAGAGTTCACTCTCACCATCAGCAGCCTGCAGTC<br>TGAAGATTTTGCAGTTTATTACTGTCAGCAGTACCACTCCTTCCCTTTC<br>ACTTTTGGCGGAGGGACCAAGGTTGAGATCAAA (SEQ ID NO: 234) |
| 20502 and 20502.1 | GAAATAGTGATGACGCAGTCTCCAGCCACCCTGTCTGTGTCTCCAGGG<br>GAAAGAGCCACCCTCTCCTGCAGGGCCAGTCAGAGTGTTAGCAGCAA<br>CTTAGCCTGGTACCAGCAGAAACCTGGCCAGGCTCCCAGGCTCCTCAT<br>CTATGGTGCATCCACCAGGGCCACTGGTATCCCAGCCAGGTTCAGTGG<br>CAGTGGGTCTGGGACAGAGTTCACTCTCACCATCAGCAGCCTGCAGTC<br>TGAAGATTTTGCAGTTTATTACTGTCAGCAGTACCACTCCTTCCCTTTC<br>ACTTTTGGCGGAGGGACCAAGGTTGAGATCAAA (SEQ ID NO: 244) |
| 22208 | GAAATAGTGATGACGCAGTCTCCAGCCACCCTGTCTGTGTCTCCAGGG<br>GAAAGAGCCACCCTCTCCTGCAGGGCCAGTCAGTCCGTTAGCACCAAC<br>TTAGCCTGGTACCAGCAGAAACCTGGCCAGGCTCCCAGGCTCCTCATC<br>TATGACGCATCCGCCAGGGTCACTGGTATCCCAGCCAGGTTCAGTGGC<br>AGTGGGTCTGGGACAGAGTTCACTCTCACCATCAGCAGCCTGCAGTCT<br>GAAGATTTTGCAGTTTATTACTGTCAGCAGTACCACTCCTTCCCTTTCA<br>CTTTTGGCGGAGGGACCAAGGTTGAGATCAAA (SEQ ID NO: 254) |
| 15462 | GAAATTGTGTTGACGCAGTCTCCAGGCACCCTGTCTTTGTCTCCAGGG<br>GAAAGAGCCACCCTCTCCTGCAGGGCCAGTCAGAGTGTTAGCAGCAG<br>CTACTTAGCCTGGTACCAGCAGAAACCTGGCCAGGCTCCCAGGCTCCT |

TABLE 10-continued

Variable light chain-encoding polynucleotide sequences

| Antibody | Variable Light Chain-Encoding Polynucleotide Sequence (SEQ ID NO) |
|---|---|
| | CATCTATGGTGCATCCAGCAGGGCCACTGGCATCCCAGACAGGTTCAG<br>TGGCAGTGGGTCTGGGACAGACTTCACTCTCACCATCAGCAGACTGGA<br>GCCTGAAGATTTTGCAGTGTATTACTGTCAGCAGGCCGCCAGTTACCC<br>TCTCACTTTTGGCGGAGGGACCAAGGTTGAGATCAAA (SEQ ID NO: 264) |
| 22213 | GAAATTGTGTTGACGCAGTCTCCAGGCACCCTGTCTTTGTCTCCAGGG<br>GAAAGAGCCACCCTCTCCTGCAGGGCCAGTCAGAGTGTTGCCAGCAGC<br>CACTTAGCCTGGTACCAGCAGAAACCTGGCCAGGCTCCCAGGCTCCTC<br>ATCTATGACGCAGTCAGCAGGGCCACTGGCATCCCAGACAGGTTCAGT<br>GGCAGTGGGTCTGGGACAGACTTCACTCTCACCATCAGCAGACTGGAG<br>CCTGAAGATTTTGCAGTGTATTACTGTCAGCAGGCCGCCAGTTACCCT<br>CTCACTTTTGGCGGAGGGACCAAGGTTGAGATCAAA (SEQ ID NO: 274) |
| 15465 | GACATCCAGATGACCCAGTCTCCATCTTCCGTGTCTGCATCTGTAGGA<br>GACAGAGTCACCATCACTTGTCGGGCGAGTCAGGGTATTAGCAGGTGG<br>TTAGCCTGGTATCAGCAGAAACCAGGGAAAGCCCCTAAGCTCCTGATC<br>TATGCTGCATCCAGTTTGCAAAGTGGGGTCCCATCAAGGTTCAGCGGC<br>AGTGGATCTGGGACAGATTTCACTCTCACCATCAGCAGCCTGCAGCCT<br>GAAGATTTTGCAACTTATTACTGTCAGCAGGCACACACCTTCCCTTAC<br>ACTTTTGGCGGAGGGACCAAGGTTGAGATCAAA (SEQ ID NO: 284) |
| 20506 | GACATCCAGATGACCCAGTCTCCATCTTCCGTGTCTGCATCTGTAGGA<br>GACAGAGTCACCATCACTTGTCGGGCGAGTCAGGGTATTAGCAGGTGG<br>TTAGCCTGGTATCAGCAGAAACCAGGGAAAGCCCCTAAGCTCCTGATC<br>TATGCTGCATCCAGTTTGCAAAGTGGGGTCCCATCAAGGTTCAGCGGC<br>AGTGGATCTGGGACAGATTTCACTCTCACCATCAGCAGCCTGCAGCCT<br>GAAGATTTTGCAACTTATTACTGTCAGCAGGCACACACCTTCCCTTAC<br>ACTTTTGGCGGAGGGACCAAGGTTGAGATCAAA (SEQ ID NO: 294) |
| 15483 | GACATCCAGATGACCCAGTCTCCTTCCACCCTGTCTGCATCTGTAGGA<br>GACAGAGTCACCATCACTTGCCGGGCCAGTCAGAGTATTAGTAGCTGG<br>TTGGCCTGGTATCAGCAGAAACCAGGGAAAGCCCCTAAGCTCCTGATC<br>TATAAAGCCTCCAGTTTGGAAAGTGGGGTCCCATCAAGGTTCAGCGGC<br>AGTGGATCTGGGACAGAATTCACTCTCACCATCAGCAGCCTGCAGCCT<br>GATGATTTTGCAACTTATTACTGCCAGCAGGACAACAGTTACCCTTAC<br>ACTTTTGGCGGAGGGACCAAGGTTGAGATCAAA (SEQ ID NO: 304) |
| 20513 | GACATCCAGATGACCCAGTCTCCTTCCACCCTGTCTGCATCTGTAGGA<br>GACAGAGTCACCATCACTTGCCGGGCCAGTCAGAGTATTAGTAGCTGG<br>TTGGCCTGGTATCAGCAGAAACCAGGGAAAGCCCCTAAGCTCCTGATC<br>TATAAAGCCTCCAGTTTGGAAAGTGGGGTCCCATCAAGGTTCAGCGGC<br>AGTGGATCTGGGACAGAATTCACTCTCACCATCAGCAGCCTGCAGCCT<br>GATGATTTTGCAACTTATTACTGCCAGCAGGACAACAGTTACCCTTAC<br>ACTTTTGGCGGAGGGACCAAGGTTGAGATCAAA (SEQ ID NO: 314) |
| 22216 | GACATCCAGATGACCCAGTCTCCTTCCACCCTGTCTGCATCTGTAGGA<br>GACAGAGTCACCATCACTTGCCGGGCCAGTAAAAGTATTAGTTCCTGG<br>TTGGCCTGGTATCAGCAGAAACCAGGAAAAGCCCCTAAGCTCCTGATC<br>TATGAAGCCTCCTCCTTGCACAGTGGGGTCCCATCAAGGTTCAGCGGC<br>AGTGGATCTGGGACAGAATTCACTCTCACCATCAGCAGCCTGCAGCCT<br>GATGATTTTGCAACTTATTACTGCCAGCAGGACAACAGTTACCCTTAC<br>ACTTTTGGCGGAGGGACCAAGGTTGAGATCAAA (SEQ ID NO: 324) |
| 15489 | GACATCCAGATGACCCAGTCTCCTTCCACCCTGTCTGCATCTGTAGGA<br>GACAGAGTCACCATCACTTGCCGGGCCAGTCAGAGTATTAGTAGCTGG<br>TTGGCCTGGTATCAGCAGAAACCAGGGAAAGCCCCTAAGCTCCTGATC<br>TATAAAGCCTCCAGTTTGGAAAGTGGGGTCCCATCAAGGTTCAGCGGC<br>AGTGGATCTGGGACAGAATTCACTCTCACCATCAGCAGCCTGCAGCCT<br>GATGATTTTGCAACTTATTACTGCCAGCAGGACAATAGCTTCCCTTTCA<br>CTTTTGGCGGAGGGACCAAGGTTGAGATCAAA (SEQ ID NO: 334) |
| 20516 | GACATCCAGATGACCCAGTCTCCTTCCACCCTGTCTGCATCTGTAGGA<br>GACAGAGTCACCATCACTTGCCGGGCCAGTCAGAGTATTAGTAGCTGG<br>TTGGCCTGGTATCAGCAGAAACCAGGGAAAGCCCCTAAGCTCCTGATC<br>TATAAAGCCTCCAGTTTGGAAAGTGGGGTCCCATCAAGGTTCAGCGGC<br>AGTGGATCTGGGACAGAATTCACTCTCACCATCAGCAGCCTGCAGCCT<br>GATGATTTTGCAACTTATTACTGCCAGCAGGACAATAGCTTCCCTTTCA<br>CTTTTGGCGGAGGGACCAAGGTTGAGATCAAA (SEQ ID NO: 344) |
| 15472 | GACATCCAGATGACCCAGTCTCCATCCTCCCTGTCTGCATCTGTAGGA<br>GACAGAGTCACCATCACTTGCCGGGCAAGTCAGAGCATTAGCAGCTAT<br>TTAAATTGGTATCAGCAGAAACCAGGGAAAGCCCCTAAGCTCCTGATC<br>TATGCTGCATCCAGTTTGCAAAGTGGGGTCCCATCAAGGTTCAGTGGC |

TABLE 10-continued

Variable light chain-encoding polynucleotide sequences

| Antibody | Variable Light Chain-Encoding Polynucleotide Sequence (SEQ ID NO) |
|---|---|
| | AGTGGATCTGGGACAGATTTCACTCTCACCATCAGCAGTCTGCAACCT<br>GAAGATTTTGCAACTTACTACTGTCAGCAACTATACAGTCTCCCTCCTA<br>CTTTTGGCGGAGGGACCAAGGTTGAGATCAAA (SEQ ID NO: 354) |
| 15503 | GACATCCAGTTGACCCAGTCTCCATCTTCCGTGTCTGCATCTGTAGGAG<br>ACAGAGTCACCATCACTTGTCGGGCGAGTCAGGATATTAGCAGCTGGT<br>TAGCCTGGTATCAGCAGAAACCAGGGAAAGCCCCTAAGCTCCTGATCT<br>ATGCTGCATCCAGTTTGCAAAGTGGGGTCCCATCAAGGTTCAGCGGCA<br>GTGGATCTGGGACAGATTTCACTCTCACCATCAGCAGCCTGCAGCCTG<br>AAGATTTTGCAACTTATTACTGTCAGCAGGCAACCAGTTACCCTCCTTG<br>GACTTTTGGCGGAGGGACCAAGGTTGAGATCAAA (SEQ ID NO: 364) |
| 15495 | GAAATAGTGATGACGCAGTCTCCAGCCACCCTGTCTGTGTCTCCAGGG<br>GAAAGAGCCACCCTCTCCTGCAGGGCCAGTCAGAGTGTTAGCAGCAA<br>CTTAGCCTGGTACCAGCAGAAACCTGGCCAGGCTCCCAGGCTCCTCAT<br>CTATAGCGCATCCACCAGGGCCACTGGTATCCCAGCCAGGTTCAGTGG<br>CAGTGGGTCTGGGACAGAGTTCACTCTCACCATCAGCAGCCTGCAGTC<br>TGAAGATTTTGCAGTTTATTACTGTCAGCAGGTCAACGTCTGGCCTCCT<br>ACTTTTGGCGGAGGGACCAAGGTTGAGATCAAA (SEQ ID NO: 374) |
| 15478 | GACATCCAGATGACCCAGTCTCCTTCCACCCTGTCTGCATCTGTAGGA<br>GACAGAGTCACCATCACTTGCCGGGCCAGTCAGAGTATTAGTAGCTGG<br>TTGGCCTGGTATCAGCAGAAACCAGGGAAAGCCCCTAAGCTCCTGATC<br>TATAAAGCCTCCAGTTTGGAAAGTGGGGTCCCATCAAGGTTCAGCGGC<br>AGTGGATCTGGGACAGAATTCACTCTCACCATCAGCAGCCTGCAGCCT<br>GATGATTTTGCAACTTATTACTGCCAGCAGTACAATAGCTACCCTCCTT<br>TCACTTTTGGCGGAGGGACCAAGGTTGAGATCAAA (SEQ ID NO: 384) |
| 15441 | GACATCCAGATGACCCAGTCTCCTTCCACCCTGTCTGCATCTGTAGGA<br>GACAGAGTCACCATCACTTGCCGGGCCAGTCAGAGTATTAGTAGCTGG<br>TTGGCCTGGTATCAGCAGAAACCAGGGAAAGCCCCTAAGCTCCTGATC<br>TATGATGCCTCCAGTTTGGAAAGTGGGGTCCCATCAAGGTTCAGCGGC<br>AGTGGATCTGGGACAGAATTCACTCTCACCATCAGCAGCCTGCAGCCT<br>GATGATTTTGCAACTTATTACTGCCAGCAGTCCAAAAGTTACCCTAGG<br>ACTTTTGGCGGAGGGACCAAGGTTGAGATCAAA (SEQ ID NO: 394) |
| 20496 | GACATCCAGATGACCCAGTCTCCATCCTCCCTGTCTGCATCTGTAGGA<br>GACAGAGTCACCATCACTTGCCGGGCAAGTCAGAGCATTAGCAGCTAT<br>TTAAATTGGTATCAGCAGAAACCAGGGAAAGCCCCTAAGCTCCTGATC<br>TATGGTGCATCCAGTTTGCAAAGTGGGGTCCCATCAAGGTTCAGTGGC<br>AGTGGATCTGGGACAGATTTCACTCTCACCATCAGCAGTCTGCAACCT<br>GAAGATTTTGCAACTTACTACTGTCAGCAAAGCTACGACCCCCCTTGG<br>ACTTTTGGCGGAGGGACCAAGGTTGAGATCAAA (SEQ ID NO: 404) |

Also provided herein are polynucleotides comprising the nucleotide sequence of SEQ ID NO:213, 214, 223, 224, 233, 234, 243, 470, 244, 253, 254, 263, 264, 273, 274, 283, 284, 293, 294, 303, 304, 313, 314, 323, 324, 333, 334, 343, 344, 353, 354, 363, 364, 373, 374, 383, 384, 393, 394, 403, or 404. Also provided herein are polynucleotides comprising (i) the nucleotide sequence of SEQ ID NO:213, 214, 223, 224, 233, 234, 243, 470, 244, 253, 254, 263, 264, 273, 274, 283, 284, 293, 294, 303, 304, 313, 314, 323, 324, 333, 334, 343, 344, 353, 354, 363, 364, 373, 374, 383, 384, 393, 394, 403, or 404 and (ii) the nucleotide sequence of SEQ ID NO:408 or 406.

Also provided herein are polynucleotides comprising a nucleotide sequence that encodes SEQ ID NO:11, 12, 21, 22, 31, 32, 41, 464, 42, 51, 52, 61, 62, 71, 72, 81, 82, 91, 92, 101, 102, 111, 112, 121, 122, 131, 132, 141, 142, 151, 152, 161, 162, 171, 172, 181, 182, 191, 192, 201, or 202 and is at least about 80%, 85%, or 90% identical to SEQ ID NO:213, 214, 223, 224, 233, 234, 243, 470, 244, 253, 254, 263, 264, 273, 274, 283, 284, 293, 294, 303, 304, 313, 314, 323, 324, 333, 334, 343, 344, 353, 354, 363, 364, 373, 374, 383, 384, 393, 394, 403, or 404, respectively.

Also provided herein are polynucleotides comprising a nucleotide sequence that encodes SEQ ID NO:11, 12, 21, 22, 31, 32, 41, 464, 42, 51, 52, 61, 62, 71, 72, 81, 82, 91, 92, 101, 102, 111, 112, 121, 122, 131, 132, 141, 142, 151, 152, 161, 162, 171, 172, 181, 182, 191, 192, 201, or 202 and is at least about 95% identical to SEQ ID NO:213, 214, 223, 224, 233, 234, 243, 470, 244, 253, 254, 263, 264, 273, 274, 283, 284, 293, 294, 303, 304, 313, 314, 323, 324, 333, 334, 343, 344, 353, 354, 363, 364, 373, 374, 383, 384, 393, 394, 403, or 404, respectively.

Also provided herein are polynucleotides comprising a nucleotide sequence that encodes SEQ ID NO:11, 12, 21, 22, 31, 32, 41, 464, 42, 51, 52, 61, 62, 71, 72, 81, 82, 91, 92, 101, 102, 111, 112, 121, 122, 131, 132, 141, 142, 151, 152, 161, 162, 171, 172, 181, 182, 191, 192, 201, or 202 and is at least about 96% identical to SEQ ID NO:213, 214, 223, 224, 233, 234, 243, 470, 244, 253, 254, 263, 264, 273, 274, 283, 284, 293, 294, 303, 304, 313, 314, 323, 324, 333, 334, 343, 344, 353, 354, 363, 364, 373, 374, 383, 384, 393, 394, 403, or 404, respectively.

Also provided herein are polynucleotides comprising a nucleotide sequence that encodes SEQ ID NO:11, 12, 21, 22, 31, 32, 41, 464, 42, 51, 52, 61, 62, 71, 72, 81, 82, 91, 92, 101, 102, 111, 112, 121, 122, 131, 132, 141, 142, 151, 152, 161, 162, 171, 172, 181, 182, 191, 192, 201, or 202 and is at least about 97% identical to SEQ ID NO:213, 214, 223, 224, 233, 234, 243, 470, 244, 253, 254, 263, 264, 273, 274, 283, 284, 293, 294, 303, 304, 313, 314, 323, 324, 333, 334, 343, 344, 353, 354, 363, 364, 373, 374, 383, 384, 393, 394, 403, or 404, respectively.

Also provided herein are polynucleotides comprising a nucleotide sequence that encodes SEQ ID NO:11, 12, 21, 22, 31, 32, 41, 464, 42, 51, 52, 61, 62, 71, 72, 81, 82, 91, 92, 101, 102, 111, 112, 121, 122, 131, 132, 141, 142, 151, 152, 161, 162, 171, 172, 181, 182, 191, 192, 201, or 202 and is at least about 98% identical to SEQ ID NO:213, 214, 223, 224, 233, 234, 243, 470, 244, 253, 254, 263, 264, 273, 274, 283, 284, 293, 294, 303, 304, 313, 314, 323, 324, 333, 334, 343, 344, 353, 354, 363, 364, 373, 374, 383, 384, 393, 394, 403, or 404, respectively.

Also provided herein are polynucleotides comprising a nucleotide sequence that encodes SEQ ID NO:11, 12, 21, 22, 31, 32, 41, 464, 42, 51, 52, 61, 62, 71, 72, 81, 82, 91, 92, 101, 102, 111, 112, 121, 122, 131, 132, 141, 142, 151, 152, 161, 162, 171, 172, 181, 182, 191, 192, 201, or 202 and is at least about 99% identical to SEQ ID NO:213, 214, 223, 224, 233, 234, 243, 470, 244, 253, 254, 263, 264, 273, 274, 283, 284, 293, 294, 303, 304, 313, 314, 323, 324, 333, 334, 343, 344, 353, 354, 363, 364, 373, 374, 383, 384, 393, 394, 403, or 404, respectively.

In certain aspects, provided herein are polynucleotides comprising a nucleotide sequence encoding the light chain or heavy chain of an antibody or an antigen-binding fragment described herein. The polynucleotides can comprise nucleotide sequences encoding a heavy chain comprising the VH FRs and CDRs of antibodies described herein (see, e.g., Tables 1 and 5). The polynucleotides can comprise nucleotide sequences encoding a light chain comprising the VL FRs and CDRs of antibodies described herein (see, e.g., Tables 2 and 6).

In specific embodiments, a polynucleotide described herein encodes a VH domain comprising the amino acid sequence set forth in SEQ ID NO:464. In specific embodiments, a polynucleotide described herein encodes a VL domain comprising the amino acid sequence set forth in SEQ ID NO:42.

In specific embodiments, a polynucleotide described herein encodes a VH domain comprising the amino acid sequence set forth in SEQ ID NO:41. In specific embodiments, a polynucleotide described herein encodes a VL domain comprising the amino acid sequence set forth in SEQ ID NO:42.

In specific embodiments, a polynucleotide described herein encodes a VH domain comprising the amino acid sequence set forth in SEQ ID NO:71. In specific embodiments, a polynucleotide described herein encodes a VL domain comprising the amino acid sequence set forth in SEQ ID NO:72.

In particular embodiments, provided herein are polynucleotides comprising a nucleotide sequence encoding an anti-B7-H4 antibody comprising three VH chain CDRs, e.g., containing VH CDR1, VH CDR2, VH VL CDR3 of any one of antibodies described herein (e.g., see Table 1). In specific embodiments, provided herein are polynucleotides comprising three VL chain CDRs, e.g., containing VL CDR1, VL CDR2, and VL CDR3 of any one of antibodies described herein (e.g., see Table 2). In specific embodiments, provided herein are polynucleotides comprising a nucleotide sequence encoding an anti-B7-H4 antibody comprising three VH chain CDRs, e.g., containing VH CDR1, VH CDR2, and VH CDR3 of any one of antibodies described herein (e.g., see Table 1) and three VL chain CDRs, e.g., containing VL CDR1, VL CDR2, and VL CDR3 of any one of antibodies described herein (e.g., see Table 2).

In particular embodiments, provided herein are polynucleotides comprising a nucleotide sequence encoding an anti-B7-H4 antibody or an antigen-binding fragment thereof or a fragment thereof comprising a VH domain, e.g., containing FR1-CDR1-FR2-CDR2-FR3-CDR3-FR4, comprising an amino acid sequence described herein (e.g., see Tables 1 and 5, e.g., the VH CDRs and VH FRs of a particular antibody identified by name in the tables). In specific embodiments, provided herein are polynucleotides comprising a nucleotide sequence encoding an anti-B7-H4 antibody or antigen-binding fragment thereof or a fragment thereof comprising a VL domain, e.g., containing FR1-CDR1-FR2-CDR2-FR3-CDR3-FR4, comprising an amino acid sequence described herein (e.g., see Tables 2 and 6, e.g., the VL CDRs and VL FRs of a particular antibody identified by name in the Tables).

In certain embodiments, a polynucleotide described herein comprises a nucleotide sequence encoding a heavy chain variable region comprising an amino acid sequence described herein (e.g., SEQ ID NO:464, 41, or 71), wherein an antibody containing the heavy chain variable region immunospecifically binds to B7-H4 (e.g., human B7-H4). In a certain embodiment, a polynucleotide described herein comprises a heavy chain variable region-encoding sequence provided herein (e.g., the variable region-encoding portion of SEQ ID NO:470, 243, or 273), wherein an antibody containing the heavy chain variable region immunospecifically binds to B7-H4 (e.g., human B7-H4).

In certain embodiments, a polynucleotide described herein comprises a nucleotide sequence encoding a light chain variable region comprising an amino acid sequence described herein (e.g., SEQ ID NO:42 or 72), wherein an antibody containing the light chain variable region immunospecifically binds to B7-H4 (e.g., human B7-H4). In a certain embodiment, a polynucleotide described herein comprises a light chain variable region-encoding sequence provided herein (e.g., the variable region-encoding portion of SEQ ID NO:244 or 274), wherein an antibody containing the heavy chain variable region immunospecifically binds to B7-H4 (e.g., human B7-H4).

In a particular embodiment, a polynucleotide or combination of polynucleotides provided herein comprises a nucleotide sequence or combination of nucleotide sequences encoding an antibody or antigen-binding fragment thereof that immunospecifically binds to B7-H4 (e.g., human B7-H4), wherein the antibody or antigen-binding fragment thereof comprises a heavy chain, wherein the heavy chain comprises a heavy chain variable domain comprising an amino acid sequence set forth in Table 3 (e.g., SEQ ID NO:464, 41, or 71) and a constant region comprising the amino acid sequence of a human gamma (γ) heavy chain constant region.

In a particular embodiment, a polynucleotide or combination of polynucleotides provided herein comprises a nucleotide sequence or combination of nucleotide sequences encoding an antibody or antigen-binding fragment thereof that immunospecifically binds to B7-H4 (e.g., human B7-H4), wherein the antibody or antigen-binding fragment thereof comprises a light chain, wherein the light chain comprises a light chain variable domain comprising an amino acid sequence set forth in Table 4 (e.g., SEQ ID NO:42 or 72) and a constant region comprising the amino acid sequence of a human lambda light chain constant region.

In a particular embodiment, a polynucleotide or combination of polynucleotides provided herein comprises a nucleotide sequence or combination of nucleotide sequences encoding an antibody or antigen-binding fragment thereof that immunospecifically binds to B7-H4 (e.g., human B7-H4), wherein the antibody or antigen-binding fragment thereof comprises (i) a heavy chain, wherein heavy chain comprises a heavy chain variable domain comprising an amino acid sequence set forth in Table 3 (e.g., SEQ ID NO:464, 41, or 71) and a constant region comprising the amino acid sequence of a human gamma (γ) heavy chain constant region and (ii) a light chain, wherein light chain comprises a light chain variable domain comprising an amino acid sequence set forth in Table 4 (e.g., SEQ ID NO:42 or 72) and a constant region comprising the amino acid sequence of a human lambda light chain constant region.

In one embodiment, a combination of polynucleotides provided herein comprises a polynucleotide comprising the nucleotide sequence of SEQ ID NO:470 and a polynucleotide comprising the nucleotide sequence of SEQ ID NO:244.

In one embodiment, a combination of polynucleotides provided herein comprises a polynucleotide comprising the nucleotide sequence of SEQ ID NO:243 and a polynucleotide comprising the nucleotide sequence of SEQ ID NO:244.

In one embodiment, a combination of polynucleotides provided herein comprises a polynucleotide comprising the nucleotide sequence of SEQ ID NO:273 and a polynucleotide comprising the nucleotide sequence of SEQ ID NO:274.

In a specific embodiment, provided herein are polynucleotides comprising a nucleotide sequence encoding an anti-B7-H4 antibody or antigen-binding fragment thereof or a domain thereof, designated herein, see, e.g., Tables 1-8.

Also provided herein are polynucleotides encoding an anti-B7-H4 antibody or antigen-binding fragment thereof described herein or a domain thereof that are optimized, e.g., by codon/RNA optimization, replacement with heterologous signal sequences, and elimination of mRNA instability elements. Methods to generate optimized nucleic acids encoding an anti-B7-H4 antibody or antigen-binding fragment thereof or a domain thereof (e.g., heavy chain, light chain, VH domain, or VL domain) for recombinant expression by introducing codon changes (e.g., a codon change that encodes the same amino acid due to the degeneracy of the genetic code) and/or eliminating inhibitory regions in the mRNA can be carried out by adapting the optimization methods described in, e.g., U.S. Pat. Nos. 5,965,726; 6,174,666; 6,291,664; 6,414,132; and 6,794,498, accordingly.

A polynucleotide encoding an antibody or antigen-binding fragment thereof described herein or a domain thereof can be generated from nucleic acid from a suitable source (e.g., a hybridoma) using methods well known in the art (e.g., PCR and other molecular cloning methods). For example, PCR amplification using synthetic primers hybridizable to the 3' and 5' ends of a known sequence can be performed using genomic DNA obtained from hybridoma cells producing the antibody of interest. Such PCR amplification methods can be used to obtain nucleic acids comprising the sequence encoding the light chain and/or heavy chain of an antibody or antigen-binding fragment thereof. Such PCR amplification methods can be used to obtain nucleic acids comprising the sequence encoding the variable light chain region and/or the variable heavy chain region of an antibody or antigen-binding fragment thereof. The amplified nucleic acids can be cloned into vectors for expression in host cells and for further cloning, for example, to generate chimeric and humanized antibodies or antigen-binding fragments thereof.

Polynucleotides provided herein can be, e.g., in the form of RNA or in the form of DNA. DNA includes cDNA, genomic DNA, and synthetic DNA, and DNA can be double-stranded or single-stranded. If single stranded, DNA can be the coding strand or non-coding (anti-sense) strand. In certain embodiments, the polynucleotide is a cDNA or a DNA lacking one more endogenous introns. In certain embodiments, a polynucleotide is a non-naturally occurring polynucleotide. In certain embodiments, a polynucleotide is recombinantly produced. In certain embodiments, the polynucleotides are isolated. In certain embodiments, the polynucleotides are substantially pure. In certain embodiments, a polynucleotide is purified from natural components.

1.2.2 Cells and Vectors

In certain aspects, provided herein are vectors (e.g., expression vectors) comprising polynucleotides comprising nucleotide sequences encoding anti-B7-H4 antibodies and antigen-binding fragments thereof or a domain thereof for recombinant expression in host cells, preferably in mammalian cells. Also provided herein are cells, e.g. host cells, comprising such vectors for recombinantly expressing anti-B7-H4 antibodies or antigen-binding fragments thereof described herein (e.g., human or humanized antibodies or antigen-binding fragments thereof). In a particular aspect, provided herein are methods for producing an antibody or antigen-binding fragments thereof described herein, comprising expressing such antibody or antigen-binding fragment thereof in a host cell.

In certain embodiments, recombinant expression of an antibody or antigen-binding fragment thereof or domain thereof described herein (e.g., a heavy or light chain described herein) that specifically binds to B7-H4 (e.g., human B7-H4) involves construction of an expression vector containing a polynucleotide that encodes the antibody or antigen-binding fragment thereof or domain thereof. Once a polynucleotide encoding an antibody or antigen-binding fragment thereof or domain thereof (e.g., heavy or light chain variable domain) described herein has been obtained, the vector for the production of the antibody or antigen-binding fragment thereof can be produced by recombinant DNA technology using techniques well known in the art. Thus, methods for preparing a protein by expressing a polynucleotide containing an antibody or antigen-binding fragment thereof or domain thereof (e.g., light chain or heavy chain) encoding nucleotide sequence are described herein. Methods which are well known to those skilled in the art can be used to construct expression vectors containing antibody or antigen-binding fragment thereof or domain thereof (e.g., light chain or heavy chain) coding sequences and appropriate transcriptional and translational control signals. These methods include, for example, in vitro recombinant DNA techniques, synthetic techniques, and in vivo genetic recombination. Also provided are replicable vectors comprising a nucleotide sequence encoding an antibody or antigen-binding fragment thereof described herein, a heavy or light chain, a heavy or light chain variable domain, or a heavy or light chain CDR, operably linked to a promoter. Such vectors can, for example, include the nucleotide sequence encoding the constant region of the antibody or antigen-binding fragment thereof (see, e.g., International Publication Nos. WO 86/05807 and WO 89/01036; and U.S. Pat. No. 5,122,464), and variable domains of the antibody or antigen-binding fragment thereof can be cloned into such a vector for expression of the entire heavy, the entire light chain, or both the entire heavy and light chains.

An expression vector can be transferred to a cell (e.g., host cell) by conventional techniques and the resulting cells can then be cultured by conventional techniques to produce an antibody or antigen-binding fragment thereof described herein (e.g., an antibody or antigen-binding fragment thereof comprising the six CDRs, the VH, the VL, the VH and the VL, the heavy chain, the light chain, or the heavy and the light chain of 20502, 20502.1, or 22213) or a domain thereof (e.g., the VH, the VL, the VH and the VL, the heavy chain, or the light chain of 20502, 20502.1, or 22213). Thus, provided herein are host cells containing a polynucleotide encoding an antibody or antigen-binding fragment thereof described herein (e.g., an antibody or antigen-binding fragment thereof comprising the six CDRs, the VH, the VL, the VH and the VL, the heavy chain, the light chain, or the heavy and the light chain of 20502, 20502.1, or 22213) or a domain thereof (e.g., the VH, the VL, the VH and the VL, the heavy chain, or the light chain of 20502, 20502.1, or 22213), operably linked to a promoter for expression of such sequences in the host cell. In certain embodiments, for the expression of double-chained antibodies or antigen-binding fragments thereof, vectors encoding both the heavy and light chains, individually, can be co-expressed in the host cell for expression of the entire immunoglobulin, as detailed below. In certain embodiments, a host cell contains a vector comprising a polynucleotide encoding both the heavy chain and light chain of an antibody described herein (e.g., the heavy and the light chain of 20502, 20502.1, or 22213), or a domain thereof (e.g., the VH and the VL of 20502, 20502.1, or 22213). In specific embodiments, a host cell contains two different vectors, a first vector comprising a polynucleotide encoding a heavy chain or a heavy chain variable region of an antibody or antigen-binding fragment thereof described herein, and a second vector comprising a polynucleotide encoding a light chain or a light chain variable region of an antibody described herein (e.g., an antibody comprising the six CDRs of 20502, 20502.1, or 22213), or a domain thereof. In other embodiments, a first host cell comprises a first vector comprising a polynucleotide encoding a heavy chain or a heavy chain variable region of an antibody or antigen-binding fragment thereof described herein, and a second host cell comprises a second vector comprising a polynucleotide encoding a light chain or a light chain variable region of an antibody or antigen-binding fragment thereof described herein (e.g., an antibody or antigen-binding fragment thereof comprising the six CDRs of 20502, 20502.1, or 22213). In specific embodiments, a heavy chain/heavy chain variable region expressed by a first cell associated with a light chain/light chain variable region of a second cell to form an anti-B7-H4 antibody or antigen-binding fragment thereof described herein (e.g., antibody or antigen-binding fragment thereof comprising the six CDRs of 20502, 20502.1, or 22213). In certain embodiments, provided herein is a population of host cells comprising such first host cell and such second host cell.

In a particular embodiment, provided herein is a population of vectors comprising a first vector comprising a polynucleotide encoding a light chain/light chain variable region of an anti-B7-H4 antibody or antigen-binding fragment thereof described herein, and a second vector comprising a polynucleotide encoding a heavy chain/heavy chain variable region of an anti-B7-H4 antibody or antigen-binding fragment thereof described herein (e.g., antibody or antigen-binding fragment thereof comprising the CDRs of 20502, 20502.1, or 22213). Alternatively, a single vector can be used which encodes, and is capable of expressing, both heavy and light chain polypeptides.

A variety of host-expression vector systems can be utilized to express antibodies and antigen-binding fragments thereof described herein (e.g., an antibody or antigen-binding fragment thereof comprising the CDRs of 20502, 20502.1, or 22213) (see, e.g., U.S. Pat. No. 5,807,715). Such host-expression systems represent vehicles by which the coding sequences of interest can be produced and subsequently purified, but also represent cells which can, when transformed or transfected with the appropriate nucleotide coding sequences, express an antibody or antigen-binding fragment thereof described herein in situ. These include but are not limited to microorganisms such as bacteria (e.g., *E. coli* and *B. subtilis*) transformed with recombinant bacteriophage DNA, plasmid DNA or cosmid DNA expression vectors containing antibody coding sequences; yeast (e.g., *Saccharomyces Pichia*) transformed with recombinant yeast expression vectors containing antibody coding sequences; insect cell systems infected with recombinant virus expression vectors (e.g., baculovirus) containing antibody coding sequences; plant cell systems (e.g., green algae such as *Chlamydomonas reinhardtii*) infected with recombinant virus expression vectors (e.g., cauliflower mosaic virus, CaMV; tobacco mosaic virus, TMV) or transformed with recombinant plasmid expression vectors (e.g., Ti plasmid) containing antibody coding sequences; or mammalian cell systems (e.g., COS (e.g., COS1 or COS), CHO, BHK, MDCK, HEK 293, NS0, PER.C6, VERO, CRL7O3O, HsS78Bst, HeLa, and NIH 3T3, HEK-293T, HepG2, SP210, R1.1, B-W, L-M, BSC1, BSC40, YB/20 and BMT10 cells) harboring recombinant expression constructs containing promoters derived from the genome of mammalian cells (e.g., metallothionein promoter) or from mammalian viruses (e.g., the adenovirus late promoter; the vaccinia virus 7.5K promoter). In a specific embodiment, cells for expressing antibodies and antigen-binding fragments thereof described herein (e.g., an antibody or antigen-binding fragment thereof comprising the CDRs of 20502, 20502.1, or 22213) are CHO cells, for example CHO cells from the CHO GS System™ (Lonza). In a particular embodiment, cells for expressing antibodies described herein are human cells, e.g., human cell lines. In a specific embodiment, a mammalian expression vector is pOptiVEC™ or pcDNA3.3. In a particular embodiment, bacterial cells such as *Escherichia coli*, or eukaryotic cells (e.g., mammalian cells), especially for the expression of whole recombinant antibody molecule, are used for the expression of a recombinant antibody molecule. For example, mammalian cells such as Chinese hamster ovary (CHO) cells in conjunction with a vector such as the major intermediate early gene promoter element from human cytomegalovirus is an effective expression system for antibodies (Foecking M K & Hofstetter H (1986) Gene 45: 101-105; and Cockett M I et al., (1990) Biotechnology 8: 662-667). In certain embodiments, antibodies or antigen-binding fragments thereof described herein are produced by CHO cells or NS0 cells.

In addition, a host cell strain can be chosen which modulates the expression of the inserted sequences, or modifies and processes the gene product in the specific fashion desired. Such modifications (e.g., glycosylation) and processing (e.g., cleavage) of protein products can contribute to the function of the protein. To this end, eukaryotic host cells which possess the cellular machinery for proper processing of the primary transcript, glycosylation, and phosphorylation of the gene product can be used. Such mammalian host cells include but are not limited to CHO, VERO, BHK, Hela, MDCK, HEK 293, NIH 3T3, W138, BT483, Hs578T, HTB2, BT2O and T47D, NS0 (a murine myeloma cell line that does not endogenously produce any immunoglobulin chains), CRL7O3O, COS (e.g., COS1 or COS), PER.C6, VERO, HsS78Bst, HEK-293T, HepG2, SP210, R1.1, B-W, L-M, BSC1, BSC40, YB/20, BMT10 and HsS78Bst cells. In certain embodiments, anti-B7-H4 antibodies described herein (e.g., an antibody or antigen-binding fragment thereof comprising the CDRs of 20502, 20502.1, or 22213) are produced in mammalian cells, such as CHO cells.

In certain embodiments, anti-B7-H4 antibodies described herein (e.g., an antibody or antigen-binding fragment thereof comprising the CDRs of 20502, 20502.1, or 22213) are produced in Potelligent® CHOK1SV cells.

In some embodiments, host cells are provided that comprise nucleic acid encoding a B7-H4 antibody or antigen-binding fragment thereof described herein, wherein the host cell lacks a functional alpha-1,6-fucosyltransferase gene (FUT8) gene. In some embodiments, the host cell is a CHO cell.

Once an antibody or antigen-binding fragment thereof described herein has been produced by recombinant expression, it can be purified by any method known in the art for purification of an immunoglobulin molecule, for example, by chromatography (e.g., ion exchange, affinity, particularly by affinity for the specific antigen after Protein A, and sizing column chromatography), centrifugation, differential solubility, or by any other standard technique for the purification of proteins. Further, the antibodies or antigen-binding fragments thereof described herein can be fused to heterologous polypeptide sequences described herein or otherwise known in the art to facilitate purification.

In specific embodiments, an antibody or antigen-binding fragment thereof described herein is isolated or purified. Generally, an isolated antibody or antigen-binding fragment thereof is one that is substantially free of other antibodies or antigen-binding fragments thereof with different antigenic specificities than the isolated antibody or antigen-binding fragment thereof. For example, in a particular embodiment, a preparation of an antibody or antigen-binding fragment thereof described herein is substantially free of cellular material and/or chemical precursors.

1.3 Pharmaceutical Compositions

Provided herein are compositions comprising an antibody or antigen-binding fragment thereof described herein having the desired degree of purity in a physiologically acceptable carrier, excipient or stabilizer (Remington's Pharmaceutical Sciences (1990) Mack Publishing Co., Easton, Pa.). Acceptable carriers, excipients, or stabilizers are nontoxic to recipients at the dosages and concentrations employed.

In various embodiments, compositions comprising an anti-B7-H4 antibody or antigen-binding fragment thereof are provided in formulations with a pharmaceutically acceptable carrier (see, e.g., Gennaro, Remington: The Science and Practice of Pharmacy with Facts and Comparisons: Drugfacts Plus, 20th ed. (2003); Ansel et al., Pharmaceutical Dosage Forms and Drug Delivery Systems, 7th ed., Lippencott Williams and Wilkins (2004); Kibbe et al., Handbook of Pharmaceutical Excipients, 3rd ed., Pharmaceutical Press (2000)).

Pharmaceutical compositions described herein can be useful in blocking the inhibitory activity of B7-H4 against T cells and/or in ADCC-dependent depletion of B7-H4 expressing cells. Pharmaceutical compositions described herein can be useful in treating a condition such as cancer. Examples of cancer that can be treated in accordance with the methods described herein include, but are not limited to, breast cancer (e.g., triple negative breast cancer, ductal carcinoma), endometrial carcinoma, ovarian cancer, and non-small cell lung cancer (e.g., squamous cell carcinoma), pancreatic cancer, thyroid cancer, kidney cancer (e.g., renal cell carcinoma), and bladder cancer (e.g., urothelial cell carcinoma). A non-small cell lung cancer can be, e.g., an adenocarcinoma. Additional examples of cancer that can be treated in accordance with the methods described herein include, but are not limited to, head and neck cancer, small cell lung cancer, gastric cancer, melanoma, and cholangiocarcinoma. In one embodiment, the ovarian cancer is a serous adenocarcinoma. In one embodiment, the breast cancer is a ductal adenocarcinoma.

The pharmaceutical compositions described herein are in one embodiment for use as a medicament. The pharmaceutical compositions described herein are in one embodiment for use as a diagnostic, e.g., to detect the presence of B7-H4 in a sample obtained from a patient (e.g., a human patient).

The compositions to be used for in vivo administration can be sterile. This is readily accomplished by filtration through, e.g., sterile filtration membranes.

In some embodiments, pharmaceutical compositions are provided, wherein the pharmaceutical composition comprises anti-B7-H4 antibodies or antigen-binding fragments thereof described herein and a pharmaceutically acceptable carrier. In some embodiments, pharmaceutical compositions are provided, wherein the pharmaceutical composition comprises afucosylated anti-B7-H4 antibodies or antigen-binding fragments thereof described herein and a pharmaceutically acceptable carrier. In specific embodiments, such pharmaceutical composition comprises afucosylated anti-B7-H4 antibodies or antigen-binding fragments e.g., wherein at least 80% of the antibodies in the composition are afucosylated. In specific embodiments, such pharmaceutical composition comprises afucosylated anti-B7-H4 antibodies or antigen-binding fragments e.g., wherein at least 85% of the antibodies in the composition are afucosylated. In specific embodiments, such pharmaceutical composition comprises afucosylated anti-B7-H4 antibodies or antigen-binding fragments e.g., wherein at least 90% of the antibodies in the composition are afucosylated. In specific embodiments, such pharmaceutical composition comprises afucosylated anti-B7-H4 antibodies or antigen-binding fragments e.g., wherein at least 95% of the antibodies in the composition are afucosylated. In specific embodiments, such pharmaceutical composition comprises afucosylated anti-B7-H4 antibodies or antigen-binding fragments e.g., wherein at least 96% of the antibodies in the composition are afucosylated. In specific embodiments, such pharmaceutical composition comprises afucosylated anti-B7-H4 antibodies or antigen-binding fragments e.g., wherein at least 97% of the antibodies in the composition are afucosylated. In specific embodiments, such pharmaceutical composition comprises afucosylated anti-B7-H4 antibodies or antigen-binding fragments e.g., wherein at least 98% of the antibodies in the composition are afucosylated. In specific embodiments, such pharmaceutical composition comprises afucosylated anti-B7-H4 antibodies or antigen-binding fragments e.g., wherein at least 99% of the antibodies in the composition are afucosylated. In specific embodiments, such pharmaceutical composition comprises afucosylated anti-B7-H4 antibodies or antigen-binding fragments wherein fucose is undetectable in the composition.

In some embodiments, a pharmaceutical composition comprises (i) an isolated antibody or antigen-binding fragment thereof that specifically binds to human B7-H4, comprising (a) the heavy chain variable region (VH) complementarity determining region (CDR) 1, VH CDR2, VH CDR3 and light chain variable region (VL) CDR1, CDR2, and CDR3 sequences of SEQ ID NOs:458-463, respectively, (b) a variable heavy chain region comprising the amino acid sequence of SEQ ID NO:464 and a variable light chain region comprising the amino acid sequence of SEQ ID NO:42, or (c) a heavy chain comprising the amino acid sequence of SEQ ID NO:469 and a light chain comprising the amino acid sequence of SEQ ID NO:44, and (ii) a pharmaceutically acceptable excipient.

Also provided herein is a pharmaceutical composition comprising (i) antibodies or antigen-binding fragments thereof that specifically bind to human B7-H4 and comprise the heavy chain variable region (VH) complementarity determining region (CDR) 1, VH CDR2, VH CDR3 and light chain variable region (VL) CDR1, CDR2, and CDR3 sequences of SEQ ID NOs:458-463, respectively and (ii) a pharmaceutically acceptable excipient, wherein at least 80%, at least 85%, at least 90%, at least 95%, at least 96%, at least 97%, at least 98%, or at least 99% of the antibodies or antigen-binding fragments thereof in the composition are afucosylated. In one embodiment, (i) the antibody or antigen-binding fragment thereof comprises a variable heavy chain region comprising the amino acid sequence of SEQ ID NO:464 and a variable light chain region comprising the amino acid sequence of SEQ ID NO:42 or (ii) the antibody comprises a heavy chain comprising the amino acid sequence of SEQ ID NO:469 and a light chain comprising the amino acid sequence of SEQ ID NO:44.

In some embodiments, a pharmaceutical composition comprises (i) an isolated antibody or antigen-binding fragment thereof that specifically binds to human B7-H4, comprising (a) the heavy chain variable region (VH) complementarity determining region (CDR) 1, VH CDR2, VH CDR3 and light chain variable region (VL) CDR1, CDR2, and CDR3 sequences of SEQ ID NOs:35-40, respectively, (b) a variable heavy chain region comprising the amino acid sequence of SEQ ID NO:41 and a variable light chain region comprising the amino acid sequence of SEQ ID NO:42, or (c) a heavy chain comprising the amino acid sequence of SEQ ID NO:43 and a light chain comprising the amino acid sequence of SEQ ID NO:44, and (ii) a pharmaceutically acceptable excipient.

Also provided herein is a pharmaceutical composition comprising (i) antibodies or antigen-binding fragments thereof that specifically bind to human B7-H4 and comprise the heavy chain variable region (VH) complementarity determining region (CDR) 1, VH CDR2, VH CDR3 and light chain variable region (VL) CDR1, CDR2, and CDR3 sequences of SEQ ID NOs:35-40, respectively and (ii) a pharmaceutically acceptable excipient, wherein at least 80%, at least 85%, at least 90%, at least 95%, at least 96%, at least 97%, at least 98%, or at least 99% of the antibodies or antigen-binding fragments thereof in the composition are afucosylated. In one embodiment, (i) the antibody or antigen-binding fragment thereof comprises a variable heavy chain region comprising the amino acid sequence of SEQ ID NO:41 and a variable light chain region comprising the amino acid sequence of SEQ ID NO:42 or (ii) the antibody comprises a heavy chain comprising the amino acid sequence of SEQ ID NO:43 and a light chain comprising the amino acid sequence of SEQ ID NO:44.

In some embodiments, a pharmaceutical composition comprises (i) an isolated antibody or antigen-binding fragment thereof that specifically binds to human B7-H4, comprising (a) the heavy chain variable region (VH) complementarity determining region (CDR) 1, VH CDR2, VH CDR3 and light chain variable region (VL) CDR1, CDR2, and CDR3 sequences of SEQ ID NOs:65-70, respectively, (b) a variable heavy chain region comprising the amino acid sequence of SEQ ID NO:71 and a variable light chain region comprising the amino acid sequence of SEQ ID NO:72, or (c) a heavy chain comprising the amino acid sequence of SEQ ID NO:73 and a light chain comprising the amino acid sequence of SEQ ID NO:74, and (ii) a pharmaceutically acceptable excipient.

Also provided herein is a pharmaceutical composition comprising (i) antibodies or antigen-binding fragments thereof that specifically bind to human B7-H4 and comprise the heavy chain variable region (VH) complementarity determining region (CDR) 1, VH CDR2, VH CDR3 and light chain variable region (VL) CDR1, CDR2, and CDR3 sequences of SEQ ID NOs:65-70, respectively and (ii) a pharmaceutically acceptable excipient, wherein at least 80%, at least 85%, at least 90%, at least 95%, at least 96%, at least 97%, at least 98%, or at least 99% of the antibodies or antigen-binding fragments thereof in the composition are afucosylated. In one embodiment, (i) the antibody or antigen-binding fragment thereof comprises a variable heavy chain region comprising the amino acid sequence of SEQ ID NO:71 and a variable light chain region comprising the amino acid sequence of SEQ ID NO:72 or (ii) the antibody comprises a heavy chain comprising the amino acid sequence of SEQ ID NO:73 and a light chain comprising the amino acid sequence of SEQ ID NO:74.

1.4 Uses and Methods
1.4.1 Therapeutic Uses and Methods

In one aspect, presented herein are methods for modulating one or more immune functions in a subject, comprising administering to a subject in need thereof an anti-B7-H4 antibody or antigen-binding fragment thereof described herein, or a pharmaceutical composition thereof as described above and herein.

In another embodiment, an anti-B7-H4 antibody or antigen-binding fragment thereof, or pharmaceutical composition, is administered to a patient (e.g., a human patient) to increase the proliferation of T cells, CD4+ T cells, or CD8+ T cells in the patient. In another embodiment, an anti-B7-H4 antibody or antigen-binding fragment thereof, or pharmaceutical composition, is administered to a patient (e.g., a human patient) to increase interferon-gamma (IFNγ) production in the patient. In another embodiment, an anti-B7-H4 antibody or antigen-binding fragment thereof, or pharmaceutical composition, is administered to a patient (e.g., a human patient) to block the inhibitory activity of B7-H4 against T cells in the patient. In another embodiment, an anti-B7-H4 antibody or antigen-binding fragment thereof, or pharmaceutical composition, is administered to a patient (e.g., a human patient) to deplete B7-H4 expressing cancer cells in the patient. In another embodiment, the anti-B7-H4 antibody or antigen-binding fragment thereof, or pharmaceutical composition, is administered to achieve two or more of the above effects.

In a certain embodiment, provided herein are methods of treating a cancer, e.g., a B7-H4 expressing cancer. The method of treating cancer can comprise administering an anti-B7-H4 antibody or antigen-binding fragment thereof provided herein or a pharmaceutical composition comprising an anti-B7-H4 antibody or antigen-binding fragment thereof provided herein to a patient (e.g., a human patient) in need thereof.

In a certain embodiment, provided herein are methods of treating a cancer selected from the group consisting of:

breast cancer (e.g., triple negative breast cancer, ductal carcinoma), endometrial carcinoma, ovarian cancer, non-small cell lung cancer (e.g., squamous cell carcinoma), pancreatic cancer, thyroid cancer, kidney cancer (e.g., renal cell carcinoma), and bladder cancer (e.g., urothelial cell carcinoma). In a certain embodiment, provided herein are methods of treating a non-small cell lung cancer that is an adenocarcinoma. In a certain embodiment, provided herein are methods of treating a cancer selected from the group consisting of: head and neck cancer, small cell lung cancer, gastric cancer, melanoma, and cholangiocarcinoma. In one embodiment, the ovarian cancer is a serous adenocarcinoma. In one embodiment, the breast cancer is a ductal adenocarcinoma. In some embodiments, such methods comprise administering an anti-B7-H4 antibody or antigen-binding fragment thereof provided herein or a pharmaceutical composition comprising an anti-B7-H4 antibody or antigen-binding fragment thereof provided herein to a patient (e.g., a human patient) in need thereof. In some embodiments, the cancer is a B7-H4 expressing cancer.

In a certain embodiment, provided herein is a method of treating a cancer that is a PD-1/PD-L1 inhibitor inadequate responder. A cancer that is a PD-1/PD-L1 inhibitor inadequate responder, may have previously responded to a PD-1/PD-L1 inhibitor, but may have become less responsive to the PD-1/PD-L1 inhibitor, or the cancer may have never responded to the PD-1/PD-L1 inhibitor. Inadequate response to a PD-1/PD-L1 inhibitor means that aspects of the cancer that would be expected to improve following a standard dose of the PD-1/PD-L1 inhibitor do not improve, and/or improvement only occurs if greater than a standard dose is administered. In some embodiments, a subject with a cancer that is a PD-1/PD-L1 inhibitor inadequate responder has experienced, or is experiencing, an inadequate response to the PD-1/PD-L1 inhibitor after receiving a standard dose for at least two weeks, at least three weeks, at least four weeks, at least six weeks, or at least twelve weeks. A "standard" dose is determined by a medical professional, and may depend on the subject's age, weight, healthy history, severity of disease, the frequency of dosing, etc. In some embodiments, subject with a cancer that is a PD-1/PD-L1 inhibitor inadequate responder has experienced, or is experiencing, an inadequate response to an anti-PD-1 antibody and/or an anti-PD-L1 antibody. In some embodiments, a subject with cancer that is a PD-1/PD-L1 inhibitor inadequate responder has experienced, or is experiencing, an inadequate response to AMP-224. In some embodiments, a subject with cancer that is a PD-1/PD-L1 inhibitor inadequate responder has experienced, or is experiencing, an inadequate response to a PD-1/PD-L1 inhibitor selected from nivolumab, pembrolizumab, and atezolizumab.

In a certain embodiment, provided herein is a method of treating a cancer that expresses a low level of PD-L1. In some embodiments, a cancer that expresses a "low level of PD-L1," or expresses "PD-L1 at a low level," denotes that the level of PD-L1 is under the level of expression for a cancer that is indicated for treatment with a PD-1 or PD-L1 antagonist in which patients are selected for treatment based on PD-L1 expression levels. In some embodiments, a "low level of PD-L1" is one in which less than 1% of the cells in the tumor have membrane staining. In some embodiments, a "low level" in regard to PD-L1 is less than 1% staining, for example, 0.9, 0.8, 0.7, 0.6, 0.5, 0.4, 0.3, 0.2, 0.1% or 0% of the cells of the tumor are stained. In some embodiments, PD-L1 expression levels can be measured by chromogenic IHC or immunofluorescence IHC (Aqua scoring). In certain embodiments, PD-L1 staining of 5% or less (including tumor and/or immune cells) can indicate that a sample expresses a "low level of PD-L1." In certain embodiments, PD-L1 staining of 10% or less (including tumor and/or immune cells) can indicate that a sample expresses a "low level of PD-L1." Unless indicated otherwise herein, a 5% threshold is used herein (i.e., 5% or less indicates a "low level of PD-L1").

In another embodiment, an anti-B7-H4 antibody or antigen-binding fragment thereof, or pharmaceutical composition, is administered to a patient (e.g., a human patient) diagnosed with cancer to increase the proliferation of T cells, CD4+ T cells, or CD8+ T cells in the patient. In another embodiment, an anti-B7-H4 antibody or antigen-binding fragment thereof, or pharmaceutical composition, is administered to a patient (e.g., a human patient) diagnosed with cancer to increase interferon-gamma (IFNγ) production in the patient. In another embodiment, an anti-B7-H4 antibody or antigen-binding fragment thereof, or pharmaceutical composition, is administered to a patient (e.g., a human patient) diagnosed with cancer to block the inhibitory activity of B7-H4 against T cells in the patient. In another embodiment, an anti-B7-H4 antibody or antigen-binding fragment thereof, or pharmaceutical composition, is administered to a patient (e.g., a human patient) diagnosed with cancer to deplete B7-H4 expressing cancer cells in the patient.

In further embodiments, an anti-B7-H4 antibody or antigen-binding fragment thereof, or pharmaceutical composition, is administered to a patient as provided above, and further in combination with an additional therapeutic agent, e.g., a chemotherapeutic agent or an immune stimulating agent, such as a T cell checkpoint inhibitor.

In an exemplary embodiment, the additional therapeutic agent is a PD-1 antagonist, such as an antagonistic PD-1 antibody. Suitable PD-1 antibodies include, for example, OPDIVO (nivolumab), KEYTRUDA (pembrolizumab), or MEDI-0680 (AMP-514; WO2012/145493). Suitable PD-1 antibodies also include, for example, camrelizumab (SHR-1210), tislelizumab (BGB-A317), or spartalizumab (NPVPDR001, NVS240118, PDR001). The additional therapeutic agent may also include pidilizumab (CT-011). A recombinant protein composed of the extracellular domain of PD-L2 (B7-DC) fused to the Fc portion of IgG1, called AMP-224, can also be used to antagonize the PD-1 receptor.

In another exemplary embodiment, the additional therapeutic agent is a PD-L1 antagonist, such as an antagonistic PD-L1 antibody. Suitable PD-L1 antibodies include, for example, TECENTRIQ (atezolizumab), durvalumab (MEDI4736), BMS-936559 (WO2007/005874), MSB0010718C (WO2013/79174) or rHigM12B7.

In yet another exemplary embodiment, the additional therapeutic agent is a GITR agonist, such as an agonistic GITR antibody. Suitable GITR antibodies include, for example, TRX-518 (WO06/105021, WO09/009116), MK-4166 (WO11/028683), or a GITR antibody disclosed in WO2015/031667. In another embodiment, the additional therapeutic agent is a GITR antibody disclosed in WO2017/015623. In a particular embodiment, the GITR antibody is selected from: a) an antibody comprising a GITR binding domain (GITR-BD) comprising a CDR1 comprising the sequence of SEQ ID NO:411, a CDR2 comprising the sequence of SEQ ID NO:412, and a CDR3 comprising the sequence of SEQ ID NO:413; b) an antibody comprising a GITR-BD comprising the sequence of SEQ ID NO:414; c) a tetravalent molecule comprising two copies of a polypeptide having the structure (GITR-BD)-Linker-(GITR-BD)-Linker-Hinge-Fc, wherein (i) the GITR-BD comprises a CDR1 comprising the sequence of SEQ ID NO:411, a CDR2 comprising the sequence of SEQ ID NO:412, and a CDR3 comprising the sequence of SEQ ID NO:413, (ii) the Linker is a polypeptide, (iii) the Hinge is a polypeptide derived from an immunoglobulin hinge region, and (iv) the Fc is an immunoglobulin Fc polypeptide; d) a tetravalent molecule comprising two copies of a polypeptide having the structure (GITR-BD)-Linker-(GITR-BD)-Linker-Hinge-Fc, wherein (i) the GITR-BD comprises the amino acid sequence of SEQ ID NO:414, (ii) the Linker is a polypeptide, (iii) the Hinge is a polypeptide derived from an immunoglobulin hinge region, and (iv) the Fc is an immunoglobulin Fc polypeptide; and e) a tetravalent molecule comprising two copies of a polypeptide comprising the sequence of SEQ ID NO: 415. In any of the above embodiments of a tetravalent molecule, a Hinge may comprise the sequence of SEQ ID NO:416, 417 or 418. In any of the above embodiments of a tetravalent molecule, a Linker may comprise an amino acid sequence selected from GG, GGG, and SEQ ID NOs:419-425. In certain embodiments, the Hinge comprises SEQ ID NO:417 and the Linker comprises any one of SEQ ID NOs:419-423.

In yet another exemplary embodiment, the additional therapeutic agent is a CD80 extracellular domain (CD80 ECD), e.g., SEQ ID NO:426; or a CD80 ECD fusion molecule comprising CD80 ECD and a fusion partner, as disclosed in WO2017/079117. In certain embodiments, the CD80 ECD fusion molecule is a CD80 ECD-Fc fusion protein. In a specific embodiment, the CD80 ECD-Fc fusion protein comprises the sequence of SEQ ID NO:427 or 428.

In yet another exemplary embodiment, the additional therapeutic agent is an anti-CSF1R antibody disclosed in U.S. Pat. Nos. 8,182,813, 8,206,715, 8,263,079, 8,513,199 or 9,221,910. In a particular embodiment, the anti-CSF1R antibody is selected from: a) an antibody comprising a heavy chain comprising the sequence of SEQ ID NO:429 and a light chain comprising the sequence of SEQ ID NO:430; b) an antibody comprising a heavy chain comprising a heavy chain (HC) complementarity determining region 1 (CDR1) comprising the sequence of SEQ ID NO:431, an HC CDR2 comprising the sequence of SEQ ID NO:432, and an HC CDR3 comprising the sequence of SEQ ID NO:433, and a light chain comprising a light chain (LC) CDR1 comprising the sequence of SEQ ID NO:434, a LC CDR2 comprising the sequence of SEQ ID NO:435, and a LC CDR3 comprising the sequence of SEQ ID NO:436; and c) an antibody comprising a heavy chain comprising the sequence of SEQ ID NO:437 and a light chain comprising the sequence of SEQ ID NO:438.

Usually, the patient is a human but non-human mammals including transgenic mammals can also be treated.

In some embodiments, the present invention relates to an antibody or antigen-binding fragment thereof or pharmaceutical composition provided herein for use as a medicament. In some aspects, the present invention relates to an antibody or antigen-binding fragment thereof or pharmaceutical composition provided herein, for use in a method for the treatment of cancer. In some aspects, the present invention relates to an antibody or antigen-binding fragment thereof or pharmaceutical composition provided herein, for use in a method for the treatment of cancer in a subject, comprising administering to the subject an effective amount of an antibody or antigen-binding fragment thereof or pharmaceutical composition provided herein.

1.4.1.1 Routes of Administration & Dosage

An antibody or antigen-binding fragment thereof or composition described herein can be delivered to a subject by a variety of routes, such as parenteral, subcutaneous, intravenous, intradermal, transdermal, intranasal, intratumoral, and administration to a tumor draining lymph node. In one embodiment, the antibody or antigen-binding fragment thereof or composition is administered by an intravenous route.

The amount of an antibody or antigen-binding fragment thereof or composition which will be effective in the treatment of a condition will depend on the nature of the disease. The precise dose to be employed in a composition will also depend on the route of administration, and the seriousness of the disease.

1.4.2 Detection & Diagnostic Uses

An anti-B7-H4 antibody or antigen-binding fragment thereof described herein (see, e.g., Section 5.2) can be used to assay B7-H4 protein levels in a biological sample using classical methods known to those of skill in the art, including immunoassays, such as the enzyme linked immunosorbent assay (ELISA), immunoprecipitation, or Western blotting. Suitable antibody assay labels are known in the art and include enzyme labels, such as, glucose oxidase; radioisotopes, such as iodine (125I, 121I), carbon (14C), sulfur (35S), tritium (3H), indium (121In), and technetium (99Tc); luminescent labels, such as luminol; and fluorescent labels, such as fluorescein and rhodamine, and biotin. Such labels can be used to label an antibody or antigen-binding fragment thereof described herein. Alternatively, a second antibody or antigen-binding fragment thereof that recognizes an anti-B7-H4 antibody or antigen-binding fragment thereof described herein can be labeled and used in combination with an anti-B7-H4 antibody or antigen-binding fragment thereof to detect B7-H4 protein levels.

Assaying for the expression level of B7-H4 protein is intended to include qualitatively or quantitatively measuring or estimating the level of a B7-H4 protein in a first biological sample either directly (e.g., by determining or estimating absolute protein level) or relatively (e.g., by comparing to the disease associated protein level in a second biological sample). B7-H4 polypeptide expression level in the first biological sample can be measured or estimated and compared to a standard B7-H4 protein level, the standard being taken from a second biological sample obtained from an individual not having the disorder or being determined by averaging levels from a population of individuals not having the disorder. As will be appreciated in the art, once the "standard" B7-H4 polypeptide level is known, it can be used repeatedly as a standard for comparison.

As used herein, the term "biological sample" refers to any biological sample obtained from a subject, cell line, tissue, or other source of cells potentially expressing B7-H4. Methods for obtaining tissue biopsies and body fluids from animals (e.g., humans) are well known in the art. Biological samples include peripheral mononuclear blood cells. A biological sample may also be a blood sample, in which circulating tumor cells (or "CTCs") may express B7-H4 and be detected.

An anti-B7-H4 antibody described herein can be used for prognostic, diagnostic, monitoring and screening applications, including in vitro and in vivo applications well known and standard to the skilled artisan and based on the present description. Prognostic, diagnostic, monitoring and screening assays and kits for in vitro assessment and evaluation of immune system status and/or immune response may be utilized to predict, diagnose and monitor to evaluate patient samples including those known to have or suspected of having an immune system-dysfunction or cancer. This type of prognostic and diagnostic monitoring and assessment is already in practice utilizing antibodies against the HER2 protein in breast cancer (HercepTest™, Dako) where the assay is also used to evaluate patients for antibody therapy using Herceptin®. In vivo applications include directed cell therapy and immune system modulation and radio imaging of immune responses.

Anti-B7-H4 antibodies and antigen-binding fragments thereof described herein can carry a detectable or functional label. When fluorescence labels are used, currently available microscopy and fluorescence-activated cell sorter analysis (FACS) or combination of both methods procedures known in the art may be utilized to identify and to quantitate the specific binding members. Anti-B7-H4 antibodies or antigen-binding fragments thereof described herein can carry a fluorescence label. Exemplary fluorescence labels include, for example, reactive and conjugated probes, e.g., Aminocoumarin, Fluorescein and Texas red, Alexa Fluor dyes, Cy dyes and DyLight dyes. An anti-B7-H4 antibody can carry a radioactive label, such as the isotopes 3H, 14C, 32P, 35S, 36Cl, 51Cr, 57Co, 58Co, 59Fe, 67Cu, 90Y, 99Tc, 111In, 117Lu, 121I, 124I, 125I, 131I, 198Au, 211At, 213Bi, 225Ac and 186Re. When radioactive labels are used, currently available counting procedures known in the art may be utilized to identify and quantitate the specific binding of anti-B7-H4 antibody or antigen-binding fragment to B7-H4 (e.g., human B7-H4). In the instance where the label is an enzyme, detection may be accomplished by any of the presently utilized colorimetric, spectrophotometric, fluorospectrophotometric, amperometric or gasometric techniques as known in the art. This can be achieved by contacting a sample or a control sample with an anti-B7-H4 antibody or antigen-binding fragment thereof under conditions that allow for the formation of a complex between the antibody or antigen-binding fragment thereof and B7-H4. Any complexes formed between the antibody or antigen-binding fragment thereof and B7-H4 are detected and compared in the sample and the control. In light of the specific binding of the antibodies or antigen-binding fragments thereof described herein for B7-H4, the antibodies or antigen-binding fragments thereof can be used to specifically detect B7-H4 expression on the surface of cells. The antibodies or antigen-binding fragments thereof described herein can also be used to purify B7-H4 via immunoaffinity purification.

Also included herein is an assay system which may be prepared in the form of a test kit for the quantitative analysis of the extent of the presence of, for instance, B7-H4. The system or test kit may comprise a labeled component, e.g., a labeled antibody or antigen-binding fragment, and one or more additional immunochemical reagents. See, e.g., Section 5.6 below for more on kits.

In some aspects, methods for in vitro detecting B7-H4 in a sample, comprising contacting said sample with an antibody or antigen-binding fragment thereof, are provided herein. In some aspects, provided herein is the use of an antibody or antigen-binding fragment thereof provided herein, for in vitro detecting B7-H4 in a sample. In one aspect, provided herein is an antibody or antigen-binding fragment thereof or pharmaceutical composition provided herein for use in the detection of B7-H4 in a subject or a sample obtained from a subject. In one aspect, provided herein is an antibody or antigen-binding fragment thereof or pharmaceutical composition provided herein for use as a diagnostic. In one preferred embodiment, the antibody comprises a detectable label. In one preferred embodiment, B7-H4 is human B7-H4. In one preferred embodiment, the subject is a human.

1.5 Kits

Provided herein are kits comprising one or more antibodies or antigen-binding fragments thereof described herein or conjugates thereof. In a specific embodiment, provided herein is a pharmaceutical pack or kit comprising one or more containers filled with one or more of the ingredients of the pharmaceutical compositions described herein, such as one or more antibodies or antigen-binding fragments thereof provided herein. Optionally associated with such container(s) can be a notice in the form prescribed by a governmental agency regulating the manufacture, use, or sale of pharmaceuticals or biological products, which notice reflects approval by the agency of manufacture, use or sale for human administration.

Also provided herein are kits that can be used in diagnostic methods. In one embodiment, a kit comprises an antibody or antigen-binding fragment thereof described herein, preferably a purified antibody or antigen-binding fragment thereof, in one or more containers. In a specific embodiment, kits described herein contain a substantially isolated B7-H4 antigen (e.g., human B7-H4) that can be used as a control. In another specific embodiment, the kits described herein further comprise a control antibody or antigen-binding fragment thereof which does not react with a B7-H4 antigen. In another specific embodiment, kits described herein contain one or more elements for detecting the binding of an antibody or antigen-binding fragment thereof to a B7-H4 antigen (e.g., the antibody or antigen-binding fragment thereof can be conjugated to a detectable substrate such as a fluorescent compound, an enzymatic substrate, a radioactive compound or a luminescent compound, or a second antibody or antigen-binding fragment thereof which recognizes the first antibody or antigen-binding fragment thereof can be conjugated to a detectable substrate). In specific embodiments, a kit provided herein can include a recombinantly produced or chemically synthesized B7-H4 antigen. The B7-H4 antigen provided in the kit can also be attached to a solid support. In a more specific embodiment, the detecting means of the above described kit includes a solid support to which a B7-H4 antigen is attached. Such a kit can also include a non-attached reporter-labeled anti-human antibody or antigen-binding fragment thereof or anti-mouse/rat antibody or antigen-binding fragment thereof. In this embodiment, binding of the antibody or antigen-binding fragment thereof to the B7-H4 antigen can be detected by binding of the said reporter-labeled antibody or antigen-binding fragment thereof.

The following examples are offered by way of illustration and not by way of limitation.

EXAMPLES

The examples in this Section (i.e., Section 6) are offered by way of illustration, and not by way of limitation.

Example 1

Assessment of Prevalence of B7-H4 Expression in Multiple Indications

The B7-H4 mouse monoclonal antibody A57.1 (ATCC Catalog No. PTA-5180) was used to detect the presence of B7-H4 on archival samples, a mixture of whole sections, and tumor microarrays. The samples were treated with the primary antibody and detected using a polymer detection system attached to DAB (Ventana Medical Systems).

B7-H4 was readily detected in the membrane and the cytosol in tumor tissues harvested from a variety of cancer patients, including invasive ductal carcinoma, triple negative breast cancer, ovarian cancer, non-small cell lung cancer and endometrial cancer. (FIG. 1). Moreover, frequency of expression was also high in the indications listed in Table 11.

TABLE 11

B7-H4 detection in tumors

| Tumor Type | #Total | #Positive | Percent Positive |
|---|---|---|---|
| Triple Negative Breast Cancer | 74 | 58 | 78% |
| Invasive Ductal Carcinoma | 51 | 38 | 74.50% |
| Endometrial Carcinoma | 77 | 54 | 70% |
| Ovarian Cancer | 141 | 85 | 60% |
| Non-Small Cell Lung Cancer (Squamous) | 47 | 19 | 40% |

B7-H4 is expressed in other cancers, such as kidney cancer (e.g., renal cell carcinoma), bladder cancer (e.g., urothelial cell carcinoma), pancreatic cancer, and thyroid cancer. See e.g., Zhu, J., et al., Asian Pacific J. Cancer Prev. 14: 3011-3015 (2011), Krambeck A, et al., PNAS 103: 10391-10396 (2006), Fan, M. et al., Int. J. Clin. Exp. Pathol. 7: 6768-6775 (2014), Xu, H., et al., Oncology Letters 11: 1841-1846 (2016), and Liu, W., et al., Oncology Letters 8: 2527-2534 (2014).

Figure 1B:
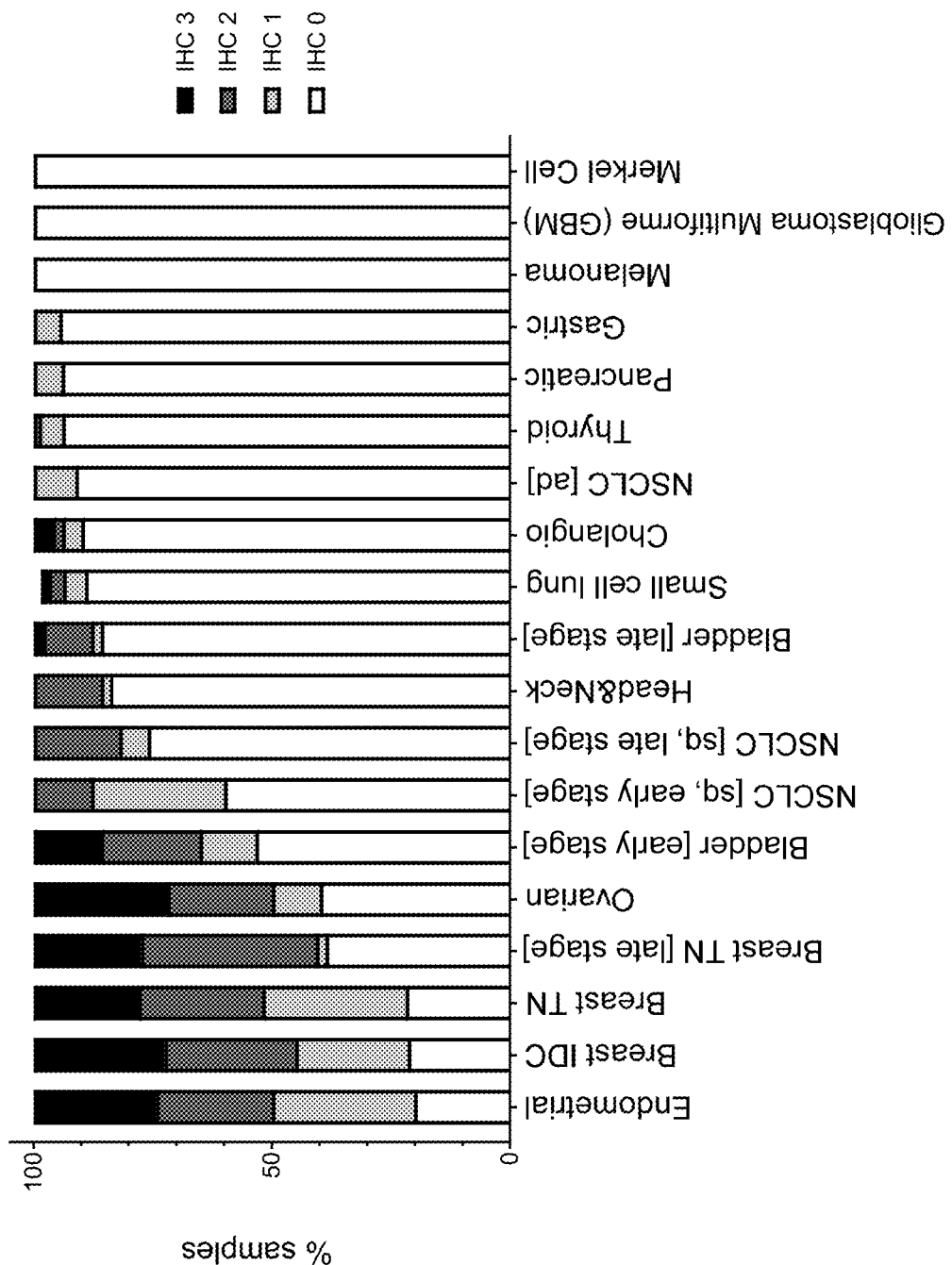
FIG. 1B shows B7-H4 prevalence in various tumor types by IHC. (See Example 1.)

In a subsequent experiment, B7-H4 prevalence in various tumor types was assessed by immunohistochemistry (IHC) (FIG. 1B). The following tumor types and stages of disease were tested: endometrial, breast invasive ductal carcinoma (IDC), breast triple negative (TN), breast triple negative (late stage), ovarian cancer, bladder cancer (early stage), non-small cell lung cancer (sq (squamous), early stage), non-small cell lung cancer (sq, late stage), head and neck cancer, bladder (late stage), small cell lung cancer, cholangiocarcinoma, non-small cell lung cancer (ad (adenocarcinoma)), thyroid cancer, pancreatic cancer, gastric cancer, melanoma, glioblastoma or glioblastoma multiforme (GBM), and merkel cell carcinoma. B7-H4 surface protein expression on tumor cells was evaluated on procured tumor samples from various tumor types and stages of disease where available (early stage (I/II), late stage (III/IV)). IHC intensity with the antibody A57.1 was scored by category 0 to 3, and samples were attributed a single IHC score by the highest intensity observed in a minimum of 10% of all tumor cells per whole section. A total of 50 to 100 samples per tumor type were evaluated.

Example 2

Generation of Novel Antibodies Against Human B7-H4

B7-H4-specific antibodies were isolated from full-length human IgG1 naïve antibody libraries using an in vitro yeast presentation system. The libraries are designed to mimic the immune system; they do not contain pre-defined heavy and light chain pairs. Libraries were subjected to multiple rounds of positive and negative selection strategies using B7-H4 protein to enrich for IgG that were cross-reactive to human, cynomolgus, and murine B7-H4 target. After four rounds of selection, the resulting IgG were sequenced, and unique antibodies were produced and evaluated for both avid and monomeric binding affinity to recombinant B7-H4 ectodomain, for epitope binning, and for target-specific cell binding.

A more detailed description of the selection, affinity maturation, and analytical methods that were used to generate and characterize the B7-H4 antibodies is provided below.

Materials and Methods

Antigens were biotinylated using the EZ-Link Sulfo-NHS-Biotinylation Kit from Pierce. Goat F(ab')2 anti-human kappa-FITC (LC-FITC), ExtrAvidin-PE (EA-PE) and Streptavidin-AF633 (SA-633) were obtained from Southern Biotech, Sigma, and Molecular Probes, respectively. Streptavidin MicroBeads and MACS LC separation columns were purchased from Miltenyi Biotec. Goat anti-human IgG-PE Human-PE) was obtained from Southern Biotech.

Naïve Discovery

Eight naïve human synthetic yeast libraries each of ~109 diversity were propagated as previously described (see Y. Xu et al, Addressing polyspecificity of antibodies selected from an in vitro yeast presentation system: a FACS-based, high-throughput selection and analytical tool. PEDS 26.10, 663-70 (2013); WO2009036379; WO2010105256; and WO2012009568.) For the first two rounds of selection, a magnetic bead sorting technique utilizing the Miltenyi MACS system was performed, as previously described (see Siegel et al, High efficiency recovery and epitope-specific sorting of an scFv yeast display library." J Immunol Methods 286(1-2), 141-153 (2004).) Briefly, yeast cells (~1010 cells/library) were incubated with 10 ml of 10 nM biotinylated Fc fusion antigen for 30 min at 30° C. in wash buffer (phosphate-buffered saline (PBS)/0.1% bovine serum albumin (BSA)). After washing once with 40 ml ice-cold wash buffer, the cell pellet was resuspended in 20 mL wash buffer, and Streptavidin MicroBeads (500 µl) were added to the yeast and incubated for 15 min at 4° C. Next, the yeast were pelleted, resuspended in 20 mL wash buffer, and loaded onto a Miltenyi LS column. After the 20 mL were loaded, the column was washed 3 times with 3 ml wash buffer. The column was then removed from the magnetic field, and the yeast were eluted with 5 mL of growth media and then grown overnight. The following rounds of selection were performed using flow cytometry. Approximately 2×107 yeast were pelleted, washed three times with wash buffer, and incubated at 30° C. with either decreasing concentrations of biotinylated Fc fusion antigen (10 to 1 nM) under equilibrium conditions, 10 nM biotinylated Fc fusion antigens of different species in order to obtain species cross-reactivity, or with a poly-specificity depletion reagent (PSR) to remove non-specific antibodies from the selection. For the PSR depletion the libraries were incubated with a 1:10 dilution of biotinylated PSR reagent as previously described (see Y. Xu et al., addressing polyspecificity of antibodies selected from an in vitro yeast presentation system: a FACS-based, high-throughput selection and analytical tool. PEDS 26.10, 663-70 (2013).) Yeast were then washed twice with wash buffer and stained with LC-FITC (diluted 1:100) and either SA-633 (diluted 1:500) or EAPE (diluted 1:50) secondary reagents for 15 min at 4° C. After washing twice with wash buffer, the cell pellets were resuspended in 0.3 mL wash buffer and transferred to strainer-capped sort tubes. Sorting was performed using a FACS ARIA sorter (BD Biosciences) and sort gates were determined to select for antibodies with desired characteristics. Selection rounds were repeated until a population with all of the desired characteristics was obtained. After the final round of sorting, yeast were plated and individual colonies were picked for characterization.

Antibody Optimization

Optimization of antibodies was performed via a light chain batch shuffle method, and then by introducing diversities into the heavy chain and light chain variable regions as described below. A combination of some of these approaches was used for each antibody.

Light chain batch shuffle: Heavy chain plasmids from a naïve selection output were extracted from the yeast via smash and grab, propagated in and subsequently purified from E.coli, and transformed into a light chain library with a diversity of 5×106. Selections were performed with one round of MACS and four rounds of FACS employing the same conditions as the naïve discovery.

CDRH1 and CDRH2 selection: The CDRH3 of a single antibody was recombined into a premade library with CDRH1 and CDRH2 variants of a diversity of 1×108 and selections were performed with one round of MACS and four rounds of FACS as described in the naïve discovery. For each FACS round the libraries were looked at for PSR binding, species cross-reactivity, and affinity pressure, and sorting was performed in order to obtain a population with the desired characteristics. For these selections affinity pressures were applied by using decreasing concentrations of biotinylated HIS-B7-H4 antigen (100 to 1 nM) under equilibrium conditions at 30° C.

VH Mut selection: The heavy chain variable region (VH) was mutagenized via error prone PCR. The library was then created by transforming this mutagenized VH and the heavy chain expression vector into yeast already containing the light chain plasmid of the parent. Selections were performed similar to previous cycles using FACS sorting for two rounds. For each FACS round the libraries were looked at for PSR binding and affinity pressure, and sorting was performed in order to obtain a population with the desired characteristics. Affinity pressures for these selections were performed as described above in the CDRH1 and CDRH2 selection.

CDRL1 and CDRL2 selection: The CDRL3 of a single antibody was recombined into a premade library with CDRL1 and CDRL2 variants of a diversity of ~5×105 and selections were performed similar to previous cycles using FACS sorting for three rounds. For each FACS round the libraries were looked at for PSR binding and affinity pressure, and sorting was performed in order to obtain a population with the desired characteristics. Affinity pressures for these selections were performed as described above in the CDRH1 and CDRH2 selection.

Antibody Production and Purification

Yeast clones were grown to saturation and then induced for 48 h at 30° C. with shaking. After induction, yeast cells were pelleted and the supernatants were harvested for purification. IgGs were purified using a Protein A column and eluted with acetic acid, pH 2.0. Fab fragments were generated by papain digestion and purified over KappaSelect (GE Healthcare LifeSciences).

ForteBio $K_D$ Measurements

ForteBio affinity measurements were performed on an Octet RED384 generally as previously described (see Estep et al, High throughput solution-based measurement of antibody-antigen affinity and epitope binning. Mabs 5(2), 270-278 (2013)). Briefly, ForteBio affinity measurements were performed by loading IgGs on-line onto AHQ sensors. Sensors were equilibrated off-line in assay buffer for 30 min and then monitored on-line for 60 seconds for baseline establishment. Sensors with loaded IgGs were exposed to 100 nM antigen for 3 minutes, and afterwards were transferred to assay buffer for 3 min for off-rate measurement. For monovalent affinity assessment Fabs were used instead of IgGs. For this assessment the unbiotinylated Fc fusion antigen was loaded on-line onto the AHQ sensors. Sensors were equilibrated off-line in assay buffer for 30 min and then monitored on-line for 60 seconds for baseline establishment. Sensors with loaded antigen were exposed to 100 nM Fab for 3 minutes, and afterwards they were transferred to assay buffer for 3 min for off-rate measurement. All kinetics were analyzed using the 1:1 binding model.

ForteBio Epitope Binning/Ligand Blocking

Epitope binning/ligand blocking was performed using a standard sandwich format cross-blocking assay. Control anti-target IgG was loaded onto AHQ sensors and unoccupied Fc-binding sites on the sensor were blocked with an irrelevant human IgG1 antibody. The sensors were then exposed to 100 nM target antigen followed by a second anti-target antibody or ligand. Additional binding by the second antibody or ligand after antigen association indicates an unoccupied epitope (non-competitor), while no binding indicates epitope blocking (competitor or ligand blocking).

Four non-competing antibodies ("binning antibodies" 1, 2, 3, and 4) were used to identify four distinct portions of the B7-H4 ectodomain by SPR. All of the antibodies generated during this campaign were then assessed for competitive binding with these four binning antibodies to the B7-H4 ectodomain. If a B7-H4 antibody competed with one of the four binning antibodies (e.g., binning antibody 1), the B7-H4 antibody was determined to be in that BIN (e.g., BIN 1). If a B7-H4 antibody competed with two of the four binning antibodies (e.g, binning antibodies 2 and 3), the B7-H4 antibody was determined to be in both of those BINS (e.g., BIN2/3).

The IgG antibodies fell into at least four binding bins, with >90% of the antibodies binding to human/cyno or mouse B7-H4 with an affinity response ranging between >0.1 nm and <100 nM. Of the recombinant protein binders, approximately 75% also bind to B7-H4 on cells.

Cell Binding Analysis 100,000 cells overexpressing the antigen were washed with wash buffer and incubated with 100 ul 100 nM IgG for 5 minutes at room temperature. Cells were then washed twice with wash buffer and incubated with 100 ul of 1:100 anti-human IgGPE for 15 minutes on ice. Cells were then washed twice with wash buffer and analyzed on a FACS Canto II analyzer (BD Biosciences.)

PSR Binding Assay

The PSR assay was done as previously described (see Xu Y, et al. (2013) Addressing polyspecificity of antibodies selected from an in vitro yeast presentation system: A FACS-based, high-throughput selection and analytical tool. Protein Eng Des Sel 26(10):663-670). In short, soluble membrane proteins were prepared from CHO cells. The enriched membrane fraction was biotinylated using NHS-LCBiotin (Pierce, Thermo Fisher). This polyspecificity reagent was incubated with IgG-presenting yeast, followed by washing. Then secondary labeling mix (Extravidin-R-PE, anti-human LC-FITC, and propidium iodide) was added to the mixture. Samples were analyzed on a FACSCanto II analyzer (BD Biosciences) using an HTS sample injector. Flow cytometry data were analyzed for mean fluorescence intensity (MFI) in the R-PE channel to assess nonspecific binding. MFI values were normalized from 0 to 1 based on three reference antibodies exhibiting low, medium, and high PSR MFI values.

Dynamic Scanning Fluorimetry 10 uL of 20× Sypro Orange is added to 20 uL of 0.2-1 mg/mL mAb or Fab solution. A RT-PCR instrument (BioRad CFX96 RT PCR) is used to ramp the sample plate temperature from 40 to 95 C at 0.5 C increment, with 2 min equilibrate at each temperature. The negative of first derivative for the raw data is used to extract Tm.

AC-SINS

The AC-SINS assay was performed as described previously (see Liu Y, et al. (2014) High-throughput screening for developability during early-stage antibody discovery using self-interaction nanoparticle spectroscopy. *MAbs* 6(2):483-492). In short, gold nanoparticles (Ted Pella Inc.) were coated with 80% capturing anti-human goat IgG Fc (Jackson ImmunoResearch) and 20% with polyclonal goat nonspecific antibody (Jackson ImmunoResearch). The antibodies of interest were then incubated with the particles for 2 h and the wavelength shift was measured using Molecular Devices SpectraMax M2 with SoftMax Pro6 software. The self-interacting clones show a higher wavelength shift away from the PBS sample.

Example 3

Structural Characterization of Human Monoclonal Antibodies Against B7-H4

The B7-H4 antibodies are human IgG1/kappa isotype. The variable heavy (VH) regions are comprised of alleles from the germline genes VH1, VH3, and VH4, and the variable light (VL) of alleles from germline genes that include Vk1 and Vk3. Some subsets of the antibodies share high identity within the respective CDR regions of the VH and VL that can range from 72-100%. Antibodies that share the same germline allele have high identity in their VH and VL framework (FR) regions that ranges from 88-100%. Sequences of the B7-H4 antibodies are provided in Tables 1-10.

Example 4

Characterization of Monoclonal Antibody Binding to B7-H4 Protein

Binding affinities of anti-B7-H4 antibodies to B7-H4-extracellular domain (ECD) were determined by biolayer interferometry (BLI). ForteBio affinity assays are described in more detail above in Example 2. Briefly, the recombinant human B7-H4-huIgG1 (SEQ ID NO:409) protein was immobilized on Protein A tips, followed by an isotype control hIgG1 in order to saturate any remaining binding sites on the capturing tip. Anti-B7-H4 antibodies were then evaluated for binding. In addition, antibody binding to cynomolgus monkey (SEQ ID NO: 2) and mouse B7-H4 (SEQ ID NO: 3) was also assessed using the same protocol. The results are summarized in Table 12.

B7-H4-huIgG1:
(SEQ ID NO: 409)
MASLGQILFWSIISIIIILAGAIALIIGFGISGRHSITVTTVASAGNIGE

DGILSCTFEPDIKLSDIVIQWLKEGVLGLVHEFKEGKDELSEQDEMFRGR

TAVFADQVIVGNASLRLKNVQLTDAGTYKCYIITSKGKGNANLEYKTGAF

SMPEVNVDYNASSETLRCEAPRWFPQPTVVWASQVDQGANFSEVSNTSFE

LNSENVTMKVVSVLYNVTINNTYSCMIENDIAKATGDIKVTESEIKRRSH

LQLLNSKASGSEPKSSDKTHTCPPCPAPELLGGPSVFLFPPKPKDTLMIS

RTPEVTCVVVDVSHEDPEVKFNWYVDGVEVHNAKTKPREEQYNSTYRVVS

VLTVLHQDWLNGKEYKCKVSNKALPAPIEKTISKAKGQPREPQVYTLPPS

RDELTKNQVSLTCLVKGFYPSDIAVEWESNGQPENNYKTTPPVLDSDGSF

FLYSKLTVDKSRWQQGNVFSCSVMHEALHNHYTQKSLSLSPGK

TABLE 12

B7-H4 Antibody Binding to Extracellular Domain by Biolayer Interferometry

| Anti-body | BIN | Human B7-H4 | | | Cynomolgus B7-H4 | | | Mouse B7-H4 | | |
|---|---|---|---|---|---|---|---|---|---|---|
| | | $K_D$ (M) | $k_{on}$ (1/Ms) | $k_{off}$ (1/s) | $K_D$ (M) | $k_{on}$ (1/Ms) | $k_{off}$ (1/s) | $K_D$ (M) | $k_{on}$ (1/Ms) | $k_{off}$ (1/s) |
| 15441 | 2 | 7.15E−09 | 1.22E+06 | 8.72E−03 | 5.46E−08 | 1.33E+06 | 7.27E−02 | NB | — | — |
| 15461 | 2/3 | 6.29E−08 | 3.81E+05 | 2.40E−02 | 6.21E−08 | 4.34E+05 | 2.70E−02 | 5.57E−08 | 3.05E+05 | 1.70E−02 |
| 15462 | 2/3 | PF | — | — | 6.65E−08 | 6.72E+05 | 4.47E−02 | 8.31E−08 | 4.59E+05 | 3.81E−02 |
| 15465 | 2/3 | 5.13E−08 | 4.84E+05 | 2.48E−02 | 5.11E−08 | 5.44E+05 | 2.78E−02 | 8.96E−08 | 2.96E+05 | 2.65E−02 |
| 15472 | 4 | 7.11E−09 | 7.00E+05 | 4.97E−03 | 7.80E−09 | 7.46E+05 | 5.82E−03 | 3.80E−08 | 4.22E+05 | 1.60E−02 |
| 15478 | 4 | 3.25E−08 | 4.77E+05 | 1.55E−02 | 3.11E−08 | 5.44E+05 | 1.69E−02 | NB | — | — |
| 15483 | 2/3 | PF | — | — | 1.08E−07 | 3.80E+05 | 4.09E−02 | 2.63E−07 | 2.65E+05 | 6.95E−02 |
| 15489 | 2/3 | 6.37E−08 | 3.66E+05 | 2.33E−02 | 7.21E−08 | 3.98E+05 | 2.87E−02 | 2.01E−07 | 2.93E+05 | 5.90E−02 |
| 15495 | 2 | 9.44E−09 | 2.89E+06 | 2.72E−02 | 5.17E−09 | 3.25E+06 | 1.68E−02 | NB | — | — |
| 15503 | 2 | 1.04E−08 | 1.96E+06 | 2.05E−02 | 6.32E−09 | 1.82E+06 | 1.15E−02 | NB | — | — |
| 20496 | other | 8.05E−10 | 6.89E+05 | 5.55E−04 | 7.21E−10 | 7.90E+05 | 5.69E−04 | 2.46E−08 | 6.92E+05 | 1.71E−02 |
| 20500 | 3 | 5.97E−09 | 3.91E+05 | 2.33E−03 | 5.47E−09 | 4.18E+05 | 2.29E−03 | 8.25E−09 | 4.08E+05 | 3.36E−03 |
| 20501 | 3 | 2.56E−09 | 9.80E+05 | 2.51E−03 | 2.42E−09 | 1.02E+06 | 2.46E−03 | 3.35E−09 | 1.12E+06 | 3.75E−03 |
| 20502 | 3 | 1.20E−09 | 9.36E+05 | 1.15E−03 | 1.20E−09 | 9.62E+05 | 1.12E−03 | 3.40E−09 | 6.32E+05 | 2.13E−03 |
| 20502.1 | 3 | 3.07E−09 | 4.87E+05 | 1.50E−03 | 2.64E−09 | 5.28E+05 | 1.39E−03 | 3.99E−09 | 5.20E+05 | 2.07E−03 |
| 20506 | 3 | 1.69E−09 | 4.41E+05 | 7.46E−04 | 1.48E−09 | 4.58E+05 | 6.78E−04 | 3.53E−09 | 4.66E+05 | 1.64E−03 |
| 20513 | 3 | 3.98E−09 | 4.53E+05 | 1.80E−03 | 3.67E−09 | 4.91E+05 | 1.80E−03 | 4.57E−09 | 5.17E+05 | 2.36E−03 |
| 20516 | 3 | 1.80E−08 | 4.10E+05 | 7.38E−03 | 1.76E−08 | 4.45E+05 | 7.83E−03 | 4.14E−08 | 3.98E+05 | 1.65E−02 |
| 22208 | 3 | 5.67E−09 | 1.84E+05 | 1.04E−03 | 5.44E−09 | 1.99E+05 | 1.08E−03 | 1.67E−08 | 9.95E+04 | 1.67E−03 |
| 22213 | 3 | 1.44E−08 | 4.96E+04 | 7.13E−04 | 7.48E−09 | 6.44E+04 | 4.82E−04 | 1.37E−08 | 4.03E+04 | 5.52E−04 |
| 22216 | 3 | 1.47E−09 | 2.45E+05 | 3.59E−04 | 1.47E−09 | 2.45E+05 | 3.59E−04 | 1.47E−09 | 2.45E+05 | 3.59E−04 |

In addition, the binding affinities of selected anti-B7-H4 antibodies to the N-terminal domain of human B7-H4 (B7-H4 IgV-huIgG1; SEQ ID NO:410) were determined by surface plasmon resonance (SPR). Briefly, anti-human Fab antibody was immobilized on a carboxyl-derivatized SPR chip surface, and anti-B7-H4 antibodies were captured on the resulting surface at 5 ug/ml for 30 seconds. B7-H4 IgV-huIgG1 at various concentrations (0 nM, 3.7 nM, 11.1 nM, 33.3 nM, 100 nM, and 300 nM) was then flowed over the surface and allowed to bind to the anti-B7-H4 antibodies during the association phase, followed by a buffer wash during the dissociation phase. Data was fitted using a 1:1 binding model, and the results are summarized in Table 13.

B7-H4 IgV-huIgG1:
(SEQ ID NO: 410)
MASLGQILFWSIISIIIILAGAIALIIGFGISGRHSITVTTVASAGNIGE

DGILSCTFEPDIKLSDIVIQWLKEGVLGLVHEFKEGKDELSEQDEMFRGR

TAVFADQVIVGNASLRLKNVQLTDAGTYKCYIITSKGKGNANLEYKTGAF

SGSEPKSSDKTHTCPPCPAPELLGGPSVFLFPPKPKDTLMISRTPEVTCV

VVDVSHEDPEVKFNWYVDGVEVHNAKTKPREEQYNSTYRVVSVLTVLHQD

WLNGKEYKCKVSNKALPAPIEKTISKAKGQPREPQVYTLPPSRDELTKNQ

VSLTCLVKGFYPSDIAVEWESNGQPENNYKTTPPVLDSDGSFFLYSKLTV

DKSRWQQGNVFSCSVMHEALHNHYTQKSLSLSPGK

TABLE 13

B7-H4 Antibody Binding to N-terminal Domain by Surface Plasmon Resonance

| | | Human B7-H4 | |
| --- | --- | --- | --- |
| Antibody | BIN | $K_D$ (M) | $k_{on}$ (1/Ms) | $k_{off}$ (1/s) |
| 15461 | 2/3 | 3.04E−08 | 1.71E+05 | 5.19E−03 |
| 15462 | 2/3 | 1.69E−08 | 2.95E+05 | 4.98E−03 |
| 15465 | 2/3 | 1.73E−08 | 2.41E+05 | 4.17E−03 |
| 15483 | 2/3 | 1.84E−08 | 2.41E+05 | 4.43E−03 |
| 15489 | 2/3 | 2.37E−08 | 1.64E+05 | 3.89E−03 |
| 20502 | 3 | 2.03E−09 | 1.78E+05 | 3.61E−04 |

Thus, multiple assays demonstrate that the antibodies bind to B7-H4.

Example 5

Epitope Mapping

Anti-B7-H4 antibody binding bins were determined by biolayer interferometry (BLI). Epitope mapping assays are described in more detail above in Example 2. Briefly, a first anti-B7-H4 antibody was captured on Protein A tips, followed by a control huIgG1 antibody to saturate additional binding sites on the tips. Next, the sensor tips were exposed to the antigen (B7-H4-huIgG1) (SEQ ID NO:409) followed by the second anti-B7-H4 antibody, which was then evaluated for binding. Epitope bins were determined by comparison to binding after a non-B7-H4 antibody was used as the first antibody. Results are summarized in Table 12.

Example 6

Characterization of Monoclonal Antibody Binding to B7-H4 Expressed on the Surface of Cells HEK293T cell lines were transfected to express full-length human, cynomolgus monkey, mouse, or rat B7-H4. In addition, the endogenous human B7-H4 expressing SK-BR-3 breast cancer cell line was used to assess the ability of the antibodies to bind B7-H4 expressed on the cell surface. $1\times10^5$ parental HEK293T or transfected HEK293T cell lines were incubated with 100 nM of the B7-H4 antibodies. Following incubation, cells were pelleted, washed, and incubated with a secondary labeling antibody, and samples were acquired on a flow cytometer. Fold binding over the parental cell line (FOP) was calculated as follows: MFI transfected HKE293T cells/MFI parental HEK293T cells. A FOP value greater than 10 was considered to demonstrate specific binding.

To assess the cell binding potency of the B7-H4 antibodies, 1×105 SK-BR-3 cells or 293 cells transfected to express cynomolgus monkey, mouse or rat B7-H4 were incubated with titrating doses of the B7-H4 antibodies. Following incubation, cells were pelleted, washed and incubated with a secondary labeling antibody and samples were acquired on a flow cytometer. Data was analyzed using the FlowJo software and MFI was plotted vs. antibody concentration. The EC50 cell binding potency was calculated using non-linear regression curve fit (GraphPad Prism).

Figure 2A:
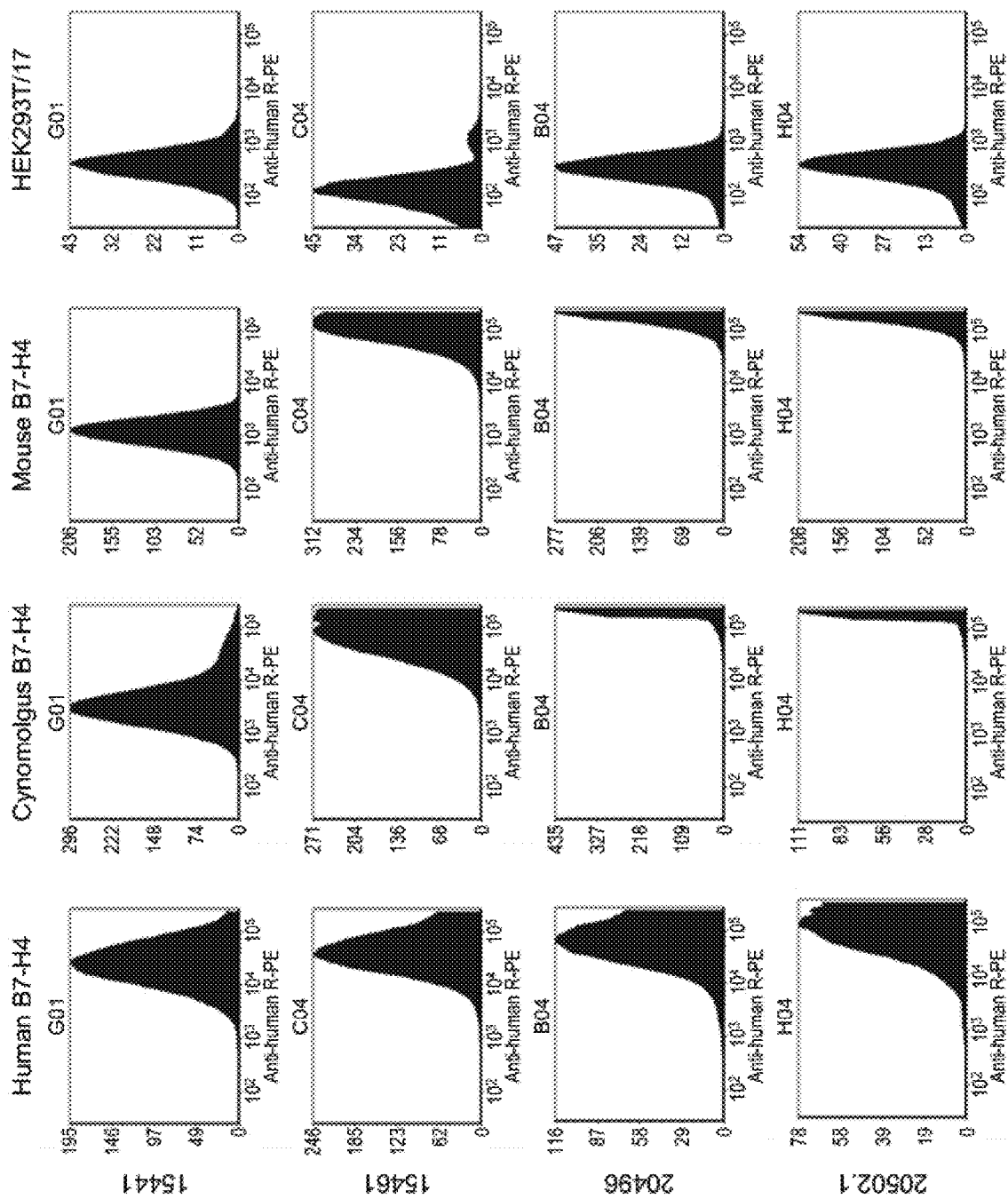
FIG. 2A shows the binding of B7-H4 antibodies to HEK293T cells expressing human, cynomolgus monkey, or mouse B7-H4. (See Example 6.)
Figure 2B:
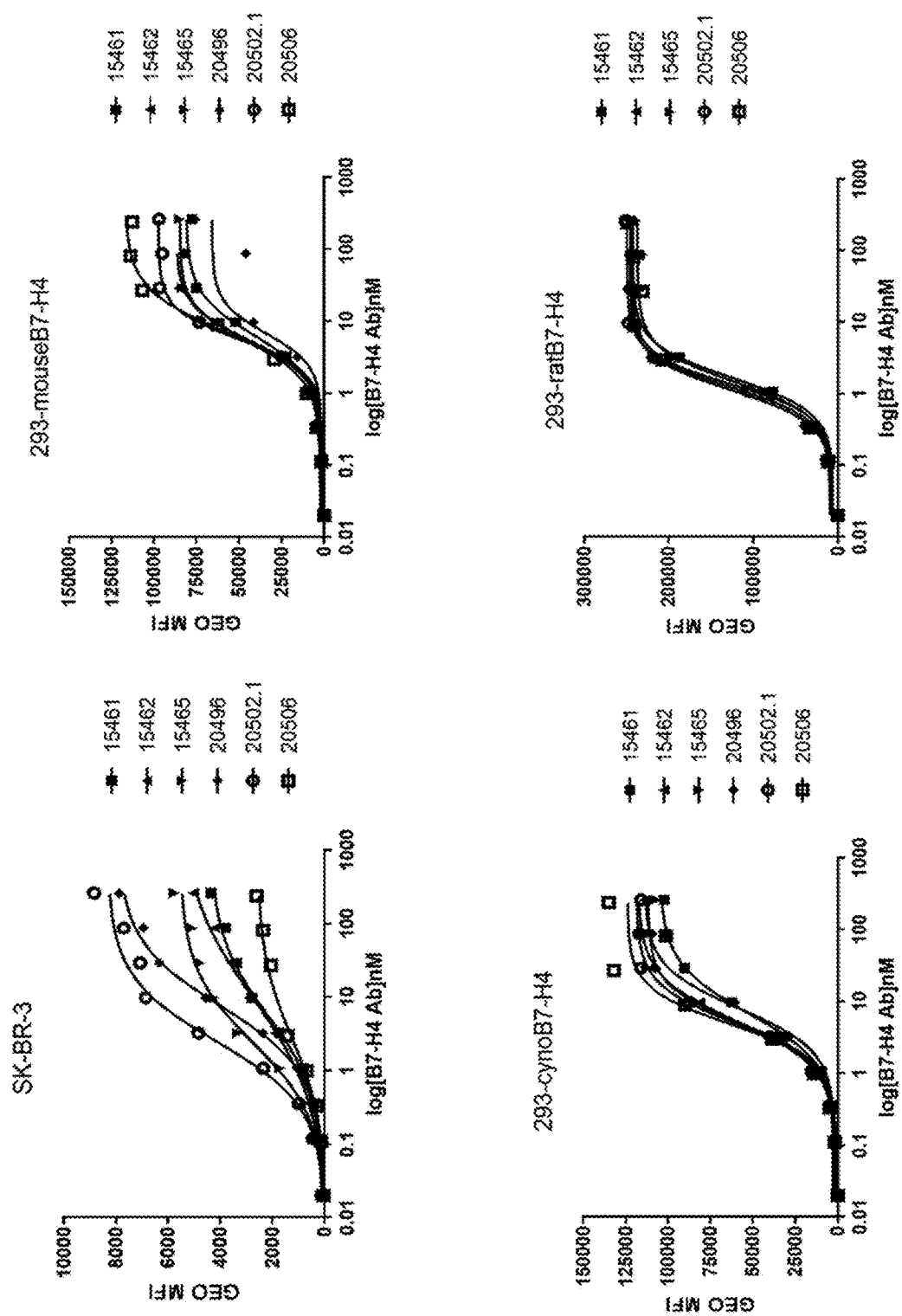
FIG. 2B shows the binding of B7-H4 antibodies to SK-BR-3 cells and to HEK293T cells expressing mouse, cynomolgus monkey, or rat B7-H4. (See Example 6.)

All B7-H4 antibodies demonstrated binding to HEK293T cells that expressed human B7-H4, cynomolgus monkey B7-H4, or mouse B7-H4. Antibodies also demonstrated potent dose-dependent binding to SK-BR-3 cells endogenously expressing human B7-H4 on the cell surface or HEK293T cell lines transfected to express cynomolgus monkey, mouse, or rat B7-H4 on the cell surface. These data demonstrate that the majority of B7-H4 antibodies are fully cross-reactive to cynomolgus monkey, mouse, and rat B7-H4 (FIGS. 2A and 2B, Table 14).

TABLE 14

B7-H4 Antibody Binding to Cell-Surface B7-H4

| Antibody | BIN | 293-huB7-H4 (FOP) | 293-cynoB7-H4 (FOP) | 293-moB7-H4 (FOP) | SK-BR-3 (EC50; nM) | 293-cynoB7-H4 (EC50; nM) | 293-mouseB7-H4 (EC50; nM) | 293-ratB7-H4 (EC50; nM) |
| --- | --- | --- | --- | --- | --- | --- | --- | --- |
| 15441 | 2 | 67 | 9 | 3 | 34.29 | ND | ND | ND |
| 15461 | 2/3 | 333 | 610 | 887 | 5.66 | 6.77 | 6.37 | 1.67 |
| 15462 | 2/3 | 530 | 416 | 456 | 4.55 | 5.29 | 5.40 | 1.13 |
| 15465 | 2/3 | 626 | 1324 | 690 | 2.13 | 4.90 | 5.34 | 1.47 |
| 15472 | 4 | 580 | 1279 | 685 | 8.86 | — | — | — |
| 15478 | 4 | 518 | 1130 | 125 | PF | — | — | — |

TABLE 14-continued

| | | | | | | 293- | 293- | 293- |
| | | 293- | 293- | 293- | SK-BR-3 | cynoB7- | mouseB7- | ratB7- |
| | | huB7-H4 | cynoB7-H4 | moB7-H4 | (EC50; | H4 (EC50; | H4 (EC50; | H4 (EC50; |
| Antibody | BIN | (FOP) | (FOP) | (FOP) | nM) | nM) | nM) | nM) |
|---|---|---|---|---|---|---|---|---|
| 15483 | 2/3 | 805 | 1012 | 1402 | 14.81 | 17.4 | 8.82 | 1.87 |
| 15489 | 2/3 | 612 | 1118 | 674 | 31.73 | 13.7 | 17.5 | 4.55 |
| 15495 | 2 | 619 | 524 | 6 | 61.2 | — | — | — |
| 15503 | 2 | 289 | 877 | 5 | PF | — | — | — |
| 20496 | other | 179 | 758 | 604 | 7.60 | 7.91 | 6.70 | ND |
| 20500 | 3 | 182 | 630 | 478 | 1.54 | 3.38 | 4.00 | 1.14 |
| 20501 | 3 | 205 | 728 | 546 | 1.90 | 3.89 | 4.67 | 1.15 |
| 20502.1 | 3 | 200 | 683 | 559 | 2.50 | 4.94 | 5.57 | 1.26 |

Example 7

Characterization of Monoclonal Antibody T Cell Checkpoint Blockade Activity

In order to characterize the T cell checkpoint blockade activity of the B7-H4 antibodies, primary human T cells were enriched from peripheral blood mononuclear cells (PBMCs) using the EasySep™ Human T Cell Enrichment Kit based on manufacturer's instructions. Enriched T cells were incubated at $2\times10^5$ cell/mL with anti-CD3/anti-CD28 Dynabeads, at a one bead per cell ratio, at 37° C. Six days later, the beads were magnetically removed, and the T cells were washed and incubated at $1\times10^6$ cell/mL with 10 U/mL IL-2 at 37° C. Four days later, T cells were washed and incubated at a $1\times10^6$ cells/mL along with artificial antigen presenting cells (aAPCs) at $2\times10^6$ cells/mL at 37° C. in the presence of 10 ug/mL of antibody or an antibody dose titration. aAPCs are a HEK293T cell line that has been transfected to co-express a scFv format of anti-human CD3 clone OKT3 and full-length human B7-H4 on the cell surface. aAPCs were treated with Mitomycin C for one hour at 37° C. and then thoroughly washed prior to adding to the T cell co-culture. 72 hours after co-culture of T cells, aAPCs and B7-H4 antibodies, plates were centrifuged, supernatants harvested and assessed for IFNγ production by ELISA, and cells were harvested and stained to assess proliferation by FACS (specifically, the cells in each well were incubated with antibodies against CD4 and CD8). Cells were then washed, fixed, permeabilized, and incubated with the Edu-Click reagent according the manufacturer's instructions. Cells were washed, and the number of proliferating CD4+, CD8+ or total T cells was measured using flow cytometry. Data was analyzed using the FlowJo software. For samples only treated with a single concentration of antibody, the data was calculated and reported as a fold increase over control-huIgG treated samples. For samples treated with a dose titration of antibody, IFNγ production was plotted vs. antibody concentration and the EC50 potency was calculated using nonlinear regression curve fit (GraphPad Prism).

Figure 3A:
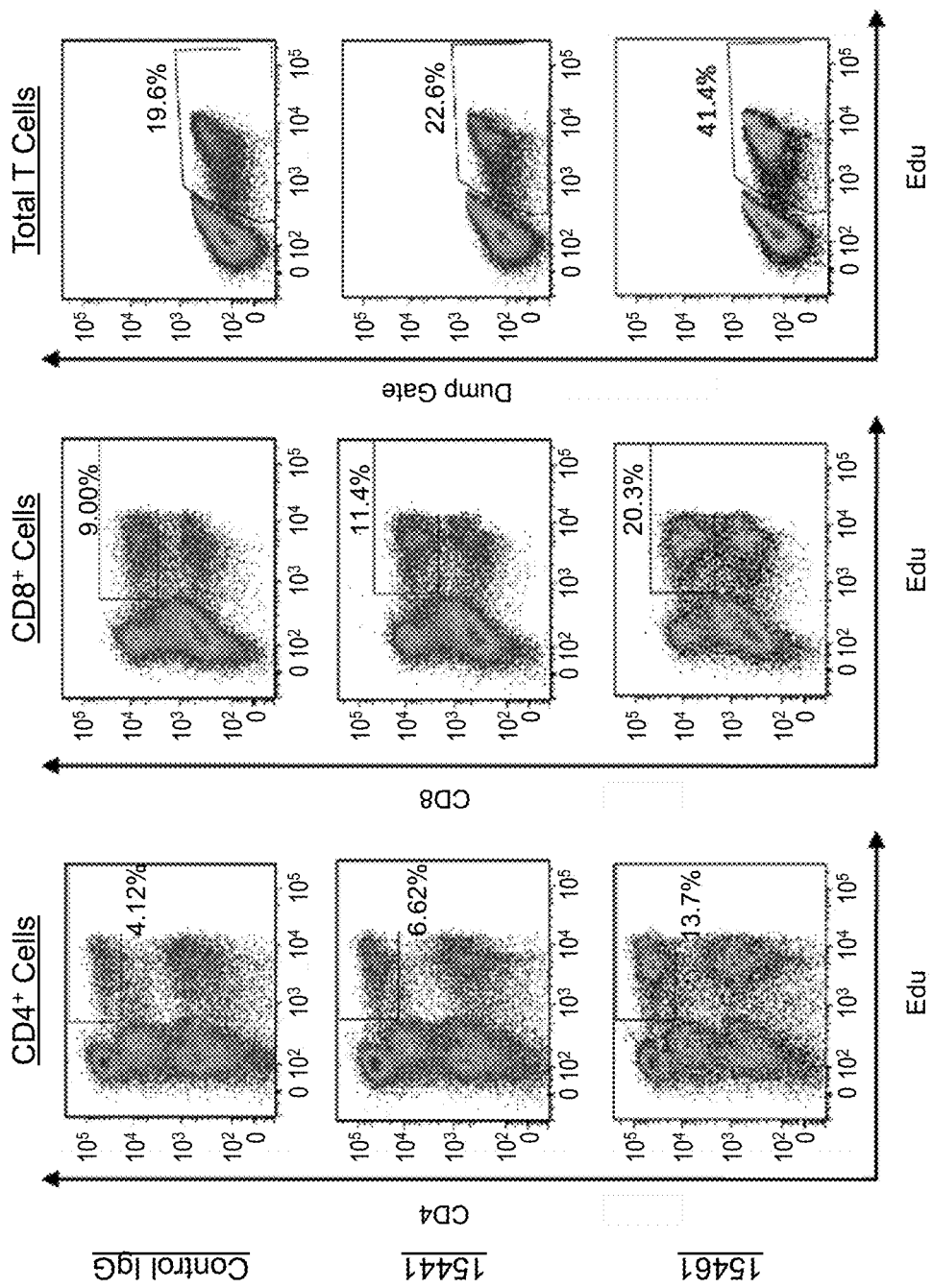
FIG. 3A shows the effect of B7-H4 antibodies on $CD4^+$, $CD8^+$ or total T cell proliferation. (See Example 7.)
Figure 3B:
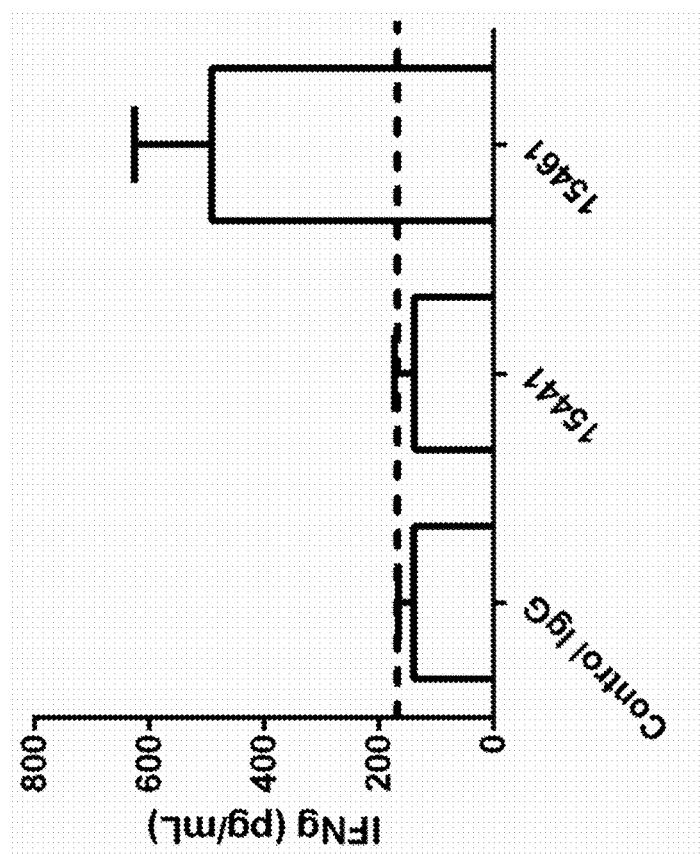
FIG. 3B shows the effect of B7-H4 antibodies on interferon-gamma (IFNγ) production. (See Example 7.)
Figure 3C:
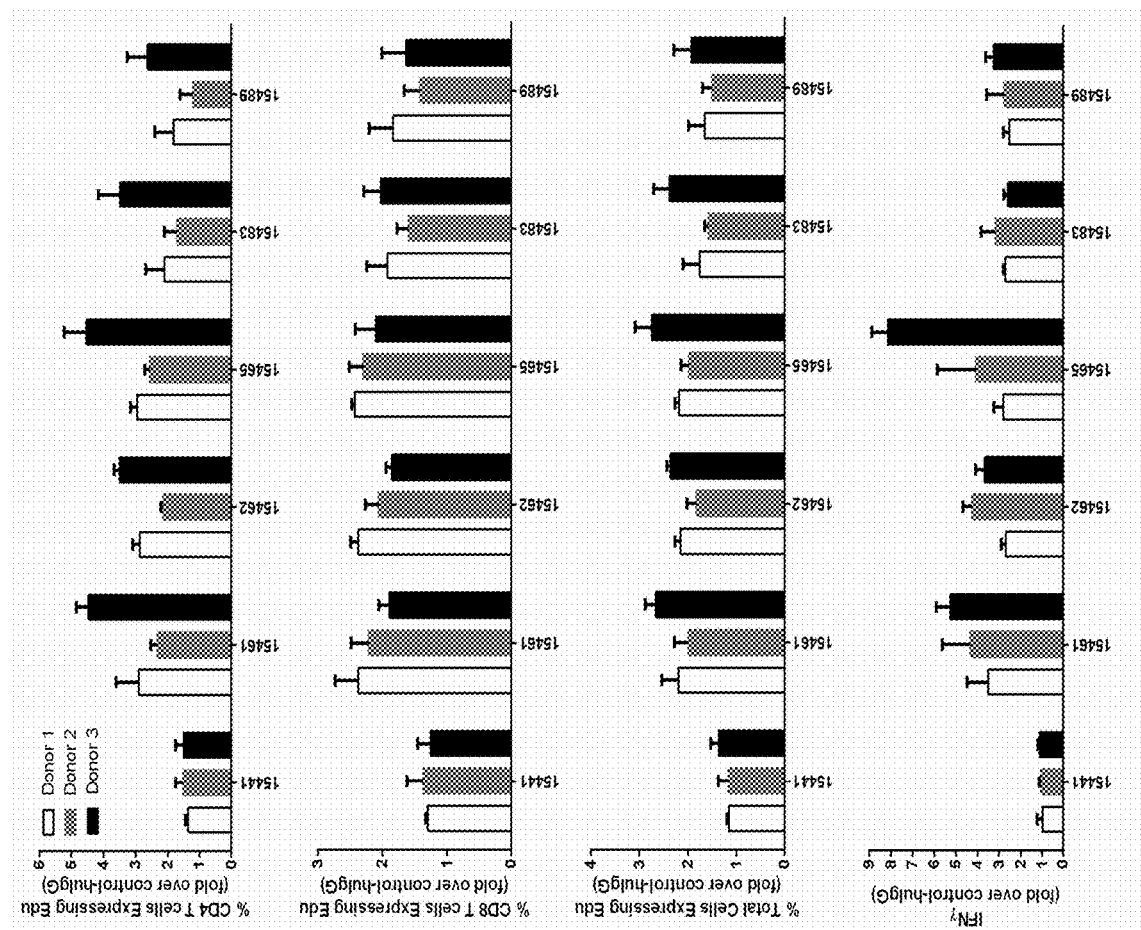
FIG. 3C shows the effect of B7-H4 antibodies on $CD4^+$, $CD8^+$ or total T cell proliferation and on interferon-gamma (IFNγ) production. (See Example 7.)
Figure 3D:
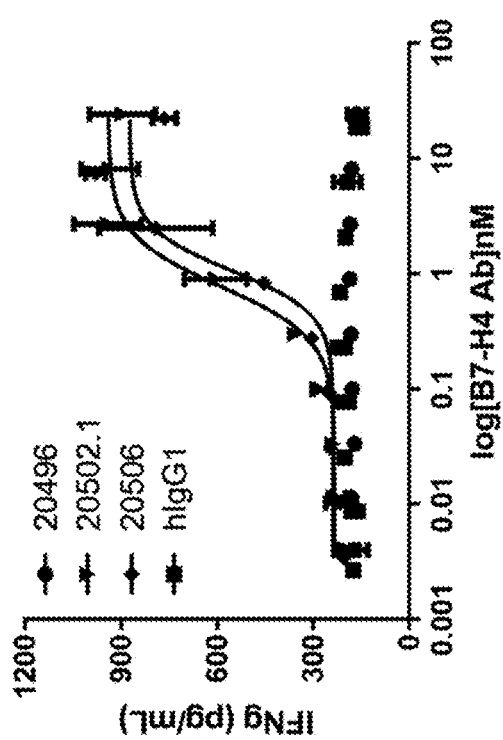
FIG. 3D shows the effect of various concentrations of B7-H4 antibodies on interferon-gamma (IFNγ) production. (See Example 7.)
Figure 4A:
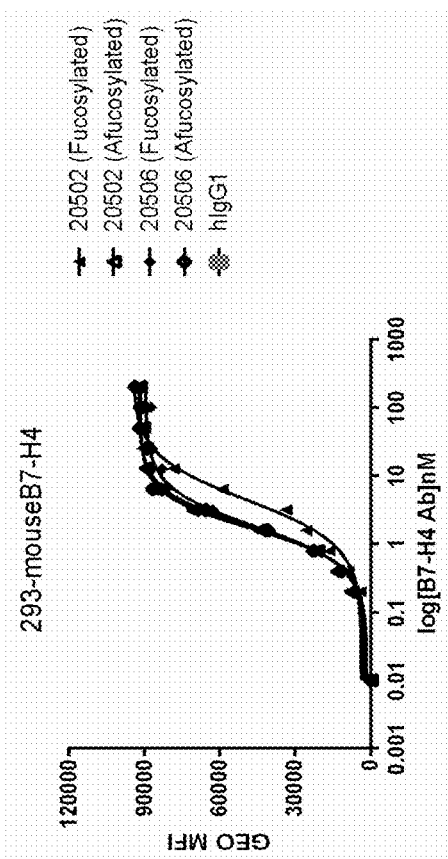
FIGS. 4A-4D show the binding of fucosylated and afucosylated antibodies to B7-H4 on SK-BR-3 cells (FIG. 4A) and to HEK293T cells expressing mouse (FIG. 4B), cynomolgus monkey (FIG. 4C), or rat B7-H4 (FIG. 4D). (See Example 9.)
Figure 4B:
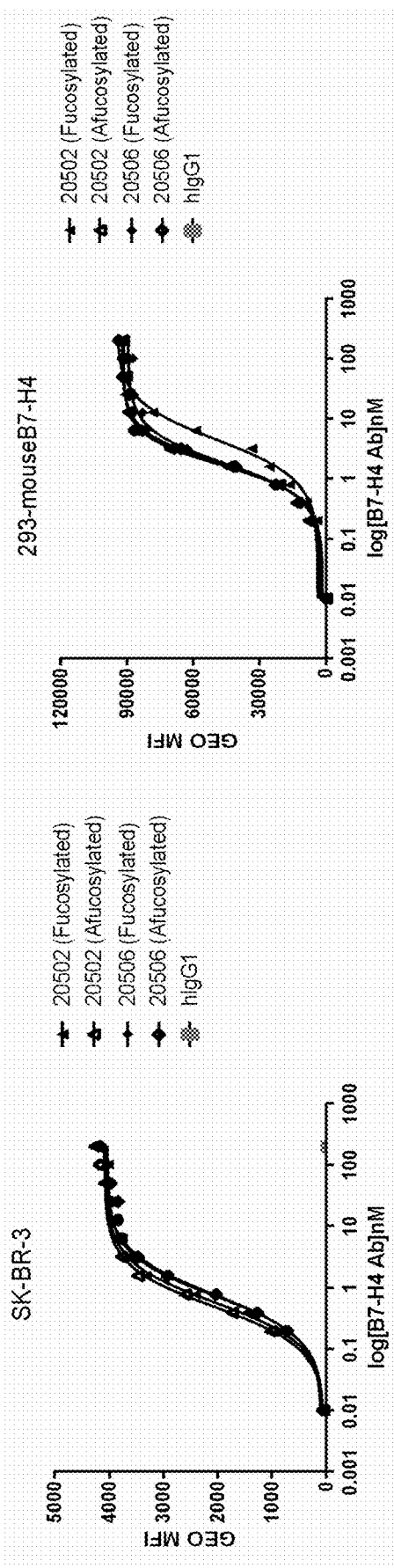
Figure 4C:
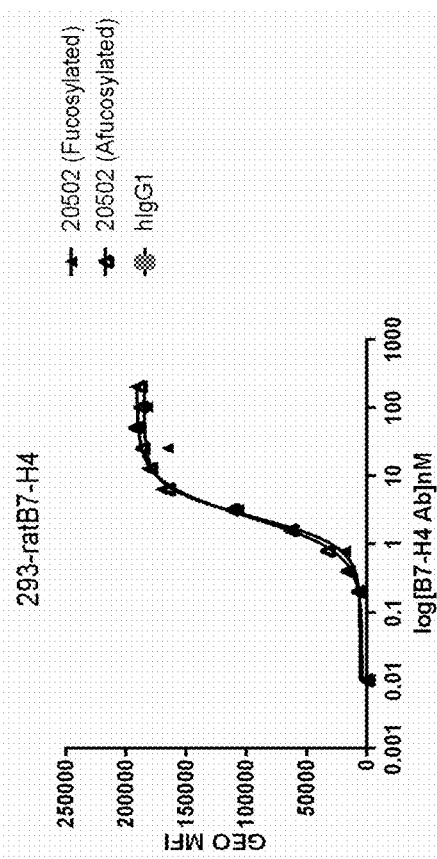
Figure 4D:
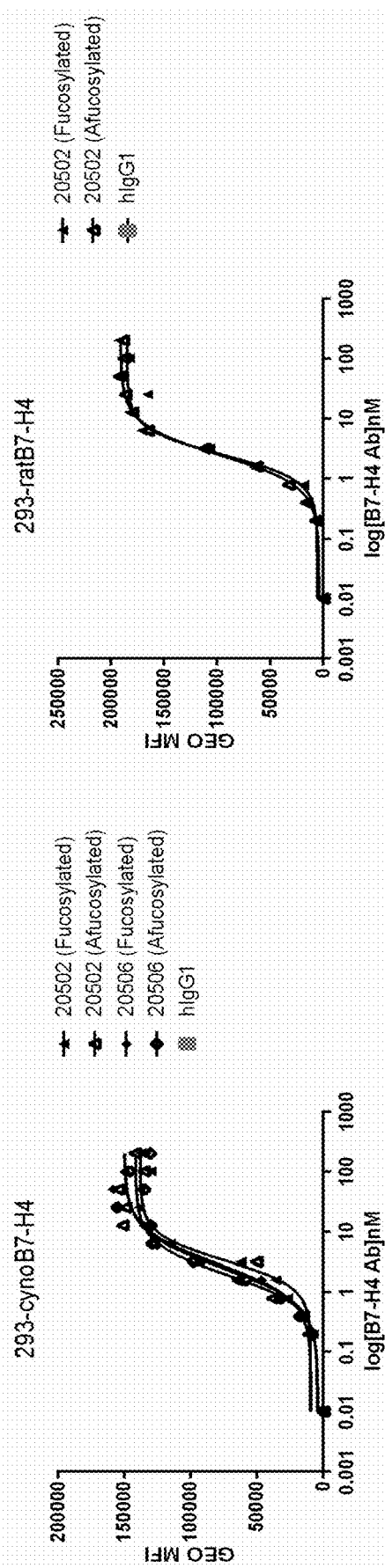

All BIN2/3 and BIN3 antibodies reproducibly resulted in T cell checkpoint blockade activity as measured by an increase in IFNγ production and/or CD4+, CD8+ or total T cell proliferation. FIG. 3A shows that antibody 15441 increases T cell proliferation by at least 3% and increases CD4+ and CD8+ T cell proliferation by at least 2%. FIG. 3A also shows that antibody 15461 increases T cell proliferation by at least 21%, increases CD4+ T cell proliferation by at least 9%, and increases CD8+ T cell proliferation by at least 11%. FIGS. 3B-3D show other dose-dependent T cell checkpoint blockade activities.

TABLE 15

B7-H4 Antibody - T Cell Checkpoint Blockade Activity

| Antibody | BIN | aAPC Assay (EC50 +/− STD; nM) | Donor 1 (Max IFNγ, pg/mL) | Donor 2 (Max IFNγ, pg/mL) | Donor 3 (Max IFNγ, pg/mL) | Donor 4 (Max IFNγ, pg/mL) |
|---|---|---|---|---|---|---|
| 15461 | 2/3 | 531.18 +/− 403.66 | 311.64 | 164.66 | 1957.34 | 986.73 |
| 15462 | 2/3 | 1312.01 +/− 1112.5 | 205.72 | 176.33 | 1661.59 | 484.8 |
| 15465 | 2/3 | 4310.72 +/− 7642.6 | 230.45 | 133.64 | 1523.82 | 865.22 |
| 15483 | 2/3 | 728.84 +/− 711.1 | 93.2 | 87.84 | 1382.03 | 939.04 |
| 15489 | 2/3 | 291.31 +/− 327.82 | 82.47 | 96.63 | 1133.02 | 799.9 |

TABLE 16

B7-H4 Antibody Binding to Cell-Surface B7-H4

| Antibody | BIN | aAPC Assay (EC50 +/− SID; nM) | Donor 1 (Max IFNγ, pg/mL) | Donor 2 (Max IFNγ, pg/mL) | Donor 3 (Max IFNγ, pg/mL) | Donor 4 (Max IFNγ, pg/mL) |
|---|---|---|---|---|---|---|
| 20496 | other | PF | 185.88 | ND | ND | ND |
| 20500 | 3 | 0.84 +/− 0.35 | 821 | 273.83 | 117.9 | 4027.1 |
| 20501 | 3 | 0.79 +/− 0.18 | 849.6 | 310 | 135.6 | 4493.1 |
| 20502.1 | 3 | 0.79 +/− 0.03 | 937 | 303.9 | 174.02 | 4269.7 |

TABLE 16-continued

| | | B7-H4 Antibody Binding to Cell-Surface B7-H4 | | | | |
|---|---|---|---|---|---|---|
| Antibody | BIN | aAPC Assay (EC50 +/- SID; nM) | Donor 1 (Max IFNγ, pg/mL) | Donor 2 (Max IFNγ, pg/mL) | Donor 3 (Max IFNγ, pg/mL) | Donor 4 (Max IFNγ, pg/mL) |
| 20506 | 3 | 1.25 +/- 0.26 | 980.8 | 258.8 | 86.1 | 2301.8 |
| 20513 | 3 | 1.16 +/- 0.16 | 658.8 | 240.3 | 91.1 | 1634.5 |
| 20516 | 3 | PF | ND | 441.1 | ND | ND |
| 22213 | 3 | 1.79 +/- 1.83 | ND | ND | ND | ND |

Example 8

Generation of Afucosylated and Fucosylated Monoclonal Antibodies

Antibodies with Fc regions having reduced fucose content in glycan moieties may exhibit higher ADCC activity compared to a fully fucosylated antibody (Niwa R et al., *Clinical Cancer Research* 11(6):2327-36 (2005)). B7-H4 antibodies were generated in CHO-x cells (Yamane-Ohnuki N, et al. *Biotechnology and Bioengineering* 87(5): 614-22 (2004)) to produce normally fucosylated antibodies and in a CHO cell line engineered to produce afucosylated antibodies (CHO-y cells) (id.).

Example 9

Characterization of Binding of Afucosylated and Fucosylated Monoclonal Antibodies The fucosylated and afucosylated anti B7-H4 antibodies were characterized by SPR following protocol as described in Example 4. The antibodies showed similar binding to human B7-H4 protein and thus there is no impact of the glycosylation on binding (Table 17).

vs. antibody concentration, and the EC50 cell binding potency was calculated using nonlinear regression curve fit (GraphPad Prism).

The B7-H4 antibodies demonstrated potent dose-dependent binding to SK-BR-3 cells endogenously expressing B7-H4 on the cell surface or 293 cell lines transfected to express cynomolgus monkey, mouse, or rat B7-H4 on the cell surface. Binding potency and species cross-reactivity was not impacted by whether an antibody was fucosylated or afucosylated (FIGS. 4A-4D and Table 17).

Example 10

Binding of Afucosylated and Fucosylated Monoclonal Antibodies to Human Fcγ Receptor IIIa (FcγRIIIa) V158 Allele Antibody 20502 was produced as both fucosylated (Ab-F) and afucosylated (Ab-A) and tested for the binding affinity of the Fc region to FcgRIIIa (V158) by surface plasmon resonance (SPR). Briefly, Protein A was covalently attached to a dextran chip using the amine coupling kit with 100 mM ethylenediamine in 100 mM Sodium Borate buffer, pH 8.0 as the blocking reagent. Ab-A or Ab-F was captured at 2

TABLE 17

| | | | Binding of afucosylated and fucosylated antibodies | | | | | | |
|---|---|---|---|---|---|---|---|---|---|
| | | | Human B7-H4 | | | SK-BR-3 | 293-cynoB7-H4 | 293-mouseB7-H4 | 293-ratB7-H4 |
| Antibody | BIN | | $K_D$ (M) | $k_{on}$ (1/Ms) | $k_{off}$ (1/s) | (EC50; nM) | (EC50; nM) | (EC50; nM) | (EC50; nM) |
| 20502 | 3 | Fucosylated | 2.58E−09 | 4.28E+05 | 1.10E−03 | 0.571 | 3.291 | 4.371 | 2.486 |
| 20502 | 3 | Afucosylated | 2.74E−09 | 4.19E+05 | 1.15E−03 | 0.483 | 2.923 | 1.655 | 2.446 |
| 20506 | 3 | Fucosylated | 1.93E−09 | 3.65E+05 | 7.03E−04 | 0.739 | 1.770 | 1.77 | 3.249 |
| 20506 | 3 | Afucosylated | 2.01E−09 | 3.60E+05 | 7.25E−04 | 0.767 | 1.769 | 1.769 | PF |
| 22213 | 3 | Fucosylated | 5.81E−09 | 1.53E+05 | 8.88E−04 | 0.651 | 5.199 | 2.445 | 4.401 |
| 22213 | 3 | Afucosylated | 5.11E−09 | 1.69E+05 | 8.62E−04 | 0.667 | 3.878 | 2.453 | 3.545 |

Figure 5A:
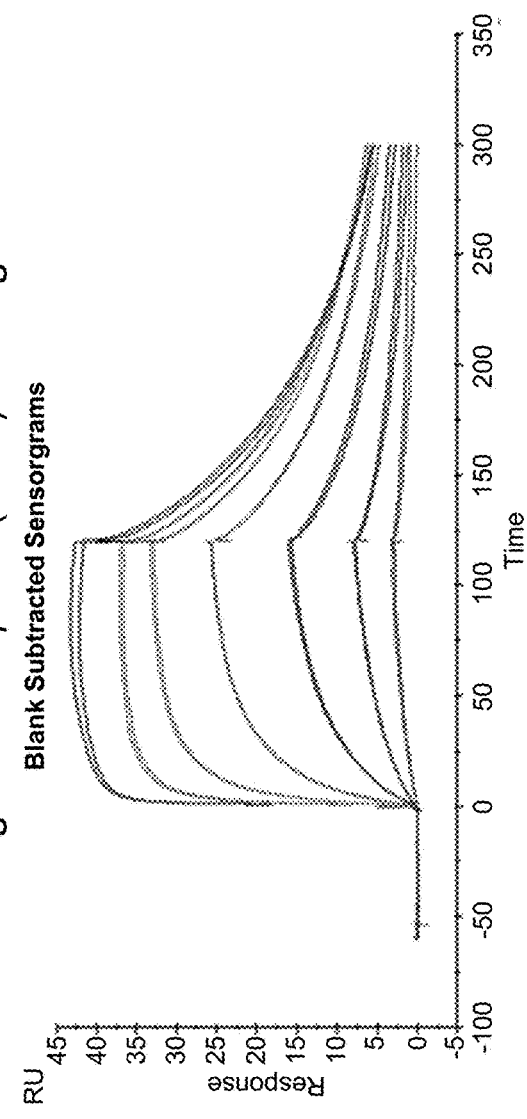
FIGS. 5A and 5B show the binding of afucosylated and fucosylated B7-H4 antibodies (respectively) to human Fcγ receptor IIIa (FcγRIIIa) V158 allele. (See Example 10.)
Figure 5B:
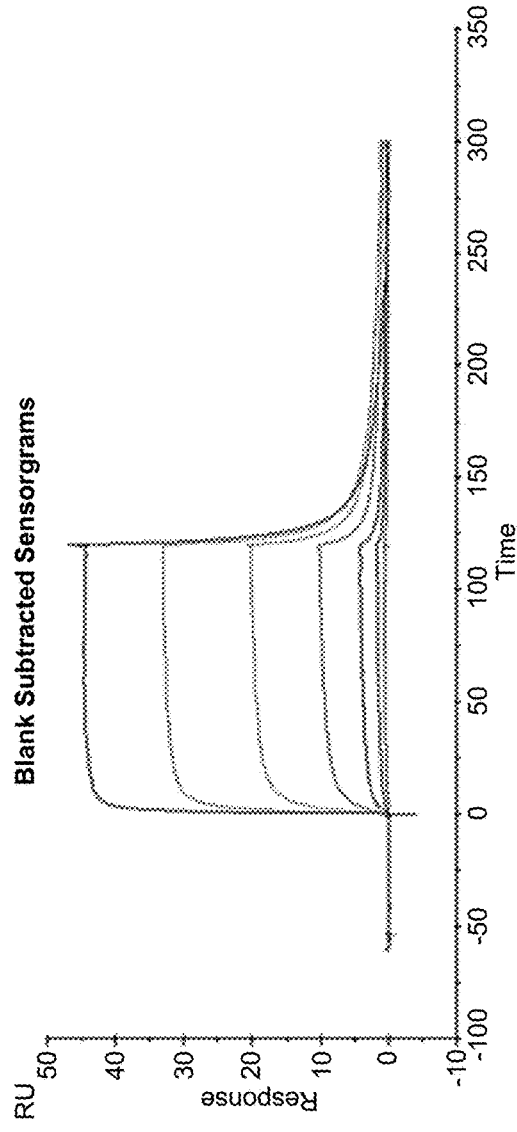

The fucosylated and afucosylated anti B7-H4 antibodies were also characterized by flow cytometry. In these experiments, HEK293T cell lines were transfected to express full-length cynomolgus monkey, mouse, or rat B7-H4. In addition, the endogenous human B7-H4 expressing SK-BR-3 breast cancer cell lines were used to assess the cell binding potency of B7-H4 antibodies. 1×10⁵ SK-BR-3 cells or 293 cells transfected to express full-length human, cynomolgus monkey, mouse, or rat B7-H4 were incubated with titrating doses of the B7-H4 antibodies. Following incubation, cells were pelleted, washed, incubated with a secondary labeling antibody, and run on a flow cytometer. Data were analyzed using the FlowJo software. MFI was plotted densities on separate flow cells, and a Protein A derivatized flow served as a reference control. Fc gamma RIIIA (V158) was diluted in HBS-P+ running buffer and injected at 6 concentrations (0 nM, 1.37 nM, 12.3 nM, 37 nM, 111 nM, 333 nM, and 1000 nM) in duplicate. The association constant, dissociation constant, and affinity for Ab-A binding were calculated using the Biacore T200 Evaluation Software 1:1 binding model. The affinity constant for Ab-A and Ab-F binding were determined using the Biacore T200 Evaluation Software steady state affinity model. The afucosylated B7-H4 antibody (Ab-A) has a 140-fold higher affinity for Fc gamma receptor IIIA (V158) than the same antibody with a fucosylated Fc (Ab-F) (FIGS. 5A and 5B, Table 18).

TABLE 18

| | Fcγ receptor IIIa (FcγRIIIa) V158 allele binding | | |
|---|---|---|---|
| | ka (1/Ms) | kd (1/s) | $K_D$ (nM) |
| Ab-A | 6.46E+05 | 9.54E-10 | 15 |
| Ab-F | N/A | N/A | 210 |

Example 11

Afucosylated and Fucosylated Monoclonal Antibodies T Cell Checkpoint Blockade Activity Primary human T cells were enriched from PBMCs using the EasySep™ Human T Cell Enrichment Kit based on the manufacturer's instructions. Enriched T cells were incubated at $2\times10^5$ cell/mL with anti-CD3/anti-CD28 Dynabeads, at a one bead per cell ratio, at 37° C. Six days later, the beads were magnetically removed, and T cells were washed and incubated at $1\times10^6$ cell/mL with 10 U/mL IL-2 at 37° C. Four days later, T cells were washed and incubated at $1\times10^6$ cells/mL along with artificial antigen presenting cells (aAPCs) at a $2\times10^6$ cells/mL concentration at 37° C. in the presence of B7-H4 antibody dose titration. aAPCs were treated with Mitomycin C for one hour at 37° C. and then thoroughly washed prior to adding to the T cell co-culture. 72 hours after co-culture of T cells, aAPCs, and B7-H4 antibodies, plates were centrifuged and supernatants were harvested and assessed for IFNγ production by ELISA. IFNγ production was plotted vs. antibody concentration and the EC50 potency was calculated using nonlinear regression curve fit (GraphPad Prism).

Figure 6A:
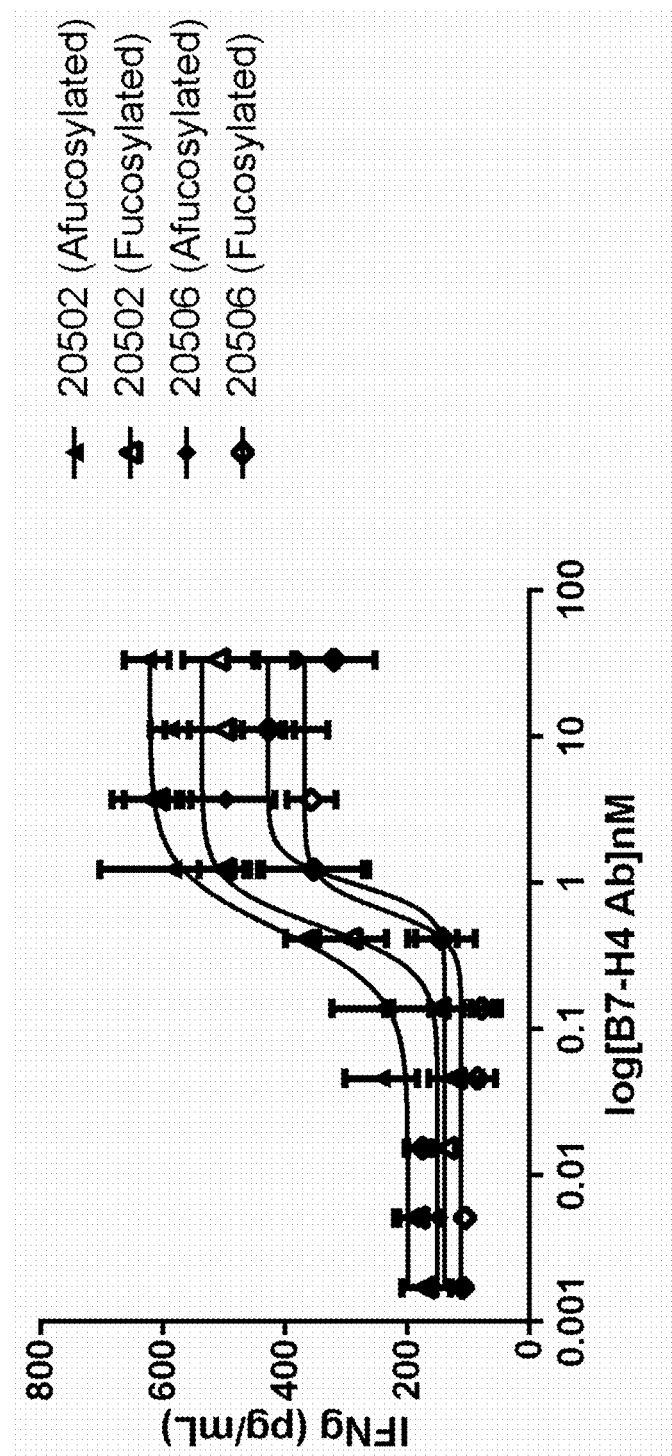
FIG. 6A shows the T cell checkpoint blockade activity of fucosylated and afucosylated B7-H4 antibodies. (See Example 11.)

The B7-H4 antibodies demonstrated potent T cell checkpoint blockade activity as measured by an increase in IFNγ production. Moreover, there was no demonstrable difference in potency between afucosylated and fucosylated antibodies (FIG. 6A and Table 19.)

TABLE 19

| | | T Cell Checkpoint blockade potency | |
|---|---|---|---|
| | | aAPC Assay (EC50 +/- STD; nM) | |
| Antibody | BIN | Afucosylated | Fucosylated |
| 20502 | 3 | 0.89 +/- 0.44 | 0.74 +/- 0.39 |
| 20506 | 3 | 1.05 +/- 0.28 | 0.95 +/- 0.46 |
| 22213 | 3 | 0.16 +/- 0.05 | 0.17 +/- 0.08 |

Next, primary human T cells were enriched from HLA-A2+ donor PBMCs using the Human Pan T Cell Isolation Kit following the manufacturer's instructions. MART-I TCR expressing T cells were generated by first activating 5×106 enriched Pan T cells with 1.5×107 anti-CD3/anti-CD28 Dynabeads, 100 ng/mL IL-2 and 15 ng/mL IL-7 for 48 hours. 5×106 activated T cells were then transduced with MART-I TCR lentiviral particles in the presence of 200 ng/mL IL-2, 30 ng/mL IL-7 and 10 ug/mL polybrene. 24 hours post transduction, MART-I TCR+ Pan T cells were expanded over a 15-day period in the presence of 33.3 ng/mL IL-2 and 5 ng/mL IL-7. To generate HLA-A2 expressing target cell lines, the endogenous B7-H4 expressing human breast cancer cell lines MDA-MB-468 and SK-BR-3 were transduced with HLA-A2 lentiviral particles for 48 hours. Furthermore, B7-H4 was knocked-out of the HLA-A2+SK-BR-3 cell line. MART-I TCR+ Pan T cells were co-cultured in the presence of the various target cell lines at a 1:1 E:T ratio, 500 µg/mL of MART-I peptide and 67 nM of the B7-H4 antibody 20502 (afucosylated) or a human isotype control. 24 hours post co-incubation, plates were centrifuged and supernatants were harvested and assessed for IL-2 production by AlphaLisa, according to the manufacturer's instructions.

Figure 6B:
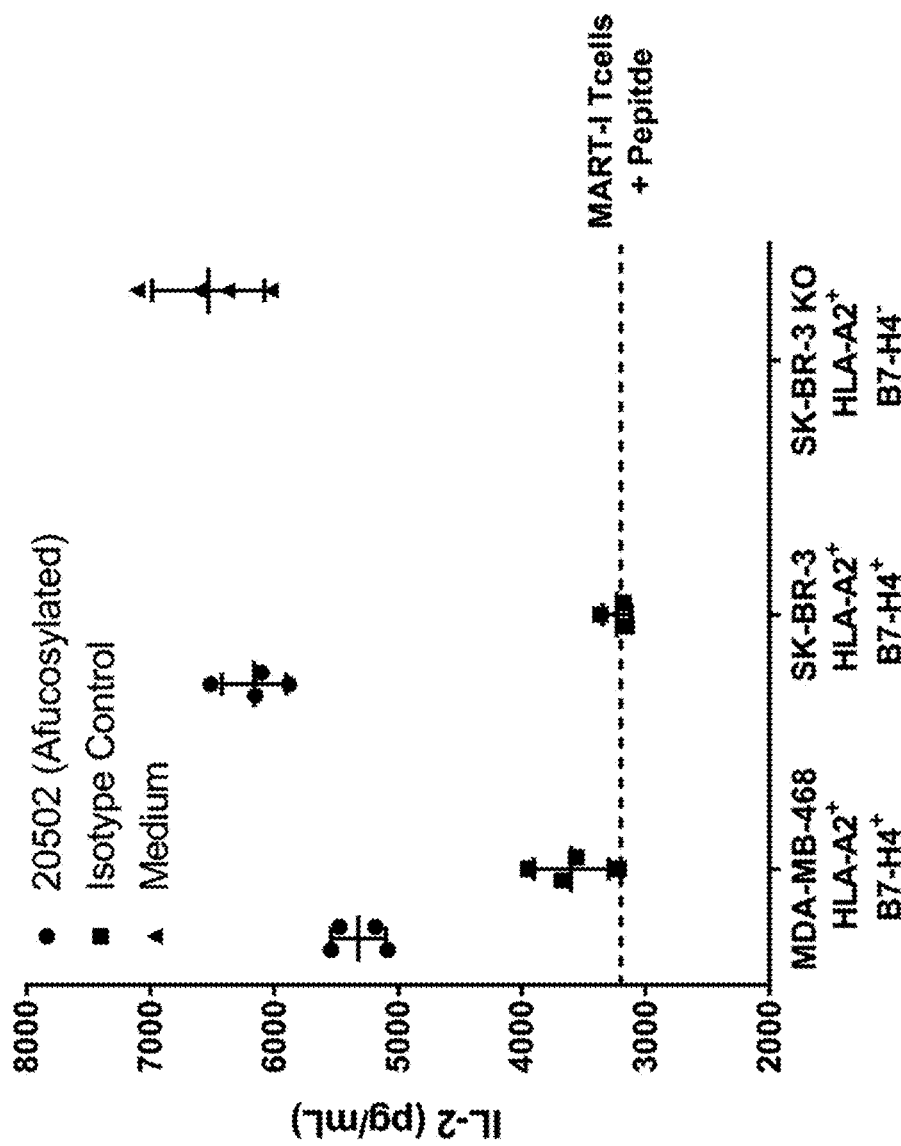
FIG. 6B shows T cell checkpoint ligand activity of afucosylated B7-H4 antibodies compared to isotype control treated cells as measured by IL-2 production. (See Example 11.)

As shown in FIG. 6B, B7-H4 demonstrated T cell checkpoint ligand activity in this assay when endogenously expressed at physiologic levels as IL-2 production was reduced in wells containing SK-BR-3 B7-H4+ cells relative to SK-BR-3 KO cells. Moreover, the B7-H4 antibody also demonstrated T cell checkpoint blockade activity as measured by an increase in IL-2 production relative to isotype control treated cells (FIG. 6B). Thus, this data confirm the T cell checkpoint blockade activity of B7-H4 antibody 20502 (afucosylated) and show that the B7-H4 antibody 20502 provides T cell checkpoint blockade activity in cells that endogenously express B7-H4.

Example 12

Afucosylated and Fucosylated Monoclonal Antibodies ADCC Activity

B7-H4 antibodies were assessed for ADCC activity against a B7-H4-expressing target cell line. Specifically, primary human PBMCs cells were cytokine activated at $1\times10^6$ cells/mL with 200 IU/mL IL-2 at 37° C. The next day, cells were washed and incubated at a 40:1 Effector:Target ratio with SK-BR-3 target cells that were labeled with Calcein-AM. 4 hours after incubation, target cell lysis was quantified using a fluorimeter. A Triton/X treated sample served as the max lysis control sample, whereas a media alone treated sample served as the background lysis control sample. The percent (%) specific lysis was calculated as follows: [1-((sample- media control)/(max lysis-media control))]×100. The percent (%) specific lysis was plotted vs. antibody concentration and the EC50 potency was calculated using nonlinear regression curve fit (GraphPad Prism).

Figure 7:
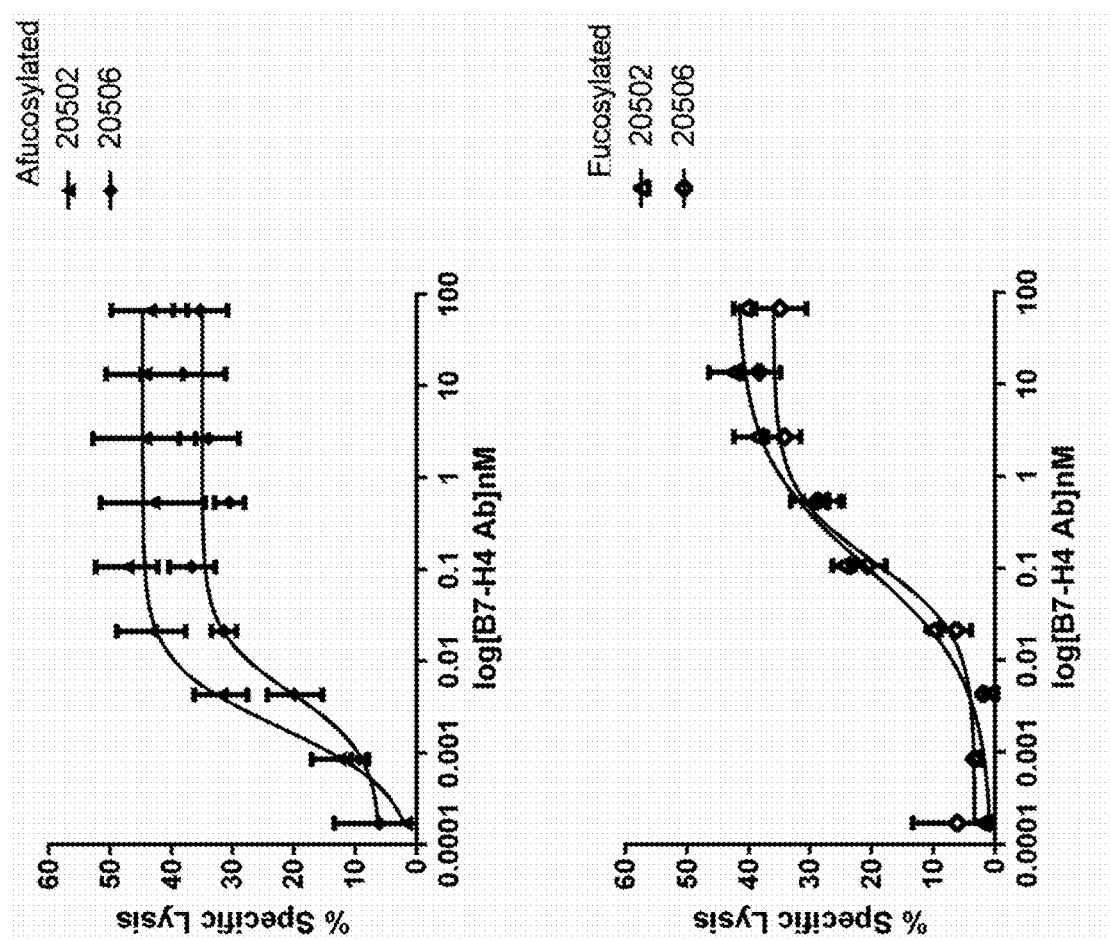
FIG. 7 shows the ADCC activity of fucosylated and afucosylated B7-H4 antibodies against a B7-H4 expressing cell line. (See Example 12.)

The B7-H4 antibodies demonstrated potent dose-dependent ADCC activity against the endogenous B7-H4 expressing breast cell line SK-BR-3. Moreover, the afucosylated antibodies demonstrated significantly more potent ADCC activity in comparison to the fucosylated antibodies (FIG. 7 and Table 20).

TABLE 20

| | | ADCC activity | |
|---|---|---|---|
| | | ADCC Assay (EC50 +/- STD; nM) | |
| Antibody | BIN | Afucosylated | Fucosylated |
| 20502 | 3 | 0.0007 +/- 1.1 × 10E-3 | 0.0370 +/- 6.2E-2 |
| 20506 | 3 | 0.0015 +/- 2.5 × 10E-3 | 0.0135 +/- 2.1E-2 |
| 22213 | 3 | 0.0015 | 0.014 |

Example 13

Correlation of ADCC Activity with Receptor Density

B7-H4 density was quantified on the surface of SK-BR-3, HCC1569, ZR-75-1, MDA-MB-48, and HCC1964 cells by FACS according to the manufacturer's specifications. Specifically, 1×10$^5$ cells were incubated with 15 ug/mL B7-H4 antibody on ice for 25 minutes. In parallel, one drop of Quantum™ Simply Cellular (QSC) microspheres (pre-coated with increasing concentrations of anti-mouse IgG capture antibody) was also incubated with 15 ug/mL B7-H4 antibody on ice for 25 minutes. Following incubation, cells and QSC microspheres were pelleted and washed, and samples were acquired on a flow cytometer. Data was analyzed using the FlowJo software. Mean fluorescence intensity (MFI) was calculated and entered into the Quick-Cal® spreadsheet. A regression associating each bead's fluorescence channel value to its pre-assigned Antibody Binding Capacity (ABC) value will be calculated automatically. An ABC value was assigned once the MFI values for the labeled cells are also added into the template).

B7-H4 antibodies were assessed for ADCC activity against B7-H4 expressing target cell lines with different levels of B7-H4 cell surface density. Specifically, 1×10$^4$ SK-BR-3, HCC1569, ZR-75-1, MDA-MB-468, or HCC1964 target cells were co-incubated with dose-titrations of B7-H4 antibody at 4° C. 25 minutes later, a single use vial of Jurkat-huCD16 reporter cells from Promega was thawed, and 7.5×10$^4$ cells were added to the target cell/B7-H4 antibody mixture and incubated at 37° C. 24 hours later, the samples were brought to room temperature (RT) and incubated with Bio-Glo buffer. The substrate and luminescence were quantified on an EnVision multi-label reader. The data was plotted as luminescence vs. antibody concentration and the EC50 potency was calculated using nonlinear regression curve fit (GraphPad Prism).

Figure 8:
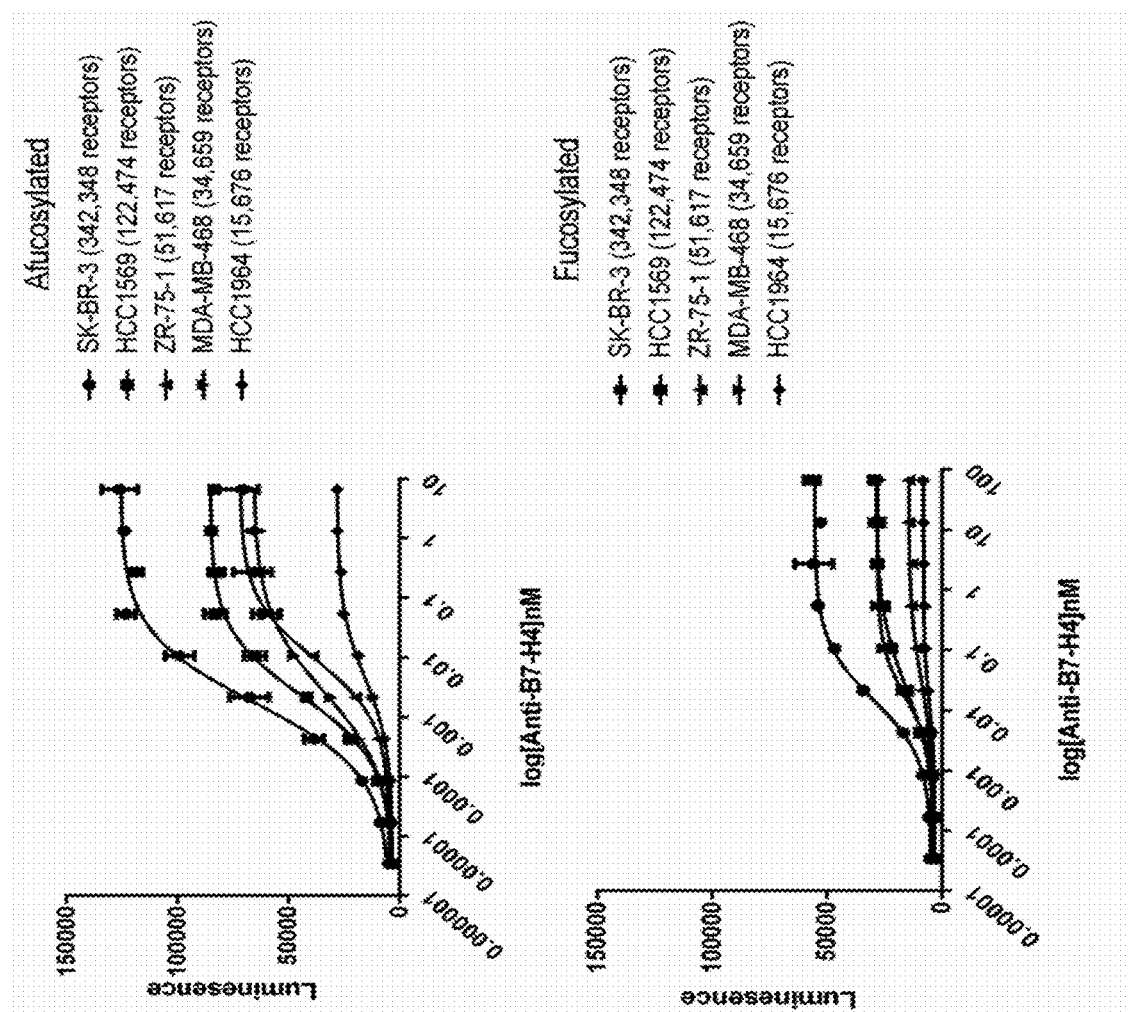
FIG. 8 shows the ADCC activity of fucosylated and afucosylated B7-H4 antibodies against cells with various B7-H4 expression levels. (See Example 13.)

B7-H4 antibody ADCC activity was dependent on B7-H4 cell surface density: as the numbers of cell surface molecules decreased, the amount of maximal ADCC activity also decreased. Moreover, afucosylated antibodies demonstrated improved ADCC activity in comparison to the fucosylated antibodies, especially against target cells with lower levels of B7-H4 cell surface density (FIG. 8).

Example 14

In Vivo Anti-Tumor Efficacy

Seven week old female BALB/c mice were purchased from Charles River Laboratories (Hollister, Calif.) and were acclimated for up to three weeks before the start of the studies. The murine colorectal carcinoma cell line CT26 was engineered to express a chimeric protein consisting of the extracellular domain of murine B7-H4 with the transmembrane domain of murine B7H3. These tumor cells were implanted subcutaneously over the right flank of the mice at 1.0×10$^6$ cells/200 µl/mouse. Prior to inoculation, the cells were cultured for no more than three passages in RPMI 1640 medium supplemented with 10% heat-inactivated Fetal Bovine Serum (FBS), 2 mM L-Glutamine. Cells were grown at 37° C. in a humidified atmosphere with 5% $CO_2$. Upon reaching 80-85% confluence, cells were harvested and resuspended in a 1:1 mixture of serum-free RPMI 1640 and Matrigel at 5×10$^6$ cells per milliliter).

Figure 9A:
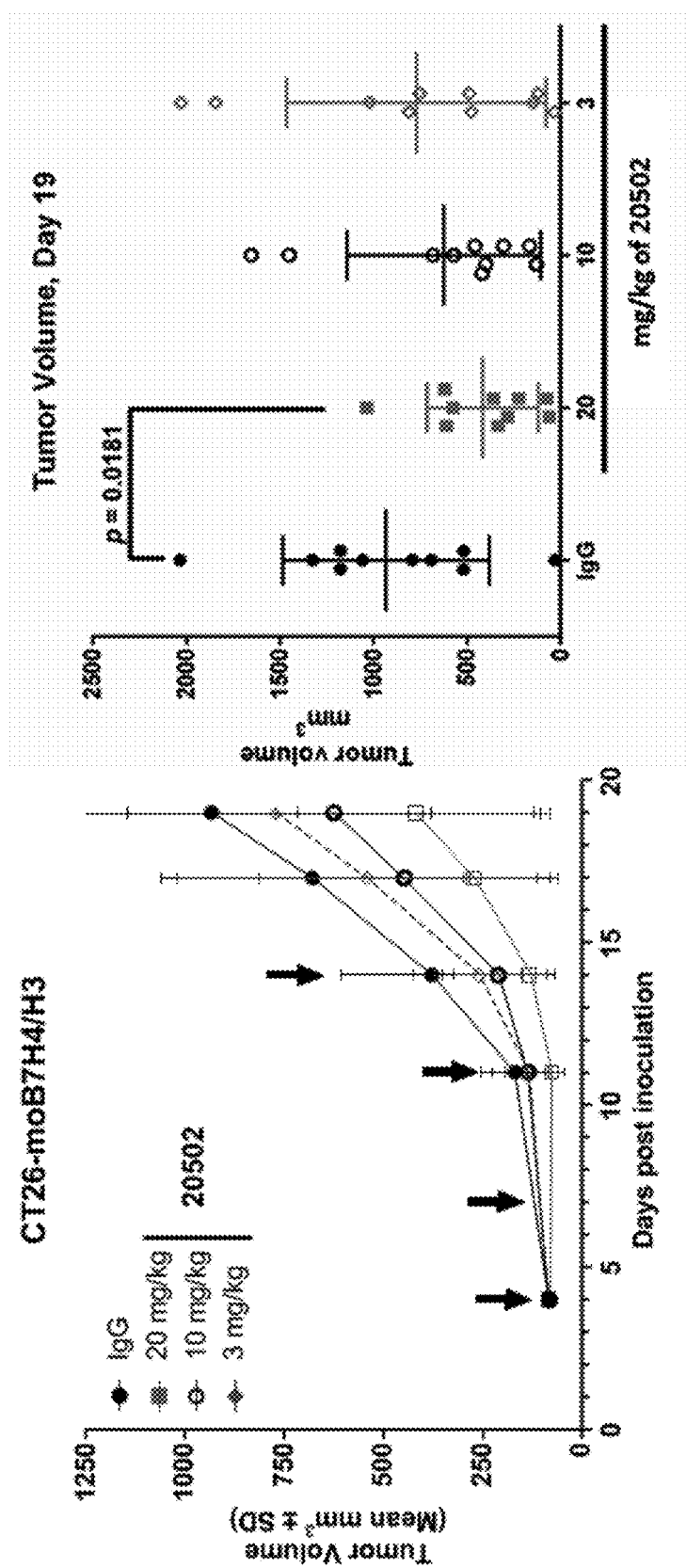
FIG. 9A shows the in vivo anti-tumor efficacy of the B7-H4 antibody 20502. (See Example 14.)
Figure 9B:
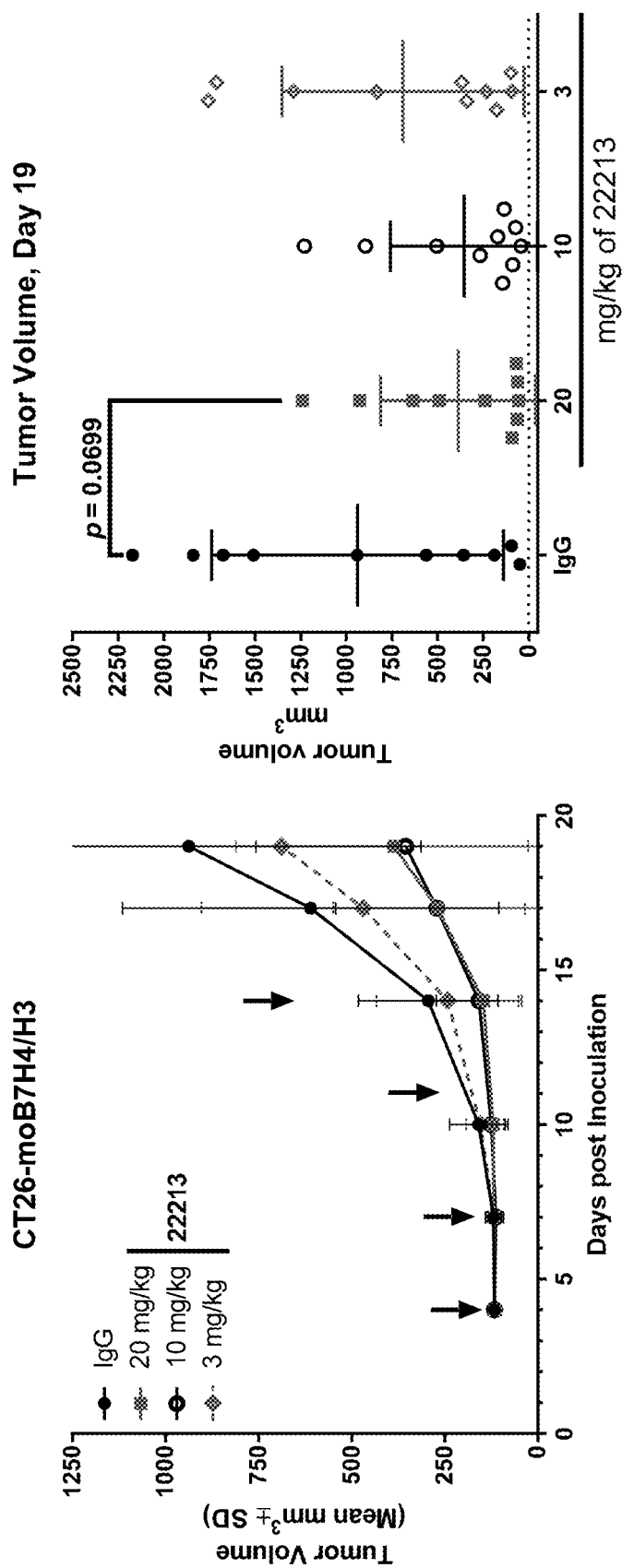
FIG. 9B shows the in vivo anti-tumor efficacy of the B7-H4 antibody 22213. (See Example 14.)

Mice were monitored twice weekly following cell implantation for tumor growth. For tumor measurements, the length and width of each tumor was measured using calipers and volume was calculated according to the formula: tumor volume (mm3)=(width (mm)×length (mm2)/2. On the day of treatment initiation, all tumors were measured, outliers were excluded, and mice were randomly assigned to treatment groups. For anti-B7-H4 treatment, antibodies used include 20502 (FIG. 9A) and 22213 (FIG. 9B). As controls, mice were administered polyclonal human IgG (Bio X Cell, BE0092) or mouse IgG2a (Bio X Cell, BE0085). The antibodies were administered four times via intravenous (i.v.) injection twice weekly beginning on Day 4 or 5 after inoculation.

Tumors continued to be measured at least twice per week until tumor volume exceeded 10% of animal weight, or approximately 2000 mm3. The change in tumor size is shown by graphing individual tumors relative to the day upon which animals were inoculated with CT26 cells. P-values were calculated using unpaired, two-tailed t-test analyses of the calculated tumor volumes on each day of the study. Treatment with 20502 or 22213 significantly reduced tumor growth compared to human IgG control ($p<0.05$) when administered between doses of 10-20 mg/kg (FIGS. 9A and 9B).

Figure 10:
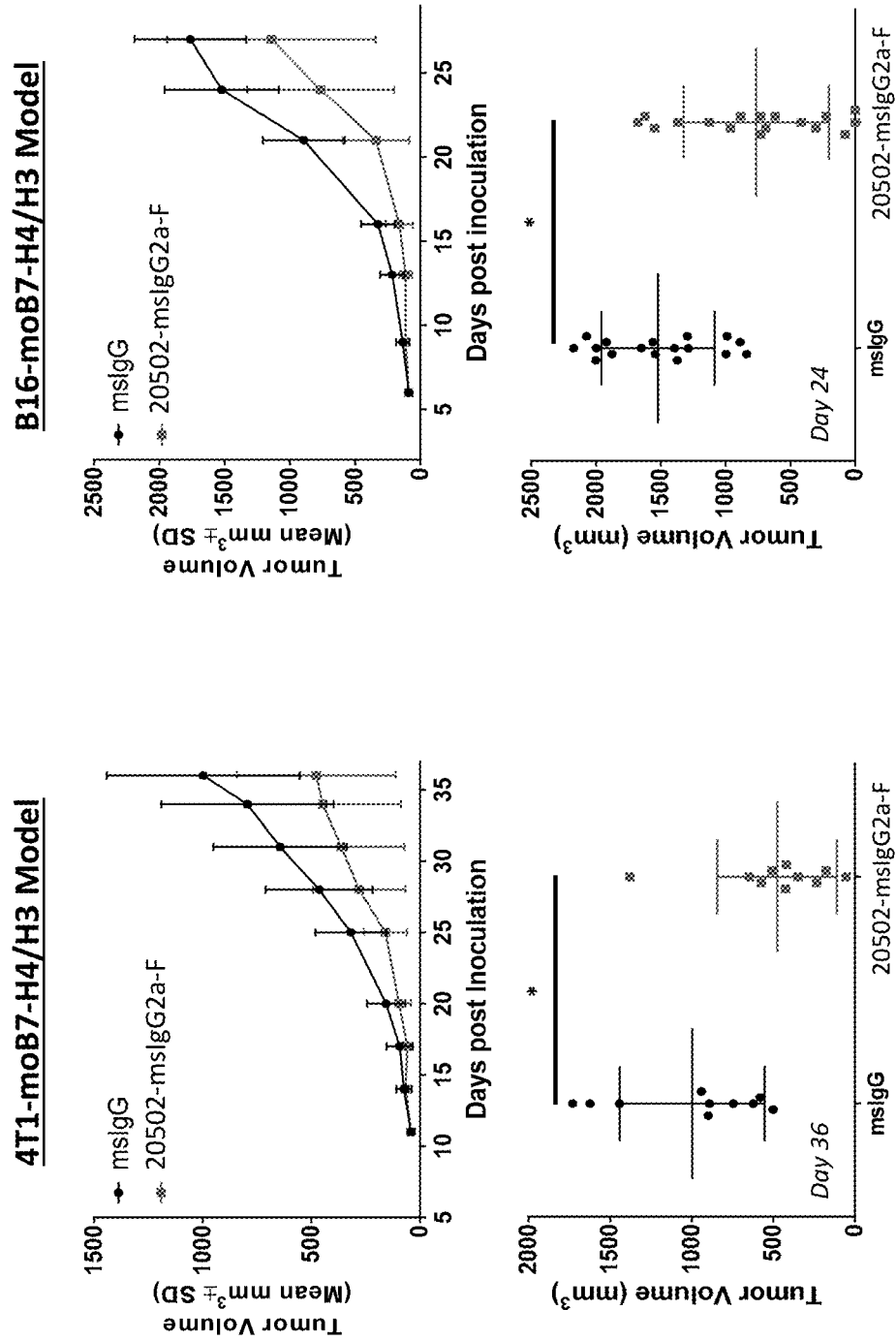
FIG. 10 shows the in vivo anti-tumor efficacy of a murine version of the B7-H4 antibody 20502 in mice implanted with 4T1 (breast carcinoma) and B16 (melanoma) cells. (See Example 14.)

Similar experiments were performed using mice with implanted 4T1 cells (a murine breast carcinoma cell line) or B16 (a murine melanoma cell line). These mice were treated with 20 mg/kg of a mouse surrogate of 20502 called 20502-msIgG2a-F, which contains the 20502 variable region fused to fucosylated mouse IgG2a, or with murine IgG control antibody. Treatment with 20502-msIgG2a-F significantly reduced tumor growth compared to the murine IgG control in both the 4T1 breast carcinoma and B16 melanoma models (FIG. 10).

Additional experiments were also performed using afucosylated 20502 in a MX-1 human breast cancer xenograft model. Female NSG (NOD-scid, IL2R gammanull) mice were purchased from the Jackson Laboratory (Bar Harbor, Me.) and were acclimated for one week before the start of the studies. The human breast cancer cell line MX-1 had previously been shown to endogenously express cell-surface B7H4 protein. These tumor cells were implanted subcutaneously over the right flank of the mice at 1.0×10$^6$ cells/100 µl/mouse in a 1:1 mixture of serum-free RPMI 1640 and Matrigel at 5×10$^6$ cells per milliliter.

Mice were monitored twice weekly following cell implantation for tumor growth. For tumor measurements, the length and width of each tumor was measured using calipers, and volume was calculated according to the formula: Tumor volume (mm3)=(width (mm)×length (mm2)/2. On Day 7 after inoculation, all tumors were measured, outliers were excluded, and mice were randomly assigned to treatment groups. All animals were administered a DNA construct that induced constitutive human IL-15 expression in the circulation for the remainder of the study. On Day 9, half of the mice received an intravenous (i.v.) injection of 20×10$^6$ human peripheral blood monocytic cells (PBMCs), acquired from StemCell Technologies (Tukwila, Wash.). Beginning on Day 11, mice were administered afucosylated 20502 (20 mg/kg) or saline as a negative control. Therapeutics were administered four times via intravenous (i.v.) injection twice weekly.

Figure 11:
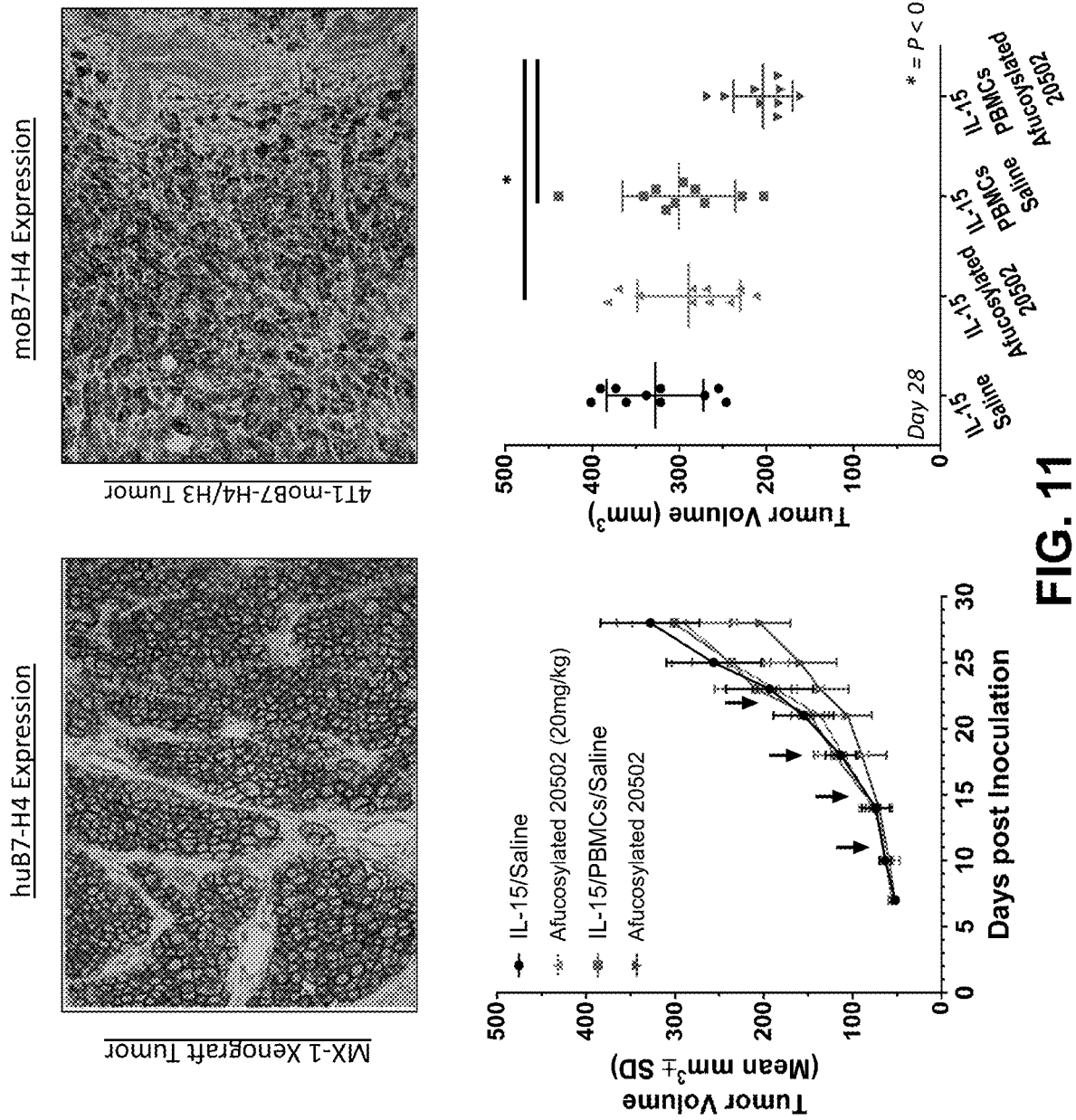
FIG. 11 shows the in vivo anti-tumor efficacy of afucosylated 20502 in an MX-1 human breast cancer xenograft model. The images show human B7-H4 expression in the MX-1 xenograft tumor (left) and murine B7-H4 expression in the 4T1 tumors (right). (See Example 14.)

Tumors continued to be measured at least twice per week until tumor volume exceeded 10% of animal weight or until the animals demonstrated a 15% or greater loss of initial body weight. P-values were calculated using One-Way ANOVA comparing the mean tumor volumes across all treatment groups on Day 28. As shown in FIG. 11, treatment with afucosylated 20502 significantly reduced tumor growth compared to saline control ($p<0.05$) only when administered to mice previously injected with human PBMCs.

Example 15

In Vivo Anti-Tumor Efficacy in Combination with Anti-PD-1 Antibody Methods

Eight week old female BALB/c mice were purchased from Charles River Laboratories (Hollister, Calif.) and were acclimated for up to two weeks before the start of the study. The murine breast carcinoma cell line 4T1 was engineered to express a chimeric protein containing the extracellular domain of murine B7-H4 and the transmembrane domain of murine B7H3. Tumor cells were implanted orthotopically in the mammary fat pad of the mice at 0.5×105 cells/50 µl/mouse. Prior to inoculation, the cells were cultured for no more than three passages in RPMI 1640 medium supplemented with 10% heat-inactivated Fetal Bovine Serum (FBS). Cells were grown at 37° C. in a humidified atmosphere with 5% $CO_2$. Upon reaching 80-85% confluence, cells were harvested and resuspended in serum-free RPMI 1640 on the ventral flank of each mouse into the mammary fat pad.

Mice were monitored twice weekly following cell implantation for tumor growth. The length and width of each tumor was measured using calipers, and the volume was calculated according to the formula: Tumor volume (mm3)=(width (mm)×length (mm)2)/2. On the day of treatment initiation, all tumors were measured, outliers were excluded, and mice were randomly assigned to treatment groups. For the anti-B7-H4 treatment, a mouse surrogate of 20502 called 20502-msIgG2a-F, which contains the 20502 variable region fused to fucosylated mouse IgG2a, was utilized. As a control, mice were administered msIgG2a (anti-HEL). 20502-msIgG2a-F or msIgG2a were administered four times via intravenous (i.v.) injection twice weekly beginning on Day 11 after inoculation. Anti-PD-1 (a modified version of RMP1-14 (Bio X Cell) containing a Fc silent msIgG2a domain) was administered three times via intraperitoneal (i.p.) injection twice weekly beginning on Day 11 after inoculation. Tumors continued to be measured at least twice per week until tumor volume exceeded 10% of animal weight, or approximately 2000 $mm^3$.

Results

Figure 12C:
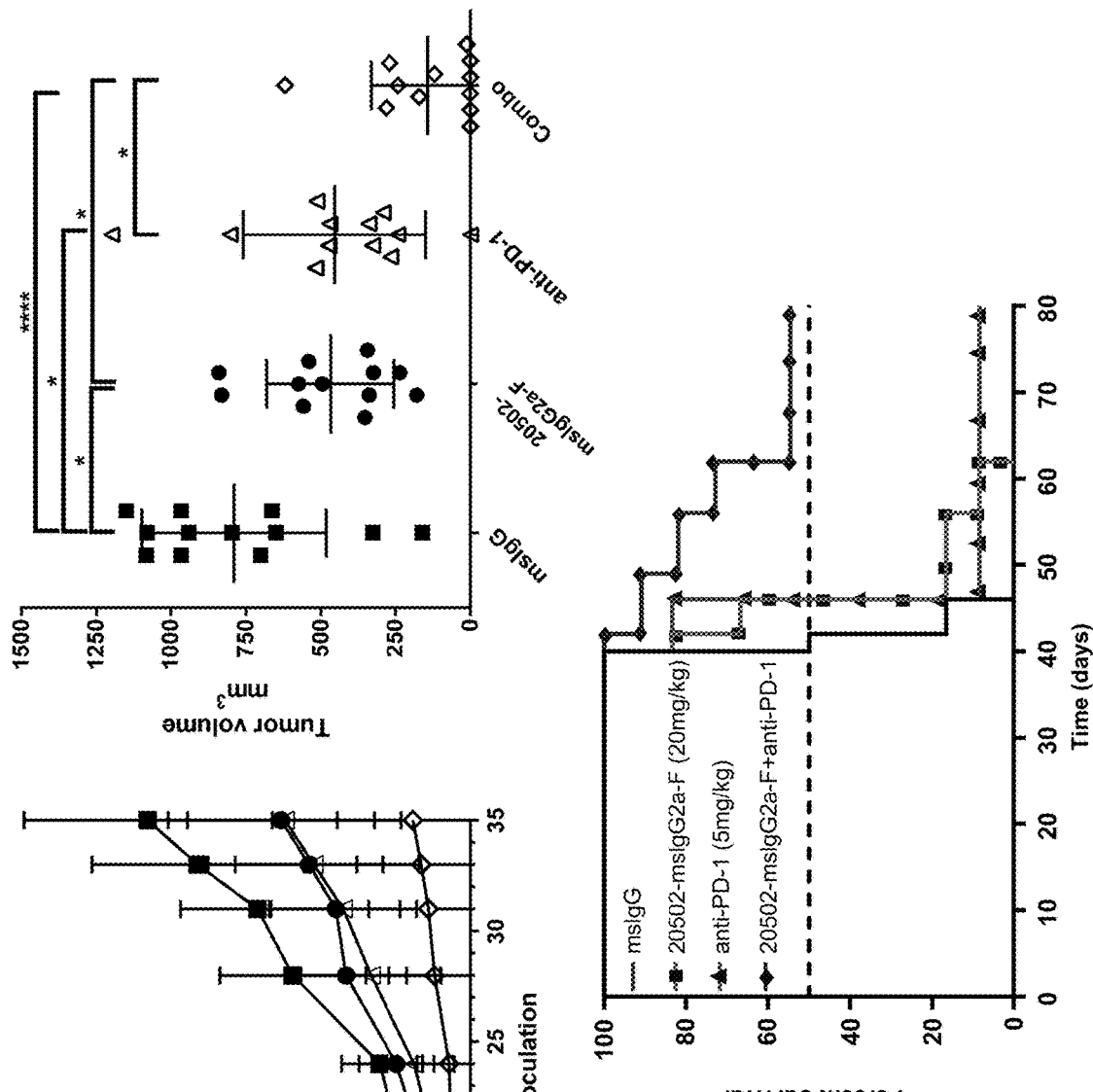

The change in tumor size, the change in mean tumor volume, and the percent survival are shown in FIGS. 12A, 12B and 12C, respectively. Treatment with either 20502-msIgG2a-F or anti-PD-1 significantly reduced tumor growth compared to msIgG2a control (p<0.05). The co-administration of 20502-msIgG2a-F and anti-PD-1 significantly enhanced tumor growth inhibition compared to either monotherapy (p<0.05). Moreover, combination therapy resulted in complete tumor regression in 5 of 12 mice. P-values were calculated using One-Way ANOVA analyses of the calculated tumor volumes on each day of the study with multiple comparisons between each group.

Example 16

Anti-B7-114 Antibody Increases NK-Cell and T-Cell Infiltration and Up-Regulates PD-L1

Eight week old female BALB/c mice were purchased from Charles River Laboratories (Hollister, Calif.) and implanted orthotopically in the mammary fat pad of the mice with 4T1+moB7-H4/H3 cells at 0.5×105 cells/50 µl/mouse. On the day of treatment initiation, all tumors were measured, outliers were excluded, and mice were randomly assigned to treatment groups. Mice were administered huIgG1 (anti-HEL) or afucosylated 20502 at 20 mg/kg via intravenous (i.v.) injection twice (Day 11 and Day 14 post-inoculation).

At 24 hours after the second dose administration, mice were euthanized and perfused with phosphate-buffered saline (PBS). Tumors were then extracted, fixed in 10% formalin for five hours, rinsed in PBS, and placed in a 30% sucrose solution for at least 24 hours. Tumors were embedded in Tissue-Tek® O.C.T. Compound and sectioned at 20 µm in a −15° C. chamber (cryostat). Tissue-mounted slides were rinsed in 0.3% Triton in PBS, blocked with 5% normal goat serum, and stained with primary antibody (anti-NKp46, anti-CD3, or anti-PD-L1; 1:500) overnight. Two serial sections from each tumor were stained.

Figure 13:
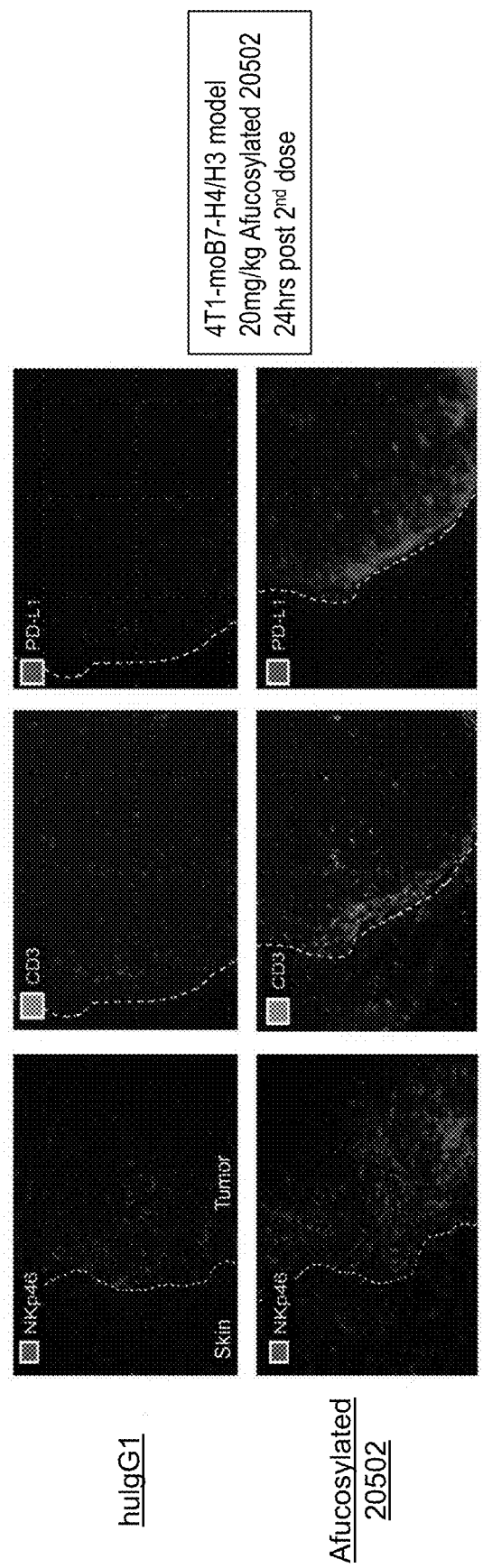
FIG. 13 shows that treatment with afucosylated 20502 (bottom panels) results in NK cell infiltration (left panels), T-cell infiltration (center panels), and PD-L1 up-regulation (right panels) as compared to treatment with a control antibody (top panels). (See Example 16.)

Following overnight incubation, slides were rinsed in 0.3% Triton then incubated with secondary antibody (1:400) for three hours in a dark humid chamber and rinsed. The tissue was then fixed in 1% paraformaldehyde and rinsed in PBS. Coverslips were mounted using Vectashield® with DAPI, sealed with Cytoseal™, and left to dry in a dark chamber. Images were acquired manually with a fluorescence microscope and camera. As shown in FIG. 13, treatment with afucosylated 20502 resulted in increased natural killer (NK) cells (as measured by the anti-NKp46 antibody) and increased CD3+ T cells at tumor edges with a moderate increase of CD3+ T cells in the tumor core. Increased PD-L1 expression was also observed.

Example 17

Anti-B7-114 Antibody Significantly Reduces Tumor Growth In Vivo in 4T1- and B16-moB7-H4/H3 Models in a Dose Dependent Manner Six- to eight-week old female BALB/c or C57B1/6 mice were purchased from Charles River Laboratories (Hollister, Calif.) and were acclimated for up to three weeks before the start of the studies. The murine breast carcinoma cell line 4T1 and melanoma cell line B16-F10 were engineered to express murine a chimeric protein consisting of the extracellular domain of murine B7-H4 with the transmembrane domain of murine B7-H3. These tumor cells were implanted orthotopically in the mammary fat pad at 0.05×$10^6$ cells/50 µl/mouse for 4T1+moB7-H4/H3 or subcutaneously over the right flank of the mice at 0.5×$10^6$ cells/100 µl/mouse for B16+moB7-H4/H3. Prior to inoculation, the cells were cultured for no more than three passages in RPMI-1640 or DMEM medium supplemented with 10% heat-inactivated Fetal Bovine Serum (FBS) and 2 mM L-Glutamine. Cells were grown at 37° C. in a humidified atmosphere with 5% $CO_2$.

Mice were monitored twice weekly following cell implantation for tumor growth. For tumor measurements, the length and width of each tumor was measured using calipers, and volume was calculated according to the formula: Tumor volume (mm3)=(width (mm)×length (mm)2)/2. On the day of treatment initiation, all tumors were measured, outliers were excluded, and mice were randomly assigned to treatment groups. Mice were administered 20502-msIgG2a-F antibody (anti-B7-H4, msIgG2a, fucosylated (also called "cmFPA150-F") or a mouse IgG2a control antibody four times via intravenous (i.v.) injection twice weekly beginning on Day 11 (4T1+moB7-H4/H3) or Day 6 (B16+moB7-H4/H3) after inoculation, except for the 20 mg/kg group, which was administered continuously twice weekly until the end of study.

Tumors continued to be measured at least twice per week until tumor volume exceeded 10% of animal weight, or approximately 2000 mm3. The change in tumor size is shown by graphing mean tumor volume relative to the day upon which animals were inoculated. Treatment with 20502-msIgG2a-F significantly reduced tumor growth compared to mouse IgG2a control (p<0.05) when administered at doses of 1 mg/kg or greater in the 4T1+moB7-H4/H3 model (see FIGS. 14A and 14B) and at doses of 3 mg/kg or greater in the B16+moB7-H4/H3 model (FIGS. 15A and 15B). Statistical significance was calculated using OneWay ANOVA comparing all treatment groups to msIgG2a.

Figure 14B:
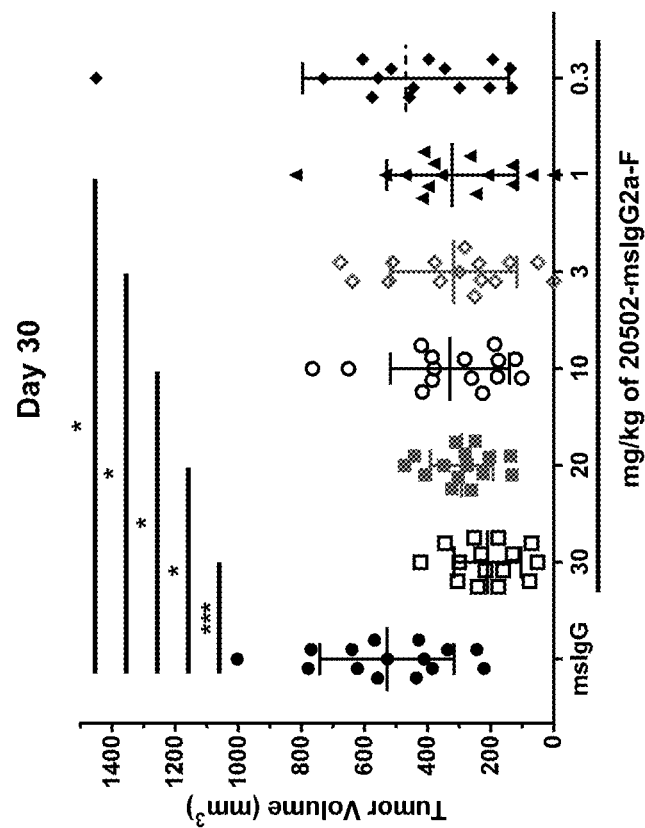
FIG. 14B shows that 20502-msIgG2a-F antibody significantly inhibits tumor growth at 30 mg/kg ($p=0.0003$), 20 mg/kg ($p=0.0103$), 10 mg/kg ($p=0.0419$), 3 mg/kg ($p=0.0277$), and 1 mg/kg ($p=0.0333$) as assessed by OneWay ANOVA on Day 30. (See Example 17.)
Figure 14A:
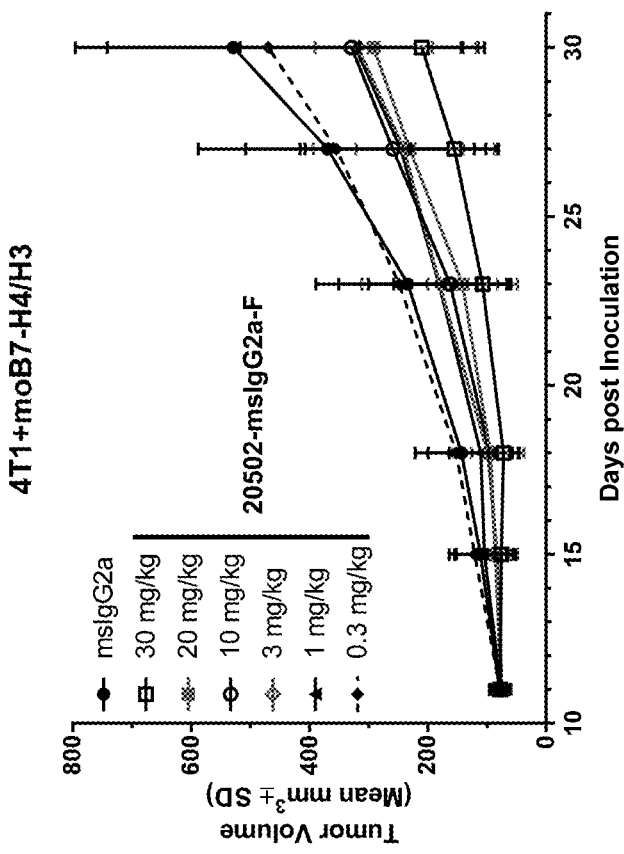
FIG. 14A shows that 20502-msIgG2a-F antibody significantly reduces tumor growth in 4T1 breast carcinoma cells in a dose dependent manner. (See Example 17.)
Figure 15B:
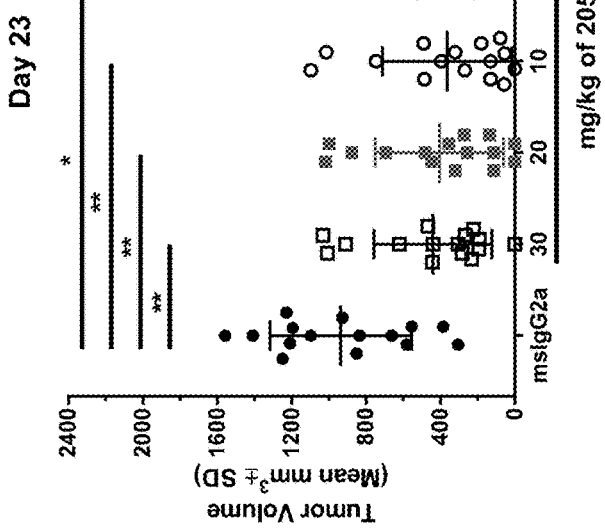
FIG. 15B shows that 20502-msIgG2a-F antibody significantly inhibits tumor growth at 30 mg/kg (p=0.0085), 20 mg/kg (p=0.0041), 10 mg/kg (p=0.0017), and 3 mg/kg (p=0.0420) as assessed by OneWay ANOVA on Day 23. (See Example 17.)
Figure 15A:
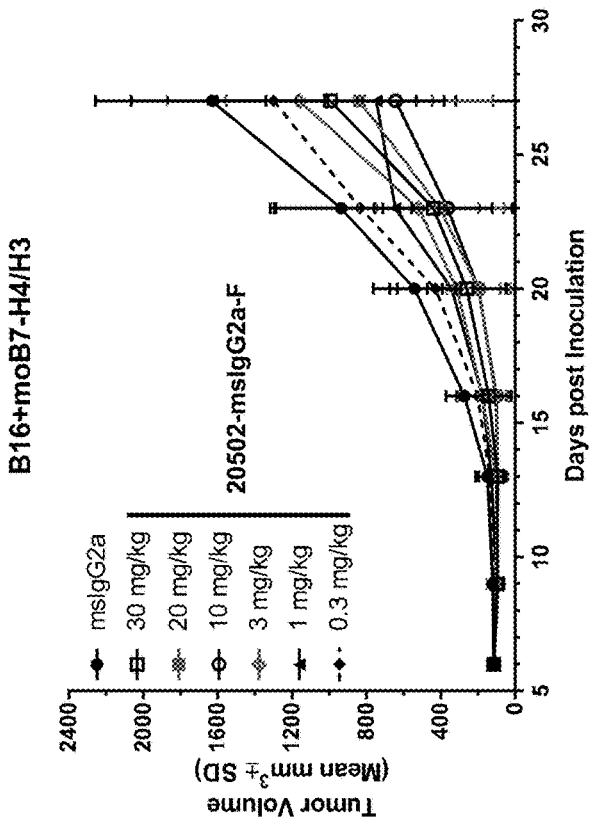
FIG. 15A shows that 20502-msIgG2a-F antibody significantly reduces growth of B16 expressing B7-H4/H3. (See Example 17.)

FIGS. 14A and 14B show that 20502-msIgG2a-F antibody significantly reduces growth of 4T1 expressing B7-H4/H3. BALB/c mice were inoculated orthotopically with 4T1 breast carcinoma cells engineered to express murine B7-H4 ECD fused to B7-H3™. Mice were administered 20502-msIgG2a-F antibody (anti-B7-H4, msIgG2a, fucosylated) twice weekly beginning on Day 11 after inoculation. 20502-msIgG2a-F antibody demonstrated a dose-dependent reduction in tumor growth, with significant tumor growth inhibition at 30 mg/kg (p=0.0003), 20 mg/kg (p=0.0103), 10 mg/kg (p=0.0419), 3 mg/kg (p=0.0277), and 1 mg/kg (p=0.0333) as assessed by OneWay ANOVA on Day 30.

FIGS. 15A and 15B show that 20502-msIgG2a-F antibody significantly reduces growth of B16 expressing B7-H4/H3. C57Bl/6 mice were inoculated subcutaneously with B16-F10 melanoma cells engineered to express murine B7-H4 ECD fused to B7-H3™. Mice were administered 20502-msIgG2a-F antibody (anti-B7-H4, msIgG2a, fucosylated) twice weekly beginning on Day 6 after inoculation. 20502-msIgG2a-F antibody demonstrated a dose-dependent reduction in tumor growth (FIG. 15A), with significant tumor growth inhibition at 30 mg/kg (p=0.0085), 20 mg/kg (p=0.0041), 10 mg/kg (p=0.0017), and 3 mg/kg (p=0.0420) as assessed by OneWay ANOVA on Day 23 (FIG. 15B).

Thus, the 20502-msIgG2a-F antibody significantly reduced tumor size in a dose-dependent manner in two different cancer models. This data in breast carcinoma and melanoma cell lines indicate that the 20502-msIgG2a-F antibody can be used to treat patients with cancer.

Sequence Tables

GITR Antibody Sequences

| SEQ ID NO | Sequence |
|---|---|
| 411 | SGSVFSIDAM |
| 412 | LSGISSAK |
| 413 | YADVSTGWGRDAHGYW |
| 414 | EVQLLESGGGEVQPGGSLRLSCAASGSVFSIDAMGWYRQAPGKQRELVAVLSGISSAKYAASAPGRFTISRDNAKNTVYLQMSSLRAEDTAVYYCYADVSTGWGRDAHGYWGQGTLVTV |
| 415 | EVQLLESGGGEVQPGGSLRLSCAASGSVFSIDAMGWYRQAPGKQRELVAVLSGISSAKYAASAPGRFTISRDNAKNTVYLQMSSLRAEDTAVYYCYADVSTGWGRDAHGYWGQGTLVTVKPGGSGGSEVQLLESGGGEVQPGGSLRLSCAASGSVFSIDAMGWYRQAPGKQRELVAVLSGISSAKYAASAPGRFTISRDNAKNTVYLQMSSLRAEDTAVYYCYADVSTGWGRDAHGYWGQGTLVTVKPGGGGDKTHTCPPCPAPELLGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVMHEALHNHYTQKSLSLSPGK |
| 416 | EPKSSDKTHTCPPC |
| 417 | DKTHTCPPC |
| 418 | ESKYGPPCPPC |
| 419 | GGSGGS |
| 420 | GGSGGSGGS |
| 421 | GGSGGSGGSGGS |
| 422 | GGSGGSGGSGGSGGS |
| 423 | GGGG |
| 424 | GGGGG |
| 425 | GGGGGG |

CD80 Sequences

| SEQ ID NO | Sequence |
|---|---|
| 426 | VIHVTKEVKEVATLSCGHNVSVEELAQTRIYWQKEKKMVLTMMSGD MNIWPEYKNRTIFDITNNLSIVILALRPSDEGTYECVVLKYEKDAFKREH LAEVTLSVKADFPTPSISDFEIPTSNIRRIICSTSGGFPEPHLSWLENGEEL NAINTTVSQDPETELYAVSSKLDFNMTTNHSFMCLIKYGHLRVNQTFN WNTTKQEHFPDN |
| 427 | VIHVTKEVKEVATLSCGHNVSVEELAQTRIYWQKEKKMVLTMMSGD MNIWPEYKNRTIFDITNNLSIVILALRPSDEGTYECVVLKYEKDAFKREH LAEVTLSVKADFPTPSISDFEIPTSNIRRIICSTSGGFPEPHLSWLENGEEL NAINTTVSQDPETELYAVSSKLDFNMTTNHSFMCLIKYGHLRVNQTFN WNTTKQEHFPDNEPKSSDKTHTCPPCPAPELLGGPSVFLFPPKPKDTLMI SRTPEVTCVVVDVSHEDPEVKFNWYVDGVEVHNAKTKPREEQYNSTY RVVSVLTVLHQDWLNGKEYKCKVSNKALPAPIEKTISKAKGQPREPQV YTLPPSRDELTKNQVSLTCLVKGFYPSDIAVEWESNGQPENNYKTTPPV LDSDGSFFLYSKLTVDKSRWQQGNVFSCSVMHEALHNHYTQKSLSLSP GK |
| 428 | VIHVTKEVKEVATLSCGHNVSVEELAQTRIYWQKEKKMVLTMMSGD MNIWPEYKNRTIFDITNNLSIVILALRPSDEGTYECVVLKYEKDAFKREH LAEVTLSVKADFPTPSISDFEIPTSNIRRIICSTSGGFPEPHLSWLENGEEL NAINTTVSQDPETELYAVSSKLDFNMTTNHSFMCLIKYGHLRVNQTFN WNTTKQEHFPDNEPKSSDKTHTCPPCPAPEFEGGPSVFLFPPKPKDTLMI SRTPEVTCVVVDVSHEDPEVKFNWYVDGVEVHNAKTKPREEQYNSTY RVVSVLTVLHQDWLNGKEYKCKVSNKALPASIEKTISKAKGQPREPQV YTLPPSRDELTKNQVSLTCLVKGFYPSDIAVEWESNGQPENNYKTTPPV LDSDGSFFLYSKLTVDKSRWQQGNVFSCSVMHEALHNHYTQKSLSLSP GK |

CSFR1 Sequences

| SEQ ID NO | Sequence |
|---|---|
| 429 | QVQLVQSGAE VKKPGSSVKV SCKASGYTFT DNYMIWVRQA PGQGLEWMGD INPYNGGTTF NQKFKGRVTI TADKSTSTAY MELSSLRSED TAVYYCARES PYFSNLYVMD YWGQGTLVTV SS |
| 430 | EIVLTQSPAT LSLSPGERAT LSCKASQSVD YDGDNYMNWY QQKPGQAPRL LIYAASNLES GIPARFSGSG SGTDFTLTIS SLEPEDFAVY YCHLSNEDLS TFGGGTKVEI K |
| 431 | GYTFTDNYMI |
| 432 | DINPYNGGTT FNQKFKG |
| 433 | ESPYFSNLYV MDY |
| 434 | KASQSVDYDG DNYMN |
| 435 | AASNLES |
| 436 | HLSNEDLST |
| 437 | QVQLVQSGAE VKKPGSSVKV SCKASGYTFT DNYMIWVRQA PGQGLEWMGD INPYNGGTTF NQKFKGRVTI TADKSTSTAY MELSSLRSED TAVYYCARES PYFSNLYVMD YWGQGTLVTV SSASTKGPSV FPLAPCSRST SESTAALGCL VKDYFPEPVT VSWNSGALTS GVHTFPAVLQ SSGLYSLSSV VTVPSSSLGT KTYTCNVDHK PSNTKVDKRV ESKYGPPCPP CPAPEFLGGP SVFLFPPKPK DTLMISRTPE VTCVVVDVSQ EDPEVQFNWY VDGVEVHNAK TKPREEQFNS TYRVVSVLTV LHQDWLNGKE YKCKVSNKGL PSSIEKTISK AKGQPREPQV YTLPPSQEEM TKNQVSLTCL VKGFYPSDIA VEWESNGQPE NNYKTTPPVL DSDGSFFLYS RLTVDKSRWQ EGNVFSCSVM HEALHNHYTQ KSLSLSLGK |
| 438 | EIVLTQSPAT LSLSPGERAT LSCKASQSVD YDGDNYMNWY QQKPGQAPRL LIYAASNLES GIPARFSGSG SGTDFTLTIS SLEPEDFAVY YCHLSNEDLS TFGGGTKVEI KRTVAAPSVF IFPPSDEQLK SGTASVVCLL NNFYPREAKV QWKVDNALQS GNSQESVTEQ DSKDSTYSLS STLTLSKADY EKHKVYACEV THQGLSSPVT KSFNRGEC |

PD-1 (Nivolumab) Antibody Sequences

| SEQ ID NO: | Description | Sequence |
|---|---|---|
| 440 | heavy chain variable region | QVQLVESGGGVVQPGRSLRLDCKASGITFSNSGMHWVRQAPGKGLEWVAVIWYDGSKRYYA DSVKGRFTISRDNSKNTLFLQMNSLRAEDTAVYYCATNDDYWGQGTLVTVSS |
| 441 | heavy chain constant region | ASTKGPSVFPLAPCSRSTSESTAALGCLVKDYFPEPVTVSWNSGALTSGVHTFPAVLQSSG LYSLSSVVTVPSSSLGTKTYTCNVDHKPSNTKVDKRVESKYGPPCPPCPAPEFLGGPSVFL FPPKPKDTLMISRTPEVTCVVVDVSQEDPEVQFNWYVDGVEVHNAKTKPREEQFNSTYRVV SVLTVLHQDWLNGKEYKCKVSNKGLPSSIEKTISKAKGQPREPQVYTLPPSQEEMTKNQVS LTCLVKGFYPSDIAVEWESNGQPENNYKTTPPVLDSDGSFFLYSRLTVDKSRWQEGNVFSC SVMHEALHNHYTQKSLSLSLGK |

| SEQ ID NO: | Description | Sequence |
|---|---|---|
| 442 | light chain variable region | EIVLTQSPATLSLSPGERATLSCRASQSVSSYLAWYQQKPGQAPRLLIYDASNRATGIPAR FSGSGSGTDFTLTISSLEPEDFAVYYCQQSSNWPRTFGQGTKVEIK |
| 443 | light chain constant region | RTVAAPSVFIFPPSDEQLKSGTASVVCLLNNFYPREAKVQWKVDNALQSGNSQESVTEQDS KDSTYSLSSTLTLSKADYEKHKVYACEVTHQGLSSPVTKSFNRGEC |
| 444 | heavy FR1 | QVQLVESGGGVVQPGRSLRLDCKASGITFS |
| 445 | heavy CDR1 | NSGMH |
| 446 | heavy FR2 | WVRQAPGKGLEWVA |
| 447 | heavy CDR2 | VIWYDGSKRYYADSVKG |
| 448 | heavy FR3 | RFTISRDNSKNTLFLQMNSLRAEDTAVYYCAT |
| 449 | heavy CDR3 | NDDY |
| 450 | heavy FR4 | WGQGTLVTVSS |
| 451 | light FR1 | EIVLTQSPATLSLSPGERATLSC |
| 452 | light CDR1 | RASQSVSSYLA |
| 453 | light FR2 | WYQQKPGQAPRLLIY |
| 454 | light CDR2 | DASNRAT |
| 455 | light FR3 | GIPARFSGSGSGTDFTLTISSLEPEDFAVYYC |
| 456 | light CDR3 | QQSSNWPRT |
| 457 | light FR4 | FGQGTKVEIK |

The invention is not to be limited in scope by the specific embodiments described herein. Indeed, various modifications of the invention in addition to those described will become apparent to those skilled in the art from the foregoing description and accompanying figures. Such modifications are intended to fall within the scope of the appended claims.

All references (e.g., publications or patents or patent applications) cited herein are incorporated herein by reference in their entirety and for all purposes to the same extent as if each individual reference (e.g., publication or patent or patent application) was specifically and individually indicated to be incorporated by reference in its entirety for all purposes.

Other embodiments are within the following claims.

What is claimed:

1. An isolated antibody or antigen-binding fragment thereof that specifically binds to human B7-H4, comprising heavy chain variable region (VH) complementarity determining region (CDR) 1, VH CDR2, VH CDR3 and light chain variable region (VL) CDR1, CDR2, and CDR3 sequences selected from the group consisting of:
   (a) SEQ ID NOs:458-463, respectively;
   (b) SEQ ID NOs:5-10, respectively;
   (c) SEQ ID NOs:15-20, respectively;
   (d) SEQ ID NOs:25-30, respectively;
   (e) SEQ ID NOs:35-40, respectively; and
   (f) SEQ ID NOs:45-50, respectively.

2. An isolated antibody or antigen-binding fragment thereof that specifically binds to human B7-H4, comprising a heavy chain variable region and a light chain variable region comprising the amino acid sequences of:
   (a) SEQ ID NOs:464 and 42, respectively;
   (b) SEQ ID NOs:11 and 12, respectively;
   (c) SEQ ID NOs:21 and 22, respectively;
   (d) SEQ ID NOs:31 and 32, respectively;
   (e) SEQ ID NOs:41 and 42, respectively; or
   (f) SEQ ID NOs:51 and 52, respectively.

3. The antibody or antigen-binding fragment thereof of claim 1, wherein the antibody or antigen-binding fragment further comprises a heavy chain constant region.

4. The antibody or antigen-binding fragment thereof of claim 3, wherein the heavy chain constant region is selected from the group consisting of human immunoglobulins IgG1, IgG2, IgG3, IgG4, IgA1, and IgA2 heavy chain constant regions.

5. The antibody or antigen-binding fragment thereof of claim 3, wherein the antibody or antigen-binding fragment further comprises a light chain constant region.

6. The antibody or antigen-binding fragment thereof of claim 5, wherein the light chain constant region is selected from the group consisting of human immunoglobulins IgGκ and IgGλ, light chain constant regions.

7. The antibody or antigen-binding fragment thereof of claim 1, wherein the antibody or antigen-binding fragment thereof comprises a heavy chain and light chain comprising the amino acid sequences of:
   (a) SEQ ID NOs:469 and 44, respectively;
   (b) SEQ ID NOs:13 and 14, respectively;
   (c) SEQ ID NOs:23 and 24, respectively;
   (d) SEQ ID NOs:33 and 34, respectively;
   (e) SEQ ID NOs:43 and 44, respectively; or
   (f) SEQ ID NOs:53 and 54, respectively.

8. An isolated antibody or antigen-binding fragment thereof that specifically binds to human B7-H4, wherein the antibody or antigen-binding fragment thereof comprises the VH CDR1, VH CDR2, VH CDR3, VL CDR1, VL CDR2, and VL CDR3 of an antibody comprising a heavy chain and a light chain comprising the amino acid sequence of:
   (a) SEQ ID NOs:469 and 44, respectively;
   (b) SEQ ID NOs:13 and 14, respectively;
   (c) SEQ ID NOs:23 and 24, respectively;
   (d) SEQ ID NOs:33 and 34, respectively;
   (e) SEQ ID NOs:43 and 44, respectively; or
   (f) SEQ ID NOs:53 and 54, respectively.

9. The antibody or antigen-binding fragment thereof of claim 8, wherein the CDRs are the Kabat-defined CDRs, the Chothia-defined CDRs, or the AbM-defined CDRs.

10. The antibody or antigen-binding fragment thereof of claim 1, wherein the antibody or antigen-binding fragment thereof is a human antibody, a chimeric antibody, or an antigen-binding fragment thereof.

11. The antibody or antigen-binding fragment thereof of claim 1, wherein contacting a cell expressing B7-H4 with the antibody or antigen-binding fragment thereof:
   (a) induces T cell proliferation when the B7-H4 cell is in a population of cells comprising T cells,
   (b) induces CD4+ T cell proliferation when the B7-H4 cell is in a population of cells comprising T cells,
   (c) induces CD8+ T cell proliferation when the B7-H4 cell is in a population of cells comprising T cells,
   (d) is capable of inducing antibody dependent cell mediated cytotoxicity (ADCC) in a B7-H4-expressing cell,
   (e) inhibits tumor growth in a murine CT26 colorectal carcinoma model, a murine breast carcinoma 4T1 model, or a melanoma cell line B16-moB7-H4/H3 model, and/or
   (f) inhibits T cell checkpoint activity of B7-H4.

12. The antibody of antigen-binding fragment thereof of claim 1, wherein contacting a cell expressing B7-H4 with the antibody or antigen-binding fragment:
   (a) increases T cell proliferation by at least 5% as compared to treatment with a control antibody when the B7-H4 cell is in a population of cells comprising T cells,
   (b) increases CD4+ T cell proliferation by at least 5% as compared to treatment with a control antibody when the B7-H4 cell is in a population of cells comprising T cells,
   (c) increases CD8+ T cell proliferation by at least 5% as compared to treatment with a control antibody when the B7-H4 cell is in a population of cells comprising T cells,
   (d) induces specific lysis in at least 20% of B7-H4 expressing cells, and/or
   (e) reduces tumor growth by at least 25% as compared to treatment with a control antibody.

13. The antibody or antigen-binding fragment thereof of claim 11, wherein the induction of T cell proliferation, the induction of CD4+ T cell proliferation, the induction of CD8+ T cell proliferation, the ADCC activity, the inhibition of tumor growth, and/or the inhibition of T cell checkpoint activity is dose-dependent.

14. The antibody or antigen-binding fragment thereof of claim 1, wherein the antibody or antigen-binding fragment thereof binds to cynomolgus monkey, rat, and/or mouse B7-H4.

15. The antibody or antigen-binding fragment thereof of claim 1, wherein the antibody or antigen-binding fragment thereof binds to the IgV domain of human B7-H4.

16. The antibody or antigen-binding fragment thereof of claim 1, wherein the antibody or antigen-binding fragment thereof is afucosylated.

17. The antibody or antigen-binding fragment thereof of claim 1, further comprising a detectable label.

18. An isolated polynucleotide comprising a nucleic acid molecule encoding the heavy chain variable region and/or the light chain variable region of claim 1.

19. An isolated vector comprising the polynucleotide of claim 18.

20. A host cell comprising the polynucleotide of claim 18.

21. A method of producing an antibody or antigen-binding fragment thereof that binds to human B7-H4 comprising culturing the host cell of claim 20 so that the nucleic acid molecule is expressed and the antibody or antigen-binding fragment thereof is produced.

22. An isolated antibody or antigen-binding fragment thereof that specifically binds to human B7-H4 and is encoded by the polynucleotide of claim 18.

23. A pharmaceutical composition comprising the antibody or antigen-binding fragment thereof of claim 1 and a pharmaceutically acceptable excipient.

24. A pharmaceutical composition comprising (i) antibodies or antigen-binding fragments of claim 1 and (ii) a pharmaceutically acceptable excipient, wherein at least 95% of the antibodies or antigen-binding fragments thereof in the composition are afucosylated.

25. The pharmaceutical composition of claim 23, further comprising an anti-PD-1 antibody or an antigen-binding fragment thereof or an anti-PD-L1 antibody or an antigen-binding fragment thereof.

26. A method for inducing T cell proliferation comprising contacting a cell expressing B7-H4 with the antibody or antigen-binding fragment thereof of claim 1, wherein the B7-H4 expressing cell is in a population of cells comprising T cells.

27. A method for inducing CD4+ T cell proliferation comprising contacting a cell expressing B7-H4 with the antibody or antigen-binding fragment thereof of claim 1, wherein the B7-H4 expressing cell is in a population of cells comprising T cells.

28. A method for inducing CD8+ T cell proliferation comprising contacting a cell expressing B7-H4 with the antibody or antigen-binding fragment thereof of claim 1, wherein the B7-H4 expressing cell is in a population of cells comprising T cells.

29. A method for killing a cell expressing B7-H4 comprising contacting the cell with the antibody or antigen-binding fragment thereof of claim 1.

30. A method for depleting B7-H4-expressing cells from a population of cells comprising contacting the population of cells with the antibody or antigen-binding fragment thereof of claim 1.

31. The method of claim 26, further comprising contacting the cell expressing B7-H4 with an anti-PD-1 antibody or an antigen-binding fragment thereof or an anti-PD-L1 antibody or an antigen-binding fragment thereof.

32. A method of treating a B7-H4 expressing cancer in a subject, the method comprising administering to the subject an effective amount of the antibody or antigen-binding fragment thereof of claim 1.

33. The method of claim 32, wherein the cancer is selected from the group consisting of head and neck cancer, small cell lung cancer, gastric cancer, melanoma, breast cancer, ductal carcinoma, endometrial carcinoma, ovarian cancer, non-small cell lung cancer, pancreatic cancer, thyroid cancer, kidney cancer and bladder cancer.

34. The method of claim 32 wherein the cancer is a PD-1 inhibitor inadequate responder, and/or wherein the cancer is a PD-L1 inhibitor inadequate responder, and/or wherein the cancer expresses a low level of PD-L1.

35. The method of claim 32, further comprising administering to the subject an anti-PD-1 antibody or an antigen-binding fragment thereof or an anti-PD-L1 antibody or an antigen-binding fragment thereof.

36. A method for detecting B7-H4 in a sample comprising contacting said sample with the antibody or antigen-binding fragment thereof of claim 1.

37. A kit comprising the antibody or antigen-binding fragment thereof of claim 1, a detection reagent, and instructions for use for detection of a B7-H4 antigen.

38. An isolated polynucleotide comprising a nucleic acid molecule encoding the heavy chain variable region or heavy chain of the antibody or antigen-binding fragment thereof of claim 7 and/or encoding the light chain variable region or light chain of the antibody or antigen-binding fragment thereof of claim 7.

39. The antibody or antigen-binding fragment thereof of claim 2, wherein the antibody or antigen-binding fragment further comprises a heavy chain constant region.

40. The antibody or antigen-binding fragment thereof of claim 2, wherein the antibody or antigen-binding fragment thereof is afucosylated.

41. The antibody or antigen-binding fragment thereof of claim 7, wherein the antibody or antigen-binding fragment thereof is afucosylated.

42. A pharmaceutical composition comprising the antibody or antigen-binding fragment thereof of claim 2 and a pharmaceutically acceptable excipient.

43. A pharmaceutical composition comprising the antibody or antigen-binding fragment thereof of claim 7 and a pharmaceutically acceptable excipient.

44. The pharmaceutical composition of claim 24, further comprising an anti-PD-1 antibody, an anti-PD-L1 antibody, or an antigen-binding fragment thereof.

45. The antibody or antigen-binding fragment of claim 39, wherein the antibody or antigen-binding fragment comprises a light chain constant chain.

\* \* \* \* \*

SEQUENCE LISTING

<160> NUMBER OF SEQ ID NOS: 469

<210> SEQ ID NO 1
<211> LENGTH: 282
<212> TYPE: PRT
<213> ORGANISM: Homo sapiens

<400> SEQUENCE: 1

Met Ala Ser Leu Gly Gln Ile Leu Phe Trp Ser Ile Ile Ser Ile Ile

```
                1               5                   10                  15
            Ile Ile Leu Ala Gly Ala Ile Ala Leu Ile Ile Gly Phe Gly Ile Ser
                            20                  25                  30
            Gly Arg His Ser Ile Thr Val Thr Val Ala Ser Ala Gly Asn Ile
                        35                  40                  45
            Gly Glu Asp Gly Ile Leu Ser Cys Thr Phe Glu Pro Asp Ile Lys Leu
                    50                  55                  60
            Ser Asp Ile Val Ile Gln Trp Leu Lys Glu Gly Val Leu Gly Leu Val
            65                  70                  75                  80
            His Glu Phe Lys Glu Gly Lys Asp Glu Leu Ser Glu Gln Asp Glu Met
                                85                  90                  95
            Phe Arg Gly Arg Thr Ala Val Phe Ala Asp Gln Val Ile Val Gly Asn
                            100                 105                 110
            Ala Ser Leu Arg Leu Lys Asn Val Gln Leu Thr Asp Ala Gly Thr Tyr
                        115                 120                 125
            Lys Cys Tyr Ile Ile Thr Ser Lys Gly Lys Gly Asn Ala Asn Leu Glu
                    130                 135                 140
            Tyr Lys Thr Gly Ala Phe Ser Met Pro Glu Val Asn Val Asp Tyr Asn
            145                 150                 155                 160
            Ala Ser Ser Glu Thr Leu Arg Cys Glu Ala Pro Arg Trp Phe Pro Gln
                                165                 170                 175
            Pro Thr Val Val Trp Ala Ser Gln Val Asp Gln Gly Ala Asn Phe Ser
                            180                 185                 190
            Glu Val Ser Asn Thr Ser Phe Glu Leu Asn Ser Glu Asn Val Thr Met
                        195                 200                 205
            Lys Val Val Ser Val Leu Tyr Asn Val Thr Ile Asn Asn Thr Tyr Ser
                    210                 215                 220
            Cys Met Ile Glu Asn Asp Ile Ala Lys Ala Thr Gly Asp Ile Lys Val
            225                 230                 235                 240
            Thr Glu Ser Glu Ile Lys Arg Arg Ser His Leu Gln Leu Leu Asn Ser
                                245                 250                 255
            Lys Ala Ser Leu Cys Val Ser Ser Phe Phe Ala Ile Ser Trp Ala Leu
                            260                 265                 270
            Leu Pro Leu Ser Pro Tyr Leu Met Leu Lys
                        275                 280

<210> SEQ ID NO 2
<211> LENGTH: 282
<212> TYPE: PRT
<213> ORGANISM: Artificial Sequence
<220> FEATURE:
<223> OTHER INFORMATION: Cynomolgus monkey B7-H4

<400> SEQUENCE: 2

Met Ala Ser Leu Gly Gln Ile Leu Phe Trp Ser Ile Ile Ser Ile Ile
1               5                   10                  15
Phe Ile Leu Ala Gly Ala Ile Ala Leu Ile Ile Gly Phe Gly Ile Ser
                20                  25                  30
Gly Arg His Ser Ile Thr Val Thr Val Ala Ser Ala Gly Asn Ile
            35                  40                  45
Gly Glu Asp Gly Ile Leu Ser Cys Thr Phe Glu Pro Asp Ile Lys Leu
        50                  55                  60
Ser Asp Ile Val Ile Gln Trp Leu Lys Glu Gly Val Ile Gly Leu Val
65                  70                  75                  80
His Glu Phe Lys Glu Gly Lys Asp Glu Leu Ser Glu Gln Asp Glu Met
```

```
                    85                  90                  95
Phe Arg Gly Arg Thr Ala Val Phe Ala Asp Gln Val Ile Val Gly Asn
                100                 105                 110

Ala Ser Leu Arg Leu Lys Asn Val Gln Leu Thr Asp Ala Gly Thr Tyr
                115                 120                 125

Lys Cys Tyr Ile Ile Thr Ser Lys Gly Lys Gly Asn Ala Asn Leu Glu
            130                 135                 140

Tyr Lys Thr Gly Ala Phe Ser Met Pro Glu Val Asn Val Asp Tyr Asn
145                 150                 155                 160

Ala Ser Ser Glu Thr Leu Arg Cys Glu Ala Pro Arg Trp Phe Pro Gln
                165                 170                 175

Pro Thr Val Val Trp Ala Ser Gln Val Asp Gln Gly Ala Asn Phe Ser
                180                 185                 190

Glu Val Ser Asn Thr Ser Phe Glu Leu Asn Ser Glu Asn Val Thr Met
                195                 200                 205

Lys Val Val Ser Val Leu Tyr Asn Val Thr Ile Asn Asn Thr Tyr Ser
            210                 215                 220

Cys Met Ile Glu Asn Asp Ile Ala Lys Ala Thr Gly Asp Ile Lys Val
225                 230                 235                 240

Thr Glu Ser Glu Ile Lys Arg Arg Ser His Leu Gln Leu Leu Asn Ser
                245                 250                 255

Lys Ala Ser Leu Cys Val Ser Ser Phe Leu Ala Ile Ser Trp Ala Leu
                260                 265                 270

Leu Pro Leu Ala Pro Tyr Leu Met Leu Lys
            275                 280

<210> SEQ ID NO 3
<211> LENGTH: 283
<212> TYPE: PRT
<213> ORGANISM: Artificial Sequence
<220> FEATURE:
<223> OTHER INFORMATION: Murine B7-H4

<400> SEQUENCE: 3

Met Ala Ser Leu Gly Gln Ile Ile Phe Trp Ser Ile Ile Asn Ile Ile
1               5                   10                  15

Ile Ile Leu Ala Gly Ala Ile Ala Leu Ile Ile Gly Phe Gly Ile Ser
                20                  25                  30

Gly Lys His Phe Ile Thr Val Thr Thr Phe Thr Ser Ala Gly Asn Ile
            35                  40                  45

Gly Glu Asp Gly Thr Leu Ser Cys Thr Phe Glu Pro Asp Ile Lys Leu
50                  55                  60

Asn Gly Ile Val Ile Gln Trp Leu Lys Glu Gly Ile Lys Gly Leu Val
65                  70                  75                  80

His Glu Phe Lys Glu Gly Lys Asp Asp Leu Ser Gln Gln His Glu Met
                85                  90                  95

Phe Arg Gly Arg Thr Ala Val Phe Ala Asp Gln Val Val Val Gly Asn
                100                 105                 110

Ala Ser Leu Arg Leu Lys Asn Val Gln Leu Thr Asp Ala Gly Thr Tyr
                115                 120                 125

Thr Cys Tyr Ile Arg Thr Ser Lys Gly Lys Gly Asn Ala Asn Leu Glu
            130                 135                 140

Tyr Lys Thr Gly Ala Phe Ser Met Pro Glu Ile Asn Val Asp Tyr Asn
145                 150                 155                 160

Ala Ser Ser Glu Ser Leu Arg Cys Glu Ala Pro Arg Trp Phe Pro Gln
```

```
                    165                 170                 175
Pro Thr Val Ala Trp Ala Ser Gln Val Asp Gln Gly Ala Asn Phe Ser
                180                 185                 190

Glu Val Ser Asn Thr Ser Phe Glu Leu Asn Ser Glu Asn Val Thr Met
            195                 200                 205

Lys Val Val Ser Val Leu Tyr Asn Val Thr Ile Asn Asn Thr Tyr Ser
        210                 215                 220

Cys Met Ile Glu Asn Asp Ile Ala Lys Ala Thr Gly Asp Ile Lys Val
225                 230                 235                 240

Thr Asp Ser Glu Val Lys Arg Arg Ser Gln Leu Gln Leu Leu Asn Ser
                245                 250                 255

Gly Pro Ser Pro Cys Val Phe Ser Ser Ala Phe Val Ala Gly Trp Ala
            260                 265                 270

Leu Leu Ser Leu Ser Cys Cys Leu Met Leu Arg
        275                 280

<210> SEQ ID NO 4
<211> LENGTH: 282
<212> TYPE: PRT
<213> ORGANISM: Artificial Sequence
<220> FEATURE:
<223> OTHER INFORMATION: Rat B7-H4

<400> SEQUENCE: 4

Met Ala Ser Leu Gly Gln Ile Ile Phe Trp Ser Ile Ile Asn Val Ile
1               5                   10                  15

Ile Ile Leu Ala Gly Ala Ile Val Leu Ile Gly Phe Gly Ile Ser
            20                  25                  30

Gly Lys His Phe Ile Thr Val Thr Thr Phe Thr Ser Ala Gly Asn Ile
        35                  40                  45

Gly Glu Asp Gly Thr Leu Ser Cys Thr Phe Glu Pro Asp Ile Lys Leu
    50                  55                  60

Asn Gly Ile Val Ile Gln Trp Leu Lys Glu Gly Ile Lys Gly Leu Val
65                  70                  75                  80

His Glu Phe Lys Glu Gly Lys Asp Asp Leu Ser Gln Gln His Glu Met
                85                  90                  95

Phe Arg Gly Arg Thr Ala Val Phe Ala Asp Gln Val Val Val Gly Asn
            100                 105                 110

Ala Ser Leu Arg Leu Lys Asn Val Gln Leu Thr Asp Ala Gly Thr Tyr
        115                 120                 125

Thr Cys Tyr Ile His Thr Ser Lys Gly Lys Gly Asn Ala Asn Leu Glu
    130                 135                 140

Tyr Lys Thr Gly Ala Phe Ser Met Pro Glu Ile Asn Val Asp Tyr Asn
145                 150                 155                 160

Ala Ser Ser Glu Ser Leu Arg Cys Glu Ala Pro Arg Trp Phe Pro Gln
                165                 170                 175

Pro Thr Val Ala Trp Ala Ser Gln Val Asp Gln Gly Ala Asn Phe Ser
            180                 185                 190

Glu Val Ser Asn Thr Ser Phe Glu Leu Asn Ser Glu Asn Val Thr Met
        195                 200                 205

Lys Val Val Ser Val Leu Tyr Asn Val Thr Ile Asn Asn Thr Tyr Ser
    210                 215                 220

Cys Met Ile Glu Asn Asp Ile Ala Lys Ala Thr Gly Asp Ile Lys Val
225                 230                 235                 240

Thr Asp Ser Glu Val Lys Arg Arg Ser Gln Leu Glu Leu Leu Asn Ser
```

```
                    245                 250                 255
Gly Pro Ser Pro Cys Val Ser Ser Val Ser Ala Ala Gly Trp Ala Leu
            260                 265                 270
Leu Ser Leu Ser Cys Cys Leu Met Leu Arg
        275                 280
```

<210> SEQ ID NO 5
<211> LENGTH: 11
<212> TYPE: PRT
<213> ORGANISM: Artificial Sequence
<220> FEATURE:
<223> OTHER INFORMATION: Antibody 15461 VH CDR1

<400> SEQUENCE: 5

```
Gly Ser Ile Ser Ser Ser Ser Tyr Tyr Trp Gly
1               5                   10
```

<210> SEQ ID NO 6
<211> LENGTH: 16
<212> TYPE: PRT
<213> ORGANISM: Artificial Sequence
<220> FEATURE:
<223> OTHER INFORMATION: Antibody 15461 VH CDR2

<400> SEQUENCE: 6

```
Asn Ile Tyr Tyr Ser Gly Ser Thr Tyr Tyr Asn Pro Ser Leu Lys Ser
1               5                   10                  15
```

<210> SEQ ID NO 7
<211> LENGTH: 12
<212> TYPE: PRT
<213> ORGANISM: Artificial Sequence
<220> FEATURE:
<223> OTHER INFORMATION: Antibody 15461 VH CDR3

<400> SEQUENCE: 7

```
Ala Arg Glu Gly Ser Tyr Pro Asn Trp Phe Asp Pro
1               5                   10
```

<210> SEQ ID NO 8
<211> LENGTH: 11
<212> TYPE: PRT
<213> ORGANISM: Artificial Sequence
<220> FEATURE:
<223> OTHER INFORMATION: Antibody 15461 VL CDR1

<400> SEQUENCE: 8

```
Arg Ala Ser Gln Ser Val Ser Ser Asn Leu Ala
1               5                   10
```

<210> SEQ ID NO 9
<211> LENGTH: 7
<212> TYPE: PRT
<213> ORGANISM: Artificial Sequence
<220> FEATURE:
<223> OTHER INFORMATION: Antibody 15461 VL CDR2

<400> SEQUENCE: 9

```
Gly Ala Ser Thr Arg Ala Thr
1               5
```

<210> SEQ ID NO 10
<211> LENGTH: 9
<212> TYPE: PRT
<213> ORGANISM: Artificial Sequence
<220> FEATURE:

<223> OTHER INFORMATION: Antibody 15461 VL CDR3

<400> SEQUENCE: 10

Gln Gln Tyr His Ser Phe Pro Phe Thr
1               5

<210> SEQ ID NO 11
<211> LENGTH: 120
<212> TYPE: PRT
<213> ORGANISM: Artificial Sequence
<220> FEATURE:
<223> OTHER INFORMATION: Antibody 15461 Variable Heavy Chain

<400> SEQUENCE: 11

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Ser
            20                  25                  30

Ser Tyr Tyr Trp Gly Trp Ile Arg Gln Pro Pro Gly Lys Gly Leu Glu
        35                  40                  45

Trp Ile Gly Asn Ile Tyr Tyr Ser Gly Ser Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Glu Gly Ser Tyr Pro Asn Trp Phe Asp Pro Trp Gly Gln
            100                 105                 110

Gly Thr Leu Val Thr Val Ser Ser
        115                 120

<210> SEQ ID NO 12
<211> LENGTH: 107
<212> TYPE: PRT
<213> ORGANISM: Artificial Sequence
<220> FEATURE:
<223> OTHER INFORMATION: Antibody 15461 Variable Light Chain

<400> SEQUENCE: 12

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Ser Ser Asn
            20                  25                  30

Leu Ala Trp Tyr Gln Gln Lys Pro Gly Gln Ala Pro Arg Leu Leu Ile
        35                  40                  45

Tyr Gly Ala Ser Thr Arg Ala Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr His Ser Phe Pro Phe
                85                  90                  95

Thr Phe Gly Gly Gly Thr Lys Val Glu Ile Lys
            100                 105

<210> SEQ ID NO 13
<211> LENGTH: 450
<212> TYPE: PRT
<213> ORGANISM: Artificial Sequence
<220> FEATURE:
<223> OTHER INFORMATION: Antibody 15461 Full-Length Heavy Chain

<400> SEQUENCE: 13

```
Gln Leu Gln Leu Gln Glu Ser Gly Pro Gly Leu Val Lys Pro Ser Glu
1               5                   10                  15

Thr Leu Ser Leu Thr Cys Thr Val Ser Gly Ser Ile Ser Ser Ser
            20                  25                  30

Ser Tyr Tyr Trp Gly Trp Ile Arg Gln Pro Pro Gly Lys Gly Leu Glu
        35                  40                  45

Trp Ile Gly Asn Ile Tyr Tyr Ser Gly Ser Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Glu Gly Ser Tyr Pro Asn Trp Phe Asp Pro Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
```

<210> SEQ ID NO 14
<211> LENGTH: 214
<212> TYPE: PRT
<213> ORGANISM: Artificial Sequence
<220> FEATURE:
<223> OTHER INFORMATION: Antibody 15461 Full-Length Light Chain

<400> SEQUENCE: 14

```
Glu Ile Val Met Thr Gln Ser Pro Ala Thr Leu Ser Val Ser Pro Gly
1               5                  10                  15
Glu Arg Ala Thr Leu Ser Cys Arg Ala Ser Gln Ser Val Ser Ser Asn
            20                  25                  30
Leu Ala Trp Tyr Gln Gln Lys Pro Gly Gln Ala Pro Arg Leu Leu Ile
        35                  40                  45
Tyr Gly Ala Ser Thr Arg Ala Thr Gly Ile Pro Ala Arg Phe Ser Gly
    50                  55                  60
Ser Gly Ser Gly Thr Glu Phe Thr Leu Thr Ile Ser Ser Leu Gln Ser
65                  70                  75                  80
Glu Asp Phe Ala Val Tyr Tyr Cys Gln Gln Tyr His Ser Phe Pro Phe
                85                  90                  95
Thr Phe Gly Gly Gly Thr Lys Val Glu Ile Lys Arg Thr Val Ala Ala
            100                 105                 110
Pro Ser Val Phe Ile Phe Pro Pro Ser Asp Glu Gln Leu Lys Ser Gly
        115                 120                 125
Thr Ala Ser Val Val Cys Leu Leu Asn Asn Phe Tyr Pro Arg Glu Ala
    130                 135                 140
Lys Val Gln Trp Lys Val Asp Asn Ala Leu Gln Ser Gly Asn Ser Gln
145                 150                 155                 160
Glu Ser Val Thr Glu Gln Asp Ser Lys Asp Ser Thr Tyr Ser Leu Ser
                165                 170                 175
Ser Thr Leu Thr Leu Ser Lys Ala Asp Tyr Glu Lys His Lys Val Tyr
            180                 185                 190
Ala Cys Glu Val Thr His Gln Gly Leu Ser Ser Pro Val Thr Lys Ser
        195                 200                 205
Phe Asn Arg Gly Glu Cys
    210
```

Preceding continuation (SEQ ID NO 13):
```
Lys Ser Arg Trp Gln Gln Gly Asn Val Phe Ser Cys Ser Val Met His
            420                 425                 430
Glu Ala Leu His Asn His Tyr Thr Gln Lys Ser Leu Ser Leu Ser Pro
        435                 440                 445
Gly Lys
    450
```

<210> SEQ ID NO 15
<211> LENGTH: 11
<212> TYPE: PRT
<213> ORGANISM: Artificial Sequence
<220> FEATURE:
<223> OTHER INFORMATION: Antibody 20500 VH CDR1

<400> SEQUENCE: 15

```
Gly Ser Ile Lys Ser Gly Ser His Tyr Trp Gly
1               5                   10
```

<210> SEQ ID NO 16
<211> LENGTH: 16

```
<212> TYPE: PRT
<213> ORGANISM: Artificial Sequence
<220> FEATURE:
<223> OTHER INFORMATION: Antibody 20500 VH CDR2

<400> SEQUENCE: 16

Asn Ile Tyr Tyr Ser Gly Ser Thr Tyr Tyr Asn Pro Ser Leu Arg Ser
1               5                   10                  15

<210> SEQ ID NO 17
<211> LENGTH: 12
<212> TYPE: PRT
<213> ORGANISM: Artificial Sequence
<220> FEATURE:
<223> OTHER INFORMATION: Antibody 20500 VH CDR3

<400> SEQUENCE: 17

Ala Arg Glu Gly Ser Tyr Pro Asn Trp Phe Asp Pro
1               5                   10

<210> SEQ ID NO 18
<211> LENGTH: 11
<212> TYPE: PRT
<213> ORGANISM: Artificial Sequence
<220> FEATURE:
<223> OTHER INFORMATION: Antibody 20500 VL CDR1

<400> SEQUENCE: 18

Arg Ala Ser Gln Ser Val Ser Ser Asn Leu Ala
1               5                   10

<210> SEQ ID NO 19
<211> LENGTH: 7
<212> TYPE: PRT
<213> ORGANISM: Artificial Sequence
<220> FEATURE:
<223> OTHER INFORMATION: Antibody 20500 VL CDR2

<400> SEQUENCE: 19

Gly Ala Ser Thr Arg Ala Thr
1               5

<210> SEQ ID NO 20
<211> LENGTH: 9
<212> TYPE: PRT
<213> ORGANISM: Artificial Sequence
<220> FEATURE:
<223> OTHER INFORMATION: Antibody 20500 VL CDR3

<400> SEQUENCE: 20

Gln Gln Tyr His Ser Phe Pro Phe Thr
1               5

<210> SEQ ID NO 21
<211> LENGTH: 120
<212> TYPE: PRT
<213> ORGANISM: Artificial Sequence
<220> FEATURE:
<223> OTHER INFORMATION: Antibody 20500 Variable Heavy Chain

<400> SEQUENCE: 21

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Lys Ser Gly
                20                  25                  30

Ser His Tyr Trp Gly Trp Ile Arg Gln Pro Pro Gly Lys Gly Leu Glu
```

```
                35                  40                  45
Trp Ile Gly Asn Ile Tyr Tyr Ser Gly Ser Thr Tyr Tyr Asn Pro Ser
         50                  55                  60

Leu Arg Ser Arg Val Thr Ile Ser Val Asp Thr Ser Lys Asn Gln Phe
 65                  70                  75                  80

Ser Leu Lys Leu Ser Ser Val Thr Ala Ala Asp Thr Ala Val Tyr Tyr
                 85                  90                  95

Cys Ala Arg Glu Gly Ser Tyr Pro Asn Trp Phe Asp Pro Trp Gly Gln
            100                 105                 110

Gly Thr Leu Val Thr Val Ser Ser
            115                 120

<210> SEQ ID NO 22
<211> LENGTH: 107
<212> TYPE: PRT
<213> ORGANISM: Artificial Sequence
<220> FEATURE:
<223> OTHER INFORMATION: Antibody 20500 Variable Light Chain

<400> SEQUENCE: 22

Glu Ile Val Met Thr Gln Ser Pro Ala Thr Leu Ser Val Ser Pro Gly
 1               5                  10                  15

Glu Arg Ala Thr Leu Ser Cys Arg Ala Ser Gln Ser Val Ser Ser Asn
             20                  25                  30

Leu Ala Trp Tyr Gln Gln Lys Pro Gly Gln Ala Pro Arg Leu Leu Ile
         35                  40                  45

Tyr Gly Ala Ser Thr Arg Ala Thr Gly Ile Pro Ala Arg Phe Ser Gly
 50                  55                  60

Ser Gly Ser Gly Thr Glu Phe Thr Leu Thr Ile Ser Ser Leu Gln Ser
 65                  70                  75                  80

Glu Asp Phe Ala Val Tyr Tyr Cys Gln Gln Tyr His Ser Phe Pro Phe
                 85                  90                  95

Thr Phe Gly Gly Gly Thr Lys Val Glu Ile Lys
            100                 105

<210> SEQ ID NO 23
<211> LENGTH: 450
<212> TYPE: PRT
<213> ORGANISM: Artificial Sequence
<220> FEATURE:
<223> OTHER INFORMATION: Antibody 20500 Full-Length Heavy Chain

<400> SEQUENCE: 23

Gln Leu Gln Leu Gln Glu Ser Gly Pro Gly Leu Val Lys Pro Ser Glu
 1               5                  10                  15

Thr Leu Ser Leu Thr Cys Thr Val Ser Gly Gly Ser Ile Lys Ser Gly
             20                  25                  30

Ser His Tyr Trp Gly Trp Ile Arg Gln Pro Pro Gly Lys Gly Leu Glu
         35                  40                  45

Trp Ile Gly Asn Ile Tyr Tyr Ser Gly Ser Thr Tyr Tyr Asn Pro Ser
         50                  55                  60

Leu Arg Ser Arg Val Thr Ile Ser Val Asp Thr Ser Lys Asn Gln Phe
 65                  70                  75                  80

Ser Leu Lys Leu Ser Ser Val Thr Ala Ala Asp Thr Ala Val Tyr Tyr
                 85                  90                  95

Cys Ala Arg Glu Gly Ser Tyr Pro Asn Trp Phe Asp Pro Trp Gly Gln
            100                 105                 110
```

Gly Thr Leu Val Thr Val Ser Ser Ala Ser Thr Lys Gly Pro Ser Val
            115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450

<210> SEQ ID NO 24
<211> LENGTH: 214
<212> TYPE: PRT
<213> ORGANISM: Artificial Sequence
<220> FEATURE:
<223> OTHER INFORMATION: Antibody 20500 Full-Length Light Chain

<400> SEQUENCE: 24

Glu Ile Val Met Thr Gln Ser Pro Ala Thr Leu Ser Val Ser Pro Gly
1               5                   10                  15

```
Glu Arg Ala Thr Leu Ser Cys Arg Ala Ser Gln Ser Val Ser Ser Asn
            20                  25                  30

Leu Ala Trp Tyr Gln Gln Lys Pro Gly Gln Ala Pro Arg Leu Leu Ile
        35                  40                  45

Tyr Gly Ala Ser Thr Arg Ala Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr His Ser Phe Pro Phe
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 25
<211> LENGTH: 11
<212> TYPE: PRT
<213> ORGANISM: Artificial Sequence
<220> FEATURE:
<223> OTHER INFORMATION: Antibody 20501 VH CDR1

<400> SEQUENCE: 25

Gly Ser Ile Lys Ser Gly Ser His Tyr Trp Gly
1               5                   10

<210> SEQ ID NO 26
<211> LENGTH: 16
<212> TYPE: PRT
<213> ORGANISM: Artificial Sequence
<220> FEATURE:
<223> OTHER INFORMATION: Antibody 20501 VH CDR2

<400> SEQUENCE: 26

Asn Ile Tyr Tyr Ser Gly Ser Thr Tyr Tyr Asn Pro Ser Leu Lys Ser
1               5                   10                  15

<210> SEQ ID NO 27
<211> LENGTH: 12
<212> TYPE: PRT
<213> ORGANISM: Artificial Sequence
<220> FEATURE:
<223> OTHER INFORMATION: Antibody 20501 VH CDR3

<400> SEQUENCE: 27

Ala Arg Glu Gly Ser Tyr Pro Asn Trp Leu Asp Pro
1               5                   10
```

```
<210> SEQ ID NO 28
<211> LENGTH: 11
<212> TYPE: PRT
<213> ORGANISM: Artificial Sequence
<220> FEATURE:
<223> OTHER INFORMATION: Antibody 20501 VL CDR1

<400> SEQUENCE: 28

Arg Ala Ser Gln Ser Val Ser Ser Asn Leu Ala
1               5                   10

<210> SEQ ID NO 29
<211> LENGTH: 7
<212> TYPE: PRT
<213> ORGANISM: Artificial Sequence
<220> FEATURE:
<223> OTHER INFORMATION: Antibody 20501 VL CDR2

<400> SEQUENCE: 29

Gly Ala Ser Thr Arg Ala Thr
1               5

<210> SEQ ID NO 30
<211> LENGTH: 9
<212> TYPE: PRT
<213> ORGANISM: Artificial Sequence
<220> FEATURE:
<223> OTHER INFORMATION: Antibody 20501 VL CDR3

<400> SEQUENCE: 30

Gln Gln Tyr His Ser Phe Pro Phe Thr
1               5

<210> SEQ ID NO 31
<211> LENGTH: 120
<212> TYPE: PRT
<213> ORGANISM: Artificial Sequence
<220> FEATURE:
<223> OTHER INFORMATION: Antibody 20501 Variable Heavy Chain

<400> SEQUENCE: 31

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Lys Ser Gly
                20                  25                  30

Ser His Tyr Trp Gly Trp Ile Arg Gln Pro Pro Gly Lys Gly Leu Glu
            35                  40                  45

Trp Ile Gly Asn Ile Tyr Tyr Ser Gly Ser Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Glu Gly Ser Tyr Pro Asn Trp Leu Asp Pro Trp Gly Gln
            100                 105                 110

Gly Thr Leu Val Thr Val Ser Ser
        115                 120

<210> SEQ ID NO 32
<211> LENGTH: 107
<212> TYPE: PRT
<213> ORGANISM: Artificial Sequence
<220> FEATURE:
<223> OTHER INFORMATION: Antibody 20501 Variable Light Chain
```

<400> SEQUENCE: 32

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Ser Ser Asn
            20                  25                  30

Leu Ala Trp Tyr Gln Gln Lys Pro Gly Gln Ala Pro Arg Leu Leu Ile
        35                  40                  45

Tyr Gly Ala Ser Thr Arg Ala Thr Gly Ile Pro Ala Arg Phe Ser Gly
50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr His Ser Phe Pro Phe
                85                  90                  95

Thr Phe Gly Gly Gly Thr Lys Val Glu Ile Lys
            100                 105

<210> SEQ ID NO 33
<211> LENGTH: 450
<212> TYPE: PRT
<213> ORGANISM: Artificial Sequence
<220> FEATURE:
<223> OTHER INFORMATION: Antibody 20501 Full-Length Heavy Chain

<400> SEQUENCE: 33

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Lys Ser Gly
            20                  25                  30

Ser His Tyr Trp Gly Trp Ile Arg Gln Pro Pro Gly Lys Gly Leu Glu
        35                  40                  45

Trp Ile Gly Asn Ile Tyr Tyr Ser Gly Ser Thr Tyr Tyr Asn Pro Ser
50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Glu Gly Ser Tyr Pro Asn Trp Leu Asp Pro Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
            245                 250                 255

Ser Arg Thr Pro Glu Val Thr Cys Val Val Val Asp Val Ser His Glu
        260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450

<210> SEQ ID NO 34
<211> LENGTH: 214
<212> TYPE: PRT
<213> ORGANISM: Artificial Sequence
<220> FEATURE:
<223> OTHER INFORMATION: Antibody 20501 Full-Length Light Chain

<400> SEQUENCE: 34

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Ser Ser Asn
            20                  25                  30

Leu Ala Trp Tyr Gln Gln Lys Pro Gly Gln Ala Pro Arg Leu Leu Ile
        35                  40                  45

Tyr Gly Ala Ser Thr Arg Ala Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr His Ser Phe Pro Phe
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

-continued

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
            165                 170                 175

Ser Thr Leu Thr Leu Ser Lys Ala Asp Tyr Glu Lys His Lys Val Tyr
        180                 185                 190

Ala Cys Glu Val Thr His Gln Gly Leu Ser Ser Pro Val Thr Lys Ser
    195                 200                 205

Phe Asn Arg Gly Glu Cys
    210

<210> SEQ ID NO 35
<211> LENGTH: 11
<212> TYPE: PRT
<213> ORGANISM: Artificial Sequence
<220> FEATURE:
<223> OTHER INFORMATION: Antibody 20502.1 VH CDR1

<400> SEQUENCE: 35

Gly Ser Ile Lys Ser Gly Ser Tyr Tyr Trp Gly
1               5                   10

<210> SEQ ID NO 36
<211> LENGTH: 16
<212> TYPE: PRT
<213> ORGANISM: Artificial Sequence
<220> FEATURE:
<223> OTHER INFORMATION: Antibody 20502.1 VH CDR2

<400> SEQUENCE: 36

Asn Ile Tyr Tyr Ser Gly Ser Thr Tyr Tyr Asn Pro Ser Leu Lys Ser
1               5                   10                  15

<210> SEQ ID NO 37
<211> LENGTH: 12
<212> TYPE: PRT
<213> ORGANISM: Artificial Sequence
<220> FEATURE:
<223> OTHER INFORMATION: Antibody 20502.1 VH CDR3

<400> SEQUENCE: 37

Ala Arg Glu Gly Ser Tyr Pro Asn Gln Phe Asp Pro
1               5                   10

<210> SEQ ID NO 38
<211> LENGTH: 11
<212> TYPE: PRT
<213> ORGANISM: Artificial Sequence
<220> FEATURE:
<223> OTHER INFORMATION: Antibody 20502.1 VL CDR1

<400> SEQUENCE: 38

Arg Ala Ser Gln Ser Val Ser Ser Asn Leu Ala
1               5                   10

<210> SEQ ID NO 39
<211> LENGTH: 7
<212> TYPE: PRT
<213> ORGANISM: Artificial Sequence
<220> FEATURE:
<223> OTHER INFORMATION: Antibody 20502.1 VL CDR2

<400> SEQUENCE: 39

Gly Ala Ser Thr Arg Ala Thr
1               5

<210> SEQ ID NO 40
<211> LENGTH: 9
<212> TYPE: PRT
<213> ORGANISM: Artificial Sequence
<220> FEATURE:
<223> OTHER INFORMATION: Antibody 20502.1 VL CDR3

<400> SEQUENCE: 40

Gln Gln Tyr His Ser Phe Pro Phe Thr
1               5

<210> SEQ ID NO 41
<211> LENGTH: 120
<212> TYPE: PRT
<213> ORGANISM: Artificial Sequence
<220> FEATURE:
<223> OTHER INFORMATION: Antibody 20502.1 Variable Heavy Chain

<400> SEQUENCE: 41

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Lys Ser Gly
            20                  25                  30

Ser Tyr Tyr Trp Gly Trp Ile Arg Gln Pro Pro Gly Lys Gly Leu Glu
        35                  40                  45

Trp Ile Gly Asn Ile Tyr Tyr Ser Gly Ser Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Glu Gly Ser Tyr Pro Asn Gln Phe Asp Pro Trp Gly Gln
            100                 105                 110

Gly Ile Leu Val Thr Val Ser Ser
        115                 120

<210> SEQ ID NO 42
<211> LENGTH: 107
<212> TYPE: PRT
<213> ORGANISM: Artificial Sequence
<220> FEATURE:
<223> OTHER INFORMATION: Antibody 20502 and 20502.1 Variable light chain

<400> SEQUENCE: 42

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Ser Ser Asn
            20                  25                  30

Leu Ala Trp Tyr Gln Gln Lys Pro Gly Gln Ala Pro Arg Leu Leu Ile
        35                  40                  45

Tyr Gly Ala Ser Thr Arg Ala Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr His Ser Phe Pro Phe
                85                  90                  95

Thr Phe Gly Gly Gly Thr Lys Val Glu Ile Lys
            100                 105

```
<210> SEQ ID NO 43
<211> LENGTH: 450
<212> TYPE: PRT
<213> ORGANISM: Artificial Sequence
<220> FEATURE:
<223> OTHER INFORMATION: Antibody 20502.1 Full-Length Heavy Chain

<400> SEQUENCE: 43

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Lys Ser Gly
            20                  25                  30

Ser Tyr Tyr Trp Gly Trp Ile Arg Gln Pro Pro Gly Lys Gly Leu Glu
        35                  40                  45

Trp Ile Gly Asn Ile Tyr Tyr Ser Gly Ser Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Glu Gly Ser Tyr Pro Asn Gln Phe Asp Pro Trp Gly Gln
            100                 105                 110

Gly Ile Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365
```

```
Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
                420                 425                 430

Glu Ala Leu His Asn His Tyr Thr Gln Lys Ser Leu Ser Leu Ser Pro
                435                 440                 445

Gly Lys
    450

<210> SEQ ID NO 44
<211> LENGTH: 214
<212> TYPE: PRT
<213> ORGANISM: Artificial Sequence
<220> FEATURE:
<223> OTHER INFORMATION: Antibody 20502 and 20502.1 Full-Length Light
      Chain

<400> SEQUENCE: 44

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Ser Ser Asn
                20                  25                  30

Leu Ala Trp Tyr Gln Gln Lys Pro Gly Gln Ala Pro Arg Leu Leu Ile
            35                  40                  45

Tyr Gly Ala Ser Thr Arg Ala Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr His Ser Phe Pro Phe
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 45
<211> LENGTH: 11
<212> TYPE: PRT
<213> ORGANISM: Artificial Sequence
<220> FEATURE:
<223> OTHER INFORMATION: Antibody 22208 VH CDR1
```

```
<400> SEQUENCE: 45

Gly Ser Ile Lys Ser Gly Ser His Tyr Trp Gly
1               5                   10

<210> SEQ ID NO 46
<211> LENGTH: 16
<212> TYPE: PRT
<213> ORGANISM: Artificial Sequence
<220> FEATURE:
<223> OTHER INFORMATION: Antibody 22208 VH CDR2

<400> SEQUENCE: 46

Asn Ile Tyr Tyr Ser Gly Ser Thr Tyr Tyr Asn Pro Ser Leu Lys Ser
1               5                   10                  15

<210> SEQ ID NO 47
<211> LENGTH: 12
<212> TYPE: PRT
<213> ORGANISM: Artificial Sequence
<220> FEATURE:
<223> OTHER INFORMATION: Antibody 22208 VH CDR3

<400> SEQUENCE: 47

Ala Arg Glu Gly Ser Tyr Pro Asn Trp Phe Asp Pro
1               5                   10

<210> SEQ ID NO 48
<211> LENGTH: 11
<212> TYPE: PRT
<213> ORGANISM: Artificial Sequence
<220> FEATURE:
<223> OTHER INFORMATION: Antibody 22208 VL CDR1

<400> SEQUENCE: 48

Arg Ala Ser Gln Ser Val Ser Thr Asn Leu Ala
1               5                   10

<210> SEQ ID NO 49
<211> LENGTH: 7
<212> TYPE: PRT
<213> ORGANISM: Artificial Sequence
<220> FEATURE:
<223> OTHER INFORMATION: Antibody 22208 VL CDR2

<400> SEQUENCE: 49

Asp Ala Ser Ala Arg Val Thr
1               5

<210> SEQ ID NO 50
<211> LENGTH: 9
<212> TYPE: PRT
<213> ORGANISM: Artificial Sequence
<220> FEATURE:
<223> OTHER INFORMATION: Antibody 22208 VL CDR3

<400> SEQUENCE: 50

Gln Gln Tyr His Ser Phe Pro Phe Thr
1               5

<210> SEQ ID NO 51
<211> LENGTH: 120
<212> TYPE: PRT
<213> ORGANISM: Artificial Sequence
<220> FEATURE:
<223> OTHER INFORMATION: Antibody 22208 Variable Heavy Chain

<400> SEQUENCE: 51
```

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Lys Ser Gly
            20                  25                  30

Ser His Tyr Trp Gly Trp Ile Arg Gln Pro Pro Gly Lys Gly Leu Glu
            35                  40                  45

Trp Ile Gly Asn Ile Tyr Tyr Ser Gly Ser Thr Tyr Tyr Asn Pro Ser
        50                  55                  60

Leu Lys Ser Arg Val Thr Met Ser Val Asp Thr Ser Lys Asn Gln Phe
65              70                  75                  80

Ser Leu Lys Leu Ser Ser Val Thr Ala Ala Asp Thr Ala Val Tyr Tyr
            85                  90                  95

Cys Ala Arg Glu Gly Ser Tyr Pro Asn Trp Phe Asp Pro Trp Gly Gln
            100                 105                 110

Gly Thr Leu Val Thr Val Ser Ser
            115                 120

<210> SEQ ID NO 52
<211> LENGTH: 107
<212> TYPE: PRT
<213> ORGANISM: Artificial Sequence
<220> FEATURE:
<223> OTHER INFORMATION: Antibody 22208 Variable Light Chain

<400> SEQUENCE: 52

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Ser Thr Asn
            20                  25                  30

Leu Ala Trp Tyr Gln Gln Lys Pro Gly Gln Ala Pro Arg Leu Leu Ile
            35                  40                  45

Tyr Asp Ala Ser Ala Arg Val Thr Gly Ile Pro Ala Arg Phe Ser Gly
        50                  55                  60

Ser Gly Ser Gly Thr Glu Phe Thr Leu Thr Ile Ser Ser Leu Gln Ser
65              70                  75                  80

Glu Asp Phe Ala Val Tyr Tyr Cys Gln Gln Tyr His Ser Phe Pro Phe
            85                  90                  95

Thr Phe Gly Gly Gly Thr Lys Val Glu Ile Lys
            100                 105

<210> SEQ ID NO 53
<211> LENGTH: 450
<212> TYPE: PRT
<213> ORGANISM: Artificial Sequence
<220> FEATURE:
<223> OTHER INFORMATION: Antibody 22208 Full-Length Heavy Chain

<400> SEQUENCE: 53

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Lys Ser Gly
            20                  25                  30

Ser His Tyr Trp Gly Trp Ile Arg Gln Pro Pro Gly Lys Gly Leu Glu
            35                  40                  45

Trp Ile Gly Asn Ile Tyr Tyr Ser Gly Ser Thr Tyr Tyr Asn Pro Ser
        50                  55                  60

Leu Lys Ser Arg Val Thr Met Ser Val Asp Thr Ser Lys Asn Gln Phe

```
                65                  70                  75                  80
        Ser Leu Lys Leu Ser Ser Val Thr Ala Ala Asp Thr Ala Val Tyr Tyr
                        85                  90                  95

Cys Ala Arg Glu Gly Ser Tyr Pro Asn Trp Phe Asp Pro Trp Gly Gln
                    100                 105                 110

Gly Thr Leu Val Thr Val Ser Ala Ser Thr Lys Gly Pro Ser Val
                115                 120                 125

Phe Pro Leu Ala Pro Ser Ser Lys Ser Thr Ser Gly Gly Thr Ala Ala
        130                 135                 140

Leu Gly Cys Leu Val Lys Asp Tyr Phe Pro Glu Pro Val Thr Val Ser
        145                 150                 155                 160

Trp Asn Ser Gly Ala Leu Thr Ser Gly Val His Thr Phe Pro Ala Val
                        165                 170                 175

Leu Gln Ser Ser Gly Leu Tyr Ser Leu Ser Ser Val Val Thr Val Pro
                    180                 185                 190

Ser Ser Ser Leu Gly Thr Gln Thr Tyr Ile Cys Asn Val Asn His Lys
                195                 200                 205

Pro Ser Asn Thr Lys Val Asp Lys Lys Val Glu Pro Lys Ser Cys Asp
        210                 215                 220

Lys Thr His Thr Cys Pro Pro Cys Pro Ala Pro Glu Leu Leu Gly Gly
        225                 230                 235                 240

Pro Ser Val Phe Leu Phe Pro Pro Lys Pro Lys Asp Thr Leu Met Ile
                        245                 250                 255

Ser Arg Thr Pro Glu Val Thr Cys Val Val Val Asp Val Ser His Glu
                    260                 265                 270

Asp Pro Glu Val Lys Phe Asn Trp Tyr Val Asp Gly Val Glu Val His
                275                 280                 285

Asn Ala Lys Thr Lys Pro Arg Glu Glu Gln Tyr Asn Ser Thr Tyr Arg
            290                 295                 300

Val Val Ser Val Leu Thr Val Leu His Gln Asp Trp Leu Asn Gly Lys
        305                 310                 315                 320

Glu Tyr Lys Cys Lys Val Ser Asn Lys Ala Leu Pro Ala Pro Ile Glu
                        325                 330                 335

Lys Thr Ile Ser Lys Ala Lys Gly Gln Pro Arg Glu Pro Gln Val Tyr
                    340                 345                 350

Thr Leu Pro Pro Ser Arg Asp Glu Leu Thr Lys Asn Gln Val Ser Leu
                355                 360                 365

Thr Cys Leu Val Lys Gly Phe Tyr Pro Ser Asp Ile Ala Val Glu Trp
        370                 375                 380

Glu Ser Asn Gly Gln Pro Glu Asn Asn Tyr Lys Thr Thr Pro Pro Val
        385                 390                 395                 400

Leu Asp Ser Asp Gly Ser Phe Phe Leu Tyr Ser Lys Leu Thr Val Asp
                        405                 410                 415

Lys Ser Arg Trp Gln Gln Gly Asn Val Phe Ser Cys Ser Val Met His
                    420                 425                 430

Glu Ala Leu His Asn His Tyr Thr Gln Lys Ser Leu Ser Leu Ser Pro
                435                 440                 445

Gly Lys
            450

<210> SEQ ID NO 54
<211> LENGTH: 214
<212> TYPE: PRT
<213> ORGANISM: Artificial Sequence
```

<220> FEATURE:
<223> OTHER INFORMATION: Antibody 22208 Full-Length Light Chain

<400> SEQUENCE: 54

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Ser Thr Asn
            20                  25                  30

Leu Ala Trp Tyr Gln Gln Lys Pro Gly Gln Ala Pro Arg Leu Leu Ile
        35                  40                  45

Tyr Asp Ala Ser Ala Arg Val Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr His Ser Phe Pro Phe
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 55
<211> LENGTH: 11
<212> TYPE: PRT
<213> ORGANISM: Artificial Sequence
<220> FEATURE:
<223> OTHER INFORMATION: Antibody 15462 VH CDR1

<400> SEQUENCE: 55

Gly Ser Ile Ser Ser Ser Ser Tyr Tyr Trp Gly
1               5                   10

<210> SEQ ID NO 56
<211> LENGTH: 16
<212> TYPE: PRT
<213> ORGANISM: Artificial Sequence
<220> FEATURE:
<223> OTHER INFORMATION: Antibody 15462 VH CDR2

<400> SEQUENCE: 56

Asn Ile Tyr Tyr Ser Gly Ser Thr Tyr Tyr Asn Pro Ser Leu Lys Ser
1               5                   10                  15

<210> SEQ ID NO 57
<211> LENGTH: 12
<212> TYPE: PRT
<213> ORGANISM: Artificial Sequence
<220> FEATURE:

-continued

<223> OTHER INFORMATION: Antibody 15462 VH CDR3

<400> SEQUENCE: 57

Ala Arg Glu Gly Ser Tyr Thr Thr Val Leu Asn Val
1               5                   10

<210> SEQ ID NO 58
<211> LENGTH: 12
<212> TYPE: PRT
<213> ORGANISM: Artificial Sequence
<220> FEATURE:
<223> OTHER INFORMATION: Antibody 15462 VL CDR1

<400> SEQUENCE: 58

Arg Ala Ser Gln Ser Val Ser Ser Ser Tyr Leu Ala
1               5                   10

<210> SEQ ID NO 59
<211> LENGTH: 7
<212> TYPE: PRT
<213> ORGANISM: Artificial Sequence
<220> FEATURE:
<223> OTHER INFORMATION: Antibody 15462 VL CDR2

<400> SEQUENCE: 59

Gly Ala Ser Ser Arg Ala Thr
1               5

<210> SEQ ID NO 60
<211> LENGTH: 9
<212> TYPE: PRT
<213> ORGANISM: Artificial Sequence
<220> FEATURE:
<223> OTHER INFORMATION: Antibody 15462 VL CDR3

<400> SEQUENCE: 60

Gln Gln Ala Ala Ser Tyr Pro Leu Thr
1               5

<210> SEQ ID NO 61
<211> LENGTH: 120
<212> TYPE: PRT
<213> ORGANISM: Artificial Sequence
<220> FEATURE:
<223> OTHER INFORMATION: Antibody 15462 Variable Heavy Chain

<400> SEQUENCE: 61

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Ser
            20                  25                  30

Ser Tyr Tyr Trp Gly Trp Ile Arg Gln Pro Pro Gly Lys Gly Leu Glu
        35                  40                  45

Trp Ile Gly Asn Ile Tyr Tyr Ser Gly Ser Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Glu Gly Ser Tyr Thr Thr Val Leu Asn Val Trp Gly Gln
            100                 105                 110

Gly Thr Met Val Thr Val Ser Ser
        115                 120

<210> SEQ ID NO 62
<211> LENGTH: 108
<212> TYPE: PRT
<213> ORGANISM: Artificial Sequence
<220> FEATURE:
<223> OTHER INFORMATION: Antibody 15462 Variable Light Chain

<400> SEQUENCE: 62

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Ala Ala Ser Tyr Pro
                85                  90                  95

Leu Thr Phe Gly Gly Gly Thr Lys Val Glu Ile Lys
            100                 105

<210> SEQ ID NO 63
<211> LENGTH: 450
<212> TYPE: PRT
<213> ORGANISM: Artificial Sequence
<220> FEATURE:
<223> OTHER INFORMATION: Antibody 15462 Full-length heavy chain

<400> SEQUENCE: 63

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Ser
            20                  25                  30

Ser Tyr Tyr Trp Gly Trp Ile Arg Gln Pro Pro Gly Lys Gly Leu Glu
        35                  40                  45

Trp Ile Gly Asn Ile Tyr Tyr Ser Gly Ser Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Glu Gly Ser Tyr Thr Thr Val Leu Asn Val Trp Gly Gln
            100                 105                 110

Gly Thr Met Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys

```
                195                 200                 205
Pro Ser Asn Thr Lys Val Asp Lys Lys Val Glu Pro Lys Ser Cys Asp
210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
                260                 265                 270

Asp Pro Glu Val Lys Phe Asn Trp Tyr Val Asp Gly Val Glu Val His
                275                 280                 285

Asn Ala Lys Thr Lys Pro Arg Glu Glu Gln Tyr Asn Ser Thr Tyr Arg
290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
                340                 345                 350

Thr Leu Pro Pro Ser Arg Asp Glu Leu Thr Lys Asn Gln Val Ser Leu
                355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
                420                 425                 430

Glu Ala Leu His Asn His Tyr Thr Gln Lys Ser Leu Ser Leu Ser Pro
                435                 440                 445

Gly Lys
    450

<210> SEQ ID NO 64
<211> LENGTH: 215
<212> TYPE: PRT
<213> ORGANISM: Artificial Sequence
<220> FEATURE:
<223> OTHER INFORMATION: Antibody 15462 Full-length light chain

<400> SEQUENCE: 64

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
                20                  25                  30

Tyr Leu Ala Trp Tyr Gln Gln Lys Pro Gly Gln Ala Pro Arg Leu Leu
            35                  40                  45

Ile Tyr Gly Ala Ser Ser Arg Ala Thr Gly Ile Pro Asp Arg Phe Ser
        50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Ala Ala Ser Tyr Pro
                85                  90                  95

Leu Thr Phe Gly Gly Gly Thr Lys Val Glu Ile Lys Arg Thr Val Ala
```

```
                100             105             110
Ala Pro Ser Val Phe Ile Phe Pro Pro Ser Asp Glu Gln Leu Lys Ser
            115                 120             125

Gly Thr Ala Ser Val Val Cys Leu Leu Asn Asn Phe Tyr Pro Arg Glu
        130                 135             140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170             175

Ser Ser Thr Leu Thr Leu Ser Lys Ala Asp Tyr Glu Lys His Lys Val
            180                 185             190

Tyr Ala Cys Glu Val Thr His Gln Gly Leu Ser Ser Pro Val Thr Lys
        195                 200             205

Ser Phe Asn Arg Gly Glu Cys
    210             215

<210> SEQ ID NO 65
<211> LENGTH: 11
<212> TYPE: PRT
<213> ORGANISM: Artificial Sequence
<220> FEATURE:
<223> OTHER INFORMATION: Antibody 22213 VH CDR1

<400> SEQUENCE: 65

Gly Ser Ile Gly Arg Gly Ser Tyr Tyr Trp Gly
1               5                   10

<210> SEQ ID NO 66
<211> LENGTH: 16
<212> TYPE: PRT
<213> ORGANISM: Artificial Sequence
<220> FEATURE:
<223> OTHER INFORMATION: Antibody 22213 VH CDR2

<400> SEQUENCE: 66

Asn Ile Tyr Tyr Ser Gly Ser Thr Tyr Tyr Asn Pro Ser Leu Lys Ser
1               5                   10                  15

<210> SEQ ID NO 67
<211> LENGTH: 12
<212> TYPE: PRT
<213> ORGANISM: Artificial Sequence
<220> FEATURE:
<223> OTHER INFORMATION: Antibody 22213 VH CDR3

<400> SEQUENCE: 67

Ala Arg Glu Gly Ser Tyr Thr Thr Val Leu Asn Val
1               5                   10

<210> SEQ ID NO 68
<211> LENGTH: 12
<212> TYPE: PRT
<213> ORGANISM: Artificial Sequence
<220> FEATURE:
<223> OTHER INFORMATION: Antibody 22213 VL CDR1

<400> SEQUENCE: 68

Arg Ala Ser Gln Ser Val Ala Ser Ser His Leu Ala
1               5                   10

<210> SEQ ID NO 69
<211> LENGTH: 7
<212> TYPE: PRT
```

<213> ORGANISM: Artificial Sequence
<220> FEATURE:
<223> OTHER INFORMATION: Antibody 22213 VL CDR2

<400> SEQUENCE: 69

Asp Ala Val Ser Arg Ala Thr
1               5

<210> SEQ ID NO 70
<211> LENGTH: 9
<212> TYPE: PRT
<213> ORGANISM: Artificial Sequence
<220> FEATURE:
<223> OTHER INFORMATION: Antibody 22213 VL CDR3

<400> SEQUENCE: 70

Gln Gln Ala Ala Ser Tyr Pro Leu Thr
1               5

<210> SEQ ID NO 71
<211> LENGTH: 120
<212> TYPE: PRT
<213> ORGANISM: Artificial Sequence
<220> FEATURE:
<223> OTHER INFORMATION: Antibody 22213 Variable Heavy Chain

<400> SEQUENCE: 71

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Gly Arg Gly
            20                  25                  30

Ser Tyr Tyr Trp Gly Trp Ile Arg Gln Pro Pro Gly Lys Gly Leu Glu
        35                  40                  45

Trp Ile Gly Asn Ile Tyr Tyr Ser Gly Ser Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Glu Gly Ser Tyr Thr Thr Val Leu Asn Val Trp Gly Gln
            100                 105                 110

Gly Thr Met Val Thr Val Ser Ser
        115                 120

<210> SEQ ID NO 72
<211> LENGTH: 108
<212> TYPE: PRT
<213> ORGANISM: Artificial Sequence
<220> FEATURE:
<223> OTHER INFORMATION: Antibody 22213 Variable Light Chain

<400> SEQUENCE: 72

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ala Ser Ser
            20                  25                  30

His Leu Ala Trp Tyr Gln Gln Lys Pro Gly Gln Ala Pro Arg Leu Leu
        35                  40                  45

Ile Tyr Asp Ala Val Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu

```
                65                  70                  75                  80
Pro Glu Asp Phe Ala Val Tyr Tyr Cys Gln Gln Ala Ala Ser Tyr Pro
                    85                  90                  95

Leu Thr Phe Gly Gly Gly Thr Lys Val Glu Ile Lys
                100                 105

<210> SEQ ID NO 73
<211> LENGTH: 450
<212> TYPE: PRT
<213> ORGANISM: Artificial Sequence
<220> FEATURE:
<223> OTHER INFORMATION: Antibody 22213 Full-Length Heavy Chain

<400> SEQUENCE: 73

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Gly Arg Gly
                20                  25                  30

Ser Tyr Tyr Trp Gly Trp Ile Arg Gln Pro Pro Gly Lys Gly Leu Glu
            35                  40                  45

Trp Ile Gly Asn Ile Tyr Tyr Ser Gly Ser Thr Tyr Tyr Asn Pro Ser
        50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Glu Gly Ser Tyr Thr Thr Val Leu Asn Val Trp Gly Gln
            100                 105                 110

Gly Thr Met Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
```

```
                    325                 330                 335
Lys Thr Ile Ser Lys Ala Lys Gly Gln Pro Arg Glu Pro Gln Val Tyr
                340                 345                 350

Thr Leu Pro Pro Ser Arg Asp Glu Leu Thr Lys Asn Gln Val Ser Leu
            355                 360                 365

Thr Cys Leu Val Lys Gly Phe Tyr Pro Ser Asp Ile Ala Val Glu Trp
        370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
                420                 425                 430

Glu Ala Leu His Asn His Tyr Thr Gln Lys Ser Leu Ser Leu Ser Pro
                435                 440                 445

Gly Lys
    450

<210> SEQ ID NO 74
<211> LENGTH: 215
<212> TYPE: PRT
<213> ORGANISM: Artificial Sequence
<220> FEATURE:
<223> OTHER INFORMATION: Antibody 22213 Full-Length Light Chain

<400> SEQUENCE: 74

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ala Ser Ser
            20                  25                  30

His Leu Ala Trp Tyr Gln Gln Lys Pro Gly Gln Ala Pro Arg Leu Leu
        35                  40                  45

Ile Tyr Asp Ala Val Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Ala Ala Ser Tyr Pro
                85                  90                  95

Leu Thr Phe Gly Gly Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215
```

-continued

```
<210> SEQ ID NO 75
<211> LENGTH: 11
<212> TYPE: PRT
<213> ORGANISM: Artificial Sequence
<220> FEATURE:
<223> OTHER INFORMATION: Antibody 15465 VH CDR1

<400> SEQUENCE: 75

Gly Ser Ile Ser Ser Gly Gly Tyr Tyr Trp Ser
1               5                   10

<210> SEQ ID NO 76
<211> LENGTH: 16
<212> TYPE: PRT
<213> ORGANISM: Artificial Sequence
<220> FEATURE:
<223> OTHER INFORMATION: Antibody 15465 VH CDR2

<400> SEQUENCE: 76

Asn Ile Tyr Tyr Ser Gly Ser Thr Tyr Tyr Asn Pro Ser Leu Lys Ser
1               5                   10                  15

<210> SEQ ID NO 77
<211> LENGTH: 13
<212> TYPE: PRT
<213> ORGANISM: Artificial Sequence
<220> FEATURE:
<223> OTHER INFORMATION: Antibody 15465 VH CDR3

<400> SEQUENCE: 77

Ala Arg Glu Ser Ser Thr Ile Ser Ala Asp Phe Asp Leu
1               5                   10

<210> SEQ ID NO 78
<211> LENGTH: 11
<212> TYPE: PRT
<213> ORGANISM: Artificial Sequence
<220> FEATURE:
<223> OTHER INFORMATION: Antibody 15465 VL CDR1

<400> SEQUENCE: 78

Arg Ala Ser Gln Gly Ile Ser Arg Trp Leu Ala
1               5                   10

<210> SEQ ID NO 79
<211> LENGTH: 7
<212> TYPE: PRT
<213> ORGANISM: Artificial Sequence
<220> FEATURE:
<223> OTHER INFORMATION: Antibody 15465 VL CDR2

<400> SEQUENCE: 79

Ala Ala Ser Ser Leu Gln Ser
1               5

<210> SEQ ID NO 80
<211> LENGTH: 9
<212> TYPE: PRT
<213> ORGANISM: Artificial Sequence
<220> FEATURE:
<223> OTHER INFORMATION: Antibody 15465 VL CDR3

<400> SEQUENCE: 80

Gln Gln Ala His Thr Phe Pro Tyr Thr
1               5

<210> SEQ ID NO 81
```

-continued

<211> LENGTH: 121
<212> TYPE: PRT
<213> ORGANISM: Artificial Sequence
<220> FEATURE:
<223> OTHER INFORMATION: Antibody 15465 Variable Heavy Chain

<400> SEQUENCE: 81

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Ser Gly
            20                  25                  30

Gly Tyr Tyr Trp Ser Trp Ile Arg Gln His Pro Gly Lys Gly Leu Glu
        35                  40                  45

Trp Ile Gly Asn Ile Tyr Tyr Ser Gly Ser Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Glu Ser Ser Thr Ile Ser Ala Asp Phe Asp Leu Trp Gly
            100                 105                 110

Arg Gly Thr Leu Val Thr Val Ser Ser
        115                 120

<210> SEQ ID NO 82
<211> LENGTH: 107
<212> TYPE: PRT
<213> ORGANISM: Artificial Sequence
<220> FEATURE:
<223> OTHER INFORMATION: Antibody 15465 Variable Light Chain

<400> SEQUENCE: 82

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Ser Arg Trp
            20                  25                  30

Leu Ala Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala His Thr Phe Pro Tyr
                85                  90                  95

Thr Phe Gly Gly Gly Thr Lys Val Glu Ile Lys
            100                 105

<210> SEQ ID NO 83
<211> LENGTH: 451
<212> TYPE: PRT
<213> ORGANISM: Artificial Sequence
<220> FEATURE:
<223> OTHER INFORMATION: Antibody 15465 Full-Length Heavy Chain

<400> SEQUENCE: 83

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Ser Gly
            20                  25                  30

```
Gly Tyr Tyr Trp Ser Trp Ile Arg Gln His Pro Gly Lys Gly Leu Glu
         35                  40                  45

Trp Ile Gly Asn Ile Tyr Tyr Ser Gly Ser Thr Tyr Tyr Asn Pro Ser
 50                  55                  60

Leu Lys Ser Arg Val Thr Ile Ser Val Asp Thr Ser Lys Asn Gln Phe
 65                  70                  75                  80

Ser Leu Lys Leu Ser Ser Val Thr Ala Ala Asp Thr Ala Val Tyr Tyr
                 85                  90                  95

Cys Ala Arg Glu Ser Ser Thr Ile Ser Ala Asp Phe Asp Leu Trp Gly
            100                 105                 110

Arg Gly Thr Leu Val Thr Val Ser Ser Ala Ser Thr Lys Gly Pro Ser
            115                 120                 125

Val Phe Pro Leu Ala Pro Ser Ser Lys Ser Thr Ser Gly Gly Thr Ala
130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
            195                 200                 205

Lys Pro Ser Asn Thr Lys Val Asp Lys Lys Val Glu Pro Lys Ser Cys
        210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
            275                 280                 285

His Asn Ala Lys Thr Lys Pro Arg Glu Glu Gln Tyr Asn Ser Thr Tyr
290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Asp Glu Leu Thr Lys Asn Gln Val Ser
            355                 360                 365

Leu Thr Cys Leu Val Lys Gly Phe Tyr Pro Ser Asp Ile Ala Val Glu
        370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
            435                 440                 445

Pro Gly Lys
```

<210> SEQ ID NO 84
<211> LENGTH: 214
<212> TYPE: PRT
<213> ORGANISM: Artificial Sequence
<220> FEATURE:
<223> OTHER INFORMATION: Antibody 15465 Full-Length Light Chain

<400> SEQUENCE: 84

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Ser Arg Trp
            20                  25                  30

Leu Ala Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala His Thr Phe Pro Tyr
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 85
<211> LENGTH: 11
<212> TYPE: PRT
<213> ORGANISM: Artificial Sequence
<220> FEATURE:
<223> OTHER INFORMATION: Antibody 20506 VH CDR1

<400> SEQUENCE: 85

Gly Ser Ile Ser His Gly Gly Tyr Tyr Trp Ser
1               5                   10

<210> SEQ ID NO 86
<211> LENGTH: 16
<212> TYPE: PRT
<213> ORGANISM: Artificial Sequence
<220> FEATURE:
<223> OTHER INFORMATION: Antibody 20506 VH CDR2

<400> SEQUENCE: 86

Asn Ile Tyr Tyr Ser Gly Ser Thr Tyr Tyr Asn Pro Ser Leu Lys Ser
1               5                   10                  15

<210> SEQ ID NO 87
<211> LENGTH: 13
<212> TYPE: PRT
<213> ORGANISM: Artificial Sequence
<220> FEATURE:
<223> OTHER INFORMATION: Antibody 20506 VH CDR3

<400> SEQUENCE: 87

Ala Arg Glu Ser Ser Thr Ile Ser Ala Asp Phe Asp Leu
1               5                   10

<210> SEQ ID NO 88
<211> LENGTH: 11
<212> TYPE: PRT
<213> ORGANISM: Artificial Sequence
<220> FEATURE:
<223> OTHER INFORMATION: Antibody 20506 VL CDR1

<400> SEQUENCE: 88

Arg Ala Ser Gln Gly Ile Ser Arg Trp Leu Ala
1               5                   10

<210> SEQ ID NO 89
<211> LENGTH: 7
<212> TYPE: PRT
<213> ORGANISM: Artificial Sequence
<220> FEATURE:
<223> OTHER INFORMATION: Antibody 20506 VL CDR2

<400> SEQUENCE: 89

Ala Ala Ser Ser Leu Gln Ser
1               5

<210> SEQ ID NO 90
<211> LENGTH: 9
<212> TYPE: PRT
<213> ORGANISM: Artificial Sequence
<220> FEATURE:
<223> OTHER INFORMATION: Antibody 20506 VL CDR3

<400> SEQUENCE: 90

Gln Gln Ala His Thr Phe Pro Tyr Thr
1               5

<210> SEQ ID NO 91
<211> LENGTH: 121
<212> TYPE: PRT
<213> ORGANISM: Artificial Sequence
<220> FEATURE:
<223> OTHER INFORMATION: Antibody 20506 Variable Heavy Chain

<400> SEQUENCE: 91

Gln Leu Gln Leu Gln Glu Ser Gly Pro Gly Leu Val Lys Pro Ser Glu
1               5                   10                  15

Thr Leu Ser Leu Thr Cys Thr Ala Ser Gly Gly Ser Ile Ser His Gly
            20                  25                  30

Gly Tyr Tyr Trp Ser Trp Ile Arg Gln His Pro Gly Lys Gly Leu Glu
        35                  40                  45

Trp Ile Gly Asn Ile Tyr Tyr Ser Gly Ser Thr Tyr Tyr Asn Pro Ser
    50                  55                  60

Leu Lys Ser Arg Val Thr Met Ser Val Asp Thr Ser Lys Asn Gln Phe
65                  70                  75                  80

Ser Leu Lys Leu Ser Ser Val Thr Ala Ala Asp Thr Ala Val Tyr Tyr

```
                    85                  90                  95

Cys Ala Arg Glu Ser Ser Thr Ile Ser Ala Asp Phe Asp Leu Trp Gly
                100                 105                 110

Arg Gly Thr Leu Val Thr Val Ser Ser
            115                 120

<210> SEQ ID NO 92
<211> LENGTH: 107
<212> TYPE: PRT
<213> ORGANISM: Artificial Sequence
<220> FEATURE:
<223> OTHER INFORMATION: Antibody 20506 Variable Light Chain

<400> SEQUENCE: 92

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Ser Arg Trp
            20                  25                  30

Leu Ala Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala His Thr Phe Pro Tyr
                85                  90                  95

Thr Phe Gly Gly Gly Thr Lys Val Glu Ile Lys
            100                 105

<210> SEQ ID NO 93
<211> LENGTH: 451
<212> TYPE: PRT
<213> ORGANISM: Artificial Sequence
<220> FEATURE:
<223> OTHER INFORMATION: Antibody 20506 Full-Length Heavy Chain

<400> SEQUENCE: 93

Gln Leu Gln Leu Gln Glu Ser Gly Pro Gly Leu Val Lys Pro Ser Glu
1               5                   10                  15

Thr Leu Ser Leu Thr Cys Thr Ala Ser Gly Gly Ser Ile Ser His Gly
            20                  25                  30

Gly Tyr Tyr Trp Ser Trp Ile Arg Gln His Pro Gly Lys Gly Leu Glu
        35                  40                  45

Trp Ile Gly Asn Ile Tyr Tyr Ser Gly Ser Thr Tyr Tyr Asn Pro Ser
50                  55                  60

Leu Lys Ser Arg Val Thr Met Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Glu Ser Ser Thr Ile Ser Ala Asp Phe Asp Leu Trp Gly
                100                 105                 110

Arg Gly Thr Leu Val Thr Val Ser Ser Ala Ser Thr Lys Gly Pro Ser
            115                 120                 125

Val Phe Pro Leu Ala Pro Ser Ser Lys Ser Thr Ser Gly Gly Thr Ala
        130                 135                 140

Ala Leu Gly Cys Leu Val Lys Asp Tyr Phe Pro Glu Pro Val Thr Val
145                 150                 155                 160
```

```
Ser Trp Asn Ser Gly Ala Leu Thr Ser Gly Val His Thr Phe Pro Ala
            165                 170                 175

Val Leu Gln Ser Ser Gly Leu Tyr Ser Leu Ser Ser Val Val Thr Val
        180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
        210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
            245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
        290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
            325                 330                 335

Glu Lys Thr Ile Ser Lys Ala Lys Gly Gln Pro Arg Glu Pro Gln Val
            340                 345                 350

Tyr Thr Leu Pro Pro Ser Arg Asp Glu Leu Thr Lys Asn Gln Val Ser
        355                 360                 365

Leu Thr Cys Leu Val Lys Gly Phe Tyr Pro Ser Asp Ile Ala Val Glu
370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
            405                 410                 415

Asp Lys Ser Arg Trp Gln Gln Gly Asn Val Phe Ser Cys Ser Val Met
        420                 425                 430

His Glu Ala Leu His Asn His Tyr Thr Gln Lys Ser Leu Ser Leu Ser
        435                 440                 445

Pro Gly Lys
    450

<210> SEQ ID NO 94
<211> LENGTH: 214
<212> TYPE: PRT
<213> ORGANISM: Artificial Sequence
<220> FEATURE:
<223> OTHER INFORMATION: Antibody 20506 Full-Length Light Chain

<400> SEQUENCE: 94

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Ser Arg Trp
            20                  25                  30

Leu Ala Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60
```

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Ala His Thr Phe Pro Tyr
                 85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 95
<211> LENGTH: 11
<212> TYPE: PRT
<213> ORGANISM: Artificial Sequence
<220> FEATURE:
<223> OTHER INFORMATION: Antibody 15483 VH CDR1

<400> SEQUENCE: 95

Gly Ser Ile Ser Ser Gly Gly Tyr Tyr Trp Ser
1               5                   10

<210> SEQ ID NO 96
<211> LENGTH: 16
<212> TYPE: PRT
<213> ORGANISM: Artificial Sequence
<220> FEATURE:
<223> OTHER INFORMATION: Antibody 15483 VH CDR2

<400> SEQUENCE: 96

Asn Ile Tyr Tyr Ser Gly Ser Thr Tyr Tyr Asn Pro Ser Leu Lys Ser
1               5                   10                  15

<210> SEQ ID NO 97
<211> LENGTH: 13
<212> TYPE: PRT
<213> ORGANISM: Artificial Sequence
<220> FEATURE:
<223> OTHER INFORMATION: Antibody 15483 VH CDR3

<400> SEQUENCE: 97

Ala Arg Gly Leu Ser Thr Ile Asp Glu Ala Phe Asp Pro
1               5                   10

<210> SEQ ID NO 98
<211> LENGTH: 11
<212> TYPE: PRT
<213> ORGANISM: Artificial Sequence
<220> FEATURE:
<223> OTHER INFORMATION: Antibody 15483 VL CDR1

<400> SEQUENCE: 98

```
Arg Ala Ser Gln Ser Ile Ser Ser Trp Leu Ala
1               5                   10
```

<210> SEQ ID NO 99
<211> LENGTH: 7
<212> TYPE: PRT
<213> ORGANISM: Artificial Sequence
<220> FEATURE:
<223> OTHER INFORMATION: Antibody 15483 VL CDR2

<400> SEQUENCE: 99

```
Lys Ala Ser Ser Leu Glu Ser
1               5
```

<210> SEQ ID NO 100
<211> LENGTH: 9
<212> TYPE: PRT
<213> ORGANISM: Artificial Sequence
<220> FEATURE:
<223> OTHER INFORMATION: Antibody 15483 VL CDR3

<400> SEQUENCE: 100

```
Gln Gln Asp Asn Ser Tyr Pro Tyr Thr
1               5
```

<210> SEQ ID NO 101
<211> LENGTH: 121
<212> TYPE: PRT
<213> ORGANISM: Artificial Sequence
<220> FEATURE:
<223> OTHER INFORMATION: Antibody 15483 Variable Heavy Chain

<400> SEQUENCE: 101

```
Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Ser Gly
            20                  25                  30

Gly Tyr Tyr Trp Ser Trp Ile Arg Gln His Pro Gly Lys Gly Leu Glu
        35                  40                  45

Trp Ile Gly Asn Ile Tyr Tyr Ser Gly Ser Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Gly Leu Ser Thr Ile Asp Glu Ala Phe Asp Pro Trp Gly
            100                 105                 110

Gln Gly Thr Leu Val Thr Val Ser Ser
        115                 120
```

<210> SEQ ID NO 102
<211> LENGTH: 107
<212> TYPE: PRT
<213> ORGANISM: Artificial Sequence
<220> FEATURE:
<223> OTHER INFORMATION: Antibody 15483 Variable Light Chain

<400> SEQUENCE: 102

```
Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30
```

```
Leu Ala Trp Tyr Gln Gln Lys Pro Gly Lys Ala Pro Lys Leu Leu Ile
         35                  40                  45

Tyr Lys Ala Ser Ser Leu Glu Ser Gly Val Pro Ser Arg Phe Ser Gly
 50                  55                  60

Ser Gly Ser Gly Thr Glu Phe Thr Leu Thr Ile Ser Ser Leu Gln Pro
 65                  70                  75                  80

Asp Asp Phe Ala Thr Tyr Tyr Cys Gln Gln Asp Asn Ser Tyr Pro Tyr
                 85                  90                  95

Thr Phe Gly Gly Gly Thr Lys Val Glu Ile Lys
             100                 105
```

<210> SEQ ID NO 103
<211> LENGTH: 451
<212> TYPE: PRT
<213> ORGANISM: Artificial Sequence
<220> FEATURE:
<223> OTHER INFORMATION: Antibody 15483 Full-Length Heavy Chain

<400> SEQUENCE: 103

```
Gln Val Gln Leu Gln Glu Ser Gly Pro Gly Leu Val Lys Pro Ser Gln
 1               5                  10                  15

Thr Leu Ser Leu Thr Cys Thr Val Ser Gly Gly Ser Ile Ser Ser Gly
             20                  25                  30

Gly Tyr Tyr Trp Ser Trp Ile Arg Gln His Pro Gly Lys Gly Leu Glu
         35                  40                  45

Trp Ile Gly Asn Ile Tyr Tyr Ser Gly Ser Thr Tyr Tyr Asn Pro Ser
 50                  55                  60

Leu Lys Ser Arg Val Thr Ile Ser Val Asp Thr Ser Lys Asn Gln Phe
 65                  70                  75                  80

Ser Leu Lys Leu Ser Ser Val Thr Ala Ala Asp Thr Ala Val Tyr Tyr
                 85                  90                  95

Cys Ala Arg Gly Leu Ser Thr Ile Asp Glu Ala Phe Asp Pro Trp Gly
             100                 105                 110

Gln Gly Thr Leu Val Thr Val Ser Ser Ala Ser Thr Lys Gly Pro Ser
         115                 120                 125

Val Phe Pro Leu Ala Pro Ser Ser Lys Ser Thr Ser Gly Gly Thr Ala
     130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285
```

His Asn Ala Lys Thr Lys Pro Arg Glu Glu Gln Tyr Asn Ser Thr Tyr
290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Asp Glu Leu Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys
    450

<210> SEQ ID NO 104
<211> LENGTH: 214
<212> TYPE: PRT
<213> ORGANISM: Artificial Sequence
<220> FEATURE:
<223> OTHER INFORMATION: Antibody 15483 Full-Length Light Chain

<400> SEQUENCE: 104

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Lys Ala Ser Ser Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Asp Asn Ser Tyr Pro Tyr
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

```
Ala Cys Glu Val Thr His Gln Gly Leu Ser Ser Pro Val Thr Lys Ser
        195                 200                 205

Phe Asn Arg Gly Glu Cys
    210

<210> SEQ ID NO 105
<211> LENGTH: 11
<212> TYPE: PRT
<213> ORGANISM: Artificial Sequence
<220> FEATURE:
<223> OTHER INFORMATION: Antibody 20513 VH CDR1

<400> SEQUENCE: 105

Gly Ser Ile Ser Asp Gly Ser Tyr Tyr Trp Ser
1               5                   10

<210> SEQ ID NO 106
<211> LENGTH: 16
<212> TYPE: PRT
<213> ORGANISM: Artificial Sequence
<220> FEATURE:
<223> OTHER INFORMATION: Antibody 20513 VH CDR2

<400> SEQUENCE: 106

Asn Ile Tyr Tyr Ser Gly Ser Thr Tyr Tyr Asn Pro Ser Leu Arg Ser
1               5                   10                  15

<210> SEQ ID NO 107
<211> LENGTH: 13
<212> TYPE: PRT
<213> ORGANISM: Artificial Sequence
<220> FEATURE:
<223> OTHER INFORMATION: Antibody 20513 VH CDR3

<400> SEQUENCE: 107

Ala Arg Gly Leu Ser Thr Ile Asp Glu Ala Phe Asp Pro
1               5                   10

<210> SEQ ID NO 108
<211> LENGTH: 11
<212> TYPE: PRT
<213> ORGANISM: Artificial Sequence
<220> FEATURE:
<223> OTHER INFORMATION: Antibody 20513 VL CDR1

<400> SEQUENCE: 108

Arg Ala Ser Gln Ser Ile Ser Ser Trp Leu Ala
1               5                   10

<210> SEQ ID NO 109
<211> LENGTH: 7
<212> TYPE: PRT
<213> ORGANISM: Artificial Sequence
<220> FEATURE:
<223> OTHER INFORMATION: Antibody 20513 VL CDR2

<400> SEQUENCE: 109

Lys Ala Ser Ser Leu Glu Ser
1               5

<210> SEQ ID NO 110
<211> LENGTH: 9
<212> TYPE: PRT
<213> ORGANISM: Artificial Sequence
<220> FEATURE:
<223> OTHER INFORMATION: Antibody 20513 VL CDR3
```

<400> SEQUENCE: 110

Gln Gln Asp Asn Ser Tyr Pro Tyr Thr
1               5

<210> SEQ ID NO 111
<211> LENGTH: 121
<212> TYPE: PRT
<213> ORGANISM: Artificial Sequence
<220> FEATURE:
<223> OTHER INFORMATION: Antibody 20513 Variable Heavy Chain

<400> SEQUENCE: 111

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Asp Gly
                20                  25                  30

Ser Tyr Tyr Trp Ser Trp Ile Arg Gln His Pro Gly Lys Gly Leu Glu
            35                  40                  45

Trp Ile Gly Asn Ile Tyr Tyr Ser Gly Ser Thr Tyr Tyr Asn Pro Ser
        50                  55                  60

Leu Arg Ser Arg Val Thr Met Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Gly Leu Ser Thr Ile Asp Glu Ala Phe Asp Pro Trp Gly
            100                 105                 110

Gln Gly Thr Leu Val Thr Val Ser Ser
        115                 120

<210> SEQ ID NO 112
<211> LENGTH: 107
<212> TYPE: PRT
<213> ORGANISM: Artificial Sequence
<220> FEATURE:
<223> OTHER INFORMATION: Antibody 20513 Variable Light Chain

<400> SEQUENCE: 112

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
                20                  25                  30

Leu Ala Trp Tyr Gln Gln Lys Pro Gly Lys Ala Pro Lys Leu Leu Ile
            35                  40                  45

Tyr Lys Ala Ser Ser Leu Glu Ser Gly Val Pro Ser Arg Phe Ser Gly
        50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Asp Asn Ser Tyr Pro Tyr
                85                  90                  95

Thr Phe Gly Gly Gly Thr Lys Val Glu Ile Lys
            100                 105

<210> SEQ ID NO 113
<211> LENGTH: 451
<212> TYPE: PRT
<213> ORGANISM: Artificial Sequence
<220> FEATURE:
<223> OTHER INFORMATION: Antibody 20513 Full-Length Heavy Chain

<400> SEQUENCE: 113

```
Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Asp Gly
            20                  25                  30

Ser Tyr Tyr Trp Ser Trp Ile Arg Gln His Pro Gly Lys Gly Leu Glu
        35                  40                  45

Trp Ile Gly Asn Ile Tyr Tyr Ser Gly Ser Thr Tyr Tyr Asn Pro Ser
    50                  55                  60

Leu Arg Ser Arg Val Thr Met Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Gly Leu Ser Thr Ile Asp Glu Ala Phe Asp Pro Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Asp Glu Leu Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415
```

```
Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
            435                 440                 445

Pro Gly Lys
    450

<210> SEQ ID NO 114
<211> LENGTH: 214
<212> TYPE: PRT
<213> ORGANISM: Artificial Sequence
<220> FEATURE:
<223> OTHER INFORMATION: Antibody 20513 Full-Length Light Chain

<400> SEQUENCE: 114

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Lys Ala Ser Ser Leu Glu Ser Gly Val Pro Ser Arg Phe Ser Gly
50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Asp Asn Ser Tyr Pro Tyr
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 115
<211> LENGTH: 11
<212> TYPE: PRT
<213> ORGANISM: Artificial Sequence
<220> FEATURE:
<223> OTHER INFORMATION: Antibody 22216 VH CDR1

<400> SEQUENCE: 115

Gly Ser Ile Ser Asp Gly Ser Tyr Tyr Trp Ser
1               5                   10

<210> SEQ ID NO 116
<211> LENGTH: 16
<212> TYPE: PRT
<213> ORGANISM: Artificial Sequence
```

```
<220> FEATURE:
<223> OTHER INFORMATION: Antibody 22216 VH CDR2

<400> SEQUENCE: 116

Asn Ile Tyr Tyr Ser Gly Ser Thr Tyr Tyr Asn Pro Ser Leu Arg Ser
1               5                   10                  15

<210> SEQ ID NO 117
<211> LENGTH: 13
<212> TYPE: PRT
<213> ORGANISM: Artificial Sequence
<220> FEATURE:
<223> OTHER INFORMATION: Antibody 22216 VH CDR3

<400> SEQUENCE: 117

Ala Arg Gly Leu Ser Thr Ile Asp Glu Ala Phe Asp Pro
1               5                   10

<210> SEQ ID NO 118
<211> LENGTH: 11
<212> TYPE: PRT
<213> ORGANISM: Artificial Sequence
<220> FEATURE:
<223> OTHER INFORMATION: Antibody 22216 VL CDR1

<400> SEQUENCE: 118

Arg Ala Ser Lys Ser Ile Ser Ser Trp Leu Ala
1               5                   10

<210> SEQ ID NO 119
<211> LENGTH: 7
<212> TYPE: PRT
<213> ORGANISM: Artificial Sequence
<220> FEATURE:
<223> OTHER INFORMATION: Antibody 22216 VL CDR2

<400> SEQUENCE: 119

Glu Ala Ser Ser Leu His Ser
1               5

<210> SEQ ID NO 120
<211> LENGTH: 9
<212> TYPE: PRT
<213> ORGANISM: Artificial Sequence
<220> FEATURE:
<223> OTHER INFORMATION: Antibody 22216 VL CDR3

<400> SEQUENCE: 120

Gln Gln Asp Asn Ser Tyr Pro Tyr Thr
1               5

<210> SEQ ID NO 121
<211> LENGTH: 121
<212> TYPE: PRT
<213> ORGANISM: Artificial Sequence
<220> FEATURE:
<223> OTHER INFORMATION: Antibody 22216 Variable Heavy Chain

<400> SEQUENCE: 121

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Asp Gly
                20                  25                  30

Ser Tyr Tyr Trp Ser Trp Ile Arg Gln His Pro Gly Lys Gly Leu Glu
            35                  40                  45
```

Trp Ile Gly Asn Ile Tyr Tyr Ser Gly Ser Thr Tyr Tyr Asn Pro Ser
            50                  55                  60

Leu Arg Ser Arg Val Thr Met Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Gly Leu Ser Thr Ile Asp Glu Ala Phe Asp Pro Trp Gly
            100                 105                 110

Gln Gly Thr Leu Val Thr Val Ser Ser
            115                 120

<210> SEQ ID NO 122
<211> LENGTH: 107
<212> TYPE: PRT
<213> ORGANISM: Artificial Sequence
<220> FEATURE:
<223> OTHER INFORMATION: Antibody 22216 Variable Light Chain

<400> SEQUENCE: 122

Asp Ile Gln Met Thr Gln Ser Pro Ser Thr Leu Ser Ala Ser Val Gly
1               5                   10                  15

Asp Arg Val Thr Ile Thr Cys Arg Ala Ser Lys Ser Ile Ser Ser Trp
            20                  25                  30

Leu Ala Trp Tyr Gln Gln Lys Pro Gly Lys Ala Pro Lys Leu Leu Ile
        35                  40                  45

Tyr Glu Ala Ser Ser Leu His Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Asp Asn Ser Tyr Pro Tyr
                85                  90                  95

Thr Phe Gly Gly Gly Thr Lys Val Glu Ile Lys
            100                 105

<210> SEQ ID NO 123
<211> LENGTH: 451
<212> TYPE: PRT
<213> ORGANISM: Artificial Sequence
<220> FEATURE:
<223> OTHER INFORMATION: Antibody 22216 Full-Length Heavy Chain

<400> SEQUENCE: 123

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Asp Gly
            20                  25                  30

Ser Tyr Tyr Trp Ser Trp Ile Arg Gln His Pro Gly Lys Gly Leu Glu
        35                  40                  45

Trp Ile Gly Asn Ile Tyr Tyr Ser Gly Ser Thr Tyr Tyr Asn Pro Ser
    50                  55                  60

Leu Arg Ser Arg Val Thr Met Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Gly Leu Ser Thr Ile Asp Glu Ala Phe Asp Pro Trp Gly
            100                 105                 110

Gln Gly Thr Leu Val Thr Val Ser Ser Ala Ser Thr Lys Gly Pro Ser
            115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Val Glu Pro Lys Ser Cys
210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Asp Glu Leu Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys
    450

<210> SEQ ID NO 124
<211> LENGTH: 214
<212> TYPE: PRT
<213> ORGANISM: Artificial Sequence
<220> FEATURE:
<223> OTHER INFORMATION: Antibody 22216 Full-Length Light Chain

<400> SEQUENCE: 124

Asp Ile Gln Met Thr Gln Ser Pro Ser Thr Leu Ser Ala Ser Val Gly
1               5                   10                  15

Asp Arg Val Thr Ile Thr Cys Arg Ala Ser Lys Ser Ile Ser Ser Trp
            20                  25                  30

```
Leu Ala Trp Tyr Gln Gln Lys Pro Gly Lys Ala Pro Lys Leu Leu Ile
        35                  40                  45

Tyr Glu Ala Ser Ser Leu His Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Asp Asn Ser Tyr Pro Tyr
                85                  90                  95

Thr Phe Gly Gly Gly Thr Lys Val Glu Ile Lys Arg Thr Val Ala Ala
                100                 105                 110

Pro Ser Val Phe Ile Phe Pro Pro Ser Asp Glu Gln Leu Lys Ser Gly
                115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
                180                 185                 190

Ala Cys Glu Val Thr His Gln Gly Leu Ser Ser Pro Val Thr Lys Ser
                195                 200                 205

Phe Asn Arg Gly Glu Cys
        210

<210> SEQ ID NO 125
<211> LENGTH: 9
<212> TYPE: PRT
<213> ORGANISM: Artificial Sequence
<220> FEATURE:
<223> OTHER INFORMATION: Antibody 15489 VH CDR1

<400> SEQUENCE: 125

Gly Ser Ile Ser Ser Tyr Tyr Trp Ser
1               5

<210> SEQ ID NO 126
<211> LENGTH: 16
<212> TYPE: PRT
<213> ORGANISM: Artificial Sequence
<220> FEATURE:
<223> OTHER INFORMATION: Antibody 15489 VH CDR2

<400> SEQUENCE: 126

Tyr Ile Tyr Ser Ser Gly Ser Thr Asn Tyr Asn Pro Ser Leu Lys Ser
1               5                   10                  15

<210> SEQ ID NO 127
<211> LENGTH: 16
<212> TYPE: PRT
<213> ORGANISM: Artificial Sequence
<220> FEATURE:
<223> OTHER INFORMATION: Antibody 15489 VH CDR3

<400> SEQUENCE: 127

Ala Arg Gly Ser Gly Gln Tyr Ala Ala Pro Asp Tyr Gly Met Asp Val
1               5                   10                  15

<210> SEQ ID NO 128
<211> LENGTH: 11
```

-continued

```
<212> TYPE: PRT
<213> ORGANISM: Artificial Sequence
<220> FEATURE:
<223> OTHER INFORMATION: Antibody 15489 VL CDR1

<400> SEQUENCE: 128

Arg Ala Ser Gln Ser Ile Ser Ser Trp Leu Ala
1               5                   10

<210> SEQ ID NO 129
<211> LENGTH: 7
<212> TYPE: PRT
<213> ORGANISM: Artificial Sequence
<220> FEATURE:
<223> OTHER INFORMATION: Antibody 15489 VL CDR2

<400> SEQUENCE: 129

Lys Ala Ser Ser Leu Glu Ser
1               5

<210> SEQ ID NO 130
<211> LENGTH: 9
<212> TYPE: PRT
<213> ORGANISM: Artificial Sequence
<220> FEATURE:
<223> OTHER INFORMATION: Antibody 15489 VL CDR3

<400> SEQUENCE: 130

Gln Gln Asp Asn Ser Phe Pro Phe Thr
1               5

<210> SEQ ID NO 131
<211> LENGTH: 122
<212> TYPE: PRT
<213> ORGANISM: Artificial Sequence
<220> FEATURE:
<223> OTHER INFORMATION: Antibody 15489 Variable Heavy Chain

<400> SEQUENCE: 131

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Tyr
            20                  25                  30

Tyr Trp Ser Trp Ile Arg Gln Pro Pro Gly Lys Gly Leu Glu Trp Ile
        35                  40                  45

Gly Tyr Ile Tyr Ser Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Gly Ser Gly Gln Tyr Ala Ala Pro Asp Tyr Gly Met Asp Val Trp
            100                 105                 110

Gly Gln Gly Thr Thr Val Thr Val Ser Ser
        115                 120

<210> SEQ ID NO 132
<211> LENGTH: 107
<212> TYPE: PRT
<213> ORGANISM: Artificial Sequence
<220> FEATURE:
<223> OTHER INFORMATION: Antibody 15489 Variable Light Chain

<400> SEQUENCE: 132
```

```
Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Lys Ala Ser Ser Leu Glu Ser Gly Val Pro Ser Arg Phe Ser Gly
50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Asp Asn Ser Phe Pro Phe
                85                  90                  95

Thr Phe Gly Gly Gly Thr Lys Val Glu Ile Lys
            100                 105
```

<210> SEQ ID NO 133
<211> LENGTH: 452
<212> TYPE: PRT
<213> ORGANISM: Artificial Sequence
<220> FEATURE:
<223> OTHER INFORMATION: Antibody 15489 Full-Length Heavy Chain

<400> SEQUENCE: 133

```
Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Tyr
            20                  25                  30

Tyr Trp Ser Trp Ile Arg Gln Pro Pro Gly Lys Gly Leu Glu Trp Ile
        35                  40                  45

Gly Tyr Ile Tyr Ser Ser Gly Ser Thr Asn Tyr Asn Pro Ser Leu Lys
50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Gly Ser Gly Gln Tyr Ala Ala Pro Asp Tyr Gly Met Asp Val Trp
            100                 105                 110

Gly Gln Gly Thr Thr Val Thr Val Ser Ser Ala Ser Thr Lys Gly Pro
        115                 120                 125

Ser Val Phe Pro Leu Ala Pro Ser Ser Lys Ser Thr Ser Gly Gly Thr
130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Lys Val Glu Pro Lys Ser
210                 215                 220

Cys Asp Lys Thr His Thr Cys Pro Pro Cys Pro Ala Pro Glu Leu Leu
225                 230                 235                 240

Gly Gly Pro Ser Val Phe Leu Phe Pro Pro Lys Pro Lys Asp Thr Leu
                245                 250                 255
```

```
Met Ile Ser Arg Thr Pro Glu Val Thr Cys Val Val Asp Val Ser
            260                 265                 270

His Glu Asp Pro Glu Val Lys Phe Asn Trp Tyr Val Asp Gly Val Glu
        275                 280                 285

Val His Asn Ala Lys Thr Lys Pro Arg Glu Glu Gln Tyr Asn Ser Thr
    290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Arg Asp Glu Leu Thr Lys Asn Gln Val
        355                 360                 365

Ser Leu Thr Cys Leu Val Lys Gly Phe Tyr Pro Ser Asp Ile Ala Val
    370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
                405                 410                 415

Val Asp Lys Ser Arg Trp Gln Gln Gly Asn Val Phe Ser Cys Ser Val
            420                 425                 430

Met His Glu Ala Leu His Asn His Tyr Thr Gln Lys Ser Leu Ser Leu
        435                 440                 445

Ser Pro Gly Lys
    450

<210> SEQ ID NO 134
<211> LENGTH: 214
<212> TYPE: PRT
<213> ORGANISM: Artificial Sequence
<220> FEATURE:
<223> OTHER INFORMATION: Antibody 15489 Full-Length Light Chain

<400> SEQUENCE: 134

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Lys Ala Ser Ser Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Asp Asn Ser Phe Pro Phe
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160
```

Glu Ser Val Thr Glu Gln Asp Ser Lys Asp Ser Thr Tyr Ser Leu Ser
            165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 135
<211> LENGTH: 9
<212> TYPE: PRT
<213> ORGANISM: Artificial Sequence
<220> FEATURE:
<223> OTHER INFORMATION: Antibody 20516 VH CDR1

<400> SEQUENCE: 135

Gly Ser Ile Ile Ser Tyr Tyr Trp Gly
1               5

<210> SEQ ID NO 136
<211> LENGTH: 16
<212> TYPE: PRT
<213> ORGANISM: Artificial Sequence
<220> FEATURE:
<223> OTHER INFORMATION: Antibody 20516 VH CDR2

<400> SEQUENCE: 136

Tyr Ile Tyr Ser Ser Gly Ser Thr Ser Tyr Asn Pro Ser Leu Lys Ser
1               5                   10                  15

<210> SEQ ID NO 137
<211> LENGTH: 16
<212> TYPE: PRT
<213> ORGANISM: Artificial Sequence
<220> FEATURE:
<223> OTHER INFORMATION: Antibody 20516 VH CDR3

<400> SEQUENCE: 137

Ala Arg Gly Ser Gly Leu Tyr Ala Ala Pro Asp Tyr Gly Leu Asp Val
1               5                   10                  15

<210> SEQ ID NO 138
<211> LENGTH: 11
<212> TYPE: PRT
<213> ORGANISM: Artificial Sequence
<220> FEATURE:
<223> OTHER INFORMATION: Antibody 20516 VL CDR1

<400> SEQUENCE: 138

Arg Ala Ser Gln Ser Ile Ser Ser Trp Leu Ala
1               5                   10

<210> SEQ ID NO 139
<211> LENGTH: 7
<212> TYPE: PRT
<213> ORGANISM: Artificial Sequence
<220> FEATURE:
<223> OTHER INFORMATION: Antibody 20516 VL CDR2

<400> SEQUENCE: 139

Lys Ala Ser Ser Leu Glu Ser
1               5

```
<210> SEQ ID NO 140
<211> LENGTH: 9
<212> TYPE: PRT
<213> ORGANISM: Artificial Sequence
<220> FEATURE:
<223> OTHER INFORMATION: Antibody 20516 VL CDR3

<400> SEQUENCE: 140

Gln Gln Asp Asn Ser Phe Pro Phe Thr
1               5

<210> SEQ ID NO 141
<211> LENGTH: 122
<212> TYPE: PRT
<213> ORGANISM: Artificial Sequence
<220> FEATURE:
<223> OTHER INFORMATION: Antibody 20516 Variable Heavy Chain

<400> SEQUENCE: 141

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ile Ser Tyr
            20                  25                  30

Tyr Trp Gly Trp Ile Arg Gln Pro Pro Gly Lys Gly Leu Glu Trp Ile
        35                  40                  45

Gly Tyr Ile Tyr Ser Ser Gly Ser Thr Ser Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Gly Ser Gly Leu Tyr Ala Ala Pro Asp Tyr Gly Leu Asp Val Trp
            100                 105                 110

Gly Gln Gly Thr Thr Val Thr Val Ser Ser
        115                 120

<210> SEQ ID NO 142
<211> LENGTH: 107
<212> TYPE: PRT
<213> ORGANISM: Artificial Sequence
<220> FEATURE:
<223> OTHER INFORMATION: Antibody 20516 Variable Light Chain

<400> SEQUENCE: 142

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Lys Ala Ser Ser Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Asp Asn Ser Phe Pro Phe
                85                  90                  95

Thr Phe Gly Gly Gly Thr Lys Val Glu Ile Lys
            100                 105

<210> SEQ ID NO 143
```

<211> LENGTH: 452
<212> TYPE: PRT
<213> ORGANISM: Artificial Sequence
<220> FEATURE:
<223> OTHER INFORMATION: Antibody 20516 Full-Length Heavy Chain

<400> SEQUENCE: 143

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ile Ser Tyr
            20                  25                  30

Tyr Trp Gly Trp Ile Arg Gln Pro Pro Gly Lys Gly Leu Glu Trp Ile
        35                  40                  45

Gly Tyr Ile Tyr Ser Ser Gly Ser Thr Ser Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
            85                  90                  95

Arg Gly Ser Gly Leu Tyr Ala Ala Pro Asp Tyr Gly Leu Asp Val Trp
        100                 105                 110

Gly Gln Gly Thr Thr Val Thr Val Ser Ser Ala Ser Thr Lys Gly Pro
    115                 120                 125

Ser Val Phe Pro Leu Ala Pro Ser Ser Lys Ser Thr Ser Gly Gly Thr
130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
            165                 170                 175

Ala Val Leu Gln Ser Ser Gly Leu Tyr Ser Leu Ser Ser Val Val Thr
        180                 185                 190

Val Pro Ser Ser Ser Leu Gly Thr Gln Thr Tyr Ile Cys Asn Val Asn
    195                 200                 205

His Lys Pro Ser Asn Thr Lys Val Asp Lys Lys Val Glu Pro Lys Ser
210                 215                 220

Cys Asp Lys Thr His Thr Cys Pro Pro Cys Pro Ala Pro Glu Leu Leu
225                 230                 235                 240

Gly Gly Pro Ser Val Phe Leu Phe Pro Pro Lys Pro Lys Asp Thr Leu
            245                 250                 255

Met Ile Ser Arg Thr Pro Glu Val Thr Cys Val Val Val Asp Val Ser
        260                 265                 270

His Glu Asp Pro Glu Val Lys Phe Asn Trp Tyr Val Asp Gly Val Glu
    275                 280                 285

Val His Asn Ala Lys Thr Lys Pro Arg Glu Glu Gln Tyr Asn Ser Thr
290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
            325                 330                 335

Ile Glu Lys Thr Ile Ser Lys Ala Lys Gly Gln Pro Arg Glu Pro Gln
        340                 345                 350

Val Tyr Thr Leu Pro Pro Ser Arg Asp Glu Leu Thr Lys Asn Gln Val
    355                 360                 365

Ser Leu Thr Cys Leu Val Lys Gly Phe Tyr Pro Ser Asp Ile Ala Val
370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
            405                 410                 415

Val Asp Lys Ser Arg Trp Gln Gln Gly Asn Val Phe Ser Cys Ser Val
        420                 425                 430

Met His Glu Ala Leu His Asn His Tyr Thr Gln Lys Ser Leu Ser Leu
    435                 440                 445

Ser Pro Gly Lys
    450

<210> SEQ ID NO 144
<211> LENGTH: 214
<212> TYPE: PRT
<213> ORGANISM: Artificial Sequence
<220> FEATURE:
<223> OTHER INFORMATION: Antibody 20516 Full-Length Light Chain

<400> SEQUENCE: 144

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Lys Ala Ser Ser Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Asn Ser Phe Pro Phe
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 145
<211> LENGTH: 9
<212> TYPE: PRT
<213> ORGANISM: Artificial Sequence
<220> FEATURE:
<223> OTHER INFORMATION: Antibody 15472 VH CDR1

<400> SEQUENCE: 145

Phe Thr Phe Ser Ser Tyr Ala Met Ser

```
<210> SEQ ID NO 146
<211> LENGTH: 17
<212> TYPE: PRT
<213> ORGANISM: Artificial Sequence
<220> FEATURE:
<223> OTHER INFORMATION: Antibody 15472 VH CDR2

<400> SEQUENCE: 146

Thr Ile Ser Gly Ser Gly Gly Ser Thr Tyr Tyr Ala Asp Ser Val Lys
1               5                   10                  15
Gly

<210> SEQ ID NO 147
<211> LENGTH: 13
<212> TYPE: PRT
<213> ORGANISM: Artificial Sequence
<220> FEATURE:
<223> OTHER INFORMATION: Antibody 15472 VH CDR3

<400> SEQUENCE: 147

Ala Arg Gly Ala Gly His Tyr Asp Leu Val Gly Arg Tyr
1               5                   10

<210> SEQ ID NO 148
<211> LENGTH: 11
<212> TYPE: PRT
<213> ORGANISM: Artificial Sequence
<220> FEATURE:
<223> OTHER INFORMATION: Antibody 15472 VL CDR1

<400> SEQUENCE: 148

Arg Ala Ser Gln Ser Ile Ser Ser Tyr Leu Asn
1               5                   10

<210> SEQ ID NO 149
<211> LENGTH: 7
<212> TYPE: PRT
<213> ORGANISM: Artificial Sequence
<220> FEATURE:
<223> OTHER INFORMATION: Antibody 15472 VL CDR2

<400> SEQUENCE: 149

Ala Ala Ser Ser Leu Gln Ser
1               5

<210> SEQ ID NO 150
<211> LENGTH: 9
<212> TYPE: PRT
<213> ORGANISM: Artificial Sequence
<220> FEATURE:
<223> OTHER INFORMATION: Antibody 15472 VL CDR3

<400> SEQUENCE: 150

Gln Gln Leu Tyr Ser Leu Pro Pro Thr
1               5

<210> SEQ ID NO 151
<211> LENGTH: 120
<212> TYPE: PRT
<213> ORGANISM: Artificial Sequence
<220> FEATURE:
<223> OTHER INFORMATION: Antibody 15472 Variable Heavy Chain

<400> SEQUENCE: 151
```

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Thr Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Ala Gly His Tyr Asp Leu Val Gly Arg Tyr Trp Gly Gln
            100                 105                 110

Gly Thr Leu Val Thr Val Ser Ser
            115                 120

<210> SEQ ID NO 152
<211> LENGTH: 107
<212> TYPE: PRT
<213> ORGANISM: Artificial Sequence
<220> FEATURE:
<223> OTHER INFORMATION: Antibody 15472 Variable Light Chain

<400> SEQUENCE: 152

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Leu Tyr Ser Leu Pro Pro
                85                  90                  95

Thr Phe Gly Gly Gly Thr Lys Val Glu Ile Lys
            100                 105

<210> SEQ ID NO 153
<211> LENGTH: 450
<212> TYPE: PRT
<213> ORGANISM: Artificial Sequence
<220> FEATURE:
<223> OTHER INFORMATION: Antibody 15472 Full-Length Heavy Chain

<400> SEQUENCE: 153

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Thr Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

-continued

```
Leu Gln Met Asn Ser Leu Arg Ala Glu Asp Thr Ala Val Tyr Tyr Cys
                 85                  90                  95

Ala Arg Gly Ala Gly His Tyr Asp Leu Val Gly Arg Tyr Trp Gly Gln
            100                 105                 110

Gly Thr Leu Val Thr Val Ser Ala Ser Thr Lys Gly Pro Ser Val
        115                 120                 125

Phe Pro Leu Ala Pro Ser Ser Lys Ser Thr Ser Gly Gly Thr Ala Ala
130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450

<210> SEQ ID NO 154
<211> LENGTH: 214
<212> TYPE: PRT
<213> ORGANISM: Artificial Sequence
<220> FEATURE:
```

<223> OTHER INFORMATION: Antibody 15472 Full-Length Light Chain

<400> SEQUENCE: 154

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Leu Tyr Ser Leu Pro Pro
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 155
<211> LENGTH: 9
<212> TYPE: PRT
<213> ORGANISM: Artificial Sequence
<220> FEATURE:
<223> OTHER INFORMATION: Antibody 15503 VH CDR1

<400> SEQUENCE: 155

Phe Thr Phe Ser Ser Tyr Ala Met Ser
1               5

<210> SEQ ID NO 156
<211> LENGTH: 17
<212> TYPE: PRT
<213> ORGANISM: Artificial Sequence
<220> FEATURE:
<223> OTHER INFORMATION: Antibody 15503 VH CDR2

<400> SEQUENCE: 156

Ala Ile Ser Gly Ser Gly Gly Ser Thr Tyr Tyr Ala Asp Ser Val Lys
1               5                   10                  15

Gly

<210> SEQ ID NO 157
<211> LENGTH: 10
<212> TYPE: PRT
<213> ORGANISM: Artificial Sequence

```
<220> FEATURE:
<223> OTHER INFORMATION: Antibody 15503 VH CDR3

<400> SEQUENCE: 157

Ala Arg Val Gly Phe Arg Ala Leu Asn Tyr
1               5                   10

<210> SEQ ID NO 158
<211> LENGTH: 11
<212> TYPE: PRT
<213> ORGANISM: Artificial Sequence
<220> FEATURE:
<223> OTHER INFORMATION: Antibody 15503 VL CDR1

<400> SEQUENCE: 158

Arg Ala Ser Gln Asp Ile Ser Ser Trp Leu Ala
1               5                   10

<210> SEQ ID NO 159
<211> LENGTH: 7
<212> TYPE: PRT
<213> ORGANISM: Artificial Sequence
<220> FEATURE:
<223> OTHER INFORMATION: Antibody 15503 VL CDR2

<400> SEQUENCE: 159

Ala Ala Ser Ser Leu Gln Ser
1               5

<210> SEQ ID NO 160
<211> LENGTH: 10
<212> TYPE: PRT
<213> ORGANISM: Artificial Sequence
<220> FEATURE:
<223> OTHER INFORMATION: Antibody 15503 VL CDR3

<400> SEQUENCE: 160

Gln Gln Ala Thr Ser Tyr Pro Pro Trp Thr
1               5                   10

<210> SEQ ID NO 161
<211> LENGTH: 117
<212> TYPE: PRT
<213> ORGANISM: Artificial Sequence
<220> FEATURE:
<223> OTHER INFORMATION: Antibody 15503 Variable Heavy Chain

<400> SEQUENCE: 161

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Val Gly Phe Arg Ala Leu Asn Tyr Trp Gly Gln Gly Thr Thr
            100                 105                 110

Val Thr Val Ser Ser
```

```
            115

<210> SEQ ID NO 162
<211> LENGTH: 108
<212> TYPE: PRT
<213> ORGANISM: Artificial Sequence
<220> FEATURE:
<223> OTHER INFORMATION: Antibody 15503 Variable Light Chain

<400> SEQUENCE: 162

Asp Ile Gln Leu Thr Gln Ser Pro Ser Ser Val Ser Ala Ser Val Gly
1               5                   10                  15

Asp Arg Val Thr Ile Thr Cys Arg Ala Ser Gln Asp Ile Ser Ser Trp
            20                  25                  30

Leu Ala Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Thr Ser Tyr Pro Pro
                85                  90                  95

Trp Thr Phe Gly Gly Gly Thr Lys Val Glu Ile Lys
            100                 105

<210> SEQ ID NO 163
<211> LENGTH: 447
<212> TYPE: PRT
<213> ORGANISM: Artificial Sequence
<220> FEATURE:
<223> OTHER INFORMATION: Antibody 15503 Full-Length Heavy Chain

<400> SEQUENCE: 163

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Val Gly Phe Arg Ala Leu Asn Tyr Trp Gly Gln Gly Thr Thr
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190
```

Leu Gly Thr Gln Thr Tyr Ile Cys Asn Val Asn His Lys Pro Ser Asn
            195                 200                 205

Thr Lys Val Asp Lys Lys Val Glu Pro Lys Ser Cys Asp Lys Thr His
    210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Asp Glu Leu Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
        435                 440                 445

<210> SEQ ID NO 164
<211> LENGTH: 215
<212> TYPE: PRT
<213> ORGANISM: Artificial Sequence
<220> FEATURE:
<223> OTHER INFORMATION: Antibody 15503 Full-Length Light Chain

<400> SEQUENCE: 164

Asp Ile Gln Leu Thr Gln Ser Pro Ser Ser Val Ser Ala Ser Val Gly
1               5                   10                  15

Asp Arg Val Thr Ile Thr Cys Arg Ala Ser Gln Asp Ile Ser Ser Trp
            20                  25                  30

Leu Ala Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Thr Ser Tyr Pro Pro
                85                  90                  95

Trp Thr Phe Gly Gly Gly Thr Lys Val Glu Ile Lys Arg Thr Val Ala
            100                 105                 110

Ala Pro Ser Val Phe Ile Phe Pro Ser Asp Glu Gln Leu Lys Ser
         115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 165
<211> LENGTH: 9
<212> TYPE: PRT
<213> ORGANISM: Artificial Sequence
<220> FEATURE:
<223> OTHER INFORMATION: Antibody 15495 VH CDR1

<400> SEQUENCE: 165

Gly Thr Phe Ser Ser Tyr Ala Ile Ser
1               5

<210> SEQ ID NO 166
<211> LENGTH: 17
<212> TYPE: PRT
<213> ORGANISM: Artificial Sequence
<220> FEATURE:
<223> OTHER INFORMATION: Antibody 15495 VH CDR2

<400> SEQUENCE: 166

Gly Ile Ile Pro Ile Phe Gly Thr Ala Ser Tyr Ala Gln Lys Phe Gln
1               5                   10                  15

Gly

<210> SEQ ID NO 167
<211> LENGTH: 13
<212> TYPE: PRT
<213> ORGANISM: Artificial Sequence
<220> FEATURE:
<223> OTHER INFORMATION: Antibody 15495 VH CDR3

<400> SEQUENCE: 167

Ala Arg Gln Gln Tyr Asp Gly Arg Tyr Phe Gly Leu
1               5                   10

<210> SEQ ID NO 168
<211> LENGTH: 11
<212> TYPE: PRT
<213> ORGANISM: Artificial Sequence
<220> FEATURE:
<223> OTHER INFORMATION: Antibody 15495 VL CDR1

<400> SEQUENCE: 168

Arg Ala Ser Gln Ser Val Ser Ser Asn Leu Ala
1               5                   10

<210> SEQ ID NO 169
<211> LENGTH: 7
<212> TYPE: PRT

<213> ORGANISM: Artificial Sequence
<220> FEATURE:
<223> OTHER INFORMATION: Antibody 15495 VL CDR2

<400> SEQUENCE: 169

Ser Ala Ser Thr Arg Ala Thr
1               5

<210> SEQ ID NO 170
<211> LENGTH: 9
<212> TYPE: PRT
<213> ORGANISM: Artificial Sequence
<220> FEATURE:
<223> OTHER INFORMATION: Antibody 15495 VL CDR3

<400> SEQUENCE: 170

Gln Gln Val Asn Val Trp Pro Pro Thr
1               5

<210> SEQ ID NO 171
<211> LENGTH: 120
<212> TYPE: PRT
<213> ORGANISM: Artificial Sequence
<220> FEATURE:
<223> OTHER INFORMATION: Antibody 15495 Variable Heavy Chain

<400> SEQUENCE: 171

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Ser Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gln Gln Tyr Asp Gly Arg Arg Tyr Phe Gly Leu Trp Gly Arg
            100                 105                 110

Gly Thr Leu Val Thr Val Ser Ser
        115                 120

<210> SEQ ID NO 172
<211> LENGTH: 107
<212> TYPE: PRT
<213> ORGANISM: Artificial Sequence
<220> FEATURE:
<223> OTHER INFORMATION: Antibody 15495 Variable Light Chain

<400> SEQUENCE: 172

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Ser Ser Asn
            20                  25                  30

Leu Ala Trp Tyr Gln Gln Lys Pro Gly Gln Ala Pro Arg Leu Leu Ile
        35                  40                  45

Tyr Ser Ala Ser Thr Arg Ala Thr Gly Ile Pro Ala Arg Phe Ser Gly
    50                  55                  60

Ser Gly Ser Gly Thr Glu Phe Thr Leu Thr Ile Ser Ser Leu Gln Ser

```
                65                  70                  75                  80
Glu Asp Phe Ala Val Tyr Tyr Cys Gln Gln Val Asn Val Trp Pro Pro
                    85                  90                  95

Thr Phe Gly Gly Gly Thr Lys Val Glu Ile Lys
                100                 105

<210> SEQ ID NO 173
<211> LENGTH: 450
<212> TYPE: PRT
<213> ORGANISM: Artificial Sequence
<220> FEATURE:
<223> OTHER INFORMATION: Antibody 15495 Full-Length Heavy Chain

<400> SEQUENCE: 173

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
                20                  25                  30

Ala Ile Ser Trp Val Arg Gln Ala Pro Gly Gln Gly Leu Glu Trp Met
            35                  40                  45

Gly Gly Ile Ile Pro Ile Phe Gly Thr Ala Ser Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gln Gln Tyr Asp Gly Arg Arg Tyr Phe Gly Leu Trp Gly Arg
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
```

```
            325                 330                 335
Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
            355                 360                 365

Thr Cys Leu Val Lys Gly Phe Tyr Pro Ser Asp Ile Ala Val Glu Trp
            370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
            405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
            435                 440                 445

Gly Lys
    450

<210> SEQ ID NO 174
<211> LENGTH: 214
<212> TYPE: PRT
<213> ORGANISM: Artificial Sequence
<220> FEATURE:
<223> OTHER INFORMATION: Antibody 15495 Full-Length Light Chain

<400> SEQUENCE: 174

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Ser Ser Asn
            20                  25                  30

Leu Ala Trp Tyr Gln Gln Lys Pro Gly Gln Ala Pro Arg Leu Leu Ile
        35                  40                  45

Tyr Ser Ala Ser Thr Arg Ala Thr Gly Ile Pro Ala Arg Phe Ser Gly
50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Val Asn Val Trp Pro Pro
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
            165                 170                 175

Ser Thr Leu Thr Leu Ser Lys Ala Asp Tyr Glu Lys His Lys Val Tyr
        180                 185                 190

Ala Cys Glu Val Thr His Gln Gly Leu Ser Ser Pro Val Thr Lys Ser
            195                 200                 205

Phe Asn Arg Gly Glu Cys
    210
```

```
<210> SEQ ID NO 175
<211> LENGTH: 9
<212> TYPE: PRT
<213> ORGANISM: Artificial Sequence
<220> FEATURE:
<223> OTHER INFORMATION: Antibody 15478 VH CDR1

<400> SEQUENCE: 175

Gly Thr Phe Ser Ser Tyr Ala Ile Ser
1               5

<210> SEQ ID NO 176
<211> LENGTH: 17
<212> TYPE: PRT
<213> ORGANISM: Artificial Sequence
<220> FEATURE:
<223> OTHER INFORMATION: Antibody 15478 VH CDR2

<400> SEQUENCE: 176

Gly Ile Ile Pro Ile Phe Gly Thr Ala Asn Tyr Ala Gln Lys Phe Gln
1               5                   10                  15

Gly

<210> SEQ ID NO 177
<211> LENGTH: 9
<212> TYPE: PRT
<213> ORGANISM: Artificial Sequence
<220> FEATURE:
<223> OTHER INFORMATION: Antibody 15478 VH CDR3

<400> SEQUENCE: 177

Ala Arg Gly Gly Pro Trp Phe Asp Pro
1               5

<210> SEQ ID NO 178
<211> LENGTH: 11
<212> TYPE: PRT
<213> ORGANISM: Artificial Sequence
<220> FEATURE:
<223> OTHER INFORMATION: Antibody 15478 VL CDR1

<400> SEQUENCE: 178

Arg Ala Ser Gln Ser Ile Ser Ser Trp Leu Ala
1               5                   10

<210> SEQ ID NO 179
<211> LENGTH: 7
<212> TYPE: PRT
<213> ORGANISM: Artificial Sequence
<220> FEATURE:
<223> OTHER INFORMATION: Antibody 15478 VL CDR2

<400> SEQUENCE: 179

Lys Ala Ser Ser Leu Glu Ser
1               5

<210> SEQ ID NO 180
<211> LENGTH: 10
<212> TYPE: PRT
<213> ORGANISM: Artificial Sequence
<220> FEATURE:
<223> OTHER INFORMATION: Antibody 15478 VL CDR3

<400> SEQUENCE: 180

Gln Gln Tyr Asn Ser Tyr Pro Pro Phe Thr
1               5                   10
```

```
<210> SEQ ID NO 181
<211> LENGTH: 116
<212> TYPE: PRT
<213> ORGANISM: Artificial Sequence
<220> FEATURE:
<223> OTHER INFORMATION: Antibody 15478 Variable Heavy Chain

<400> SEQUENCE: 181

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Gly Pro Trp Phe Asp Pro Trp Gly Gln Gly Thr Leu Val
            100                 105                 110

Thr Val Ser Ser
        115

<210> SEQ ID NO 182
<211> LENGTH: 108
<212> TYPE: PRT
<213> ORGANISM: Artificial Sequence
<220> FEATURE:
<223> OTHER INFORMATION: Antibody 15478 Variable Light Chain

<400> SEQUENCE: 182

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Lys Ala Ser Ser Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Asn Ser Tyr Pro Pro
                85                  90                  95

Phe Thr Phe Gly Gly Gly Thr Lys Val Glu Ile Lys
            100                 105

<210> SEQ ID NO 183
<211> LENGTH: 446
<212> TYPE: PRT
<213> ORGANISM: Artificial Sequence
<220> FEATURE:
<223> OTHER INFORMATION: Antibody 15478 Full-Length Heavy Chain

<400> SEQUENCE: 183

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
```

```
                20                  25                  30
Ala Ile Ser Trp Val Arg Gln Ala Pro Gly Gln Gly Leu Glu Trp Met
                35                  40                  45

Gly Gly Ile Ile Pro Ile Phe Gly Thr Ala Asn Tyr Ala Gln Lys Phe
        50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Gly Pro Trp Phe Asp Pro Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Lys Thr His Thr
    210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Asp Glu Leu Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly Lys
        435                 440                 445
```

<210> SEQ ID NO 184
<211> LENGTH: 215
<212> TYPE: PRT
<213> ORGANISM: Artificial Sequence
<220> FEATURE:
<223> OTHER INFORMATION: Antibody 15478 Full-Length Light Chain

<400> SEQUENCE: 184

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Lys Ala Ser Ser Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Asn Ser Tyr Pro Pro
                85                  90                  95

Phe Thr Phe Gly Gly Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 185
<211> LENGTH: 9
<212> TYPE: PRT
<213> ORGANISM: Artificial Sequence
<220> FEATURE:
<223> OTHER INFORMATION: Antibody 15441 VH CDR1

<400> SEQUENCE: 185

Phe Thr Phe Ser Ser Tyr Ala Met Ser
1               5

<210> SEQ ID NO 186
<211> LENGTH: 17
<212> TYPE: PRT
<213> ORGANISM: Artificial Sequence
<220> FEATURE:
<223> OTHER INFORMATION: Antibody 15441 VH CDR2

<400> SEQUENCE: 186

Ala Ile Ser Gly Ser Gly Gly Thr Ser Tyr Ala Asp Ser Val Lys
1               5                   10                  15

Gly

<210> SEQ ID NO 187
<211> LENGTH: 13
<212> TYPE: PRT
<213> ORGANISM: Artificial Sequence
<220> FEATURE:
<223> OTHER INFORMATION: Antibody 15441 VH CDR3

<400> SEQUENCE: 187

Ala Lys Pro Ser Leu Ala Thr Met Leu Ala Phe Asp Ile
1               5                   10

<210> SEQ ID NO 188
<211> LENGTH: 11
<212> TYPE: PRT
<213> ORGANISM: Artificial Sequence
<220> FEATURE:
<223> OTHER INFORMATION: Antibody 15441 VL CDR1

<400> SEQUENCE: 188

Arg Ala Ser Gln Ser Ile Ser Ser Trp Leu Ala
1               5                   10

<210> SEQ ID NO 189
<211> LENGTH: 7
<212> TYPE: PRT
<213> ORGANISM: Artificial Sequence
<220> FEATURE:
<223> OTHER INFORMATION: Antibody 15441 VL CDR2

<400> SEQUENCE: 189

Asp Ala Ser Ser Leu Glu Ser
1               5

<210> SEQ ID NO 190
<211> LENGTH: 9
<212> TYPE: PRT
<213> ORGANISM: Artificial Sequence
<220> FEATURE:
<223> OTHER INFORMATION: Antibody 15441 VL CDR3

<400> SEQUENCE: 190

Gln Gln Ser Lys Ser Tyr Pro Arg Thr
1               5

<210> SEQ ID NO 191
<211> LENGTH: 120
<212> TYPE: PRT
<213> ORGANISM: Artificial Sequence
<220> FEATURE:
<223> OTHER INFORMATION: Antibody 15441 Variable Heavy Chain

<400> SEQUENCE: 191

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
                20                  25                  30

Ala Met Ser Trp Val Arg Gln Ala Pro Gly Lys Gly Leu Glu Trp Val
            35                  40                  45

Ser Ala Ile Ser Gly Ser Gly Gly Ser Thr Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

```
Leu Gln Met Asn Ser Leu Arg Ala Glu Asp Thr Ala Val Tyr Tyr Cys
                85                  90                  95

Ala Lys Pro Ser Leu Ala Thr Met Leu Ala Phe Asp Ile Trp Gly Gln
            100                 105                 110

Gly Thr Met Val Thr Val Ser Ser
        115                 120

<210> SEQ ID NO 192
<211> LENGTH: 107
<212> TYPE: PRT
<213> ORGANISM: Artificial Sequence
<220> FEATURE:
<223> OTHER INFORMATION: Antibody 15441 Variable Light Chain

<400> SEQUENCE: 192

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Asp Ala Ser Ser Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Ser Lys Ser Tyr Pro Arg
                85                  90                  95

Thr Phe Gly Gly Gly Thr Lys Val Glu Ile Lys
            100                 105

<210> SEQ ID NO 193
<211> LENGTH: 450
<212> TYPE: PRT
<213> ORGANISM: Artificial Sequence
<220> FEATURE:
<223> OTHER INFORMATION: Antibody 15441 Full-Length Heavy Chain

<400> SEQUENCE: 193

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Pro Ser Leu Ala Thr Met Leu Ala Phe Asp Ile Trp Gly Gln
            100                 105                 110

Gly Thr Met Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160
```

Trp Asn Ser Gly Ala Leu Thr Ser Gly Val His Thr Phe Pro Ala Val
            165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
            195                 200                 205

Pro Ser Asn Thr Lys Val Asp Lys Lys Val Glu Pro Lys Ser Cys Asp
            210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
            245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
            275                 280                 285

Asn Ala Lys Thr Lys Pro Arg Glu Glu Gln Tyr Asn Ser Thr Tyr Arg
            290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
            325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
            355                 360                 365

Thr Cys Leu Val Lys Gly Phe Tyr Pro Ser Asp Ile Ala Val Glu Trp
            370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
            405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
            435                 440                 445

Gly Lys
    450

<210> SEQ ID NO 194
<211> LENGTH: 214
<212> TYPE: PRT
<213> ORGANISM: Artificial Sequence
<220> FEATURE:
<223> OTHER INFORMATION: Antibody 15441 Full-Length Light Chain

<400> SEQUENCE: 194

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
            35                  40                  45

Tyr Asp Ala Ser Ser Leu Glu Ser Gly Val Pro Ser Arg Phe Ser Gly
    50                  55                  60

```
Ser Gly Ser Gly Thr Glu Phe Thr Leu Thr Ile Ser Ser Leu Gln Pro
 65                  70                  75                  80

Asp Asp Phe Ala Thr Tyr Tyr Cys Gln Gln Ser Lys Ser Tyr Pro Arg
                 85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 195
<211> LENGTH: 11
<212> TYPE: PRT
<213> ORGANISM: Artificial Sequence
<220> FEATURE:
<223> OTHER INFORMATION: Antibody 20496 VH CDR1

<400> SEQUENCE: 195

Gly Ser Ile Ser Ser Ser Val Tyr Tyr Trp Ser
1               5                   10

<210> SEQ ID NO 196
<211> LENGTH: 16
<212> TYPE: PRT
<213> ORGANISM: Artificial Sequence
<220> FEATURE:
<223> OTHER INFORMATION: Antibody 20496 VH CDR2

<400> SEQUENCE: 196

Ser Ile Leu Val Ser Gly Ser Thr Tyr Tyr Asn Pro Ser Leu Lys Ser
1               5                   10                  15

<210> SEQ ID NO 197
<211> LENGTH: 9
<212> TYPE: PRT
<213> ORGANISM: Artificial Sequence
<220> FEATURE:
<223> OTHER INFORMATION: Antibody 20496 VH CDR3

<400> SEQUENCE: 197

Ala Arg Ala Val Ser Phe Leu Asp Val
1               5

<210> SEQ ID NO 198
<211> LENGTH: 11
<212> TYPE: PRT
<213> ORGANISM: Artificial Sequence
<220> FEATURE:
<223> OTHER INFORMATION: Antibody 20496 VL CDR1

<400> SEQUENCE: 198
```

Arg Ala Ser Gln Ser Ile Ser Ser Tyr Leu Asn
1               5                   10

<210> SEQ ID NO 199
<211> LENGTH: 7
<212> TYPE: PRT
<213> ORGANISM: Artificial Sequence
<220> FEATURE:
<223> OTHER INFORMATION: Antibody 20496 VL CDR2

<400> SEQUENCE: 199

Gly Ala Ser Ser Leu Gln Ser
1               5

<210> SEQ ID NO 200
<211> LENGTH: 9
<212> TYPE: PRT
<213> ORGANISM: Artificial Sequence
<220> FEATURE:
<223> OTHER INFORMATION: Antibody 20496 VL CDR3

<400> SEQUENCE: 200

Gln Gln Ser Tyr Asp Pro Pro Trp Thr
1               5

<210> SEQ ID NO 201
<211> LENGTH: 117
<212> TYPE: PRT
<213> ORGANISM: Artificial Sequence
<220> FEATURE:
<223> OTHER INFORMATION: Antibody 20496 Variable Heavy Chain

<400> SEQUENCE: 201

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Ser
            20                  25                  30

Val Tyr Tyr Trp Ser Trp Ile Arg Gln Pro Pro Gly Lys Gly Leu Glu
        35                  40                  45

Trp Ile Gly Ser Ile Leu Val Ser Gly Ser Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Ala Val Ser Phe Leu Asp Val Trp Gly Gln Gly Thr Met
            100                 105                 110

Val Ile Val Ser Ser
        115

<210> SEQ ID NO 202
<211> LENGTH: 107
<212> TYPE: PRT
<213> ORGANISM: Artificial Sequence
<220> FEATURE:
<223> OTHER INFORMATION: Antibody 20496 Variable Light Chain

<400> SEQUENCE: 202

Asp Ile Gln Met Thr Gln Ser Pro Ser Leu Ser Ala Ser Val Gly
1               5                   10                  15

Asp Arg Val Thr Ile Thr Cys Arg Ala Ser Gln Ser Ile Ser Ser Tyr
            20                  25                  30

```
Leu Asn Trp Tyr Gln Gln Lys Pro Gly Lys Ala Pro Lys Leu Leu Ile
             35                  40                  45

Tyr Gly Ala Ser Ser Leu Gln Ser Gly Val Pro Ser Arg Phe Ser Gly
         50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Ser Tyr Asp Pro Pro Trp
                 85                  90                  95

Thr Phe Gly Gly Gly Thr Lys Val Glu Ile Lys
                100                 105

<210> SEQ ID NO 203
<211> LENGTH: 447
<212> TYPE: PRT
<213> ORGANISM: Artificial Sequence
<220> FEATURE:
<223> OTHER INFORMATION: Antibody 20496 Full-Length Heavy Chain

<400> SEQUENCE: 203

Gln Leu Gln Leu Gln Glu Ser Gly Pro Gly Leu Val Lys Pro Ser Glu
1               5                  10                  15

Thr Leu Ser Leu Thr Cys Thr Val Ser Gly Gly Ser Ile Ser Ser Ser
             20                  25                  30

Val Tyr Tyr Trp Ser Trp Ile Arg Gln Pro Pro Gly Lys Gly Leu Glu
         35                  40                  45

Trp Ile Gly Ser Ile Leu Val Ser Gly Ser Thr Tyr Tyr Asn Pro Ser
 50                  55                  60

Leu Lys Ser Arg Val Thr Ile Ser Val Asp Thr Ser Lys Asn Gln Phe
 65                  70                  75                  80

Ser Leu Lys Leu Ser Ser Val Thr Ala Ala Asp Thr Ala Val Tyr Tyr
                 85                  90                  95

Cys Ala Arg Ala Val Ser Phe Leu Asp Val Trp Gly Gln Gly Thr Met
            100                 105                 110

Val Ile Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys Asp Lys Thr His
    210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285
```

```
Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
                340                 345                 350

Pro Ser Arg Asp Glu Leu Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
                420                 425                 430

His Asn His Tyr Thr Gln Lys Ser Leu Ser Leu Ser Pro Gly Lys
        435                 440                 445
```

<210> SEQ ID NO 204
<211> LENGTH: 214
<212> TYPE: PRT
<213> ORGANISM: Artificial Sequence
<220> FEATURE:
<223> OTHER INFORMATION: Antibody 20496 Full-Length Light Chain

<400> SEQUENCE: 204

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Gly Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Asp Pro Pro Trp
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205
```

```
Phe Asn Arg Gly Glu Cys
    210

<210> SEQ ID NO 205
<211> LENGTH: 26
<212> TYPE: PRT
<213> ORGANISM: Artificial Sequence
<220> FEATURE:
<223> OTHER INFORMATION: Antibody 15461 VH FR1

<400> SEQUENCE: 205

Gln Leu Gln Leu Gln Glu Ser Gly Pro Gly Leu Val Lys Pro Ser Glu
1               5                   10                  15

Thr Leu Ser Leu Thr Cys Thr Val Ser Gly
            20                  25

<210> SEQ ID NO 206
<211> LENGTH: 14
<212> TYPE: PRT
<213> ORGANISM: Artificial Sequence
<220> FEATURE:
<223> OTHER INFORMATION: Antibody 15461 VH FR2

<400> SEQUENCE: 206

Trp Ile Arg Gln Pro Pro Gly Lys Gly Leu Glu Trp Ile Gly
1               5                   10

<210> SEQ ID NO 207
<211> LENGTH: 30
<212> TYPE: PRT
<213> ORGANISM: Artificial Sequence
<220> FEATURE:
<223> OTHER INFORMATION: Antibody 15461 VH FR3

<400> SEQUENCE: 207

Arg Val Thr Ile Ser Val Asp Thr Ser Lys Asn Gln Phe Ser Leu Lys
1               5                   10                  15

Leu Ser Ser Val Thr Ala Ala Asp Thr Ala Val Tyr Tyr Cys
            20                  25                  30

<210> SEQ ID NO 208
<211> LENGTH: 11
<212> TYPE: PRT
<213> ORGANISM: Artificial Sequence
<220> FEATURE:
<223> OTHER INFORMATION: Antibody 15461 VH FR4

<400> SEQUENCE: 208

Trp Gly Gln Gly Thr Leu Val Thr Val Ser Ser
1               5                   10

<210> SEQ ID NO 209
<211> LENGTH: 23
<212> TYPE: PRT
<213> ORGANISM: Artificial Sequence
<220> FEATURE:
<223> OTHER INFORMATION: Antibody 15461 VL FR1

<400> SEQUENCE: 209

Glu Ile Val Met Thr Gln Ser Pro Ala Thr Leu Ser Val Ser Pro Gly
1               5                   10                  15

Glu Arg Ala Thr Leu Ser Cys
            20
```

<210> SEQ ID NO 210
<211> LENGTH: 15
<212> TYPE: PRT
<213> ORGANISM: Artificial Sequence
<220> FEATURE:
<223> OTHER INFORMATION: Antibody 15461 VL FR2

<400> SEQUENCE: 210

Trp Tyr Gln Gln Lys Pro Gly Gln Ala Pro Arg Leu Leu Ile Tyr
1               5                   10                  15

<210> SEQ ID NO 211
<211> LENGTH: 32
<212> TYPE: PRT
<213> ORGANISM: Artificial Sequence
<220> FEATURE:
<223> OTHER INFORMATION: Antibody 15461 VL FR3

<400> SEQUENCE: 211

Gly Ile Pro Ala Arg Phe Ser Gly Ser Gly Ser Gly Thr Glu Phe Thr
1               5                   10                  15

Leu Thr Ile Ser Ser Leu Gln Ser Glu Asp Phe Ala Val Tyr Tyr Cys
            20                  25                  30

<210> SEQ ID NO 212
<211> LENGTH: 10
<212> TYPE: PRT
<213> ORGANISM: Artificial Sequence
<220> FEATURE:
<223> OTHER INFORMATION: Antibody 15461 VL FR4

<400> SEQUENCE: 212

Phe Gly Gly Gly Thr Lys Val Glu Ile Lys
1               5                   10

<210> SEQ ID NO 213
<211> LENGTH: 360
<212> TYPE: DNA
<213> ORGANISM: Artificial Sequence
<220> FEATURE:
<223> OTHER INFORMATION: Antibody 15461 Variable Heavy Chain-Encoding
      Polynucleotide Sequence

<400> SEQUENCE: 213
cagctgcagc tgcaggagtc gggcccagga ctggtgaagc cttcggagac cctgtccctc      60
acctgcactg tctctggtgg ctccatcagc agtagtagtt actactgggg ctggatccgc     120
cagcccccag gaaggggct ggagtggatt gggaacatct attatagtgg gagcacctac      180
tacaacccgt ccctcaagag tcgagtcacc atatccgtag acacgtccaa gaaccagttc     240
tccctgaagc tgagttctgt gaccgccgca gacacggcgg tgtactactg cgccagagaa     300
ggatcttacc ccaattggtt tgatccatgg ggacagggta cattggtcac cgtctcctca     360

<210> SEQ ID NO 214
<211> LENGTH: 321
<212> TYPE: DNA
<213> ORGANISM: Artificial Sequence
<220> FEATURE:
<223> OTHER INFORMATION: Antibody 15461 Variable Light Chain-Encoding
      Polynucleotide Sequence

<400> SEQUENCE: 214
gaaatagtga tgacgcagtc tccagccacc ctgtctgtgt ctccagggga aagagccacc      60
ctctcctgca gggccagtca gagtgttagc agcaacttag cctggtacca gcagaaacct     120

```
ggccaggctc ccaggctcct catctatggt gcatccacca gggccactgg tatcccagcc    180
aggttcagtg gcagtgggtc tgggacagag ttcactctca ccatcagcag cctgcagtct    240
gaagattttg cagtttatta ctgtcagcag taccactcct cccttttcac ttttggcgga    300
gggaccaagg ttgagatcaa a                                              321
```

<210> SEQ ID NO 215
<211> LENGTH: 26
<212> TYPE: PRT
<213> ORGANISM: Artificial Sequence
<220> FEATURE:
<223> OTHER INFORMATION: Antibody 20500 VH FR1

<400> SEQUENCE: 215

Gln Leu Gln Leu Gln Glu Ser Gly Pro Gly Leu Val Lys Pro Ser Glu
1               5                   10                  15

Thr Leu Ser Leu Thr Cys Thr Val Ser Gly
            20                  25

<210> SEQ ID NO 216
<211> LENGTH: 14
<212> TYPE: PRT
<213> ORGANISM: Artificial Sequence
<220> FEATURE:
<223> OTHER INFORMATION: Antibody 20500 VH FR2

<400> SEQUENCE: 216

Trp Ile Arg Gln Pro Pro Gly Lys Gly Leu Glu Trp Ile Gly
1               5                   10

<210> SEQ ID NO 217
<211> LENGTH: 30
<212> TYPE: PRT
<213> ORGANISM: Artificial Sequence
<220> FEATURE:
<223> OTHER INFORMATION: Antibody 20500 VH FR3

<400> SEQUENCE: 217

Arg Val Thr Ile Ser Val Asp Thr Ser Lys Asn Gln Phe Ser Leu Lys
1               5                   10                  15

Leu Ser Ser Val Thr Ala Ala Asp Thr Ala Val Tyr Tyr Cys
            20                  25                  30

<210> SEQ ID NO 218
<211> LENGTH: 11
<212> TYPE: PRT
<213> ORGANISM: Artificial Sequence
<220> FEATURE:
<223> OTHER INFORMATION: Antibody 20500 VH FR4

<400> SEQUENCE: 218

Trp Gly Gln Gly Thr Leu Val Thr Val Ser Ser
1               5                   10

<210> SEQ ID NO 219
<211> LENGTH: 23
<212> TYPE: PRT
<213> ORGANISM: Artificial Sequence
<220> FEATURE:
<223> OTHER INFORMATION: Antibody 20500 VL FR1

<400> SEQUENCE: 219

Glu Ile Val Met Thr Gln Ser Pro Ala Thr Leu Ser Val Ser Pro Gly
1               5                   10                  15

Glu Arg Ala Thr Leu Ser Cys
            20

<210> SEQ ID NO 220
<211> LENGTH: 15
<212> TYPE: PRT
<213> ORGANISM: Artificial Sequence
<220> FEATURE:
<223> OTHER INFORMATION: Antibody 20500 VL FR2

<400> SEQUENCE: 220

Trp Tyr Gln Gln Lys Pro Gly Gln Ala Pro Arg Leu Leu Ile Tyr
1               5                   10                  15

<210> SEQ ID NO 221
<211> LENGTH: 32
<212> TYPE: PRT
<213> ORGANISM: Artificial Sequence
<220> FEATURE:
<223> OTHER INFORMATION: Antibody 20500 VL FR3

<400> SEQUENCE: 221

Gly Ile Pro Ala Arg Phe Ser Gly Ser Gly Ser Gly Thr Glu Phe Thr
1               5                   10                  15

Leu Thr Ile Ser Ser Leu Gln Ser Glu Asp Phe Ala Val Tyr Tyr Cys
            20                  25                  30

<210> SEQ ID NO 222
<211> LENGTH: 10
<212> TYPE: PRT
<213> ORGANISM: Artificial Sequence
<220> FEATURE:
<223> OTHER INFORMATION: Antibody 20500 VL FR4

<400> SEQUENCE: 222

Phe Gly Gly Gly Thr Lys Val Glu Ile Lys
1               5                   10

<210> SEQ ID NO 223
<211> LENGTH: 360
<212> TYPE: DNA
<213> ORGANISM: Artificial Sequence
<220> FEATURE:
<223> OTHER INFORMATION: Antibody 20500 Variable Heavy Chain-Encoding
      Polynucleotide Sequence

<400> SEQUENCE: 223
cagctgcagc tgcaggagtc gggcccagga ctggtgaagc cttcggagac cctgtccctc      60
acctgcactg tctctggtgg ctccatcaag agtggtagtc actactgggg ctggatccgc     120
cagcccccag ggaaggggct ggagtggatt gggaacatct attatagtgg gagcacctac     180
tacaacccgt ccctcaggag tcgagtcacc atatccgtag acacgtccaa gaaccagttc     240
tccctgaagc tgagttctgt gaccgccgca gacacggcgg tgtactactg cgccagggaa     300
ggatcttacc ccaattggtt tgatccatgg ggacagggta cattggtcac cgtctcctca     360

<210> SEQ ID NO 224
<211> LENGTH: 321
<212> TYPE: DNA
<213> ORGANISM: Artificial Sequence
<220> FEATURE:
<223> OTHER INFORMATION: Antibody 20500 Variable Light Chain-Encoding
      Polynucleotide Sequence

<400> SEQUENCE: 224

-continued

```
gaaatagtga tgacgcagtc tccagccacc ctgtctgtgt ctccagggga aagagccacc    60
ctctcctgca gggccagtca gagtgttagc agcaacttag cctggtacca gcagaaacct   120
ggccaggctc ccaggctcct catctatggt gcatccacca gggccactgg tatcccagcc   180
aggttcagtg gcagtgggtc tgggacagag ttcactctca ccatcagcag cctgcagtct   240
gaagattttg cagtttatta ctgtcagcag taccactcct tccctttcac ttttggcgga   300
gggaccaagg ttgagatcaa a                                             321
```

<210> SEQ ID NO 225
<211> LENGTH: 26
<212> TYPE: PRT
<213> ORGANISM: Artificial Sequence
<220> FEATURE:
<223> OTHER INFORMATION: Antibody 20501 VH FR1

<400> SEQUENCE: 225

Gln Leu Gln Leu Gln Glu Ser Gly Pro Gly Leu Val Lys Pro Ser Glu
1               5                   10                  15

Thr Leu Ser Leu Thr Cys Thr Val Ser Gly
            20                  25

<210> SEQ ID NO 226
<211> LENGTH: 14
<212> TYPE: PRT
<213> ORGANISM: Artificial Sequence
<220> FEATURE:
<223> OTHER INFORMATION: Antibody 20501 VH FR2

<400> SEQUENCE: 226

Trp Ile Arg Gln Pro Pro Gly Lys Gly Leu Glu Trp Ile Gly
1               5                   10

<210> SEQ ID NO 227
<211> LENGTH: 30
<212> TYPE: PRT
<213> ORGANISM: Artificial Sequence
<220> FEATURE:
<223> OTHER INFORMATION: Antibody 20501 VH FR3

<400> SEQUENCE: 227

Arg Val Thr Ile Ser Val Asp Thr Ser Lys Asn Gln Phe Ser Leu Lys
1               5                   10                  15

Leu Ser Ser Val Thr Ala Ala Asp Thr Ala Val Tyr Tyr Cys
            20                  25                  30

<210> SEQ ID NO 228
<211> LENGTH: 11
<212> TYPE: PRT
<213> ORGANISM: Artificial Sequence
<220> FEATURE:
<223> OTHER INFORMATION: Antibody 20501 VH FR4

<400> SEQUENCE: 228

Trp Gly Gln Gly Thr Leu Val Thr Val Ser Ser
1               5                   10

<210> SEQ ID NO 229
<211> LENGTH: 23
<212> TYPE: PRT
<213> ORGANISM: Artificial Sequence
<220> FEATURE:
<223> OTHER INFORMATION: Antibody 20501 VL FR1

<400> SEQUENCE: 229

Glu Ile Val Met Thr Gln Ser Pro Ala Thr Leu Ser Val Ser Pro Gly
1               5                   10                  15

Glu Arg Ala Thr Leu Ser Cys
                20

<210> SEQ ID NO 230
<211> LENGTH: 15
<212> TYPE: PRT
<213> ORGANISM: Artificial Sequence
<220> FEATURE:
<223> OTHER INFORMATION: Antibody 20501 VL FR2

<400> SEQUENCE: 230

Trp Tyr Gln Gln Lys Pro Gly Gln Ala Pro Arg Leu Leu Ile Tyr
1               5                   10                  15

<210> SEQ ID NO 231
<211> LENGTH: 32
<212> TYPE: PRT
<213> ORGANISM: Artificial Sequence
<220> FEATURE:
<223> OTHER INFORMATION: Antibody 20501 VL FR3

<400> SEQUENCE: 231

Gly Ile Pro Ala Arg Phe Ser Gly Ser Gly Ser Gly Thr Glu Phe Thr
1               5                   10                  15

Leu Thr Ile Ser Ser Leu Gln Ser Glu Asp Phe Ala Val Tyr Tyr Cys
                20                  25                  30

<210> SEQ ID NO 232
<211> LENGTH: 10
<212> TYPE: PRT
<213> ORGANISM: Artificial Sequence
<220> FEATURE:
<223> OTHER INFORMATION: Antibody 20501 VL FR4

<400> SEQUENCE: 232

Phe Gly Gly Gly Thr Lys Val Glu Ile Lys
1               5                   10

<210> SEQ ID NO 233
<211> LENGTH: 360
<212> TYPE: DNA
<213> ORGANISM: Artificial Sequence
<220> FEATURE:
<223> OTHER INFORMATION: Antibody 20501 Variable Heavy Chain-Encoding
      Polynucleotide Sequence

<400> SEQUENCE: 233
cagctgcagc tgcaggagtc gggcccagga ctggtgaagc cttcggagac cctgtccctc      60
acctgcactg tctctggtgg ctccatcaag agtggtagtc actactgggg ctggatccgc     120
cagcccccag ggaagggact ggagtggatt gggaacatct attatagtgg agcacctac     180 tacaacccgt ccctcaagag tcgagtcacc atatccgtag acacgtccaa gaaccagttc     240
tccctgaagc tgagttctgt gaccgccgca gacacggcgg tgtactactg cgccagagaa     300
ggatcttacc ccaattggtt ggatccatgg ggacagggta cattggtcac cgtctcctca     360

<210> SEQ ID NO 234
<211> LENGTH: 321
<212> TYPE: DNA
<213> ORGANISM: Artificial Sequence
<220> FEATURE:
<223> OTHER INFORMATION: Antibody 20501 Variable Light Chain-Encoding -continued Polynucleotide Sequence

<400> SEQUENCE: 234

```
gaaatagtga tgacgcagtc tccagccacc ctgtctgtgt ctccagggga aagagccacc    60
ctctcctgca gggccagtca gagtgttagc agcaacttag cctggtacca gcagaaacct   120
ggccaggctc ccaggctcct catctatggt gcatccacca gggccactgg tatcccagcc   180
aggttcagtg gcagtgggtc tgggacagag ttcactctca ccatcagcag cctgcagtct   240
gaagattttg cagtttatta ctgtcagcag taccactcct tcccttttcac ttttggcgga   300
gggaccaagg ttgagatcaa a                                             321
```

<210> SEQ ID NO 235
<211> LENGTH: 26
<212> TYPE: PRT
<213> ORGANISM: Artificial Sequence
<220> FEATURE:
<223> OTHER INFORMATION: Antibody 20502.1 VH FR1

<400> SEQUENCE: 235

Gln Leu Gln Leu Gln Glu Ser Gly Pro Gly Leu Val Lys Pro Ser Glu
1               5                   10                  15
Thr Leu Ser Leu Thr Cys Thr Val Ser Gly
            20                  25

<210> SEQ ID NO 236
<211> LENGTH: 14
<212> TYPE: PRT
<213> ORGANISM: Artificial Sequence
<220> FEATURE:
<223> OTHER INFORMATION: Antibody 20502.1 VH FR2

<400> SEQUENCE: 236

Trp Ile Arg Gln Pro Pro Gly Lys Gly Leu Glu Trp Ile Gly
1               5                   10

<210> SEQ ID NO 237
<211> LENGTH: 30
<212> TYPE: PRT
<213> ORGANISM: Artificial Sequence
<220> FEATURE:
<223> OTHER INFORMATION: Antibody 20502.1 VH FR3

<400> SEQUENCE: 237

Arg Val Thr Ile Ser Val Asp Thr Ser Lys Asn Gln Phe Ser Leu Lys
1               5                   10                  15
Leu Ser Ser Val Thr Ala Ala Asp Thr Ala Val Tyr Tyr Cys
            20                  25                  30

<210> SEQ ID NO 238
<211> LENGTH: 11
<212> TYPE: PRT
<213> ORGANISM: Artificial Sequence
<220> FEATURE:
<223> OTHER INFORMATION: Antibody 20502.1 VH FR4

<400> SEQUENCE: 238

Trp Gly Gln Gly Ile Leu Val Thr Val Ser Ser
1               5                   10

<210> SEQ ID NO 239
<211> LENGTH: 23
<212> TYPE: PRT
<213> ORGANISM: Artificial Sequence

```
<220> FEATURE:
<223> OTHER INFORMATION: Antibody 20502 and 20502.1  VL FR1

<400> SEQUENCE: 239

Glu Ile Val Met Thr Gln Ser Pro Ala Thr Leu Ser Val Ser Pro Gly
1               5                   10                  15

Glu Arg Ala Thr Leu Ser Cys
            20

<210> SEQ ID NO 240
<211> LENGTH: 15
<212> TYPE: PRT
<213> ORGANISM: Artificial Sequence
<220> FEATURE:
<223> OTHER INFORMATION: Antibody 20502 and 20502.1  VL FR2

<400> SEQUENCE: 240

Trp Tyr Gln Gln Lys Pro Gly Gln Ala Pro Arg Leu Leu Ile Tyr
1               5                   10                  15

<210> SEQ ID NO 241
<211> LENGTH: 32
<212> TYPE: PRT
<213> ORGANISM: Artificial Sequence
<220> FEATURE:
<223> OTHER INFORMATION: Antibody 20502 and 20502.1  VL FR3

<400> SEQUENCE: 241

Gly Ile Pro Ala Arg Phe Ser Gly Ser Gly Ser Gly Thr Glu Phe Thr
1               5                   10                  15

Leu Thr Ile Ser Ser Leu Gln Ser Glu Asp Phe Ala Val Tyr Tyr Cys
            20                  25                  30

<210> SEQ ID NO 242
<211> LENGTH: 10
<212> TYPE: PRT
<213> ORGANISM: Artificial Sequence
<220> FEATURE:
<223> OTHER INFORMATION: Antibody20502 and 20502.1  VL FR4

<400> SEQUENCE: 242

Phe Gly Gly Gly Thr Lys Val Glu Ile Lys
1               5                   10

<210> SEQ ID NO 243
<211> LENGTH: 360
<212> TYPE: DNA
<213> ORGANISM: Artificial Sequence
<220> FEATURE:
<223> OTHER INFORMATION: Antibody 20502.1  Variable Heavy Chain-Encoding
      Polynucleotide Sequence

<400> SEQUENCE: 243
cagctgcagc tgcaggagtc gggcccagga ctggtgaagc cttcggagac cctgtccctc      60
acctgcactg tctctggtgg ctccatcaag agtggtagtt actactgggg ctggatccgc     120
cagcccccag ggaaggggct ggagtggatt gggaacatct attatagtgg gagcacctac     180
tacaacccgt ccctcaagag tcgagtcacc atatccgtag acacgtccaa gaaccagttc     240
tccctgaagc tgagttctgt gaccgccgca gacacggcgg tgtactactg cgccagagaa     300
ggatcttacc ccaatcagtt tgatccatgg ggacagggta tattggtcac cgtctcctca     360

<210> SEQ ID NO 244
<211> LENGTH: 321
```

<212> TYPE: DNA
<213> ORGANISM: Artificial Sequence
<220> FEATURE:
<223> OTHER INFORMATION: Antibody 20502 and 20502.1  Variable Light
      Chain-Encoding Polynucleotide Sequence

<400> SEQUENCE: 244
gaaatagtga tgacgcagtc tccagccacc ctgtctgtgt ctccagggga aagagccacc    60
ctctcctgca gggccagtca gagtgttagc agcaacttag cctggtacca gcagaaacct   120
ggccaggctc ccaggctcct catctatggt gcatccacca gggccactgg tatcccagcc   180
aggttcagtg gcagtgggtc tgggacagag ttcactctca ccatcagcag cctgcagtct   240
gaagattttg cagtttatta ctgtcagcag taccactcct tcccttttcac ttttggcgga   300 gggaccaagg ttgagatcaa a                                              321

<210> SEQ ID NO 245
<211> LENGTH: 26
<212> TYPE: PRT
<213> ORGANISM: Artificial Sequence
<220> FEATURE:
<223> OTHER INFORMATION: Antibody 22208 VH FR1

<400> SEQUENCE: 245

Gln Leu Gln Leu Gln Glu Ser Gly Pro Gly Leu Val Lys Pro Ser Glu
1               5                   10                  15

Thr Leu Ser Leu Thr Cys Thr Val Ser Gly
            20                  25

<210> SEQ ID NO 246
<211> LENGTH: 14
<212> TYPE: PRT
<213> ORGANISM: Artificial Sequence
<220> FEATURE:
<223> OTHER INFORMATION: Antibody 22208  VH FR2

<400> SEQUENCE: 246

Trp Ile Arg Gln Pro Pro Gly Lys Gly Leu Glu Trp Ile Gly
1               5                   10

<210> SEQ ID NO 247
<211> LENGTH: 30
<212> TYPE: PRT
<213> ORGANISM: Artificial Sequence
<220> FEATURE:
<223> OTHER INFORMATION: Antibody 22208  VH FR3

<400> SEQUENCE: 247

Arg Val Thr Met Ser Val Asp Thr Ser Lys Asn Gln Phe Ser Leu Lys
1               5                   10                  15

Leu Ser Ser Val Thr Ala Ala Asp Thr Ala Val Tyr Tyr Cys
            20                  25                  30

<210> SEQ ID NO 248
<211> LENGTH: 11
<212> TYPE: PRT
<213> ORGANISM: Artificial Sequence
<220> FEATURE:
<223> OTHER INFORMATION: Antibody 22208  VH FR4

<400> SEQUENCE: 248

Trp Gly Gln Gly Thr Leu Val Thr Val Ser Ser
1               5                   10

-continued

```
<210> SEQ ID NO 249
<211> LENGTH: 23
<212> TYPE: PRT
<213> ORGANISM: Artificial Sequence
<220> FEATURE:
<223> OTHER INFORMATION: Antibody 22208  VL FR1

<400> SEQUENCE: 249

Glu Ile Val Met Thr Gln Ser Pro Ala Thr Leu Ser Val Ser Pro Gly
1               5                   10                  15

Glu Arg Ala Thr Leu Ser Cys
            20

<210> SEQ ID NO 250
<211> LENGTH: 15
<212> TYPE: PRT
<213> ORGANISM: Artificial Sequence
<220> FEATURE:
<223> OTHER INFORMATION: Antibody 22208  VL FR2

<400> SEQUENCE: 250

Trp Tyr Gln Gln Lys Pro Gly Gln Ala Pro Arg Leu Leu Ile Tyr
1               5                   10                  15

<210> SEQ ID NO 251
<211> LENGTH: 32
<212> TYPE: PRT
<213> ORGANISM: Artificial Sequence
<220> FEATURE:
<223> OTHER INFORMATION: Antibody 22208  VL FR3

<400> SEQUENCE: 251

Gly Ile Pro Ala Arg Phe Ser Gly Ser Gly Ser Gly Thr Glu Phe Thr
1               5                   10                  15

Leu Thr Ile Ser Ser Leu Gln Ser Glu Asp Phe Ala Val Tyr Tyr Cys
            20                  25                  30

<210> SEQ ID NO 252
<211> LENGTH: 10
<212> TYPE: PRT
<213> ORGANISM: Artificial Sequence
<220> FEATURE:
<223> OTHER INFORMATION: Antibody 22208  VL FR4

<400> SEQUENCE: 252

Phe Gly Gly Gly Thr Lys Val Glu Ile Lys
1               5                   10

<210> SEQ ID NO 253
<211> LENGTH: 360
<212> TYPE: DNA
<213> ORGANISM: Artificial Sequence
<220> FEATURE:
<223> OTHER INFORMATION: Antibody 22208  Variable Heavy Chain-Encoding
      Polynucleotide Sequence

<400> SEQUENCE: 253
cagctgcagc tgcaggagtc gggcccagga ctggtgaagc cttcggagac cctgtccctc      60
acctgcactg tctctggtgg ctccatcaag agtggtagtc actactgggg ctggatccgc     120
cagcccccag ggaaggggct ggagtggatt gggaacatct attatagtgg gagcacctac     180
tacaacccgt ccctcaagag tcgagtcacc atgtccgtag acacgtccaa gaaccagttc     240
tccctgaagc tgagttctgt gaccgccgca gacacggcgg tgtactactg cgccagagaa     300
ggatcttacc ccaattggtt tgatccatgg ggacagggta cattggtcac cgtctcctca     360
```

<210> SEQ ID NO 254
<211> LENGTH: 321
<212> TYPE: DNA
<213> ORGANISM: Artificial Sequence
<220> FEATURE:
<223> OTHER INFORMATION: Antibody 22208  Variable Light Chain-Encoding
      Polynucleotide Sequence

<400> SEQUENCE: 254
gaaatagtga tgacgcagtc tccagccacc ctgtctgtgt ctccagggga aagagccacc    60
ctctcctgca gggccagtca gtccgttagc accaacttag cctggtacca gcagaaacct   120
ggccaggctc ccaggctcct catctatgac gcatccgcca gggtcactgg tatcccagcc   180
aggttcagtg gcagtgggtc tgggacagag ttcactctca ccatcagcag cctgcagtct   240
gaagattttg cagtttatta ctgtcagcag taccactcct tcccttt cac ttttggcgga   300 gggaccaagg ttgagatcaa a                                             321

<210> SEQ ID NO 255
<211> LENGTH: 26
<212> TYPE: PRT
<213> ORGANISM: Artificial Sequence
<220> FEATURE:
<223> OTHER INFORMATION: Antibody 15462 VH FR1

<400> SEQUENCE: 255

Gln Leu Gln Leu Gln Glu Ser Gly Pro Gly Leu Val Lys Pro Ser Glu
1               5                   10                  15

Thr Leu Ser Leu Thr Cys Thr Val Ser Gly
            20                  25

<210> SEQ ID NO 256
<211> LENGTH: 14
<212> TYPE: PRT
<213> ORGANISM: Artificial Sequence
<220> FEATURE:
<223> OTHER INFORMATION: Antibody 15462  VH FR2

<400> SEQUENCE: 256

Trp Ile Arg Gln Pro Pro Gly Lys Gly Leu Glu Trp Ile Gly
1               5                   10

<210> SEQ ID NO 257
<211> LENGTH: 30
<212> TYPE: PRT
<213> ORGANISM: Artificial Sequence
<220> FEATURE:
<223> OTHER INFORMATION: Antibody 15462  VH FR3

<400> SEQUENCE: 257

Arg Val Thr Ile Ser Val Asp Thr Ser Lys Asn Gln Phe Ser Leu Lys
1               5                   10                  15

Leu Ser Ser Val Thr Ala Ala Asp Thr Ala Val Tyr Tyr Cys
            20                  25                  30

<210> SEQ ID NO 258
<211> LENGTH: 11
<212> TYPE: PRT
<213> ORGANISM: Artificial Sequence
<220> FEATURE:
<223> OTHER INFORMATION: Antibody 15462  VH FR4

<400> SEQUENCE: 258

```
Trp Gly Gln Gly Thr Met Val Thr Val Ser Ser
1               5                   10
```

<210> SEQ ID NO 259
<211> LENGTH: 23
<212> TYPE: PRT
<213> ORGANISM: Artificial Sequence
<220> FEATURE:
<223> OTHER INFORMATION: Antibody 15462  VL FR1

<400> SEQUENCE: 259

```
Glu Ile Val Leu Thr Gln Ser Pro Gly Thr Leu Ser Leu Ser Pro Gly
1               5                   10                  15

Glu Arg Ala Thr Leu Ser Cys
            20
```

<210> SEQ ID NO 260
<211> LENGTH: 15
<212> TYPE: PRT
<213> ORGANISM: Artificial Sequence
<220> FEATURE:
<223> OTHER INFORMATION: Antibody 15462  VL FR2

<400> SEQUENCE: 260

```
Trp Tyr Gln Gln Lys Pro Gly Gln Ala Pro Arg Leu Leu Ile Tyr
1               5                   10                  15
```

<210> SEQ ID NO 261
<211> LENGTH: 32
<212> TYPE: PRT
<213> ORGANISM: Artificial Sequence
<220> FEATURE:
<223> OTHER INFORMATION: Antibody 15462  VL FR3

<400> SEQUENCE: 261

```
Gly Ile Pro Asp Arg Phe Ser Gly Ser Gly Ser Gly Thr Asp Phe Thr
1               5                   10                  15

Leu Thr Ile Ser Arg Leu Glu Pro Glu Asp Phe Ala Val Tyr Tyr Cys
            20                  25                  30
```

<210> SEQ ID NO 262
<211> LENGTH: 10
<212> TYPE: PRT
<213> ORGANISM: Artificial Sequence
<220> FEATURE:
<223> OTHER INFORMATION: Antibody 15462  VL FR4

<400> SEQUENCE: 262

```
Phe Gly Gly Gly Thr Lys Val Glu Ile Lys
1               5                   10
```

<210> SEQ ID NO 263
<211> LENGTH: 360
<212> TYPE: DNA
<213> ORGANISM: Artificial Sequence
<220> FEATURE:
<223> OTHER INFORMATION: Antibody 15462  Variable Heavy Chain-Encoding
      Polynucleotide Sequence

<400> SEQUENCE: 263

```
cagctgcagc tgcaggagtc gggcccagga ctggtgaagc cttcggagac cctgtccctc      60
acctgcactg tctctggtgg ctccatcagc agtagtagtt actactgggg ctggatccgc     120
cagcccccag ggaaggggct ggagtggatt gggaacatct attatagtgg gagcacctac     180
tacaacccgt ccctcaagag tcgagtcacc atatccgtag acacgtccaa gaaccagttc     240
```

```
tccctgaagc tgagttctgt gaccgccgca gacacggcgg tgtactactg cgccagagaa    300
ggatcttaca caaccgtgtt aaacgtatgg ggtcagggta caatggtcac cgtctcctca    360
```

<210> SEQ ID NO 264
<211> LENGTH: 324
<212> TYPE: DNA
<213> ORGANISM: Artificial Sequence
<220> FEATURE:
<223> OTHER INFORMATION: Antibody 15462   Variable Light Chain-Encoding
      Polynucleotide Sequence

<400> SEQUENCE: 264

```
gaaattgtgt tgacgcagtc tccaggcacc ctgtctttgt ctccagggga aagagccacc     60
ctctcctgca gggccagtca gagtgttagc agcagctact tagcctggta ccagcagaaa    120
cctggccagg ctcccaggct cctcatctat ggtgcatcca gcagggccac tggcatccca    180
gacaggttca gtggcagtgg gtctgggaca gacttcactc tcaccatcag cagactggag    240
cctgaagatt ttgcagtgta ttactgtcag caggccgcca gttaccctct cacttttggc    300
ggagggacca aggttgagat caaa                                           324
```

<210> SEQ ID NO 265
<211> LENGTH: 26
<212> TYPE: PRT
<213> ORGANISM: Artificial Sequence
<220> FEATURE:
<223> OTHER INFORMATION: Antibody 22213 VH FR1

<400> SEQUENCE: 265

```
Gln Leu Gln Leu Gln Glu Ser Gly Pro Gly Leu Val Lys Pro Ser Glu
1               5                   10                  15

Thr Leu Ser Leu Thr Cys Thr Val Ser Gly
            20                  25
```

<210> SEQ ID NO 266
<211> LENGTH: 14
<212> TYPE: PRT
<213> ORGANISM: Artificial Sequence
<220> FEATURE:
<223> OTHER INFORMATION: Antibody 22213   VH FR2

<400> SEQUENCE: 266

```
Trp Ile Arg Gln Pro Pro Gly Lys Gly Leu Glu Trp Ile Gly
1               5                   10
```

<210> SEQ ID NO 267
<211> LENGTH: 30
<212> TYPE: PRT
<213> ORGANISM: Artificial Sequence
<220> FEATURE:
<223> OTHER INFORMATION: Antibody 22213   VH FR3

<400> SEQUENCE: 267

```
Arg Val Thr Ile Ser Val Asp Thr Ser Lys Asn Gln Phe Ser Leu Lys
1               5                   10                  15

Leu Ser Ser Val Thr Ala Ala Asp Thr Ala Val Tyr Tyr Cys
            20                  25                  30
```

<210> SEQ ID NO 268
<211> LENGTH: 11
<212> TYPE: PRT
<213> ORGANISM: Artificial Sequence
<220> FEATURE:

<223> OTHER INFORMATION: Antibody 22213 VH FR4

<400> SEQUENCE: 268

Trp Gly Gln Gly Thr Met Val Thr Val Ser Ser
1               5                   10

<210> SEQ ID NO 269
<211> LENGTH: 23
<212> TYPE: PRT
<213> ORGANISM: Artificial Sequence
<220> FEATURE:
<223> OTHER INFORMATION: Antibody 22213 VL FR1

<400> SEQUENCE: 269

Glu Ile Val Leu Thr Gln Ser Pro Gly Thr Leu Ser Leu Ser Pro Gly
1               5                   10                  15

Glu Arg Ala Thr Leu Ser Cys
            20

<210> SEQ ID NO 270
<211> LENGTH: 15
<212> TYPE: PRT
<213> ORGANISM: Artificial Sequence
<220> FEATURE:
<223> OTHER INFORMATION: Antibody 22213 VL FR2

<400> SEQUENCE: 270

Trp Tyr Gln Gln Lys Pro Gly Gln Ala Pro Arg Leu Leu Ile Tyr
1               5                   10                  15

<210> SEQ ID NO 271
<211> LENGTH: 32
<212> TYPE: PRT
<213> ORGANISM: Artificial Sequence
<220> FEATURE:
<223> OTHER INFORMATION: Antibody 22213 VL FR3

<400> SEQUENCE: 271

Gly Ile Pro Asp Arg Phe Ser Gly Ser Gly Ser Gly Thr Asp Phe Thr
1               5                   10                  15

Leu Thr Ile Ser Arg Leu Glu Pro Glu Asp Phe Ala Val Tyr Tyr Cys
            20                  25                  30

<210> SEQ ID NO 272
<211> LENGTH: 10
<212> TYPE: PRT
<213> ORGANISM: Artificial Sequence
<220> FEATURE:
<223> OTHER INFORMATION: Antibody 22213 VL FR4

<400> SEQUENCE: 272

Phe Gly Gly Gly Thr Lys Val Glu Ile Lys
1               5                   10

<210> SEQ ID NO 273
<211> LENGTH: 360
<212> TYPE: DNA
<213> ORGANISM: Artificial Sequence
<220> FEATURE:
<223> OTHER INFORMATION: Antibody 22213 Variable Heavy Chain-Encoding
      Polynucleotide Sequence

<400> SEQUENCE: 273
cagctgcagc tgcaggagtc gggcccagga ctggtgaagc cttcggagac cctgtccctc      60
acctgcactg tctctggtgg ctccatcggg agggggagtt actactgggg ctggatccgc     120

```
cagcccccag ggaaggggct ggagtggatt gggaacatct attatagtgg gagcacctac      180
tacaacccgt ccctcaagag tcgagtcacc atatccgtag acacgtccaa gaaccagttc      240
tccctgaagc tgagttctgt gaccgccgca gacacggcgg tgtactactg cgccagagaa      300
ggatcttaca caaccgtgtt aaacgtatgg ggtcaggggta caatggtcac cgtctcctca      360

<210> SEQ ID NO 274
<211> LENGTH: 324
<212> TYPE: DNA
<213> ORGANISM: Artificial Sequence
<220> FEATURE:
<223> OTHER INFORMATION: Antibody 22213  Variable Light Chain-Encoding
      Polynucleotide Sequence

<400> SEQUENCE: 274
gaaattgtgt tgacgcagtc tccaggcacc ctgtctttgt ctccagggga aagagccacc       60
ctctcctgca gggccagtca gagtgttgcc agcagccact tagcctggta ccagcagaaa      120
cctggccagg ctcccaggct cctcatctat gacgcagtca gcagggccac tggcatccca      180
gacaggttca gtggcagtgg gtctgggaca gacttcactc tcaccatcag cagactggag      240
cctgaagatt ttgcagtgta ttactgtcag caggccgcca gttaccctct cacttttggc      300
ggagggacca aggttgagat caaa                                             324

<210> SEQ ID NO 275
<211> LENGTH: 26
<212> TYPE: PRT
<213> ORGANISM: Artificial Sequence
<220> FEATURE:
<223> OTHER INFORMATION: Antibody 15465 VH FR1

<400> SEQUENCE: 275

Gln Val Gln Leu Gln Glu Ser Gly Pro Gly Leu Val Lys Pro Ser Gln
1               5                   10                  15

Thr Leu Ser Leu Thr Cys Thr Val Ser Gly
            20                  25

<210> SEQ ID NO 276
<211> LENGTH: 14
<212> TYPE: PRT
<213> ORGANISM: Artificial Sequence
<220> FEATURE:
<223> OTHER INFORMATION: Antibody 15465  VH FR2

<400> SEQUENCE: 276

Trp Ile Arg Gln His Pro Gly Lys Gly Leu Glu Trp Ile Gly
1               5                   10

<210> SEQ ID NO 277
<211> LENGTH: 30
<212> TYPE: PRT
<213> ORGANISM: Artificial Sequence
<220> FEATURE:
<223> OTHER INFORMATION: Antibody 15465  VH FR3

<400> SEQUENCE: 277

Arg Val Thr Ile Ser Val Asp Thr Ser Lys Asn Gln Phe Ser Leu Lys
1               5                   10                  15

Leu Ser Ser Val Thr Ala Ala Asp Thr Ala Val Tyr Tyr Cys
            20                  25                  30

<210> SEQ ID NO 278
```

<210> SEQ ID NO 278
<211> LENGTH: 11
<212> TYPE: PRT
<213> ORGANISM: Artificial Sequence
<220> FEATURE:
<223> OTHER INFORMATION: Antibody 15465  VH FR4

<400> SEQUENCE: 278

Trp Gly Arg Gly Thr Leu Val Thr Val Ser Ser
1               5                   10

<210> SEQ ID NO 279
<211> LENGTH: 23
<212> TYPE: PRT
<213> ORGANISM: Artificial Sequence
<220> FEATURE:
<223> OTHER INFORMATION: Antibody 15465  VL FR1

<400> SEQUENCE: 279

Asp Ile Gln Met Thr Gln Ser Pro Ser Ser Val Ser Ala Ser Val Gly
1               5                   10                  15

Asp Arg Val Thr Ile Thr Cys
            20

<210> SEQ ID NO 280
<211> LENGTH: 15
<212> TYPE: PRT
<213> ORGANISM: Artificial Sequence
<220> FEATURE:
<223> OTHER INFORMATION: Antibody 15465  VL FR2

<400> SEQUENCE: 280

Trp Tyr Gln Gln Lys Pro Gly Lys Ala Pro Lys Leu Leu Ile Tyr
1               5                   10                  15

<210> SEQ ID NO 281
<211> LENGTH: 32
<212> TYPE: PRT
<213> ORGANISM: Artificial Sequence
<220> FEATURE:
<223> OTHER INFORMATION: Antibody 15465  VL FR3

<400> SEQUENCE: 281

Gly Val Pro Ser Arg Phe Ser Gly Ser Gly Ser Gly Thr Asp Phe Thr
1               5                   10                  15

Leu Thr Ile Ser Ser Leu Gln Pro Glu Asp Phe Ala Thr Tyr Tyr Cys
            20                  25                  30

<210> SEQ ID NO 282
<211> LENGTH: 10
<212> TYPE: PRT
<213> ORGANISM: Artificial Sequence
<220> FEATURE:
<223> OTHER INFORMATION: Antibody 15465  VL FR4

<400> SEQUENCE: 282

Phe Gly Gly Gly Thr Lys Val Glu Ile Lys
1               5                   10

<210> SEQ ID NO 283
<211> LENGTH: 363
<212> TYPE: DNA
<213> ORGANISM: Artificial Sequence
<220> FEATURE:
<223> OTHER INFORMATION: Antibody 15465  Variable Heavy Chain-Encoding
      Polynucleotide Sequence

<400> SEQUENCE: 283

```
caggtgcagc tgcaggagtc gggcccagga ctggtgaagc cttcacagac cctgtccctc    60
acctgtactg tctctggtgg ctccatcagc agtggtggtt actactggag ctggatccgc   120
cagcacccag ggaagggcct ggagtggatt gggaacatct attacagtgg gagcacctac   180
tacaacccgt ccctcaagag tcgagttacc atatcagtag acacgtctaa gaaccagttc   240
tccctgaagc tgagttctgt gaccgccgca gacacggcgg tgtactactg cgccagagaa   300
tctagcacca tatctgccga cttcgaccta tggggagag gtaccttggt caccgtctcc   360
tca                                                                   363
```

```
<210> SEQ ID NO 284
<211> LENGTH: 321
<212> TYPE: DNA
<213> ORGANISM: Artificial Sequence
<220> FEATURE:
<223> OTHER INFORMATION: Antibody 15465  Variable Light Chain-Encoding
      Polynucleotide Sequence

<400> SEQUENCE: 284
```

```
gacatccaga tgacccagtc tccatcttcc gtgtctgcat ctgtaggaga cagagtcacc    60
atcacttgtc gggcgagtca gggtattagc aggtggttag cctggtatca gcagaaacca   120
gggaaagccc ctaagctcct gatctatgct gcatccagtt tgcaaagtgg ggtcccatca   180
aggttcagcg gcagtggatc tgggacagat ttcactctca ccatcagcag cctgcagcct   240
gaagattttg caacttatta ctgtcagcag gcacacacct tcccttacac ttttggcgga   300
gggaccaagg ttgagatcaa a                                              321
```

```
<210> SEQ ID NO 285
<211> LENGTH: 26
<212> TYPE: PRT
<213> ORGANISM: Artificial Sequence
<220> FEATURE:
<223> OTHER INFORMATION: Antibody 20506 VH FR1

<400> SEQUENCE: 285
```

Gln Leu Gln Leu Gln Glu Ser Gly Pro Gly Leu Val Lys Pro Ser Glu
1               5                   10                  15

Thr Leu Ser Leu Thr Cys Thr Ala Ser Gly
            20                  25

```
<210> SEQ ID NO 286
<211> LENGTH: 14
<212> TYPE: PRT
<213> ORGANISM: Artificial Sequence
<220> FEATURE:
<223> OTHER INFORMATION: Antibody 20506  VH FR2

<400> SEQUENCE: 286
```

Trp Ile Arg Gln His Pro Gly Lys Gly Leu Glu Trp Ile Gly
1               5                   10

```
<210> SEQ ID NO 287
<211> LENGTH: 30
<212> TYPE: PRT
<213> ORGANISM: Artificial Sequence
<220> FEATURE:
<223> OTHER INFORMATION: Antibody 20506  VH FR3

<400> SEQUENCE: 287
```

Arg Val Thr Met Ser Val Asp Thr Ser Lys Asn Gln Phe Ser Leu Lys
1               5                   10                  15

```
Leu Ser Ser Val Thr Ala Ala Asp Thr Ala Val Tyr Tyr Cys
            20                  25                  30

<210> SEQ ID NO 288
<211> LENGTH: 11
<212> TYPE: PRT
<213> ORGANISM: Artificial Sequence
<220> FEATURE:
<223> OTHER INFORMATION: Antibody 20506  VH FR4

<400> SEQUENCE: 288

Trp Gly Arg Gly Thr Leu Val Thr Val Ser Ser
1               5                   10

<210> SEQ ID NO 289
<211> LENGTH: 23
<212> TYPE: PRT
<213> ORGANISM: Artificial Sequence
<220> FEATURE:
<223> OTHER INFORMATION: Antibody 20506  VL FR1

<400> SEQUENCE: 289

Asp Ile Gln Met Thr Gln Ser Pro Ser Ser Val Ser Ala Ser Val Gly
1               5                   10                  15

Asp Arg Val Thr Ile Thr Cys
            20

<210> SEQ ID NO 290
<211> LENGTH: 15
<212> TYPE: PRT
<213> ORGANISM: Artificial Sequence
<220> FEATURE:
<223> OTHER INFORMATION: Antibody 20506  VL FR2

<400> SEQUENCE: 290

Trp Tyr Gln Gln Lys Pro Gly Lys Ala Pro Lys Leu Leu Ile Tyr
1               5                   10                  15

<210> SEQ ID NO 291
<211> LENGTH: 32
<212> TYPE: PRT
<213> ORGANISM: Artificial Sequence
<220> FEATURE:
<223> OTHER INFORMATION: Antibody 20506  VL FR3

<400> SEQUENCE: 291

Gly Val Pro Ser Arg Phe Ser Gly Ser Gly Ser Gly Thr Asp Phe Thr
1               5                   10                  15

Leu Thr Ile Ser Ser Leu Gln Pro Glu Asp Phe Ala Thr Tyr Tyr Cys
            20                  25                  30

<210> SEQ ID NO 292
<211> LENGTH: 10
<212> TYPE: PRT
<213> ORGANISM: Artificial Sequence
<220> FEATURE:
<223> OTHER INFORMATION: Antibody 20506  VL FR4

<400> SEQUENCE: 292

Phe Gly Gly Gly Thr Lys Val Glu Ile Lys
1               5                   10

<210> SEQ ID NO 293
<211> LENGTH: 363
<212> TYPE: DNA
```

<213> ORGANISM: Artificial Sequence
<220> FEATURE:
<223> OTHER INFORMATION: Antibody 20506  Variable Heavy Chain-Encoding
      Polynucleotide Sequence

<400> SEQUENCE: 293

```
cagctgcagc tgcaggagtc gggcccagga ctggtgaagc cttcggagac cctgtccctc      60
acctgtactg cctctggtgg ctccatcagc catggtgggt actactggag ctggatccgc     120
cagcacccag ggaagggcct ggagtggatt gggaacatct attacagtgg gagcacctac     180
tacaatccgt ccctcaagag tcgagttacc atgtcagtag acacgtctaa gaaccagttc     240
tccctgaagc tgagttctgt gaccgccgca gacacggcgg tgtactactg cgccagagaa     300
tctagcacca tatctgccga cttcgaccta tggggagag gtaccttggt caccgtctcc     360
tca                                                                  363
```

<210> SEQ ID NO 294
<211> LENGTH: 321
<212> TYPE: DNA
<213> ORGANISM: Artificial Sequence
<220> FEATURE:
<223> OTHER INFORMATION: Antibody 20506  Variable Light Chain-Encoding
      Polynucleotide Sequence

<400> SEQUENCE: 294

```
gacatccaga tgacccagtc tccatcttcc gtgtctgcat ctgtaggaga cagagtcacc      60
atcacttgtc gggcgagtca gggtattagc aggtggttag cctggtatca gcagaaacca     120
gggaaagccc ctaagctcct gatctatgct gcatccagtt tgcaaagtgg ggtcccatca     180
aggttcagcg gcagtggatc tgggacagat ttcactctca ccatcagcag cctgcagcct     240
gaagattttg caacttatta ctgtcagcag gcacacacct cccttacac tttggcgga      300
gggaccaagg ttgagatcaa a                                              321
```

<210> SEQ ID NO 295
<211> LENGTH: 26
<212> TYPE: PRT
<213> ORGANISM: Artificial Sequence
<220> FEATURE:
<223> OTHER INFORMATION: Antibody 15483 VH FR1

<400> SEQUENCE: 295

```
Gln Val Gln Leu Gln Glu Ser Gly Pro Gly Leu Val Lys Pro Ser Gln
1               5                   10                  15

Thr Leu Ser Leu Thr Cys Thr Val Ser Gly
            20                  25
```

<210> SEQ ID NO 296
<211> LENGTH: 14
<212> TYPE: PRT
<213> ORGANISM: Artificial Sequence
<220> FEATURE:
<223> OTHER INFORMATION: Antibody 15483  VH FR2

<400> SEQUENCE: 296

```
Trp Ile Arg Gln His Pro Gly Lys Gly Leu Glu Trp Ile Gly
1               5                   10
```

<210> SEQ ID NO 297
<211> LENGTH: 30
<212> TYPE: PRT
<213> ORGANISM: Artificial Sequence
<220> FEATURE:

<223> OTHER INFORMATION: Antibody 15483   VH FR3

<400> SEQUENCE: 297

Arg Val Thr Ile Ser Val Asp Thr Ser Lys Asn Gln Phe Ser Leu Lys
1               5                   10                  15

Leu Ser Ser Val Thr Ala Ala Asp Thr Ala Val Tyr Tyr Cys
            20                  25                  30

<210> SEQ ID NO 298
<211> LENGTH: 11
<212> TYPE: PRT
<213> ORGANISM: Artificial Sequence
<220> FEATURE:
<223> OTHER INFORMATION: Antibody 15483   VH FR4

<400> SEQUENCE: 298

Trp Gly Gln Gly Thr Leu Val Thr Val Ser Ser
1               5                   10

<210> SEQ ID NO 299
<211> LENGTH: 23
<212> TYPE: PRT
<213> ORGANISM: Artificial Sequence
<220> FEATURE:
<223> OTHER INFORMATION: Antibody 15483   VL FR1

<400> SEQUENCE: 299

Asp Ile Gln Met Thr Gln Ser Pro Ser Thr Leu Ser Ala Ser Val Gly
1               5                   10                  15

Asp Arg Val Thr Ile Thr Cys
            20

<210> SEQ ID NO 300
<211> LENGTH: 15
<212> TYPE: PRT
<213> ORGANISM: Artificial Sequence
<220> FEATURE:
<223> OTHER INFORMATION: Antibody 15483   VL FR2

<400> SEQUENCE: 300

Trp Tyr Gln Gln Lys Pro Gly Lys Ala Pro Lys Leu Leu Ile Tyr
1               5                   10                  15

<210> SEQ ID NO 301
<211> LENGTH: 32
<212> TYPE: PRT
<213> ORGANISM: Artificial Sequence
<220> FEATURE:
<223> OTHER INFORMATION: Antibody 15483   VL FR3

<400> SEQUENCE: 301

Gly Val Pro Ser Arg Phe Ser Gly Ser Gly Ser Gly Thr Glu Phe Thr
1               5                   10                  15

Leu Thr Ile Ser Ser Leu Gln Pro Asp Asp Phe Ala Thr Tyr Tyr Cys
            20                  25                  30

<210> SEQ ID NO 302
<211> LENGTH: 10
<212> TYPE: PRT
<213> ORGANISM: Artificial Sequence
<220> FEATURE:
<223> OTHER INFORMATION: Antibody 15483   VL FR4

<400> SEQUENCE: 302

Phe Gly Gly Gly Thr Lys Val Glu Ile Lys

<210> SEQ ID NO 303
<211> LENGTH: 363
<212> TYPE: DNA
<213> ORGANISM: Artificial Sequence
<220> FEATURE:
<223> OTHER INFORMATION: Antibody 15483  Variable Heavy Chain-Encoding
      Polynucleotide Sequence

<400> SEQUENCE: 303

```
caggtgcagc tgcaggagtc gggcccagga ctggtgaagc cttcacagac cctgtccctc    60
acctgtactg tctctggtgg ctccatcagc agtggtggtt actactggag ctggatccgc   120
cagcacccag ggaagggcct ggagtggatt gggaacatct attacagtgg gagcacctac   180
tacaacccgt ccctcaagag tcgagttacc atatcagtag acacgtctaa gaaccagttc   240
tccctgaagc tgagttctgt gaccgccgca gacacggcgg tgtactactg cgccagaggg   300
ttgagcacca tagacgaggc attcgaccca tggggacagg gtacattggt caccgtctcc   360
tca                                                                 363
```

<210> SEQ ID NO 304
<211> LENGTH: 321
<212> TYPE: DNA
<213> ORGANISM: Artificial Sequence
<220> FEATURE:
<223> OTHER INFORMATION: Antibody 15483  Variable Light Chain-Encoding
      Polynucleotide Sequence

<400> SEQUENCE: 304

```
gacatccaga tgacccagtc tccttccacc ctgtctgcat ctgtaggaga cagagtcacc    60
atcacttgcc gggccagtca gagtattagt agctggttgg cctggtatca gcagaaacca   120
gggaaagccc ctaagctcct gatctataaa gcctccagtt tggaaagtgg ggtcccatca   180
aggttcagcg gcagtggatc tgggacagaa ttcactctca ccatcagcag cctgcagcct   240
gatgattttg caacttatta ctgccagcag gacaacagtt acccttacac ttttggcgga   300
gggaccaagg ttgagatcaa a                                             321
```

<210> SEQ ID NO 305
<211> LENGTH: 26
<212> TYPE: PRT
<213> ORGANISM: Artificial Sequence
<220> FEATURE:
<223> OTHER INFORMATION: Antibody 20513 VH FR1

<400> SEQUENCE: 305

Gln Leu Gln Leu Gln Glu Ser Gly Pro Gly Leu Val Lys Pro Ser Glu
1               5                   10                  15
Thr Leu Ser Leu Thr Cys Thr Val Ser Gly
            20                  25

<210> SEQ ID NO 306
<211> LENGTH: 14
<212> TYPE: PRT
<213> ORGANISM: Artificial Sequence
<220> FEATURE:
<223> OTHER INFORMATION: Antibody 20513  VH FR2

<400> SEQUENCE: 306

Trp Ile Arg Gln His Pro Gly Lys Gly Leu Glu Trp Ile Gly
1               5                   10

<210> SEQ ID NO 307
<211> LENGTH: 30
<212> TYPE: PRT
<213> ORGANISM: Artificial Sequence
<220> FEATURE:
<223> OTHER INFORMATION: Antibody 20513 VH FR3

<400> SEQUENCE: 307

Arg Val Thr Met Ser Val Asp Thr Ser Lys Asn Gln Phe Ser Leu Lys
1               5                   10                  15

Leu Ser Ser Val Thr Ala Ala Asp Thr Ala Val Tyr Tyr Cys
            20                  25                  30

<210> SEQ ID NO 308
<211> LENGTH: 11
<212> TYPE: PRT
<213> ORGANISM: Artificial Sequence
<220> FEATURE:
<223> OTHER INFORMATION: Antibody 20513 VH FR4

<400> SEQUENCE: 308

Trp Gly Gln Gly Thr Leu Val Thr Val Ser Ser
1               5                   10

<210> SEQ ID NO 309
<211> LENGTH: 23
<212> TYPE: PRT
<213> ORGANISM: Artificial Sequence
<220> FEATURE:
<223> OTHER INFORMATION: Antibody 20513 VL FR1

<400> SEQUENCE: 309

Asp Ile Gln Met Thr Gln Ser Pro Ser Thr Leu Ser Ala Ser Val Gly
1               5                   10                  15

Asp Arg Val Thr Ile Thr Cys
            20

<210> SEQ ID NO 310
<211> LENGTH: 15
<212> TYPE: PRT
<213> ORGANISM: Artificial Sequence
<220> FEATURE:
<223> OTHER INFORMATION: Antibody 20513 VL FR2

<400> SEQUENCE: 310

Trp Tyr Gln Gln Lys Pro Gly Lys Ala Pro Lys Leu Leu Ile Tyr
1               5                   10                  15

<210> SEQ ID NO 311
<211> LENGTH: 32
<212> TYPE: PRT
<213> ORGANISM: Artificial Sequence
<220> FEATURE:
<223> OTHER INFORMATION: Antibody 20513 VL FR3

<400> SEQUENCE: 311

Gly Val Pro Ser Arg Phe Ser Gly Ser Gly Ser Gly Thr Glu Phe Thr
1               5                   10                  15

Leu Thr Ile Ser Ser Leu Gln Pro Asp Asp Phe Ala Thr Tyr Tyr Cys
            20                  25                  30

<210> SEQ ID NO 312
<211> LENGTH: 10
<212> TYPE: PRT
<213> ORGANISM: Artificial Sequence
<220> FEATURE:
<223> OTHER INFORMATION: Antibody 20513 VL FR4

<400> SEQUENCE: 312

Phe Gly Gly Gly Thr Lys Val Glu Ile Lys
1               5                   10

<210> SEQ ID NO 313
<211> LENGTH: 363
<212> TYPE: DNA
<213> ORGANISM: Artificial Sequence
<220> FEATURE:
<223> OTHER INFORMATION: Antibody 20513 Variable Heavy Chain-Encoding
      Polynucleotide Sequence

<400> SEQUENCE: 313

```
cagctgcagc tgcaggagtc gggcccagga ctggtgaagc cttcggagac cctgtccctc      60
acctgcactg tctctggtgg ctccatcagc gatggtagtt actactggag ctggatccgc     120
cagcacccag ggaagggcct ggagtggatt gggaacatct attacagtgg gagcacctac     180
tacaacccgt ccctcaggag tcgagttacc atgtcagtag acacgtctaa gaaccagttc     240
tccctgaagc tgagttctgt gaccgccgca gacacggcgg tgtactactg cgccagaggg     300
ttgagcacca tagacgaggc attcgaccca tggggacagg gtacattggt caccgtctcc     360
tca                                                                   363
```

<210> SEQ ID NO 314
<211> LENGTH: 321
<212> TYPE: DNA
<213> ORGANISM: Artificial Sequence
<220> FEATURE:
<223> OTHER INFORMATION: Antibody 20513 Variable Light Chain-Encoding
      Polynucleotide Sequence

<400> SEQUENCE: 314

```
gacatccaga tgacccagtc tccttccacc ctgtctgcat ctgtaggaga cagagtcacc      60
atcacttgcc gggccagtca gagtattagt agctggttgg cctggtatca gcagaaacca     120
gggaaagccc ctaagctcct gatctataaa gcctccagtt tggaaagtgg ggtcccatca     180
aggttcagcg gcagtggatc tgggacagaa ttcactctca ccatcagcag cctgcagcct     240
gatgattttg caacttatta ctgccagcag gacaacagtt acccttacac ttttggcgga     300
gggaccaagg ttgagatcaa a                                               321
```

<210> SEQ ID NO 315
<211> LENGTH: 26
<212> TYPE: PRT
<213> ORGANISM: Artificial Sequence
<220> FEATURE:
<223> OTHER INFORMATION: Antibody 22216 VH FR1

<400> SEQUENCE: 315

Gln Val Gln Leu Gln Glu Ser Gly Pro Gly Leu Val Lys Pro Ser Gln
1               5                   10                  15

Thr Leu Ser Leu Thr Cys Thr Val Ser Gly
            20                  25

<210> SEQ ID NO 316
<211> LENGTH: 14
<212> TYPE: PRT
<213> ORGANISM: Artificial Sequence
<220> FEATURE:
<223> OTHER INFORMATION: Antibody 22216 VH FR2

<400> SEQUENCE: 316

Trp Ile Arg Gln His Pro Gly Lys Gly Leu Glu Trp Ile Gly
1               5                   10

<210> SEQ ID NO 317
<211> LENGTH: 30
<212> TYPE: PRT
<213> ORGANISM: Artificial Sequence
<220> FEATURE:
<223> OTHER INFORMATION: Antibody 22216 VH FR3

<400> SEQUENCE: 317

Arg Val Thr Met Ser Val Asp Thr Ser Lys Asn Gln Phe Ser Leu Lys
1               5                   10                  15

Leu Ser Ser Val Thr Ala Ala Asp Thr Ala Val Tyr Tyr Cys
            20                  25                  30

<210> SEQ ID NO 318
<211> LENGTH: 11
<212> TYPE: PRT
<213> ORGANISM: Artificial Sequence
<220> FEATURE:
<223> OTHER INFORMATION: Antibody 22216 VH FR4

<400> SEQUENCE: 318

Trp Gly Gln Gly Thr Leu Val Thr Val Ser Ser
1               5                   10

<210> SEQ ID NO 319
<211> LENGTH: 23
<212> TYPE: PRT
<213> ORGANISM: Artificial Sequence
<220> FEATURE:
<223> OTHER INFORMATION: Antibody 22216 VL FR1

<400> SEQUENCE: 319

Asp Ile Gln Met Thr Gln Ser Pro Ser Thr Leu Ser Ala Ser Val Gly
1               5                   10                  15

Asp Arg Val Thr Ile Thr Cys
            20

<210> SEQ ID NO 320
<211> LENGTH: 15
<212> TYPE: PRT
<213> ORGANISM: Artificial Sequence
<220> FEATURE:
<223> OTHER INFORMATION: Antibody 22216 VL FR2

<400> SEQUENCE: 320

Trp Tyr Gln Gln Lys Pro Gly Lys Ala Pro Lys Leu Leu Ile Tyr
1               5                   10                  15

<210> SEQ ID NO 321
<211> LENGTH: 32
<212> TYPE: PRT
<213> ORGANISM: Artificial Sequence
<220> FEATURE:
<223> OTHER INFORMATION: Antibody 22216 VL FR3

<400> SEQUENCE: 321

Gly Val Pro Ser Arg Phe Ser Gly Ser Gly Ser Gly Thr Glu Phe Thr
1               5                   10                  15

Leu Thr Ile Ser Ser Leu Gln Pro Asp Asp Phe Ala Thr Tyr Tyr Cys
            20                  25                  30

<210> SEQ ID NO 322
<211> LENGTH: 10
<212> TYPE: PRT
<213> ORGANISM: Artificial Sequence
<220> FEATURE:
<223> OTHER INFORMATION: Antibody 22216 VL FR4

<400> SEQUENCE: 322

Phe Gly Gly Gly Thr Lys Val Glu Ile Lys
1               5                   10

<210> SEQ ID NO 323
<211> LENGTH: 363
<212> TYPE: DNA
<213> ORGANISM: Artificial Sequence
<220> FEATURE:
<223> OTHER INFORMATION: Antibody 22216 Variable Heavy Chain-Encoding
      Polynucleotide Sequence

<400> SEQUENCE: 323
caggtgcagc tgcaggagtc gggcccagga ctggtgaagc cttcacagac cctgtccctc      60
acctgtactg tctctggtgg ctccatcagc gatggtagtt actactggag ctggatccgc     120
cagcacccag ggaagggcct ggagtggatt gggaacatct attacagtgg gagcacctac     180
tacaacccgt ccctcaggag tcgagttacc atgtcagtag acacgtctaa gaaccagttc     240
tccctgaagc tgagttctgt gaccgccgca gacacggcgg tgtactactg cgccagaggg     300
ttgagcacca tagacgaggc attcgaccca tggggacagg gtacattggt caccgtctcc     360
tca                                                                    363

<210> SEQ ID NO 324
<211> LENGTH: 321
<212> TYPE: DNA
<213> ORGANISM: Artificial Sequence
<220> FEATURE:
<223> OTHER INFORMATION: Antibody 22216 Variable Light Chain-Encoding
      Polynucleotide Sequence

<400> SEQUENCE: 324
gacatccaga tgacccagtc tccttccacc ctgtctgcat ctgtaggaga cagagtcacc      60
atcacttgcc gggccagtaa aagtattagt tcctggttgg cctggtatca gcagaaacca     120
ggaaaagccc ctaagctcct gatctatgaa gcctcctcct gcacagtggg gtcccatca     180 aggttcagcg gcagtggatc tgggacagaa ttcactctca ccatcagcag cctgcagcct     240
gatgattttg caacttatta ctgccagcag gacaacagtt accctacac ttttggcgga     300 gggaccaagg ttgagatcaa a                                                321

<210> SEQ ID NO 325
<211> LENGTH: 26
<212> TYPE: PRT
<213> ORGANISM: Artificial Sequence
<220> FEATURE:
<223> OTHER INFORMATION: Antibody 15489 VH FR1

<400> SEQUENCE: 325

Gln Val Gln Leu Gln Glu Ser Gly Pro Gly Leu Val Lys Pro Ser Glu
1               5                   10                  15

Thr Leu Ser Leu Thr Cys Thr Val Ser Gly
            20                  25

<210> SEQ ID NO 326
<211> LENGTH: 14
<212> TYPE: PRT
<213> ORGANISM: Artificial Sequence
<220> FEATURE:
<223> OTHER INFORMATION: Antibody 15489 VH FR2

<400> SEQUENCE: 326

Trp Ile Arg Gln Pro Pro Gly Lys Gly Leu Glu Trp Ile Gly
1               5                   10

<210> SEQ ID NO 327
<211> LENGTH: 30
<212> TYPE: PRT
<213> ORGANISM: Artificial Sequence
<220> FEATURE:
<223> OTHER INFORMATION: Antibody 15489 VH FR3

<400> SEQUENCE: 327

Arg Val Thr Ile Ser Val Asp Thr Ser Lys Asn Gln Phe Ser Leu Lys
1               5                   10                  15

Leu Ser Ser Val Thr Ala Ala Asp Thr Ala Val Tyr Tyr Cys
            20                  25                  30

<210> SEQ ID NO 328
<211> LENGTH: 11
<212> TYPE: PRT
<213> ORGANISM: Artificial Sequence
<220> FEATURE:
<223> OTHER INFORMATION: Antibody 15489 VH FR4

<400> SEQUENCE: 328

Trp Gly Gln Gly Thr Thr Val Thr Val Ser Ser
1               5                   10

<210> SEQ ID NO 329
<211> LENGTH: 23
<212> TYPE: PRT
<213> ORGANISM: Artificial Sequence
<220> FEATURE:
<223> OTHER INFORMATION: Antibody 15489 VL FR1

<400> SEQUENCE: 329

Asp Ile Gln Met Thr Gln Ser Pro Ser Thr Leu Ser Ala Ser Val Gly
1               5                   10                  15

Asp Arg Val Thr Ile Thr Cys
            20

<210> SEQ ID NO 330
<211> LENGTH: 15
<212> TYPE: PRT
<213> ORGANISM: Artificial Sequence
<220> FEATURE:
<223> OTHER INFORMATION: Antibody 15489 VL FR2

<400> SEQUENCE: 330

Trp Tyr Gln Gln Lys Pro Gly Lys Ala Pro Lys Leu Leu Ile Tyr
1               5                   10                  15

<210> SEQ ID NO 331
<211> LENGTH: 32
<212> TYPE: PRT
<213> ORGANISM: Artificial Sequence
<220> FEATURE:
<223> OTHER INFORMATION: Antibody 15489 VL FR3

<400> SEQUENCE: 331

Gly Val Pro Ser Arg Phe Ser Gly Ser Gly Ser Gly Thr Glu Phe Thr
1               5                   10                  15

Leu Thr Ile Ser Ser Leu Gln Pro Asp Asp Phe Ala Thr Tyr Tyr Cys
            20                  25                  30

<210> SEQ ID NO 332
<211> LENGTH: 10
<212> TYPE: PRT
<213> ORGANISM: Artificial Sequence
<220> FEATURE:
<223> OTHER INFORMATION: Antibody 15489 VL FR4

<400> SEQUENCE: 332

Phe Gly Gly Gly Thr Lys Val Glu Ile Lys
1               5                   10

<210> SEQ ID NO 333
<211> LENGTH: 366
<212> TYPE: DNA
<213> ORGANISM: Artificial Sequence
<220> FEATURE:
<223> OTHER INFORMATION: Antibody 15489 Variable Heavy Chain-Encoding
      Polynucleotide Sequence

<400> SEQUENCE: 333
caggtgcagc tgcaggagtc gggcccagga ctggtgaagc cttcggagac cctgtccctc       60
acctgcactg tctctggtgg ctccatcagt agttactact ggagctggat ccggcagccc      120
ccagggaagg gactggagtg gattgggtat atctatagta gtgggagcac caactacaac      180
ccctccctca agagtcgagt caccatatca gtagacacgt ccaagaacca gttctccctg      240
aagctgagtt ctgtgaccgc cgcagacacg gcggtgtact actgcgccag aggtctggga      300
cagtatgcag ctcctgatta tggaatggac gtatggggcc agggaacaac tgtcaccgtc      360
tcctca                                                                 366

<210> SEQ ID NO 334
<211> LENGTH: 321
<212> TYPE: DNA
<213> ORGANISM: Artificial Sequence
<220> FEATURE:
<223> OTHER INFORMATION: Antibody 15489 Variable Light Chain-Encoding
      Polynucleotide Sequence

<400> SEQUENCE: 334
gacatccaga tgacccagtc tccttccacc ctgtctgcat ctgtaggaga cagagtcacc       60
atcacttgcc gggccagtca gagtattagt agctggttgg cctggtatca gcagaaacca      120
gggaaagccc ctaagctcct gatctataaa gcctccagtt tggaaagtgg ggtcccatca      180
aggttcagcg gcagtggatc tgggacagaa ttcactctca ccatcagcag cctgcagcct      240
gatgattttg caacttatta ctgccagcag gacaatagct cccttttcac ttttggcgga      300
gggaccaagg ttgagatcaa a                                                321

<210> SEQ ID NO 335
<211> LENGTH: 26
<212> TYPE: PRT
<213> ORGANISM: Artificial Sequence
<220> FEATURE:
<223> OTHER INFORMATION: Antibody 20516 VH FR1

<400> SEQUENCE: 335

Gln Val Gln Leu Gln Glu Ser Gly Pro Gly Leu Val Lys Pro Ser Glu

```
1               5                  10                  15
Thr Leu Ser Leu Thr Cys Thr Val Ser Gly
            20                  25
```

<210> SEQ ID NO 336
<211> LENGTH: 14
<212> TYPE: PRT
<213> ORGANISM: Artificial Sequence
<220> FEATURE:
<223> OTHER INFORMATION: Antibody 20516  VH FR2

<400> SEQUENCE: 336

```
Trp Ile Arg Gln Pro Pro Gly Lys Gly Leu Glu Trp Ile Gly
1               5                  10
```

<210> SEQ ID NO 337
<211> LENGTH: 30
<212> TYPE: PRT
<213> ORGANISM: Artificial Sequence
<220> FEATURE:
<223> OTHER INFORMATION: Antibody 20516  VH FR3

<400> SEQUENCE: 337

```
Arg Val Thr Ile Ser Val Asp Thr Ser Lys Asn Gln Phe Ser Leu Lys
1               5                  10                  15

Leu Ser Ser Val Thr Ala Ala Asp Thr Ala Val Tyr Tyr Cys
            20                  25                  30
```

<210> SEQ ID NO 338
<211> LENGTH: 11
<212> TYPE: PRT
<213> ORGANISM: Artificial Sequence
<220> FEATURE:
<223> OTHER INFORMATION: Antibody 20516  VH FR4

<400> SEQUENCE: 338

```
Trp Gly Gln Gly Thr Thr Val Thr Val Ser Ser
1               5                  10
```

<210> SEQ ID NO 339
<211> LENGTH: 23
<212> TYPE: PRT
<213> ORGANISM: Artificial Sequence
<220> FEATURE:
<223> OTHER INFORMATION: Antibody 20516  VL FR1

<400> SEQUENCE: 339

```
Asp Ile Gln Met Thr Gln Ser Pro Ser Thr Leu Ser Ala Ser Val Gly
1               5                  10                  15

Asp Arg Val Thr Ile Thr Cys
            20
```

<210> SEQ ID NO 340
<211> LENGTH: 15
<212> TYPE: PRT
<213> ORGANISM: Artificial Sequence
<220> FEATURE:
<223> OTHER INFORMATION: Antibody 20516  VL FR2

<400> SEQUENCE: 340

```
Trp Tyr Gln Gln Lys Pro Gly Lys Ala Pro Lys Leu Leu Ile Tyr
1               5                  10                  15
```

<210> SEQ ID NO 341
<211> LENGTH: 32

<212> TYPE: PRT
<213> ORGANISM: Artificial Sequence
<220> FEATURE:
<223> OTHER INFORMATION: Antibody 20516 VL FR3

<400> SEQUENCE: 341

Gly Val Pro Ser Arg Phe Ser Gly Ser Gly Ser Gly Thr Glu Phe Thr
1               5                   10                  15
Leu Thr Ile Ser Ser Leu Gln Pro Asp Asp Phe Ala Thr Tyr Tyr Cys
            20                  25                  30

<210> SEQ ID NO 342
<211> LENGTH: 10
<212> TYPE: PRT
<213> ORGANISM: Artificial Sequence
<220> FEATURE:
<223> OTHER INFORMATION: Antibody 20516 VL FR4

<400> SEQUENCE: 342

Phe Gly Gly Gly Thr Lys Val Glu Ile Lys
1               5                   10

<210> SEQ ID NO 343
<211> LENGTH: 366
<212> TYPE: DNA
<213> ORGANISM: Artificial Sequence
<220> FEATURE:
<223> OTHER INFORMATION: Antibody 20516 Variable Heavy Chain-Encoding
      Polynucleotide Sequence

<400> SEQUENCE: 343
caggtgcagc tgcaggagtc gggcccagga ctggtgaagc cttcggagac cctgtccctc      60
acctgcactg tctctggtgg ctccatcatt agttactact ggggctggat ccggcagccc     120
ccagggaagg gactggagtg gattgggtat atctattcta gtgggagcac ctcgtacaac     180
ccctccctca gagtcgagt caccatatca gtagacacgt ccaagaacca gttctccctg     240
aagctgagtt ctgtgaccgc cgcagacacg gcggtgtact actgcgccag aggctctgga     300
ctgtatgcag ctcctgatta tggacttgac gtatggggtc agggaacaac tgtcaccgtc     360
tcctca                                                               366

<210> SEQ ID NO 344
<211> LENGTH: 321
<212> TYPE: DNA
<213> ORGANISM: Artificial Sequence
<220> FEATURE:
<223> OTHER INFORMATION: Antibody 20516 Variable Light Chain-Encoding
      Polynucleotide Sequence

<400> SEQUENCE: 344
gacatccaga tgacccagtc tccttccacc ctgtctgcat ctgtaggaga cagagtcacc      60
atcacttgcc gggccagtca gagtattagt agctggttgg cctggtatca gcagaaacca     120
gggaaagccc ctaagctcct gatctataaa gcctccagtt tggaaagtgg ggtcccatca     180
aggttcagcg gcagtggatc tgggacagaa ttcactctca ccatcagcag cctgcagcct     240
gatgattttg caacttatta ctgccagcag gacaatagct cccttttcac ttttggcgga     300
gggaccaagg ttgagatcaa a                                              321

<210> SEQ ID NO 345
<211> LENGTH: 26
<212> TYPE: PRT
<213> ORGANISM: Artificial Sequence
<220> FEATURE:
<223> OTHER INFORMATION: Antibody 15472 VH FR1

<400> SEQUENCE: 345

Glu Val Gln Leu Leu Glu Ser Gly Gly Gly Leu Val Gln Pro Gly Gly
1               5                   10                  15

Ser Leu Arg Leu Ser Cys Ala Ala Ser Gly
            20                  25

<210> SEQ ID NO 346
<211> LENGTH: 14
<212> TYPE: PRT
<213> ORGANISM: Artificial Sequence
<220> FEATURE:
<223> OTHER INFORMATION: Antibody 15472 VH FR2

<400> SEQUENCE: 346

Trp Val Arg Gln Ala Pro Gly Lys Gly Leu Glu Trp Val Ser
1               5                   10

<210> SEQ ID NO 347
<211> LENGTH: 30
<212> TYPE: PRT
<213> ORGANISM: Artificial Sequence
<220> FEATURE:
<223> OTHER INFORMATION: Antibody 15472 VH FR3

<400> SEQUENCE: 347

Arg Phe Thr Ile Ser Arg Asp Asn Ser Lys Asn Thr Leu Tyr Leu Gln
1               5                   10                  15

Met Asn Ser Leu Arg Ala Glu Asp Thr Ala Val Tyr Tyr Cys
            20                  25                  30

<210> SEQ ID NO 348
<211> LENGTH: 11
<212> TYPE: PRT
<213> ORGANISM: Artificial Sequence
<220> FEATURE:
<223> OTHER INFORMATION: Antibody 15472 VH FR4

<400> SEQUENCE: 348

Trp Gly Gln Gly Thr Leu Val Thr Val Ser Ser
1               5                   10

<210> SEQ ID NO 349
<211> LENGTH: 23
<212> TYPE: PRT
<213> ORGANISM: Artificial Sequence
<220> FEATURE:
<223> OTHER INFORMATION: Antibody 15472 VL FR1

<400> SEQUENCE: 349

Asp Ile Gln Met Thr Gln Ser Pro Ser Ser Leu Ser Ala Ser Val Gly
1               5                   10                  15

Asp Arg Val Thr Ile Thr Cys
            20

<210> SEQ ID NO 350
<211> LENGTH: 15
<212> TYPE: PRT
<213> ORGANISM: Artificial Sequence
<220> FEATURE:
<223> OTHER INFORMATION: Antibody 15472 VL FR2

<400> SEQUENCE: 350

Trp Tyr Gln Gln Lys Pro Gly Lys Ala Pro Lys Leu Leu Ile Tyr
1               5                   10                  15

<210> SEQ ID NO 351
<211> LENGTH: 32
<212> TYPE: PRT
<213> ORGANISM: Artificial Sequence
<220> FEATURE:
<223> OTHER INFORMATION: Antibody 15472 VL FR3

<400> SEQUENCE: 351

Gly Val Pro Ser Arg Phe Ser Gly Ser Gly Ser Gly Thr Asp Phe Thr
1               5                   10                  15

Leu Thr Ile Ser Ser Leu Gln Pro Glu Asp Phe Ala Thr Tyr Tyr Cys
            20                  25                  30

<210> SEQ ID NO 352
<211> LENGTH: 10
<212> TYPE: PRT
<213> ORGANISM: Artificial Sequence
<220> FEATURE:
<223> OTHER INFORMATION: Antibody 15472 VL FR4

<400> SEQUENCE: 352

Phe Gly Gly Gly Thr Lys Val Glu Ile Lys
1               5                   10

<210> SEQ ID NO 353
<211> LENGTH: 360
<212> TYPE: DNA
<213> ORGANISM: Artificial Sequence
<220> FEATURE:
<223> OTHER INFORMATION: Antibody 15472 Variable Heavy Chain-Encoding
      Polynucleotide Sequence

<400> SEQUENCE: 353
gaggtgcagc tgttggagtc tgggggaggc ttggtacagc ctggggggtc cctgagactc      60
tcctgtgcag cctctggatt cacctttagc agctatgcca tgagctgggt ccgccaggct     120
ccagggaagg gcctggagtg ggtctcaacc attagtggta gtggtggtag cacatactac     180
gcagactccg tgaagggccg gttcaccatc tccagagaca attccaagaa cacgctgtat     240
ctgcaaatga acagcctgag agccgaggac acggcggtgt actactgcgc cagaggtgcc     300
ggacactacg acctcgtcgg acgatactgg ggacagggta cattggtcac cgtctcctca     360

<210> SEQ ID NO 354
<211> LENGTH: 321
<212> TYPE: DNA
<213> ORGANISM: Artificial Sequence
<220> FEATURE:
<223> OTHER INFORMATION: Antibody 15472 Variable Light Chain-Encoding
      Polynucleotide Sequence

<400> SEQUENCE: 354
gacatccaga tgacccagtc tccatcctcc ctgtctgcat ctgtaggaga cagagtcacc      60
atcacttgcc gggcaagtca gagcattagc agctatttaa attggtatca gcagaaacca     120
gggaaagccc ctaagctcct gatctatgct gcatccagtt tgcaaagtgg ggtcccatca     180
aggttcagtg gcagtggatc tgggacagat ttcactctca ccatcagcag tctgcaacct     240
gaagattttg caacttacta ctgtcagcaa ctatacagtc ccctcctac ttttggcgga      300 gggaccaagg ttgagatcaa a                                               321

```
<210> SEQ ID NO 355
<211> LENGTH: 26
<212> TYPE: PRT
<213> ORGANISM: Artificial Sequence
<220> FEATURE:
<223> OTHER INFORMATION: Antibody 15503 VH FR1

<400> SEQUENCE: 355

Glu Val Gln Leu Leu Glu Ser Gly Gly Gly Leu Val Gln Pro Gly Gly
1               5                   10                  15

Ser Leu Arg Leu Ser Cys Ala Ala Ser Gly
            20                  25

<210> SEQ ID NO 356
<211> LENGTH: 14
<212> TYPE: PRT
<213> ORGANISM: Artificial Sequence
<220> FEATURE:
<223> OTHER INFORMATION: Antibody 15503 VH FR2

<400> SEQUENCE: 356

Trp Val Arg Gln Ala Pro Gly Lys Gly Leu Glu Trp Val Ser
1               5                   10

<210> SEQ ID NO 357
<211> LENGTH: 30
<212> TYPE: PRT
<213> ORGANISM: Artificial Sequence
<220> FEATURE:
<223> OTHER INFORMATION: Antibody 15503 VH FR3

<400> SEQUENCE: 357

Arg Phe Thr Ile Ser Arg Asp Asn Ser Lys Asn Thr Leu Tyr Leu Gln
1               5                   10                  15

Met Asn Ser Leu Arg Ala Glu Asp Thr Ala Val Tyr Tyr Cys
            20                  25                  30

<210> SEQ ID NO 358
<211> LENGTH: 11
<212> TYPE: PRT
<213> ORGANISM: Artificial Sequence
<220> FEATURE:
<223> OTHER INFORMATION: Antibody 15503 VH FR4

<400> SEQUENCE: 358

Trp Gly Gln Gly Thr Thr Val Thr Val Ser Ser
1               5                   10

<210> SEQ ID NO 359
<211> LENGTH: 23
<212> TYPE: PRT
<213> ORGANISM: Artificial Sequence
<220> FEATURE:
<223> OTHER INFORMATION: Antibody 15503 VL FR1

<400> SEQUENCE: 359

Asp Ile Gln Leu Thr Gln Ser Pro Ser Ser Val Ser Ala Ser Val Gly
1               5                   10                  15

Asp Arg Val Thr Ile Thr Cys
            20

<210> SEQ ID NO 360
<211> LENGTH: 15
<212> TYPE: PRT
<213> ORGANISM: Artificial Sequence
<220> FEATURE:
```

<223> OTHER INFORMATION: Antibody 15503 VL FR2

<400> SEQUENCE: 360

Trp Tyr Gln Gln Lys Pro Gly Lys Ala Pro Lys Leu Leu Ile Tyr
1               5                   10                  15

<210> SEQ ID NO 361
<211> LENGTH: 32
<212> TYPE: PRT
<213> ORGANISM: Artificial Sequence
<220> FEATURE:
<223> OTHER INFORMATION: Antibody 15503 VL FR3

<400> SEQUENCE: 361

Gly Val Pro Ser Arg Phe Ser Gly Ser Gly Ser Gly Thr Asp Phe Thr
1               5                   10                  15

Leu Thr Ile Ser Ser Leu Gln Pro Glu Asp Phe Ala Thr Tyr Tyr Cys
            20                  25                  30

<210> SEQ ID NO 362
<211> LENGTH: 10
<212> TYPE: PRT
<213> ORGANISM: Artificial Sequence
<220> FEATURE:
<223> OTHER INFORMATION: Antibody 15503 VL FR4

<400> SEQUENCE: 362

Phe Gly Gly Gly Thr Lys Val Glu Ile Lys
1               5                   10

<210> SEQ ID NO 363
<211> LENGTH: 351
<212> TYPE: DNA
<213> ORGANISM: Artificial Sequence
<220> FEATURE:
<223> OTHER INFORMATION: Antibody 15503 Variable Heavy Chain-Encoding
      Polynucleotide Sequence

<400> SEQUENCE: 363
gaggtgcagc tgttggagtc tgggggaggc ttggtacagc ctggggggtc cctgagactc        60
tcctgtgcag cctctggatt cacctttagc agctatgcca tgagctgggt ccgccaggct       120
ccagggaagg gctggagtg gtctcagct attagtggta gtggtggtag cacatactac         180
gcagactccg tgaagggccg gttcaccatc tccagagaca attccaagaa cacgctgtat       240
ctgcaaatga acagcctgag agccgaggac acggcggtgt actactgcgc cagagtggga       300
ttcagagcat taaactactg gggacagggt acaactgtca ccgtctcctc a                351

<210> SEQ ID NO 364
<211> LENGTH: 324
<212> TYPE: DNA
<213> ORGANISM: Artificial Sequence
<220> FEATURE:
<223> OTHER INFORMATION: Antibody 15503 Variable Light Chain-Encoding
      Polynucleotide Sequence

<400> SEQUENCE: 364
gacatccagt tgacccagtc tccatcttcc gtgtctgcat ctgtaggaga cagagtcacc        60
atcacttgtc gggcgagtca ggatattagc agctggttag cctggtatca gcagaaacca      120
gggaaagccc ctaagctcct gatctatgct gcatccagtt tgcaaagtgg ggtcccatca      180
aggttcagcg gcagtggatc tgggacagat ttcactctca ccatcagcag cctgcagcct      240
gaagattttg caacttatta ctgtcagcag gcaaccagtt accctccttg gacttttggc      300
ggagggacca aggttgagat caaa                                         324

<210> SEQ ID NO 365
<211> LENGTH: 26
<212> TYPE: PRT
<213> ORGANISM: Artificial Sequence
<220> FEATURE:
<223> OTHER INFORMATION: Antibody 15495 VH FR1

<400> SEQUENCE: 365

Gln Val Gln Leu Val Gln Ser Gly Ala Glu Val Lys Lys Pro Gly Ser
1               5                   10                  15

Ser Val Lys Val Ser Cys Lys Ala Ser Gly
            20                  25

<210> SEQ ID NO 366
<211> LENGTH: 14
<212> TYPE: PRT
<213> ORGANISM: Artificial Sequence
<220> FEATURE:
<223> OTHER INFORMATION: Antibody 15495 VH FR2

<400> SEQUENCE: 366

Trp Val Arg Gln Ala Pro Gly Gln Gly Leu Glu Trp Met Gly
1               5                   10

<210> SEQ ID NO 367
<211> LENGTH: 30
<212> TYPE: PRT
<213> ORGANISM: Artificial Sequence
<220> FEATURE:
<223> OTHER INFORMATION: Antibody 15495 VH FR3

<400> SEQUENCE: 367

Arg Val Thr Ile Thr Ala Asp Glu Ser Thr Ser Thr Ala Tyr Met Glu
1               5                   10                  15

Leu Ser Ser Leu Arg Ser Glu Asp Thr Ala Val Tyr Tyr Cys
            20                  25                  30

<210> SEQ ID NO 368
<211> LENGTH: 11
<212> TYPE: PRT
<213> ORGANISM: Artificial Sequence
<220> FEATURE:
<223> OTHER INFORMATION: Antibody 15495 VH FR4

<400> SEQUENCE: 368

Trp Gly Arg Gly Thr Leu Val Thr Val Ser Ser
1               5                   10

<210> SEQ ID NO 369
<211> LENGTH: 23
<212> TYPE: PRT
<213> ORGANISM: Artificial Sequence
<220> FEATURE:
<223> OTHER INFORMATION: Antibody 15495 VL FR1

<400> SEQUENCE: 369

Glu Ile Val Met Thr Gln Ser Pro Ala Thr Leu Ser Val Ser Pro Gly
1               5                   10                  15

Glu Arg Ala Thr Leu Ser Cys
            20

<210> SEQ ID NO 370

```
<211> LENGTH: 15
<212> TYPE: PRT
<213> ORGANISM: Artificial Sequence
<220> FEATURE:
<223> OTHER INFORMATION: Antibody 15495 VL FR2

<400> SEQUENCE: 370

Trp Tyr Gln Gln Lys Pro Gly Gln Ala Pro Arg Leu Leu Ile Tyr
1               5                   10                  15

<210> SEQ ID NO 371
<211> LENGTH: 32
<212> TYPE: PRT
<213> ORGANISM: Artificial Sequence
<220> FEATURE:
<223> OTHER INFORMATION: Antibody 15495 VL FR3

<400> SEQUENCE: 371

Gly Ile Pro Ala Arg Phe Ser Gly Ser Gly Ser Gly Thr Glu Phe Thr
1               5                   10                  15

Leu Thr Ile Ser Ser Leu Gln Ser Glu Asp Phe Ala Val Tyr Tyr Cys
            20                  25                  30

<210> SEQ ID NO 372
<211> LENGTH: 10
<212> TYPE: PRT
<213> ORGANISM: Artificial Sequence
<220> FEATURE:
<223> OTHER INFORMATION: Antibody 15495 VL FR4

<400> SEQUENCE: 372

Phe Gly Gly Gly Thr Lys Val Glu Ile Lys
1               5                   10

<210> SEQ ID NO 373
<211> LENGTH: 360
<212> TYPE: DNA
<213> ORGANISM: Artificial Sequence
<220> FEATURE:
<223> OTHER INFORMATION: Antibody 15495 Variable Heavy Chain-Encoding
      Polynucleotide Sequence

<400> SEQUENCE: 373
caggtgcagc tggtgcagtc tggggctgag gtgaagaagc ctgggtcctc ggtgaaggtc     60
tcctgcaagg cttctggagg caccttcagc agctatgcta tcagctgggt gcgacaggcc    120
cctggacaag gcttgagtg gatgggaggg atcatcccta tctttggtac agcaagctac    180
gcacagaagt tccagggcag agtcacgatt accgcggacg aatccacgag cacagcctac    240
atggagctga gcagcctgag atctgaggac acggcggtgt actactgcgc aagacagcaa    300
tacgacggta acgatactt cggcctatgg gggagaggta ccttggtcac cgtctcctca    360

<210> SEQ ID NO 374
<211> LENGTH: 321
<212> TYPE: DNA
<213> ORGANISM: Artificial Sequence
<220> FEATURE:
<223> OTHER INFORMATION: Antibody 15495 Variable Light Chain-Encoding
      Polynucleotide Sequence

<400> SEQUENCE: 374
gaaatagtga tgacgcagtc tccagccacc ctgtctgtgt ctccagggga aagagccacc     60
ctctcctgca gggccagtca gagtgttagc agcaacttag cctggtacca gcagaaacct    120
ggccaggctc ccaggctcct catctatagc gcatccacca gggccactgg tatcccagcc    180
```

-continued

```
aggttcagtg gcagtgggtc tgggacagag ttcactctca ccatcagcag cctgcagtct    240
gaagattttg cagtttatta ctgtcagcag gtcaacgtct ggcctcctac ttttggcgga    300
gggaccaagg ttgagatcaa a                                              321
```

<210> SEQ ID NO 375
<211> LENGTH: 26
<212> TYPE: PRT
<213> ORGANISM: Artificial Sequence
<220> FEATURE:
<223> OTHER INFORMATION: Antibody 15478 VH FR1

<400> SEQUENCE: 375

Gln Val Gln Leu Val Gln Ser Gly Ala Glu Val Lys Lys Pro Gly Ser
1               5                   10                  15

Ser Val Lys Val Ser Cys Lys Ala Ser Gly
            20                  25

<210> SEQ ID NO 376
<211> LENGTH: 14
<212> TYPE: PRT
<213> ORGANISM: Artificial Sequence
<220> FEATURE:
<223> OTHER INFORMATION: Antibody 15478 VH FR2

<400> SEQUENCE: 376

Trp Val Arg Gln Ala Pro Gly Gln Gly Leu Glu Trp Met Gly
1               5                   10

<210> SEQ ID NO 377
<211> LENGTH: 30
<212> TYPE: PRT
<213> ORGANISM: Artificial Sequence
<220> FEATURE:
<223> OTHER INFORMATION: Antibody 15478 VH FR3

<400> SEQUENCE: 377

Arg Val Thr Ile Thr Ala Asp Glu Ser Thr Ser Thr Ala Tyr Met Glu
1               5                   10                  15

Leu Ser Ser Leu Arg Ser Glu Asp Thr Ala Val Tyr Tyr Cys
            20                  25                  30

<210> SEQ ID NO 378
<211> LENGTH: 11
<212> TYPE: PRT
<213> ORGANISM: Artificial Sequence
<220> FEATURE:
<223> OTHER INFORMATION: Antibody 15478 VH FR4

<400> SEQUENCE: 378

Trp Gly Gln Gly Thr Leu Val Thr Val Ser Ser
1               5                   10

<210> SEQ ID NO 379
<211> LENGTH: 23
<212> TYPE: PRT
<213> ORGANISM: Artificial Sequence
<220> FEATURE:
<223> OTHER INFORMATION: Antibody 15478 VL FR1

<400> SEQUENCE: 379

Asp Ile Gln Met Thr Gln Ser Pro Ser Thr Leu Ser Ala Ser Val Gly
1               5                   10                  15

Asp Arg Val Thr Ile Thr Cys

```
<210> SEQ ID NO 380
<211> LENGTH: 15
<212> TYPE: PRT
<213> ORGANISM: Artificial Sequence
<220> FEATURE:
<223> OTHER INFORMATION: Antibody 15478 VL FR2

<400> SEQUENCE: 380

Trp Tyr Gln Gln Lys Pro Gly Lys Ala Pro Lys Leu Leu Ile Tyr
1               5                   10                  15

<210> SEQ ID NO 381
<211> LENGTH: 32
<212> TYPE: PRT
<213> ORGANISM: Artificial Sequence
<220> FEATURE:
<223> OTHER INFORMATION: Antibody 15478 VL FR3

<400> SEQUENCE: 381

Gly Val Pro Ser Arg Phe Ser Gly Ser Gly Ser Gly Thr Glu Phe Thr
1               5                   10                  15

Leu Thr Ile Ser Ser Leu Gln Pro Asp Asp Phe Ala Thr Tyr Tyr Cys
            20                  25                  30

<210> SEQ ID NO 382
<211> LENGTH: 10
<212> TYPE: PRT
<213> ORGANISM: Artificial Sequence
<220> FEATURE:
<223> OTHER INFORMATION: Antibody 15478 VL FR4

<400> SEQUENCE: 382

Phe Gly Gly Gly Thr Lys Val Glu Ile Lys
1               5                   10

<210> SEQ ID NO 383
<211> LENGTH: 348
<212> TYPE: DNA
<213> ORGANISM: Artificial Sequence
<220> FEATURE:
<223> OTHER INFORMATION: Antibody 15478 Variable Heavy Chain-Encoding
      Polynucleotide Sequence

<400> SEQUENCE: 383
caggtgcagc tggtgcagtc tggggctgag gtgaagaagc ctgggtcctc ggtgaaggtc      60
tcctgcaagg cttctggagg caccttcagc agctatgcta tcagctgggt gcgacaggcc    120
cctggacaag gcttgagtg gatgggaggg atcatcccta tctttggtac agcaaactac    180
gcacagaagt tccagggcag agtcacgatt accgcggacg aatccacgag cacagcctac    240
atggagctga gcagcctgag atctgaggac acggcggtgt actactgcgc cagaggtggg    300
ccttggtttg atcatggggg acagggtaca ttggtcaccg tctcctca                348

<210> SEQ ID NO 384
<211> LENGTH: 324
<212> TYPE: DNA
<213> ORGANISM: Artificial Sequence
<220> FEATURE:
<223> OTHER INFORMATION: Antibody 15478 Variable Light Chain-Encoding
      Polynucleotide Sequence

<400> SEQUENCE: 384
gacatccaga tgacccagtc tccttccacc ctgtctgcat ctgtaggaga cagagtcacc      60
```

```
atcacttgcc gggccagtca gagtattagt agctggttgg cctggtatca gcagaaacca    120
gggaaagccc ctaagctcct gatctataaa gcctccagtt tggaaagtgg ggtcccatca    180
aggttcagcg gcagtggatc tgggacagaa ttcactctca ccatcagcag cctgcagcct    240
gatgattttg caacttatta ctgccagcag tacaatagct accctccttt cacttttggc    300
ggagggacca aggttgagat caaa                                           324
```

<210> SEQ ID NO 385
<211> LENGTH: 26
<212> TYPE: PRT
<213> ORGANISM: Artificial Sequence
<220> FEATURE:
<223> OTHER INFORMATION: Antibody 15441 VH FR1

<400> SEQUENCE: 385

Glu Val Gln Leu Leu Glu Ser Gly Gly Gly Leu Val Gln Pro Gly Gly
1               5                   10                  15

Ser Leu Arg Leu Ser Cys Ala Ala Ser Gly
            20                  25

<210> SEQ ID NO 386
<211> LENGTH: 14
<212> TYPE: PRT
<213> ORGANISM: Artificial Sequence
<220> FEATURE:
<223> OTHER INFORMATION: Antibody 15441 VH FR2

<400> SEQUENCE: 386

Trp Val Arg Gln Ala Pro Gly Lys Gly Leu Glu Trp Val Ser
1               5                   10

<210> SEQ ID NO 387
<211> LENGTH: 30
<212> TYPE: PRT
<213> ORGANISM: Artificial Sequence
<220> FEATURE:
<223> OTHER INFORMATION: Antibody 15441 VH FR3

<400> SEQUENCE: 387

Arg Phe Thr Ile Ser Arg Asp Asn Ser Lys Asn Thr Leu Tyr Leu Gln
1               5                   10                  15

Met Asn Ser Leu Arg Ala Glu Asp Thr Ala Val Tyr Tyr Cys
            20                  25                  30

<210> SEQ ID NO 388
<211> LENGTH: 11
<212> TYPE: PRT
<213> ORGANISM: Artificial Sequence
<220> FEATURE:
<223> OTHER INFORMATION: Antibody 15441 VH FR4

<400> SEQUENCE: 388

Trp Gly Gln Gly Thr Met Val Thr Val Ser Ser
1               5                   10

<210> SEQ ID NO 389
<211> LENGTH: 23
<212> TYPE: PRT
<213> ORGANISM: Artificial Sequence
<220> FEATURE:
<223> OTHER INFORMATION: Antibody 15441 VL FR1

<400> SEQUENCE: 389

Asp Ile Gln Met Thr Gln Ser Pro Ser Thr Leu Ser Ala Ser Val Gly
1               5                   10                  15

Asp Arg Val Thr Ile Thr Cys
            20

<210> SEQ ID NO 390
<211> LENGTH: 15
<212> TYPE: PRT
<213> ORGANISM: Artificial Sequence
<220> FEATURE:
<223> OTHER INFORMATION: Antibody 15441 VL FR2

<400> SEQUENCE: 390

Trp Tyr Gln Gln Lys Pro Gly Lys Ala Pro Lys Leu Leu Ile Tyr
1               5                   10                  15

<210> SEQ ID NO 391
<211> LENGTH: 32
<212> TYPE: PRT
<213> ORGANISM: Artificial Sequence
<220> FEATURE:
<223> OTHER INFORMATION: Antibody 15441 VL FR3

<400> SEQUENCE: 391

Gly Val Pro Ser Arg Phe Ser Gly Ser Gly Ser Gly Thr Glu Phe Thr
1               5                   10                  15

Leu Thr Ile Ser Ser Leu Gln Pro Asp Asp Phe Ala Thr Tyr Tyr Cys
            20                  25                  30

<210> SEQ ID NO 392
<211> LENGTH: 10
<212> TYPE: PRT
<213> ORGANISM: Artificial Sequence
<220> FEATURE:
<223> OTHER INFORMATION: Antibody 15441 VL FR4

<400> SEQUENCE: 392

Phe Gly Gly Gly Thr Lys Val Glu Ile Lys
1               5                   10

<210> SEQ ID NO 393
<211> LENGTH: 360
<212> TYPE: DNA
<213> ORGANISM: Artificial Sequence
<220> FEATURE:
<223> OTHER INFORMATION: Antibody 15441 Variable Heavy Chain-Encoding
      Polynucleotide Sequence

<400> SEQUENCE: 393
gaggtgcagc tgttggagtc tgggggaggc ttggtacagc ctggggggtc cctgagactc      60
tcctgtgcag cctctggatt cacctttagc agctatgcca tgagctgggt ccgccaggct     120
ccagggaagg ggctggagtg ggtctcagct attagtggta gtggtggtag cacatcctac     180
gcagactccg tgaagggccg gttcaccatc tccagagaca attccaagaa cacgctgtat     240
ctgcaaatga acagcctgag agccgaggac acggcggtgt actactgcgc caagccttct     300
ttggcaacaa tgttagcctt cgatatctgg ggtcaggta caatggtcac cgtctcctca     360

<210> SEQ ID NO 394
<211> LENGTH: 321
<212> TYPE: DNA
<213> ORGANISM: Artificial Sequence
<220> FEATURE:
<223> OTHER INFORMATION: Antibody 15441 Variable Light Chain-Encoding
      Polynucleotide Sequence

<400> SEQUENCE: 394

```
gacatccaga tgacccagtc tccttccacc ctgtctgcat ctgtaggaga cagagtcacc    60
atcacttgcc gggccagtca gagtattagt agctggttgg cctggtatca gcagaaacca   120
gggaaagccc ctaagctcct gatctatgat gcctccagtt tggaaagtgg ggtcccatca   180
aggttcagcg gcagtggatc tgggacagaa ttcactctca ccatcagcag cctgcagcct   240
gatgattttg caacttatta ctgccagcag tccaaaagtt accctaggac ttttggcgga   300
gggaccaagg ttgagatcaa a                                             321
```

<210> SEQ ID NO 395
<211> LENGTH: 26
<212> TYPE: PRT
<213> ORGANISM: Artificial Sequence
<220> FEATURE:
<223> OTHER INFORMATION: Antibody 20496 VH FR1

<400> SEQUENCE: 395

Gln Leu Gln Leu Gln Glu Ser Gly Pro Gly Leu Val Lys Pro Ser Glu
1               5                   10                  15

Thr Leu Ser Leu Thr Cys Thr Val Ser Gly
            20                  25

<210> SEQ ID NO 396
<211> LENGTH: 14
<212> TYPE: PRT
<213> ORGANISM: Artificial Sequence
<220> FEATURE:
<223> OTHER INFORMATION: Antibody 20496 VH FR2

<400> SEQUENCE: 396

Trp Ile Arg Gln Pro Pro Gly Lys Gly Leu Glu Trp Ile Gly
1               5                   10

<210> SEQ ID NO 397
<211> LENGTH: 30
<212> TYPE: PRT
<213> ORGANISM: Artificial Sequence
<220> FEATURE:
<223> OTHER INFORMATION: Antibody 20496 VH FR3

<400> SEQUENCE: 397

Arg Val Thr Ile Ser Val Asp Thr Ser Lys Asn Gln Phe Ser Leu Lys
1               5                   10                  15

Leu Ser Ser Val Thr Ala Ala Asp Thr Ala Val Tyr Tyr Cys
            20                  25                  30

<210> SEQ ID NO 398
<211> LENGTH: 11
<212> TYPE: PRT
<213> ORGANISM: Artificial Sequence
<220> FEATURE:
<223> OTHER INFORMATION: Antibody 20496 VH FR4

<400> SEQUENCE: 398

Trp Gly Gln Gly Thr Met Val Ile Val Ser Ser
1               5                   10

<210> SEQ ID NO 399
<211> LENGTH: 23
<212> TYPE: PRT
<213> ORGANISM: Artificial Sequence
<220> FEATURE:

<223> OTHER INFORMATION: Antibody 20496 VL FR1

<400> SEQUENCE: 399

Asp Ile Gln Met Thr Gln Ser Pro Ser Ser Leu Ser Ala Ser Val Gly
1               5                   10                  15

Asp Arg Val Thr Ile Thr Cys
            20

<210> SEQ ID NO 400
<211> LENGTH: 15
<212> TYPE: PRT
<213> ORGANISM: Artificial Sequence
<220> FEATURE:
<223> OTHER INFORMATION: Antibody 20496 VL FR2

<400> SEQUENCE: 400

Trp Tyr Gln Gln Lys Pro Gly Lys Ala Pro Lys Leu Leu Ile Tyr
1               5                   10                  15

<210> SEQ ID NO 401
<211> LENGTH: 32
<212> TYPE: PRT
<213> ORGANISM: Artificial Sequence
<220> FEATURE:
<223> OTHER INFORMATION: Antibody 20496 VL FR3

<400> SEQUENCE: 401

Gly Val Pro Ser Arg Phe Ser Gly Ser Gly Ser Gly Thr Asp Phe Thr
1               5                   10                  15

Leu Thr Ile Ser Ser Leu Gln Pro Glu Asp Phe Ala Thr Tyr Tyr Cys
            20                  25                  30

<210> SEQ ID NO 402
<211> LENGTH: 10
<212> TYPE: PRT
<213> ORGANISM: Artificial Sequence
<220> FEATURE:
<223> OTHER INFORMATION: Antibody 20496 VL FR4

<400> SEQUENCE: 402

Phe Gly Gly Gly Thr Lys Val Glu Ile Lys
1               5                   10

<210> SEQ ID NO 403
<211> LENGTH: 351
<212> TYPE: DNA
<213> ORGANISM: Artificial Sequence
<220> FEATURE:
<223> OTHER INFORMATION: Antibody 20496 Variable Heavy Chain-Encoding
      Polynucleotide Sequence

<400> SEQUENCE: 403
cagctgcagc tgcaggagtc gggcccagga ctggtgaagc cttcggagac cctgtccctc      60
acctgcactg tctctggtgg ctccatcagc agtagtgttt actactggag ttggatccgc     120
cagcccccag ggaaggggtt ggagtggatt gggagtatcc tggtgagtgg gagcacctac     180
tacaacccgt ccctcaagag tcgagtcacc atatccgtag acacgtccaa gaaccagttc     240
tccctgaagc tgagttctgt gaccgccgca gacacggcgg tgtactactg cgccagagct     300
gtatccttct tagacgtatg gggtcagggt acaatggtca tcgtctcctc a              351

<210> SEQ ID NO 404
<211> LENGTH: 321
<212> TYPE: DNA

<213> ORGANISM: Artificial Sequence
<220> FEATURE:
<223> OTHER INFORMATION: Antibody 20496 Variable Light Chain-Encoding
      Polynucleotide Sequence

<400> SEQUENCE: 404

```
gacatccaga tgacccagtc tccatcctcc ctgtctgcat ctgtaggaga cagagtcacc    60
atcacttgcc gggcaagtca gagcattagc agctatttaa attggtatca gcagaaacca   120
gggaaagccc ctaagctcct gatctatggt gcatccagtt tgcaaagtgg ggtcccatca   180
aggttcagtg gcagtggatc tgggacagat ttcactctca ccatcagcag tctgcaacct   240
gaagattttg caacttacta ctgtcagcaa agctacgacc ccccttggac ttttggcgga   300
gggaccaagg ttgagatcaa a                                              321
```

<210> SEQ ID NO 405
<211> LENGTH: 107
<212> TYPE: PRT
<213> ORGANISM: Homo sapiens

<400> SEQUENCE: 405

```
Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105
```

<210> SEQ ID NO 406
<211> LENGTH: 321
<212> TYPE: DNA
<213> ORGANISM: Homo sapiens

<400> SEQUENCE: 406

```
cggaccgtgg ctgcaccatc tgtcttcatc ttcccgccat ctgatgagca gttgaaatct    60
ggaactgcct ctgttgtgtg cctgctgaat aacttctatc ccagagaggc caaagtacag   120
tggaaggtgg ataacgccct ccaatcgggt aactcccagg agagtgtcac agagcaggac   180
agcaaggaca gcacctacag cctcagcagc accctgacgc tgagcaaagc agactacgag   240
aaacacaaag tctacgcctg cgaagtcacc catcagggcc tgagctcgcc cgtcacaaag   300
agcttcaaca ggggagagtg t                                              321
```

<210> SEQ ID NO 407
<211> LENGTH: 330
<212> TYPE: PRT
<213> ORGANISM: Homo sapiens

<400> SEQUENCE: 407

```
Ala Ser Thr Lys Gly Pro Ser Val Phe Pro Leu Ala Pro Ser Ser Lys
1               5                   10                  15
```

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 408
<211> LENGTH: 990
<212> TYPE: DNA
<213> ORGANISM: Homo sapiens

<400> SEQUENCE: 408
gcctccacca agggcccatc ggtcttcccc ctggcaccct cctccaagag cacctctggg      60
ggcacagcgg ccctgggctg cctggtcaag gactacttcc ccgaaccggt gacggtgtcg     120
tggaactcag gcgccctgac cagcggcgtg cacaccttcc cggctgtcct acagtcctca     180
ggactctact ccctcagcag cgtggtgacc gtgccctcca gcagcttggg cacccagacc     240
tacatctgca acgtgaatca caagcccagc aacaccaagg tggacaagaa agttgagccc     300
aaatcttgtg acaaaactca cacatgccca ccgtgcccag cacctgaact cctgggggga     360

```
ccgtcagtct tcctcttccc cccaaaaccc aaggacaccc tcatgatctc ccggacccct    420
gaggtcacat gcgtggtggt ggacgtgagc cacgaagacc ctgaggtcaa gttcaactgg    480
tacgtggacg gcgtggaggt gcataatgcc aagacaaagc cgcgggagga gcagtacaac    540
agcacgtacc gggtggtcag cgtcctcacc gtcctgcacc aggactggct gaatggcaag    600
gagtacaagt gcaaggtctc caacaaagcc ctcccagccc ccatcgagaa aaccatctcc    660
aaagccaaag ggcagccccg agaaccacag gtgtacaccc tgcccccatc ccgggatgag    720
ctgaccaaga accaggtcag cctgacctgc ctggtcaaag gcttctatcc cagcgacatc    780
gccgtggagt gggagagcaa tgggcagccg gagaacaact acaagaccac gcctcccgtg    840
ctggactccg acggctcctt cttcctctac agcaagctca ccgtggacaa gagcaggtgg    900
cagcagggga acgtcttctc atgctccgtg atgcatgagg ctctgcacaa ccactacacg    960
cagaagagcc tctccctgtc tccgggtaaa                                    990
```

<210> SEQ ID NO 409
<211> LENGTH: 493
<212> TYPE: PRT
<213> ORGANISM: Artificial Sequence
<220> FEATURE:
<223> OTHER INFORMATION: B7-H4-huIgG1

<400> SEQUENCE: 409

```
Met Ala Ser Leu Gly Gln Ile Leu Phe Trp Ser Ile Ile Ser Ile Ile
1               5                   10                  15

Ile Ile Leu Ala Gly Ala Ile Ala Leu Ile Ile Gly Phe Gly Ile Ser
            20                  25                  30

Gly Arg His Ser Ile Thr Val Thr Thr Val Ala Ser Ala Gly Asn Ile
        35                  40                  45

Gly Glu Asp Gly Ile Leu Ser Cys Thr Phe Glu Pro Asp Ile Lys Leu
    50                  55                  60

Ser Asp Ile Val Ile Gln Trp Leu Lys Glu Gly Val Leu Gly Leu Val
65                  70                  75                  80

His Glu Phe Lys Glu Gly Lys Asp Glu Leu Ser Glu Gln Asp Glu Met
                85                  90                  95

Phe Arg Gly Arg Thr Ala Val Phe Ala Asp Gln Val Ile Val Gly Asn
            100                 105                 110

Ala Ser Leu Arg Leu Lys Asn Val Gln Leu Thr Asp Ala Gly Thr Tyr
        115                 120                 125

Lys Cys Tyr Ile Ile Thr Ser Lys Gly Lys Gly Asn Ala Asn Leu Glu
    130                 135                 140

Tyr Lys Thr Gly Ala Phe Ser Met Pro Glu Val Asn Val Asp Tyr Asn
145                 150                 155                 160

Ala Ser Ser Glu Thr Leu Arg Cys Glu Ala Pro Arg Trp Phe Pro Gln
                165                 170                 175

Pro Thr Val Val Trp Ala Ser Gln Val Asp Gln Gly Ala Asn Phe Ser
            180                 185                 190

Glu Val Ser Asn Thr Ser Phe Glu Leu Asn Ser Glu Asn Val Thr Met
        195                 200                 205

Lys Val Val Ser Val Leu Tyr Asn Val Thr Ile Asn Asn Thr Tyr Ser
    210                 215                 220

Cys Met Ile Glu Asn Asp Ile Ala Lys Ala Thr Gly Asp Ile Lys Val
225                 230                 235                 240

Thr Glu Ser Glu Ile Lys Arg Arg Ser His Leu Gln Leu Leu Asn Ser
```

```
                 245                 250                 255
Lys Ala Ser Gly Ser Glu Pro Lys Ser Ser Asp Lys Thr His Thr Cys
            260                 265                 270

Pro Pro Cys Pro Ala Pro Glu Leu Leu Gly Gly Pro Ser Val Phe Leu
        275                 280                 285

Phe Pro Pro Lys Pro Lys Asp Thr Leu Met Ile Ser Arg Thr Pro Glu
    290                 295                 300

Val Thr Cys Val Val Val Asp Val Ser His Glu Asp Pro Glu Val Lys
305                 310                 315                 320

Phe Asn Trp Tyr Val Asp Gly Val Glu Val His Asn Ala Lys Thr Lys
                325                 330                 335

Pro Arg Glu Glu Gln Tyr Asn Ser Thr Tyr Arg Val Val Ser Val Leu
            340                 345                 350

Thr Val Leu His Gln Asp Trp Leu Asn Gly Lys Glu Tyr Lys Cys Lys
        355                 360                 365

Val Ser Asn Lys Ala Leu Pro Ala Pro Ile Glu Lys Thr Ile Ser Lys
    370                 375                 380

Ala Lys Gly Gln Pro Arg Glu Pro Gln Val Tyr Thr Leu Pro Pro Ser
385                 390                 395                 400

Arg Asp Glu Leu Thr Lys Asn Gln Val Ser Leu Thr Cys Leu Val Lys
                405                 410                 415

Gly Phe Tyr Pro Ser Asp Ile Ala Val Glu Trp Glu Ser Asn Gly Gln
            420                 425                 430

Pro Glu Asn Asn Tyr Lys Thr Thr Pro Pro Val Leu Asp Ser Asp Gly
        435                 440                 445

Ser Phe Phe Leu Tyr Ser Lys Leu Thr Val Asp Lys Ser Arg Trp Gln
    450                 455                 460

Gln Gly Asn Val Phe Ser Cys Ser Val Met His Glu Ala Leu His Asn
465                 470                 475                 480

His Tyr Thr Gln Lys Ser Leu Ser Leu Ser Pro Gly Lys
                485                 490
```

<210> SEQ ID NO 410
<211> LENGTH: 385
<212> TYPE: PRT
<213> ORGANISM: Artificial Sequence
<220> FEATURE:
<223> OTHER INFORMATION: B7-H4 IgV-huIgG1

<400> SEQUENCE: 410

```
Met Ala Ser Leu Gly Gln Ile Leu Phe Trp Ser Ile Ile Ser Ile Ile
1               5                   10                  15

Ile Ile Leu Ala Gly Ala Ile Ala Leu Ile Ile Gly Phe Gly Ile Ser
            20                  25                  30

Gly Arg His Ser Ile Thr Val Thr Thr Val Ala Ser Ala Gly Asn Ile
        35                  40                  45

Gly Glu Asp Gly Ile Leu Ser Cys Thr Phe Glu Pro Asp Ile Lys Leu
    50                  55                  60

Ser Asp Ile Val Ile Gln Trp Leu Lys Glu Gly Val Leu Gly Leu Val
65                  70                  75                  80

His Glu Phe Lys Glu Gly Lys Asp Glu Leu Ser Glu Gln Asp Glu Met
                85                  90                  95

Phe Arg Gly Arg Thr Ala Val Phe Ala Asp Gln Val Ile Val Gly Asn
            100                 105                 110

Ala Ser Leu Arg Leu Lys Asn Val Gln Leu Thr Asp Ala Gly Thr Tyr
```

```
            115                 120                 125
Lys Cys Tyr Ile Ile Thr Ser Lys Gly Lys Gly Asn Ala Asn Leu Glu
        130                 135                 140

Tyr Lys Thr Gly Ala Phe Ser Gly Ser Glu Pro Lys Ser Ser Asp Lys
145                 150                 155                 160

Thr His Thr Cys Pro Pro Cys Pro Ala Pro Glu Leu Leu Gly Gly Pro
                165                 170                 175

Ser Val Phe Leu Phe Pro Pro Lys Pro Lys Asp Thr Leu Met Ile Ser
            180                 185                 190

Arg Thr Pro Glu Val Thr Cys Val Val Val Asp Val Ser His Glu Asp
        195                 200                 205

Pro Glu Val Lys Phe Asn Trp Tyr Val Asp Gly Val Glu Val His Asn
210                 215                 220

Ala Lys Thr Lys Pro Arg Glu Glu Gln Tyr Asn Ser Thr Tyr Arg Val
225                 230                 235                 240

Val Ser Val Leu Thr Val Leu His Gln Asp Trp Leu Asn Gly Lys Glu
                245                 250                 255

Tyr Lys Cys Lys Val Ser Asn Lys Ala Leu Pro Ala Pro Ile Glu Lys
            260                 265                 270

Thr Ile Ser Lys Ala Lys Gly Gln Pro Arg Glu Pro Gln Val Tyr Thr
        275                 280                 285

Leu Pro Pro Ser Arg Asp Glu Leu Thr Lys Asn Gln Val Ser Leu Thr
290                 295                 300

Cys Leu Val Lys Gly Phe Tyr Pro Ser Asp Ile Ala Val Glu Trp Glu
305                 310                 315                 320

Ser Asn Gly Gln Pro Glu Asn Asn Tyr Lys Thr Thr Pro Pro Val Leu
                325                 330                 335

Asp Ser Asp Gly Ser Phe Phe Leu Tyr Ser Lys Leu Thr Val Asp Lys
            340                 345                 350

Ser Arg Trp Gln Gln Gly Asn Val Phe Ser Cys Ser Val Met His Glu
        355                 360                 365

Ala Leu His Asn His Tyr Thr Gln Lys Ser Leu Ser Leu Ser Pro Gly
370                 375                 380

Lys
385

<210> SEQ ID NO 411
<211> LENGTH: 10
<212> TYPE: PRT
<213> ORGANISM: Artificial Sequence
<220> FEATURE:
<223> OTHER INFORMATION: GITR Antibody

<400> SEQUENCE: 411

Ser Gly Ser Val Phe Ser Ile Asp Ala Met
1               5                   10

<210> SEQ ID NO 412
<211> LENGTH: 8
<212> TYPE: PRT
<213> ORGANISM: Artificial Sequence
<220> FEATURE:
<223> OTHER INFORMATION: GITR Antibody

<400> SEQUENCE: 412

Leu Ser Gly Ile Ser Ser Ala Lys
1               5
```

```
<210> SEQ ID NO 413
<211> LENGTH: 16
<212> TYPE: PRT
<213> ORGANISM: Artificial Sequence
<220> FEATURE:
<223> OTHER INFORMATION: GITR Antibody

<400> SEQUENCE: 413

Tyr Ala Asp Val Ser Thr Gly Trp Gly Arg Asp Ala His Gly Tyr Trp
1               5                   10                  15

<210> SEQ ID NO 414
<211> LENGTH: 119
<212> TYPE: PRT
<213> ORGANISM: Artificial Sequence
<220> FEATURE:
<223> OTHER INFORMATION: GITR Antibody

<400> SEQUENCE: 414

Glu Val Gln Leu Leu Glu Ser Gly Gly Gly Glu Val Gln Pro Gly Gly
1               5                   10                  15

Ser Leu Arg Leu Ser Cys Ala Ala Ser Gly Ser Val Phe Ser Ile Asp
            20                  25                  30

Ala Met Gly Trp Tyr Arg Gln Ala Pro Gly Lys Gln Arg Glu Leu Val
        35                  40                  45

Ala Val Leu Ser Gly Ile Ser Ser Ala Lys Tyr Ala Ala Ser Ala Pro
    50                  55                  60

Gly Arg Phe Thr Ile Ser Arg Asp Asn Ala Lys Asn Thr Val Tyr Leu
65                  70                  75                  80

Gln Met Ser Ser Leu Arg Ala Glu Asp Thr Ala Val Tyr Tyr Cys Tyr
                85                  90                  95

Ala Asp Val Ser Thr Gly Trp Gly Arg Asp Ala His Gly Tyr Trp Gly
            100                 105                 110

Gln Gly Thr Leu Val Thr Val
        115

<210> SEQ ID NO 415
<211> LENGTH: 479
<212> TYPE: PRT
<213> ORGANISM: Artificial Sequence
<220> FEATURE:
<223> OTHER INFORMATION: GITR Antibody

<400> SEQUENCE: 415

Glu Val Gln Leu Leu Glu Ser Gly Gly Gly Glu Val Gln Pro Gly Gly
1               5                   10                  15

Ser Leu Arg Leu Ser Cys Ala Ala Ser Gly Ser Val Phe Ser Ile Asp
            20                  25                  30

Ala Met Gly Trp Tyr Arg Gln Ala Pro Gly Lys Gln Arg Glu Leu Val
        35                  40                  45

Ala Val Leu Ser Gly Ile Ser Ser Ala Lys Tyr Ala Ala Ser Ala Pro
    50                  55                  60

Gly Arg Phe Thr Ile Ser Arg Asp Asn Ala Lys Asn Thr Val Tyr Leu
65                  70                  75                  80

Gln Met Ser Ser Leu Arg Ala Glu Asp Thr Ala Val Tyr Tyr Cys Tyr
                85                  90                  95

Ala Asp Val Ser Thr Gly Trp Gly Arg Asp Ala His Gly Tyr Trp Gly
            100                 105                 110

Gln Gly Thr Leu Val Thr Val Lys Pro Gly Gly Ser Gly Gly Ser Glu
```

```
            115                 120                 125
Val Gln Leu Leu Glu Ser Gly Gly Glu Val Gln Pro Gly Gly Ser
130                 135                 140

Leu Arg Leu Ser Cys Ala Ala Ser Gly Ser Val Phe Ser Ile Asp Ala
145                 150                 155                 160

Met Gly Trp Tyr Arg Gln Ala Pro Gly Lys Gln Arg Glu Leu Val Ala
                165                 170                 175

Val Leu Ser Gly Ile Ser Ser Ala Lys Tyr Ala Ala Ser Ala Pro Gly
                180                 185                 190

Arg Phe Thr Ile Ser Arg Asp Asn Ala Lys Asn Thr Val Tyr Leu Gln
                195                 200                 205

Met Ser Ser Leu Arg Ala Glu Asp Thr Ala Val Tyr Tyr Cys Tyr Ala
210                 215                 220

Asp Val Ser Thr Gly Trp Gly Arg Asp Ala His Gly Tyr Trp Gly Gln
225                 230                 235                 240

Gly Thr Leu Val Thr Val Lys Pro Gly Gly Gly Asp Lys Thr His
                245                 250                 255

Thr Cys Pro Pro Cys Pro Ala Pro Glu Leu Leu Gly Gly Pro Ser Val
                260                 265                 270

Phe Leu Phe Pro Pro Lys Pro Lys Asp Thr Leu Met Ile Ser Arg Thr
                275                 280                 285

Pro Glu Val Thr Cys Val Val Val Asp Val Ser His Glu Asp Pro Glu
290                 295                 300

Val Lys Phe Asn Trp Tyr Val Asp Gly Val Glu Val His Asn Ala Lys
305                 310                 315                 320

Thr Lys Pro Arg Glu Glu Gln Tyr Asn Ser Thr Tyr Arg Val Val Ser
                325                 330                 335

Val Leu Thr Val Leu His Gln Asp Trp Leu Asn Gly Lys Glu Tyr Lys
                340                 345                 350

Cys Lys Val Ser Asn Lys Ala Leu Pro Ala Pro Ile Glu Lys Thr Ile
                355                 360                 365

Ser Lys Ala Lys Gly Gln Pro Arg Glu Pro Gln Val Tyr Thr Leu Pro
370                 375                 380

Pro Ser Arg Asp Glu Leu Thr Lys Asn Gln Val Ser Leu Thr Cys Leu
385                 390                 395                 400

Val Lys Gly Phe Tyr Pro Ser Asp Ile Ala Val Glu Trp Glu Ser Asn
                405                 410                 415

Gly Gln Pro Glu Asn Asn Tyr Lys Thr Thr Pro Pro Val Leu Asp Ser
                420                 425                 430

Asp Gly Ser Phe Phe Leu Tyr Ser Lys Leu Thr Val Asp Lys Ser Arg
                435                 440                 445

Trp Gln Gln Gly Asn Val Phe Ser Cys Ser Val Met His Glu Ala Leu
                450                 455                 460

His Asn His Tyr Thr Gln Lys Ser Leu Ser Leu Ser Pro Gly Lys
465                 470                 475

<210> SEQ ID NO 416
<211> LENGTH: 14
<212> TYPE: PRT
<213> ORGANISM: Artificial Sequence
<220> FEATURE:
<223> OTHER INFORMATION: GITR Antibody

<400> SEQUENCE: 416

Glu Pro Lys Ser Ser Asp Lys Thr His Thr Cys Pro Pro Cys
```

<210> SEQ ID NO 417
<211> LENGTH: 9
<212> TYPE: PRT
<213> ORGANISM: Artificial Sequence
<220> FEATURE:
<223> OTHER INFORMATION: GITR Antibody

<400> SEQUENCE: 417

Asp Lys Thr His Thr Cys Pro Pro Cys
1               5

<210> SEQ ID NO 418
<211> LENGTH: 11
<212> TYPE: PRT
<213> ORGANISM: Artificial Sequence
<220> FEATURE:
<223> OTHER INFORMATION: GITR Antibody

<400> SEQUENCE: 418

Glu Ser Lys Tyr Gly Pro Pro Cys Pro Pro Cys
1               5                   10

<210> SEQ ID NO 419
<211> LENGTH: 6
<212> TYPE: PRT
<213> ORGANISM: Artificial Sequence
<220> FEATURE:
<223> OTHER INFORMATION: GITR Antibody

<400> SEQUENCE: 419

Gly Gly Ser Gly Gly Ser
1               5

<210> SEQ ID NO 420
<211> LENGTH: 9
<212> TYPE: PRT
<213> ORGANISM: Artificial Sequence
<220> FEATURE:
<223> OTHER INFORMATION: GITR Antibody

<400> SEQUENCE: 420

Gly Gly Ser Gly Gly Ser Gly Gly Ser
1               5

<210> SEQ ID NO 421
<211> LENGTH: 12
<212> TYPE: PRT
<213> ORGANISM: Artificial Sequence
<220> FEATURE:
<223> OTHER INFORMATION: GITR Antibody

<400> SEQUENCE: 421

Gly Gly Ser Gly Gly Ser Gly Gly Ser Gly Gly Ser
1               5                   10

<210> SEQ ID NO 422
<211> LENGTH: 15
<212> TYPE: PRT
<213> ORGANISM: Artificial Sequence
<220> FEATURE:
<223> OTHER INFORMATION: GITR Antibody

<400> SEQUENCE: 422

Gly Gly Ser Gly Gly Ser Gly Gly Ser Gly Gly Ser Gly Gly Ser
1               5                   10                  15

<210> SEQ ID NO 423
<211> LENGTH: 4
<212> TYPE: PRT
<213> ORGANISM: Artificial Sequence
<220> FEATURE:
<223> OTHER INFORMATION: GITR Antibody

<400> SEQUENCE: 423

Gly Gly Gly Gly
1

<210> SEQ ID NO 424
<211> LENGTH: 5
<212> TYPE: PRT
<213> ORGANISM: Artificial Sequence
<220> FEATURE:
<223> OTHER INFORMATION: GITR Antibody

<400> SEQUENCE: 424

Gly Gly Gly Gly Gly
1               5

<210> SEQ ID NO 425
<211> LENGTH: 6
<212> TYPE: PRT
<213> ORGANISM: Artificial Sequence
<220> FEATURE:
<223> OTHER INFORMATION: GITR Antibody

<400> SEQUENCE: 425

Gly Gly Gly Gly Gly Gly
1               5

<210> SEQ ID NO 426
<211> LENGTH: 208
<212> TYPE: PRT
<213> ORGANISM: Artificial Sequence
<220> FEATURE:
<223> OTHER INFORMATION: CD80

<400> SEQUENCE: 426

Val Ile His Val Thr Lys Glu Val Lys Glu Val Ala Thr Leu Ser Cys
1               5                   10                  15

Gly His Asn Val Ser Val Glu Glu Leu Ala Gln Thr Arg Ile Tyr Trp
            20                  25                  30

Gln Lys Glu Lys Lys Met Val Leu Thr Met Met Ser Gly Asp Met Asn
        35                  40                  45

Ile Trp Pro Glu Tyr Lys Asn Arg Thr Ile Phe Asp Ile Thr Asn Asn
    50                  55                  60

Leu Ser Ile Val Ile Leu Ala Leu Arg Pro Ser Asp Glu Gly Thr Tyr
65                  70                  75                  80

Glu Cys Val Val Leu Lys Tyr Glu Lys Asp Ala Phe Lys Arg Glu His
                85                  90                  95

Leu Ala Glu Val Thr Leu Ser Val Lys Ala Asp Phe Pro Thr Pro Ser
            100                 105                 110

Ile Ser Asp Phe Glu Ile Pro Thr Ser Asn Ile Arg Arg Ile Ile Cys
        115                 120                 125

Ser Thr Ser Gly Gly Phe Pro Glu Pro His Leu Ser Trp Leu Glu Asn
    130                 135                 140

Gly Glu Glu Leu Asn Ala Ile Asn Thr Thr Val Ser Gln Asp Pro Glu
145                 150                 155                 160

```
Thr Glu Leu Tyr Ala Val Ser Ser Lys Leu Asp Phe Asn Met Thr Thr
            165                 170                 175

Asn His Ser Phe Met Cys Leu Ile Lys Tyr Gly His Leu Arg Val Asn
            180                 185                 190

Gln Thr Phe Asn Trp Asn Thr Thr Lys Gln Glu His Phe Pro Asp Asn
        195                 200                 205

<210> SEQ ID NO 427
<211> LENGTH: 440
<212> TYPE: PRT
<213> ORGANISM: Artificial Sequence
<220> FEATURE:
<223> OTHER INFORMATION: CD80

<400> SEQUENCE: 427

Val Ile His Val Thr Lys Glu Val Lys Glu Val Ala Thr Leu Ser Cys
1               5                   10                  15

Gly His Asn Val Ser Val Glu Glu Leu Ala Gln Thr Arg Ile Tyr Trp
            20                  25                  30

Gln Lys Glu Lys Lys Met Val Leu Thr Met Met Ser Gly Asp Met Asn
        35                  40                  45

Ile Trp Pro Glu Tyr Lys Asn Arg Thr Ile Phe Asp Ile Thr Asn Asn
50                  55                  60

Leu Ser Ile Val Ile Leu Ala Leu Arg Pro Ser Asp Glu Gly Thr Tyr
65                  70                  75                  80

Glu Cys Val Val Leu Lys Tyr Glu Lys Asp Ala Phe Lys Arg Glu His
                85                  90                  95

Leu Ala Glu Val Thr Leu Ser Val Lys Ala Asp Phe Pro Thr Pro Ser
            100                 105                 110

Ile Ser Asp Phe Glu Ile Pro Thr Ser Asn Ile Arg Arg Ile Ile Cys
        115                 120                 125

Ser Thr Ser Gly Gly Phe Pro Glu Pro His Leu Ser Trp Leu Glu Asn
130                 135                 140

Gly Glu Glu Leu Asn Ala Ile Asn Thr Thr Val Ser Gln Asp Pro Glu
145                 150                 155                 160

Thr Glu Leu Tyr Ala Val Ser Ser Lys Leu Asp Phe Asn Met Thr Thr
            165                 170                 175

Asn His Ser Phe Met Cys Leu Ile Lys Tyr Gly His Leu Arg Val Asn
            180                 185                 190

Gln Thr Phe Asn Trp Asn Thr Thr Lys Gln Glu His Phe Pro Asp Asn
        195                 200                 205

Glu Pro Lys Ser Ser Asp Lys Thr His Thr Cys Pro Pro Cys Pro Ala
210                 215                 220

Pro Glu Leu Leu Gly Gly Pro Ser Val Phe Leu Phe Pro Pro Lys Pro
225                 230                 235                 240

Lys Asp Thr Leu Met Ile Ser Arg Thr Pro Glu Val Thr Cys Val Val
            245                 250                 255

Val Asp Val Ser His Glu Asp Pro Glu Val Lys Phe Asn Trp Tyr Val
            260                 265                 270

Asp Gly Val Glu Val His Asn Ala Lys Thr Lys Pro Arg Glu Glu Gln
        275                 280                 285

Tyr Asn Ser Thr Tyr Arg Val Val Ser Val Leu Thr Val Leu His Gln
        290                 295                 300

Asp Trp Leu Asn Gly Lys Glu Tyr Lys Cys Lys Val Ser Asn Lys Ala
305                 310                 315                 320
```

Leu Pro Ala Pro Ile Glu Lys Thr Ile Ser Lys Ala Lys Gly Gln Pro
            325                 330                 335

Arg Glu Pro Gln Val Tyr Thr Leu Pro Pro Ser Arg Asp Glu Leu Thr
            340                 345                 350

Lys Asn Gln Val Ser Leu Thr Cys Leu Val Lys Gly Phe Tyr Pro Ser
            355                 360                 365

Asp Ile Ala Val Glu Trp Glu Ser Asn Gly Gln Pro Glu Asn Asn Tyr
            370                 375                 380

Lys Thr Thr Pro Pro Val Leu Asp Ser Asp Gly Ser Phe Phe Leu Tyr
385                 390                 395                 400

Ser Lys Leu Thr Val Asp Lys Ser Arg Trp Gln Gln Gly Asn Val Phe
            405                 410                 415

Ser Cys Ser Val Met His Glu Ala Leu His Asn His Tyr Thr Gln Lys
            420                 425                 430

Ser Leu Ser Leu Ser Pro Gly Lys
            435                 440

<210> SEQ ID NO 428
<211> LENGTH: 440
<212> TYPE: PRT
<213> ORGANISM: Artificial Sequence
<220> FEATURE:
<223> OTHER INFORMATION: CD80

<400> SEQUENCE: 428

Val Ile His Val Thr Lys Glu Val Lys Glu Val Ala Thr Leu Ser Cys
1               5                   10                  15

Gly His Asn Val Ser Val Glu Glu Leu Ala Gln Thr Arg Ile Tyr Trp
                20                  25                  30

Gln Lys Glu Lys Lys Met Val Leu Thr Met Met Ser Gly Asp Met Asn
            35                  40                  45

Ile Trp Pro Glu Tyr Lys Asn Arg Thr Ile Phe Asp Ile Thr Asn Asn
        50                  55                  60

Leu Ser Ile Val Ile Leu Ala Leu Arg Pro Ser Asp Glu Gly Thr Tyr
65                  70                  75                  80

Glu Cys Val Val Leu Lys Tyr Glu Lys Asp Ala Phe Lys Arg Glu His
                85                  90                  95

Leu Ala Glu Val Thr Leu Ser Val Lys Ala Asp Phe Pro Thr Pro Ser
            100                 105                 110

Ile Ser Asp Phe Glu Ile Pro Thr Ser Asn Ile Arg Arg Ile Ile Cys
        115                 120                 125

Ser Thr Ser Gly Gly Phe Pro Glu Pro His Leu Ser Trp Leu Glu Asn
130                 135                 140

Gly Glu Glu Leu Asn Ala Ile Asn Thr Thr Val Ser Gln Asp Pro Glu
145                 150                 155                 160

Thr Glu Leu Tyr Ala Val Ser Ser Lys Leu Asp Phe Asn Met Thr Thr
                165                 170                 175

Asn His Ser Phe Met Cys Leu Ile Lys Tyr Gly His Leu Arg Val Asn
            180                 185                 190

Gln Thr Phe Asn Trp Asn Thr Thr Lys Gln Glu His Phe Pro Asp Asn
        195                 200                 205

Glu Pro Lys Ser Ser Asp Lys Thr His Thr Cys Pro Pro Cys Pro Ala
    210                 215                 220

Pro Glu Phe Glu Gly Gly Pro Ser Val Phe Leu Phe Pro Pro Lys Pro
225                 230                 235                 240

```
Lys Asp Thr Leu Met Ile Ser Arg Thr Pro Glu Val Thr Cys Val Val
                245                 250                 255
Val Asp Val Ser His Glu Asp Pro Glu Val Lys Phe Asn Trp Tyr Val
            260                 265                 270
Asp Gly Val Glu Val His Asn Ala Lys Thr Lys Pro Arg Glu Glu Gln
        275                 280                 285
Tyr Asn Ser Thr Tyr Arg Val Val Ser Val Leu Thr Val Leu His Gln
    290                 295                 300
Asp Trp Leu Asn Gly Lys Glu Tyr Lys Cys Lys Val Ser Asn Lys Ala
305                 310                 315                 320
Leu Pro Ala Ser Ile Glu Lys Thr Ile Ser Lys Ala Lys Gly Gln Pro
                325                 330                 335
Arg Glu Pro Gln Val Tyr Thr Leu Pro Pro Ser Arg Asp Glu Leu Thr
            340                 345                 350
Lys Asn Gln Val Ser Leu Thr Cys Leu Val Lys Gly Phe Tyr Pro Ser
        355                 360                 365
Asp Ile Ala Val Glu Trp Glu Ser Asn Gly Gln Pro Glu Asn Asn Tyr
    370                 375                 380
Lys Thr Thr Pro Pro Val Leu Asp Ser Asp Gly Ser Phe Phe Leu Tyr
385                 390                 395                 400
Ser Lys Leu Thr Val Asp Lys Ser Arg Trp Gln Gln Gly Asn Val Phe
                405                 410                 415
Ser Cys Ser Val Met His Glu Ala Leu His Asn His Tyr Thr Gln Lys
            420                 425                 430
Ser Leu Ser Leu Ser Pro Gly Lys
        435                 440

<210> SEQ ID NO 429
<211> LENGTH: 122
<212> TYPE: PRT
<213> ORGANISM: Artificial Sequence
<220> FEATURE:
<223> OTHER INFORMATION: CD80

<400> SEQUENCE: 429

Gln Val Gln Leu Val Gln Ser Gly Ala Glu Val Lys Lys Pro Gly Ser
1               5                   10                  15
Ser Val Lys Val Ser Cys Lys Ala Ser Gly Tyr Thr Phe Thr Asp Asn
                20                  25                  30
Tyr Met Ile Trp Val Arg Gln Ala Pro Gly Gln Gly Leu Glu Trp Met
            35                  40                  45
Gly Asp Ile Asn Pro Tyr Asn Gly Gly Thr Thr Phe Asn Gln Lys Phe
    50                  55                  60
Lys Gly Arg Val Thr Ile Thr Ala Asp Lys Ser Thr Ser Thr Ala Tyr
65                  70                  75                  80
Met Glu Leu Ser Ser Leu Arg Ser Glu Asp Thr Ala Val Tyr Tyr Cys
                85                  90                  95
Ala Arg Glu Ser Pro Tyr Phe Ser Asn Leu Tyr Val Met Asp Tyr Trp
            100                 105                 110
Gly Gln Gly Thr Leu Val Thr Val Ser Ser
        115                 120

<210> SEQ ID NO 430
<211> LENGTH: 111
<212> TYPE: PRT
<213> ORGANISM: Artificial Sequence
```

-continued

<220> FEATURE:
<223> OTHER INFORMATION: CD80

<400> SEQUENCE: 430

Glu Ile Val Leu Thr Gln Ser Pro Ala Thr Leu Ser Leu Ser Pro Gly
1               5                   10                  15

Glu Arg Ala Thr Leu Ser Cys Lys Ala Ser Gln Ser Val Asp Tyr Asp
            20                  25                  30

Gly Asp Asn Tyr Met Asn Trp Tyr Gln Gln Lys Pro Gly Gln Ala Pro
        35                  40                  45

Arg Leu Leu Ile Tyr Ala Ala Ser Asn Leu Glu Ser Gly Ile Pro Ala
    50                  55                  60

Arg Phe Ser Gly Ser Gly Ser Gly Thr Asp Phe Thr Leu Thr Ile Ser
65                  70                  75                  80

Ser Leu Glu Pro Glu Asp Phe Ala Val Tyr Tyr Cys His Leu Ser Asn
                85                  90                  95

Glu Asp Leu Ser Thr Phe Gly Gly Gly Thr Lys Val Glu Ile Lys
            100                 105                 110

<210> SEQ ID NO 431
<211> LENGTH: 10
<212> TYPE: PRT
<213> ORGANISM: Artificial Sequence
<220> FEATURE:
<223> OTHER INFORMATION: GITR Antibody

<400> SEQUENCE: 431

Gly Tyr Thr Phe Thr Asp Asn Tyr Met Ile
1               5                   10

<210> SEQ ID NO 432
<211> LENGTH: 17
<212> TYPE: PRT
<213> ORGANISM: Artificial Sequence
<220> FEATURE:
<223> OTHER INFORMATION: CD80

<400> SEQUENCE: 432

Asp Ile Asn Pro Tyr Asn Gly Gly Thr Thr Phe Asn Gln Lys Phe Lys
1               5                   10                  15
Gly

<210> SEQ ID NO 433
<211> LENGTH: 13
<212> TYPE: PRT
<213> ORGANISM: Artificial Sequence
<220> FEATURE:
<223> OTHER INFORMATION: CD80

<400> SEQUENCE: 433

Glu Ser Pro Tyr Phe Ser Asn Leu Tyr Val Met Asp Tyr
1               5                   10

<210> SEQ ID NO 434
<211> LENGTH: 15
<212> TYPE: PRT
<213> ORGANISM: Artificial Sequence
<220> FEATURE:
<223> OTHER INFORMATION: CD80

<400> SEQUENCE: 434

Lys Ala Ser Gln Ser Val Asp Tyr Asp Gly Asp Asn Tyr Met Asn
1               5                   10                  15

<210> SEQ ID NO 435
<211> LENGTH: 7
<212> TYPE: PRT
<213> ORGANISM: Artificial Sequence
<220> FEATURE:
<223> OTHER INFORMATION: CD80

<400> SEQUENCE: 435

Ala Ala Ser Asn Leu Glu Ser
1               5

<210> SEQ ID NO 436
<211> LENGTH: 9
<212> TYPE: PRT
<213> ORGANISM: Artificial Sequence
<220> FEATURE:
<223> OTHER INFORMATION: CD80

<400> SEQUENCE: 436

His Leu Ser Asn Glu Asp Leu Ser Thr
1               5

<210> SEQ ID NO 437
<211> LENGTH: 449
<212> TYPE: PRT
<213> ORGANISM: Artificial Sequence
<220> FEATURE:
<223> OTHER INFORMATION: CD80

<400> SEQUENCE: 437

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Asp Asn
                20                  25                  30

Tyr Met Ile Trp Val Arg Gln Ala Pro Gly Gln Gly Leu Glu Trp Met
            35                  40                  45

Gly Asp Ile Asn Pro Tyr Asn Gly Gly Thr Thr Phe Asn Gln Lys Phe
    50                  55                  60

Lys Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Ser Pro Tyr Phe Ser Asn Leu Tyr Val Met Asp Tyr Trp
                100                 105                 110

Gly Gln Gly Thr Leu Val Thr Val Ser Ser Ala Ser Thr Lys Gly Pro
            115                 120                 125

Ser Val Phe Pro Leu Ala Pro Cys Ser Arg Ser Thr Ser Glu Ser Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Lys Thr Tyr Thr Cys Asn Val Asp
        195                 200                 205

His Lys Pro Ser Asn Thr Lys Val Asp Lys Arg Val Glu Ser Lys Tyr
    210                 215                 220

-continued

Gly Pro Pro Cys Pro Cys Pro Ala Pro Glu Phe Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser Gln Glu Asp
            260                 265                 270

Pro Glu Val Gln Phe Asn Trp Tyr Val Asp Gly Val Glu Val His Asn
        275                 280                 285

Ala Lys Thr Lys Pro Arg Glu Glu Gln Phe Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Gly Leu Pro Ser Ser Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Gln Glu Glu Met Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Arg Leu Thr Val Asp Lys
                405                 410                 415

Ser Arg Trp Gln Glu Gly Asn Val Phe Ser Cys Ser Val Met His Glu
            420                 425                 430

Ala Leu His Asn His Tyr Thr Gln Lys Ser Leu Ser Leu Ser Leu Gly
        435                 440                 445

Lys

<210> SEQ ID NO 438
<211> LENGTH: 218
<212> TYPE: PRT
<213> ORGANISM: Artificial Sequence
<220> FEATURE:
<223> OTHER INFORMATION: CD80

<400> SEQUENCE: 438

Glu Ile Val Leu Thr Gln Ser Pro Ala Thr Leu Ser Leu Ser Pro Gly
1               5                   10                  15

Glu Arg Ala Thr Leu Ser Cys Lys Ala Ser Gln Ser Val Asp Tyr Asp
            20                  25                  30

Gly Asp Asn Tyr Met Asn Trp Tyr Gln Gln Lys Pro Gly Gln Ala Pro
        35                  40                  45

Arg Leu Leu Ile Tyr Ala Ala Ser Asn Leu Glu Ser Gly Ile Pro Ala
    50                  55                  60

Arg Phe Ser Gly Ser Gly Ser Gly Thr Asp Phe Thr Leu Thr Ile Ser
65                  70                  75                  80

Ser Leu Glu Pro Glu Asp Phe Ala Val Tyr Tyr Cys His Leu Ser Asn
                85                  90                  95

Glu Asp Leu Ser Thr Phe Gly Gly Gly Thr Lys Val Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr

```
            130                 135                 140
Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215

<210> SEQ ID NO 439
<211> LENGTH: 268
<212> TYPE: PRT
<213> ORGANISM: Homo sapiens

<400> SEQUENCE: 439

Pro Gly Trp Phe Leu Asp Ser Pro Asp Arg Pro Trp Asn Pro Pro Thr
1               5                   10                  15

Phe Ser Pro Ala Leu Leu Val Val Thr Glu Gly Asp Asn Ala Thr Phe
            20                  25                  30

Thr Cys Ser Phe Ser Asn Thr Ser Glu Ser Phe Val Leu Asn Trp Tyr
        35                  40                  45

Arg Met Ser Pro Ser Asn Gln Thr Asp Lys Leu Ala Ala Phe Pro Glu
    50                  55                  60

Asp Arg Ser Gln Pro Gly Gln Asp Cys Arg Phe Arg Val Thr Gln Leu
65                  70                  75                  80

Pro Asn Gly Arg Asp Phe His Met Ser Val Val Arg Ala Arg Arg Asn
                85                  90                  95

Asp Ser Gly Thr Tyr Leu Cys Gly Ala Ile Ser Leu Ala Pro Lys Ala
            100                 105                 110

Gln Ile Lys Glu Ser Leu Arg Ala Glu Leu Arg Val Thr Glu Arg Arg
        115                 120                 125

Ala Glu Val Pro Thr Ala His Pro Ser Pro Ser Pro Arg Pro Ala Gly
    130                 135                 140

Gln Phe Gln Thr Leu Val Val Gly Val Val Gly Gly Leu Leu Gly Ser
145                 150                 155                 160

Leu Val Leu Leu Val Trp Val Leu Ala Val Ile Cys Ser Arg Ala Ala
                165                 170                 175

Arg Gly Thr Ile Gly Ala Arg Arg Thr Gly Gln Pro Leu Lys Glu Asp
            180                 185                 190

Pro Ser Ala Val Pro Val Phe Ser Val Asp Tyr Gly Glu Leu Asp Phe
        195                 200                 205

Gln Trp Arg Glu Lys Thr Pro Glu Pro Pro Val Pro Cys Val Pro Glu
    210                 215                 220

Gln Thr Glu Tyr Ala Thr Ile Val Phe Pro Ser Gly Met Gly Thr Ser
225                 230                 235                 240

Ser Pro Ala Arg Arg Gly Ser Ala Asp Gly Pro Arg Ser Ala Gln Pro
                245                 250                 255

Leu Arg Pro Glu Asp Gly His Cys Ser Trp Pro Leu
            260                 265

<210> SEQ ID NO 440
<211> LENGTH: 113
```

```
<212> TYPE: PRT
<213> ORGANISM: Artificial Sequence
<220> FEATURE:
<223> OTHER INFORMATION: PD-1 heavy chain variable region

<400> SEQUENCE: 440

Gln Val Gln Leu Val Glu Ser Gly Gly Gly Val Val Gln Pro Gly Arg
1               5                   10                  15

Ser Leu Arg Leu Asp Cys Lys Ala Ser Gly Ile Thr Phe Ser Asn Ser
            20                  25                  30

Gly Met His Trp Val Arg Gln Ala Pro Gly Lys Gly Leu Glu Trp Val
        35                  40                  45

Ala Val Ile Trp Tyr Asp Gly Ser Lys Arg Tyr Tyr Ala Asp Ser Val
    50                  55                  60

Lys Gly Arg Phe Thr Ile Ser Arg Asp Asn Ser Lys Asn Thr Leu Phe
65                  70                  75                  80

Leu Gln Met Asn Ser Leu Arg Ala Glu Asp Thr Ala Val Tyr Tyr Cys
                85                  90                  95

Ala Thr Asn Asp Asp Tyr Trp Gly Gln Gly Thr Leu Val Thr Val Ser
            100                 105                 110

Ser

<210> SEQ ID NO 441
<211> LENGTH: 327
<212> TYPE: PRT
<213> ORGANISM: Artificial Sequence
<220> FEATURE:
<223> OTHER INFORMATION: PD-1 heavy chain constant region

<400> SEQUENCE: 441

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205
```

Pro Ser Ser Ile Glu Lys Thr Ile Ser Lys Ala Lys Gly Gln Pro Arg
210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
                275                 280                 285

Arg Leu Thr Val Asp Lys Ser Arg Trp Gln Glu Gly Asn Val Phe Ser
290                 295                 300

Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 442
<211> LENGTH: 107
<212> TYPE: PRT
<213> ORGANISM: Artificial Sequence
<220> FEATURE:
<223> OTHER INFORMATION: PD-1 light chain variable region

<400> SEQUENCE: 442

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Ser Ser Asn Trp Pro Arg
                85                  90                  95

Thr Phe Gly Gln Gly Thr Lys Val Glu Ile Lys
            100                 105

<210> SEQ ID NO 443
<211> LENGTH: 107
<212> TYPE: PRT
<213> ORGANISM: Artificial Sequence
<220> FEATURE:
<223> OTHER INFORMATION: PD-1 light chain constant region

<400> SEQUENCE: 443

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

-continued

```
Lys His Lys Val Tyr Ala Cys Glu Val Thr His Gln Gly Leu Ser Ser
                85                  90                  95
Pro Val Thr Lys Ser Phe Asn Arg Gly Glu Cys
            100                 105

<210> SEQ ID NO 444
<211> LENGTH: 30
<212> TYPE: PRT
<213> ORGANISM: Artificial Sequence
<220> FEATURE:
<223> OTHER INFORMATION: PD-1 heavy FR1

<400> SEQUENCE: 444

Gln Val Gln Leu Val Glu Ser Gly Gly Val Val Gln Pro Gly Arg
1               5                   10                  15

Ser Leu Arg Leu Asp Cys Lys Ala Ser Gly Ile Thr Phe Ser
            20                  25                  30

<210> SEQ ID NO 445
<211> LENGTH: 5
<212> TYPE: PRT
<213> ORGANISM: Artificial Sequence
<220> FEATURE:
<223> OTHER INFORMATION: PD-1 heavy CDR1

<400> SEQUENCE: 445

Asn Ser Gly Met His
1               5

<210> SEQ ID NO 446
<211> LENGTH: 14
<212> TYPE: PRT
<213> ORGANISM: Artificial Sequence
<220> FEATURE:
<223> OTHER INFORMATION: PD-1 heavy FR2

<400> SEQUENCE: 446

Trp Val Arg Gln Ala Pro Gly Lys Gly Leu Glu Trp Val Ala
1               5                   10

<210> SEQ ID NO 447
<211> LENGTH: 17
<212> TYPE: PRT
<213> ORGANISM: Artificial Sequence
<220> FEATURE:
<223> OTHER INFORMATION: PD-1 heavy CDR2

<400> SEQUENCE: 447

Val Ile Trp Tyr Asp Gly Ser Lys Arg Tyr Tyr Ala Asp Ser Val Lys
1               5                   10                  15

Gly

<210> SEQ ID NO 448
<211> LENGTH: 32
<212> TYPE: PRT
<213> ORGANISM: Artificial Sequence
<220> FEATURE:
<223> OTHER INFORMATION: PD-1 heavy FR3

<400> SEQUENCE: 448

Arg Phe Thr Ile Ser Arg Asp Asn Ser Lys Asn Thr Leu Phe Leu Gln
1               5                   10                  15

Met Asn Ser Leu Arg Ala Glu Asp Thr Ala Val Tyr Tyr Cys Ala Thr
            20                  25                  30
```

<210> SEQ ID NO 449
<211> LENGTH: 4
<212> TYPE: PRT
<213> ORGANISM: Artificial Sequence
<220> FEATURE:
<223> OTHER INFORMATION: PD-1 heavy CDR3

<400> SEQUENCE: 449

Asn Asp Asp Tyr
1

<210> SEQ ID NO 450
<211> LENGTH: 11
<212> TYPE: PRT
<213> ORGANISM: Artificial Sequence
<220> FEATURE:
<223> OTHER INFORMATION: PD-1 heavy FR4

<400> SEQUENCE: 450

Trp Gly Gln Gly Thr Leu Val Thr Val Ser Ser
1               5                   10

<210> SEQ ID NO 451
<211> LENGTH: 23
<212> TYPE: PRT
<213> ORGANISM: Artificial Sequence
<220> FEATURE:
<223> OTHER INFORMATION: PD-1 light FR1

<400> SEQUENCE: 451

Glu Ile Val Leu Thr Gln Ser Pro Ala Thr Leu Ser Leu Ser Pro Gly
1               5                   10                  15

Glu Arg Ala Thr Leu Ser Cys
            20

<210> SEQ ID NO 452
<211> LENGTH: 11
<212> TYPE: PRT
<213> ORGANISM: Artificial Sequence
<220> FEATURE:
<223> OTHER INFORMATION: PD-1 light CDR1

<400> SEQUENCE: 452

Arg Ala Ser Gln Ser Val Ser Ser Tyr Leu Ala
1               5                   10

<210> SEQ ID NO 453
<211> LENGTH: 15
<212> TYPE: PRT
<213> ORGANISM: Artificial Sequence
<220> FEATURE:
<223> OTHER INFORMATION: PD-1 light FR2

<400> SEQUENCE: 453

Trp Tyr Gln Gln Lys Pro Gly Gln Ala Pro Arg Leu Leu Ile Tyr
1               5                   10                  15

<210> SEQ ID NO 454
<211> LENGTH: 7
<212> TYPE: PRT
<213> ORGANISM: Artificial Sequence
<220> FEATURE:
<223> OTHER INFORMATION: PD-1 light CDR2

<400> SEQUENCE: 454

Asp Ala Ser Asn Arg Ala Thr
1               5

<210> SEQ ID NO 455
<211> LENGTH: 32
<212> TYPE: PRT
<213> ORGANISM: Artificial Sequence
<220> FEATURE:
<223> OTHER INFORMATION: PD-1 light FR3

<400> SEQUENCE: 455

Gly Ile Pro Ala Arg Phe Ser Gly Ser Gly Ser Gly Thr Asp Phe Thr
1               5                   10                  15

Leu Thr Ile Ser Ser Leu Glu Pro Glu Asp Phe Ala Val Tyr Tyr Cys
            20                  25                  30

<210> SEQ ID NO 456
<211> LENGTH: 9
<212> TYPE: PRT
<213> ORGANISM: Artificial Sequence
<220> FEATURE:
<223> OTHER INFORMATION: PD-1 light CDR3

<400> SEQUENCE: 456

Gln Gln Ser Ser Asn Trp Pro Arg Thr
1               5

<210> SEQ ID NO 457
<211> LENGTH: 10
<212> TYPE: PRT
<213> ORGANISM: Artificial Sequence
<220> FEATURE:
<223> OTHER INFORMATION: PD-1 light FR4

<400> SEQUENCE: 457

Phe Gly Gln Gly Thr Lys Val Glu Ile Lys
1               5                   10

<210> SEQ ID NO 458
<211> LENGTH: 11
<212> TYPE: PRT
<213> ORGANISM: Artificial Sequence
<220> FEATURE:
<223> OTHER INFORMATION: Antibody 20502 VH CDR1

<400> SEQUENCE: 458

Gly Ser Ile Lys Ser Gly Ser Tyr Tyr Trp Gly
1               5                   10

<210> SEQ ID NO 459
<211> LENGTH: 16
<212> TYPE: PRT
<213> ORGANISM: Artificial Sequence
<220> FEATURE:
<223> OTHER INFORMATION: Antibody 20502 VH CDR2

<400> SEQUENCE: 459

Asn Ile Tyr Tyr Ser Gly Ser Thr Tyr Tyr Asn Pro Ser Leu Arg Ser
1               5                   10                  15

<210> SEQ ID NO 460
<211> LENGTH: 12
<212> TYPE: PRT
<213> ORGANISM: Artificial Sequence
<220> FEATURE:
<223> OTHER INFORMATION: Antibody 20502 VH CDR3

```
<400> SEQUENCE: 460

Ala Arg Glu Gly Ser Tyr Pro Asn Gln Phe Asp Pro
1               5                   10

<210> SEQ ID NO 461
<211> LENGTH: 11
<212> TYPE: PRT
<213> ORGANISM: Artificial Sequence
<220> FEATURE:
<223> OTHER INFORMATION: Antibody 20502 VL CDR1

<400> SEQUENCE: 461

Arg Ala Ser Gln Ser Val Ser Ser Asn Leu Ala
1               5                   10

<210> SEQ ID NO 462
<211> LENGTH: 7
<212> TYPE: PRT
<213> ORGANISM: Artificial Sequence
<220> FEATURE:
<223> OTHER INFORMATION: Antibody 20502 VL CDR2

<400> SEQUENCE: 462

Gly Ala Ser Thr Arg Ala Thr
1               5

<210> SEQ ID NO 463
<211> LENGTH: 9
<212> TYPE: PRT
<213> ORGANISM: Artificial Sequence
<220> FEATURE:
<223> OTHER INFORMATION: Antibody 20502 VL CDR3

<400> SEQUENCE: 463

Gln Gln Tyr His Ser Phe Pro Phe Thr
1               5

<210> SEQ ID NO 464
<211> LENGTH: 120
<212> TYPE: PRT
<213> ORGANISM: Artificial Sequence
<220> FEATURE:
<223> OTHER INFORMATION: Antibody 20502 Variable Heavy Chain

<400> SEQUENCE: 464

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Lys Ser Gly
            20                  25                  30

Ser Tyr Tyr Trp Gly Trp Ile Arg Gln Pro Pro Gly Lys Gly Leu Glu
        35                  40                  45

Trp Ile Gly Asn Ile Tyr Tyr Ser Gly Ser Thr Tyr Tyr Asn Pro Ser
    50                  55                  60

Leu Arg Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Glu Gly Ser Tyr Pro Asn Gln Phe Asp Pro Trp Gly Gln
            100                 105                 110

Gly Thr Leu Val Thr Val Ser Ser
        115                 120
```

```
<210> SEQ ID NO 465
<211> LENGTH: 26
<212> TYPE: PRT
<213> ORGANISM: Artificial Sequence
<220> FEATURE:
<223> OTHER INFORMATION: Antibody 20502 VH FR1

<400> SEQUENCE: 465
```

Gln Leu Gln Leu Gln Glu Ser Gly Pro Gly Leu Val Lys Pro Ser Glu
1               5                   10                  15

Thr Leu Ser Leu Thr Cys Thr Val Ser Gly
            20                  25

```
<210> SEQ ID NO 466
<211> LENGTH: 14
<212> TYPE: PRT
<213> ORGANISM: Artificial Sequence
<220> FEATURE:
<223> OTHER INFORMATION: Antibody 20502 VH FR2

<400> SEQUENCE: 466
```

Trp Ile Arg Gln Pro Pro Gly Lys Gly Leu Glu Trp Ile Gly
1               5                   10

```
<210> SEQ ID NO 467
<211> LENGTH: 30
<212> TYPE: PRT
<213> ORGANISM: Artificial Sequence
<220> FEATURE:
<223> OTHER INFORMATION: Antibody 20502 VH FR3

<400> SEQUENCE: 467
```

Arg Val Thr Ile Ser Val Asp Thr Ser Lys Asn Gln Phe Ser Leu Lys
1               5                   10                  15

Leu Ser Ser Val Thr Ala Ala Asp Thr Ala Val Tyr Tyr Cys
            20                  25                  30

```
<210> SEQ ID NO 468
<211> LENGTH: 11
<212> TYPE: PRT
<213> ORGANISM: Artificial Sequence
<220> FEATURE:
<223> OTHER INFORMATION: Antibody 20502 VH FR4

<400> SEQUENCE: 468
```

Trp Gly Gln Gly Thr Leu Val Thr Val Ser Ser
1               5                   10

```
<210> SEQ ID NO 469
<211> LENGTH: 450
<212> TYPE: PRT
<213> ORGANISM: Artificial Sequence
<220> FEATURE:
<223> OTHER INFORMATION: Antibody 20502 Full Length Heavy Chain

<400> SEQUENCE: 469
```

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Lys Ser Gly
            20                  25                  30

Ser Tyr Tyr Trp Gly Trp Ile Arg Gln Pro Pro Gly Lys Gly Leu Glu
        35                  40                  45

Trp Ile Gly Asn Ile Tyr Tyr Ser Gly Ser Thr Tyr Tyr Asn Pro Ser
    50                  55                  60

-continued

```
Leu Arg Ser Arg Val Thr Ile Ser Val Asp Thr Ser Lys Asn Gln Phe
 65                  70                  75                  80

Ser Leu Lys Leu Ser Ser Val Thr Ala Ala Asp Thr Ala Val Tyr Tyr
                 85                  90                  95

Cys Ala Arg Glu Gly Ser Tyr Pro Asn Gln Phe Asp Pro Trp Gly Gln
            100                 105                 110

Gly Thr Leu Val Thr Val Ser Ser Ala Ser Thr Lys Gly Pro Ser Val
            115                 120                 125

Phe Pro Leu Ala Pro Ser Ser Lys Ser Thr Ser Gly Gly Thr Ala Ala
130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
            195                 200                 205

Pro Ser Asn Thr Lys Val Asp Lys Lys Val Glu Pro Lys Ser Cys Asp
210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
            275                 280                 285

Asn Ala Lys Thr Lys Pro Arg Glu Glu Gln Tyr Asn Ser Thr Tyr Arg
290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
            355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
            435                 440                 445

Gly Lys
450
```